US012545685B2

(12) United States Patent
Sugimoto et al.

(10) Patent No.: US 12,545,685 B2
(45) Date of Patent: *Feb. 10, 2026

(54) DISPIROPYRROLIDINE DERIVATIVES

(71) Applicant: Daiichi Sankyo Company, Limited, Tokyo (JP)

(72) Inventors: Yuuichi Sugimoto, Tokyo (JP); Kouichi Uoto, Tokyo (JP); Takanori Wakabayashi, Tokyo (JP); Masaki Miyazaki, Tokyo (JP); Masaki Setoguchi, Tokyo (JP); Toru Taniguchi, Tokyo (JP); Keisuke Yoshida, Tokyo (JP); Akitake Yamaguchi, Tokyo (JP); Shoko Yoshida, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 203 days.

This patent is subject to a terminal disclaimer.

(21) Appl. No.: 18/450,009

(22) Filed: Aug. 15, 2023

(65) Prior Publication Data

US 2024/0246989 A1 Jul. 25, 2024

Related U.S. Application Data

(60) Division of application No. 17/234,404, filed on Apr. 19, 2021, now abandoned, which is a continuation of application No. 14/080,589, filed on Nov. 14, 2013, now abandoned, which is a continuation of application No. 13/416,061, filed on Mar. 9, 2012, now Pat. No. 8,629,133.

(60) Provisional application No. 61/546,805, filed on Oct. 13, 2011.

(30) Foreign Application Priority Data

Mar. 10, 2011 (JP) ................................ 2011-052687

(51) Int. Cl.

| | |
|---|---|
| ***C07D 487/20*** | (2006.01) |
| ***A61K 9/14*** | (2006.01) |
| ***A61K 9/16*** | (2006.01) |
| ***A61K 9/20*** | (2006.01) |
| ***C07D 471/20*** | (2006.01) |
| ***C07D 487/10*** | (2006.01) |

(52) U.S. Cl.

CPC .............. *C07D 487/20* (2013.01); *A61K 9/14* (2013.01); *A61K 9/1623* (2013.01); *A61K 9/1652* (2013.01); *A61K 9/2018* (2013.01); *A61K 9/2054* (2013.01); *A61K 9/2059* (2013.01); *C07D 471/20* (2013.01); *C07D 487/10* (2013.01)

(58) Field of Classification Search

USPC .......................................................... 514/210

See application file for complete search history.

(56) References Cited

U.S. PATENT DOCUMENTS

| | | | |
|---|---|---|---|
| 8,629,133 | B2 | 1/2014 | Sugimoto et al. |
| 9,359,368 | B2 | 6/2016 | Yoshida et al. |
| 9,540,386 | B2 | 1/2017 | Yoshida et al. |
| 9,718,830 | B2 | 8/2017 | Yoshida et al. |
| 9,718,831 | B2 | 8/2017 | Yoshida et al. |
| 9,745,315 | B2 | 8/2017 | Yoshida et al. |
| 9,884,871 | B2 | 2/2018 | Yoshida et al. |
| 10,023,578 | B2 | 7/2018 | Yoshida et al. |
| 10,030,030 | B2 | 7/2018 | Yoshida et al. |
| 10,485,794 | B2 | 11/2019 | Seki |
| 11,058,673 | B2 | 7/2021 | Tse et al. |
| 2004/0259867 | A1 | 12/2004 | Fotouhi et al. |
| 2004/0259884 | A1 | 12/2004 | Haley et al. |
| 2007/0213341 | A1 | 9/2007 | Chen et al. |

(Continued)

FOREIGN PATENT DOCUMENTS

| | | |
|---|---|---|
| CN | 103635473 A | 3/2014 |
| CN | 104812757 A | 7/2015 |

(Continued)

OTHER PUBLICATIONS

Babu, et al (2006) "Heteropoly Acid-silica Mediated [3+2] Cycloaddition of Azomethine Ylides-a Facile Multicomponent One-pot Synthesis of Novel Dispiroheterocycles", Tetrahedron Letters, 47(52):9221-9225.

(Continued)

*Primary Examiner* — Ana Z Muresan

(74) *Attorney, Agent, or Firm* — Polsinelli PC

(57) ABSTRACT

The present invention provides a dispiropyrrolidine derivative represented by the following formula (1), which has various substituents, inhibits interaction between Mdm2 protein and p53 protein and exhibits anti-tumor activity, wherein $R^1$, $R^2$, $R^3$, ring A, and ring B in formula (1) respectively have the same meanings as defined in the specification.

(1)

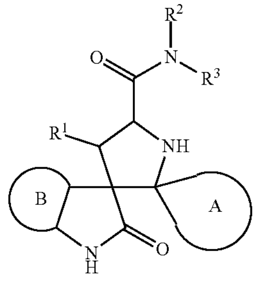

5 Claims, No Drawings

(56) References Cited

U.S. PATENT DOCUMENTS

| | | | |
|---|---|---|---|
| 2008/0125430 | A1 | 5/2008 | Wang et al. |
| 2011/0301176 | A1 | 12/2011 | Uoto et al. |
| 2012/0122947 | A1 | 5/2012 | Wang et al. |
| 2012/0264738 | A1 | 10/2012 | Sugimoto et al. |
| 2012/0289494 | A1 | 11/2012 | Wang et al. |
| 2014/0121196 | A1 | 5/2014 | Sugimoto et al. |
| 2015/0210707 | A1 | 7/2015 | Yoshida et al. |
| 2017/0216302 | A1 | 8/2017 | Seki |
| 2018/0296547 | A1 | 10/2018 | Tse et al. |
| 2022/0106324 | A1 | 4/2022 | Sugimoto et al. |

FOREIGN PATENT DOCUMENTS

| | | | |
|---|---|---|---|
| EP | 2707372 | A2 | 3/2014 |
| EP | 2894156 | A1 | 7/2015 |
| EP | 3284466 | A1 | 2/2018 |
| WO | 9912904 | A1 | 3/1999 |
| WO | 0175145 | A2 | 10/2001 |
| WO | 03051360 | A1 | 6/2003 |
| WO | 03076608 | A1 | 9/2003 |
| WO | 2005110996 | A1 | 11/2005 |
| WO | 2006024837 | A1 | 3/2006 |
| WO | 2006032466 | A2 | 3/2006 |
| WO | 2006091646 | A2 | 8/2006 |
| WO | 2006125974 | A1 | 11/2006 |
| WO | 2006136606 | A2 | 12/2006 |
| WO | 2007104664 | A1 | 9/2007 |
| WO | 2007104714 | A1 | 9/2007 |
| WO | 2008034736 | A2 | 3/2008 |
| WO | 2008036168 | A2 | 3/2008 |
| WO | 2008055812 | A1 | 5/2008 |
| WO | 2008119741 | A2 | 10/2008 |
| WO | 2008141917 | A1 | 11/2008 |
| WO | 2008141975 | A1 | 11/2008 |
| WO | 2009077357 | A1 | 6/2009 |
| WO | 2009080488 | A1 | 7/2009 |
| WO | 2009115425 | A1 | 9/2009 |
| WO | 2010027500 | A1 | 3/2010 |
| WO | 2010028862 | A1 | 3/2010 |
| WO | 2010031713 | A1 | 3/2010 |
| WO | 2010082612 | A1 | 7/2010 |
| WO | 2010084097 | A1 | 7/2010 |
| WO | 2010091979 | A1 | 8/2010 |
| WO | 2010094622 | A1 | 8/2010 |
| WO | 2010121995 | A1 | 10/2010 |
| WO | 2011045257 | A1 | 4/2011 |
| WO | 2011060049 | A2 | 5/2011 |
| WO | 2011061139 | A1 | 5/2011 |
| WO | 2011067185 | A1 | 6/2011 |
| WO | 2011098398 | A1 | 8/2011 |
| WO | 2011101297 | A1 | 8/2011 |
| WO | 2011127058 | A2 | 10/2011 |
| WO | 2011134925 | A1 | 11/2011 |
| WO | 2012007409 | A1 | 1/2012 |
| WO | 2012022707 | A1 | 2/2012 |
| WO | 2012034954 | A1 | 3/2012 |
| WO | 2012038307 | A1 | 3/2012 |
| WO | 2012065022 | A2 | 5/2012 |
| WO | 2012076513 | A1 | 6/2012 |
| WO | 2012121361 | A1 | 9/2012 |
| WO | 2012155066 | A2 | 11/2012 |
| WO | 2015108175 | A1 | 7/2015 |
| WO | 2016133194 | A1 | 8/2016 |
| WO | 2016167236 | A1 | 10/2016 |

OTHER PUBLICATIONS

Babu, et al. (2007) "Ultrasonic Assisted-silica Mediated [3+2] Cycloaddition of Azomethine Ylides-a Facile Multicomponent One-pot Synthesis of Novel Dispiroheterocycles", Tetrahedron Letters, 48(38):6809-6813.

Babu, et al. (2007) "Zrocl2. 8h20-mediated Microwave Induced [3+2] Cycloaddition of Azomethine Ylides. Facile One-pot Synthesis of Novel Dispiroheterocycles", Tetrahedron Letters, 48(2):305-308.

Casaschi, et al. (1993) "Retention of the Configuration of Oxoindolin-3-ylidene Dipolarophiles in the Reaction With Azomethine Ylides From Ninhydrin and Secondary Amino Acids", Gazzetta Chimica Italiana, 123(3):137-143.

Datrika, et al. (2016) "Stereoselective Synthesis of (R)-(?) and (S)-(+)-phoracantholide I From (R)-(+)-c-valerolactone", Tetrahedron: Asymmetry, 27(14-15):603-607.

Ding, et al. (2005) "Structure-Based Design of Potent Non-Peptide MDM2 Inhibitors", J. Am. Chem. Soc., 127:10130-10131.

Ding, et al. (2006) "Structure-Based Design of Spiro-oxindoles as Potent, Specific Small-Molecule Inhibitors of the MDM2-p53 Interaction", J. Med. Chem., 49:3432-3435.

Ding, et al. (2005) "Synthesis of Spirooxindoles via Asymmetric 1,3-dipolar Cycloaddition", Tetrahedron Letters, 46:5949-5951.

Giuseppetti, et al. (1994) "The Crystal Structure of 2-(5,7-dichloro-I-methyloxoindol)-3-spiro-I'-(2'-Benzoylhexahydropyrrolizin)-3'-spiro-2"-indan-1",3"-dion", Zeitschrift Fuer Kristallographie, 209(4):360-362.

Grigg, et al. (1984) "Decarboxylative Transamination. A New Route to Spirocyclic and Bridgehead-nitrogen Compounds. Relevance to A-amino Acid Decarboxylases", Journal of the Chemical Society, 3:182-183.

Hardcastle, et al. (2006) "Small-Molecule Inhibitors of the MDM2-p53 Protein-Protein Interaction Based on an Isoindolinone Scaffold", J. Med. Chem., 49:6209-6221.

Jayashankaran, et al. (2006) "Synthesis of Novel Ferrocenyl Oxindole and Ferrocene Substituted Dispiroheterocycles Through [3+2] Cycloaddition of Azomethine Ylides", Synthetic Communications, 36(7):979-986.

Katritzky, et al (2003) "A General Route to 5-Aminotetrazoles", J. Org. Chem., 68(12):4941-4943.

Katritzky, et al (2000) "Di(benzotriazol-1-yl)methanimine: A New Reagent for the Synthesis of Tri- and Tetrasubstituted Guanidines", J. Org. Chem., 65(23):8080-8082.

Kriek et al. (2003) "Synthesis of Novel Tetrahydropyran-Based Dipeptide Isosters by Overman Rearrangement of 2,3-Didehydroglycosides", European Journal of Organic Chemistry, pp. 2418-2427.

Lakshmi, et al. (2010) "An Expedient Approach for the Synthesis of Dispiropyrrolidine Bisoxindoles, Spiropyrrolidine Oxindoles and Spiroindane-1,3-diones Through 1,3-dipolar Cycloaddition Reactions", Tetrahedron Letters, 51:(7)1064-1068.

Liu, et al. (2010) "Regio- and Stereoselective Synthesis of Novel Dispiropyrrolidine Bisoxindole Derivatives via Multicomponent Reactions", J. Comb. Chem., 12(2):292-294.

Neidle, Stephen (2008) Cancer Drug Design and Discovery, pp. 427-431.

Pellegrini, et al. (1996) "Total Synthesis of (+)-Elacomine and (−)-Isoelacomine, Two Hitherto Unnamed Oxindole Alkaloids from Elaeagnus commutata", Helvetica Chimica Acta, 79:151-168.

Sebahar, et al. (2000) "The Asymmetric Total Synthesis of(+)-and(−)- Spirotryprostatin B", Journal of the American Chemical Society, 122:5666-5667.

Shanmugam, et al. (2008) "A Facile and Efficient Synthesis of Highly Functionalized 3,3'-dispiropyrrolidine- and 3,3'-dispiropyrrolizidine Bisoxindoles via [3+2] Cycloaddition", Tetrahedron Letters, 49:(16)2611-2615. 2008.

Suresh, et al. (2007) "Ti02-silica Mediated One Pot Three Component 1,3-dipolar Cycloaddition Reaction: a Facile and Rapid Synthesis of Dispiro Acenaphthenone/oxindole [indanedione/oxindole] Pyrroloisoquinoline Ring Systems", Tetrahedron, 63(33):8010-8016.

Thorn, et al. (1996) "Organozinc Reagents for the Nucleophilic C-Glycosylation of Glycals", Synlett, 1996 (2):185-186.

Vassilev, et al. (Feb. 6, 2004) "In Vivo Activation of the p53 Pathway by Small-Molevule Antagonists of MDM2", Science, 303:844-848.

Williams, et al. (1992) "Asymmetric [1,3]-Dipolar Cycloaddition Reactions: Synthesis of Highly Substituted Proline Derivates", J. Org. Chem., 57(24):6527-6532.

(56) References Cited

OTHER PUBLICATIONS

Yu, et al. (2009) "Potent and Orally Active Small-Molecule Inhibitors of the MDM2-p53 Interaction", J. Med. Chem., 52:7970-7973.
Anonymous. (2016) "Sarcoma," Oncology Forum. Diagnosis and Treatment and Case Discussion. Tumor Forum [online]. Retrieved from: http://www.cancertreatmentcn.com/solid-tumor/%E8%82%89%E7%98%A4/, retrieved on Jul. 6, 2020; 3 pages with 3 pages of translation.
Babu A. R., et al., "Regioselective Synthesis of Novel Dispiro-Oxindoloindenoquinoxaline Pyrrolidines Through 1, 3-Dipolar Cycloaddition Methodology, Synthetic Communications," 2008, vol. 38, No. 9, pp. 1433-1438.
clinicaltrials.gov (Jan. 1, 20203) "ALRN-6924 in Patients With Advanced Solid Tumors or Lymphomas," Identifier: NCT02264613: First Posted Oct. 15, 2014. American Association for Cancer Research [online]. Retrieved from: clincancerres.aacrjournals.org on Apr. 10, 2020; 9 pages.
Coindre J.M., et al., "Well-Differentiated and Dedifferentiated Liposarcomas," Virchows Arch, Feb. 2010, vol. 456, pp. 167-179.
Communication pursuant to Article 94(3) for European Patent application No. EP16798291.7, mailed on Apr. 3, 2025, 6 pages.
Coquard I., et al.,"Effect of the MDM2 Antagonist RG7112 on the P53 Pathway in Patients with MDM2-Amplified, Well-Differentiated or Dedifferentiated Liposarcoma: an Exploratory Proof of-Mechanism Study," The Lancet Oncology, Nov. 2012, vol. 13, No. 11, pp. 1133-1140.
Extended European Search Report for European Application No. 12755073.9, dated Jun. 24, 2014, 6 pages.
Flaherty K.T., et al., "Phase I, Dose-Escalation Trial of the Oral Cyclin-Dependent Kinase 4/6 Inhibitor PD 0332991, Administered Using a 21-Day Schedule in Patients with Advanced Cancer," Clinical Cancer Research, Jan. 15, 2012, vol. 18, No. 2, pp. 568-576.
Gounder M.M., "A Phase 1 Study of the MDM2 Inhibitor DS-3032b in Patients (Pts) with Advanced Solid Tumors and Lymphomas," 2016, 3 Pages.
International Preliminary Report on Patentability for Application No. PCT/JP2012/056066, mailed on Sep. 19, 2013, 14 pages.
International Search Report and Written Opinion for International Application No. PCT/JP2016/081975. dated Feb. 1, 2017, 12 pages.
International Search Report and Written Opinion issued in PCT application No. PCT/JP2012/056066 on May 22, 2012, 21 pages.
Momand J., et al., "Survey and Summary: The MDM2 Gene Amplification Database," Nucleic Acids Research, Aug. 1998, vol. 26, No. 15, pp. 3453-3459.
Office Action for Chinese Patent Application No. 201680061650.4, mailed Mar. 16, 2020, 8 pages.
Rayburn E., et al., "MDM2 and Human Malignancies: Expression, Clinical Pathology, Prognostic Markers, and Implications for Chemotherapy," Current Cancer Drug Targets, Feb. 2004, vol. 5, No. 1, pp. 27-41.
Sankyo D., "A Multiple Ascending Dose Study of Milademetan in Subjects With Advanced Solid Tumors or Lymphomas," National Library of Medicine National Center for Biotechnology Information, 2015, 20 Pages.
Sankyo D., "Safety, Tolerability and Pharmacokinetics of Milademetan Alone and With 5-Azacitidine (AZA) in Acute Myelogenous Leukemia (AML) or High-Risk Myelodysplastic Syndrome (MDS)," National Library of Medicine National Center for Biotechnology Information, 2015, 19 pages.
Siu L.L., et al., "Phase 1 Dose Escalation, Food Effect, and Biomarker Study of RG7388, a More Potent Second-Generation MDM2 Antagonist, in Patients (pts) with Solid Tumors," Journal of Clinical Oncology, May 20, 2014 , vol. 32, No. 15, pp. 2.
Steinman H.A., et al., "An Alternative Splice Form of Mdm2 Induces P53-independent Cell Growth and Tumorigenesis," Journal Biological Chemistry, vol. 279, No. 6, pp. 4877-4886.
Zhang Ruming, "General Knowlege Evidence 1: Modern Surgical Treatment of Soft Tissue Sarcomas," 2nd Edition, Tianjin Science and Technology Press, Feb. 28, 2010, p. 72.

DISPIROPYRROLIDINE DERIVATIVES

CROSS REFERENCE TO RELATED APPLICATIONS

This application is a divisional application of U.S. application Ser. No. 17/234,404, filed Apr. 19, 2021, which is a continuation application of U.S. application Ser. No. 14/080,589, filed Nov. 14, 2013, which is a continuation application of U.S. application Ser. No. 13/416,061, filed on Mar. 9, 2012, now U.S. Pat. No. 8,629,133, which claims priority to Application No. 61/546,805, filed on Oct. 13, 2011, and Japanese Application No. 2011-052687 filed on Mar. 10, 2011. The entire disclosures of each of the above-referenced applications are incorporated herein by reference.

BACKGROUND OF THE INVENTION

Field of the Invention

The present invention relates to a dispiropyrrolidine compound having anti-tumor activity by inhibition of murine double minute 2 (Mdm2) or a salt thereof.

Description of the Related Art p53 is known as an important factor for inhibiting canceration of cells. p53 is a transcription factor that induces the expression of genes involved in the cell cycle and cellular apoptosis in response to various stresses. p53 is thought to inhibit canceration of cells by a transcription regulating function thereof. In fact, deletion or mutation of the p53 gene is observed in about half of human cancer cases.

Meanwhile, overexpression of murine double minute 2 (Mdm2), a type of E3 ubiquitin ligase, is known as a factor for canceration of cells that are cancerated in spite of the presence of normal p53. Mdm2 is a protein the expression of which is induced by p53. Mdm2 negatively regulates p53 by mediating degradation of p53 by binding to the transcription activity domain of p53 to decrease the transcription activity of p53, exporting p53 out of the nucleus, and further acting as a ubiquitination ligase against p53. Therefore, it is thought that inactivation of functions of and degradation of p53 are promoted in cells in which Mdm2 is overexpressed, resulting in canceration (J. Am. Chem. Soc., 2005, 127, 10130-10131).

Paying attention to such functions of Mdm2, many approaches have been attempted using substances that inhibit the suppression of p53 functions by Mdm2 as candidate anti-tumor agents. Examples of the Mdm2 inhibitors targeting the Mdm2-p53 binding site have been reported, which include spirooxindole derivatives (WO2006/091646, WO2006/136606, WO2007/104664, WO2007/104714, WO2008/034736, WO2008/036168, WO2008/055812, WO2008/141917, WO2008/141975, WO2009/077357, WO2009/080488, WO2010/084097, WO2010/091979, WO2010/094622. WO2010/121995; J. Am. Chem. Soc., 2005, 127, 10130-10131; J. Med. Chem., 2006, 49, 3432-3435; and J. Med. Chem., 2009, 52, 7970-7973), indole derivatives (WO2008/119741), pyrrolidine-2-carboxamide derivatives (WO2010/031713), pyrrolidinone derivatives (WO2010/028862), and isoindolinone derivatives (WO2006/024837; and J. Med. Chem, 2006, 49, 6209-6221).

The present invention provides a novel Mdm2 inhibiting compound. Furthermore, the present invention provides an anti-tumor agent containing the Mdm2 inhibiting compound.

SUMMARY OF THE INVENTION

As a result of extensive studies, the present inventors have found that a compound having a structure represented by the following general formula (1) or a salt thereof has potent Mdm2 inhibiting activity and they accomplished the present invention.

More specifically, the present invention provides:

[1]A compound represented by general formula (1) of a salt thereof:

(1)

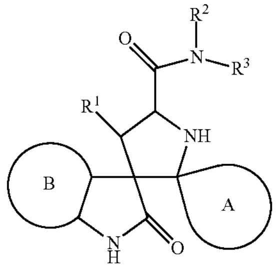

wherein ring A represents a spiro-linked 4- to 6-membered saturated hydrocarbon ring which may have one or more substituents selected from Group 1, or a spiro-linked 6-membered saturated heterocyclic ring which may have one or more substituents selected from Group 1;

ring B represents a benzene ring which may have one or more substituents selected from Group 2, a pyridine ring which may have one or more substituents selected from Group 2, or a pyrimidine ring which may have one or more substituents selected from: Group 2;

$R^1$ represents an aryl group which may have one or more substituents selected from Group 3, a heteroaryl group which may have one or more substituents selected from Group 3, a $C_3$-$C_6$ cycloalkyl group which may have one or more substituents selected from Group 3, or a $C_3$-$C_6$ cycloalkenyl group which may have one or more substituents selected from Group 3;

$R^2$ represents a $C_1$-$C_6$ alkyl group which may be substituted with one to three halogen atoms or one to three hydroxy groups, or a hydrogen atom; and $R^3$ represents a group represented by the following general formula (2), (3), or (4):

(2)

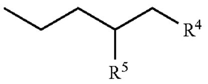

(3)

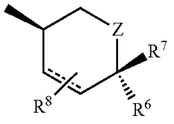

-continued (4)

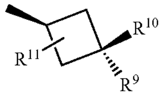

wherein in formula (2), $R^4$ and $R^5$ each independently represent a hydroxy group, a $C_1$-$C_6$ alkyl group, or a $C_1$-$C_6$ alkoxy group, or $R^4$ and $R^5$ together with the carbon atoms to which the $R^4$ and $R^5$ groups are respectively bonded may together form a 4- to 6-membered saturated hydrocarbon ring;

in formula (3), the broken line in the ring structure indicates that the bond may be a double bond, $R^6$ represents a $C_1$-$C_6$ alkyl group which may have one or more substituents selected from Group 4, a carbamoyl group which may have one or more substituents selected from Group 5, a 5- or 6-membered nitrogen-containing heteroaryl group which may be substituted with an oxo group or one or more $C_1$-$C_6$ alkyl groups which may be substituted with an oxo group or one hydroxy group, a hydroxy group, or —NR'R", wherein R' and R" each independently represent a $C_1$-$C_6$ alkyl group which may be substituted with one to three halogen atoms, an oxo group, or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group which may have one or more substituents selected from a $C_1$-$C_6$ alkyl group and a hydroxy group, $R^7$ represents a $C_1$-$C_6$ alkyl group which may be substituted with one hydroxy group, a hydroxy group, or a hydrogen atom, of $R^6$ and $R^7$ may together form a spiro-linked 4- to 6-membered hydrocarbon ring or a spiro-linked 4- to 6-membered nitrogen-containing heterocyclic ring, $R^8$ represents one or more substituents selected from a hydroxy group, a $C_1$-$C_6$ alkyl group, and a $C_1$-$C_6$ alkoxy group, and Z represents $CH_2$, NH, or an oxygen atom; and in formula (4), $R^9$ represents a $C_1$-$C_6$ alkyl group which may have one or more substituents selected from Group 4, a carbamoyl group which may have one or more substituents selected from Group 5, a 5- or 6-membered nitrogen-containing heteroaryl group which may be substituted with an oxo group or one or more $C_1$-$C_6$ alkyl groups which may be substituted with an oxo group or one hydroxy group, a hydroxy group, or —NR'R", wherein R' and R" each independently represent a $C_1$-$C_6$ alkyl group which may be substituted with one to three halogen atoms, an oxo group, or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group which may have one or more substituents selected from a $C_1$-$C_6$ alkyl group and a hydroxy group, $R^{10}$ represents a $C_1$-$C_6$ alkyl group which may be substituted with one hydroxy group, a hydroxy group, or a hydrogen atom, or $R^9$ and $R^{10}$ may together form a spiro-linked 4- to 6-membered hydrocarbon ring or a spiro-linked 4- to 6-membered nitrogen-containing heterocyclic ring, and $R^{11}$ represents one or more substituents selected from a hydroxy group, a $C_1$-$C_6$ alkyl group, and a $C_1$-$C_6$ alkoxy group, wherein Group 1 represents a halogen atom, a $C_1$-$C_6$ alkyl group which may be substituted with one to three halogen atoms, a $C_1$-$C_6$ alkoxy group, or a cyano group, Group 2 represents a halogen atom, a $C_1$-$C_6$ alkyl group which may be substituted with one to three halogen atoms, a $C_3$-$C_4$ cycloalkyl group which may be substituted with one to three halogen atoms, a vinyl group, an ethinyl group, a cyano group, or a $C_1$-$C_6$ alkoxy group, Group 3 represents a halogen atom, a $C_1$-$C_6$ alkyl group which may be substituted with one to three halogen atoms or one to three hydroxy groups, a $C_3$-$C_4$ cycloalkyl group which may be substituted with one to three halogen atoms or one to three hydroxy groups, a vinyl group, an ethinyl group, a cyano group, —OR', —NR'R", —COOR', or —CONHR', wherein R' and R" each independently represent a $C_1$-$C_6$ alkyl group which may be substituted with one to three halogen atoms or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group which may have one or more substituents selected from a $C_1$-$C_6$ alkyl group and a hydroxy group, Group 4 represents a halogen atom, a hydroxy group, a carbamoyl group, a morpholino group, a $C_1$-$C_6$ alkoxy group, a $C_1$-$C_6$ alkylsulfonyl group, or —NR'R", wherein R' and R" each independently represent a $C_1$-$C_6$ alkyl group which may be substituted with one to three halogen atoms, one to three hydroxy groups, or an oxo group, a $C_3$-$C_4$ cycloalkyl group which may be substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group which may have one or more substituents selected from a $C_1$-$C_6$ alkyl group and a hydroxy group, and Group 5 represents a $C_1$-$C_6$ alkyl group which may be substituted with one to three halogen atoms, one to three hydroxy groups, or a $C_1$-$C_6$ alkoxy group, a $C_3$-$C_6$ cycloalkyl group, a $C_1$-$C_6$ alkoxy group, or a tetrahydropyranyl group.

[2] A compound according to [1] represented by general formula (5) or a salt thereof;

(5)

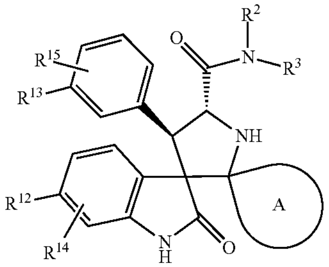

wherein in formula (5), ring A, $R^2$, and $R^3$ have the same meanings as ring A, $R^2$, and $R^3$, respectively, in [1];

$R^{12}$ and $R^{13}$ represent a group selected from a halogen atom, a $C_1$-$C_6$ alkyl group which may be substituted with one to three halogen atoms or one to three hydroxy groups, and a cyano group;

$R^{14}$ represents one or more substituents selected from halogen atom, a $C_1$-$C_6$ alkyl group which may be substituted with one to three halogen atoms or one to three hydroxy groups, and a cyano group; and $R^{15}$ represents one or more substituents selected from Group 3, wherein Group 3 has the same meaning as Group 3 in [1].

[3] A compound according to [1] represented by general formula (6) or a salt thereof;

(6)

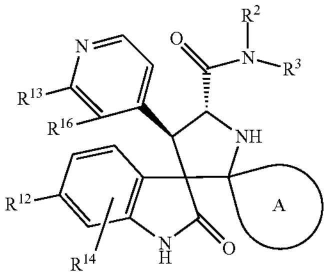

wherein in formula (6), ring A, $R^2$, and $R^3$ have the same meanings as ring A, $R^2$, and $R^3$, respectively, in [1];

$R^{12}$, $R^{13}$, and $R^{16}$ represent a group selected from a halogen atom, a $C_1$-$C_6$ alkyl group which may be substituted with one to three halogen atoms or one to three hydroxy groups, and a cyano group; and $R^{14}$ represents one or more substituents selected from a halogen atom, a $C_1$-$C_6$ alkyl group which may be substituted with one to three halogen atoms or one to three hydroxy groups, and a cyano group.

[4] A compound according to [1] represented by general formula (7) or a salt thereof:

(7)

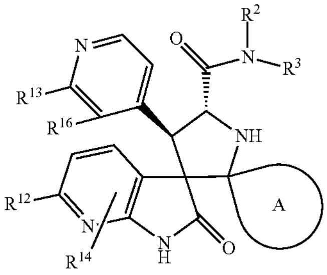

wherein in formula (7), ring A, $R^2$, and $R^3$ have the same meanings as ring A, $R^2$, and $R^3$, respectively, in [1];

$R^{12}$, $R^{13}$, and $R^{16}$ represent a group selected from a halogen atom, a $C_1$-$C_6$ alkyl group which may be substituted with one to three halogen atoms or one to three hydroxy groups, and a cyano group; and $R^{14}$ represents one or more substituents selected from a halogen atom, a $C_1$-$C_6$ alkyl group which may be substituted with one to three halogen atoms or one to three hydroxy groups, and a cyano group.

[5] A compound according to [1] represented by general formula (8) or a salt thereof:

(8)

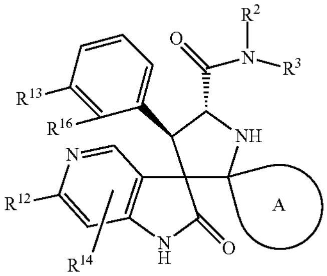

wherein in formula (8), ring A, $R^2$, and $R^3$ have the same meanings as ring A, $R^2$, and $R^3$, respectively, in [1];

$R^{12}$, $R^{13}$, and $R^{16}$ represent a group selected from a halogen atom, a $C_1$-$C_6$ alkyl group which may be substituted with one to three halogen atoms or one to three hydroxy groups, and a cyano group; and $R^{14}$ represents one or more substituents selected from a halogen atom, a $C_1$-$C_6$ alkyl group which may be substituted with one to three halogen atoms or one to three hydroxy groups, and a cyano group.

[6] A compound selected from the following group or a salt thereof:

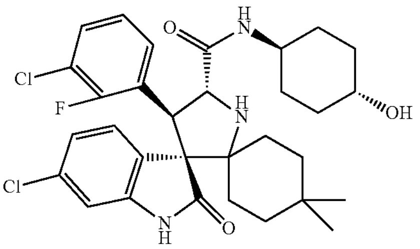

-continued
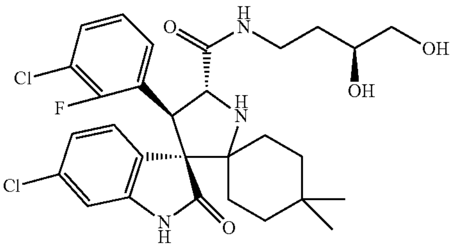
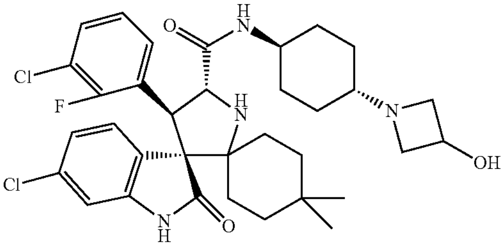
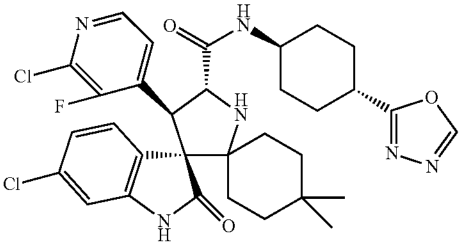
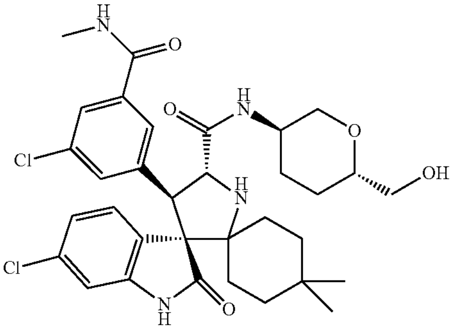
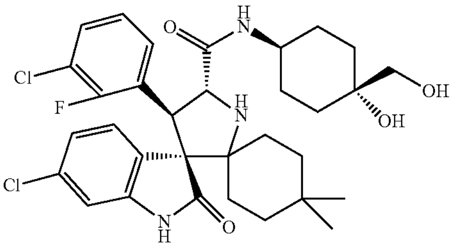
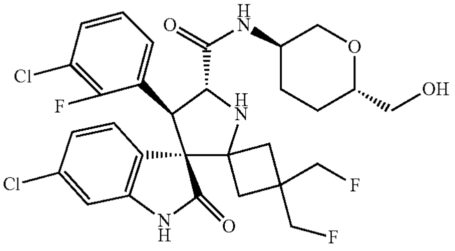
-continued
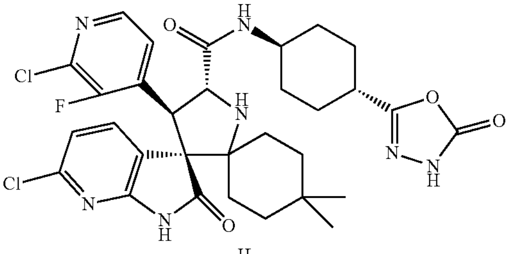
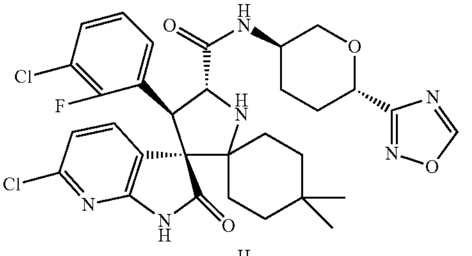
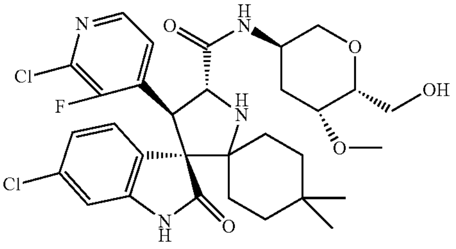
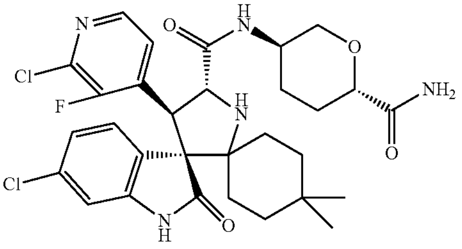
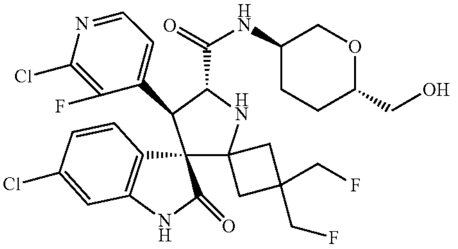
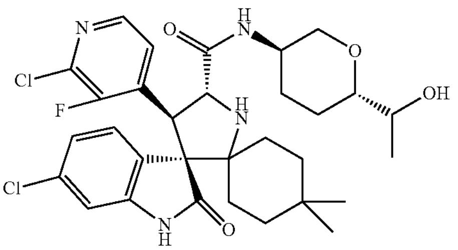
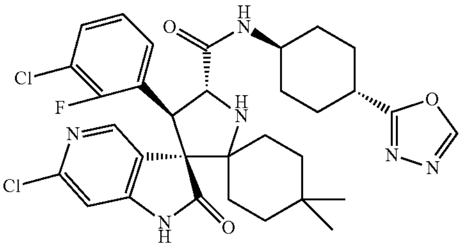

-continued

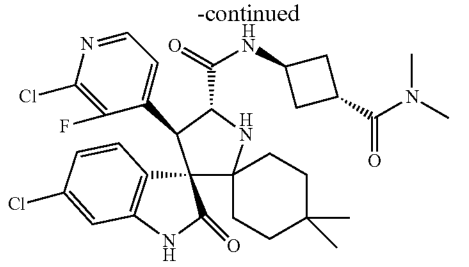

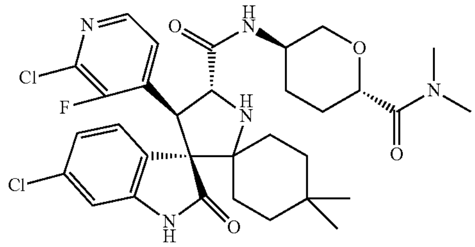

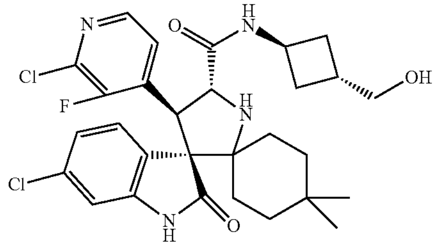

[7] (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide hydrochloride.

[8] (3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2'"-dihydrodispiro[cyclohexane-1,2'-pyrrolidine-3',3"-indole]-S'-carboxamide sulfate.

[9] (3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide methanesulfonate.

[10] (3'R, 4'S, S'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"=dihydrodispiro[cyclohexane-1,2'-pyrrolidine-3',3"-indole]-5'-carboxamide ethanesulfonate.

[11] (3'R, 4'S,5'R)—N-[(5R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide benzenesulfonate.

[12] (3"R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5-carboxamide p-toluenesulfonate.

[13] (3'R, 4'S,5'R)-6"-chloro-4'-(2-chloro-3-fluoropyridin-4-yl)-N-((3R,6S)-6-[1-hydroxyethyl]tetrahydro-2H-pyran-3-yl)-4,4-dimethyl-2"-oxo-1",2"-dihydrodispiro[cyclohexane-1,2'-pyrrolidine-3',3"-indole]-5'-carboxamide benzenesulfonate.

[14] An inhibitor of Mdm2 comprising a compound according to any one of [1] to or a salt thereof.

[15] An inhibitor of Mdm2 ubiquitin ligase comprising a compound according to any one of [1] to or a salt thereof.

[16] An inhibitor of p53-Mdm2 binding comprising a compound according to any one of [1] to or a salt thereof.

[17] An inhibitor of suppression of p53 transcription activity comprising a compound according to any one of [1] to [13] or a salt thereof.

[18] An inhibitor of p53 degradation comprising a compound according to any one of [1] to [13] or a salt thereof;

[19] A medicament comprising a compound according to any one of [1] to or a salt thereof as an active ingredient.

[20] An anticancer agent comprising a compound according to any one of [1] to or a salt thereof as an active ingredient.

[21] An anticancer agent according to [20], wherein the cancer is lung cancer, breast cancer, prostate cancer, colon cancer, acute myeloid leukemia, malignant lymphoma, malignant melanoma, retinoblastoma, neuroblastoma, or sarcoma.

[22] A pharmaceutical composition comprising a compound according to any one of [1] to [13] of a salt thereof and a pharmaceutically acceptable carrier.

[23] A method for treating cancer, comprising administering a compound according to any one of [1] to [13] or a salt thereof.

[24] A method for treating cancer according to [23], wherein the cancer is lung cancer, breast cancer, prostate cancer, colon cancer, acute myeloid leukemia, malignant lymphoma, malignant melanoma, retinoblastoma, neuroblastoma, or sarcoma.

[25] Use of a compound according to any one of [1] to [13] or a salt thereof for the manufacture of a medicament.

[26] Use of a compound according to any one of [1] to [13] or a salt thereof for the manufacture of an anticancer agent.

The present invention provides novel spiroprolinamide derivatives represented by the above formula (1), which have Mdm2 inhibiting activity. Such novel compounds are useful as an anti-tumor agent.

DETAILED DESCRIPTION OF THE PREFERRED EMBODIMENTS

In the present invention, “Mdm2” means a protein encoded by the murine double minute 2 gene. “Mdm2” includes Mdm2 proteins encoded by a complete length of the Mdm2 gene, Mdm2 proteins encoded by mutated Mdm2 genes (including deletion mutants, substitution mutants, and addition mutants), and so forth. In the present invention, “Mdm2” also includes homologues derived from various animal species such as, for example, human Mdm2 homologue (HDM2).

In the present invention, “p53” means a protein encoded by the p53 gene, “p53” means the p53 protein encoded by a full length p53 gene or a p53 protein that has a mutation (including mutations by deletion, substitution, or addition), but functions normally.

In the present invention, “Mdm2 inhibitor” means a factor that restores p53 functions suppressed by Mdm2 by acting on either Mdm2 or p53, or on both Mdm2 and p53. The p53 functions are not particularly limited so long as they are functions that p53 normally has. Examples thereof include inhibition of canceration of cells by inducing the expression of genes involved in the cell cycle or cellular apoptosis. Examples of Mdm2 inhibitors include factors that inhibit binding of Mdm2 to p53 (hereinafter, referred to as p53-

Mdm2 binding inhibitors) or factors that inhibit ubiquitination of p53 by Mdm2 (hereinafter, referred to as Mdm2 ubiquitin ligase inhibitors).

In the present invention, "inhibitor of suppression of p53 transcription activity" means a factor that restores the functions of p53 as a transcription factor previously suppressed by Mdm2.

In the present invention, "inhibitor of p53 degradation" means a factor that inhibits degradation of p53 in proteasomes by inhibiting ubiquitination of p53 by Mdm2.

In the present invention, the terms "tumor" and "cancer" are used interchangeably. Furthermore, in the present invention, tumor, malignant tumor, cancer, malignant neoplasm, carcinoma, sarcoma, and the like may be collectively referred to as a "tumor" or "cancer."

In the present invention, "$C_1$-$C_6$ alkyl group" means a straight or branched alkyl group having 1 to 6 carbon atoms. Examples of a "$C_1$-$C_6$ alkyl group" include a methyl group, an ethyl group, a propyl group, an isopropyl group, a butyl group, and a tert-butyl group.

"$C_1$-$C_6$ alkoxy group" means an alkoxy group having a straight or branched alkyl group having 1 to 6 carbon atoms. Examples of a "$C_1$-$C_6$ alkoxy group" include a methoxy group, an ethoxy group, a propoxy group, an isopropoxy group, and a butoxy group.

Examples of "halogen atom" include a fluorine atom, a chlorine atom, a bromine atom, and an iodine atom.

"Oxo group" means a group represented by "=O" unless otherwise specified.

"Carbamoyl group" also includes a cyclic carbamoyl group.

Hereafter, each substituent in formula (1) will be explained.

In the following general formula (1),

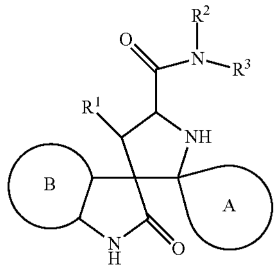
(1)

ring A represents a spiro-linked 4- to 6-membered saturated hydrocarbon ring which may have one or more substituents selected from Group 1 above or a spiro-linked 6-membered saturated heterocyclic ring which may have one or more substituents selected from Group 1 above. Here, "spiro-linked" means that ring A and the pyrrolidine ring to which ring A is bonded form a spiro ring, as illustrated in, for example, the compounds of the Examples:

A substituent bonded to ring A may be positioned at any position. A plurality of substituents may be the same or different and two identical substituents are preferably bonded at the 2- to 6-positions.

The substituent (s) is preferably a $C_1$-$C_6$ alkyl group which may be substituted with one to three halogen atoms, more preferably a $C_1$-$C_6$ alkyl group which may be substituted with one fluorine atom, yet more preferably two methyl groups, ethyl groups, or fluoromethyl groups bonded at the 2-position for a 4-membered ring A, bonded at the 3- and 4-positions for a 5-membered ring A, or bonded at the 4-position for a 6-membered ring A.

The 6-membered saturated heterocyclic ring represented by ring A is preferably dioxane or hexahydropyrimidine. The 5-position in these rings is preferably bonded to the pyrrolidine ring in a compound of formula (1).

Ring A is more preferably a 4- or 6-membered saturated hydrocarbon ring.

Ring B represents a benzene ring which may have one or more substituents selected from Group 2 above, a pyridine ring which may have one or more substituents selected from Group 2 above, or a pyrimidine ring which may have one or more substituents selected from Group 2 above.

A substituent bonded to ring B may be positioned at any position. A plurality of substituents may be the same or different. For the benzene ring, one or two substituents are preferably bonded at the 5- or 6-position. For the pyridine ring, one substituent is preferably bonded at the 6-position. For the pyrimidine ring, one substituent is preferably bonded at the 2-position.

The substituent (s) is preferably a halogen atom, a $C_1$-$C_6$ alkyl group which may be substituted with one to three halogen atoms, a cyano group, or a $C_1$-$C_6$ alkoxy group, more preferably a halogen atom or a cyano group, yet more preferably a halogen atom. The halogen atom is preferably a fluorine atom or a chlorine atom.

$R^1$ represents an aryl group which may have one or more substituents selected from Group 3 above, a heteroaryl group which may have one or more substituents selected from Group 3 above, a $C_3$-$C_6$ cycloalkyl group which may have one of more substituents selected from Group 3 above, or a $C_3$-$C_6$ cycloalkenyl group which may have one or more substituents selected from Group 3 above.

Here, examples of the aryl group include a phenyl group, a benzyl group, an indenyl group, a naphthyl group, a fluorenyl group, an anthranil group, and a phenanthrenyl group. A phenyl group is particularly preferred.

Here, examples of the heteroaryl group include a pyrolyl group, a pyrazolyl group, a triazolyl group, an oxazolyl group, an oxadiazolyl group, a thiophenyl group, a thiazolyl group, a thiadiazolyl group, a pyridyl group, a pyrimidyl group, a pyridazinyl group, a pyrazinyl group, a benzimidazolyl group, a benzotriazolyl group, a benzofuranyl group, a benzothiophenyl group, a quinolyl group, a carbazolyl group, and a dibenzofuranyl group. A pyridyl group and a benzimidazolyl group are particularly preferred. The position of binding of the heteroaryl group to the pyrrolidine ring is not particularly limited and a pyridyl group, for example, is more preferably bonded at the 4-position.

Here, examples of the $C_3$-$C_6$ cycloalkyl group include a cyclopropyl group, a cyclobutanyl group, a cyclopentanyl group, and a cyclohexyl group. The $C_3$-$C_6$ cycloalkyl group is preferably a cyclopentanyl group or a cyclohexyl group, more preferably a cyclohexyl group.

Here, examples of the $C_3$-$C_6$ cycloalkenyl group include a cyclopropenyl group, a cyclobutenyl group, a cyclopentenyl group, and a cyclohexenyl group. The $C_3$-$C_6$ cycloalkenyl group is preferably a cyclopentenyl group or a cyclohexenyl group, more preferably a cyclohexenyl group.

The number and position of the substituent (s) bonded to the aryl group, the heteroaryl group, the $C_3$-$C_6$ cycloalkyl group, and the $C_3$-$C_6$ cycloalkenyl group are not limited and a plurality of substituents may be the same or different.

Examples of the types of substituents include a halogen atom, a $C_3$-$C_6$ alkyl group which may be substituted with one to three halogen atoms or one to three hydroxy groups, a $C_3$-$C_4$ cycloalkyl group which may be substituted with one to three halogen atoms or one to three hydroxy groups, a vinyl group, an ethinyl group, a cyano group, —OR', —NR'R", —COOR', and —CONHR', wherein R' and R" each independently represent a $C_1$-$C_6$ alkyl group which may be substituted with one to three halogen atoms or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group which may have one or more substituents selected from a $C_1$-$C_6$ alkyl group and a hydroxy group.

Here, examples of the "4- to 7-membered nitrogen-containing heterocyclic group" in the phrase "R' and R" together with the nitrogen atom to which R' and R" are bonded may together form a 4- to 7-membered nitrogen-containing heterocyclic group which may have one or more substituents selected from a $C_1$-$C_6$ alkyl group, a hydroxy group, and an oxo group" include an azetidinyl group, a pyrrolidinyl group, a piperidinyl group, a piperazinyl group, a morpholinyl group, a hexamethyleneiminyl group, a homopiperazinyl group, and a homomorpholinyl group. Examples of preferable substitutes include a halogen atom, a $C_1$-$C_6$ alkyl group which may be substituted with one to three halogen atoms or one to three hydroxy groups, —NR'R", —CONHR', and a cyano group. A halogen atom, a hydroxy-$C_1$-$C_3$ alkyl group, an amino group, CONHR' wherein R' is a $C_1$-$C_3$ alkyl group, or a cyano group is more preferred.

The position of a substituent on the R' group when R' represents a ring is not particularly limited. For the phenyl group and cyclohexyl group, particularly preferably, one chlorine atom is bonded at the 3-position, or a chlorine atom and a fluorine atom are bonded at the 3- and 2-positions, respectively. For the cyclohexenyl group, the position of the double bond is not particularly limited. Particularly preferably, one chlorine atom is bonded at the 3-position with respect to the position of binding to the pyrrolidine ring, or a chlorine atom and a fluorine atom are bonded at the 3- and 2-positions, respectively. For the pyridyl group, particularly preferably, one chlorine atom is bonded at the 2-position, or a chlorine atom and a fluorine atom are bonded at the 2- and 3-positions, respectively.

$R^2$ represents a $C_1$-$C_5$ alkyl group which may be substituted with one to three halogen atoms or one to three hydroxy groups, or a hydrogen atom. The substituent bonded to the $C_2$-$C_6$ alkyl group is preferably a fluorine atom or a hydroxy group, $R^2$ is preferably a hydrogen atom, a methyl group, or an ethyl group, particularly preferably a hydrogen atom.

$R^3$ represents a group represented by the following general formula (2), (3), or (4):

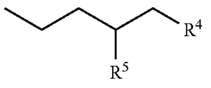

(2)

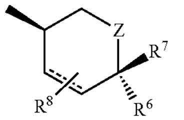

(3)

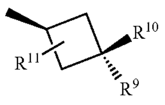

(4)

In formula (2); $R^4$ and $R^5$ each independently represent a hydroxy group, a $C_1$-$C_6$ alkyl group, or a $C_1$-$C_6$ alkoxy group, or $R^4$ and $R^5$ together with the carbon atoms to which the $R^4$ and $R^5$ groups are respectively bonded may form a 4- to 6-membered saturated hydrocarbon ring.

Preferably, both of $R^4$ and $R^5$ are a hydroxy group, or $R^4$ and $R^5$ together with the carbon atoms to which the $R^4$ and $R^5$ groups are respectively bonded form a 4- to 6-membered saturated hydrocarbon ring. More preferably, both $R^4$ and $R^5$ are a hydroxy group.

In formula (3), the broken line in the ring structure indicates that the bond may be a double bond;

$R^6$ represents a $C_2$-$C_6$ alkyl group which may have one or more substituents selected from Group 4 above, a carbamoyl group which may have one or more substituents selected from Group 5 above, a 5- or 6-membered nitrogen-containing heteroaryl group which may be substituted with an oxo group or one or more $C_1$-$C_6$ alkyl groups which may be substituted with an oxo group or one hydroxy group, a hydroxy group, or —NR'R", wherein R' and R" each independently represent a $C_1$-$C_6$ alkyl group which may be substituted with one to three halogen atoms, an oxo group, or one to three hydroxy groups, a $C_3$-$C_4$ cycloalkyl group which may be substituted with one to three halogen atoms or one to three hydroxy groups, of a hydrogen atom, or R' and R" together with the nitrogen atom to which. R' and R" are bonded may form a 4- to 7-membered nitrogen-containing heterocyclic group which may have one or more substituents selected from a $C_1$-$C_6$ alkyl group and a hydroxy group;

$R^7$ represents a $C_1$-$C_6$ alkyl group which may be substituted with one hydroxy group, a hydroxy group, or a hydrogen atom, or $R^6$ and $R^7$ may together form a spiro-linked 4- to 6-membered hydrocarbon ring or a spiro-linked 4- to 6-membered nitrogen-containing heterocyclic ring (wherein "spiro-linked" means that a ring formed by R' and R' together and the z-containing 6-membered ring form a spiro ring);

$R^8$ represents one or more substituents selected from a hydroxy group, a $C_1$-$C_6$ alkyl group, and a $C_1$-$C_6$ alkoxy group; and Z represents $CH_2$, NH, of an oxygen atom.

When $R^6$ is a "$C_1$-$C_6$ alkyl group which may have one or more substituents", examples of the substituent(s) include a halogen atom, a hydroxy group, a carbamoyl group, a morpholino group, a $C_1$-$C_6$ alkoxy group, a $C_1$-$C_6$ alkylsulfonyl group, and —NR'R". Here, R' and R" each independently represent a $C_1$-$C_6$ alkyl group which may be substituted with one to three halogen atoms, one to three hydroxy groups, or an oxo group, a $C_3$-$C_4$ cycloalkyl group which may be substituted with one to three halogen atoms or one to three hydroxy groups, or a hydrogen atom, or R' and R" together with the nitrogen atom to which R' and R" are bonded may form a 4- to 7-membered nitrogen-containing heterocyclic group which may have one or more substituents selected from a $C_1$-$C_6$ alkyl group and a hydroxy group. Here, examples of the "4- to 7-membered nitrogen-containing heterocyclic group" when "R' and R" together with the nitrogen atom to which R' and R" are bonded form a 4- to 7-membered nitrogen-containing heterocyclic group which may have one or more substituents selected from a $C_1$-$C_6$ alkyl group and a hydroxy group" include an azetidinyl group, a pyrrolidinyl group, and a piperidinyl group.

The "$C_1$-$C_6$ alkyl group which may have one or more substituents", represented by R", is preferably a hydroxymethyl group, a 1-hydroxyethyl group, a 2-hydroxypropyl group, a hydroxyethyl group, a 1-hydroxy-1-methylethyl group, a 3,4-dihydroxybutyl group, a methoxymethyl group, a methylsulfonylmethyl group, an aminomethyl group, a di-$C_1$-$C_3$ alkylaminomethyl group, a (hydroxyethyl)aminomethyl group, a $C_1$-$C_3$ alkyloxy (hydroxyethyl)aminomethyl group, an aminooxoethyl group, or a di-$C_1$-$C_3$ alkylaminooxoethyl group.

When $R^6$ is a "carbamoyl group which may have one or more substituents", examples of the substituent (s) include a $C_1$-$C_6$ alkyl group which may be substituted with one to three halogen atoms, one to three hydroxy groups, or a $C_1$-$C_6$ alkoxy group, a $C_3$-$C_6$ cycloalkyl group, a $C_1$-$C_6$ alkoxy group, and a tetrahydropyranyl group.

The "carbamoyl group which may have one or more substituents", represented by $R^6$, is preferably an unsubstituted carbamoyl group, a methylcarbamoyl group, a dimethylcarbamoyl group, an ethylcarbamoyl group, a diethylcarbamoyl group, a methylethylcarbamoyl group, an isopropylcarbamoyl group, a cyclopropylcarbamoyl group, a 2-hydroxyethylcarbamoyl group, a 2-methoxyethylcarbamoyl group, a 2-methoxyethyl-$C_1$-$C_3$ alkylcarbamoyl group, or a 2-fluoroethylcarbamoyl group.

When $R^6$ is a "5- or 6-membered nitrogen-containing heteroaryl group which may be substituted with an oxo group or one or more $C_1$-$C_6$ alkyl groups which may be substituted with an oxo group or one hydroxy group", examples of the "5- or 6-membered nitrogen-containing heteroaryl group" include an oxadiazolyl group, a triazolyl group, an imidazolyl group, a thiazolyl group, a thiadiazolyl group, a pyrrolyl group, a pyridyl group, a pyrimidyl group, a pyridazinyl group, and a triazinyl group. An oxadiazolyl group or a triazolyl group is preferred. An oxadiazolyl group, for example, is preferably bonded at the 2-position. The position of the substituent bonded to the "5- or 6-membered nitrogen-containing heteroaryl group" is not particularly limited. For the 6-membered nitrogen-containing heteroaryl group, the substituent is positioned at any position. For the 5-membered nitrogen-containing heteroaryl group, the substituent is preferably substituted at the 5-position.

The "5- or 6-membered nitrogen-containing heteroaryl group which may be substituted with an oxo group or one or more $C_1$-$C_6$ alkyl groups which may be substituted with an oxo group or one hydroxy group", represented by R", is preferably an unsubstituted oxadiazolyl group, a triazolyl group, or a pyridyl group, particularly preferably an oxadiazolyl group.

Furthermore, $R^6$ may be a hydroxy group or —NR'R".

When $R^6$ is "—NR'R"", R' and R" each independently represent a $C_1$-$C_6$ alkyl group which may be substituted with one to three halogen atoms, an oxo group, or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may form a 4- to 7-membered nitrogen-containing heterocyclic group which may have one or more substituents selected from a $C_1$-$C_6$ alkyl group and a hydroxy group. Here, examples of the "4- to 7-membered nitrogen-containing heterocyclic group" when "R' and R" together with the nitrogen atom to which R' and R" are bonded form a 4- to 7-membered nitrogen-containing heterocyclic group which may have one or more substituents selected from a $C_1$-$C_6$ alkyl group and a hydroxy group" include an azetidinyl group, a pyrrolidinyl group, a piperidinyl group, a piperazinyl group, a 2-oxopiperazinyl group, a morpholinyl group, a homopiperidinyl group, a homopiperazinyl group, and a 1,4-oxazepanyl group.

"—NR'R"" represented by $R^6$ preferably forms an azetidinyl group, a piperazinyl group, or a morpholinyl group.

$R^6$ is preferably a hydroxymethyl group, a 1-hydroxyethyl group, a 2-hydroxypropyl group, a hydroxyethyl group, a 1-hydroxy-1-methylethyl group, an oxazolyl group, an oxadiazolyl group, an oxathiazolyl group, or a carbamoyl group which may have an alkyl group having 1 to 6 carbon atoms as a substituent, more preferably a 1-hydroxyethyl group, an oxadiazolyl group, or an unsubstituted carbamoyl group.

$R^7$ represents a $C_1$-$C_6$ alkyl group which may be substituted with one hydroxy group, a hydroxy group, or a hydrogen atom.

$R^7$ is more preferably a methyl group, an ethyl group, a hydroxymethyl group, a hydroxyethyl group, a hydroxy group, or a hydrogen atom, yet more preferably a hydroxy group or a hydrogen atom.

Furthermore, $R^6$ and $R^7$ may together form a 4- to 6-membered spiro-linked hydrocarbon ring or a 4- to 6-membered spiro-linked nitrogen-containing heterocyclic ring. Examples of the ring formed include a cyclobutane ring, a cyclopentane ring, a cyclohexane ring, an azetidine ring, a pyrrolidine ring, and a tetrahydropyran ring. A cyclobutane ring or an azetidine ring is more preferred.

$R^8$ is a substituent on the 6-membered ring in formula (3) and represents one or more substituents selected from a hydroxy group, a $C_1$-$C_6$ alkyl group, and a $C_1$-$C_6$ alkoxy group.

The position of $R^8$ bonded to the 6-membered ring in formula (3) is not particularly limited so long as it is other than the position to which $R^6$ and $R^7$ are bonded. The number of the substituent is not limited. Furthermore, $R^8$ is not required to be present. Ra is preferably a hydroxy group, a methoxy group, or a methyl group. More preferably, $R^8$ is absent, or one $R^8$ group is present. Yet more preferably, $R^8$ is absent, or a methoxy group is bonded in the same positional configuration as in $R^6$ on the carbon atom adjacent to the carbon to atom which $R^6$ is bonded.

In formula (4), $R^8$ represents a $C_1$-$C_6$ alkyl group which may have one or more substituents selected from Group 4 above, a carbamoyl group which may have one or more substituents selected from Group 5 above, a 5- or 6-membered nitrogen-containing heteroaryl group which may be substituted with an oxo group or one or more $C_1$-$C_6$ alkyl groups which may be substituted with an oxo group or one hydroxy group, a hydroxy group, or —NR'R", wherein R' and R" each independently represent a $C_1$-$C_6$ alkyl group which may be substituted with one to three halogen atoms, an oxo group, or one to three hydroxy groups, a $C_3$-$C_4$ cycloalkyl group which may be substituted with one to three halogen atoms or one to three hydroxy groups, or a hydrogen atom, or R' and R" together with the nitrogen atom to which R' and R" are bonded may form a 4- to 7-membered nitrogen-containing heterocyclic group which may have one or more substituents selected from a $C_1$-$C_6$ alkyl group and a hydroxy group.

$R^{10}$ represents a $C_1$-$C_6$ alkyl group which may be substituted with one hydroxy group, a hydroxy group, or a hydrogen atom, or $R^9$ and $R^{10}$ may together form a spiro-linked 4- to 6-membered hydrocarbon ring or a spiro-linked 4- to 6-membered nitrogen-containing heterocyclic ring, and $R^{11}$ represents one or more substituents selected from a hydroxy group, a $C_1$-$C_6$ alkyl group, and a $C_1$-$C_6$ alkoxy group.

$R^9$ has the same meaning as defined above in $R^6$ in formula (3) and also has the same preferred examples.

$R^{10}$ has the same meaning as defined above in $R^7$ in formula (3) and also has the same preferred examples.

$R^{11}$ has the same meaning as defined above in $R^8$ in formula (3) and also has the same preferred examples. The phrase "$R^9$ and $R^{10}$ may together form a spiro-linked 4- to 6-membered hydrocarbon ring or a spiro-linked 4- to 6-membered nitrogen-containing heterocyclic ring" means that $R^9$ and $R^{10}$ together form a ring structure and this ring and the cyclobutane ring to which $R^9$ and $R^{10}$ are bonded form a spiro ring.

A compound represented by general formula (1) of the present invention is more preferably a compound represented by any of the following general formulas (5) to (8) (in formulas (5) to (8), ring A, $R^2$, and $R^3$ have the same meanings as defined above and also have the same preferred examples):

(5)

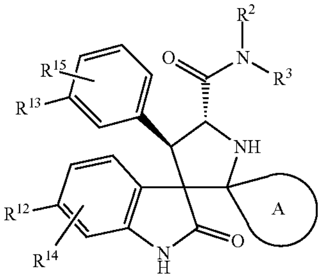

(6)

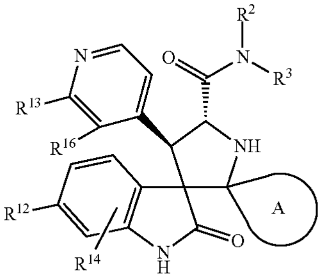

(7)

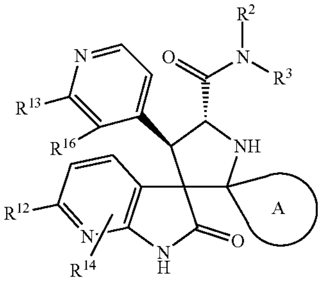

(8)

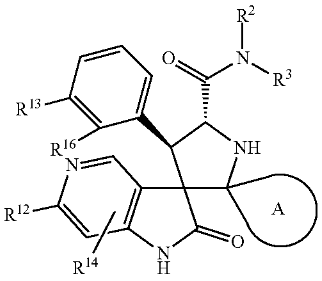

$R^{12}$, $R^{13}$, and $R^{15}$ represent a group selected from a halogen atom, a $C_1$-$C_6$ alkyl group which may be substituted with one to three halogen atoms or one to three hydroxy groups, and a cyano group and are preferably a halogen atom or a cyano group, more preferably a halogen atom, yet more preferably a chlorine atom or a fluorine atom.

$R^{14}$ represents one or more substituents selected from a halogen atom, a $C_1$-$C_6$ alkyl group which may be substituted with one to three halogen atoms or one to three hydroxy groups, and a cyano group and is not required to be present. Preferably, $R^{14}$ is absent or $R^{14}$, if present, is a fluorine atom. The position of the substituent bonded to the ring is not limited.

$R^{15}$ represents one or more substituents selected from Group 3 above and is not required to be present. More preferably, $R^{15}$ is absent or $R^{15}$, if present, is a halogen atom, a hydroxy-$C_1$-$C_3$ alkyl group, an amino group, —CONHR' wherein R' is a $C_1$-$C_3$ alkyl group, or a cyano group.

A compound represented by general formula (1) of the present invention is more preferably a compound selected from the following group:

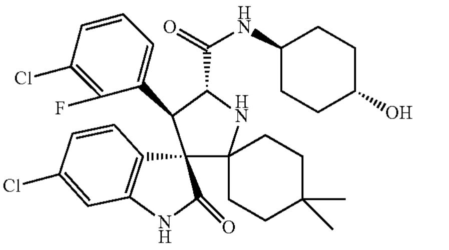

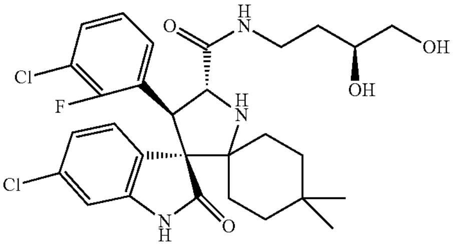

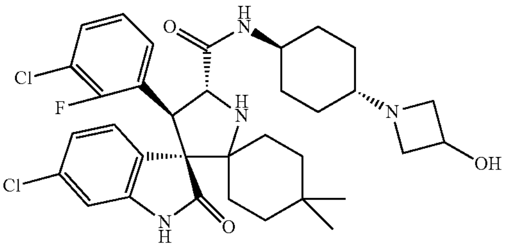

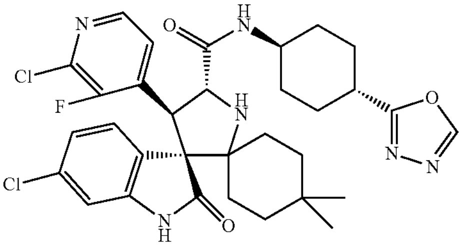

-continued
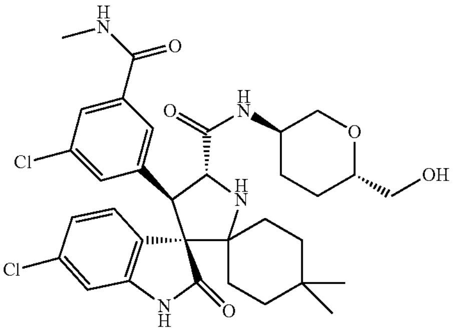
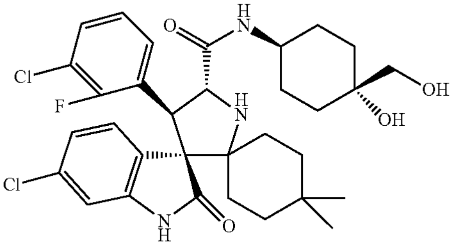
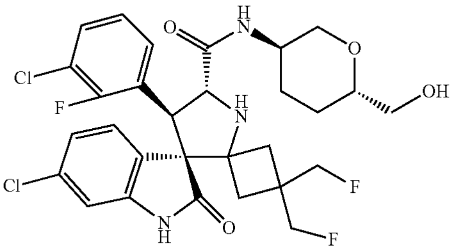
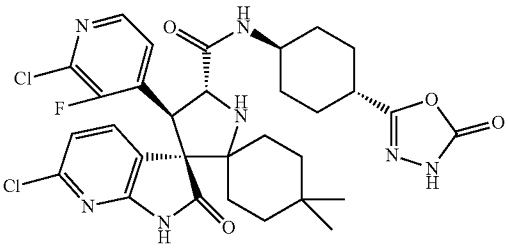
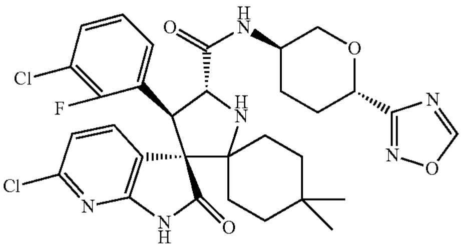
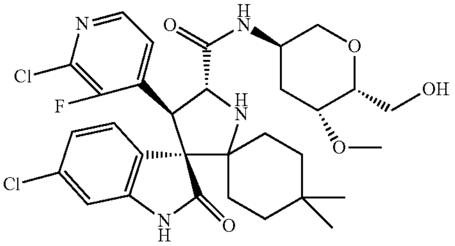
-continued
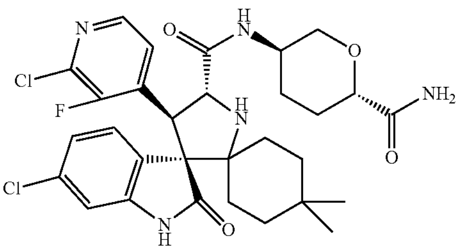
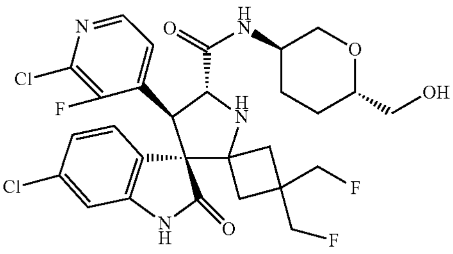
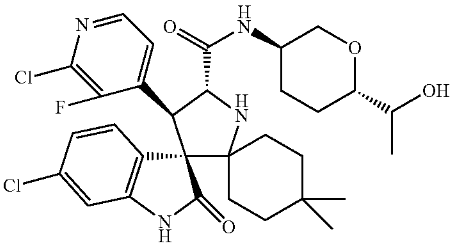
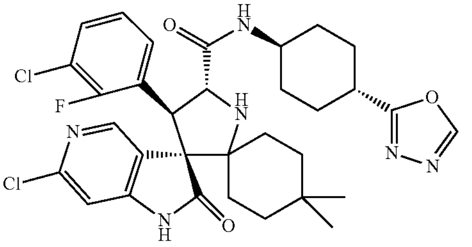
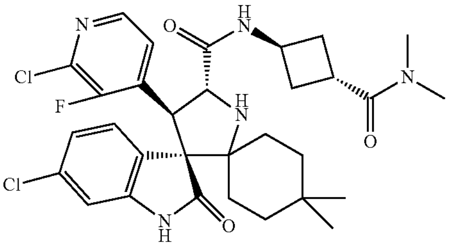
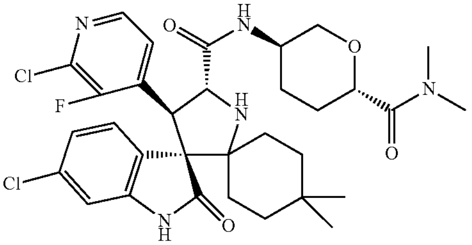

-continued

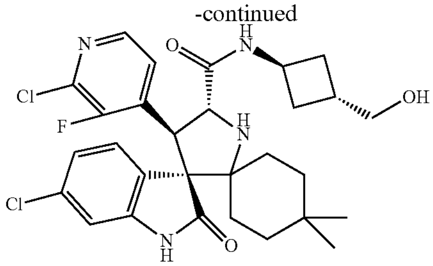

A compound represented by formula (1) of the present invention may have stereoisomers or optical isomers due to asymmetric carbon atoms, and all these stereoisomers, optical isomers, and mixtures thereof are included in the present invention.

In one embodiment of the present invention, a compound having an absolute configuration represented by the following formula is preferred:

(9)

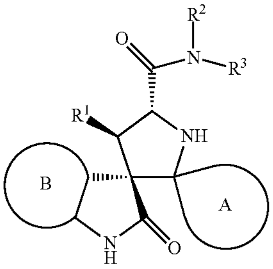

From previous studies, it is known that in a compound having a 6-oxo-2,7-diazaspiro[4.4]nonane-3-carboxamide structure, the central skeleton of general formula (9), which is unsubstituted or monosubstituted at the 2-position in the pyrrolidine ring, cleavage and recyclization at the C2-C3 carbon bond of the pyrrolidine ring occur in a polar solvent to facilitate isomerization of the spiro ring structure at the 3-position (Helv. Chim. Acta, 1996, 79, 151-168, etc.). The present inventors have found that introduction of the spiro ring structure A to the 2-position of the pyrrolidine ring can prevent the progression of this isomerization. The present inventors have also found that the compound group having an absolute configuration represented by general formula (9) is far superior in the ability to inhibit Mdm2-p53 binding to that reported in the previous studies. Furthermore, the present inventors have obtained co-crystals with Mdm2 protein from compounds of Examples 18, 38, and 70 of the present application, which are described later, and consequently found that these compounds bind to Mdm2 protein in a manner different from that predicted in silico in J. Am. Chem. Soc., 2005, 127, 10130-10131 and J. Med. Chem., 2006, 49, 3432-3435.

A compound represented by general formula (1) of the present invention can form a pharmaceutically acceptable salt, if desired, when having a basic group such as an amino group. Examples of such salts can include the following: hydrohalides such as hydrochloride and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as formic acid, acetic acid, malic acid, fumarate, succinate, citrate, tartrate, oxalate, and maleate; and amino acid salts such as ornithine salt, glutamate, and aspartate. Hydrohalides and organic acid salts are preferred.

A compound represented by general formula (1) of the present invention may generally form a base addition salt when having an acidic group such as a carboxy group. Examples of pharmaceutically acceptable salts can include the following: alkali metal salts such as sodium salt, potassium salt, and lithium salt, alkaline earth metal salts such as calcium salt and magnesium salt; inorganic salts such as ammonium salt; and Organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N, N'-dibenzylethylenediamine salt, diethanolamine salt, N-benzyl-N-(2-phenylethoxy)amine salt, piperazine salt, tetramethylammonium salt, and tris (hydroxymethyl)aminomethane salt.

A compound represented by general formula (1) of the present invention of the salt thereof may be present in a free or solvate form. A compound represented by general formula (1) of the present invention or a salt thereof may be present in a hydrate form, for example, by absorbing moisture in the air. The solvate is not particularly limited so long as it is pharmaceutically acceptable. Specifically, the solvate is preferably a hydrate, an ethanol solvate, a 2-propanol solvate, or the like. Moreover, a compound represented by general formula (1) of the present invention may be in an N-oxide form when containing a nitrogen atom. These solvate and N-oxide forms are also included in the present invention.

A compound represented by general formula (1) of the present invention may have various isomers such as geometrical isomers (e.g., cis and trans forms), tautomers, and optical isomers (e.g., d and l forms), depending on the types of Combinations of substituents. The compounds of the present invention also encompasses all of these isomers, stereoisomers, and mixtures of these isomers and stereoisomers in any ratio, unless otherwise specified.

A compound represented by general formula (1) of the present invention may contain an isotope in a non-natural proportion as one or more constituent atoms. Examples of an isotope include deuterium ($^{2}H$), tritium ($^{3}H$), iodine-125 ($^{125}I$), and carbon-14 ($^{14}C$). These compounds are useful as a therapeutic or preventive agent, a research reagent (e.g., an assay reagent), and a diagnostic agent (e.g., an in vivo diagnostic imaging agent). All isotopic variants of the compounds represented by general formula (1) are included in the scope of the present invention, regardless of the presence or absence of radioactivity.

Moreover, the present invention also encompasses compounds that are converted to the compounds represented by general formula (1) as an active ingredient in the pharmaceutical composition of the present invention due to a reaction induced by an enzyme, gastric acid, or the like under physiological conditions in vivo, i.e., a compound that is converted to a compound represented by general formula (1) through enzymatic oxidation, reduction, hydrolysis, or the like or a pharmaceutically acceptable prodrug compound that is converted to a compound represented by general formula (1) through hydrolysis or the like induced by gastric acid or the like.

Examples of a prodrug can include the following: compounds in which an amino group in a compound represented by general formula (1) is acylated, alkylated, or phosphorylated (e.g., compounds in which the amino group is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, or tert-butylated); compounds in which a hydroxy group in a compound represented by general formula (1) is acylated, alkylated, phosphorylated, or borated (e.g., compounds in which the hydroxy group is acetylated, palmitoylated, propanoylated, pivaloylated, succinylated, fumarylated, alanylated, or dimethylaminomethylcarbonylated); and compounds in which a carboxy group in a compound represented by general formula (1) is esterified or amidated (e.g., compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated).

A prodrug of a compound of the present invention can be produced from a compound represented by general formula (1) according to any method known in the art. Moreover, a prodrug of a compound of the present invention also includes those converted to a compound represented by general formula (1) under physiological conditions as described in "Development of Pharmaceutical Products", vol. 7, Molecule Design, p. 163-198, Hirokawa-Shoten Ltd. (1990).

Next, a representative method for producing a compound represented by general formula (1) will be explained. A compound of the present invention can be produced by various production methods and the following production methods are illustrative and should not be construed in any limitive way Reactions shown Below can be performed by protecting substituents with appropriate protective groups, if necessary and the types of protective groups are not particularly limited;

Production Method 1

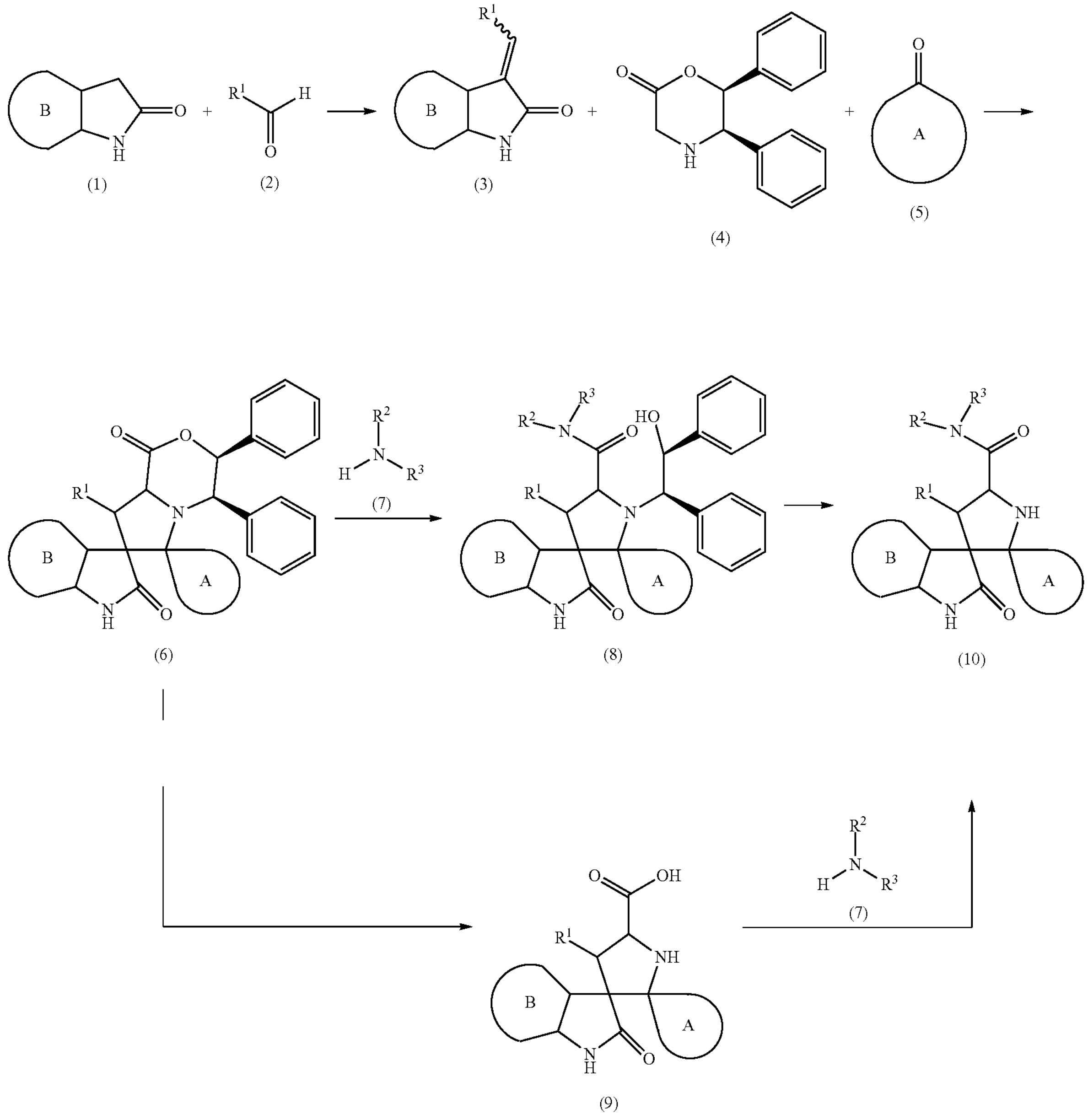

wherein ring A, ring B, $R^1$, $R^2$, and $R^3$ have the same 2 meanings as defined above.

Synthesis of Compound (3)

A compound (3) can be obtained by subjecting an oxindole compound (1) and an aldehyde compound (2) to a dehydration reaction through treatment with an organic base such as pyrrolidine, piperidine, or diisobutylethylamine as a catalyst. Here, the solvent used in the reaction is not particularly limited and examples thereof include lower alcohols such as methanol and ethanol, and mixed solvents in which any of these solvents are mixed with water in an arbitrary ratio. The reaction temperature is not particularly limited and examples thereof include room temperature to 120° C., Moreover, the compound can also be obtained by a cyclodehydration reaction using an organic acid such as p-toluenesulfonic acid or camphorsulfonic acid as a catalyst. Here, the solvent used in the reaction is not particularly limited and examples thereof include benzene, toluene, and xylene. The reaction temperature is preferably in the range from 80° C. to 100° C. or the boiling point of the solvent.

Synthesis of Compound (6)

A compound (6) can be obtained by reacting compound (3) with a morpholinone compound. (4) as a chiral auxiliary compound and a ketone compound (5) using a dehydrating agent such as a molecular sieve and a Lewis acid such as copper sulfate, zinc bromide, or a boron trifluoride-diethyl ether complex as a catalyst. Here, the solvent used in the reaction is not particularly limited and examples thereof include tetrahydrofuran, dioxane, chloroform, benzene, toluene, and mixed solvents thereof. However, dried solvents are preferred. The reaction temperature is usually preferably in the range from room temperature to 100° C. or the boiling point of the solvent (J. Am. Chem. Soc., 2000, 122, 5666-5667; and Tetrahedron Lett., 2005, 5949-5951).

Synthesis of Compound (8)

A compound (8) can be obtained by reacting compound (6) with an amine compound (7). In this reaction, an organic base such as triethylamine, diisopropylethylamine, 4-dimethylaminopyridine, N-methylmorpholine, pyridine, 2,6-lutidine, or diazabicyclo[5.4.0]undec-7-ene, or an inorganic base such as potassium carbonate, sodium carbonate, potassium bicarbonate, or sodium bicarbonate can also be added. Here, examples of the solvent used in the reaction can include dichloromethane, chloroform, diethyl ether, tetrahydrofuran, toluene, methanol, ethanol, isopropyl alcohol, and mixed solvents thereof. The reaction temperature is usually preferably in the range from 0° ° C. to 100° C. or the boiling point of the solvent.

Synthesis of Compound (9)

A compound (9) can be obtained by hydrolyzing compound (6) with a base such as sodium hydroxide, potassium hydroxide, lithium hydroxide, potassium tert-butoxide, potassium carbonate, or sodium carbonate, then neutralizing the hydrolysate with an acid such as hydrochloric acid, sulfuric acid, or methanesulfonic acid, then reacting the reaction mixture with lead (IV) acetate or cerium (IV) diammonium nitrate, and neutralizing the reaction product with for example, an inorganic base such as sodium hydroxide, potassium hydroxide, potassium carbonate, sodium carbonate, potassium bicarbonate, or sodium bicarbonate. Alternatively, the compound can also be obtained by reacting compound (6) under the hydrolysis conditions above, then reacting the hydrolysate with lead (IV) acetate or cerium (IV) diammonium nitrate without neutralizing it, and then neutralizing the reaction product under the conditions above. Here, examples of the solvent used in the reaction include methanol, ethanol, tetrahydrofuran, dioxane, acetonitrile, dichloromethane, water, and mixed solvents thereof. However, organic solvents that can be mixed with water in an arbitrary ratio are preferred. The reaction temperature is usually preferably in the range from −20° ° C. to room temperature.

Synthesis of Compound (10) [Via Compound (8)]

A compound (10) can be obtained by reacting compound. (8) with lead (IV) acetate or cerium (IV) diammonium nitrate. Here, examples of the solvent used in the reaction include methanol, ethanol, tetrahydrofuran, dioxane, acetonitrile, dichloromethane, water, and mixed solvents thereof. However, organic solvents that can be mixed with water in an arbitrary ratio are preferred. The reaction temperature is usually preferably in the range from −20° ° C. to room temperature. Subsequently, the reaction mixture is preferably treated with an inorganic base such as potassium carbonate or sodium carbonate. The treatment temperature is usually preferably in the range from −20° C. to room temperature.

The product obtained by the production method above is more preferably converted to a compound that is thermodynamically stable and has the desired positional configuration by heating, usually in the range from room temperature to 80° C. or the boiling point of the solvent, using methanol, ethanol, tetrahydrofuran, dioxane, water, acetonitrile, or the like ox a mixed solvent thereof, or an organic solvent that can be mixed with water in an arbitrary ratio.

Synthesis of Compound (10) [Via Compound (9)]

A compound (10) can be obtained by reacting compound (9) with an amine compound (7) in the presence of a condensing agent. Here, examples of the condensing agent used can include N, N'-dicyclohexylcarbodiimide (DCC), 1-ethyl-3-(3-dimethylaminopropyl) carbodiimide (EDCI), carbonyldiimidazole (CDI), 2-(2H-benzotriazol-2-yl)-4-(1, 1,3,3-tetramethylbutyl)phenol (BOP), 1H-benzotriazol-1-yloxytripyrrolidinophosphoniumhexafluorophosphate (PyBOP), and O-(7-azabenzotriazol-1-yl)-N, N, N',N'-tetramethyluronium hexafluorophosphate (HATU). The solvent used in the reaction is not particularly limited and examples thereof include dichloromethane, dimethylformamide, tetrahydrofuran, ethyl acetate, and mixed solvents thereof. The reaction temperature is usually in the range from −20° C. to 100° C. or the boiling point of the solvent, preferably in the range from −5° C. to 50° C. Moreover, an organic base such as triethylamine, diisopropylethylamine, N-methylmorpholine, or 4-dimethylaminopyridine, or an inorganic base such as potassium carbonate, sodium carbonate, potassium bicarbonate, or sodium bicarbonate can be added, if necessary. Furthermore, 1-hydroxybenzotriazole, N-hydroxysuccinimide, or the like can be added as a reaction accelerator.

The product obtained by the production method above is more preferably converted to a compound that is thermodynamically stable and has the desired positional configuration by heating, usually in the range from room temperature to 80° C. or the boiling point of the solvent, using methanol, ethanol, tetrahydrofuran, dioxane, water, acetonitrile, or the like or a mixed solvent thereof, or an organic solvent that can be mixed with water in an arbitrary ratio.

Production Method 2

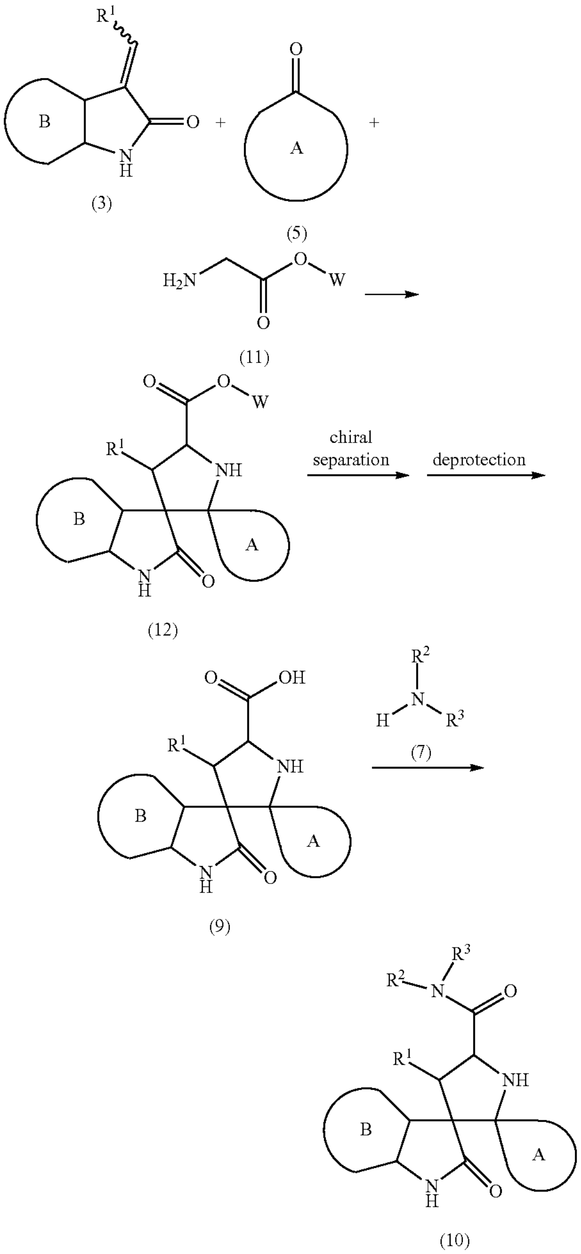

(3) (5) (11) (12) (9) (7) (10)

wherein ring A, ring B, $R^1$, $R^2$, and $R^3$ have the same meanings as defined above, and W means a protective group for the carboxy group. Examples of the protective group for the carboxy group include substituted or unsubstituted alkyl groups of aralkyl groups such as a methyl group, an ethyl group, a tert-butyl group, and a benzyl group.

Synthesis of Compound (12)

A compound (12) can be obtained by reacting a compound (3), a ketone compound (5), and a compound (11) such as a glycine ester or hydrochloride thereof with a dehydrating agent such as a molecular sieve or magnesium sulfate. Here, the solvent used in the reaction is not particularly limited and examples thereof include tetrahydrofuran, dioxane, chloroform, 1,2-dichloroethane, benzene, toluene, and mixed solvents thereof. However, dried solvents are preferred. The reaction temperature is usually preferably in the range from room temperature to 100° C. or the boiling point of the solvent (Tetrahedron, 2001, 57, 1129-1137). Moreover, silver acetate, silver fluoride, or the like can also be added as a catalyst in the reaction (Tetrahedron, 2003, 59, 335-340; and WO2010/031713).

Synthesis of Compound (9)

Because the compound synthesized by the production method above is a racemate, the compound of interest can be obtained by optical resolution using a chiral column or a crystallization method involving formation of an optically active salt or the like of tartaric acid, bromocamphorsulfonic acid, chlorocamphorsulfonic acid, camphorsulfonic acid, or the like, followed by deprotection of the ester (W). Although reaction conditions differ depending on the type of W, this reaction may be hydrolysis. When W is a methyl group, an ethyl group, a benzyl group, or the like, the compound can be obtained by treating compound (12) with a base such as sodium hydroxide, potassium hydroxide, lithium hydroxide, or potassium tert-butoxide, or an acid such as hydrochloric acid or p-toluenesulfonic acid. Here, examples of the solvent used in the reaction include methanol, ethanol, water, tetrahydrofuran, dioxane, and mixed solvents thereof. However, organic solvents that can be mixed with water in an arbitrary ratio are preferred. The reaction temperature is usually preferably in the range from −20° C. to 100° C. or the boiling point of the solvent. When W is a tert-butyl group or the like, the compound can be obtained by treating compound (12) with, for example, trifluoroacetic acid or hydrochloric acid. Here, the solvent used in the reaction is not particularly limited and examples thereof include dichloromethane, chloroform, 1,2-dichloroethane, and mixed solvents thereof. The reaction temperature is usually in the range from −20° C. to 80° ° C. or the boiling point of the solvent, preferably in the range from 0° C. to around room temperature.

Synthesis of Compound (10)

A compound (10) can be obtained according to the method for producing compound (10) with compound (9) as a starting material described in [Production Method 1] above.

The starting material compounds (1), (2), (3), (4), (S), (7), (11), and (12) are commercially available products or can be synthesized according to methods described in the Reference Examples section.

In one embodiment of the present invention, a compound of the present invention can be used as a p53-Mdm2 binding inhibitor and/or an Mdm2 ubiquitin ligase inhibitor because it inhibits the binding of p53 with Mdm2 and the ubiquitination of p53 by Mdm2.

The condition of the p53-Mdm2 binding can be examined by a method conventionally used by those skilled in the art to examine binding conditions between proteins (for example, immunological techniques, surface plasmon resonance techniques, etc.). Examples of methods for examining the condition of the Mdm2-p53 binding using an immunological technique include an immuno-sedimentation method and enzyme-linked-immunosorbent assay (ELISA). An antibody used in such immunological techniques may be an anti-Mdm2 antibody and/or an anti-p53 antibody that can directly detect Mdm2 and/or p53. When Mdm2 and/or p53 is labeled with a tag (for example, a GST tag or a histidine tag) or the like, an antibody suitable for labeling (for example, an anti-GST antibody or an anti-histidine antibody) can be used. Methods for examining the condition of the Mdm2-p53 binding using an immunological technique are described in, for example, WO2003/51359, WO2003/

51360, U.S. Patent Application Publication No. 2004/259867 or 2004/259884, and WO2005/110996. Methods for examining the condition of the Mdm2-p53 binding using a surface plasmon resonance technique are described in, for example, Science, vol. 303, p. 844-848, 2004.

Ubiquitin ligase activity of Mdm2 against p53 can be examined by a ubiquitin ligase assay conventionally used by those skilled in the art. The ubiquitin ligase activity can be detected by, for example, comparing ubiquitination of p53 by ubiquitin activation enzyme (E1), ubiquitin binding enzyme (E2), and ubiquitin ligase (E3) (Mdm2) in the presence and absence of a test compound (for example, refer to WO2001/75145 and WO2003/76608), In another embodiment, a compound of the present invention can be used as an inhibitor of suppression of the p53 transcription activity because it restores functions of p53 as a transcription factor that is suppressed by Mdm2 by inhibiting the binding of Mdm2 to the p53 transcription activation domain. The inhibitor of suppression of the p53 transcription activity can be obtained by, for example, measuring the mRNA level or the protein level of a protein whose transcription is regulated by p53 (for example, $p21^{Waf1/Cip1}$) in the presence or absence of a test compound by an mRNA measuring method (for example, Northern blot) or a protein measuring method (for example, Western blot) conventionally used by those skilled in the art, and selecting the test compound as an inhibitor of suppression of the p53 transcription activity when the mRNA level or the protein level is increased in the presence of the test compound as compared with that in the absence of the test compound. Furthermore, the inhibitor of suppression of the p53 transcription activity can also be identified by a reporter assay using the reporter activity of a reporter gene that includes a p53 responsive element as an indicator.

In another embodiment, a compound of the present invention can be used as a p53 degradation inhibitor because it inhibits ubiquitination of p53 by Mdm2 and thereby prevents the degradation of p53 in proteasomes. The p53 degradation inhibitor can be obtained by, for example, measuring the protein level of p53 in the presence or absence of a test compound by a protein measuring method (for example, Western blot) conventionally used by those skilled in the art and selecting the best compound as a p53 degradation inhibitor when the protein level is increased in the presence of the test compound as compared with that in the absence of the test compound.

In another embodiment, a compound of the present invention can be used as an anti-tumor agent because it normalizes functions of p53 as a cancer-restraining gene by inhibition of the Mdm2-p53 binding and/or ubiquitination of p53 by Mdm2.

Cellular growth inhibiting activity can be examined by methods for testing growth inhibition conventionally used by those skilled in the art. The cell growth inhibition activity can be determined by, for example, comparing the levels of cellular growth (for example, tumor cells) in the presence and absence of a test compound as described in the following Test Example 2. The levels of cellular growth can be examined by using, for example, a test system for measuring living cells. Examples of methods for measuring living cells include the [$^3$H]-thymidine uptake test, the BrdU method, the MTT assay, and so forth.

Moreover, in vivo anti-tumor activity can be examined by methods for testing anti-tumor activity conventionally used by those skilled in the art. The in vivo anti-tumor activity of a compound of the present invention can be confirmed by, for example, transplanting various tumor cells into mice, rats, or the like, after confirming the engraftment of the transplanted cells, orally or intravenously administering a compound of the present invention to the animals; a few days or a few weeks later, comparing tumor growth in the non-compound-administered group with that in the compound-administered group.

A compound of the present invention can be used for the treatment of tumors or cancers, for example, lung cancer, digestive system cancer, ovary cancer, uterine cancer, breast, cancer, prostate cancer, liver cancer, head/neck region cancer, blood cancer, renal cancer, skin cancer (malignant melanoma, etc.), retinoblastoma, testicular tumors, and sarcoma, more preferably lung cancer, breast cancer, prostate cancer, colon cancer, acute myeloid leukemia, malignant lymphoma, malignant melanoma, retinoblastoma, neuroblastoma, and sarcoma. However, the present invention is not limited to these cancers.

A pharmaceutical composition of the present invention can contain a compound of the present invention and a pharmaceutically acceptable carrier and can be administered as various injections such as intravenous injection, intramuscular injection, and subcutaneous injection or by various methods such as oral administration or percutaneous administration. "Pharmaceutically acceptable carrier" means a pharmacologically acceptable material that is involved in transport of a compound of the present invention or a composition containing a compound of present invention (for example, an excipient, a diluent, an additive, a solvent, etc.) from a given organ to another organ.

A formulation can be prepared by selecting a suitable formulation form (for example, oral formulation or injection) depending on the administration method and using various conventionally used methods for preparing a formulation. Examples of oral formulations include tablets, powders, granules, capsules, pills, lozenges, solutions, syrups, elixirs, emulsions, oily or aqueous suspensions, and so forth. In oral administration, the free compound or a salt form may be used. An aqueous formulation can be prepared by forming an acid adduct with a pharmacologically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization of the like. Furthermore, one dose may be filled in one vessel, or two or more doses may be filled in a vessel.

Examples of solid formulations include tablets, powders, granules, capsules, pills, and lozenges. These solid formulations may contain pharmaceutically acceptable additives together with a compound of the present invention. Examples of additives include fillers, extenders, binders, disintegrating agents, dissolution promoting agents, skin wetting agents, and lubricants, and these can be selected and mixed as required to prepare a formulation.

Examples of liquid formulations include solutions, syrups, elixirs, emulsions, and suspensions. These liquid formulations may contain pharmaceutically acceptable additives together with a compound of the present invention. Examples of additives include suspending agents and emulsifiers, and these are selected and mixed as required to prepare a formulation.

The compound of the present invention can be used in cancer treatment of mammals, in particular, humans. The dose and the administration interval can be suitably selected depending on the site of the disease, the patient's height, body weight, sex, or medical history, according to a physician's judgment. When the compound of the present invention is administered to a human, the dose range is approx. 0.01 to 500 mg/kg body weight per day, preferably, approx. 0.1 to 100 mg/kg body weight. Preferably, the compound of the present invention is administered to a human once a day, or the dose is divided two to four times, and administration is repeated at an appropriate interval. Furthermore, the daily dose may exceed the above-mentioned dose at a physician's discretion, if necessary.

The compound of the present invention may be used in combination with an additional anti-tumor agent. Examples thereof include anti-tumor antibiotics, anti-tumor plant constituents, BRMs (biological response modifiers), hormones, vitamins, anti-tumor antibodies, molecular target drugs, and other anti-tumor agents.

More specifically, examples of alkylating agents include the following: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and busulfan, improsulfan tosylate, and dacarbazine.

Examples of various metabolic antagonists include the following: purine metabolic antagonists such as 6-mercaptopurine, 6-thioguanine, and thioinosine; pyrimidine metabolic antagonists such as fluorouracil, tegafur, tegafur-uracil, carmofur, doxifluridine, broxuridine, cytarabine, and enocitabine; and folic acid metabolic antagonists such as methotrexate and trimetrexate.

Examples of anti-tumor antibiotics include the following: anti-tumor anthracycline antibiotics such as mitomycin C, bleomycin, peplomycin, daunorubicin, aclarubicin, doxorubicin, pirarubicin, THP-adriamycin, 4'-epidoxorubicin, and epirubicin; and chromomycin A3 and actinomycin D.

Examples of anti-tumor plant constituents include the following: vinca alkaloids such as vindesine, vincristine, and vinblastine; taxanes such as paclitaxel and docetaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, imatinib mesilate, gefitinib, erlotinib, sunitinib, lapatinib, and sorafenib.

Examples of other anti-tumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

The present invention also includes a method for preventing and/or treating cancer comprising administering a compound of the present invention or a salt thereof.

The present invention further includes use of a compound of the present invention, a salt, or a solvate thereof for the manufacture of the medicament.

Hereinafter, the present invention will be specifically explained with reference to the Examples. However, the present invention is not limited to these examples, and they should not be construed in any limitive way. Furthermore, reagents, solvents, and starting materials in the specification can be readily obtained from commercially available supply sources unless otherwise specified, Hereinafter, the present invention will be specifically explained with reference to the Examples. However, the present invention is not limited to these examples, and they should not be construed in any limitative way. Furthermore, reagents, solvents, and starting materials in the specification can be readily obtained from commercially available supply sources unless otherwise specified.

EXAMPLES

Example 1

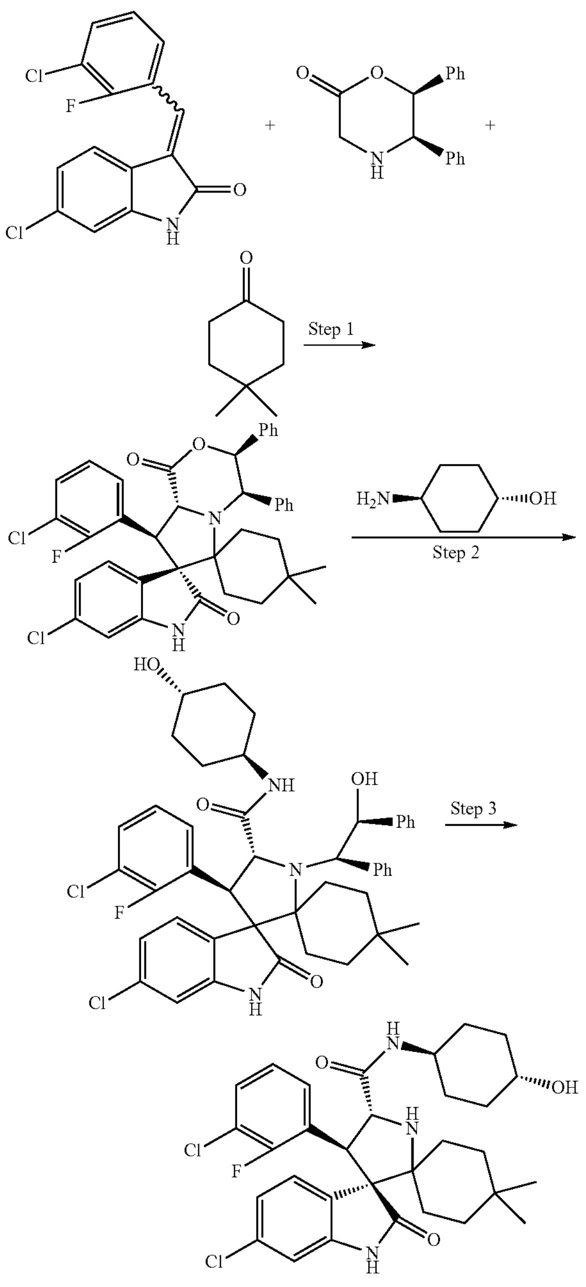

Step 1

(3'S,4'R, 7'S,8'S,8a'R)-6"-chloro-8'-(3-chloro-2-fluorophenyl)-4,4-dimethyl-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione (5R,6S)-5,6-diphenylmorpholin-2-one (506 mg, 2.00 mmol), 4,4-dimethylcyclohexanone (252 mg, 2.00 mmol), and molecular sieves 4 A (powder) (2 g) were added to a toluene (20 ml) solution of (3E/Z)-6-chloro-3-(3-chloro-2-fluorobenzylidene)-1,3-dihydro-2H-indol-2-one (WO2006/091646) (616 mg, 2.00 mmol) under nitrogen atmosphere and the resulting mixture was stirred under heating at 70° ° C. for 5 days. After cooling, insoluble matter was removed by filtration through celite and the filtrate was concentrated under reduced pressure. The residue was dissolved in ethyl acetate and the organic layer was washed with 1N hydrochloric acid and brine and then dried over anhydrous sodium sulfate. The solvent was evaporated under reduced pressure and the residue was purified by silica gel column chromatography [n-hexane:ethyl acetate=9:1→6:1 (v/v)] to give 194 mg (14%) of the title compound as a yellow amorphous solid.

$^1$H-NMR (400 MHz, $CDCl_3$) δ: 0.19 (3H, s), 0.52 (3H, s), 0.94-1.00 (3H, m), 1.29-1.41 (3H, m), 1.80 (1H, d, J=11.0 Hz), 2.27 (1H, d, J=14.2 Hz), 4.61 (1H, d, J=11.0 Hz), 4.86 (1H, d, J=2.7 Hz), 5.35 (1H, d, J=11.4 Hz), 6.23 (1H, d, J=8.2 Hz), 6.60 (1H, dd, J=8.2, 1.8 Hz), 6.72-6.78 (2H, m), 6.88 (1H, d, J=1.8 Hz), 7.07-7.26 (11H, m), 7.67 (1H, s), 7.77 (1H, t, J=6.4 Hz).

Step 2

(4'S,5'R)-6"-chloro-4'-(3-chloro-2-fluorophenyl)-N-(trans-4-hydroxycyclohexyl)=1'-[(1R,2S)-2-hydroxy-1,2-diphenylethyl]-4,4-dimethyl-2"-oxo-1", 2"-dihydrodispiro[cyclohexane-1,2'-pyrrolidine-3', 3"-indole]-5'-carboxamide Trans-4-aminocyclohexanol (167 mg, 1.45 mmol) was added to a tetrahydrofuran (10 ml) solution of the compound (194 mg, 0.29 mmol) obtained in Step 1 above and the resulting mixture was heated to reflux for 6 days. After cooling, saturated ammonium chloride solution was added, followed by extraction with ethyl acetate. The organic layer was washed with brine and then dried over anhydrous sodium sulfate. The solvent was evaporated under reduced pressure and the residue was: purified by silica gel column chromatography [chloroform:methanol=100:0→30:1 (v/v)] to give 230 mg (100%) of the title compound as a pale yellow amorphous solid.

$^1$H-NMR (400 MHz, $CDCl_3$) δ: 0.51-0.57 (1H, m), 0.85-0.89 (5H, m), 1.05 (3H, s), 1.29-1.35 (6H, m), 1.69-1.71 (3H, m), 1.82-1.97 (2H, m), 2.26-2.42 (2H, m), 2.90 (1H, d, J=12.8 Hz), 3.43-3.46 (2H, m), 3.73-3.74 (1H, m), 4.15 (1H, d, J=7.8 Hz), 4.64 (1H, d, J=11.0 Hz), 4.90 (1H, d, J=2.7 Hz), 5.55 (1H, s), 6.13 (1H, s), 6.41 (1H, t, J=6.4 Hz), 6.64 (1H, t, J=7.8 Hz), 6.75 (1H, d, J=1.8 Hz), 7.00-7.03 (2H, m), 7.09-7.11 (4H, m), 7.19-7.20 (5H, m), 7.36 (1H, s), 7.42 (2H, s).

Step 3

(3'R, 4'S,5'R)-6"-chloro-4'-(3-chloro-2-fluorophenyl)-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide The compound (230 mg, 0.29 mmol) obtained in Step 2 above was dissolved in acetonitrile (10 ml) and water (3 ml), cerium. (IV) diammonium nitrate (318 mg, 0.58 mmol) was added under ice cooling and the resulting mixture was stirred for 10 minutes. Potassium carbonate (160 mg, 1.16 mmol) was added to the reaction mixture, the resulting mixture was stirred and then insoluble matter was removed by filtration through celite. The filtrate was diluted with ethyl acetate, washed with brine and then dried over anhydrous sodium sulfate. The solvent was evaporated under reduced pressure and the residue was purified by silica gel column chromatography [chloroform:methanol=100:0→30:1→20:1 (v/v)] to give 90 mg (53%) of the title compound as a pale yellow solid.

$^1$H-NMR (400 MHz, $CD_3OD$) δ: 0.68 (3H, s), 0.94 (3H, s), 1.06-1.23 (2H, m), 1.25-1.44 (5H, m), 1.48-1.63 (2H, m), 1.71-2.06 (7H, m), 3.50-3.65 (2H, m), 4.48 (1H, d, J=9.2 Hz), 4.66 (1H, d, J=9.2 Hz), 6.73 (1H, d, J=2.3 Hz), 7.00-7.06 (2H, m), 7.16-7.24 (1H, m), 7.39-7.45 (1H, m), 7.57-7.64 (1H, m).

MS (ESI) m/z: 588 $(M+H)^+$.

Example 2

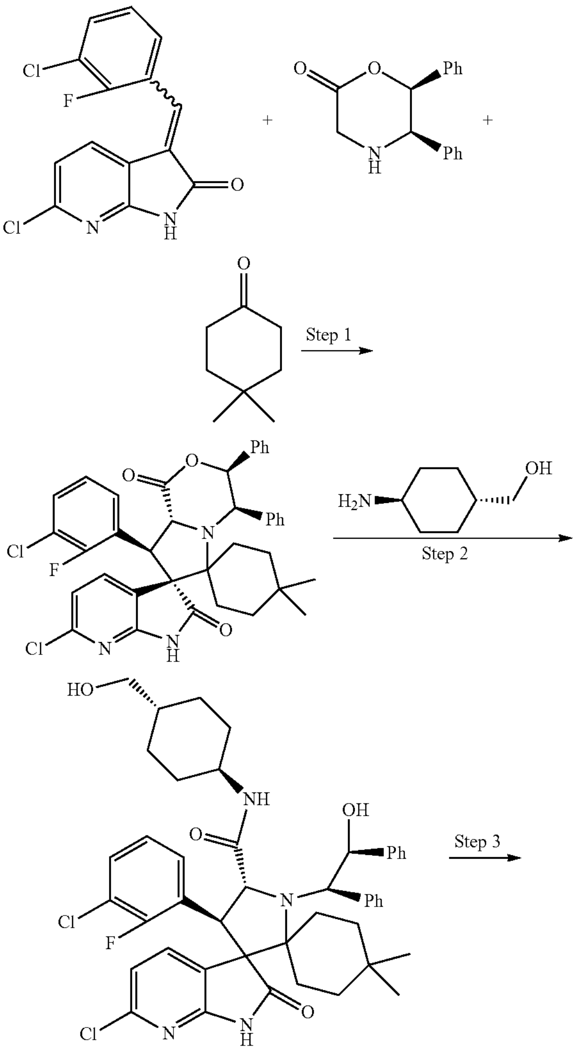

-continued

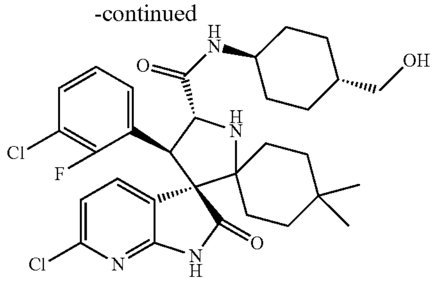

Step 1

(3'S,4'R, 7'S,8'S,8a'R)-6"-chloro-8'-(3-chloro-2-fluorophenyl)-4,4-dimethyl-3',4'-diphenyl-3',4',8',8a'-tetrahydro-1'H-dispiro[cyclohexane-1,6'-pyrrolo[2,1-c][1,4) oxazine-7',3"-pyrrolo[2,3-b]pyridine]-]', 2"(1"H)-dione (5R,6S)-5,6-diphenylmorpholin-2-one (2.62 g, 10.3 mmol), 4,4-dimethylcyclohexanone (1.30 g, 10.3 mmol), and anhydrous copper sulfate (16.4 g, 103 mmol) were added to a toluene (80 ml) solution of the compound (2.67 g, 8.60 mmol) obtained in Reference Example 1 and the resulting mixture was heated to reflux for 24 hours under nitrogen atmosphere. After cooling, insoluble matter was removed by filtration through celite and the filtrate was concentrated under reduced pressure. The residue was dissolved in ethyl acetate and the organic layer was washed with 1N hydrochloric acid solution and brine and then dried over anhydrous sodium sulfate. The solvent was evaporated under reduced pressure and the residue was purified by silica gel column chromatography [n-hexane:ethyl acetate=9:1→6:1 (v/v)] to give 5.1 g (90%) of the title compound as a yellow amorphous solid.

$^1$H-NMR (400 MHz, $CDCl_3$) δ: 0.20 (3H, s), 0.55 (3H, s), 0.90-1.08 (3H, m), 1.21-1.32 (1H, m), 1.33-1.47 (2H, m), 1.76-1.86 (1H, m), 2.26-2.36 (1H, m), 4.65 (1H, d, J=11.2 Hz), 4.88 (1H, d, J=3.2 Hz), 5.36 (1H, d, J=11.2 Hz), 6.52 (1H, d, J=7.8 Hz), 6.64 (1H, d, J=8.2 Hz), 6.71-6.78 (2H, m), 7.06-7.24 (10H, m), 7.25-7.32 (1H, m), 7.74-7.83 (1H, m), 9.00 (1H, s).

Step 2

(4'S,5'R)-6'-chloro-4'-(3-chloro-2-fluorophenyl)-1'-[(1R,2S)-2-hydroxy-1,2-diphenylethyl]-N-[trans-4-(hydroxymethyl)cyclohexyl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (260 mg, 0.39 mmol) obtained in Step 1 above and (trans-4-aminocyclohexyl)methanol (100 mg, 0.77 mmol) were used as starting materials and treated: in the same way as in Step 2 of Example 1 to give 260 mg (83%) of the title compound as a pale yellow oil.

MS (ESI) m/z; 799 $(M+H)^+$.

Step 3

(3'R, 4'S,5'R)-6"-chloro-4'-(3-chloro-2-fluorophenyl)-N-[trans-4-(hydroxymethyl)cyclohexyl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (260 mg, 0.33 mmol) obtained in Step 2 above was used as a starting material and treated in the same way as in Step 3 of Example 1 to give 63 mg (33%) of the title compound as a colorless solid.

$^1$H-NMR (400 MHz, $CD_3OD$) δ: 0.71 (3H, s), 0.95 (3H, s), 1.04-1.10 (2H, m), 1.20-1.32 (5H, m), 1.45-1.46 (1H, m), 1.56-1.59 (2H, m), 1.71-1.78 (2H, m), 1.85-2.01 (5H, m), 3.37 (2H, d, J=6.0 Hz), 3.55-3.57 (1H, m), 4.52 (1H, d, J=9.6 Hz), 4.68 (1H, d, J=9.6 Hz), 7.04-7.07 (2H, m), 7.24 (1H, t, J=7.1 Hz), 7.59 (1H, t, J=6.9 Hz), 7.83 (1H, dd, J=7.8, 2.3 Hz).

MS (ESI) m/z: 603 $(M+H)^+$.

Example 3

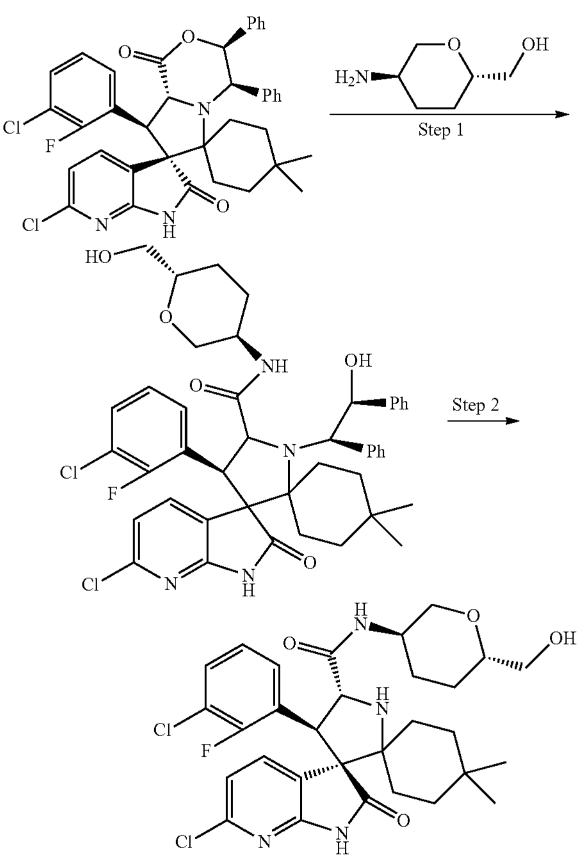

Step 1

(4'S,5'R)-6"-chloro-4'-(3-chloro-2-fluorophenyl)-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (670 mg, 1.00 mmol) obtained in Step 1 of Example 2 and the compound (262 mg, 2.0 mmol) obtained in Step 3 of Reference Example 2 were used as starting materials and treated in the same way as in Step 2 of Example 1 to give 200 mg (25%) of the title compound as a light brown amorphous solid, MS (ESI) m/z: 801 $(M+H)^+$.

Step 2

(3'R, 4'S,5'R)-6"-chloro-4'-(3-chloro-2-fluorophenyl)-N-[(3R,6S)-6-(hydroxymethyl)tetrahydro-2H-pyran-3-yl]-4,4-dimethyl-2"-oxo-1",2"-dihydro-dispiro[cyclohexane-1,2'-pyrrolidine-3',3"-pyrrolo[2,3-b]pyridine]-5'-carboxamide The compound (200 mg, 0.25 mmol) obtained in Step 2 above was used as a starting material and treated in the same way as in Step 3 of Example 1 to give 77 mg (51%) of the title compound as a colorless solid.

$^1$H-NMR (400 MHz, $CD_3OD$) δ: 0.71 (3H, s), 0.95 (3H, s), 1.16-1.20 (2H, m), 1.36-1.45 (2H, m), 1.58-1.61 (3H, m), 1.71-1.84 (4H, m), 2.01-2.11 (1H, m), 3.15 (1H, t, J=10.5 Hz), 3.36-3.39 (1H, m), 3.49 (2H, d, J=5.0 Hz), 3.73-3.81 (1H, m), 3.88-3.96 (1H, m), 4.53 (1H, d, J=9.2 Hz), 4.70 (1H, d, J=9.2 Hz), 7.03-7.08 (2H, m), 7.21-7.27 (1H, m), 7.57 (1H, t, J=6.9 Hz), 7.83 (1H, dd, J=7.8, 2.3 Hz).

MS (ESI) m/z: 605 $(M+H)^+$.

Example 4

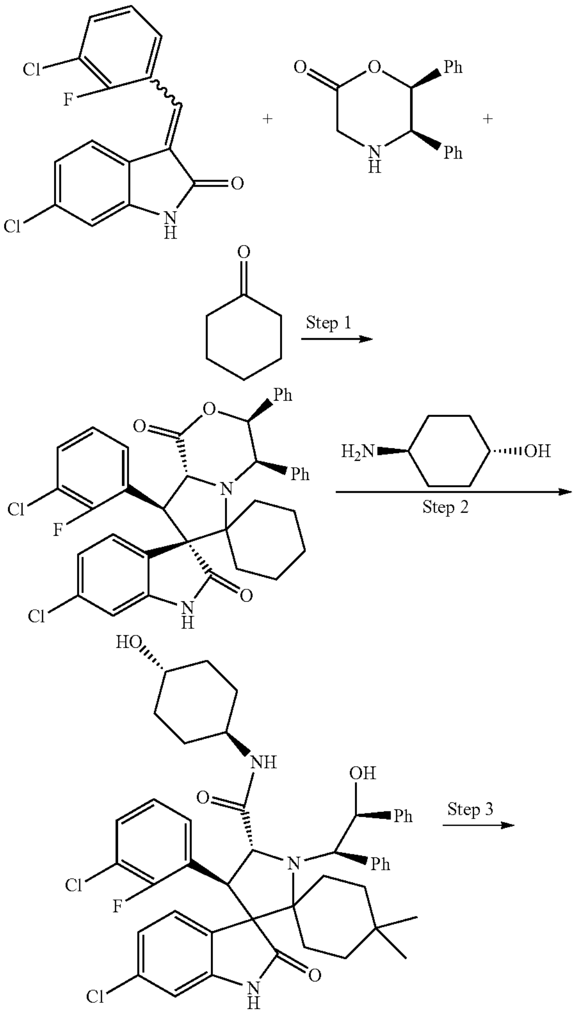

-continued

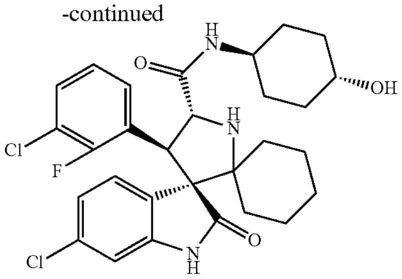

Step 1

(3'S,4'R, 7'S,8'S, 8a'R)-6"-chloro-8'-(3-chloro-2-fluorophenyl)-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione Cyclohexanone (0.25 ml, 2.40 mmol) was used as a starting material and treated in the same way as in Step 1 of Example 1 to give 900 mg. (70%) of the title compound as a yellow solid.

$^1$H-NMR (400 MHz, $CDCl_3$) δ: 1.15-1.32 (8H, m), 2.01 (1H, d, J=12.9 Hz), 2.45 (1H, d, J=13.4 Hz), 4.61 (1H; d, J=11.0 Hz), 4.88 (1H, d, J=2.9 Hz), 5.36 (1H, d, J=11.5 Hz), 6.23 (1H, d, J=8.3 Hz), 6.60 (1H, dd, J=8.2, 1.8 Hz), 6.76 (28, d, J=6.8 Hz), 6.87 (1H, d, J=1.7 Hz), 7.05-7.23 (11H, m), 7.42 (1H, s), 7.75 (1H, t, J=6.6 Hz).

Step 2

(4'S,5'R)-6"-chloro-4'-(3-chloro-2-fluorophenyl)-N-(trans-4-hydroxycyclohexyl)-1'-[(1R,2S)-2-hydroxy-1,2-diphenylethyl]-2"-oxo-1",2"-dihydrodispiro[cyclohexane-1,2'-pyrrolidine-3',3"-indole]-5'-carboxamide The compound (320 mg, 0.50 mmol) obtained in Step 1 above was used as a starting material and treated in the same way as in Step 2 of Example 1 to give 228 mg (60%) of the title compound as a colorless solid.

$^1$H-NMR (400 MHz, $CDCl_3$) δ: 0.49-0.53 (1H, m), 0.82-0.90 (3H, m), 1.28-1.30 (4M, m), 1.58-1.62 (2H, m), 1.80-1.90 (6H, m), 2.09 (1H, t, J=11.4 Hz), 2.16-2.23 (1H, m), 3.03 (1H, d, J=14.7 Hz), 3.43-3.45 (2H, m), 3.72-3.73, (1H, m), 4.12 (1H, d, J=8.2 Hz), 4.65 (1H, d, J=10.5 Hz), 4.90 (1H, d, J=3.2 Hz), 5.53 (1H, d, J=2.7 Hz), 6.18 (15, s), 6.41 (1H, t, J=6.6 Hz), 6.64 (1H, t, J=8.0 Hz), 6.75 (1H, d, J=1.8 Hz), 7.00-7.03 (2H, m), 7.10 (4H, q. J=7.6 Hz), 7.17 (3H, t, J=3.0 Hz), 7.21 (2H, d, J=7.3 Hz), 7.34 (1H, s), 7.43 (2H, br s).

Step 3

(3'R, 4'S,5'R)-6"-chloro-4'-(3-chloro-2-fluorophenyl)-N-(trans-4-hydroxycyclohexyl)-2"-oxo-1",2"-dihydrodispiro[cyclohexane-1,2'-pyrrolidine-3',3"-indole]-5'-carboxamide The compound (228 mg, 0.30 mmol) obtained in Step 2 above was used as a starting material and treated in the same way as in Step 3 of Example 1 to give 76 mg (45%) of the title compound as a colorless solid.

$^1$H-NMR (400 MHz, $CD_3OD$) δ: 0.88-0.97 (2H, m), 1.05-1.08 (1H, m), 1.29-1.43 (5H, m), 1.54-1.59 (2H, m), 1.64-1.79 (3H, m), 1.87-1.99 (5H, m), 3.56-3.58 (2H, m), 4.50 (1H, d, J=9.2 Hz), 4.65 (1H, d, J=9.6 Hz), 6.71 (1H, d, J=2.3 Hz), 7.00-7.04 (2H, m), 7.18-7.22 (1H, m), 7.39 (1H, dd, J=8.2, 2.3 Hz), 7.61 (1H, t, J=6.6 Hz).

MS (ESI) m/z: 560 $(M+H)^+$.

Example 5

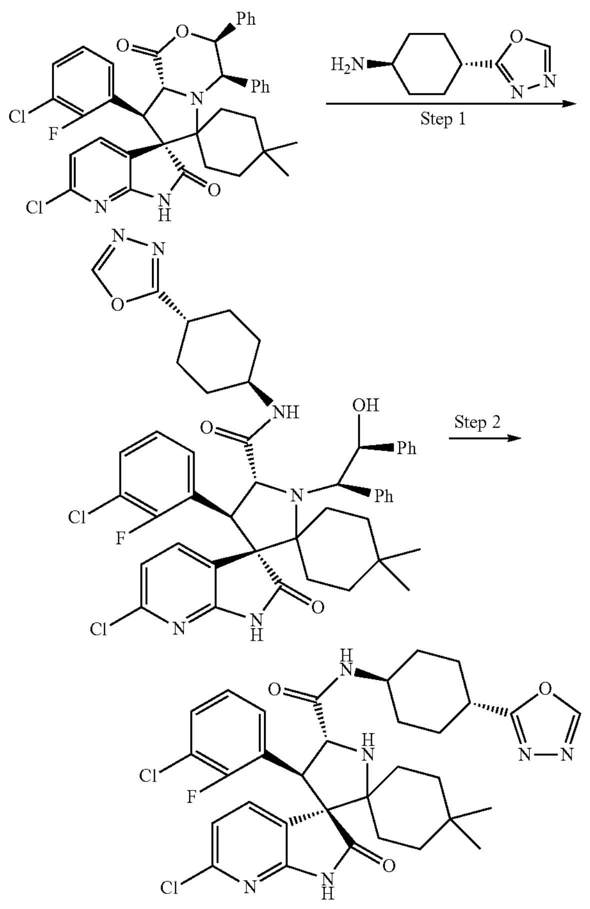

Step 1

(4'S,5'R)-6"-chloro-4'-(3-chloro-2=fluorophenyl)-1'-[(1R,2S)-2-hydroxy-1,2-diphenylethyl]-4,4-dimethyl-N-[trans-4-(1,3,4-oxadiazol-2-yl)cyclohexyl]-2"-oxo-1",2"-dihydrodispiro[cyclohexane-1,2"pyrrolidine-3',3"-pyrrolo[2,3-b]pyridine]-5'-carboxamide A methanol (18 ml) solution of the compound (3.61 g, 21.0 mmol) obtained in Step 3 of Reference Example 3 was added to a methanol (6 ml) solution of the compound (3.42 q, 4.82 mmol) obtained in Step 1 of Example 2 under nitrogen atmosphere and the resulting mixture was stirred under heating at 60° C. for 2 days. After cooling, dichloromethane was added and the organic layer was washed with saturated ammonium chloride solution. The organic layer was dried over anhydrous sodium sulfate, the solvent was concentrated under reduced pressure and the residue obtained was purified by silica gel column chromatography [dichloromethane:methanol=99:1→49:1 (v/v)] to give 3.26 g of the title compound as a mixture of isomers.

MS (ESI) m/z: 837 $(M+H)^+$.

Step 2

(3'R, 4'S,5'R)-6"-chloro-4'-(3-chloro-2-fluorophenyl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-pyrrolo[2,3-b]pyridine]-5'-carboxamide The compound (3.26 g, 3.89 mmol) obtained in Step 1 above was used as a starting material and treated in the same way as in Step 3 of Example 1 to give 1.00 g (31%) of the title compound as a pale yellow solid.

$^1$H-NMR (400 MHz, $CDCl_3$) δ: 0.71 (3H, s), 0.97 (3H, s), 1.14-1.28 (2H, m), 1.30-1.44 (3H, m), 1.46-1.61 (2M, m), 1.62-1.81 (5H, m), 2.09-2.29 (4H, m), 2.91-2.99 (1H, m), 3.17-3.30 (1H, m), 3.74-3.84, (1H, m), 4.48 (1H, d, J=9.2 Hz), 4.70 (1H, d, J=9.2 Hz), 6.97 (1H, t, J=7.7 Hz), 7.06 (1H, d, J=8.0 Hz), 7.14-7.19 (1H, m), 7.46-7.51 (1H, m), 7.56 (1H, d, J=8.6 Hz), 7.64 (1H, dd, J=7.5, 2.3 Hz), 7.85 (1H, s), 8.33 (1H, s).

MS (ESI) m/z: 641 $(M+H)^+$.

Example 6

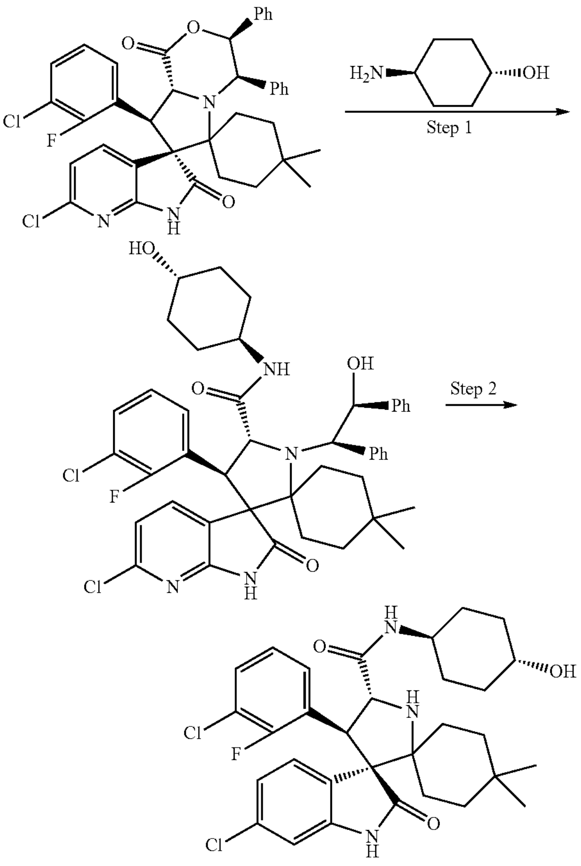

Step 1

(4'S,5'R)-6"-chloro-4'-(3-chloro-2-fluorophenyl)-N-(trans-4-hydroxycyclohexyl)-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (335 mg, 0.50 mmol) obtained in Step 1 of Example 2 was used as a starting material and treated in the same way as in Step 2 of Example 1 to give 160 mg (40%) of the title compound as a pale yellow amorphous solid.

$^1$H-NMR (400 MHz, $CDCl_3$) δ: 0.55-0.59 (1H, m), 0.87 (3H, s), 0.95-1.01 (1H, m), 1.05 (3H, s), 1.25-1.44 (6H, m), 1.63-1.69 (2H, m), 1.85-1.97 (2H, m), 2.29-2.33 (2H, m), 2.82 (1H, d, J=15.9 Hz), 3.45 (1H, s), 3.70-3.73 (3H, m), 4.42 (1H, d, J=7.8 Hz), 4.54 (1H, d, J=10.5 Hz), 4.85 (1H, d, J=3.4 Hz), 5.56 (1H, s), 5.67 (1H, s), 6.58 (1H, s), 6.77 (1H, t, J=7.8 Hz), 6.95 (1H, d, J=7.8 Hz), 7.03-7.05 (2H, m), 7.14-7.24 (9H, m), 7.38-7.46 (2H, m), 7.48 (1H, s).

Step 2

(3'R, 4'S,5'R)-6"-chloro-4'-(3-chloro-2-fluorophenyl)-N-(trans-4-hydroxycyclohexyl)-4,4-dimethyl-2"-oxo-1",2"-dihydrodispiro[cyclohexane-1,2'-pyrrolidine-3',3"-pyrrolo[2,3-b]pyridine]-5'-carboxamide The compound (160 mg, 0.20 mmol) obtained in Step 1 above was used as a starting material and treated in the same way as in Step 3 of Example 1 to give 30 mg (25%) of the title compound as a colorless solid.

$^1$H-NMR (400 MHz, $CD_3OD$) δ: 0.71 (3H, s), 0.95 (3H, s), 1.09-1.25 (2H, m), 1.26-1.43 (5H, m), 1.51-1.63 (2H, m), 1.64-4.68 (1H, d, J=9.3 Hz), 7.01-7.09 (2H, m), 7.20-7.28 (1H, m), 7.54-7.62 (1H, m), 7.83 (1H, dd, J=7.9, 2.6 Hz).)

MS (ESI) m/z: 589 $(M+H)^+$.

Example 7

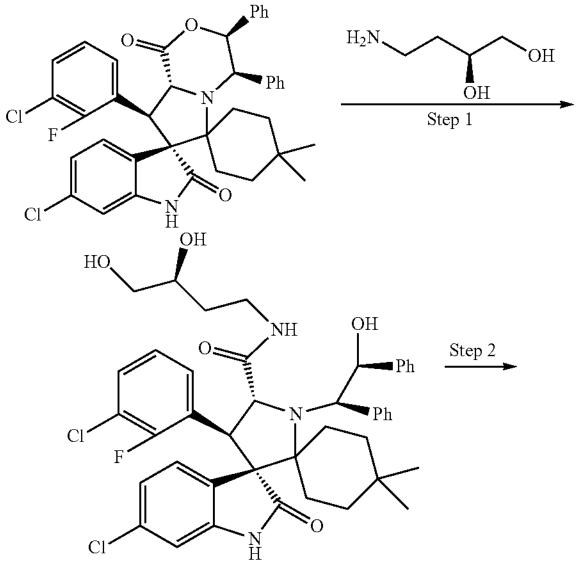

-continued

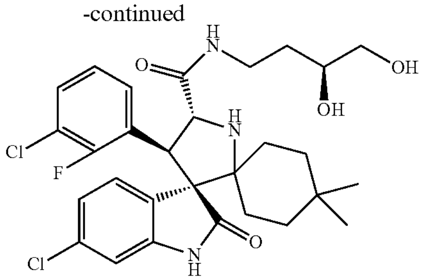

Step 1

(4'S,5'R)-6"-chloro-4'-(3-chloro-2-fluorophenyl)-N-[(3S)-3,4-dihydroxybutyl]-1'-[(1R,2S)-2-hydroxy-1,2-diphenylethyl]-4,4-dimethyl-2"-oxo-1",2"-dihydrodispiro(cyclohexane-1,2'-pyrrolidine-3',3"-indole)-5'-carboxamide The compound (1.01 g, 1.51 mmol) obtained in Step 1 of Example 1 and (28)-4-aminobutane-1,2-diol (WO2007/011162) (475 mg, 4.53 mmol) were used as starting materials and treated in the same way as in Step 2 of Example 1 to give 644 mg (55%) of the title compound as a colorless amorphous solid.

MS (ESI) m/z: 774 $(M+H)^+$.

Step 2

(3'R, 4'S,5'R)-6"-chloro-4'-(3-chloro-2-fluorophenyl)-N-[(35)-3,4-dihydroxybutyl]-4,4-dimethyl-2"-oxo-1",2"-dihydrodispiro[cyclohexane-1,2'-pyrrolidine-3',3"-indole]-5'-carboxamide The compound (644 mg, 0.83 mmol) obtained in Step 1 above was used as a starting material and treated in the same way as in Step 3 of Example 1 to give 330 mg (67%) of the title compound as a colorless amorphous solid.

$^1$H-NMR (400 MHz, DMSO-dd) δ: 0.58 (3H, s), 0.88 (3H, s), 0.94 (1H, td, J=13.9, 4.3 Hz), 1.09 (1H, d, J=13.3 Hz), 1.18 (1H, d, J=13.4 Hz), 1.30-1.63 (5H, m), 1.71-1.81 (2H, m), 3.05-3.08 (1H, m), 3.19-3.32 (3H, m), 3.40-3.47 (2H, m)+4.38 (1H, t, J=9.8 Hz), 4.49 (2H, dd, J=12.1, 5.3 Hz), 4.55 (1H, d, J=9.2 Hz), 6.66 (1H, d, J=1.8 Hz), 7.02 (1H, dd, J=8.2, 1.8 Hz), 7.09 (1H, t, J=8.0 Hz), 7.30 (1H, td, J=7.6, 1.4 Hz), 7.42 (1H, dd, J=8.0, 2.1 Hz), 7.56 (1H, t, J=6.6 Hz), 7.98 (1H, t, J=6.2 Hz), 10.50 (1H, br s).

MS (ESI) m/z: 578 $(M+H)^+$.

Example 8

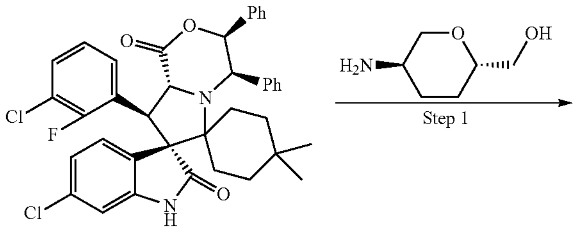

-continued

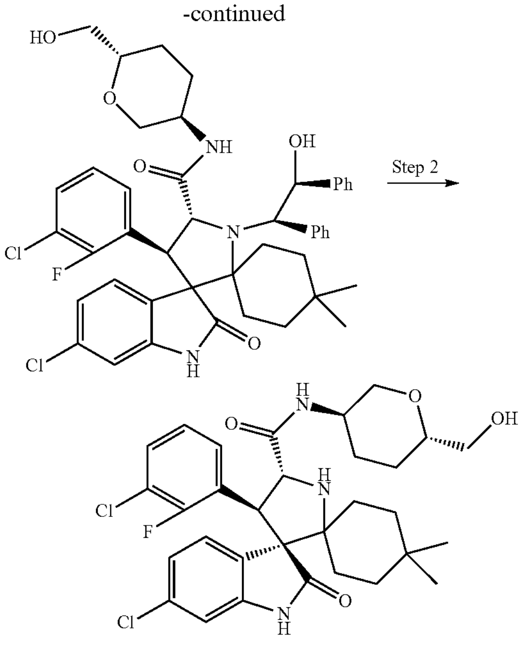

Step 1

(4'S,5'R)-6"-chloro-4'-(3-chloro-2-fluorophenyl)-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (164 mg, 0.24 mmol) obtained in Step 1 of Example 1 and the compound (79.0 mg, 0.49 mmol) obtained in Step 3 of Reference Example 2 were used as starting materials and treated in the same way as in Step 1 of Example 5 to give 92.5 mg of the title compound as a mixture of isomers.

MS (ESI) m/z: 800 $(M+H)^+$.

Step 2

(3'R, 4'S,5'R)-6"-chloro-4'-(3-chloro-2-fluorophenyl)-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (92.5 mg, 0.12 mmol) obtained in Step 1 above was used as a starting material and treated in the same way as in Step 3 of Example 1 to give 28.1 mg (19%) of the title compound as a pale yellow solid.

$^1H$-NMR (400 MHz, $CDCl_3$) δ: 0.68 (3H, s), 0.95 (3H, s), 1.09-1.27 (3H, m), 1.32-1.39 (1H, m), 1.41-1.79 (6H, m), 1.97-2.06 (1H, m), 2.08-2.14 (1H, m), 3.12 (1H, t, J=10.6 Hz), 3.40-3.46 (1H, m), 3.51-3.57 (1H, m), 3.58-3.65 (1H, m), 3.84-3.95 (1H, m), 4.06-4.11 (1H, m), 4.45 (1H, d, J=9.2 Hz), 4.67 (1H, d, J=9.2 Hz), 6.69 (1H, d, J=2.0 Hz), 6.88-6.93 (1H, m); 7.05 (1H, dd, J=8.3, 2.0 Hz), 7, 10-7.14 (1H, m), 7.31-7.35 (1H, m), 7.41 (1H, s), 7.47-7.55 (2H, m),

MS (ESI) m/z: 604 $(M+H)^+$.

Example 9

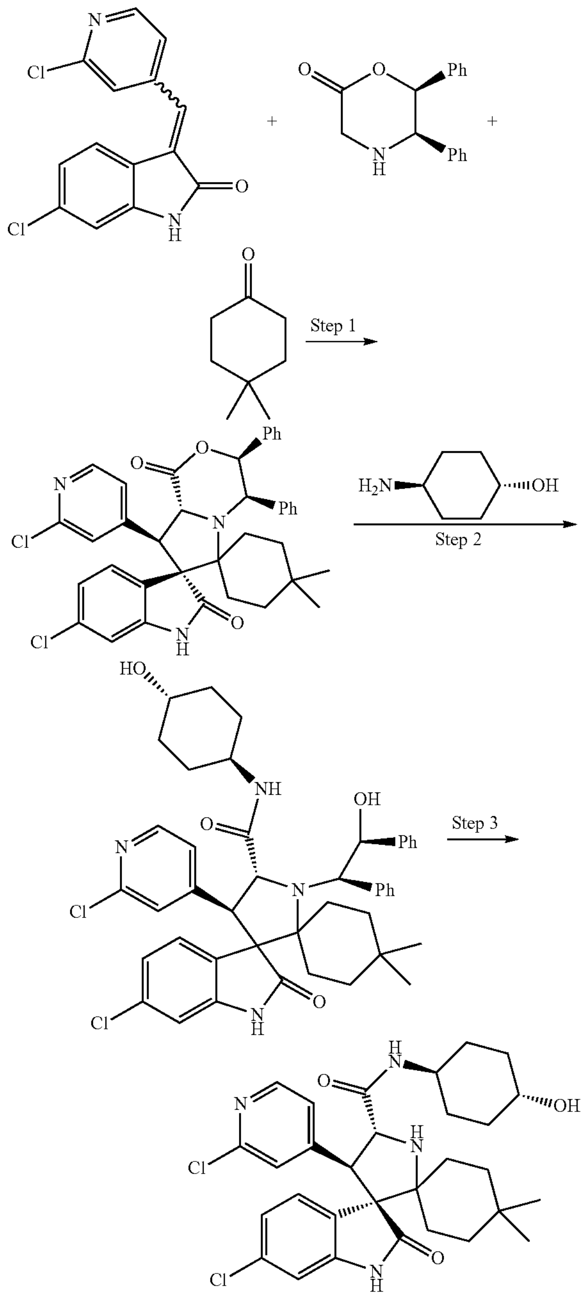

Step 1

(3'S,4'R, 7'S,8'R, 8a'R)-6"-chloro-8'-(2-chloropyridin-4-yl)-4,4-dimethyl-3',4'-diphenyl-3',4',8',8a'-tetrahydro-1'H-dispiro [cyclohexane-1,6'-pyrrolo[2,1-c][1,4]oxazine-7',3"-indole]-1',2" (1"H)-dione A boron trifluoride-diethyl ether complex (0.038 ml, 0.30 mmol) and molecular sieves 4 A (powder) (3 g) were added to a tetrahydrofuran (30 ml) solution of the compound (873 mg, 3.00 mmol) obtained in Reference Example 4, (5R,6S)-5,6-diphenylmorpholin-2-one (760 mg, 3.00 mmol), and 4,4-dimethylcyclohexanone (379 mg, 3.00 mmol) under nitrogen atmosphere and the resulting mixture was stirred under heating at 70° ° C. for 7 days. After cooling, insoluble matter was removed by filtration through celite and the filtrate was washed with brine and then dried over anhydrous sodium sulfate. The solvent was evaporated under reduced pressure and the residue was purified by silica gel column chromatography [n-hexane:ethyl acetate=4:1→1:1 (v/v)] to give 1.18 g (60%) of the title compound as a pale yellow amorphous solid.

$^1$H-NMR (400 MHz, $CDCl_3$) δ: 0.54 (3H, s), 0.67 (3H, 8), 0.80-0.92 (1H, m), 1.15-1.41 (4H, m), 1.71-1.82 (1H, m), 1.82-1.94 (1H, m), 2.15-2.26 (1H, m), 4.42 (1H, d, J=10.7 Hz), 4.81 (1H, d, J=3.7 Hz), 5.03 (1H, d, J=10.7 Hz), 6.60-6.68 (2H, m), 6.78-6.84 (2H, m), 6.95-6.89 (1H, m), 6.91-6.98 (2H, m), 7.06-7.31 (9H, m), 7.47 (1H, s), 8.14 (1H, d, J=5.1 Hz).

Step 2

(4'R, 5'R)-6"-chloro-4'-(2-chloropyridine-4-yl)-N-(trans-4-hydroxycyclohexyl)-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-5'-carboxamide The compound (195 mg, 0.30 mmol) obtained in Step 1 above was used as a starting material and treated in the same way as in Step 2 of Example 1 to give 184 mg (80%) of the title compound as a yellow amorphous solid.

MS (ESI) m/z: 767 $(M+H)^+$.

Step 3

(3'R, 4'R, 5'R)-6"-chloro-4'-(2-chloropyridin-4-yl)-N-(trans-4-hydroxycyclohexyl)-4,4-dimethyl-2"-oxo-1",2"-dihydrodispiro[cyclohexane-1,2"-pyrrolidine-3',3"-indole]-5'-carboxamide The compound (184 mg, 0.24 mmol) obtained in Step 2 above was used as a starting material and treated in the same way as in Step 3 of Example 1 to give 81 mg (59%) of the title compound as a colorless solid.

$^1$H-NMR (400 MHz, $CD_3OD$) δ: 0.68 (3H, s), 0.94 (3M, s), 1.13-1.19 (2H, m), 1.33-1.41 (5H, m), 1.50-1.60 (2H, m), 1.76-1.78 (3H, m), 1.95-1.99 (4H, m), 3.58-3.60 (2H, m), 4.21 (1H, d, J=9.2 Hz), 4.60 (1H, d, J=9.2 Hz), 6.79 (1H, d, J=1.8 Hz), 7.06 (1H, dd, J=5.3, 1.6 Hz), 7.10 (1H, dd, J=8.2, 1.8 Hz), 7.23 (1H, s), 7.52 (1H, d, J=8.2 Hz), 8.06 (1H, d, J=5.5 Hz).

MS (ESI) m/z: 575 $(M+H)^+$.

Example 10

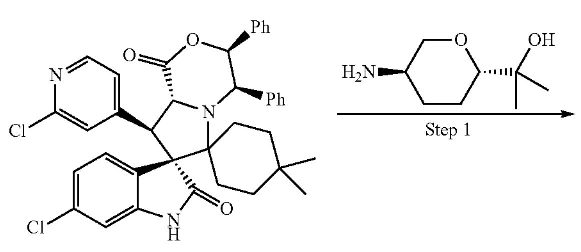

-continued

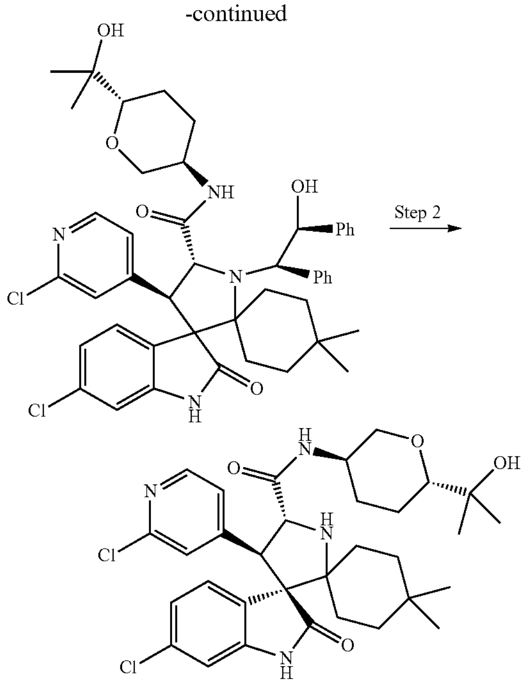

Step 1

(4'R, 5'R)-6"-chloro-4'-(2-chloropyridin-4-yl)-1'-[(1R,2S)-2-hydroxy-1,2-diphenylethyl]-N-[(3R,6S)-6-{1-hydroxy-1-methylethyl}tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (159 mg, 1.00 mmol) obtained in Step 2 of Reference Example 5 and triethylamine (0.14 ml, 1.00 mmol) were added to a 2-propanol (4 ml) solution of the compound (195 mg, 0.30 mmol) obtained in Step 1 of Example 9 and the resulting mixture was stirred under heating at 70° C. for 4 days. After cooling, the reaction mixture was diluted with ethyl acetate, washed with saturated ammonium chloride solution and brine and then dried over anhydrous sodium sulfate. The solvent was evaporated under reduced pressure and the residue was purified by silica gel column chromatography [chloroform:methanol=100:0→40:1 (v/v)] to give 98 mg (40%) of the title compound as a pale yellow amorphous solid.

MS (ESI) m/z: 811 $(M+H)^+$.

Step 2

(3'R, 4'R, 5'R)-6"-chloro-4'-(2-chloropyridin-4-yl)-N-[(3R,6S)-6-(1-hydroxy-1-methylethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide Cerium (IV) diammonium nitrate (132 mg, 0.24 mmol) was added to an acetonitrile (10 ml)/water (3 ml) solution of the compound (98 mg, 0.12 mmol) obtained in Step 1 above under ice cooling and the resulting mixture was stirred for 10 minutes. Potassium carbonate (65 mg, 0.48 mmol) was added to the reaction mixture and insoluble matter was removed by filtration through celite. The filtrate was diluted with ethyl acetate, washed with brine and then dried over anhydrous sodium sulfate. The solvent was evaporated under reduced pressure, the residue was dissolved in chloroform (9 ml) and methanol (1 ml), silica gel (980 mg) was added and the resulting mixture was stirred overnight at room temperature. Insoluble matter was removed by filtration and the residue was purified by NH-silica gel column chromatography (chloroform) to give 39 mg (53%) of the title compound as a colorless solid.

$^1$H-NMR (400 MHz, $CD_3OD$) δ: 0.68 (3H, s), 0.95 (3H, s), 1.14-1.16 (9H, m), 1.31-1.34 (1H, m), 1.48-1.58 (3H, m), 1.77-1.79 (3H, m), 1.83-1.86 (1H, m), 2.06-2.08 (1H, m), 3.11-3.16 (2H, m), 3.74-3.75 (1H, m), 3.98-4.01 (1H, m), 4.23 (1H, d, J=9.2 Hz), 4.61 (1H, d, J=8.7 Hz), 6.79 (1H, d, J=1.8 Hz), 7.06 (1H, dd, J=5.3, 1.6 Hz), 7.11 (1H, dd, J=8.0, 2.1 Hz), 7.22-7.30 (1H, m), 7.52 (1H, d, J=8.2 Hz), 8.06 (1H, d, J=3.5 Hz).

MS (ESI) m/z: 615 $(M+H)^+$.

Example 11

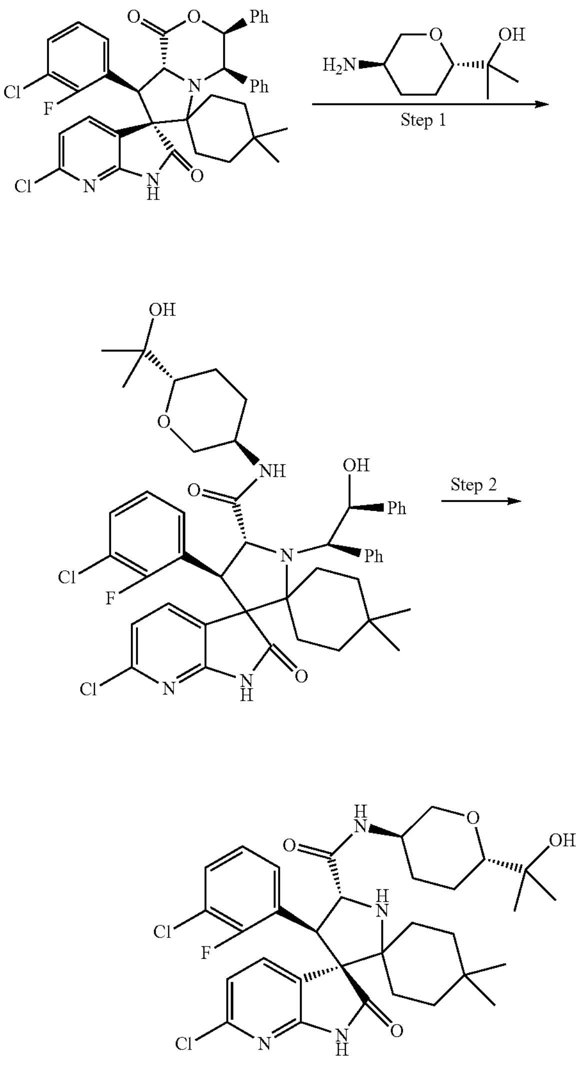

Step 1

(4'S,5'R)-6"-chloro-4'-(3-chloro-2-fluorophenyl)-1'-[(1R,2S)-2-hydroxy-1,2-diphenylethyl]-N-[(3R,6S)-6-(1-hydroxy-1-methylethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide Trimethylaluminum (2.0 mol/l, n-hexane solution, 0.5 ml, 1, 00 mmol) was added to a tetrahydrofuran (6.0 ml) solution of the compound (201 mg, 0.30 mmol) obtained in Step 1 of Example 2 under ice cooling under nitrogen atmosphere and the resulting mixture was stirred for 30 minutes. A tetrahydrofuran (4 ml) solution of the compound (159 mg, 1.00 mmol) obtained in Step 2 of Reference Example 5 was added to the reaction mixture and the resulting mixture was warmed to 50° C. and stirred overnight. After cooling, 1N hydrochloric acid was added, followed by extraction with ethyl acetate. The organic layer was washed with brine and then dried over anhydrous sodium sulfate. The solvent was evaporated under reduced pressure and the residue was purified by silica gel column chromatography [chloroform:methanol=50:0→30:1 (v/v)] to give 56 mg (22%) of the title compound as a purple amorphous solid.

$^1$H-NMR (400 MHz, $CDCl_3$) δ: 0.86 (3H, s), 1.05 (3H, s), 1.08-1.14 (6H, m), 1.23-1.34 (2H, m), 1.38-1.70 (5H, m), 1.98-2.07 (1H, m), 2.20-2.41 (4H, m), 2.75-2.94 (1H, m), 2.85-2.91 (1H, m), 3.61-3.69 (1H, m), 3.71-3.78 (1H, m), 3.80-3.92 (1H, m), 4.37-4.44 (1H, m), 4.45-4.52 (1H, m), 4.82-4.87 (1H, m), 5.37 (2H, s), 5.52-5.57 (1H, m), 6.56-6.64 (1H, m), 6.78, (1H, t, J=7.8 Hz), 6.94 (1H, d, J=7.8 Hz), 7.02-7.08 (1H, m), 7.09-7.15 (2H, m), 7.16-7.25 (8H, m), 7.38-7.46 (2H, m), 7.64 (1H, s).

Step 2

(3'R, 4'S,5'R)-6"-chloro-4'-(3-chloro-2-fluorophenyl)-N-[(3R,6S)-6-(1-hydroxy-1-methylethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (56 mg, 0.067 mmol) obtained in Step 1 above was used as a starting material and treated in the same way as in Step 3 of Example 1 to give 30 mg (70%) of the title compound as a colorless solid.

$^1$H-NMR (400 MHz, $CD_3OD$) δ: 0.71 (3H, s), 0.95 (3H, s), 1.09-1.39 (9H, m), 1.43-1.90 (8H, m), 2.04-2.13 (1H, m), 3.04-3.17 (2H, m), 3.69-3.80 (1H, m), 3.91-3.99 (1H, m), 4.52 (1H, d, J=9.2 Hz), 4.70 (1H, d, J=9.2 Hz), 7.02-7.10 (2H, m), 7.20-7.28 (1H, m), 7.54-7.61 (1H, m), 7.83 (1H, dd, J=7.8, 2.3. H %).

MS (ESI) m/z: 633 $(M+H)^+$.

Example 12

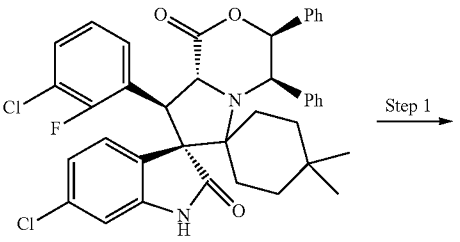

-continued

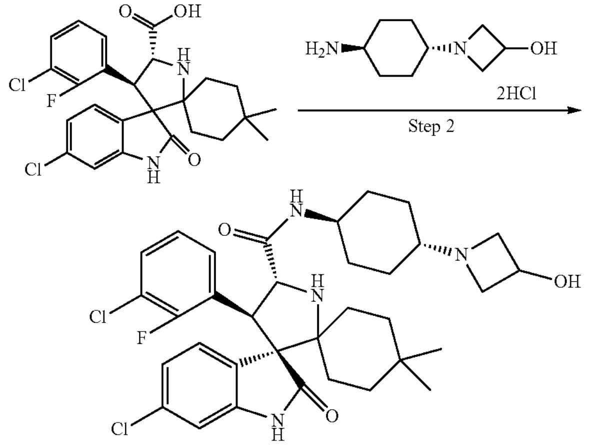

Step 1

(4'S,5'R)-6"-chloro-4'-(3-chloro-2-fluorophenyl)-4,4-dimethyl-2"-oxo-1",2"-dihydrodispiro[cyclohexane-1,2'-pyrrolidine-3',3"-indole]-5'-carboxylic acid 1N sodium hydroxide solution (50 ml, 50 mmol) was added to a methanol (250 ml) solution of the compound (15.7 g, 23, 4 mmol) obtained in Step 1 of Example 1 and the resulting mixture was heated to reflux overnight. After cooling, methanol (500 ml) and water (200 ml) were added to the reaction mixture and then the resulting mixture was neutralized by addition of 1N hydrochloric acid (50 ml) under ice cooling. Cerium (IV) diammonium nitrate (26.9 g, 49.1 mmol) was added under ice cooling, the resulting mixture was stirred for 20 minutes, then potassium carbonate (13.6 g, 98.3 mmol) was added and the resulting mixture was further stirred for 30 minutes. Insoluble matter was removed by filtration through celite and the filtrate was concentrated under reduced pressure. The residue was diluted with water, followed by extraction with ethyl acetate. The aqueous layer was further subjected to extraction with chloroform:methanol [5:1 (v/v)], the organic layers were combined and dried over anhydrous sodium sulfate, then the solvent was evaporated under reduced pressure and the residue was dried to give 6.54 g (578) of the title compound as a pale yellow solid.

$^{1}$H-NMR (400 MHz, $CD_3OD$) δ: 0.75 (3H, s), 1.02 (3H, s), 1.26-1.36 (1H, m), 1.39-1.45 (1H, m), 1.46-1.54 (1H, m), 1.60-1.67 (1H, m), 1.74-1.83 (1H, m), 1.94-2.00 (1H, m), 2.06-2.14 (1H, m), 2.34-2.43 (1H, m), 4.50-4.98 (2H, m), 6.76 (1H, d, J=2.3 Hz), 7.08-7.14 (2H, m), 7.28-7.32 (1H, m), 7.56 (1H, dd, J=8.0, 2.3 Hz), 7.60-7.65 (1H, m).

MS (ESI) m/z: 491 $(M+H)^+$.

Step 2

(3'R, 4'S,5'R)-6"-chloro-4'-(3-chloro-2-fluorophenyl)-N-[trans-4-(3-hydroxyazetidin-1-yl)cyclohexyl]-4,4-dimethyl-2"-oxo-1",2"-dihydrodispiro [cyclohexane-1,2'-pyrrolidine-3',3"-indole]-5'-carboxamide The compound (146 mg, 0.60 mmol) obtained in Step 2 of Reference Example 13, triethylamine (0.14 ml, 1.00 mmol), 1-hydroxybenzotriazole (74 mg, 0.55 mmol), and 1-ethyl-3-(3-dimethylaminopropyl) carbodiimide hydrochloride (105 mg, 0.55 mmol) were added to an N,N-dimethylformamide (5 ml) solution of the compound (246 mg, 0.50 mmol) obtained in Step 1 above and the resulting mixture was stirred at room temperature for 18 hours. The reaction mixture was diluted with ethyl acetate, washed with water, saturated sodium bicarbonate solution, and brine in that order and then dried over anhydrous sodium sulfate. The solvent was evaporated under reduced pressure, then the residue was purified by silica gel column chromatography [chloroform:methanol=70:1 (v/v)] and the purified product obtained was dissolved in methanol (10 ml) and stirred at 60° C. for 24 hours. The solvent was evaporated under reduced pressure to give 150 mg (47%) of the title compound as a pale yellow solid.

$^{1}$H-NMR (400 MHz, $CD_3OD$) δ: 0.71 (3H, s), 0.95 (3H, s), 1.06-1.39 (7H, m), 1.53-1.63 (1H, m), 1.75-2.03 (7H, m), 2.10-2.18 (1H, m), 2.88-2.96 (2H, m), 3.26-3.32 (1H, m), 3.53-3.62 (1H, m), 3.62-3.71 (2H, m), 4.30-4.36 (1H, m), 4.50 (1H, d, J=9.2 Hz), 4.68 (1H, d, J=9.7 Hz), 6.75 (1H, d, J=2.3 Hz), 7.02-7.07 (2H, m), 7.22 (1H, t, J=8.0 Hz), 7.44 (1H, dd, J=8.0, 2.3 Hz), 7.63 (1H, t, J=6.6 Hz).

MS (ESI) m/z: 643 $(M+H)^+$.

Example 13

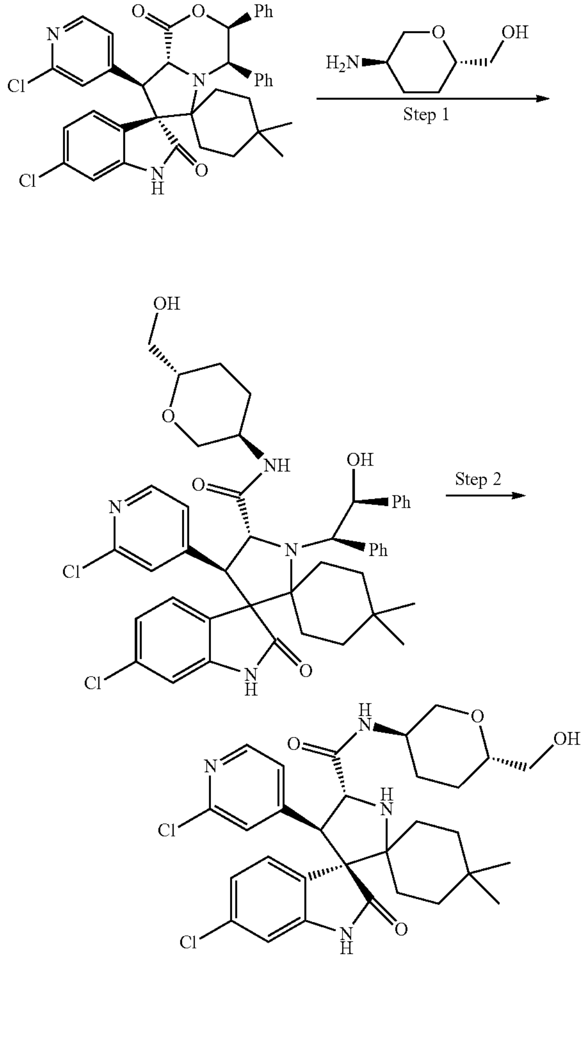

Step 1

(4'R, 5'R)-6"-chloro-4'-(2-chloropyridin-4-yl)-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (195 mg, 0.30 mmol) obtained in Step 1 of Example 9 and the compound (131 mg, 1.00 mmol) obtained in Step 3 of Reference Example 2 were used as starting materials and treated in the same way as in Step 1 of Example 10 to give 233 mg (99%) of the title compound as a colorless amorphous solid.

$^1$H-NMR (400 MHz, $CDCl_3$) δ: 0.87 (38, s), 1.05 (3H, s), 1.07-1.19 (1H, m), 1.21-1.32 (1H, m), 1.35-1.54 (2H, m); 1.58-1.76 (3H, m), 1.89-1.98 (1H, m), 2.00-2.08 (1H, m), 2.20-2.37 (2H, m), 2.51 (1H, t, J=10.5 Hz), 2.75-2.85 (1H, m), 3.19-3.28 (1H, m), 3.43-3.61 (3H, m), 3.68-3.76 (1H, m), 3.84-3.97 (1H, m), 4.12 (1H, d, J=11.0 Hz), 4.66-4.78 (1H, m), 4.84-4.91 (1H, m), 5.20-5.30 (1H, m), 5.50-5.57 (1H, m), 6.51-6.55 (1H, m), 6.71-6.76 (2H, m), 6.92 (1H, d, J=8.2 Hz), 6.99 (1H, dd, J=8.2, 1.8 Hz), 7.01-7.08 (1H, m), 7.08-7.18 (4H, m), 7.21-7.28 (4H, m), 7.35 (1H, s), 7.39-7.47 (2H, m), 8.00 (1H, d, J=5.0 Hz).

Step 2

(3'R, 4'R, 5'R)-6"-chloro-4'-(2-chloropyridin-4-yl)-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (233 mg, 0.30 mmol) obtained in Step 1 above was used as a starting material and treated in the same way as in Step 2 of Example 10 to give 90 mg (52%) of the title compound as a colorless solid.

$^1$H-NMR (400 MHz, $CD_3OD$) δ: 0.68 (3H, s), 0.94 (3H, s), 1.17-1.19 (2H, m), 1.31-1.33 (1H, m), 1.41-1.62 (4H, m), 1.75-1.79 (4H, m), 2.05 (1H, d, δ=11.0 Hz), 3.18 (1H, t, J=10.5 Hz), 3.37-3.41 (1H, m), 3.50 (2H, d, J=5.0 Hz), 3.77-3.81 (1H, m), 3.95-3.98 (1H, m), 4.23 (1H, d, J=8.7 Hz), 4.61 (1H, d, J=9.2 Hz), 6.79 (1H, d, J=1.8 Hz), 7.06 (1H, dd, J=5.3, 1.6 Hz), 7.11 (1H, dd, J=8.2, 1.8 Hz), 7.22 (1H, s), 7.52 (1H, d, J=8.2 Hz), 8.06 (1H, d, J=5.0 Hz).

MS (ESI) m/z: 587 (M+R)$^+$.

Example 14

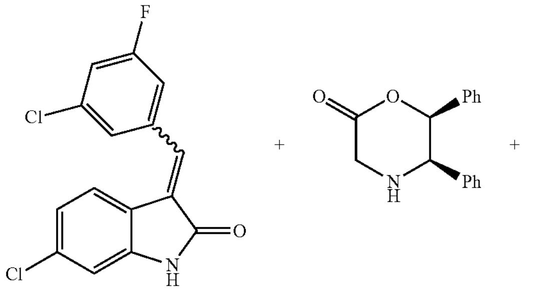

-continued

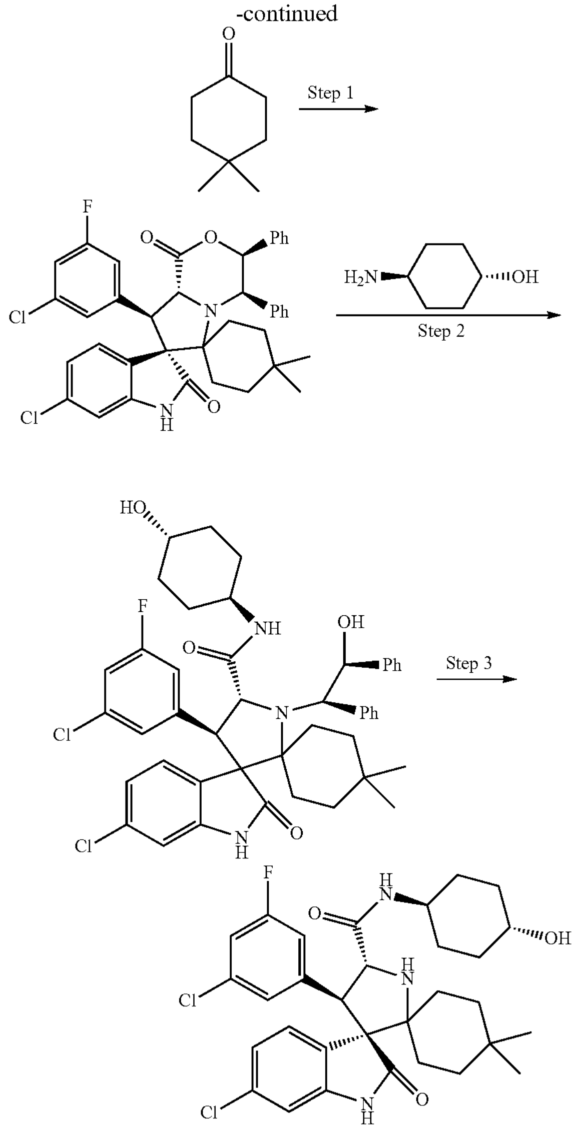

Step 1

(3'S,4'R, 7'S,8'R, 8a'R)-6"-chloro-8'-(3-chloro-5-fluorophenyl)-4,4-dimethyl-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione The compound (1.55 g, 5.00 mmol) obtained in Reference Example 6 was used and treated in the same way as in Step 1 of Example 9 to give 2.03 g (618) of the title compound as a colorless solid.

$^1$H-NMR (400 MHz, $CDCl_3$) δ: 0.48 (3H, s), 0.64 (3H, s), 0.83-0.92 (1H, m), 1.11-1.29 (3H, m), 1.33-1.41 (1H, m), 1.71-1.83 (2H, m), 2.15-2.24 (1H, m), 4.43 (1H, d, J=11.0 Hz), 4.80 (1H, d, J=3.7 Hz), 5.02 (1H, d, J=11.0 Hz), 6.64 (1H, d, J=8.7 Hz), 6.73 (2H, dd, J=6.9, 2.8 Hz), 6.79 (2H, dt, J=8.4, 2.9 Hz), 6.85-6.93 (4H, m), 7.09-7.18 (5H, m), 7.21-7.28 (3H, m), 7.44 (1H, br s).

MS (APCI) m/z: 669 (M+H)$^+$.

Step 2

(4'R, 5'R)-6"-chloro-4-(3-chloro-5-fluorophenyl)-N-(trans-4-hydroxycyclohexyl)-1'-[(1R,2S)=2-hydroxy-1,2-diphenylethyl]-4,4-dimethyl-2"-oxo-1",2"-dihydrodispiro[cyclohexane-1,2'-pyrrolidine-3',3"-indole]-5'-carboxamide The compound (1.01 g, 1.51 mmol) obtained in Step 1 above was used and treated in the same way as in Step 2 of Example 1 to give 0.75 g (63%) of the title compound as a colorless amorphous solid.

MS (APCI) m/z: 784 $(M+H)^+$.

Step 3

(3'R, 4'R, S'R)-6"-chloro-4'-(3-chloro-5-fluorophenyl)-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide The compound (0.72 g, 0.92 mmol) obtained in Step 2 above was used as a starting material and treated in the same way as in Step 3 of Example 1 to give 213 mg (40%) of the title compound as a colorless solid.

$^1$H-NMR (400 MHz, $CD_3OD$) δ: 0.68 (3H, s), 0.93 (3H, s), 1.08-1.41 (8H, m), 1.49-1.62 (2K, m), 1.70-1.82 (3H, m), 1.87-2.02 (4H, m), 3.51-3.65 (2H, m), 4.17 (1H, d, J=9.2 Hz), 4.52 (1H, d, J=9.2 Hz), 6.77 (1H, d, J=1.8 Hz), 6.84-6.89 (1H, m), 6.90-6.95 (1H, m), 6.97 (1H, s), 7.09 (1H, dd, J=8.0, 2.1 Hz), 7.49 (1H, d, J=8.3 Hz).

MS (ESI) m/z: 588 $(M+H)^+$.

Example 15

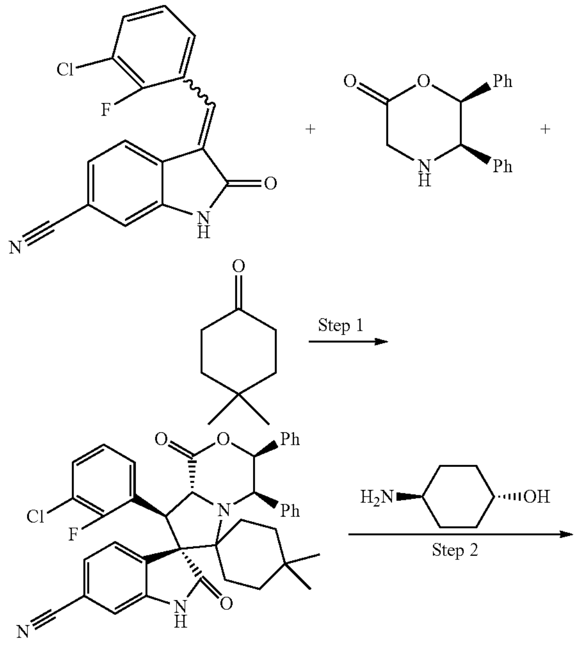

-continued

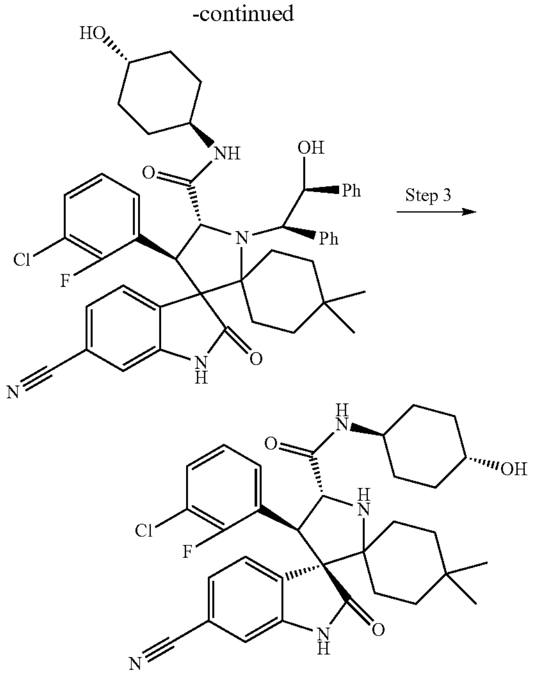

Step 1

(3'S,4'R, 7'S,8'S, 8a'R)-8'-(3-chloro-2-fluorophenyl)-4,4-dimethyl-1',2"-dioxo-3',4'-diphenyl-1",2",3',4',8',8a'-hexahydro-1'H-dispiro[cyclohexane-1,6'-pyrrolo[2,1-c][1,4]oxazine-7',3"-indole]-6"-carbonitrile The compound (869 mg, 3.00 mmol) obtained in Reference Example 7 was used as a starting material and treated in the same way as in Step 1 of Example 9 to give 49 mg (2%) of the title compound as a blackish brown solid.

$^1$H-NMR (400 MHz, $CDCl_3$) δ: 0.22 (3H, s), 0.53 (3H, s), 0.91-1.09 (3H, m), 1.21-1.28 (1H, m), 1.32-1.45 (2H, m), 1.83-1.89 (1H, m), 2.29-2.35 (1H, m), 4.67 (1H, d, J=11.5 Hz), 4.89 (1H, d, J=3.4 Hz), 5.40 (1H, d, J=11.5 Hz), 6.44 (1H, d, J=8.0 Hz), 6.77 (2H, m), 6.97 (1H, dd, J=8.0, 1.1 Hz), 7.09-7.28 (12H, m), 7.68 (1H, s), 7.84 (1H, t, J=6.6 Hz).

Step 2

(4'S,5'R)-4'-(3-chloro-2-fluorophenyl)-6"-cyano-N-(trans-4-hydroxycyclohexyl)-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-5'-carboxamide The compound (49 mg, 0.074 mmol) obtained in Step 1 above was used as a starting material and treated in the same way as in Step 2 of Example 1 to give 46 mg (80%) of the title compound as a blackish brown oil:

MS (APCI) m/z; 775 $(M+H)^+$.

Step 3

(3'R, 4'S,5'R)-4'-(3-chloro-2-fluorophenyl)-6"-cyano-N-(trans-4-hydroxycyclohexyl)-4,4-dimethyl-2"-oxo-1",2"-dihydrodispiro[cyclohexane-1,2'-pyrrolidine-3',3"-indole]-5%-carboxamide The compound (46 mg, 0.06 mmol) obtained in Step 2 above was used as a starting material and treated in the same way as in Step 3 of Example 1 to give 21 mg (628) of the title compound as a pale yellow solid.

$^1$H-NMR (400 MHz, $CD_3OD$) δ: 0.68 (3H, s), 0.96 (3H, s), 1.09-1.17 (1H, m), 1.18-1.24 (1H, m), 1.30-1.44 (5H, m), 1.55-1.64 (2H, m), 1.74-1.85 (2H, m), 1.87-2.02 (5H, m), 3.55-3.66 (2H, m), 4.55 (1H, d, J=9.2 Hz), 4.77 (1H, d, J=9.2 Hz), 7.02 (1H, br s), 7.04 (1H, t, J=8.0 Hz), 7.22 (1H, t, J=7.7 Hz), 7.44 (1H, d, J=7.7 Hz), 7.64 (1H, t, J=7.2 Hz), 7.69 (1H, d, J=8.0 Hz).

MS (ESI) m/z: 579 $(M+H)^+$.

Example 16

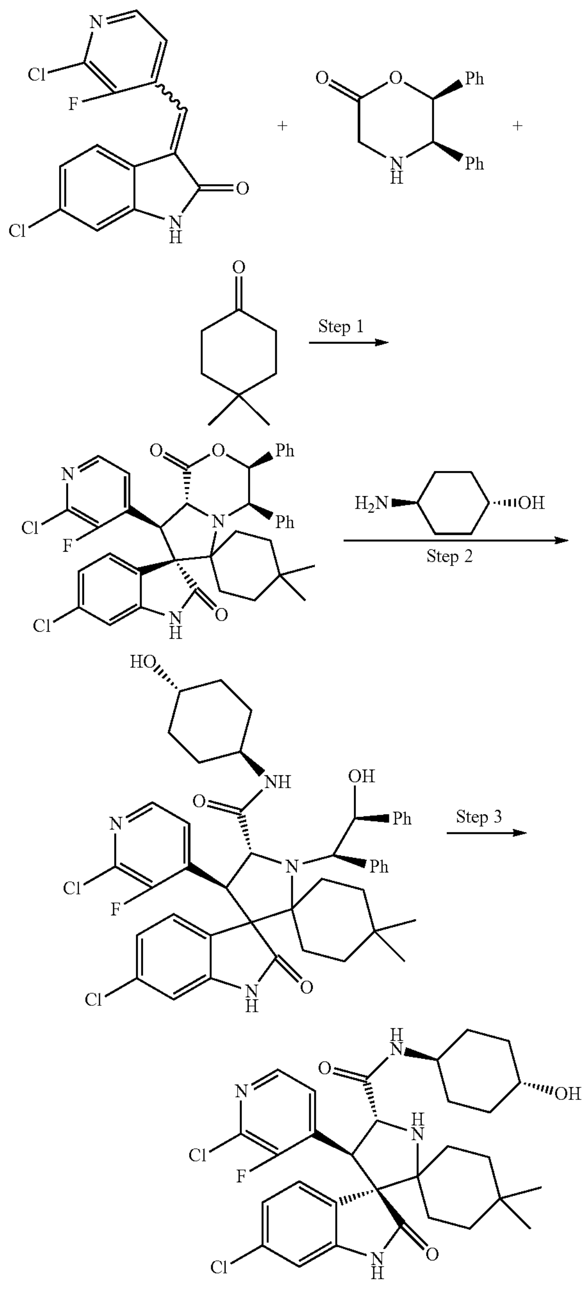

Step 1

(3'S,4'R, 7'S,8'S,8a'R)-6"-chloro-8'-(2-chloro-3-fluoropyridin-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione The compound (1.86 g, 6.00 mmol) obtained in Reference Example 8 was used as a starting material and treated in the same way as in Step 1 of Example 9 to give 3.39 g (84%) of the title compound as a yellow solid.

$^1$H-NMR (400 MHz, $CDCl_3$) δ: 0.21 (3H, s), 0.53 (3H, s), 0.89-1.08 (3H, m), 1.28-1.43 (3H, m), 1.73-1.81 (1H, m), 2.23-2.33 (1H, m), 4.58 (1H, d, J=11.0 Hz), 4.86 (1H, d, J=3.2 Hz), 5.31 (1H, d, J=11.0 Hz), 6.25 (1H, d, J=8.3 Hz), 6.67 (1H, dd, J=8, 3, 1.8 Hz), 6.72-6.77 (2H, m), 6.93 (1H, d, J=1.8 Hz), 7.04-7.17 (6H, m), 7.18-7.25 (3H, m), 7.79 (1H, t, J=4.6 Hz), 7.99 (1H, s), 8.29 (1H, d, J=5.0 Hz).

MS (APCI) m/z: 670 $(M+H)^+$.

Step 2

(4'S,5'R)-6"-chloro-4'-(2-chloro-3-fluoropyridin-4-yl)-N-(trans-4-hydroxycyclohexyl)-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-5'-carboxamide The compound (671 mg, 1.00 mmol) obtained in Step 1 above was used as a starting material and treated in the same way as in Step 2 of Example 1 to give 730 mg (93%) of the title compound as a pale yellow solid.

MS (ESI) m/z: 785 $(M+H)^+$.

Step 3

(3'R, 4'S,5'R)-6"-chloro-4'-(2-chloro-3-fluoropyridin-4-yl)-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide The compound (710 mg, 0.90 mmol) obtained in Step 2 above was used as a starting material and treated in the same way as in Step 3 of Example 14 to give 357 mg (67%) of the title compound as a colorless solid.

$^1$H-NMR (400 MHz, $CD_3OD$) δ: 0.68 (3H, s), 0.94 (3H, 3), 1.09-1.24 (2H, m), 1.28-1.42 (5H, m), 1.50-1.63 (2H, m), 1.74-1.82 (3H, m), 1.85-2.02 (4H, m), 3.51-3.65 (2H, m), 4.53 (1H, d, J=9.2 Hz), 4.65 (1H, d, J=9.2 Hz), 6.76 (14, d, J=1.8 Hz), 7.06 (1H, dd, J=8.0, 2.1 Hz), 7.45 (1H, dd, J=8.3, 2.3 Hz), 7.66 (1H, t, J=5.0 Hz), 8.06 (1H, d, J=5.0 Hz).

MS (ESI) m/z: 589 $(M+H)^+$.

Example 17

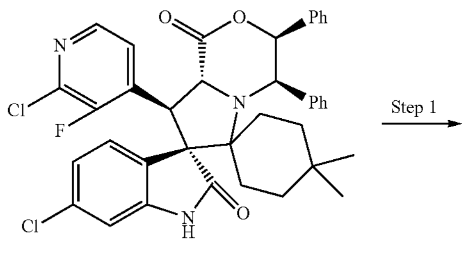

-continued

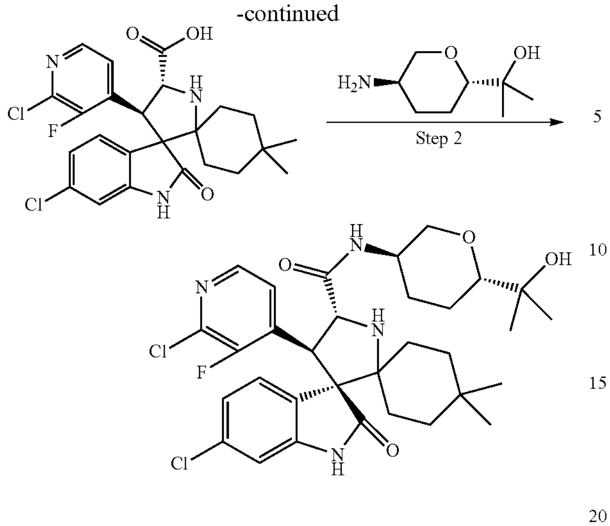

Step 1

(4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylic acid The compound (630 mg, 0.94 mmol) obtained in Step 1 of Example 16 was dissolved in acetonitrile (10 ml) and water (4 ml), potassium carbonate (130 mg, 0.94 mmol) was added and the resulting mixture was heated to reflux at 85° C. for 16 hours. After cooling, anhydrous magnesium sulfate (113 mg, 0.94 mmol) was added and the resulting mixture was stirred at room temperature for 15 minutes. After extraction with ethyl acetate, the organic layer was washed with brine and dried over anhydrous magnesium sulfate. The solvent was evaporated under reduced pressure to give (4'S,5'R)-6"-chloro-4'-(2-chloro-3-fluoropyridin-4-yl)-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-5'-carboxylic acid (650 mg, 100%) as a pale orange amorphous solid [MS (ESI) m/z: 688 $(M+H)^+$.]. The carboxylic acid (650 mg, 0.94 mmol) obtained was dissolved in methanol (30 ml) and water (8 ml), cerium (IV) diammonium nitrate (1.55 g, 2.82 mmol) was added under ice cooling and the resulting mixture was stirred at the same temperature for 30 minutes. Potassium carbonate (780 mg, 5.64 mmol) was added under ice cooling and the resulting mixture was stirred at the same temperature for 1 hour. Insoluble matter was removed by filtration through celite, then the filtrate was concentrated under reduced pressure and water was added to the residue obtained, followed by extraction with ethyl acetate. The organic layer was washed with brine and dried over anhydrous sodium sulfate. The solvent was evaporated under reduced pressure and the residue obtained was purified by silica gel column chromatography [chloroform:methanol=20:1→4:1 (v/v)] to give 152 mg (33%) of the title compound as a colorless solid.

$^1$H-NMR (500 MHz, $CD_3OD$) δ: 0.74 (3H, s), 0.9 (3H, s), 1.29-1.44 (2H, m), 1.48-1.58 (2H, m), 1.64-1.76 (1H, m), 1.94-2.02 (1H, m), 2.11 (1H, ddd, J=14.0, 14.0, 4.0 Hz), 2.43-2.53 (1H, m), 5.07 (1H, d, J=10.3 Hz), 5.32 (1H, d, J=10.3 Hz), 6.84 (1H, d, J=1.7 Hz), 7.16 (1H, dd, J=8.3, 2.0 Hz), 7.63 (1H, dd, 0=8.0, 2.3 Hz), 7.75 (1H, t, J=5.2 Hz), 8.15 (1H, d, J=5.2 Hz).

MS (ESI) m/z: 492 $(M+H)^+$.

Step 2

(3'R, 4'S,5'R)-6"-chloro-4'-(2-chloro-3-fluoropyridin-4-yl)-N-[(3R,6S)-6-(1-hydroxy-1-methylethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (70 mg, 0.14 mmol) obtained in Step 1 above and the compound (34 mg, 0.21 mmol) obtained in Step 2 of Reference Example 5 were used as starting materials and treated in the same way as in Step 2 of Example 12 to give 38 mg (42%) of the title compound as a colorless solid.

$^1$H-NMR (400 MHz, $CD_3OD$) δ: 0.68 (3H, s), 0.95 (3H, s), 1.09-1.24 (8H, m), 1.29-1.39 (1H, m), 1.44-1.63 (4H, m), 1.74-1.88 (4H, m), 2.05-2.13 (1H, m), 3.07-3.19 (2H, m), 3.71-3.81 (1H, m), 3, 93-4.00 (1H, m); 4.54, (1H, d, J=9.2 Hz), 4.67 (1H, d, J=9.2 Hz), 6.75-6.78 (1H, m), 7.07 (1H, dd, J=8.2, 1.8 Hz), 7.43-7.48 (1H, m), 7.65 (1H, t, J=5.0 Hz), 8.05 (1H, d, J=5.0 Hz).

MS (ESI) m/z: 633 $(M+H)^+$.

Example 18

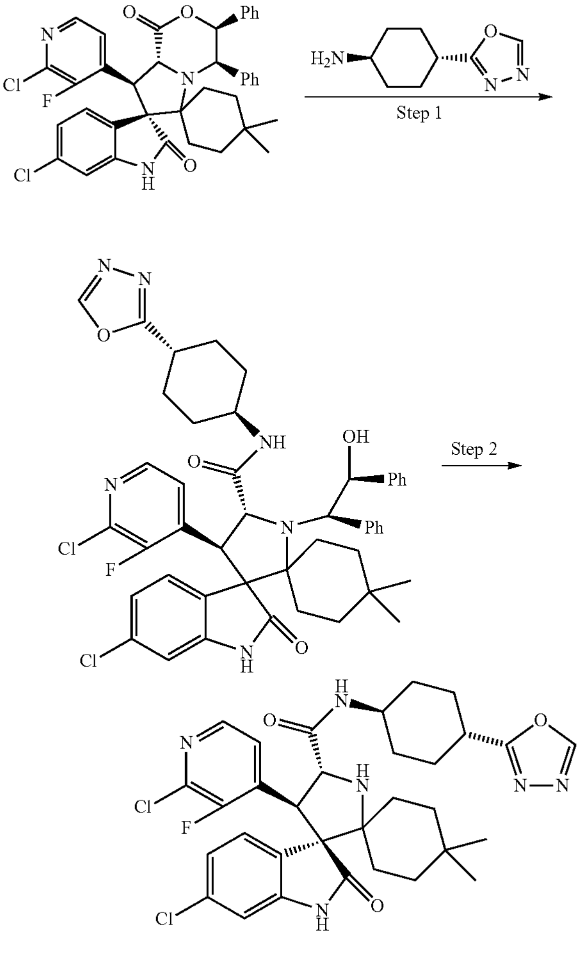

Step 1

(4'S,5'R)-6"-chloro-4'-(2-chloro-3-fluoropyridin-4-yl)-1'-[(1R,2S)-2-hydroxy-1,2-diphenylethyl]-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-indole]-5'-carboxamide The compound (180 mg, 0.27 mmol) obtained in Step 1 of Example 16 and the compound (154 mg, 0.92 mmol) obtained in Step 3 of Reference Example 3 were used as starting materials and treated in the same way as in Step 1 of Example 5 to give 134 mg of the title compound as a pale yellow amorphous solid.

MS (ESI) m/z: 837 $(M+H)^+$.

Step 2

(3'R, 4'S,5'R)-6"-chloro-4'-(2-chloro-3-fluoropyridin-4-yl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-indole]-5'-carboxamide The compound (134 mg, 0.16 mmol) obtained in Step 1 above was used as a starting material and treated in the same way as in Step 3 of Example 1 to give 73 mg (448) of the title compound as a pale yellow solid.

$^1$H-NMR (500 MHz, $CDCl_3$) δ: 0.68 (3H, s), 0.96 (3H, s), 1.12-1.27 (2H, m), 1.31-1.44 (3H, m), 1.45-1.54 (2H, m), 1.58-1.82 (5H, m), 2.10-2.29 (4H, m), 2.92-3.00 (1H, m), 3.18-3.44 (1H, m), 3.74-3.84 (1H, m), 4.45 (1H, d, J=8.9 Hz), 4.66 (1H, d, J=8.9 Hz), 6.73 (1H, d, J=1.7 Hz), 7.06 (1H, dd, J=8.0, 1.7 Hz), 7.32 (1H, dd, J=8.3, 2.0 Hz), 7.51 (1H, t, J=5.2 Hz), 7.61, (1H, d, J=8.3 Hz), 7.74 (1H, s), 8.04 (1H, d, J=5.2 Hz), 8.34 (1H, s).

MS (ESI) m/z: 641 $(M+H)^+$.

Example 19

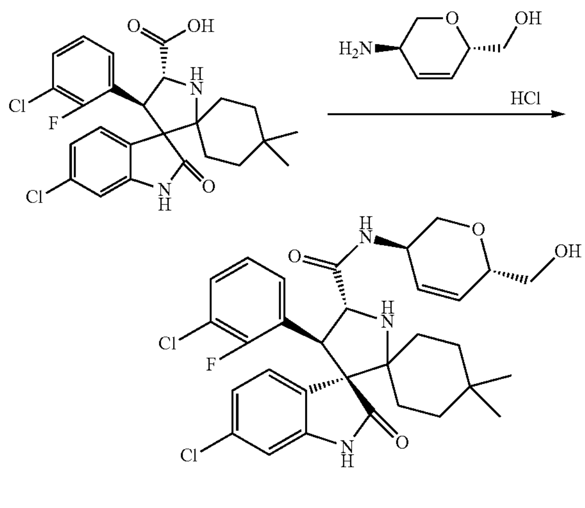

(3'R,4'S,5'R)-6"-chloro-4'-(3-chloro-2-fluorophenyl)-N-[(3R,6S)-6-(hydroxymethyl)-3,6-dihydro-2H-pyran-3-yl]-4,4-dimethyl-2"-oxo-1",2"-dihydrodispiro[cyclohexane-1,2'-pyrrolidine-3',3"-indole]-5'-carboxamide The compound (60 mg, 0.12 mmol) obtained in Step 1 of Example 12 and the compound obtained in Step 2 of Reference Example 9 were used as starting materials and treated in the same way as in Step 2 of Example 12 to give 59 mg (81%) of the title compound as a colorless solid.

$^1$H-NMR (400 MHz, $CDCl_3$) δ: 0.68 (3H, s), 0.92 (3H, s), 1.13-1.21 (2H, m), 1.29-1.35 (1H, m), 1.47-1.67 (3H, m), 1.73-1.78 (2H, m), 2.00 (1H, t, J=6.1 Hz), 3.26 (1H, br s), 3.48 (1H, dd, J=11.2, 6.3 Hz), 3.65 (2H, t, J=5.9 Hz), 4.10 (1H, dd, J=11.4, 4.8 Hz), 4.25-4.29 (1H, m), 4.45-4.52 (2H, m), 4.70 (1H, d, J=9.0 Hz), 5.84 (1H, dt, J=10.3, 1.7 Hz), 5.90 (1H, dt, J=10.0, 2.6 Hz), 6.69 (1H, d, J=1.7 Hz), 6.92 (1H, t, J=8.1 Hz), 7.05 (1H, dd, J=8.2, 1.8 Hz), 7.11-7.15 (1H, m), 7.33-7.36 (2H, m), 7.51 (1H, t, J=6.6 Hz), 7.79 (1H, d, J=9.0 Hz).

MS (ESI) m/z: 602 $(M+H)^+$.

Example 20

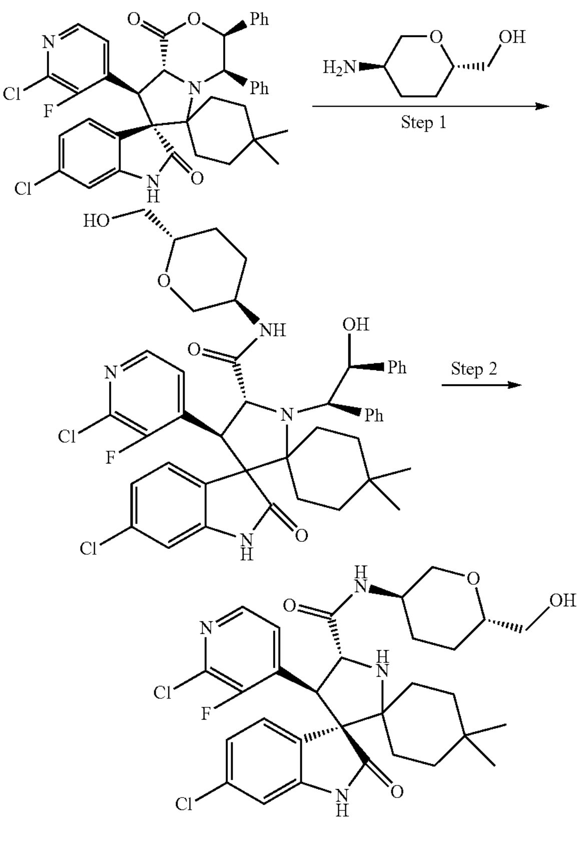

Step 1

(4'S,5'R)-6"-chloro-4'-(2-chloro-3-fluoropyridin-4-yl)-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5-carboxamide The compound (131 mg, 1.00 mmol) obtained in Step 3 of Reference Example 2 and triethylamine (0.14 mi, 1.00 mmol) were added to a methanol (4 ml) solution of the compound (268 mg, 0.40 mmol) obtained in Step 1 of Example 16 and the resulting mixture was stirred at 50° C. for 5 days. After cooling, saturated ammonium chloride solution was added, followed by extraction with ethyl acetate. The organic layer was washed with brine and then dried over anhydrous sodium sulfate. The solvent was evaporated under reduced pressure and the residue was purified by silica gel column chromatography [chloroform: methanol=100:0→30:1 (v/v)] to give 288 mg (89%) of the title compound as a colorless amorphous solid.

$^1$H-NMR (400 MHz, $CDCl_3$) δ: 0.86 (3H, s), 1.05 (3H, s), 1.12-1.18 (1H, m), 1.26-1.29 (1H, m), 1.41-1.48 (2H, m), 1.58-1.68 (5H, m), 2.05 (1H, d, J=9.6 Hz), 2.22-2.32 (2H, m), 2.61 (1H, t, J=10.5 Hz), 2.83 (1H, d, J=14.2 Hz), 3.26 (1H, s), 3.48-3.51 (1H, m), 3.56-3.58 (1H, m), 3.63 (1H, d, J=10.5 Hz), 3.82-3.84 (1H, m), 3.89-3.91 (1H, m), 4.58 (1H, d, J=10.5 Hz), 4.86 (1H, s), 4.97-5.01 (2H, m), 5.53 (1H, s), 6.40 (1H, t, J=4.6 Hz), 6.79 (1H, s), 6.93 (1H, d, J=7.8 Hz), 6.98 (1H, d, J=8.2 Hz), 7.04-7.07 (1H, m), 7.12-7.13 (4H, m), 7.21-7.23 (3H, m), 7.42 (28, s), 7.67 (1H, s), 7.75 (1H, d, J=5.0 Hz).

Step 2

(3'R, 4'S,5'R)-6"-chloro-4'-(2-chloro-3-fluoropyridin-4-yl)-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-S'-carboxamide The compound (288 mg, 0.36 mmol) obtained in Step 1 above was used as a starting material and treated in the same way as in Step 3 of Example 1 to give 140 mg (65%) of the title compound as a colorless solid.

$^1$H-NMR (400 MHz, $CD_3OD$) δ: 0.68 (3H, s), 0.95 (3H, s), 1.15-1.21 (2H, m), 1, 33-1.35 (1H, m); 1.43-1.48 (1H, m); 1.56-1.59 (3H, m), 1.76-1.79 (4H, m), 2.06 (1H, d, J=11.9 Hz), 3.17 (1H, t, J=10.8 Hz), 3.37-3.40 (1H, m), 3.49 (2H, d, J=5.5 Hz), 3.77-3.80 (1H, m), 3.93 (1H, dd, J=9.8, 3.9 Hz), 4.54 (1H, d, J=8.7 Hz), 4.67 (1H, d, J=9.2 Hz), 6.77 (1H, d, J=1.8 Hz), 7.05-7.07 (1H, m), 7.46 (1H, dd, J=8.2, 2.3 Hz), 7.65 (1H, t, J=5.0 Hz), 8.05 (1H, d, J=5.0 Hz).

MS (ESI) m/z; 605 $(M+H)^+$.

Example 21

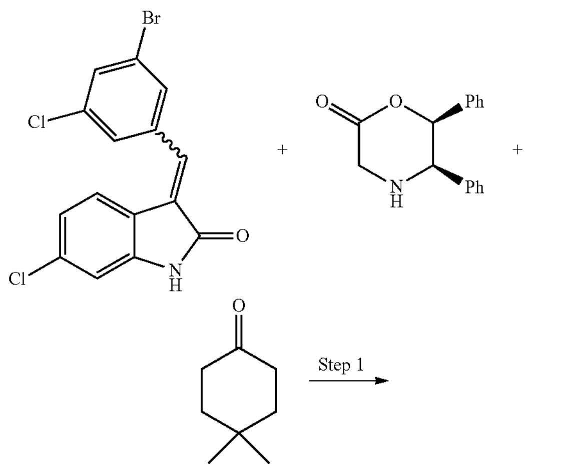

-continued

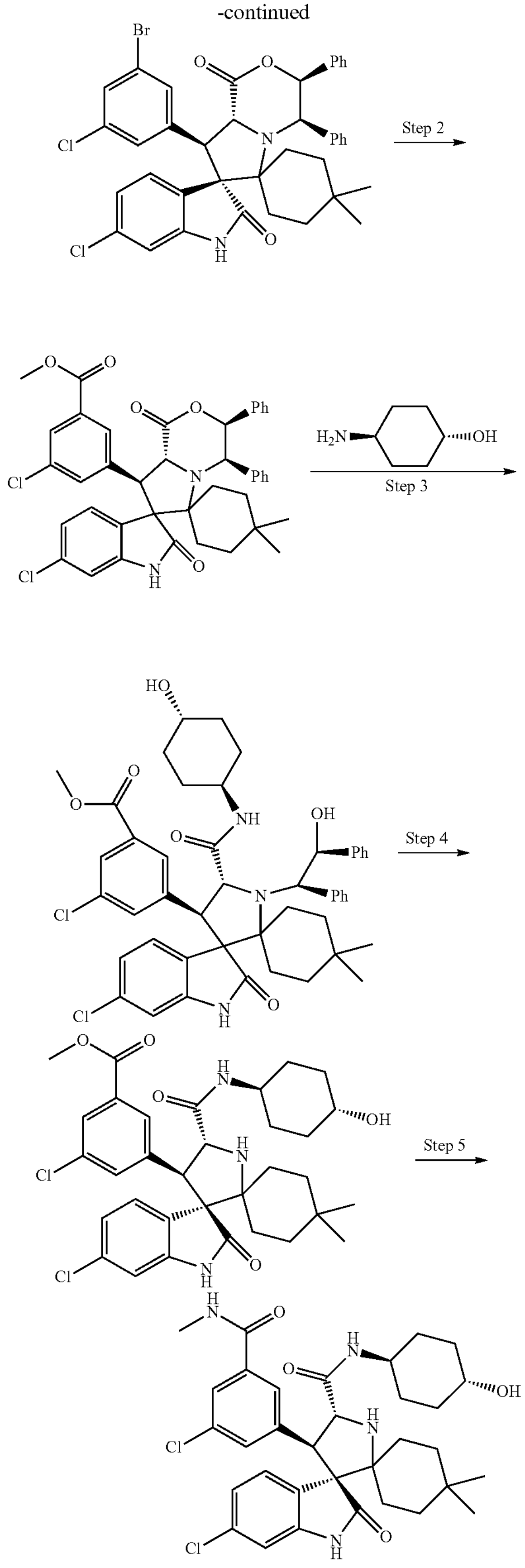

Step 1

(3'S,4'R, 7'S,8'R, 8a'R)-8'-(3-bromo-5-chlorophenyl)-6"-chloro-4,4-dimethyl-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione The compound (4.25 g, 11.5 mmol) obtained in Reference Example 10 was used as a starting material and treated in the same way as in Step 1 of Example 9 to give 3.44 g (41%) of the title compound as a yellow solid.

$^1$H-NMR (400 MHz, $CDCl_3$) δ: 0.49 (3H, s), 0.65 (3H, s), 0.83-0.93 (1H, m), 1.12-1.29 (3H, m), 1.34-1.44 (1H, m), 1.74-1.84 (2H, m), 2.14-2.25 (1H, m), 4.39 (1H, d, J=11.0 Hz), 4.80 (1H, d, J=3.7 Hz), 5.00 (1H, d, J=11.0 Hz), 6.62-6.68 (1H, m), 6.70-6.74 (1H, m), 6.79-6.85 (2H, m), 6.88-6.94 (2H, m), 6.99-7.03 (1H, m), 7.07-7.19 (6H, m), 7.20-7.25 (3H, m), 7.28-7.30 (1H, m), 7.48 (1H, s).

MS (FAB) m/z: 729 $(M+H)^+$.

Step 2

Methyl 3-chloro-5-[(3'S,4'R, 8'R, 8a'R)-6"-chloro-4,4-dimethyl-1',2"-dioxo-3',4'-diphenyl-1",2",3',4',8',8a'-hexahydro-1'H-dispiro[cyclohexane-1,6'-pyrrolo[2,1-c][1,4]oxazine-7',3"-indole]-8'-yl]benzoate The compound (3.14 g, 4.30 mmol) obtained in Step 1 above was dissolved in dimethyl sulfoxide (40 ml) and methanol (40 ml), triethylamine (0.71 ml, 5.16 mmol) and a 1,1'-bis(diphenylphosphino) ferrocene-palladium (II) dichloride dichloromethane complex (351 mg, 0.43 mmol) were added and the resulting mixture was stirred under heating at 90° C. for 2 days under carbon monoxide atmosphere. Saturated sodium bicarbonate solution was added to the reaction mixture, followed by extraction with ethyl acetate. The organic layer was washed with brine and then dried over anhydrous sodium sulfate. The solvent was evaporated under reduced pressure and the residue was purified by silica gel column chromatography [n-hexane: ethyl acetate=1:1 (v/v)] to give 0.40 q (13%) of the title compound as a yellow solid.

MS (FAB) m/z: 709 $(M+H)^+$.

Step 3

Methyl 3-chloro-5-(4'R, 5'R)-6"-chloro-5'-[(trans-4-hydroxycyclohexyl) carbamoyl]-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-4'-yl)benzoate The compound (312 mg, 0.44 mmol) obtained in Step 2 above was used as a starting material and treated in the same way as in Step 2 of Example 1 to give 302 mg (838) of the title compound as a pale yellow solid.

MS (FAB) m/z: 824 $(M+H)^+$.

Step 4

Methyl 3-chloro-5-{(3'R, 4'R, 5'R)-6"-chloro-5-[(trans-4-hydroxycyclohexyl) carbamoyl]-4,4-dimethyl-2"-oxo-1",2"-dihydrodispiro[cyclohexane-1,2'-pyrrolidine-3',3"-indole]-4'-yl}benzoate The compound (301 mg, 0.37 mmol) obtained in Step 3 above was used as a starting material and treated in the same way as in Step 3 of Example 1 under ice cooling to give 104 mg (45%) of the title compound as a colorless solid.

$^1$H-NMR (400 MHz, $CDCl_3$) δ: 0.68 (3H, s), 0.94 (38, s), 1.11-1.55 (10H, m), 1.59-1.80 (2H, m), 1.93-2.06 (4H, m), 3.26 (1H, s), 3.60-3.75 (2H, m), 3.82 (3H, s), 4.17 (1H, d, J=8.6 Hz), 4.52 (1H, d, J=8.6 Hz), 6.73 (1H, d, J=2.3 Hz), 7.10 (1H, dd, J=8.0, 1.7 Hz), 7.20-7.26 (1H, m), 7.28-7.33 (2H, m), 7.53-7.58 (1H, m), 7.63 (1H, br s), 7.72-7.77 (1H, m).

MS (ESI) m/z: 628 $(M+H)^+$.

Step 5

(3'R, 4'R, 5'R)-6"-chloro-4'-[3-chloro-5-(methylcarbamoyl)phenyl]-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide 1N sodium hydroxide solution (0.19 ml, 0.19 mmol) was added to a methanol (4 ml) solution of the compound (81 mg, 0.13 mmol) obtained in Step 4 above and the resulting mixture was stirred at 50° C. for 4 hours. The reaction mixture was neutralized by addition of 1N hydrochloric acid and then the resulting mixture was concentrated under reduced pressure. Dichloromethane (4 ml) was added to the residue, then methylamine hydrochloride (26 mg, 0.39 mmol), triethylamine (0.11 ml, 0.77 mmol), and 1-ethyl-3-(3-dimethylaminopropyl) carbodiimide hydrochloride (74 mg, 0.39 mmol) were added and the resulting mixture was stirred at room temperature for 24 hours. Saturated sodium bicarbonate solution was added to the reaction mixture, followed by extraction with ethyl acetate. The organic layer was washed with brine and then dried over anhydrous sodium sulfate. The solvent was evaporated under reduced pressure and then the residue was purified by NH-silica gel column chromatography [methanol:ethyl acetate=5:95 (v/v)] to give 42 mg (528) of the title compound as a colorless solid.

$^1$H-NMR (500 MHz, $CD_3OD$) δ: 0.69 (3H, s), 0.94 (3H, =), 1.08-1.24 (2H, m), 1.27-1.45 (5H, m), 1.48-1.63 (2H, m), 1.72-1.85 (3H, m), 1.87-2.02 (4H, m), 2.85 (3H, s), 3.51-3.67 (2H, m), 4.21 (1H, d, J=9.2 Hz), 4.62 (1H, d, J=9.2 Hz), 6.74 (1H, d, J=1.7 Hz), 7.09 (1H, dd, J=8.0, 2.3 Hz), 7.23-7.26 (1H, m), 7.51 (1H, d, J=8.0 Hz), 7.53-7.56 (2H, m).

MS (ESI) m/z: 627 $(M+H)^+$.

Example 22

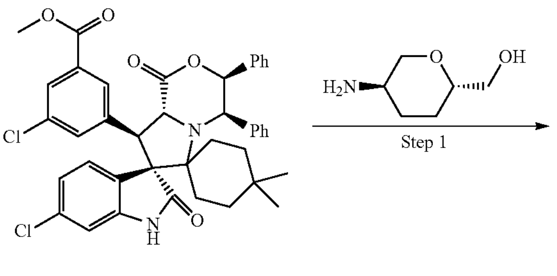

-continued

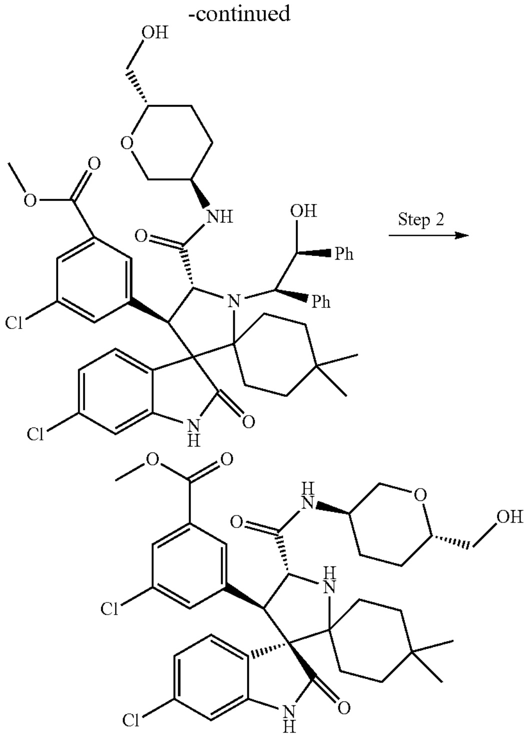

Step 1

1,5-Anhydro-2-[((4'R, 5'R)-6"-chloro-4'-[3-chloro-5-(methoxycarbonyl)phenyl]-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indol]-5'-yl)carbonyl)amino]-2,3,4-trideoxy-D-erythro-hexitol The compound (253 mg, 2.20 mmol) obtained in Step 3 of Reference Example 2 was added to a sulfolane (9 ml) solution of the compound (1.27 g, 1.79 mmol) obtained in Step 2 of Example 21 and the resulting mixture was stirred under heating at 70° C. for 28 hours. Saturated sodium bicarbonate solution was added to the reaction mixture, followed by extraction with ethyl acetate. The organic layer was washed with brine and then dried over anhydrous sodium sulfate. The solvent was evaporated under reduced pressure and the residue was purified by silica gel column chromatography [n-hexane:ethyl acetate=1:1 (v/v)] to give 511 mg (34%) of the title compound as a pale yellow solid.

MS (FAB) m/z: 840 $(M+H)^+$.

Step 2

1,5-Anhydro-2-[({(3'R, 4'R, 5'R)-6"-chloro-4'-[3-chloro-5-(methoxycarbonyl)phenyl]-4,4-dimethyl-2"-oxo-1",2"-dihydrodispiro[cyclohexane-1,2'-pyrrolidine-3',3"-indole]-5'-yl}carbonyl)amino]-2,3,4-trideoxy-D-erythro-hexitol The compound (498 mg, 0,592 mmol) obtained in Step 1 above was used as a starting material and treated in the same way as in Step 3 of Example 1 to give 252 mg (66%) of the title compound as a colorless solid.

$^1H$-NMR (400 MHz, $CD_3OD$) δ: 0.69 (3H, s), 0.95 (3H, s), 1.11-1.23 (2H, m), 1.26-1.49 (2H, m), 1.50-1.68 (3H, m), 1.71-1.87 (4H, m), 2.01-2.11 (1H, m), 3.10-3.24 (1H, m), 3.34-3.43 (1H, m), 3.44-3.54 (2H, m), 3.72-3.80 (1H, m), 3.83 (3H, s), 3.92-4.00 (1H, m), 4.26 (1H, d, J=9.2 Hz), 4.59 (1H, d, J=Hz), 7.38-7.43 (1H, m), 7.53 (1H, d, J=8.3 Hz), 7.64-7.69 (1H, m), 7.70-7.74 (1H, m).

MS (ESI) m/z: 644 $(M+H)^+$.

Example 23

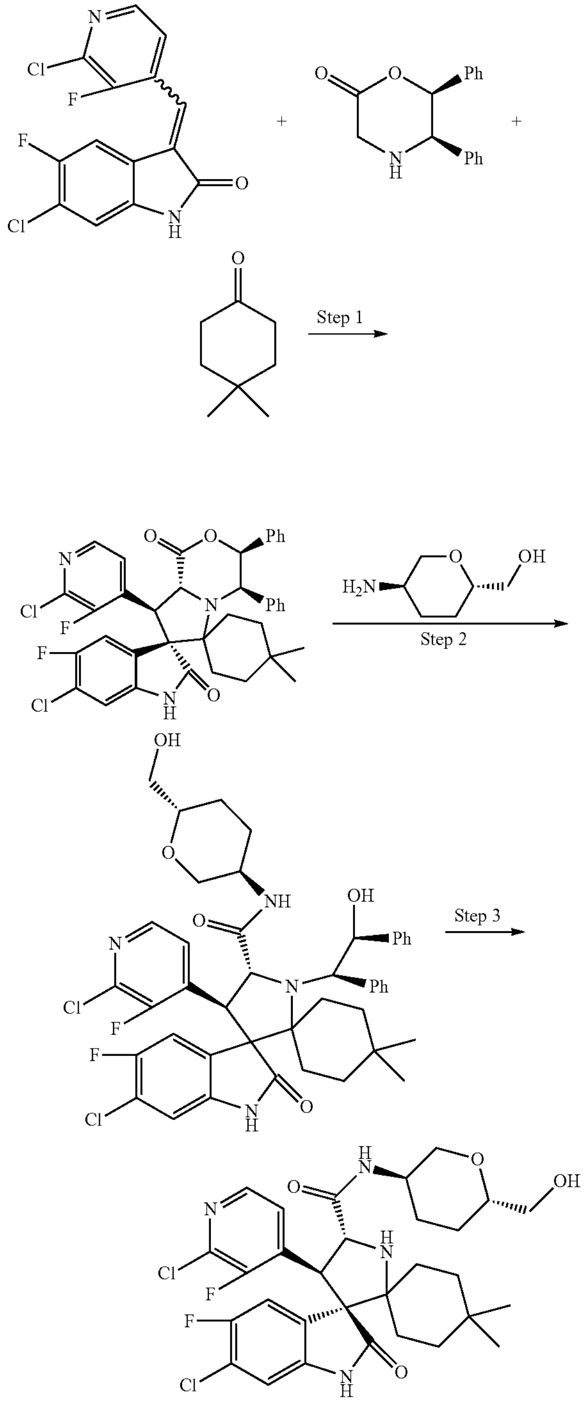

Step 1

(3'S,4'R, 7'S,8'S,8a'R)-6"-chloro-8'-(2-chloro-3-fluoropyridin-4-yl)-5"-fluoro-4,4-dimethyl-3',4'-diphenyl-3', 4',8',8a'-tetrahydro-1'H-dispiro[cyclohexane-1,6'=pyrrolo[2,1-c][1,4]oxazine-7',3"-indole]-1',2" (1"A)-dione The compound (981 mg, 3.0 mmol) obtained in Reference Example 11 was used as a starting material and treated in the same way as in Step 1 of Example 9 to give 1.20 g (58%) of the title compound as a pale pink solid.

$^1$H-NMR (400 MHz, $CDCl_3$) δ: 0.22 (3H, s), 0.55 (3H, s), 0.97-1.00 (3H, m), 1, 29-1.38 (3H, m), 1.74 (1H, d, J=11.4 Hz), 2.27 (1H, d, J=11.4 Hz), 4.58 (1H, d, J=11.4 Hz), 4.83 (1H, d, J=2.7 Hz), 5.26 (1H, d, J=11.4 Hz), 6.20 (1H, d, J=8.7 Hz), 6.74 (2H, d, J=7.3 Hz), 6.93 (1H, d, J=5.0 Hz), 7.05-7.07 (3H, m), 7.11-7.16 (3H, m), 7.21-7.22 (3H, m), 7.42 (1H, s), 7.76 (1H, t, J=4.8 Hz), 8.32 (1H, d, J=5.0 Hz).

Step 2

(4'S,5'R)-6"-chloro-4'-(2-chloro-3-fluoropyridin-4-yl)-5"-fluoro-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (275 mg, 0.40 mmol) obtained in Step 1 above and the compound (131 mg, 1.00 mmol) obtained in Step 3 of Reference Example 2 were used as starting materials and treated in the same way as in Step 1 of Example 22 to give 205 mg (62%) of the title compound as a pale yellow amorphous solid.

MS (ESI) m/z: 810 $(M+H)^+$.

Step 3

(3'R, 4'S,5'R)-6"-chloro-4'-(2-chloro-3-fluoropyridin-4-yl)-5"-fluoro-N-[(3R,6S)-6-(hydroxymethyl) tetrahydro-2H-pyran-3-yl]-4,4-dimethyl-2"-oxo-1", 2"-dihydrodispiro[cyclohexane-1,2'-pyrrolidine-3', 3"-indole]-5'-carboxamide The compound (205 mg, 0.25 mmol) obtained in Step 2 above was used as a starting material and treated in the same way as in Step 3 of Example 1 to give 73 mg (578) of the title compound as a colorless solid.

$^1$H-NMR (400 MHz, $CD_3OD$) δ: 0.70 (3H, s), 0.95 (3H, s); 1.12-1.22 (2H, m), 1.38-1.46 (2H, m), 1.57-1.63 (3H, m), 1.71-1.84 (4H, m), 2.07 (1H, d, J=11.4 Hz), 3.17 (1H, t, J=10.5 Hz), 3.39 (1H, dd, J=11.0, 5.0 Hz), 3.50 (2H, d, J=5.0 Hz), 3.74-3.82 (1H, m), 3.93 (1H, dd, J=11, 0, 4.6 Hz), 4.55 (1H, d, J=9.2 Hz), 4.67 (1H, d, J=9.2 Hz), 6.83 (1H, d, J=6.4 Hz), 7.48 (1H, dd, J=9.2, 1.8 Hz), 7.65 (1H, t, J=5.0 Hz), 8.06 (1H, d, J=5.0 Hz).

MS (ESI) m/z: 623 $(M+H)^+$.

Example 24

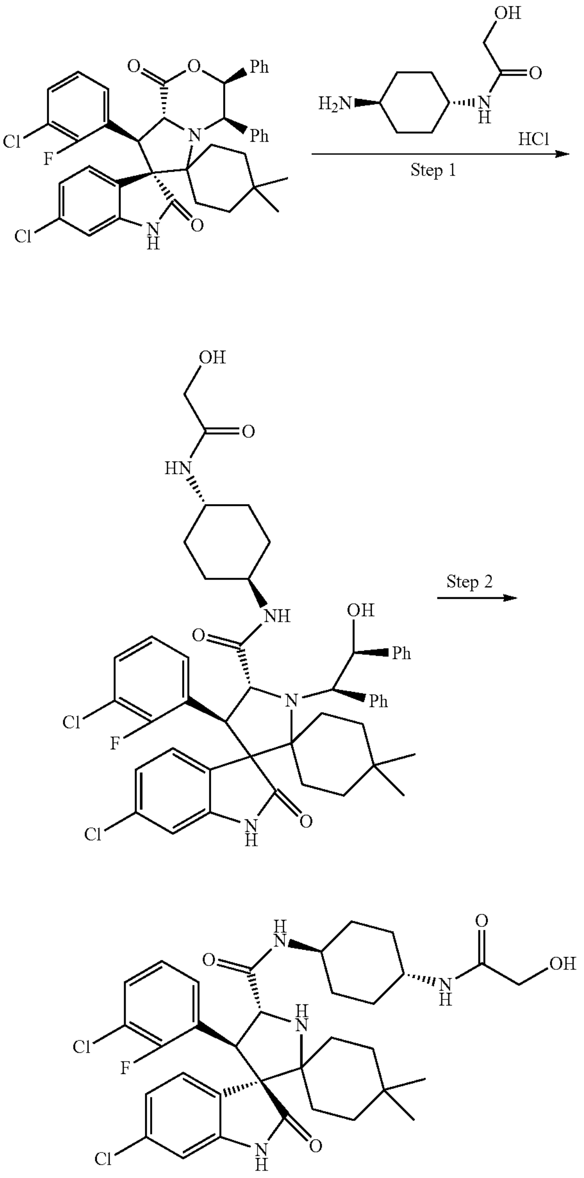

Step 1

(4'S,5'R)-6"-chloro-4'-(3-chloro-2-fluorophenyl)-N-{trans-4-[(hydroxyacetyl)amino]cyclohexyl}-1'-[(1R,2S)-2-hydroxy-1,2-diphenylethyl]-4,4-dimethyl-2"-oxo-1",2"-dihydrodispiro[cyclohexane-1,2'-pyrrolidine-3',3"-indole]-5'-carboxamide The compound (150 mg, 0.22 mmol) obtained in Step 1 of Example 1 and N-(trans-4-aminocyclohexyl)-2-hydroxyacetamide hydrochloride (331 mg, 1.23 mmol) were used as starting materials and treated in the same way as in Step 1 of Example 20 to give 58 mg (31%) of the title compound as a colorless solid.

MS (ESI) m/z: 841 $(M+H)^+$.

Step 2

(3'R, 4'S,5'R)-6"-chloro-4'-(3-chloro-2-fluorophenyl)-N-{trans-4-[(hydroxyacetyl)amino]cyclohexyl}-4,4-dimethyl-2"-oxo-1",2"-dihydrodispiro[cyclohexane-1,2'-pyrrolidine-3',3"-indole]-5'-carboxamide The compound (58 mg, 0.07 mmol) obtained in Step 1 above was used as a starting material and treated in the same way as in Step 3 of Example 1 to give 18 mg (40%) of the title compound as a colorless solid.

$^1$H-NMR (400 MHz, $CD_3OD$) δ: 0.68 (3H, s), 0.95 (3H, s), 1.07-1.65 (10H, m), 1.74-2.03 (6H, m), 3.55-3.81 (2H, m), 3.94 (2H, s), 4.49 (1H, d, J=9.2 Hz), 4.67 (1H, d, J=9.2 Hz), 6.73 (1H, d, J=1.8 Hz), 6.99-7.07 (2H, m), 7.16-7.23 (1H, m), 7.39-7.46 (1H, m), 7.57-7.65 (1H, m).

MS (ESI) m/z: 645 $(M+H)^+$.

Example 25

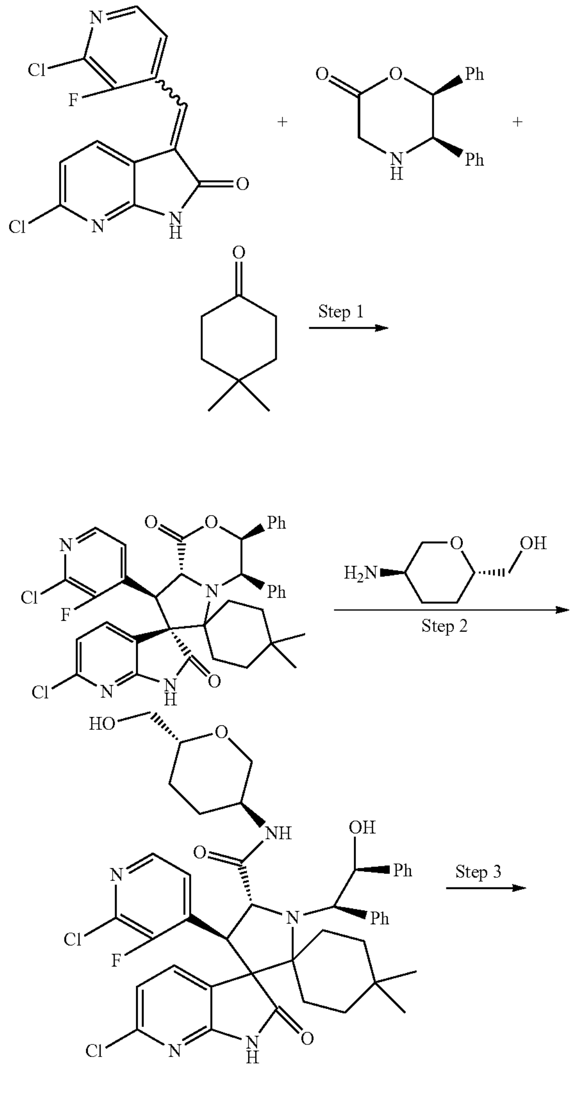

-continued

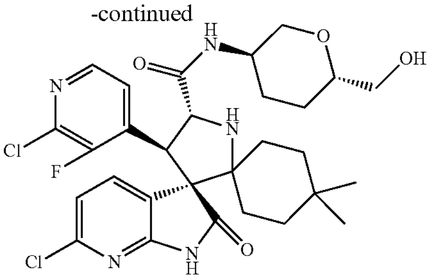

Step 1

(3'S,4'R, 7'S,8'S,8a'R)-6"-chloro-8'-(2-chloro-3-fluoropyridin-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-pyrrolo[2,3-b]pyridine]-1',2" (1"H)-dione The compound (1.46 g, 4.71 mmol) obtained in Reference Example 12 was used as a starting material and treated in the same way as in Step 1 of Example 9 to give 1.90 g (60%) of the title compound as a pale red solid.

$^1$H-NMR (500 MHz, $CDCl_3$) δ: 0.21 (3H, s), 0.55 (3H, s), 0.93-1.07 (3H, m), 1.22-1.30 (1H, m), 1.33-1.42 (2H, m), 1.72-1.79 (2H, m), 2.24-2.31 (1H, m), 4.58 (1H, d, J=11.5 Hz), 4.84 (1H, d, J=3.4 Hz), 5.29 (JH, d, J=11.5 Hz), 6.53 (1H, d, J=8.0 Hz), 6.69 (1H, d, J=7.5 Hz), 6.71-6.75 (2H, m), 7.04-7.08 (3H, m), 7.09-7.18 (3H, m), 7.19-7.25 (3H, m), 7.76-7.82 (1H, m), 8.16 (1H, s), 8.32 (1H, d, J=4.6 Hz).

Step 2

(4'S,5'R)-6"-chloro-4'-(2-chloro-3-fluoropyridin-4-yl)-1'-[(1R,2S)-2-hydroxy-1,2-diphenylethyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (204 mg, 0.30 mmol) obtained in Step 1 above and the compound (120 mg, 0.91 mmol) obtained in Step 3 of Reference Example 2 were used as starting materials and treated in the same way as in Step 1 of Example 5 to give 1.36 mg of the title compound as a brownish red amorphous solid of a mixture of isomers.

MS (ESI) m/z: 802 $(M+H)^+$.

Step 3

(3'R, 4'S,5'R)-6"-chloro-4'-(2-chloro-3-fluoropyridin-4-yl)-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (136 mg, 0.17 mmol) obtained in Step 2 above was used as a starting material and treated in the same way as in Step 3 of Example 1 to give 59 mg (32%) of the title compound as a pale yellow solid.

$^1$H-NMR (500 MHz, $CDCl_3$) δ: 0.70 (3H, s), 0.96 (3H, s), 1.13-1.28 (2H, m), 1.33-1.76 (8H, m), 1.99-2.13 (2H, m), 3.13 (1H, t, J=10.9 Hz), 3.39-3.47 (1H, m), 3.51-3.58 (1H, m); 3.59-3.66 (1H, m), 3.84-3.94 (1H, m), 4.04-4.11 (1H, m), 4.45 (1H, d, J=9.2 Hz), 4.66 (1H, d, J=9.2 Hz), 7.07 (1H, d, J=7.5 Hz, 7.40 (1H, d, J=8.6 Hz), 7.45 (1H, t, J=4.9 Hz), 7.61 (1H, dd, J=7.5, 2.3 Hz), 7.97 (1H, br s), 8.09 (1H, d, J=5.2 Hz),

MS (ESI) m/z: 606 $(M+H)^+$.

Example 26

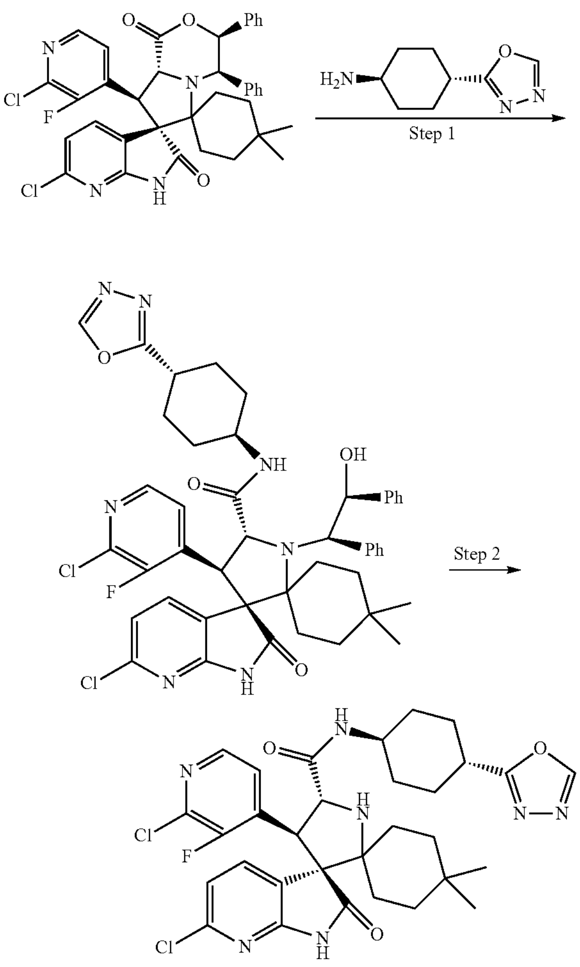

Step 1

(4'S,5'R)-6"-chloro-4'-(2-chloro-3-fluoropyridin-4-yl)-1'-[(1R,2S)-2-hydroxy-1,2-diphenylethyl]-4,4-dimethyl-N-[trans-4-(1,3,4-oxadiazol-2-yl)cyclohexyl]-2"-oxo-1",2'-dihydrodispiro[cyclohexane-1,2'-pyrrolidine-3',3"-pyrrolo[2,3-b]pyridine]-5'-carboxamide The compound (202 mg, 0.30 mmol) obtained in Step 1 of Example 25 and the compound (176 mg, 1.05 mmol) obtained in Step 3 of Reference Example 3 were used as starting materials and treated in the same way as in Step 1 of Example 5 to give 142 mg of the title compound as a brown amorphous solid.

MS (ESI) m/z: 838 $(M+H)^+$.

Step 2

(3'R, 4'S,5'R)-6"-chloro-4'-(2-chloro-3-fluoropyridin-4-yl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-pyrrolo[2,3-b]pyridine]-5'-carboxamide The compound (142 mg, 0.17 mmol) obtained in Step 1 above was used as a starting material and treated in the same way as in Step 3 of Example 1 to give 72 mg (378) of the title compound as a pale yellow solid.

$^1$H-NMR (400 MHz, $CDCl_3$) δ: 0.70 (3H, s), 0.97 (3H, s), 1.14-1.29 (2H, m), 1.31-1.44 (3H, m), 1.46-1.55 (2H, m), 1.57-1.82 (5H, m), 2.09-2.29 (4H, m), 2.92-3.00 (1H, m), 3.17-3.40 (1H, m), 3.74-3.83 (1H, m), 4.47 (1H, d, J=8.9 Hz), 4.68 (1H, d, J=8.9 Hz), 7.07 (1H, d, J=7.5 Hz), 7.48 (1H, t, J=4.9 Hz), 7.53 (1H, d, J=8.6 Hz), 7.63 (1H, dd, J=8.0, 2.3 Hz), 8.08 (1H, d, J=5.2 Hz), 8.30-8.38 (2H, m).

MS (ESI) m/z: 642 $(M+H)^+$.

Example 27

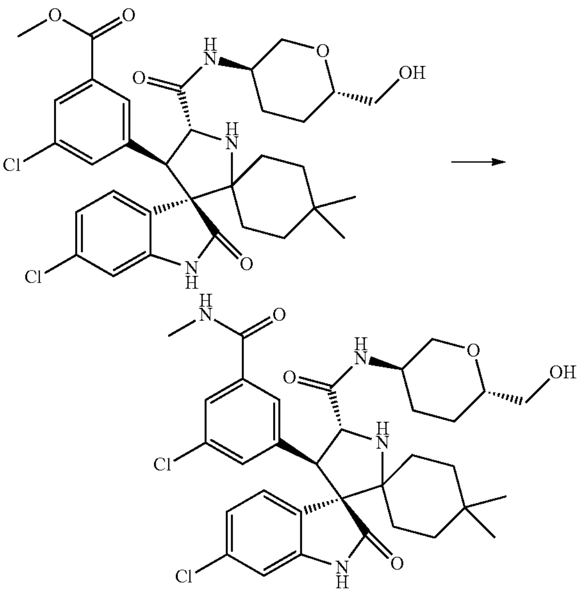

2, 5~Anhydro-2-[({(3'R, 4'R, 5'R)-6"-chloro-4'-[3-chloro-5-(methylcarbamoyl)phenyl]-4,4-dimethyl-2"-oxo-1",2"-dihydrodispiro[cyclohexane-1,2'-pyrrolidine-3',3"-indole]-5'-yl}carbonyl)amino]-2,3,4-trideoxy-D-erythro-hexitol The compound (82 mg, 0.13 mmol) obtained in Step 22 of Example 2 was used as a starting material and treated in the same way as in Step 5 of Example 21 to give 31 mg (37%) of the title compound as a colorless solid.

$^1$H-NMR (500 MHz, $CD_3OD$) δ: 0.59 (3H, s), 0.95 (3H, s), 1.09-1.24 (2H, m), 1.26-1.38 (1H, m), 1.38-1.49 (1H, m), 1.49-1.66 (3H, m), 1.70-1.86 (4H, m), 1.99-2.11 (1H, m), 2.85 (3H, s), 3.12-3.21 (1H, m), 3.35-3.42 (1H, m), 3.49 (2H, d, J=5.2 Hz), 3.73-3.83 (1H, m), 3.91-3.98 (1H, m), 4.23 (1H, d, J=9.2 Hz), 4.63 (1H, d, J=9.2 Hz), 6.74 (1H, d, J=2.3 Hz), 7.09 (1H, dd, J=8.0, 1.7 Hz), 7.23-7.26 (1H, m), 7.51 (1H, d, J=8.0 Hz), 7.52-7.57 (2H, m).

MS (ESI) m/z: 643 $(M+H)^+$.

Example 28

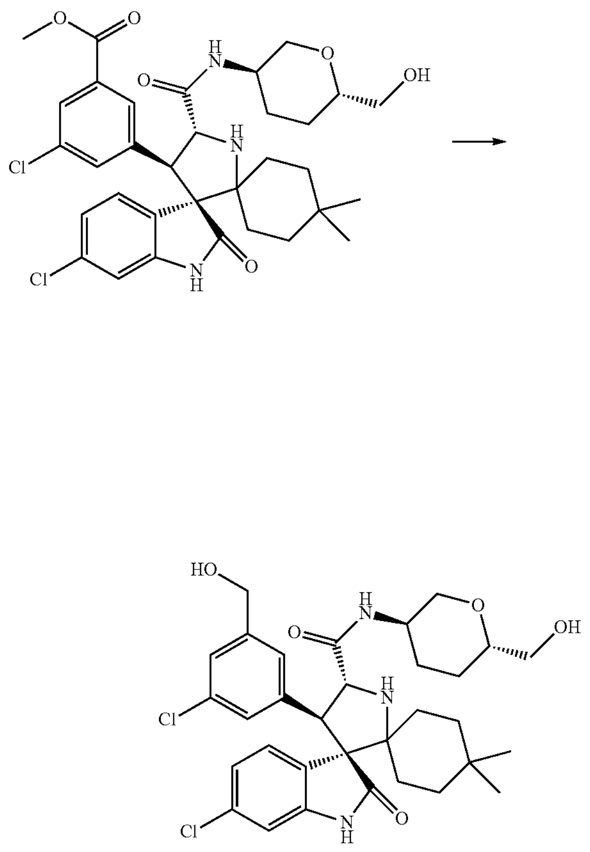

(3'R, 4'R, 5'R)-6"-chloro-4'-[3-chloro-5-(hydroxymethyl)phenyl]-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide Lithium borohydride (26 mg, 1.25 mmol) was gradually added to a tetrahydrofuran (4 ml) solution of the compound (107 mg, 0, 17 mmol) obtained in Step 2 of Example 22 at room temperature and the resulting mixture was stirred at the same temperature for 18 hours. Water was added to the reaction mixture, followed by extraction with ethyl acetate. The organic layer was washed with brine and then dried over anhydrous sodium sulfate. The solvent was evaporated under reduced pressure and then the residue was purified by silica gel column chromatography [methanol:ethyl acetate=1:9 (v/v)] to give 69 mg (68%) of the title compound as a colorless solid.

$^1$H-NMR (400 MHz, $CD_3OD$) δ: 0.68 (3H, s), 0.94 (3H, s), 1.04-1.24 (2H, m), 1.26-1.49 (2H, m), 1.50-1.65 (3H, m), 1.68-1.87 (4H, m), 2.00-2.12 (1H, m), 3.06-3.20 (1H, m), 3.34-3.43 (1H, m), 3.46-3.51 (2H, m), 3.71-3.83 (1H, m), 3.89-3.99 (1H, m), 4.18 (1H, d, J=9.2 Hz), 4.40 (2H, s), 4.56 (1H, d, J=9.2 Hz), 6.74 (1H, d, J=1.8 Hz), 6.97-7.02 (1H, m), 7.03-7.15 (3H, m), 7.49 (1H, d, J=7.8 Hz).

MS (ESI) m/z: 616 $(M+H)^+$.

Example 29

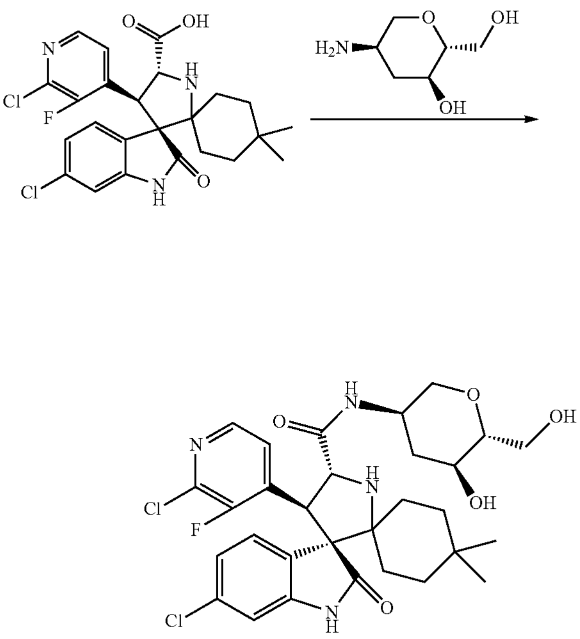

(3'R, 4'S,5'R)-6"-chloro-4'-(2-chloro-3-fluoropyridin-4-yl)-N-[(3R,5S,6R)-5-hydroxy-6-(hydroxymethyl)tetrahydro-2H-pyran-3-yl]-4,4-dimethyl-2"-oxo-1",2"-dihydrodispiro[cyclohexane-1,2'-pyrrolidine-3), 3", indole]-5'-carboxamide The compound (80 mg, 0.16 mmol) obtained in Step 1 of Example 17 and the compound (39 mg, 0.27 mmol) obtained in Step 4 of Reference Example 14 were used as starting materials and treated in the same way as in Step 2 of Example 12 to give 68 mg (67%) of the title compound as a colorless solid.

$^1$H-NMR (400 MHz, $CDCl_3$) δ: 0.68 (3H, s), 0.95 (3H, s), 1.10-1.27 (4H, m), 1.36-1.79 (5H, m), 2.32-2.42 (1H, m), 2.55 (1H, br s), 3.04-3.13 (1H, m), 3.14-3.21 (1H, m), 3.68-3.90 (3H, m), 3.95-4.07 (2H, m), 4.45 (1H, d, J=9.0 Hz), 4.63 (1H, d, J=9.0 Hz), 6.73 (1H, d, J=1.8 Hz), 7.05-7.10 (1H, m), 7.29-7.34 (1H, m), 7.47-7.60 (3H, m), 8.05 (1H, d, J=5.5 Hz).

MS (ESI) m/z: 621 $(M+H)^+$.

Example 30

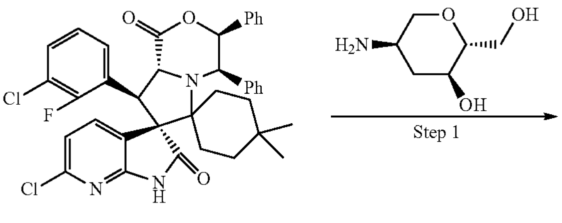

-continued

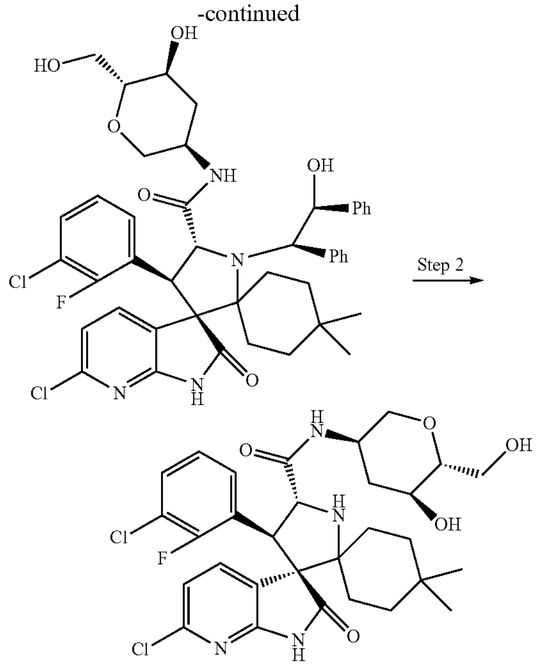

Step 1

(4'S,5'R)-6"-chloro-4'-(3-chloro-2-fluorophenyl)-1'-[(1R,2S)-2-hydroxy-1,2-diphenylethyl]-N-[(3R,5S,6R)-5-hydroxy-6-(hydroxymethyl)tetrahydro-2H-pyran-3-yl]-4,4-dimethyl-2"-oxo-1",2"-dihydrodispiro[cyclohexane-1,2'-pyrrolidine-3',3"pyrrolo[2,3-b]pyridine]-S'-carboxamide The compound (170 mg, 0.25 mmol) obtained in Step 1 of Example 2 and the compound (145 mg, 0.98 mmol) obtained in Step 4 of Reference Example 14 were used as starting materials and treated in the same way as in Step 1 of Example 5 to give 100 mg (50%) of the title compound as a colorless solid.

MS (ESI) m/z: 815 $(M-H)^-$.

Step 2

(3'R, 4'S,5'R)-6"-chloro-4'-(3-chloro-2-fluorophenyl)-N-[(3R,5S,6R)-5-hydroxy-6-(hydroxymethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (99 mg, 0.12 mmol) obtained in Step 1 above was used as a starting material and treated in the same way as in Step 3 of Example 1 to give 44 mg (58%) of the title compound as a colorless solid.

$^1$H-NMR (400 MHz, $CDCl_3$) δ: 0.70 (3H, s), 0.96 (3H, s), 1.12-1.28 (3H, m), 1.35-1.81 (6H, m), 2.31-2.56 (2H, m), 3.03-3.12 (1H, m), 3.13-3.21 (1H, m), 3.68-3.90 (3H, m), 3.94-4.08 (2H, m), 4.48 (1H, d, J=9.2 Hz), 4.67 (1H, d, J=9.2 Hz), 6.94-7.01 (1H, m), 7.06 (1H, d, J=7.8 Hz), 7.14-7.21 (1H, m), 7.43-7.56 (2H, m), 7.63 (1H, dd, J=8.0, 2.5 Hz), 7.88 (1H, br s).

MS (ESI) m/z: 621 $(M+H)^+$.

Example 31

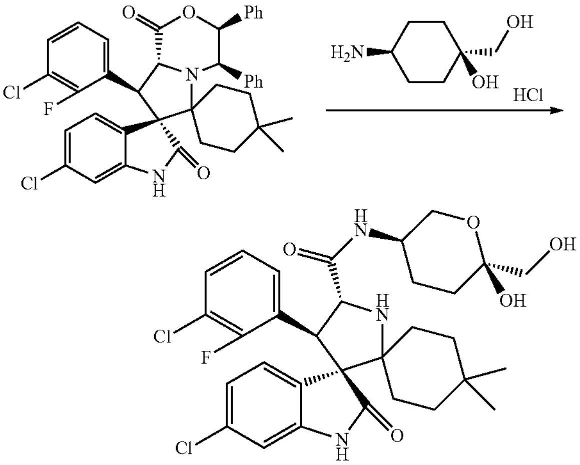

(3'R, 4'S,5'R)-6"-chloro-4'-(3-chloro-2-fluorophenyl)-N-[cis-4-hydroxy-4-(hydroxymethyl)cyclohexyl]-4,4-dimethyl-2"-oxo-1",2"-dihydrodispiro[cyclohexane-1,2'-pyrrolidine-3',3"-indole]-5'-carboxamide Triethylamine (0.22 ml, 1.58 mmol) was added to a methanol (2 ml) solution of the compound (201 mg, 0.30 mmol) obtained in Step 1 of Example 1 and the compound (278 mg, 1.53 mmol) obtained in Reference Example 15, and the resulting mixture was stirred under heating overnight at 60° C. The reaction mixture was diluted with ethyl acetate, washed with water and brine in that order and then dried over anhydrous magnesium sulfate. The solvent was concentrated under reduced pressure and the residue obtained was purified by silica gel column chromatography [methanol:chloroform=5:95 (v/v)]. The solid obtained was dissolved in acetonitrile (1.8 ml) and water (0.6 ml), cerium (IV) diammonium nitrate (136 mg, 0.25 mmol) was added under ice cooling and the resulting mixture was stirred for 30 minutes. Subsequently, potassium carbonate (69 mg, 0.50 mmol) was added and the resulting mixture was stirred for 30 minutes. Water was added, followed by extraction with chloroform. The organic layer was dried over anhydrous sodium sulfate. The solvent was concentrated under reduced pressure, chloroform (9 ml), methanol (1 ml), and silica gel (1 g) were added to the residue obtained and the resulting mixture was stirred at room temperature for 2 hours. Insoluble matter was removed by filtration through celite and the filtrate was concentrated under reduced pressure. The residue obtained was purified by silica gel column chromatography [methanol:chloroform=5:95 (v/v)] to give 32 mg (17%) of the title compound as a colorless solid.

$^1$H-NMR (400 MHz, DMSO-dc) δ: 0.60 (3H, s), 0.89 (3H, s), 0.96 (1H, td, J=14.1, 4.1 Hz), 1.10-1.14 (1H, m), 1.22-1.26 (1H, m), 1.35-1.59 (11H, m), 1.67-1.79 (2H, m), 3.14 (2H; d, J=5.5 Hz), 3.37-3.43 (1H, m), 3.49 (1H, d, J=10.1 Hz), 3.94 (1H, s), 4.36 (1H, t, J=9.2 Hz), 4.49 (1H, t, J=5.7 Hz), 4.55 (1H, d, J=9.6 Hz), 6.67 (1H, d, J=2.3 Hz), 7.04 (1H, dd, J=8.3, 1.8 Hz), 7.11 (1H, t, J=8.0 Hz), 7.30-7.34 (1H, m), 7.44 (1H, dd, J=3.0, 2.1 Hz), 7.56-7.60 (1H, m), 7.72 (1H, d, J=8.7 Hz), 10.52 (1H, s).

MS (ESI) m/z: 618 $(M+H)^+$.

Example 32

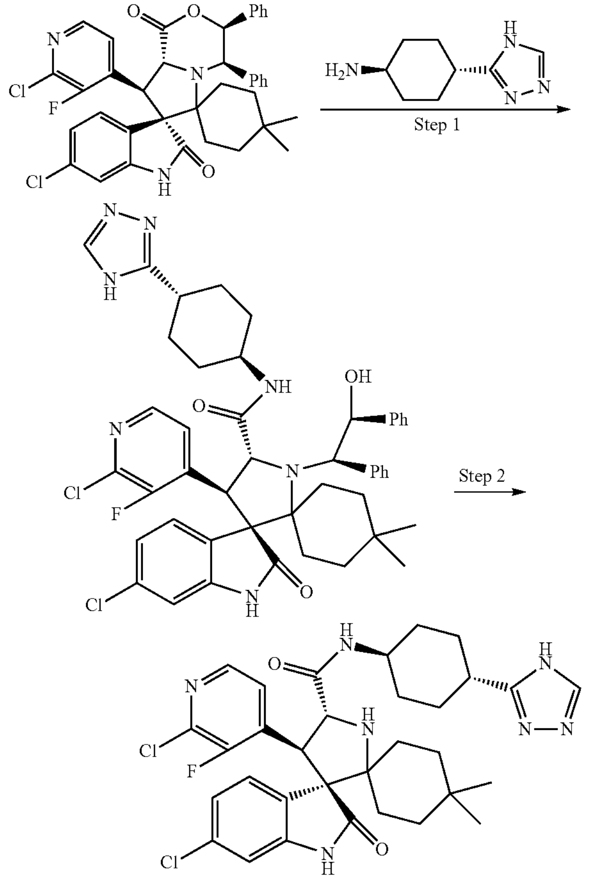

Step 1

(4'S,5'R)-6"-chloro-4'-(2-chloro-3-fluoropyridin-4-yl)-1'-[(1R,2S)-2-hydroxy-1,2-diphenylethyl]-4,4-dimethyl-2"-oxo-N-[trans-4-(4H-1,2,4-triazol-3-yl)cyclohexyl]-1",2"-dihydrodispiro[cyclohexane-1,2'-pyrrolidine-3',3"-indole]-5'-carboxamide The compound (154 mg, 0.23 mmol) obtained in Step 1 of Example 16 and the compound (115 mg, 0.69 mmol) obtained in Step 4 of Reference Example 16 were used as starting materials and treated in the same way as in Step 1 of Example 5 to give 130 mg (68%) of the title compound as a colorless solid.

MS (ESI) m/z: 835 $(M-H)^-$.

Step 2

(3'R, 4'S,5'R)-6"-chloro-4'-(2-chloro-3-fluoropyridin-4-yl)-4,4-dimethyl-2"-oxo-N-[trans-4-(4H-1,2,4-triazol-3-yl)cyclohexyl]-1",2"-dihydrodispiro[cyclohexane-1,2'-pyrrolidine-3',3"-indole]-5'-carboxamide The compound (130 mg, 0.16 mmol) obtained in Step 1 above was used as a starting material and treated in the same way as in Step 3 of Example 1 to give 77 mg (77%) of the title compound as a colorless solid.

$^1$H-NMR (400 MHz, $CDCl_3$) δ: 0.69 (3H, s), 0.96 (3H, s), 1.10-1.89 (12H, m), 2.08-2.25 (4H, m), 2.79-2.90 (1H, m), 3.72-3.87 (2H, m), 4.46 (1H, d, J=9.2 Hz), 4.67 (1H, d, J=9.2 Hz), 6.74 (1H, d, J=2.3 Hz), 7.05-7.10 (1H, m), 7.30-7.38 (2H, m), 7.49-7.54 (1H, m), 7.56-7.65 (1H, m), 8.01 (1H, s), 8.05 (1H, d, J=5.5 Hz).

MS (ESI) m/z: 640 $(M+H)^+$.

Example 33

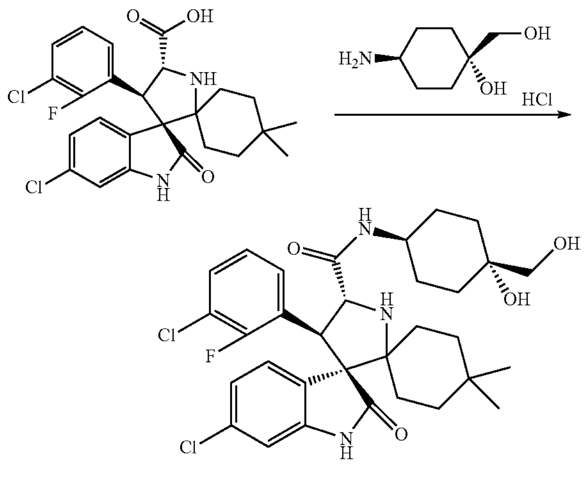

(3'R, 4'S,5'R)-6"-chloro-4'-(3-chloro-2-fluorophenyl)-N-[trans-4-hydroxy-4-(hydroxymethyl)cyclohexyl]-4,4-dimethyl-2"-oxo-1",2"-dihydrodispiro[cyclohexane-1,2'-pyrrolidine-3',3"-indole]-5'-carboxamide The compound (108 mg, 0.22 mmol) obtained in Step 1 of Example 12 and the compound (0.27 mmol) obtained in Step 3 of Reference Example 17 were used as starting materials and treated in the same way as in Step 2 of Example 12 to give 93 mg (68%) of the title compound as a colorless solid.

$^1$H-NMR (400 MHz, DMSO-$d_6$) δ: 0.60 (3H, s), 0.88 (3H, s), 0.92-1.00 (1H, m), 1.10-1.14 (1H, m), 1.24-1.63 (10H, m), 1.69-1.77 (4H, m), 3.26 (2H, d, J=6.0 Hz), 3.51 (1H, d, J=9.6 Hz), 3.68 (1H, s), 4.02 (1H, s), 4.38-4.45 (2H, m), 4.52 (1H, d, J=9.2 Hz), 6.67 (1H, d, J=1.8 Hz), 7.03 (1H, dd, J=8.3, 2.3 Hz), 7.11 (1H, t, J=8.0 Hz), 7.30-7.34 (1H, m), 7.44 (1H, dd, J=8.3, 1.8 Hz), 7.56-7.60 (1H, m), 7.85 (1H, d, J=8.3 Hz), 10.53 (1H, s).

MS (ESI) m/z: 618 $(M+H)^+$.

Example 34

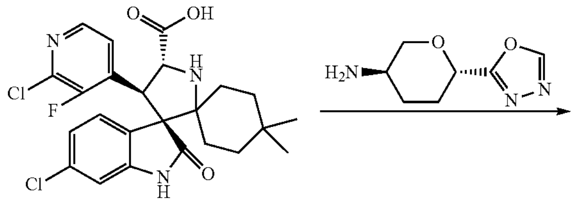

-continued

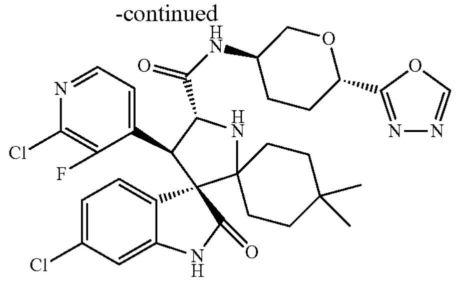

(3'R, 4'S,5'R)-6"-chloro-4'-(2-chloro-3-fluoropyridin-4-yl)-4,4-dimethyl-N-[(3R,6S)-6-(1,3,4-oxadiazol-2-yl)tetrahydro-2H-pyran-3-yl]-2"-oxo-1",2"-dihydrodispiro[cyclohexane-1,2'-pyrrolidine-3',3"-indole]-5'-carboxamide The compound (81 mg, 0.16 mmol) obtained in Step 1 of Example 17 and the compound (34 mg, 0.20 mmol) obtained in Step 6 of Reference Example 18 were used as starting materials and treated in the same way as in Step 2 of Example 12 to give 72 mg (68%) of the title compound as a pale yellow solid.

$^1$H-NMR (500 MHz, $CDCl_3$) δ: 0.69 (3H, s), 0.96 (3H, s), 1.12-1.27 (2H, m), 1.36-1.43 (1H, m), 1.45-1.55 (2H, m), 1.61-1.82 (4H, m), 2.11-2.29 (3H, m), 3.21-3.43 (2H, m), 3.99-4.08 (1H, m), 4.09-4.15 (1H, m), 4.47 (1H, d, J=9.2 Hz), 4.65 (1H, d, J=9.2 Hz), 4.78 (1H, dd, J=9.7, 2.9 Hz), 6.73 (1H, d, J=1.7 Hz), 7.06 (1H, dd, J=8.3, 2.0 Hz), 7.31 (1H, dd, J=8.3, 2.0 Hz), 7.51 (1H, t, J=4.9 Hz), 7.70 (19, d, J=8.6 Hz), 7.92 (1H, s), 8.05 (1H, d, J=5.2 Hz), 8.43 (1H, s),

MS (ESI) m/z: 643 $(M+H)^+$.

Example 35

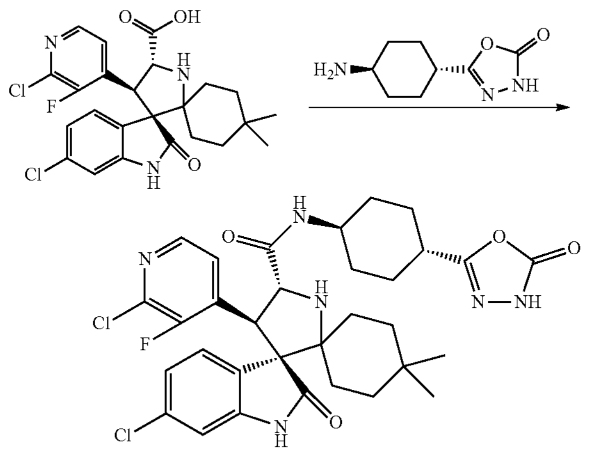

(3'R, 4'S, S'R)-6"-chloro-4'-(2-chloro-3-fluoropyridin-4-yl)-4,4-dimethyl-2"-oxo-N-[trans-4-(5-oxo-4,5-dihydro-1,3,4-oxadiazol-2-yl)cyclohexyl]-1",2"-dihydrodispiro[cyclohexane-1,2'-pyrrolidine-3',3"-indole]-5'-carboxamide The compound (70 mg, 0.14 mmol) obtained in Step 1 of Example 17 and the compound (31 mg, 0.17 mmol) obtained in Step 2 of Reference Example 19 were used as starting materials and treated in the same way as in Step 2 of Example 12 to give 53 mg (57%) of the title compound as a pale yellow solid.

$^1$H-NMR (500 MHz, $CDCl_3$) δ: 0.68 (3H, s), 0.95 (3H, s), 1.10-1.80 (12H, m), 2.06-2.19 (4H, m), 2.52-2.61 (1H, m), 3.19-3.40 (1H, m), 3.69-3.80 (1H, m), 4.44 (1H, d, J=9.2 Hz), 4.65 (1H, d, J=9.2 Hz), 6.73 (1H, d, J=2.3 Hz), 7.07 (1H, dd, J=8.0, 1.7 Hz), 7.32 (1H, dd, J=8.0, 2.3 Hz), 7.41 (1H, s), 7.50 (1H, t, J=4.9 Hz), 7.59 (1H, d, J=8.6 Hz), 8.05 (1H, d, J=5.2 Hz), 8.76 (1H, s).

MS (ESI) m/z: 657 $(M+H)^+$.

Example 36

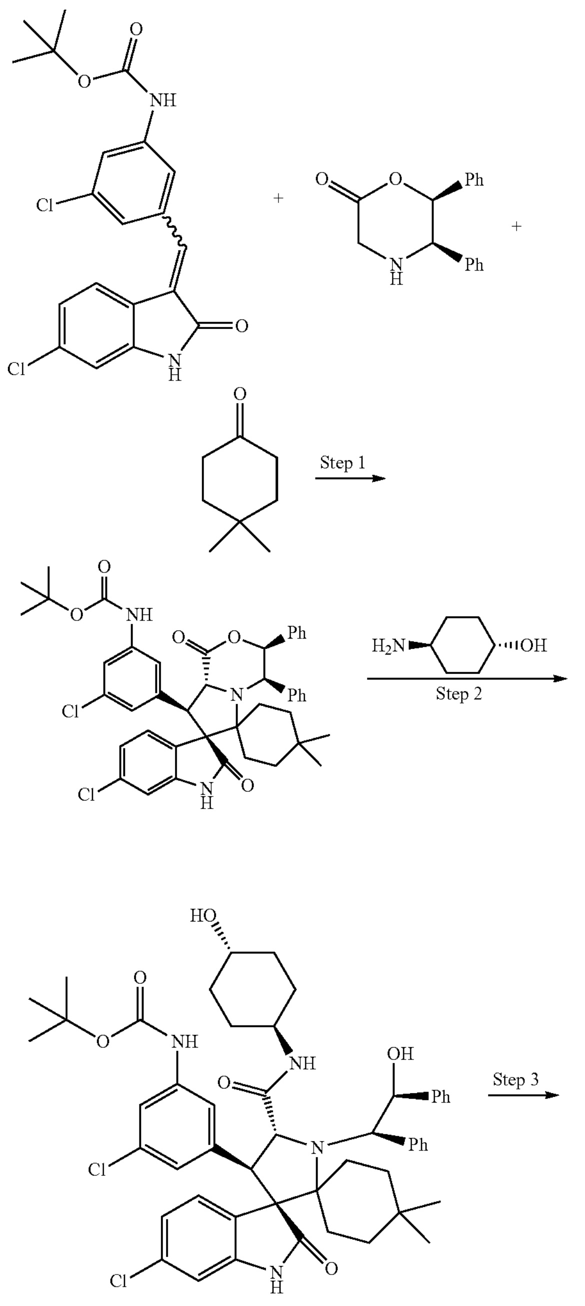

-continued

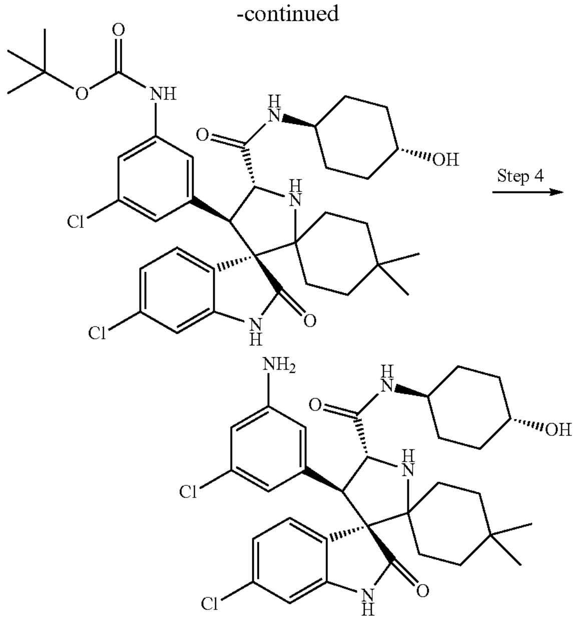

Step 1

Tert-butyl {-chloro-5-[13'S,4+R, 8'R, 8a'R)-6"-chloro-4,4-dimethyl-1',2"-dioxo-3',4'-diphenyl-1",2", 3',4',8',8a'-hexahydro-1'H-dispiro[cyclohexane-1,6'-pyrrolo[2,1-c][1,4]oxazine-7',3"-indole]-8'-yl] phenyl}carbamate The compound (2.41 g, 6.16 mmol) obtained in Step 3 of Reference Example 20 was used as a starting material and treated in the same way as in Step 1 of Example 9 to give 859 mg (18%) of the title compound as a yellow solid.

MS (FAB) m/z: 766 $(M+H)^+$.

Step 2

Tert-butyl (3-chloro-5-{(4'R, 5'8)-6"-chloro-5'-[(trans-4-hydroxycyclohexyl) carbamoyl]-1'-[(1R,2S)-2-hydroxy-1, 2-diphenylethyl]-4,4-dimethyl-2"-oxo-1",2"-dihydrodispiro [cyclohexane-1,2-pyrrolidine-3',3"-indole]-4'-yl}phenyl) carbamate The compound (842 mg, 1.10 mmol) obtained in Step 1 above was used as a starting material and treated in the same way as in Step 2 of Example 1 to give 621 mg (64%) of the title compound as a colorless solid.

MS (FAB) m/z: 881 $(M+H)^+$.

Step 3

Tert-butyl (3-chloro-5-{(3'R, 4'R, 5'R)-6"-chloro-5'-[(trans-4-hydroxycyclohexyl)carbamoyl]-4,4-dimethyl-2"-oxo-1",2"-dihydrodispiro[cyclohexane-1,2'-pyrrolidine-3',3"-indole]-4'-yl}phenyl) carbamate The compound (610 mg, 0.69 mmol) obtained in Step 2 above was used as a starting material and treated in the same way as in Step 3 of Example 1 to give 338 mg (71%) of the title compound as a colorless solid.

$^1$H-NMR (400 MHz, $CD_3OD$) δ: 0.68 (3H, s), 0.93 (3H, s), 1.08-1.64 (18H, m), 1.68-1.84 (3H, m), 1.87-2.02 (4H, m), 3.48-3.68 (2H, m), 4.10 (1H, d, J=9.2 Hz), 4.51 (1H, d, J=8.7 Hz), 6.74-6.79 (2H, m), 6.97-7.02 (1H, m), 7.08 (1H, dd, J=8.0, 2.1 Hz), 7.30-7.35 (1H, m), 7.45 (1H, d, J=8.3 Hz).

MS (FAB) m/z: 685 $(M+H)^+$.

Step 4

(3'R, 4'R, 5'R)-4'-(3-amino-5-chlorophenyl)-6"-chloro-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide 4N hydrochloric acid/1,4-dioxane solution (1.16 ml, 4.64 mmol) was added to a 1,4-dioxane (6 ml) solution of the compound (321 mg, 0.47 mmol) obtained in Step 3 above and the resulting mixture was stirred at room temperature for 24 hours; Saturated sodium bicarbonate solution was added to the reaction mixture, followed by extraction with ethyl acetate. The organic layer was washed with brine and then dried over anhydrous sodium sulfate. The solvent was evaporated under reduced pressure and then the residue was purified by silica gel column chromatography [methanol: ethyl acetate=1:4 (v/v)] to give 248 mg (91%) of the title compound as a colorless solid.

$^1$H-NMR (500 MHz, $CD_3OD$) δ: 0.68 (3H, s), 0.93 (3H, 8), 1.05-1.22 (2H, m), 1.24-1.42 (5H, m), 1.48-1.61 (2H, m), 1.69-1.82 (3H, m), 1.86-2.01 (4H, m), 3.51-3.64 (2H, m), 4.02 (1H, d, J=9.2 Hz), 4.46 (1H, d, J=9.2 Hz), 6.34-6.37 (1H, m), 6.41-6.46 (2H, m), 6.76 (1H, d, J=1.7 Hz), 7.06 (1H, dd, J=8.3, 2.0 Hz), 7.43 (1H, d, J=8.0 Hz).

MS (ESI) m/z: 585 $(M+H)^+$.

Example 37

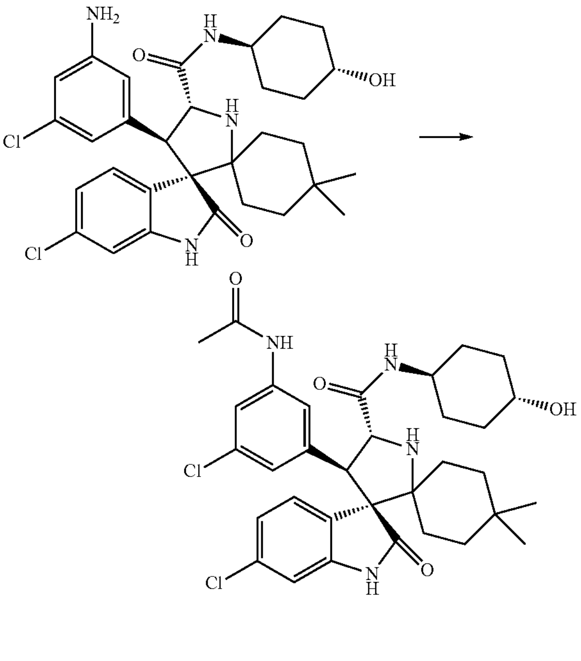

(3'R, 4'R, S'R)-4'-(3-acetamide-5-chlorophenyl)-6"-chloro-N-(trans-4-hydroxycyclohexyl)-4,4-dimethyl-2"-oxo-1",2"-dihydrodispiro[cyclohexane-1,2'-pyrrolidine-3',3"-indole]-5'-carboxamide The compound (101 mg, 0.172 mmol) obtained in Step 4 of Example 36 and acetic acid (0.015 ml, 0.26 mmol) were used as starting materials and treated in the same way as in Step 2 of Example 12 to give 53 mg (49%) of the title compound as a colorless solid.

$^1$H-NMR (500 MHz, $CD_3OD$) δ: 0.68 (3H, s), 0.93 (3H, s), 1.08-1.22 (2H, m), 1.27-1.42 (5H, m), 1.49-1.61 (2H, m), 1.71-1.82 (3H, m), 1.86-2.02 (4H, m), 2.04 (3H, s), 3.51-3.66 (2H, m), 4.11 (1H, d, J=9.2 Hz), 4.51 (1H, d, J=9.2 Hz), 6.76 (1H, d, J=1.7 Hz), 6.86-6.88 (1H, m), 7.06-7.10 (2H, m), 7.46 (1H, d, J=8.0 Hz), 7.57-7.59 (1H, m).

MS (ESI) m/z: 627 $(M+H)^+$.

Example 38

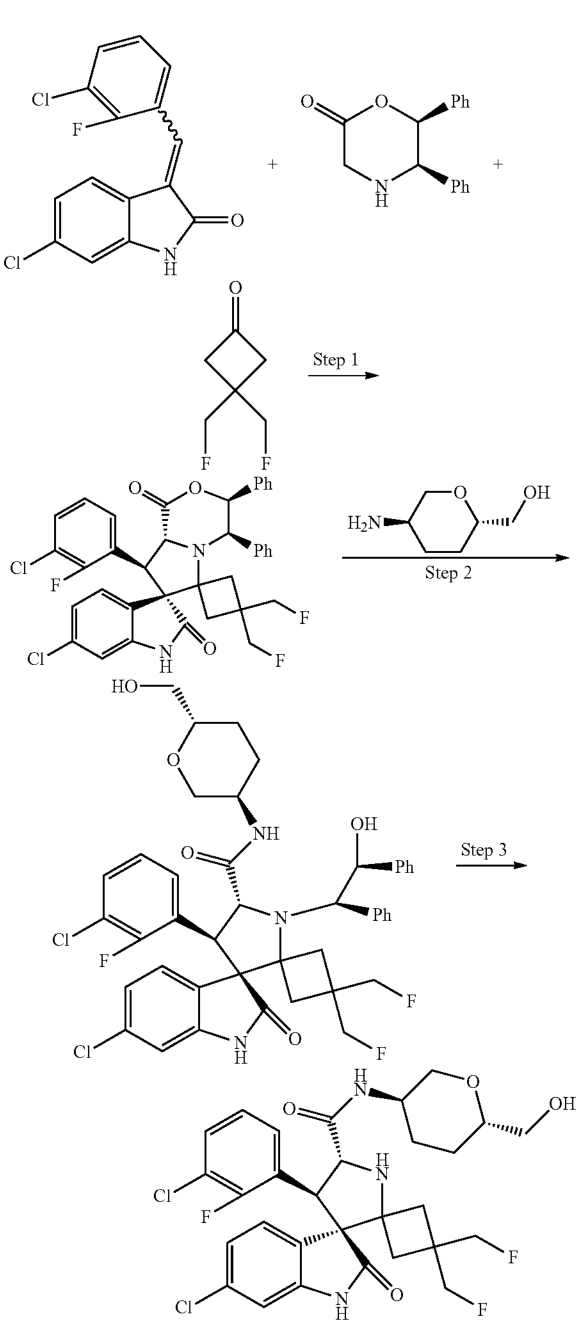

Step 1

(3'S,4'R, 7'S,8'S, 8a'R)-6"-chloro-8'-(3-chloro-2-fluorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2" (1"H)-dione The compound (WO2006/091646) (5.44 g, 21.5 mmol) used as a starting material in Step 1 of Example 1 and the compound (2.88 g, 21.5 mmol) obtained in Step 2 of Reference Example 21 were used as starting materials and treated in the same way as in Step 1 of Example 9 to give 10.2 g (87%) of the title compound as a pale yellow amorphous solid.

$^1$H-NMR (400 MHz, $CDCl_3$) δ: 1.95 (1H, d, J=14.2 Hz), 2.26 (1H, d, J=14.2 Hz), 2.79 (1H, d, J=14.2 Hz), 2.88 (1H, d, J=14.2 Hz), 3.82-4.02 (2H, m), 4.14-4.34 (2H, m), 4.55 (1H, d, J=9.6 Hz), 4.73 (1H, d, J=9.6 Hz), 5.19-5.23 (1H, m), 6.38 (1H, d, J=4.1 Hz), 6.65 (1H, d, J=7.8 Hz), 6.85-6.92 (3H, m), 6.95-7.01 (1H, m), 7.10-7.16 (2H, m), 7.18-7.25 (9H, m), 7.56 (1H, s).

Step 2

(4'S,5'R)-6"-chloro-4'-(3-chloro-2-fluorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro [cyclobutane-1,2'-pyrrolidine-3',3"-indole]-5'-carboxamide The compound (300 mg, 0.44 mmol) obtained in Step 1 above was used as a starting material and treated in the same way as in Step 1 of Example 20 to give 233 mg (65%) of the title compound as a pale yellow amorphous solid.

$^1$H-NMR (400 MHz, $CDCl_3$) δ: 1.12-1.27 (1H, m), 1.42-1.69 (3H, m), 2.04-2.13 (1H, m), 2.53-2.66 (2H, m), 2.85 (1H, d, J=14.7 Hz), 3.23-3.31 (1H, m), 3.36 (1H, d, J=14.2 Hz), 3.45-3.53 (1H, m), 3.57 (1H, dd, J=11.7, 3.0 Hz), 3.79-3.86 (2H, m), 3.91-4.02 (1H, m), 4.06-4.26 (3H, m), 4.43-4.62 (3H, m), 4.85 (1H, d, J=3.7 Hz), 5.01 (1H, d, J=8.2 Hz), 5.59-5.64 (1H, m), 6.49-5.55 (1H, m), 6.74 (1H, t, J=8.0 Hz), 6.79-6.83 (2H, m), 6.89 (1H, dd, J=8.2, 1.8 Hz), 7.06-7.30 (10H, m), 7.33-7.40 (2H, m), 7.72 (1H, s),

Step 3

(3'R, 4'S,5'R)-6"-chloro-4'-(3-chloro-2-fluorophenyl)-3,3-bis(fluoromethyl)-N-[(3R,6S)-6-(hydroxymethyl)tetrahydro-2H-pyran-3-yl]-2"-oxo-1", 2"-dihydrodispiro [cyclobutane-1,2'-pyrrolidine-3', 3"-indole]-5'-carboxamide The compound (200 mg, 0.25 mmol) obtained in Step 2 above was used as a starting material and treated in the same way as in Step 3 of Example 1 to give 66 mg (44%) of the title compound as a colorless solid.

$^1$H-NMR (400 MHz, $CD_3OD$) δ: 1.37-1.49 (1H, m, 1.52-1.64 (1H, m), 1.64-1.78 (2H, m), 1.88 (1H, d, J=13.3 Hz), 2.03-2.13 (2H, m), 2.18 (1H, d, J=12.8 Hz), 3.10 (1H, t, J=10.5 Hz), 3.32-3.40 (1H, m), 3.49 (2H, d, J=5.0 Hz), 3.74=3.94 (4H, m), 4.38 (1H, d, J=9.4 Hz), 4.45 (1H, d, J=9.4 Hz), 4.58-4.78 (2H, m), 6.81 (1H, d, J=1.8 Hz), 7.02 (1H, t, J=8.0 Hz), 7.10 (1H, dd, J=8.0, 2.1 Hz), 7.19-7.26 (1H, m), 7.50 (1H, dd, J=8.2, 2.3 Hz), 7.52-7.57 (1H, m).

MS (ESI) m/z: 612 $(M+H)^+$.

Example 39

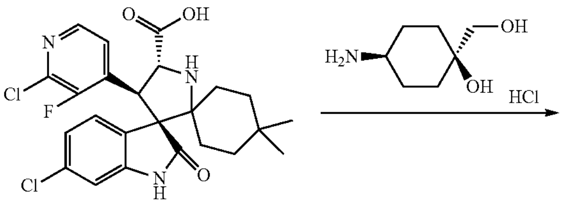

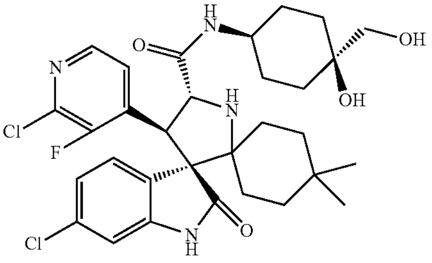

(3'R, 4'S,5'R)-6"-chloro-4'-(2-chloro-3-fluoropyridin-4-yl)-N-[cis-4-hydroxy-4-(hydroxymethyl)cyclohexyl]-4,4-dimethyl-2"-oxo-1",2"-dihydrodispiro[cyclohexane-1,2'-pyrrolidine-3',3"-indole]-5-carboxamide The compound (80 mg, 0.16 mmol) obtained in Step 1 of Example 17 and the compound (0.33 mmol) obtained in Reference Example 15 were used as starting materials and treated in the same way as in Step 2 of Example 12 to give 63 mg (62%) of the title compound as a colorless solid.

$^1$H-NMR (400 MHz, DMSO-$d_6$) δ: 0.60 (3H, s), 0.89 (3H, s), 0.93-1.00 (1H, m), 1.11-1.15 (1H, m), 1.23-1.25 (1H, m), 1.36-1.60 (11H, m), 1.67-1.77 (2H, m), 3.14 (2H, d, J=6.0 Hz), 3.38-3.47 (1H, m), 3.54-3.57 (1H, m), 3.96 (1H, s), 4.43 (1H, t, J=9.6 Hz), 4.49 (1H, t, J=5.7 Hz), 4.54 (1H, d, J=9.2 Hz), 6.71 (1H, d, J=1.8 Hz), 7.05 (1H, dd, J=8.0, 2.1 Hz), 7.50 (1H, dd, J=8.3, 1.8 Hz), 7.63 (1H, t, J=5.0 Hz), 7.72 (1H, d, J=8.3 Hz), 8.18 (1H, d, J=5.0 Hz), 10.61 (1H, s).

MS (ESI) m/z: 619 $(M+H)^+$.

Example 40

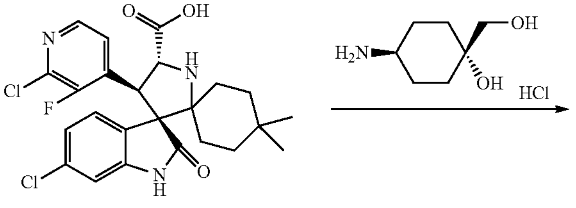

-continued

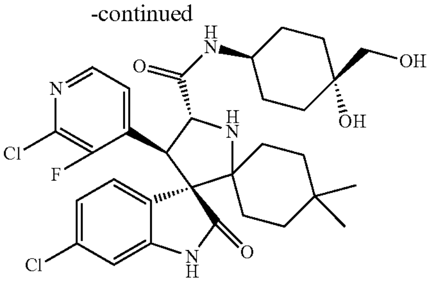

(3'R, 4'S,5R)-6"-chloro-4'-(2-chloro-3-fluoropyridin-4-yl)-N-[trans-4-hydroxy-4-(hydroxymethyl)cyclohexyl]-4,4-dimethyl-2"-oxo-1",2"-dihydrodispiro[cyclohexane-1,2'-pyrrolidine-3',3"-indole]-5'-carboxamide The compound (80 mg, 0.16 mmol) obtained in Step 1 of Example 17 and the compound (0.24 mmol) obtained in Step 3 of Reference Example 17 were used as starting materials and treated in the same way as in Step 2 of Example 12 to give 69 mg (66%) of the title compound as a colorless solid.

$^1$H-NMR (400 MHz, DMSO-$d_6$) δ: 0.60 (3H, s), 0.89 (3H, s), 0.97 (1H, dt, J=5.5, 13.3 Hz), 1.11-1.15 (1H, m), 1.24-1.75 (14H, m), 3.27 (2H, d, J=6.0 Hz), 3.56-3.59 (1H, m), 3.69 (1H, s), 4.03 (1H, s), 4.43-4.53 (3H, m), 6.71 (1H, d, J=1.8 Hz), 7.05 (1H, dd, J=8.3, 2.3 Hz), 7.50 (1H, dd, J=8.3, 1.8 Hz), 7.63 (1H, t, J=5.3 Hz), 7.85 (1H, d, J=8.3 Hz), 8.18 (1H, d, J=5.5 Hz), 10.62 (1H, s).

MS (ESI) m/z: 619 $(M+H)^+$.

Example 41

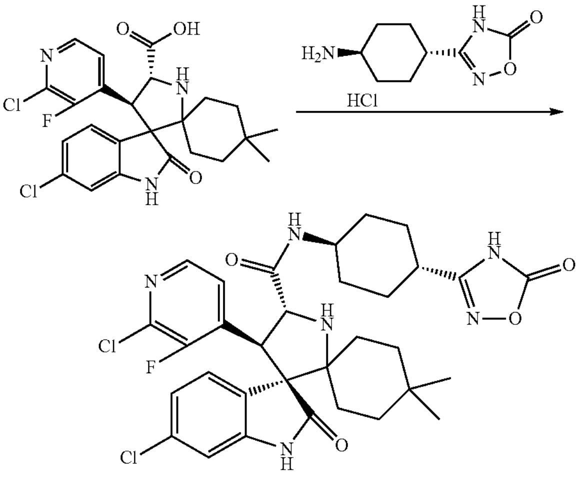

(3'R, 4'S,5'R)-6"-chloro-4'-(2-chloro-3-fluoropyridin-4-yl)-4,4-dimethyl-2"-oxo-N-[trans-4-(5-oxo-4,5-dihydro-1,2,4-oxadiazol-3-yl)cyclohexyl]-1",2"-dihydrodispiro[cyclohexane-1,2'-pyrrolidine-3',3"-indole]-5'-carboxamide The compound (84 mg, 0.17 mmol) obtained in Step 1 of Example 17 and the compound (46 mg, 0.20 mmol) obtained in Step 7 of Reference Example 22 were used as starting materials and treated in the same way as in Step 2 of Example 12 to give 87 mg (78%) of the title compound as a pale yellow solid.

$^1$H-NMR (500 MHz, $CD_3OD$) δ: 0.68 (3H, s), 0.94 (3H, s); 1.10-1.24 (2H, m); 1.32-1.67 (7H, m), 1.75-1.84 (3H, m), 1.98-2.12 (4H, m), 2.57-2.66 (1H, m); 3.62-3.71 (1H, m), 4.55 (1H, d, J=9.2 Hz), 4.67 (1H, d, J=9.2 Hz), 6.77 (1H, d, J=2.3 Hz), 7.06 (1H, dd, J=8.0, 2.3 Hz), 7.46 (1H, dd, J=8.0, 2.3 Hz), 7.65-7.69 (1H, m), 8.06 (1H, d, J=5.2 Hz).

MS (ESI) m/z: 657 $(M+H)^+$.

Example 42

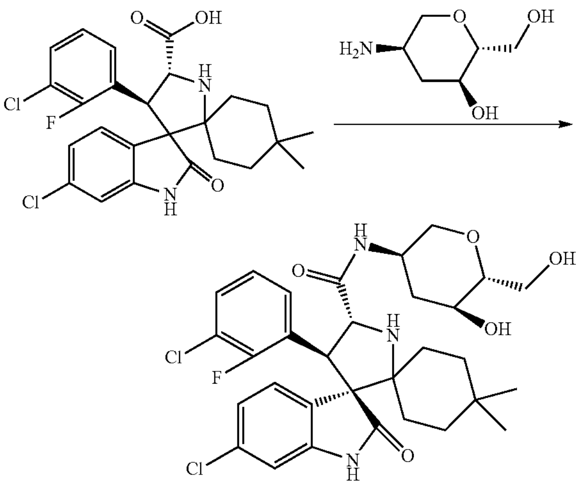

(3'R, 4'S,5'R)-6"-chloro-4'-(3-chloro-2-fluorophenyl)-N-[(3R,5S,6R)-5-hydroxy-6-(hydroxymethyl) tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (80 mg, 0.16 mmol) obtained in Step 1 of Example 12 and the compound (34 mg, 0.23 mmol) obtained in Step 4 of Reference Example 14 were used as starting materials and treated in the same way as in Step 2 of Example 12 to give 67 mg (66%) of the title compound as a colorless solid.

$^1$H-NMR (400 MHz, $CD_3OD$) δ: 0.68 (3H, s), 0.94 (3H, s), 1.07-1.88 (9H, m), 2.24-2.34 (1H, m), 3.04-3.15 (2H, m), 3.45-3.65 (2H, m), 3.80-3.95 (3H, m), 4.50 (1H, d, J=9.4 HZ), 4.59 (1H, d, J=9.4 Hz), 6.73 (1H, d, J=1.8 Hz), 6.98-7.08 (2H, m), 7.17-7.24 (1H, m), 7.39-7.46 (1H, m), 7.55-7.65 (1H, m).

MS (ESI) m/z: 620 $(M+H)^+$.

Example 43

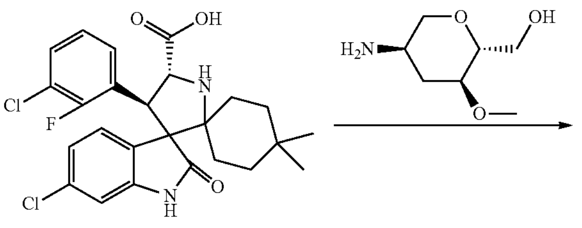

-continued

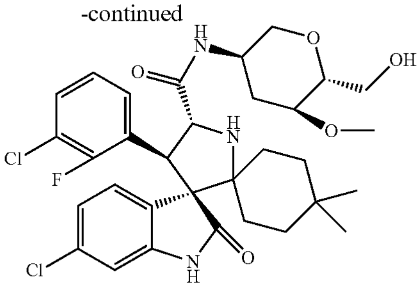

(3'R, 4'S,5'R)-6"-chloro-4'-(3-chloro-2-fluorophenyl)-N-[(3R,5S,6R)-6-(hydroxymethyl)-5-methoxytetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (80 mg, 0.16 mmol) obtained in Step 1 of Example 12 and the compound (34 mg, 0.21 mmol) obtained in Step 4 of Reference Example 23 were used as starting materials and treated in the same way as in Step 2 of Example 12 to give 69 mg (67%) of the title compound as a colorless solid.

$^1$H-NMR (400 MHz, $CD_3OD$) δ: 0.69 (3H, s), 0.95 (3H, s), 1.07-1.91 (9H, m), 2.46-2.56 (1H, m), 3.08-3.27 (3H, m), 3.39 (3H, s), 3.61 (1H, dd, J=11.7, 5.7 Hz), 3.74-3.93 (3H, m), 4.50 (1H, d, J=9.2 Hz), 4.70 (1H, d, J=9.2 Hz), 6.73 (1H, d; J=1.8 Hz), 6.98-7.08 (2H, m), 7.17-7.24 (1H, m), 7.40-7.47 (1H, m), 7.56-7.64 (1H, m).

MS (ESI) m/z: 634 $(M+H)^+$.

Example 44

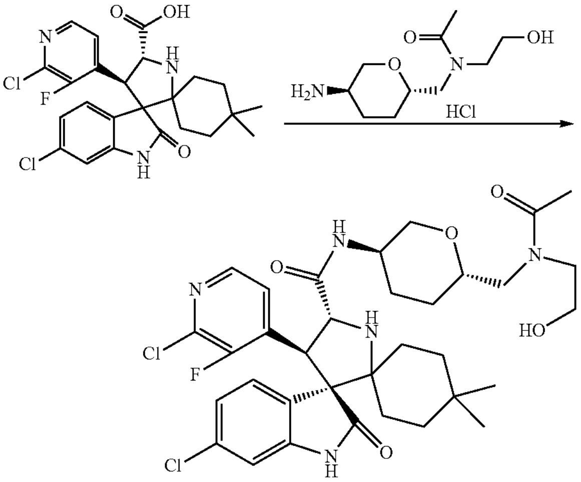

(3'R, 4'S,5'R)—N-(3R,6S)-6-{[acetyl (2-hydroxyethyl)amino methyl}tetrahydro-2H-pyran-3-yl]-6"-chloro-4'-(2-chloro-3-fluoropyridine-4-yl)-4,4-dimethyl-2"-oxo-1",2"-dihydrodispiro[cyclohexane-1,2)-pyrrolidine-3',3"-indole]-5'-carboxamide The compound (237 mg, 0.48 mmol) obtained in Step 1 of Example 17 and the compound (142 mg) obtained in Step 6 of Reference Example 24 were used as starting materials and treated in the same way as in Step 2 of Example 12 to give 171 mg (47%) of the title compound as a pale yellow amorphous solid.

$^1$H-NMR (400 MHz, $CDCl_3$) δ: 0.68 (3H, s), 0.95 (3H, s), 1.11-1.24 (2H, m), 1.32-1.84 (9H, m), 2.08-2.13 (48; m), 2.14 (3H, s), 2.82 (1H, dd, J=14.2, 9.3 Hz), 3.09 (1H, t, J=11.1 Hz), 3.18-3.31 (2H, m), 3.38-3.53 (2H, m), 3.62-3.76 (3H, m), 3.82-3.92 (2H, m), 4.02 (1H, dd, J=10.7, 2.9 Hz), 4.40-4.46 (1H, m), 4.63 (1H, dd, J=9.2, 4.3 Hz), 6.73 (1H, t, J=1.8 Hz), 7.06 (1H, dd, J=8.2, 1.8 Hz), 7.30 (1H, dd, J=8.3, 2.2 Hz), 7.43-7.52 (3H, m), 8.05 (1H, dd, 3=5.1, 2.2 Hz).

MS (ESI) m/z: 690 $(M+H)^+$.

Example 45

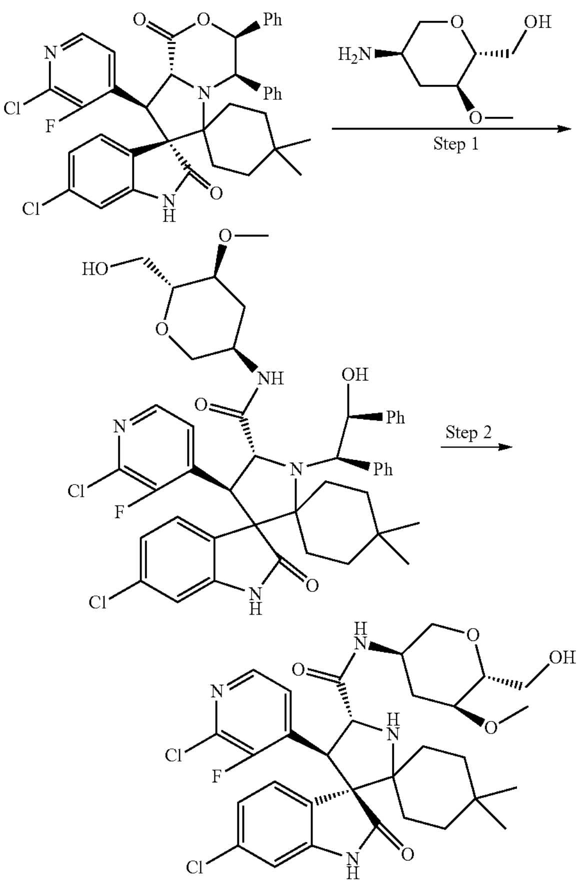

Step 1

(4'S,5'R)-6"-chloro-4'-(2-chloro-3-fluoropyridin-4-yl)-1'-[(1R,2S)-2-hydroxy-1,2-diphenylethyl]-N-[(3R,5S,6R)-6-(hydroxymethyl)-5-methoxytetrahydro-2H-pyran-3-yl]=4,4-dimethyl-2"-oxo-1",2"-dihydrodispiro[cyclohexane-1,2'-pyrrolidine-3',3"-indole]-5'-carboxamide The compound (140 mg, 0.21 mmol) obtained in Step 1 of Example 16 and the compound (101 mg, 0.63 mmol) obtained in Step 4 of Reference Example 23 were used as starting materials and treated in the same way as in Step 1 of Example 5 to give 48 mg (27%) of the title compound as a colorless solid.

MS (ESI) m/z: 833 $(M+H)^+$.

Step 2

(3'R, 4'S,5'R)-6"-chloro-4'-(2-chloro-3-fluoropyridin-4-yl)-N-[(3R,5S,6R)-6-(hydroxymethyl)-5-methoxytetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (48 mg, 0.06 mmol) obtained in Step 1 above was used as a starting material and treated in the same way as in Step 3 of Example 1 to give 26 mg (71%) of the title compound as a colorless solid.

$^1$H-NMR (400 MHz, $CDCl_3$) δ: 0.68 (3H, s), 0.95 (3H, s), 1.09-1.83 (9H, m), 2.09-2.24 (1H, m), 2.48-2.58 (1H, m), 3.08-3.38 (4H, m), 3.40 (3H, s), 3.66-4.06 (4H, m), 4.45 (1H, d, J=9.0 Hz), 4.64 (1H, d, J=9.0 Hz), 6.72 (1H, d, J=1.8 Hz), 7.03-7.09 (1H, m), 7.28-7.35 (1H, m), 7.47-7.52 (1H, m), 7.60 (1H, d, J=8.3 Hz), 7.74 (1H, s), 8.05 (1H, d, J=5.5 Hz).

MS (ESI) m/z: 635 $(M+H)^+$.

Example 46

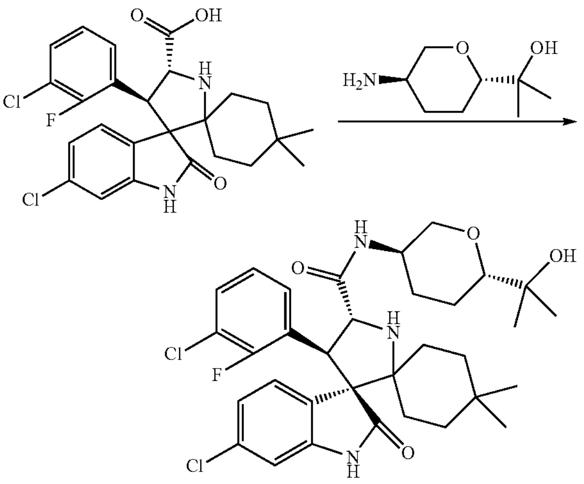

(3'R, 4'S,5'R)-6"-chloro-4'-(3-chloro-2-fluorophenyl)-N-[(3R,6S)-6-(1-hydroxy-1-methylethyl)tetrahydro-2H-pyran-3-yl]-4,4-dimethyl-2'-oxo-1"; 2"-dihydrodispiro[cyclohexane-1,2'-pyrrolidine-3',3"-indole]-5'-carboxamide The compound (40 mg, 0.08 mmol) obtained in Step 1 of Example 12 and the compound (16 mg, 0.10 mmol) obtained in Step 2 of Reference Example 5 were used as starting materials and treated in the same way as in Step 2 of Example 12 to give 15 mg (28%) of the title compound as a colorless solid.

$^1$H-NMR (400 MHz, $CDCl_3$) δ: 0.68 (3H, s), 0.95 (3H, s), 1.09-1.23 (8H, m), 1.32-1.56 (5H, m), 1.57-1.66 (1H, m), 1.69-1.80 (3H, m), 2.08-2.15 (1H, m), 3.07-3.13 (2H, m), 3.82-3.92 (1H, m), 4.06-4.12 (1H, m), 4.45 (1H, d, J=9.2 Hz), 4.67 (1H, d, J=9.2 Hz), 6.69 (1H, d, J=2.3 Hz), 6.87-6.91 (1H, m), 7.05 (1H, dd, J=8.0, 1.7 Hz), 7.10-7.14 (1H, m), 7.33 (1H, dd, J=8.0, 2.3 Hz), 7.46-7.54 (2H, m), 7.72 (1H, s).

MS (ESI) m/z: 632 $(M+H)^+$.

Example 47

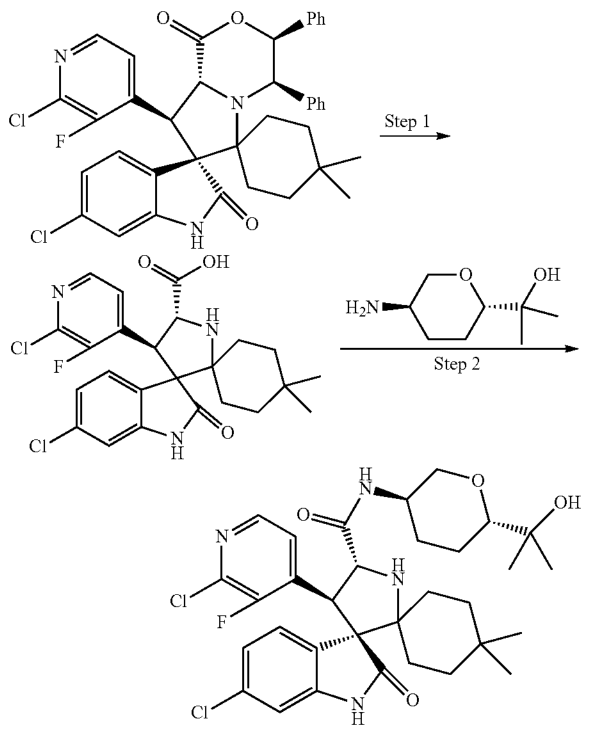

Step 1

(4'S,5'R)-6'-chloro-4'-(2-chloro-3-fluoropyridin-4-yl)-4,4-dimethyl-2"-oxo-1",2"-dihydrodispiro[cyclohexane-1,2'-pyrrolidine-3',3"-pyrrolo[2,3-b]pyridine]-5'-carboxylic acid The compound (406 mg, 0.60 mmol) obtained in Step 25 of Example 1 was used as a starting material and treated in the same way as in Step 1 of Example 12 to give 134 mg (45%) of the title compound as a brown solid.

MS (ESI) m/z: 493 $(M+H)^+$.

Step 2

(3'R, 4'S,5'R)-6"-chloro-4'-(2-chloro-3-fluoropyridin-4-yl)-N-[(3R,6S)-6-(1-hydroxy-1-methylethyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (65 mg, 0.13 mmol) obtained in Step 1 above and the compound (25 mg, 0.16 mmol) obtained in Step 2 of Reference Example 5 were used as starting materials and treated in the same way as in Step 2 of Example 12 to give 20 mg (24%) of the title compound as a pale yellow solid.

$^1$H-NMR (500 MHz, $CDCl_3$) δ: 0.70 (3H, s), 0.96 (3H, s), 1.07-1.82 (16H, m), 2.05-2.16 (1H, m), 2.37-2.49 (1H, m), 3.05-3.14 (2H, m), 3.17-3.41 (1H, m), 3.80-3.92 (1H, m), 4.04-4.12 (1H, m), 4.45 (1H, d, J=9.0 Hz), 4.66 (1H, d, J=9.0 Hz), 7.07 (1H, d, J=8.0 Hz), 7.34-7.40 (1H, m), 7.43-7.48 (1H, m), 7.62 (1H, dd, J=8.0, 2.3 Hz), 7.92 (1H, s), 8.09 (1H, d, J=5.2 Hz).

MS (ESI) m/z: 634 $(M+H)^+$.

Example 48

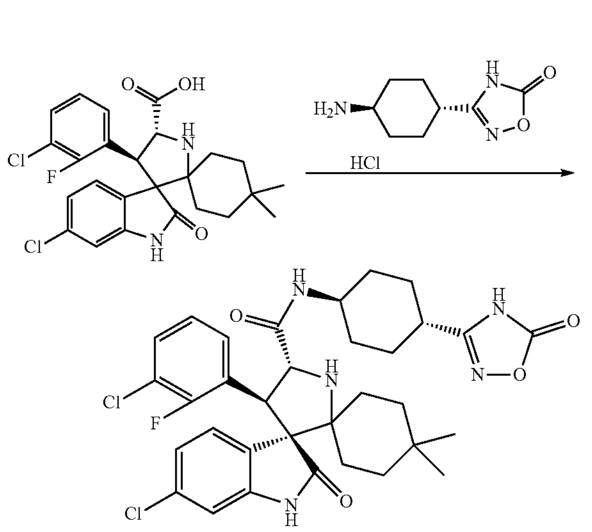

(3'S,4'S,5'R)-6'-chloro-4'-(3-chloro-2-fluorophenyl)-4,4-dimethyl-2"-oxo-N-[trans-4-(5-oxo-4,5-dihydro-1,2,4-oxadiazol-3-yl)cyclohexyl]-1",2"-dihydrodispiro[cyclohexane-1,2'-pyrrolidine-3',3"-indole]-5'-carboxamide The compound (87 mg, 0.18 mmol) obtained in Step 1 of Example 12 and the compound (48 mg, 0.21 mmol) obtained in Step 7 of Reference Example 22 were used as starting materials and treated in the same way as in Step 2 of Example 12 to give 75 mg (64%) of the title compound as a pale yellow solid.

$^1$H-NMR (500 MHz, $CD_3OD$) δ: 0.69 (3H, s), 0.94 (3H, s), 1.09-1.23 (2H, m), 1.27-1.50 (4H, m), 1.52-1.66 (4H, m), 1.76-1.88 (2H, m), 1.95-2.12 (4H, m), 2.57-2.65 (1H, m), 3.61-3.70 (1H, m), 4.48-4.53 (1H, m), 4.54-4.60 (1H, m), 4.68 (1H, d, J=9.2 Hz), 6.73 (1H, d, J=2.3 Hz), 7.00-7.06 (2H, m), 7.18-7.23 (1H, m), 7.43 (1H, dd, J=8.0, 2.3 Hz), 7.59-7.64 (4H, m).

MS (ESI) m/z: 656 $(M+H)^+$.

Example 49

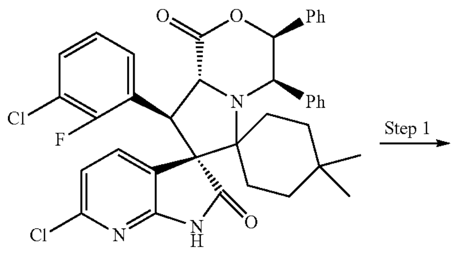

-continued

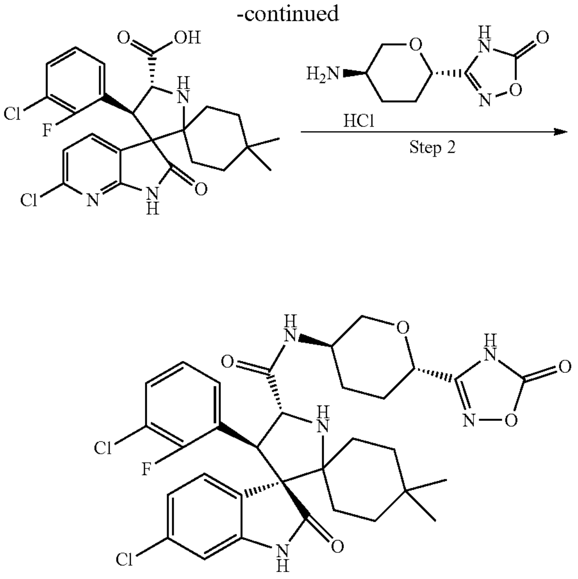

Step 1

(4'S,5'R)-6"-chloro-4'-(3-chloro-2-fluorophenyl)-4,4-dimethyl-2"-oxo-1",2"-dihydrodispiro[cyclohexane-1,2'-pyrrolidine-3',3"-pyrrolo[2,3-b]pyridine]-5'-carboxylic acid The compound (10.6 g, 15.7 mmol) obtained in Step 2 of Example 1 was used as a starting material and treated in the same way as in Step 1 of Example 12 to give 1.79 g (23%) of the title compound as a colorless solid.

$^1$H-NMR (500 MHz, DMSO-$d_6$) δ: 0.61-0.69 (3H, m), 0.84-0.92 (3H, m), 0.99-1.29 (3H, m), 1.33-1.67 (3H, m), 1.73-1.83 (1H, m), 1.96-2.05 (1H, m), 4.51-4.58 (1H, m), 4.68-4.74 (1H, m), 6.86-7.30 (3H, m), 7.37-7.43 (1H, m), 7.49-7.56 (1H, m), 7.92-7.99 (1H, m), 11.30-11.38 (1H, m).

MS (ESI) m/z: 492 $(M+H)^+$.

Step 2

(3'R, 4'S,5'R)-6"-chloro-4'-(3-chloro-2-fluorophenyl)-4,4-dimethyl-2"-oxo-N-[trans-4-(5-oxo-4,5-dihydro-1,2,4-oxadiazol-3-yl)cyclohexyl]-1",2"-dihydrodispiro[cyclohexane-1,2'-pyrrolidine-3',3"-pyrrolo[2,3-b] pyridine]-5'-carboxamide The compound (121 mg, 0.25 mmol) obtained in Step 1 above and the compound (66 mg, 0.29 mmol) obtained in Step 7 of Reference Example 22 were used as starting materials and treated in the same way as in Step 2 of Example 12 to give 56 mg (35%) of the title compound as a light brown solid.

$^1$H-NMR (500 MHz, $CD_3OD$) δ: 0.71 (3H, s), 0.95 (3H, s), 2.64 (1H, m), 3.60-3.70 (1H, m), 4.51-4.60 (2H, m), 4.70 (1H, d, J=9.2 Hz), 7.03-7.10 (1H, m), 7.17-7.29 (2H, m), 7.56-7.62 (1H, m), 7.80-7.86 (1H, m).

MS (ESI) m/z: 657 $(M+H)^+$.

Example 50

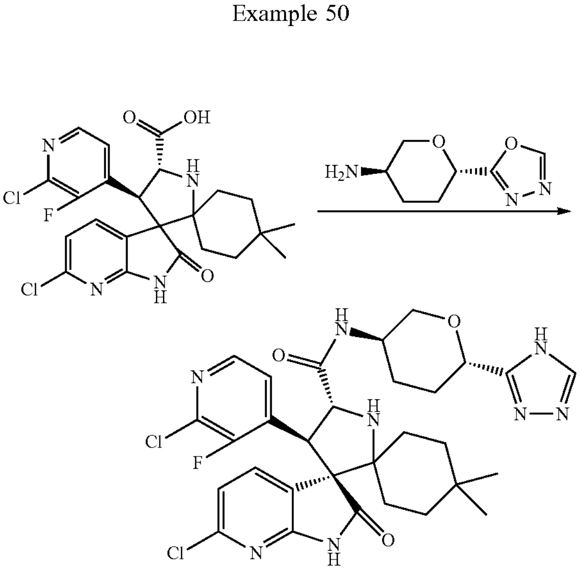

(3'R, 4'S,5'R)-6"-chloro-4'-(2-chloro-3-fluoropyridin-4-yl)-4,4-dimethyl-N-[(3R,6S)-6-(1,3,4-oxadiazol-2-yl)tetrahydro-2H-pyran-3-yl]-2"-oxo-1",2"-dihydrodispiro[cyclohexane-1,2'-pyrrolidine-3',3"-pyrrolo[2,3-b]pyridine]-3'-carboxamide The compound (69 mg, 0.14 mmol) obtained in Step 1 of Example 47 and the compound (28 mg, 0.17 mmol) obtained in Step 6 of Reference Example 18 were used as starting materials and treated in the same way as in Step 2 of Example 12 to give 12 mg (14%) of the title compound as a light brown solid.

$^1$H-NMR (500 MHz, $CDCl_3$) δ: 0.71 (3H, s), 0.98 (3H, s), 1.15-1.79 (8H, m), 2.10-2.29 (4H, m), 3.39 (1H, dd, J=10, 9, 9.2 Hz), 3.98-4.07 (1H, m), 4.09-4.14 (1H, m), 4.48 (1H, d, J=9.2 Hz), 4.67 (1H, d, J=9.2 Hz), 4.78 (1H, dd, J=9.7, 2.9 Hz), 7.09 (1H, d, J=8.0 Hz), 7.44-7.47 (1H, m), 7.58-7.65 (2H, m), 7.67-7.72 (1H, m), 8.10 (1H, d, J=5.2 Hz), 8.42 (1H, s).

MS (ESI) m/z: 644 $(M+H)^+$.

Example 51

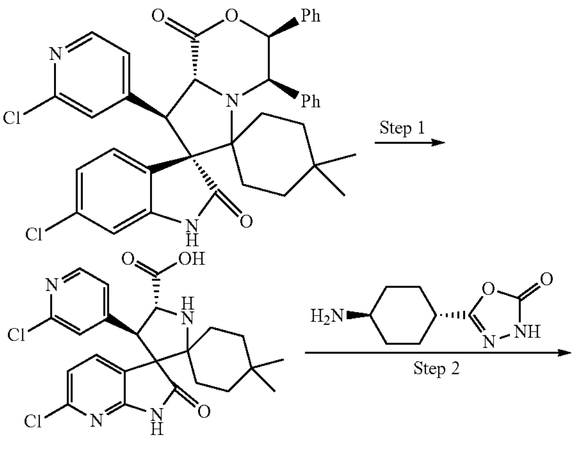

-continued

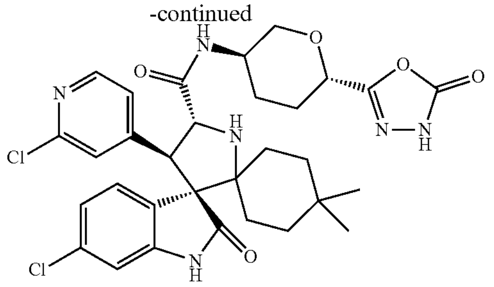

Step 1

(4'R, S'R)-6"-chloro-4'-(2-chloropyridin-4-yl)-4,4-dimethyl-2"-oxo-1",2"-dihydrodispiro[cyclohexane-1,2'-pyrrolidine-3',3"-indole]-5'-carboxylic acid The compound (192 g, 294 mmol) obtained in Step 9 of Example 1 was used as a starting material and treated in the same way as in Step 1 of Example 12 to give 53.6 g (38%) of the title compound as a colorless solid.

$^1$H-NMR (400 MHz, $CD_3OD$) δ: 0.76 (3H, s), 1.01 (3H, s), 1.33 (1H, td, J=14.1, 4.3 Hz), 1.41 (1H, dd, J=14.0, 2.3 Hz), 1.52 (1H, td, J=14.1, 3.7 Hz), 1.61 (1H, dd, J=14.0, 2.3 Hz), 1.80 (1H, td, J=14.1, 3.4 Hz), 1.95 (1H, dd, J=14.1, 2.7 Hz), 2.06 (1H, td, J=14.0, 4.1 Hz), 2.35 (1H, dd, J=14.2, 3.2 Hz), 4.43 (1H, d, J=10.1 Hz), 5.03 (1H, d, J=10.1 Hz), 6.82 (1H, d, J=1.8 Hz), 7.12 (1H, dd, J=5.5, 1.4 Hz), 7.18 (1H, dd, J=8.2, 2.3 Hz), 7.28 (1H, s), 7.66 (1H, d, J=8.2 Hz), 8.14 (1H, d, J=5.5 Hz).

Step 2

(3'R, 4'R, 5'R)-6"-chloro-4'=(2-chloropyridin-4-yl)-4,4-dimethyl-2"-oxo-N-[trans-4-(5-oxo-4,5-dihydro-1,3,4-oxadiazol-2-yl)cyclohexyl]-1",2"-dihydro-dispiro[cyclohexane-1,2'-pyrrolidine-3',3"-indole]-5'-carboxamide The compound (80 mg, 0.17 mmol) obtained in Step 1 above and the compound (37 mg, 0.20 mmol) obtained in Step 2 of Reference Example 19 were used as starting materials and treated in the same way as in Step 2 of Example 12 to give 28 mg (268) of the title compound as a colorless solid.

$^1$H-NMR (500 MHz, $CD_3OD$) δ: 0.68 (3H, s), 0.95 (3H, s), 1.10-1.82 (12H, m), 1.99-2.19 (4H, m), 2.62-2.67 (1H, m), 3.64-3.68 (1H, m), 4.22 (1H, d, J=9.2 Hz), 4.62 (1H, d, J=9.2 Hz), 6.79 (1H, d, J=2.3 Hz), 7.05-7.09 (1H, m), 7.11 (1H, dd, J=8.3, 2.0 Hz), 7.21-7.25 (1H, m), 7.52 (1H, d, J=8.0 HZ), 8.06 (1H, d, J=5.2 Hz).

MS (ESI) m/z: 639 $(M+H)^+$.

Example 52

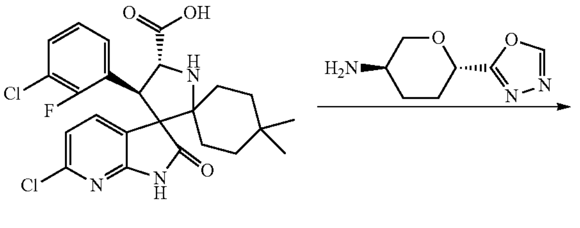

-continued

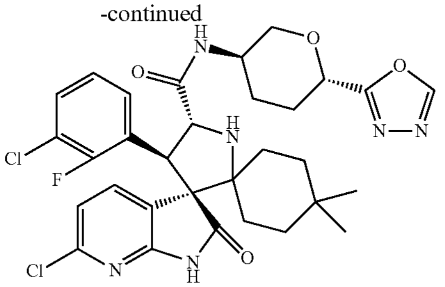

(3'R, 4'S,5'R)-6"-chloro-4'-(3-chloro-2-fluorophenyl)-4,4-dimethyl-N-[(3R,6S)-6-(1,3,4-oxadiazol-2-yl)tetrahydro-2H-pyran-3-yl]-2"-oxo-1",2"-dihydro-dispiro[cyclohexane-1,2'-pyrrolidine-3',3"-pyrrolo[2,3-b]pyridine]-5'-carboxamide The compound (84 mg, 0.17 mmol) obtained in Step 1 of Example 49 and the compound (35 mg, 0.20 mmol) obtained in Step 6 of Reference Example 18 were used as starting materials and treated in the same way as in Step 2 of Example 12 to give 97 mg (898) of the title compound as a colorless solid.

$^1$H-NMR (500 MHz, $CDCl_3$) δ: 0.71 (3H, s), 0.97 (3H, s), 1.14-1.27 (2H, m), 1.33-1.44 (1H, m), 1.46-1.58 (2H, m), 1.61-1.86 (4H, m), 2.09-2.29 (3H, m), 3.38 (1H, dd, J=11, 2, 9.5 Hz), 3.99-4.08 (1H, m), 4.09-4.15 (1H, m), 4.51 (1H, d, J=9.2 Hz), 4.70 (1H, d, J=9.2 Hz), 4.78 (1H, dd, J=10.0, 2.6 Hz), 6.94 (1H, t, J=8.0 Hz), 7.05 (1H, d, J=8.0 Hz), 7.13-7.18 (1H, m), 7.45-7.51 (1H, m), 7.62-7.68 (2H, m), 8.43 (1H, s), 8.72 (1H, s).

MS (ESI) m/z: 643 $(M+H)^+$.

Example 53

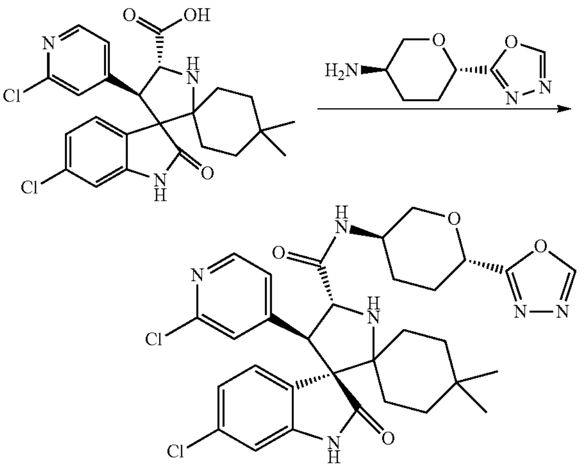

(3'R, 4'R, 5'R)-6"-chloro-4'-(2-chloropyridin-4-yl)-4,4-dimethyl-N-[(3R,6S)-6-(1,3,4-oxadiazol-2-yl)tetrahydro-2-pyran-3-yl]-2"-oxo-1",2"-dihydrodispiro[cyclohexane-1,2'-pyrrolidine-3',3"-indole]-5'-carboxamide The compound (81 mg, 0.17 mmol) obtained in Step 1 of Example 51 and the compound (35 mg, 0.20 mmol) obtained in Step 6 of Reference Example 18 were used as starting materials and treated in the same way as in Step 2 of Example 12 to give 74 mg (69%) of the title compound as a colorless solid.

$^1$H-NMR (500 MHz, $CDCl_3$) δ: 0.70 (3H, s), 0.96 (3H, s), 1.12-1.27 (2H, m), 1.33-1.41 (1H, m), 1.43-1.81 (6H, m), 2.10-2.28 (3H, m), 3.22-3.36 (1H, m), 3.41 (1H, dd, J=10.9, 9.2 Hz), 3.98-4.08 (1H, m), 4.09-4.18 (2H, m), 4.53 (1H, d, J=9.2 Hz), 4.78 (1H, dd, J=9.2, 2.9 Hz), 6.78 (1H, d, J=1.7 Hz), 6.90 (1H, dd, J=5.2, 1.7 Hz), 7.07-7.09 (1H, m), 7.12 (1H, dd, J=8.3, 2.0 Hz), 7.29 (1H, d, J=8.0 Hz), 7.44 (1H, s), 7.72 (1H, d, J=8.6 Hz), 8.11 (1H, d, J=5.2 Hz), 8.43 (1H, s).

MS (ESI) m/z: 625 $(M+H)^+$.

Example 54

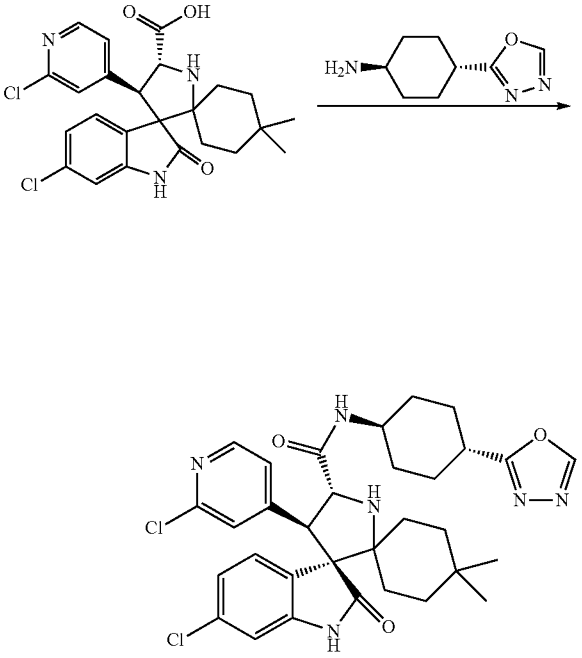

(3'R, 4'R, 5'R)-6"-chloro-4'-(2-chloropyridin-4-yl)-4, 4-dimethyl-N-[trans-4-(1,3,4-oxadiazol-2-yl)cyclohexyl]-2"-oxo-1",2"-dihydrodispiro[cyclohexane-1, 2'-pyrrolidine-3',3"-indole]-5'-carboxamide The compound (86 mg, 0.18 mmol) obtained in Step 1 of Example 51 and the compound (36 mg, 0.22 mmol) obtained in Step 3 of Reference Example 3 were used as starting materials and treated in the same way as in Step 2 of Example 12 to give 81 mg (72%) of the title compound as a colorless solid.

$^1$H-NMR (500 MHz, $CDCl_3$) δ: 0.69 (3H, s), 0.96 (3H, s), 1.12-1.24 (2H, m), 1.32-1.44 (3H, m), 1.45-1.54 (2H, m), 1.56-1.83 (5H, m), 2.06-2.29 (4H, m), 2.92-3.00 (1H, m), 3.14-3.46 (1H, m), 3.75-3.85 (1H, m), 4.12 (1H, d, J=8.6 Hz), 4.51 (1H, d, J=8.6 Hz), 6.78 (1H, d, J=1.7 Hz), 6.91 (1H, do, J=5.15, 1.7 Hz), 7.08-7.12 (2H, m), 7.29 (1H, d, J=8.0 Hz), 7.66 (1H, d, J=8.0 Hz), 7.73 (1H, s), 8.09 (1H, d, J=5.2 Hz), 8.34 (1H, s).

MS (ESI) m/z: 623 $(M+H)^+$.

Example 55

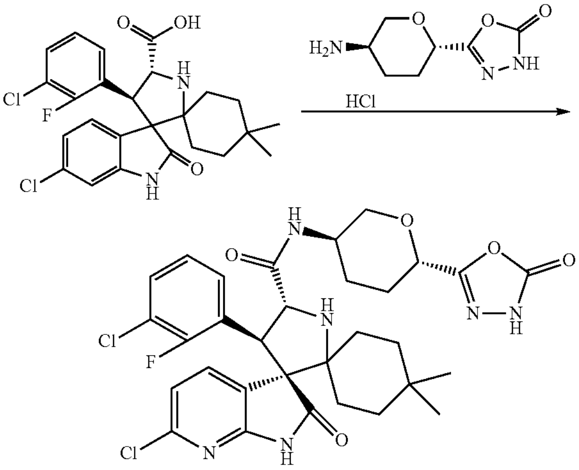

(3'R, 4'S,5'R)-6"-chloro-4'-(3-chloro-2-fluorophenyl)-4,4-dimethyl-2"-oxo-N-[(3R,6S)-6-(5-oxo-4,5-dihydro-1,3,4-oxadiazol-2-yl)tetrahydro-2H-pyran-3-yl]-1",2"-dihydrodispiro[cyclohexane-1,2'-pyrrolidine-3',3"-pyrrolo[2,3-b]pyridine]-5'-carboxamide The compound (76 mg, 0.15 mmol) obtained in Step 1 of Example 49 and the compound (41 mg, 0.18 mmol) obtained in Step 3: of Reference Example 25 were used as starting materials and treated in the same way as in Step 2 of Example 12 to give 67 mg (668) of the title compound as a colorless solid.

$^1$H-NMR (500 MHz, $CDCl_3$) δ: 0.71 (3H, s), 0.97 (3H, s), 1.14-1.81 (9H, m), 1.95-2.12 (2H, m), 2.16-2.23 (1H, m), 3.19-3.28 (1H, m), 3.28-3.35 (1H, m), 3.94-4.04 (1H, m), 4.08-4.15 (1H, m), 4.37 (1H, dd, J=10.0, 3.2 Hz), 4.46-4.52 (1H, m), 4.69 (1H, d, J=9.7 Hz), 6.95-7.01 (1H, m), 7.06 (1H, d, J=8.02 Hz), 7.15-7.20 (1H, m), 7.44-7.50 (1H, m), 7.60-7.66 (2H, m), 7.75-7.92 (1H, m).

MS (ESI) m/z: 659 $(M+H)^+$.

Example 56

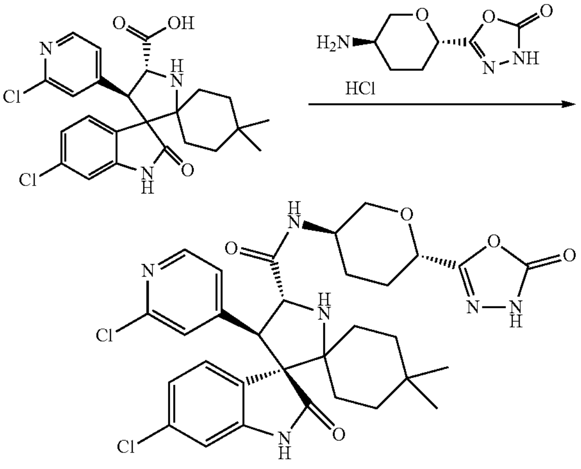

(3'R, 4'R, 5'R)-6"-chloro-4'-(2-chloropyridin-4-yl)-4,4-dimethyl-2"-Oxo-N-[(3R,6S)-6-(5-oxo-4,5-dihydro-1,3,4-oxadiazol-2-yl)tetrahydro-2H-pyran-3-yl]-1",2"-dihydrodispiro[cyclohexane-1,2'-pyrrolidine-3',3"-indole]-5'-carboxamide The compound (85 mg, 0.18 mmol) obtained in Step 1 of Example 51 and the compound (48 mg, 0.21 mmol) obtained in Step 3 of Reference Example 25 were used as starting materials and treated in the same way as in Step 2 of Example 12 to give 34 mg (29%) of the title compound as a colorless solid.

$^1$H-NMR (400 MHz, $CDCl_3$) δ: 0.69 (3H, s), 0.95 (3H, s), 1.11-1.81 (9H, m), 1.94-2.21 (3H, m), 3.30-3.38 (1H, m), 3.93-4.04 (1H, m), 4.08-4.17 (2H, m), 4.38 (1H, dd, J=9.6, 3.2 Hz), 4.52 (1H, d, J=8.7 Hz), 6.78 (1H, d, J=1.8 Hz), 6.90 (1H, dd, J=5.3, 1.6 Hz), 7.06-7.09 (1H, m), 7.11 (1H, dd, J=8.3, 1.8 Hz), 7.29 (1H, d, J=8.3 Hz), 7.70-7.75 (2H, m), 8.10 (1H, d, J=5.5 Hz).

MS (ESI) m/z: 641 $(M+H)^+$.

Example 57

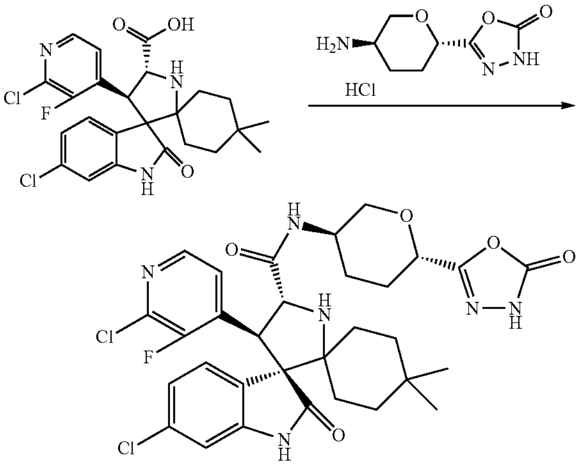

(3'R, 4'S,5'R)-6"-chloro-4'-(2-chloro-3-fluoropyridin-4-yl)-4,4-dimethyl-2"-oxo-N-[(3R,6S)-6-(5-oxo-4,5-dihydro-1,3,4-oxadiazol-2-yl)tetrahydro-2H-pyran-3-yl]-1",2"-dihydrodispiro[cyclohexane-1,2'-pyrrolidine-3',3"-indole]-5'-carboxamide The compound (81 mg, 0.17 mmol) obtained in Step 1 of Example 17 and the compound (44 mg, 0.20 mmol) obtained in Step 3 of Reference Example 25 were used as starting materials and treated in the same way as in Step 2 of Example 12 to give 57 mg (52%) of the title compound as a colorless solid.

$^1$H-NMR (400 MHz, $CDCl_3$) δ: 0.68 (3H, s), 0.95. (3H, s), 1.09-1.82 (9H, m), 1.95-2.14 (2H, m), 2.15-2.25 (1H, m), 3.21-3.39 (2H, m), 3.94-4.05 (1H, m), 4.07-4.14 (1H, m), 4.38 (1H, dd, J=9.9, 3.4 Hz), 4.47 (1H, d, J=8.7 Hz), 4.65 (1H, d, J=9.2H %), 6.73 (1H, d, J=2.3 Hz), 7.07 (1H, dd, J=8.3, 1.8 Hz), 7.32 (1H, dd, J=8.0, 2.1 Hz), 7.50 (1H, t, J=5.0 Hz), 7.62 (1H, s), 7.68 (1H, d, J=8.3 Hz), 8.05 (1H, d, J=5.0 Hz), 9.23 (1H, s).

MS (ESI) m/z: 659 $(M+H)^+$.

Example 58

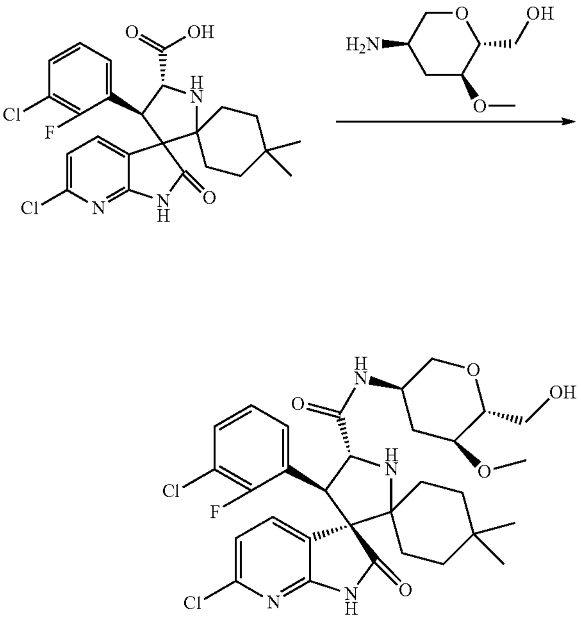

(3'R, 4'S,5'R)-6"-chloro-4'-(3-chloro-2-fluorophenyl)-N-[(3R,5S,6R)-6-(hydroxymethyl)-5-methoxytetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (80 mg, 0.16 mmol) obtained in Step 1 of Example 49 and the compound (30 mg, 0.18 mmol) obtained in Step 4 of Reference Example 23 were used as starting materials and treated in the same way as in Step 2 of Example 12 to give 48 mg (47%) of the title compound as a colorless solid.

$^1$H-NMR (400 MHz, $CDCl_3$) δ: 0.71 (3H, s), 0.96 (3H, s), 1.16-1.77 (9H, m), 1.98-2.04 (1H, m), 2.48-2.58 (1H, m), 3.07-3.30 (4H, m), 3.40 (3H, s), 3.67-3.74 (1H, m), 3.81-3.89 (1H, m), 3.94-4.05 (2H, m), 4.44-4.53 (1H, m), 4.68 (1H, d, J=9.2 Hz), 6.96-7.03 (1H, m), 7.05 (1H, d, J=7.8 Hz), 7.15-7.22 (1H, m), 7.44-7.66 (4H, m).

MS (ESI) m/z: 635 $(M+H)^+$.

Example 59

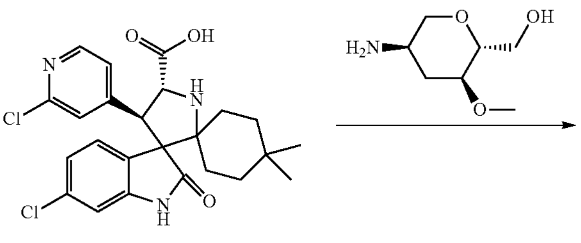

-continued

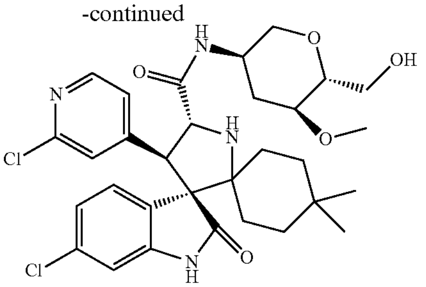

(3'R, 4'R, 5'B)-6"-chloro-4'-(2-chloropyridin-4-yl)-N-[(3R,5S,6R)-6-(hydroxymethyl)-5-methoxytetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (80 mg, 0.17 mmol) obtained in Step 1 of Example 51 and the compound (36 mg, 0.22 mmol) obtained in Step 4 of Reference Example 23 were used as starting materials and treated in the same way as in Step 2 of. Example 12 to give 48 mg (46%) of the title compound as a colorless solid.

$^{1}$H-NMR (400 MHz, $CDCl_3$) δ: 0.69 (3H, s), 0.95 (3H, s), 1.13-1.78 (9H, m), 1.99-2.05 (1H, m), 2.47-2.57 (1H, m), 3.10-3.32 (4H, m), 3.40 (3H, s), 3.67-3.76 (1H, m), 3.82-4.06 (3H, m), 4.10 (1H, d, J=8.7 Hz), 4.51 (1H, d, J=8.7 Hz), 6.78 (1H, d, J=2.3 Hz), 6.87-6.91 (1H, m), 7.06-7.13 (2H, m), 7.25-7.29 (2H, m), 7.62 (1H, d, J=8.3 Hz), 8.11 (1H, d, J=5.0 Hz).

MS (ESI) m/z: 617 $(M+H)^+$.

Example 60

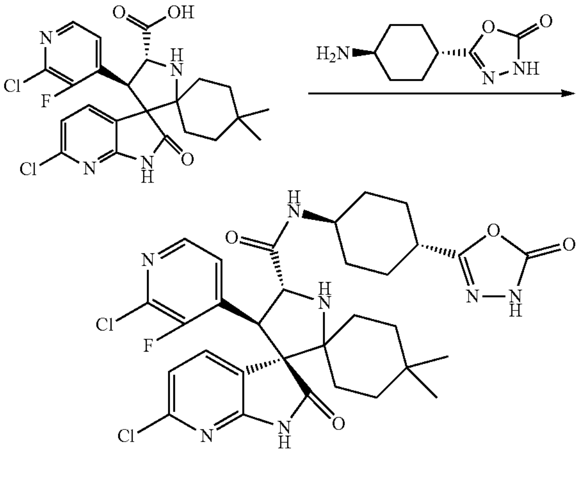

(3'R, 4'S,5'R)-5"-chloro-4'-(2-chloro-3-fluoropyridin-4-yl)-4,4-dimethyl-2"-oxo-N-[trans-4-(5-oxo-4,5-dihydro-1,3,4-oxadiazol-2-yl)cyclohexyl]-1",2"-dihydrodispiro[cyclohexane-1,2'-pyrrolidine-3',3"-pyrrolo[2,3-b]pyridine]-5'-carboxamide The compound (96 mg, 0.19 mmol) obtained in Step 1 of Example 47 and the compound (43 mg, 0.23 mmol) obtained in Step 2 of Reference Example 19 were used as starting materials and treated in the same way as in Step 2 of Example 12 to give 51 mg (40%) of the title compound as a colorless solid.

$^{1}$H-NMR (500 MHz, $CD_3OD$) δ: 0.71 (3H, s), 0.96 (3H, s), 1.15-1.84 (12H, m), 1.95-2.18 (4H, m), 2.59-2.68 (1H, m), 3.61-3.70 (1H, m), 4.58 (1H, d, J=9.2 Hz), 4.69 (1H, d, J=9.2 Hz), 7.09 (1H, d, J=8.0 Hz), 7.62-7.67 (1H, m), 7.87 (1H, dd, J=7.7, 2.0 Hz), 8.09 (1H, d, J=5.2 Hz).

MS (ESI) m/z: 658 $(M+H)^+$.

Example 61

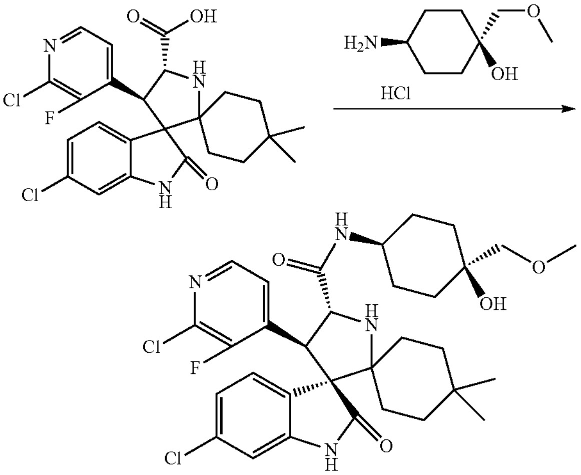

(3'R, 4'S,5'R)-6"-chloro-4'-(2-chloro-3-fluoropyridin-4-yl)-N-[cis-4-hydroxy-4-(methoxymethyl)cyclohexyl]-4,4-dimethyl-2"-oxo-1",2"-dihydrodispiro[cyclohexane-1,2'-pyrrolidine-3',3"-indole]-5'-carboxamide The compound (100 mg, 0.20 mmol) obtained in Step 1 of Example 17 and the compound (0.31 mmol) obtained in Step 2 of Reference Example 31 were used as starting materials and treated in the same way as in Step 2 of Example 12 to give 80 mg (62%) of the title compound as a colorless solid.

$^{1}$H-NMR (DMSO-$d_6$) δ: 0.60 (3H, s), 0.89 (3H, s), 0.33-1.00 (1H, m), 1.11-1.14 (1H, m), 1.22-1.30 (1H, m), 1.33-1.65 (11H, m), 1.67-1.77 (2H, m), 3.10 (2H, s), 3.26 (3H, s), 3.39-3.44 (1H, m), 3.54-3.56 (1H, m), 4.21 (1H, s), 4.43 (1H, t, J=9.2 Hz), 4.54 (1H, d, J=9.2 Hz), 6.71 (1H, d, J=1.8 Hz), 7.05 (1H, dd, J=8.0, 2.1 Hz), 7.50 (1H, dd, J=8.3, 1.8 Hz), 7.63 (1H, t, J=5.0 Hz), 7.72 (1H, d, J=8.3 Hz), 8.18 (1H, d, J=5.0 Hz), 10.61 (1H, s).

MS (ESI) m/z: 633 $(M+H)^+$.

Example 62

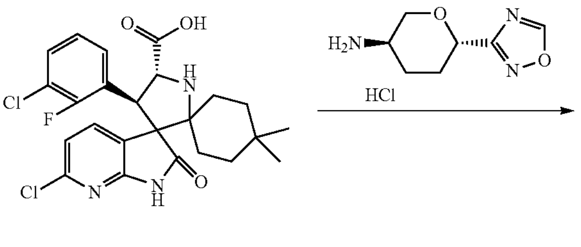

-continued

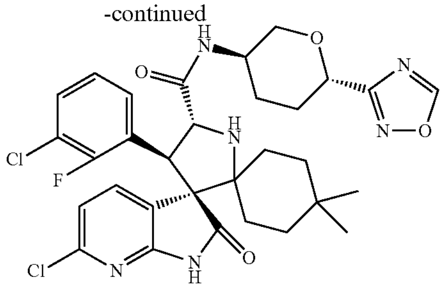

(3'R, 4'S,5'R)-6"-chloro-4'-(3-chloro-2-fluorophenyl)-4,4-dimethyl-N-[(3R,6S)-6-(1,2,4-oxadiazol-3-yl)tetrahydro-2H-pyran-3-yl]-2"-oxo-1",2"-dihydrodispiro[cyclohexane-1,2'-pyrrolidine-3',3"-pyrrolo[2,3-b]pyridine]-5'-carboxamide The compound (87 mg, 0.18 mmol) obtained in Step 1 of Example 49 and the compound (44 mg, 0.21 mmol) obtained in Step 4 of Reference Example 26 were used as starting materials and treated in the same way as in Step 2 of Example 12 to give 91 mg (80%) of the title compound as a colorless solid.

$^1$H-NMR (400 MHz, $CDCl_3$) δ: 0.71 (3H, s), 0.97 (3H, s), 1.13-1.28 (2H, m), 1.32-1.85 (7H, m), 2.01-2.12 (1H, m), 2.15-2.27 (2H, m), 3.33-3.42 (1H, m), 4.01-4.10 (1H, m), 4.16-4.23 (1H, m), 4.50 (1H, d, J=9.2 Hz), 4.68-4.74 (2H, m), 6.95 (1H, t, J=8.0 Hz), 7.06 (1H, d, J=8.0 Hz), 7.13-7.18 (1H, m), 7.45-7.50 (1H, m), 7.59-7.66 (2H, m), 8.36 (1H, s), 8.72 (1H, s).

MS (ESI) m/z: 643 $(M+H)^+$.

Example 63

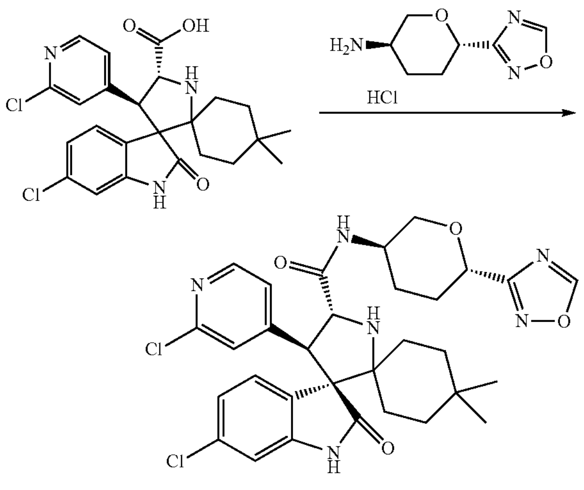

(3'R,4'R,5'R)-6"-chloro-4'-(2-chloropyridin-4-yl)-4,4-dimethyl-N-[(3R,6S)-6-(1,2,4-oxadiazol-3-yl)tetrahydro-2H-pyran-3-yl]-2"-oxo-1",2"-dihydrodispiro[cyclohexane-1,2'-pyrrolidine-3',3"-indole]-5'-carboxamide The compound (86 mg, 0.18 mmol) obtained in Step 1 of Example 51 and the compound (45 mg, 0.22 mmol) obtained in Step 4 of Reference Example 26 were used as starting materials and treated in the same way as in Step 2 of Example 12 to give 71 mg (63%) of the title compound as a colorless solid.

$^1$H-NMR (500 MHz, $CDCl_3$) δ: 0.69 (3H, s), 0.96 (3H, s), 1.12-1.27 (2H, m), 1.32-1.40 (1H, m), 1.45-1.80 (6H, m), 2.02-2.13 (1H, m), 2.15-2.24 (2H, m), 3.36-3.43 (1H, m), 4.01-4.10 (1H, m), 4.12 (1H, d, J=8.6 Hz), 4.19-4.25 (1H, m), 4.52 (1H, d, J=8.6 Hz), 4.72 (1H, dd, J=10.3, 2.3 Hz), 6.77 (1H, d, J=2.3 Hz), 6.88-6.92 (1H, m), 7.06-7.09 (1H, m), 7.11 (1H, dd, J=8.0, 1.7 Hz), 7.29 (1H, d, J=8.0 Hz), 7.56 (1H, s), 7.69 (1H, d, J=8.6 Hz), 8.10 (1H, d, J=5.2 Hz), 8.73 (1H, s).

MS (ESI) m/z: 625 $(M+H)^+$.

Example 64

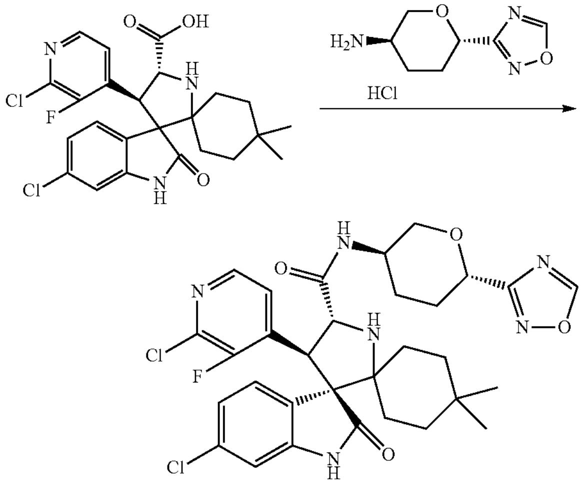

(3'R, 4'S,5'R)-6"-chloro-4'-(2-chloro-3-fluoropyridin-4-yl)-4,4-dimethyl-N-[(3R,6S)-6-(1,2,4-oxadiazol-3-yl)tetrahydro-2H-pyran-3-yl]-2"-oxo-1",2"-dihydrodispiro[cyclohexane-1,2'-pyrrolidine-3',3"-indole]-5'-carboxamide The compound (84 mg, 0.17 mmol) obtained in Step 1 of Example 17 and the compound (42 mg, 0.20 mmol) obtained in Step 4 of Reference Example 26 were used as starting materials and treated in the same way as in Step 2 of Example 12 to give 92 mg (82%) of the title compound as a colorless solid.

$^1$H-NMR (500 MHz, $CDCl_3$) δ: 0.69 (3H, s), 0.96 (3H, s), 1.12-1.27 (2H, m), 1.35-1.42 (1H, m), 1.45-1.55 (2H, m), 1.57-1.83 (4H, m), 2.03-2.13 (1H, m), 2.15-2.28 (2H, m), 3.22-3.45 (2H, m), 4.00-4.11 (1H, m), 4.15-4.22 (1H, m), 4.47 (1H, d, J=9.2 Hz), 4.65 (1H, d, J=9.2 Hz), 4.72 (1H, dd, J=10.3, 2.3 Hz), 6.72 (1H, d, J=1.7 Hz), 7.06 (1H, dd, J=8, 3, 2.0 Hz), 7.29-7.34 (1H, m), 7.50 (1H, t, J=5.2 Hz), 7.66 (1H, d, J=8.6 Hz), 7.82 (1H, s), 8.04 (1H; d, J=5.2 Hz), 8.73 (1H, s).

MS (ESI) m/z: 643 $(M+H)^+$.

Example 65

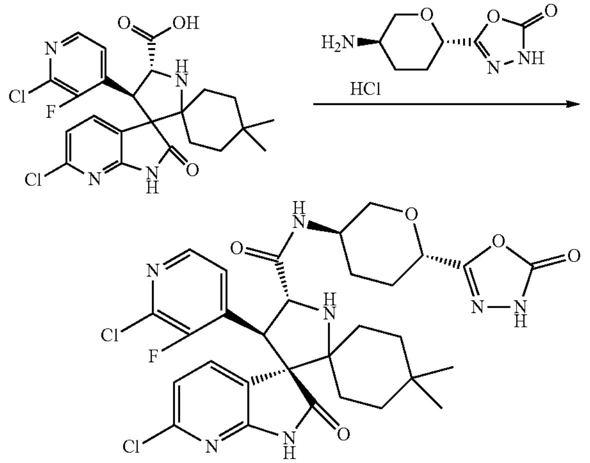

(3'R, 4'S,5'R)-6"-chloro-4'-(2-chloro-3-fluoropyridin-4-yl)-4,4-dimethyl-2"-oxo-N-[(3R,6S)-6-(5-oxo-4,5-dihydro-1,3,4-oxadiazol-2-yl)tetrahydro-2H-pyran-3-yl]-1",2"-dihydrodispiro[cyclohexane-1,2'-pyrrolidine-3',3"-pyrrolo[2,3-b]pyridine]-5'-carboxamide The compound (87 mg, 0.18 mmol) obtained in Step 1 of Example 47 and the compound (47 mg, 0.21 mmol) obtained in Step 3 of Reference Example 25 were used as starting materials and treated in the same way as in Step 2 of Example 12 to give 54 mg (46%) of the title compound as a colorless solid.

$^1$H-NMR (400 MHz, $CD_3OD$) δ: 0.71 (3H, s), 0.96 (3H, s), 1.08-2.20 (12H, m), 3.34-3.41 (1H, m), 3.82-3.91 (1H, m), 3.93-4.00 (1H, m), 4.42 (1H, dd, J=10.1, 3.2 Hz), 4.60 (1H, d, J=9.2 Hz), 4.71 (1H, d, J=9.2 Hz), 7.10 (1H, d, J=8.0 Hz), 7.61-7.66 (1H, m), 7.87 (1H, dd, J=8.0, 2.3 Hz), 8.09 (1H, d, J=5.2 Hz),

MS (ESI) m/z: 660 $(M+H)^+$.

Example 66

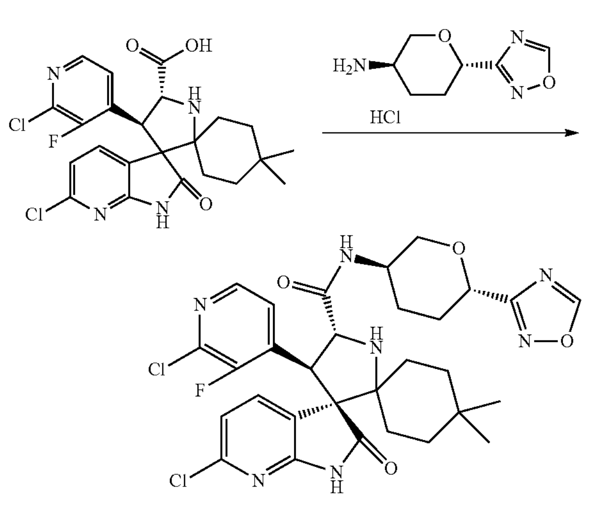

(3'R, 4'S,5'R)-6"-chloro-4'-(2-chloro-3-fluoropyridin-4-yl)-4,4-dimethyl-N-[(3R,6S)-6-(1,2,4-oxadiazol-3-yl)tetrahydro-2H-pyran-3-yl]-2"-oxo-1",2"-dihydrodispiro[cyclohexane-1,2'-pyrrolidine-3',3"-pyrrolo[2,3-b]pyridine]-5'-carboxamide The compound (88 mg, 0.18 mmol) obtained in Step 1 of Example 47 and the compound (44 mg, 0.21 mmol) obtained in Step 4 of Reference Example 26 were used as starting materials and treated in the same way as in Step 2 of. Example 12 to give 81 mg (71%) of the title compound as a colorless solid, $^1$H-NMR (500 MHz, $CDCl_3$) δ: 0.71 (3H, s), 0.97 (3H, s), 1.15-1.29 (2H, m), 1.35-1.43 (1H, m), 1.45-1.79 (6H, m), 2.02-2.13 (1H, m), 2.16-2.26 (2H, m), 3.20-3.47 (2H, m), 4.00-4.11 (1H, m), 4.16-4.22 (1H, m), 4.48 (1H, d, J=9.2 Hz), 4.65-4.74 (2H, m), 7.08 (1H, d, J=8.0 Hz), 7.46 (1H, t, J=4.3 Hz), 7.57 (1H, d, J=8.0 Hz), 7.63 (1H, dd, J=7.5, 2.3 Hz), 8.09 (1H, d, J=5.2 Hz), 8.28 (1H, br s), 8.73 (1H, s).

MS (ESI) m/z: 644 $(M+H)^+$.

Example 67

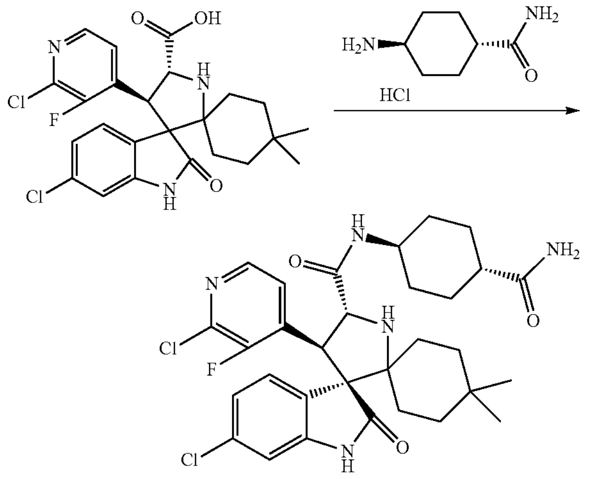

(3'R, 4'S,5'R)—N-(trans-4-carbamoylcyclohexyl)-6"-chloro-4'-(2-chloro-3-fluoropyridin-4-yl)-4,4-dimethyl-2'-oxo-1",2"-dihydrodispiro[cyclohexane-1,2'-pyrrolidine-3',3"-indole]-5'-carboxamide The compound (200 mg, 0.41 mmol) obtained in Step 1 of Example 17 and trans-4-aminocyclohexanecarboxamide hydrochloride (WO2005/058892) (87 mg, 0.49 mmol) were used as starting materials and treated in the same way as in Step 2 of Example 12 to give 53 mg (21%) of the title compound as a colorless solid.

$^1$H-NMR (400 MHz, $CD_3OD$) δ: 0.67 (3H, s), 0.93 (3H, s), 1.09-1.22 (2H, m), 1.26-1.41 (3H, m), 1.49-1.64 (4H, m), 1.76-1.81 (3H, m), 1.86-2.07 (4H, m), 2.18-2.27 (1H, m), 3.57-3.66 (1H, m), 4.52 (1H, d, J=9.2 Hz), 4.65 (1H, d, J=9.2 Hz), 6.76 (1H, d, J=1.8 Hz), 7.05 (1H, dd, J=8.0, 2.1 Hz), 7.45 (1H, dd, J=8.2, 2.3 (z), 7.65 (1H, t, J=5.0 Hz), 8.04 (1H, d, J=5.0 Hz).

MS (ESI) m/z: 616 $(M+H)^+$.

Example 68

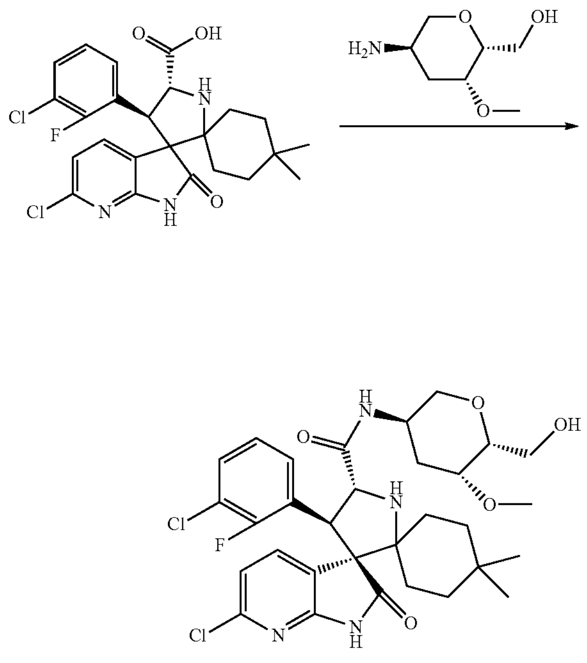

(3'R, 4'S,5'R)-6"-chloro-4'-(3-chloro-2-fluorophenyl)-N-[(3R,5R,6R)-6-(hydroxymethyl)-5-methoxytetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (70 mg, 0.14 mmol) obtained in step 1 of Example 49 and the compound (25 mg, 0:16 mmol) obtained in Step 5 of Reference Example 27 were used as starting materials and treated in the same way as in Step 2 of Example 12 to give 78 mg (86%) of the title compound as a colorless solid.

$^1$H-NMR (400 MHz, $CDCl_3$) δ: 0.70 (3H, s), 0.96 (3H, s), 1.10-1.82 (9H, m), 2.20-2.49 (2H, m), 3.18-3.28 (1H, m), 3.40 (3H, s), 3.45-3.55 (2H, m), 3.63-3.77 (1H, m), 3.84-3.94 (1H, m), 4.05-4.28 (2H, m), 4.47 (1H, d, J=9.2 Hz), 4.70 (1H, d, J=9.2 Hz), 6.91-6.99 (1H, m), 7.05 (1H, d, J=7.8 Hz), 7.11-7.19 (1H, m), 7.42-7.69 (3H, m), 8.22-8.32 (1H, m).

Example 69

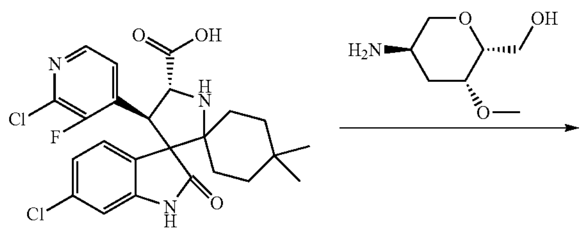

-continued

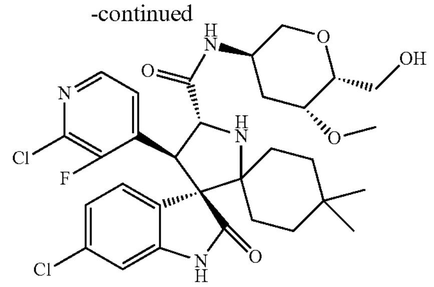

(3'R, 4'S,5'R)-6"-chloro-4'-(2-chloro-3-fluoropyridin-4-yl)-N-((3R,5R,6R)-6-(hydroxymethyl)-5-methoxytetrahydro-2H-pyran-3-yl)-4,4-dimethyl-2"-oxo-1",2"-dihydrodispiro[cyclohexane-1,2'-pyrrolidine-3',3"-indole]-5'-carboxamide The compound (70 mg, 0.14 mmol) obtained in Step 1 of Example 17 and the compound (25 mg, 0.16 mmol) obtained in Step 5 of Reference Example 27 were used as starting materials and treated in the same way as in Step 2 of Example 12 to give 66 mg (73%) of the title compound as a colorless solid.

$^1$H-NMR (400 MHz, $CDCl_3$) δ: 0.69 (3H, s), 0.95 (3H, s), 1.10-1.82 (9H, m), 2.16-2.23 (1H, m), 2.38-2.49 (1H, m), 3.20-3.28 (1H, m), 3.41 (38, s), 3.46-3.55 (2H, m), 3.66-3.76 (14, m), 3.85-3.94 (1H, m), 4.06-4.28 (2H, m), 4.44 (1H, d, J=9.2 Hz), 4.66 (1H, d, J=9.2 Hz), 6.74 (1H, d, J=1.8 Hz), 7.07 (1H, dd, J=8.3, 1.8 Hz), 7.31-7.54 (4H, m), 8.05 (1H, d, J=5.5 Hz).

MS (ESI) m/z: 6.35 $(M+H)^+$.

Example 70

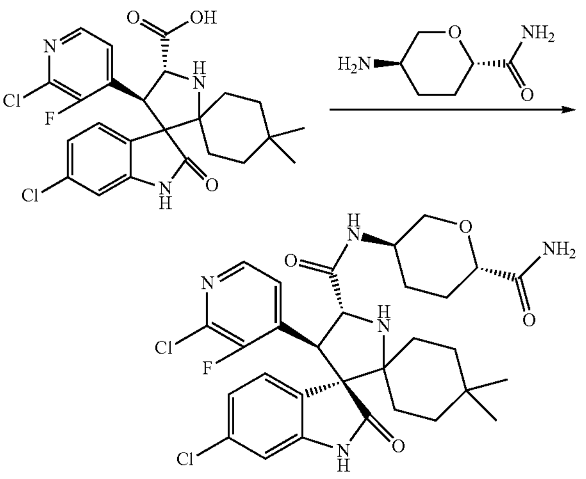

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide The compound (100 mg, 0.20 mmol) obtained in Step 1 of Example 17 and the compound (35 mg, 0.24 mmol)

obtained in Step 3 of Reference Example 28 were used as starting materials and treated in the same way as in Step 2 of Example 12 to give 94 mg (76%) of the title compound as a colorless solid, $^1$H-NMR (400 MHz, $CDCl_3$) δ: 0.68 (3H, s), 0.95 (3H, s), 1.11-1.27 (2H, m), 1.35-1.81 (8H, m), 2.10-2.17 (1H, m), 2.25-2.32 (1H, m), 3.15 (1H, t, J=10.5 Hz), 3.27 (1H, br s), 3.80 (1H, dd, J=11.0, 2.3 Hz), 3.85-3.95 (1H, m), 4.13 (1H, ddd, J=10.8, 4.5, 1.3 Hz), 4.44 (1H, d, J=9.2 Hz), 4.64 (1H, d, J=9.2 Hz), 5.46 (1H, d, J=3.7 Hz), 6.49 (1H, d, J=3.7 Hz), 6.74 (1H, d, J=1.8 Hz), 7.07 (1H, dd, J=8.2, 1.8 Hz), 7.31 (1H, dd, J=8.2, 2.3 Hz), 7.48-7.52 (2H, m), 7.62 (1H, s), 8.05 (1H, d, J=5.5 Hz).

MS (ESI) m/z: 618 $(M+H)^+$.

Example 71

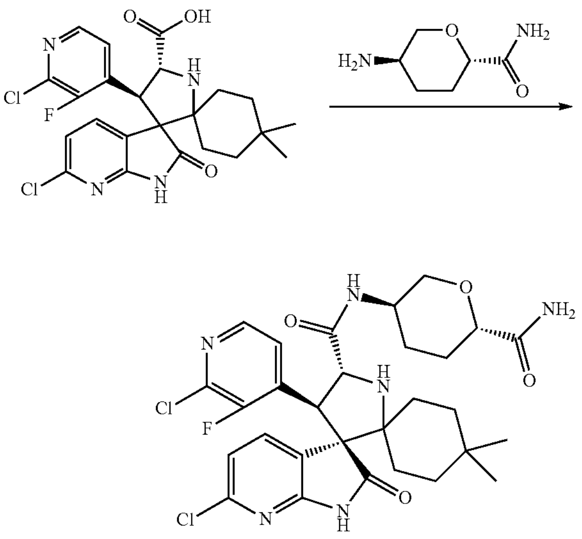

(3'R, 4'S, S'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-pyrrolo[2,3-b]pyridine]-5'-carboxamide The compound (100 mg, 0.20 mmol) obtained in Step 1 of Example 47 and the compound (35 mg, 0.24 mmol) obtained in Step 3 of Reference Example 28 were used as starting materials and treated in the same way as in Step 2 of Example 12 to give 41 mg (33%) of the title compound as a colorless solid.

$^1$H-NMR (400 MHz, $CDCl_3$) δ: 0.70 (3R, s), 0.96 (3H, s), 1.15-1.27 (2H, m), 1.34-1.40 (1H, m), 1.45-1.73 (7H, m), 2.10-2.16 (1H, m), 2.26-2.32 (1H, m), 3.15 (1H, t, J=10.8 Hz), 3.26 (1H, br s), 3.81 (1H, dd, J=11.2, 2.5 Hz), 3.87-3.93 (1H, m), 4.12 (1H, dd, J=11.0, 2.7 Hz), 4.45 (1H, d, J=8.7 Hz), 4.65 (1H, d, J=9.2 Hz), 5.52 (1H, d, J=3.2 Hz), 6.49 (1H, d, J=3.2 Hz), 7.07 (1H, d, J=7.8 Hz), 7.42-7.47 (2H, m), 7.61 (1H, dd, J=7.8, 2.3 Hz), 8.09 (1H, d, J=5.0 Hz), 8.20 (1H, br s).

MS (ESI) m/z: 619 $(M+H)^+$.

Example 72

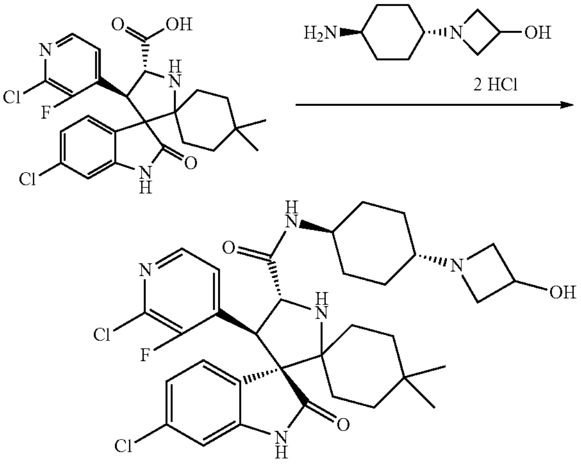

(3'R, 4'S,5'R)-6"-chloro-4'-(2-chloro-3-fluoropyridin-4-yl)-N-[trans-4-(3-hydroxyazetidine-1-yl)cyclohexyl]-4,4-dimethyl-2"-oxo-1",2"-dihydrodispiro[cyclohexane-1,2'-pyrrolidine-3',3"-indole]-5'-carboxamide The compound (197 mg, 0.40 mmol) obtained in Step 1 of Example 17 and the compound (117 mg, 0.48 mmol) obtained in Step 2 of Reference Example 13 were used as starting materials and treated in the same way as in Step 2 of Example 12 to give 107 mg (40%) of the title compound as a pale yellow solid.

$^1$H-NMR (400 MHz, $CD_3OD$) δ: 0.70 (3H, s), 0.97 (3H, s), 1.07-1.41 (7H, m), 1.53-1.64 (2H, m), 1.75-1.83 (2H, m), 1.86-2.02 (4H, m), 2.10-2.18 (1H, m), 2.90-2.96 (2H, m), 3.56-3.64 (2H, m), 3.64-3.69 (2H, m), 4.30-4.36 (1H, m), 4.55 (1H, d, J=9.2 Hz), 4.67 (1H, d, J=9.2 Hz), 6.79 (1H, d, J=2.3 Hz), 7.08 (1H, dd, J=8.3, 2.0 Hz), 7.47 (1H, dd, J=8.3, 2.0 Hz), 7.68 (1H, t, J=4.9 Hz), 8.07 (1H, d, J=5.7 Hz).

MS (ESI) m/z: 644 $(M+H)^+$.

Example 73

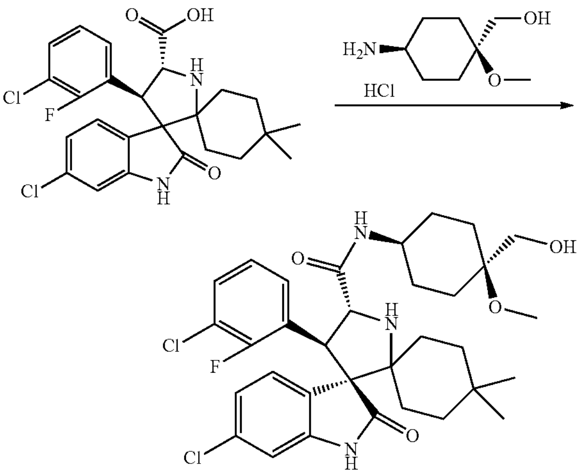

(3'R, 4'S,5'R)-6"-chloro-4'-(3-chloro-2-fluorophenyl)-N-[cis-4-(hydroxymethyl)-4-methoxycyclohexyl]-4,4-dimethyl-2"-oxo-1",2"-dihydrodispiro[cyclohexane-1,2'-pyrrolidine-3',3"-indole]-5'-carboxamide The compound (68 mg, 0.14 mmol) obtained in Step 1 of Example 12 and the compound (0.12 mmol) obtained in Step 6 of Reference Example 29 were used as starting materials and treated in the same way as in Step 2 of Example 12 to give 35 mg (48%) of the title compound as a colorless amorphous solid.

$^1$H-NMR (500 MHz, DMSO-do) δ: 0.60 (3H, s), 0.89 (3H, s), 0.93-0.98 (1H, m), 1.10-1.13 (1H, m); 1.19-1.59 (10H, m), 1.67-1.78 (4H, m), 2.09 (2H, s), 3.11 (3H, s), 3.28-3.49 (4H, m), 4.33-4.37 (1H, m), 4.45-4.47 (1H, m), 4.56 (1H, d, J=9.7 Hz), 6.68 (1H, d, J=1.7 Hz), 7.04 (1H, d, J=9.7 Hz), 7.11 (1H, t, J=7.7 Hz), 7.32 (1H, t, J=7.2 Hz), 7.44 (1H, d, J=8.0 Hz), 7.57 (1H, t, J=6.6 Hz), 7.75 (1H, d, J=8.6 Hz), 10.52 (1H, s).

MS (ESI) m/z: 632 (M+H)$^+$.

Example 74

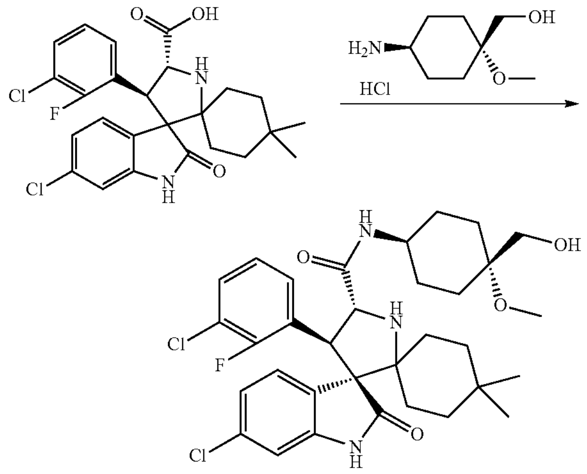

(3'R, 4'S,5'R)-6"-chloro-4'-(3-chloro-2-fluorophenyl)-N-[trans-4-(hydroxymethyl)-4-methoxycyclohexyl]-4,4-dimethyl-2"-oxo-1",2"-dihydrodispiro[cyclohexane-1,2'-pyrrolidine-3',3"-indole]-5'-carboxamide The compound (79 mg, 0.16 mmol) obtained in Step 1 of Example 12 and the compound (0.18 mmol) obtained in Step 4 of Reference Example 29 were used as starting materials and treated in the same way as in Step 2 of Example 12 to give 50 mg (51%) of the title compound as a colorless solid.

$^1$H-NMR (400 MHz, DMSO-$d_6$) δ: 0.60 (3H, s), 0.88 (3H, s), 0.92-1.00 (1H, m), 1.10-1.14 (1H, m), 1.23-1.26 (1H, m), 1.30-1.37 (1H, m), 1.44-1.79 (12H, m), 3.11 (3H, s), 3.39 (2H, d, J=5.5 Hz), 3.50 (1H, d, J=10.1 Hz), 3.65-3.72 (1H, m), 4.38-4.47 (2H, m), 4.53 (1H, d, J=9.6 Hz), 6.67 (1H, d, J=1.8 Hz), 7.03 (1H, dd, J=8.0, 2.1 Hz), 7.11 (1H, t, J=8.0 Hz), 7.30-7.34 (1H, m), 7.44 (1H, dd, J=8.3, 2.3 Hz), 7.56-7.60 (1H, m), 7.88 (1H, d, J=7.8 Hz), 10.53 (1H, s).

MS (ESI) m/z: 632 (M+H)$^+$.

Examples 75 (Isomer A) and 76 (Isomer B)

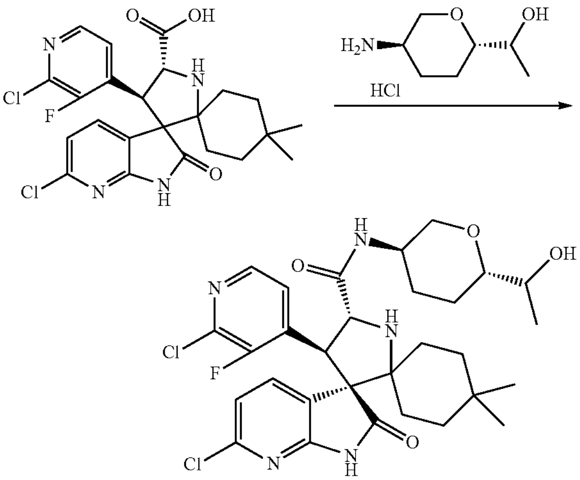

(3'R, 4'S,5'R)-6"-chloro-4'-(2-chloro-3-fluoropyridin-4-yl)-N-{(3R,6S)-6-[1-hydroxyethyl]tetrahydro-2H-pyran-3-yl}-4,4-dimethyl-2"-oxo-1",2"-dihydrodispiro[cyclohexane-1,2'-pyrrolidine-3',3"-pyrrolo[2,3-b]pyridine]-5'-carboxamide The compound (200 mg, 0.41 mmol) obtained in Step 1 of Example 47 and the compound (89 mg, 0.49 mmol) obtained in Step 3 of Reference Example 30 were used as starting materials and treated in the same way as in Step 2 of Example 12 to give a mixture of diastereomers. The mixture of diastereomers obtained was resolved and purified by chiral column liquid chromatography [fractionation conditions: CHIRALPAK IC, n-hexane; ethanol=3:2 (v/v)] to separately give 12 mg (5%; isomer A) and 82 mg (32%; isomer B) of the title compounds as colorless solids.

Isomer A:

$^1$H-NMR (400 MHz, $CDCl_3$) δ: 0.70 (3H, s), 0.96 (3H, s), 1.15 (3H, d, J=6.9 Hz), 1.16-1.27 (3H, m), 1.37-1.63 (6H, m), 1.70-1.77 (2H, m), 2.05-2.15 (2H, m), 3.12 (1H, t, J=10.5 Hz), 3.20-3.28 (2H, m), 3.81-3.90 (2H, m), 4.06 (1H, dd, J=10.3, 4.4 Hz), 4.45 (1H, d, J=8.7 Hz), 4.66 (1H, d, J=9.2 Hz), 7.07 (1H, d, J=7.8 Hz), 7.38 (1H, d, J=8.2 Hz), 7.45 (1H, t, J=4.8 Hz), 7.61 (1H, d, J=8.2 Hz), 8.02 (1H, br s), 8.08 (1H, d, J=5.0 Hz).

MS (ESI) m/z: 620 (M+H)$^+$.

Isomer B:

$^1$H-NMR (400 MHz, $CDCl_3$) δ: 0.70 (3H, s), 0.96 (3H, s), 1.16 (3H, d, J=6.0 Hz), 1.17-1.29 (3H, m), 1.34-1.63 (6H, m), 1.71-1.77 (2H, m), 2.07-2.12 (1H, m), 2.64 (1H, br s), 3.03-3.09 (1H, m), 3.10 (1H, t, J=10.8 Hz), 3.26 (1H, br. s), 3.63 (1H; t, J=6.2 Hz), 3.83-3.92 (1H, m), 4.04-4.10 (1H, m), 4.45 (1H, d, J=8.7 Hz), 4.66 (1H, d, J=8.7 Hz), 7.07 (1H, d, J=8.2 Hz), 7.39 (1H, d, J=8.7 Hz), 7.45 (1H, t, J=4.8 Hz), 7.61 (1H, dd, J=7, 6, 2.1 Hz), 8.01 (1H, br s), 8.09 (1H, d, J=5.0 Hz).

MS (ESI) m/z: 620 (M+H)$^+$.

Example 77 (Isomer A) and 78 (Isomer R)

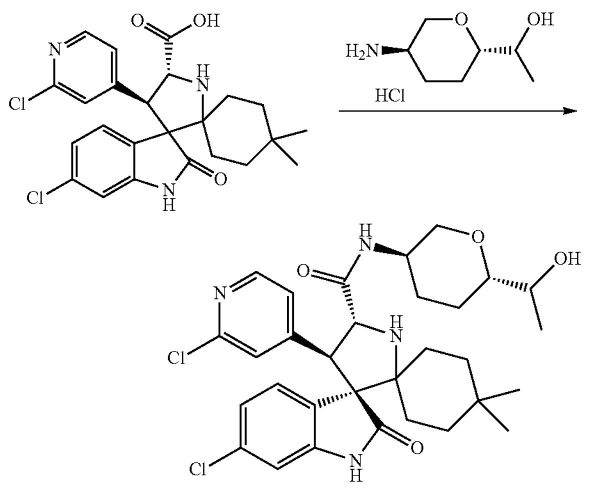

(3'R, 4'S,5'R)-6"-chloro-4'-(2-chloropyridin-4-yl)-N-((3R,6S)-6-(1-hydroxyethyl)tetrahydro-2H-pyran-3-yl)-4,4-dimethyl-2"-oxo-1",2"-dihydrodispiro[cyclohexane-1,2'-pyrrolidine-3',3"-indole]-5'-carboxamide The compound (300 mg, 0.63 mmol) obtained in Step 1 of Example 51 and the compound (137 mg, 0.76 mmol) obtained in Step 3 of Reference Example 30 were used as starting materials and treated in the same way as in Step 2 of Example 12 to give a mixture of diastereomers. The mixture of diastereomers obtained was resolved and purified by chiral column liquid chromatography [fractionation conditions: CHIRALCEL OD-H, n-hexane:ethanol=4:1 (v/v)] to separately give 45 mg (12%: isomer A) and 249 mg (66%: isomer B) of the title compounds as colorless solids.

Isomer A:

$^1$H-NMR (400 MHz, $CDCl_3$) δ: 0.68 (3H, s), 0.94 (3H, s), 1.14-1.23 (5H, m), 1.31-1.37 (1H, m), 1.40-1.53 (3H, m), 1.55-1.65 (3H, ml, 1.69-1.77 (2H, m), 2.06-2.14 (2H, m), 3.14 (1H, t, J=10.8 Hz), 3.21-3.26 (1H, m), 3.29 (1H, br s), 3.83-3.90 (2H, m), 4.09 (1H, m), 4.10 (1H, d, J=8.7 Hz), 4.49 (1H, d, J=8.2 Hz), 6.76 (1H, d, J=1.4 Hz), 6.90 (1H, d, J=5.5 Hz), 7.08 (1H, s), 7.10 (1H, dd, J=8.2, 1.4 Hz), 7.28 (1H, d, J=9.2 Hz), 7.52 (1H, d, J=8.7 Hz), 7.57 (1H, s), 8.10 (1H, d, J=5.0 Hz).

MS (ESI) m/z: 601 $(M+H)^+$.

Isomer B:

$^1$H-NMR (400 MHz, $CDCl_3$) δ: 0.68 (3H, s), 0.95 (3H, s), 1.15-1.27 (5H, m), 1.30-1.36 (1H, m), 1.41-1.53 (4H, m), 1.56-1.63 (2H, m), 1.69-1.77 (2H, m), 2.03-2.11 (1H, m), 2.68 (1H, s), 3.03-3.08 (1H, m), 3.11 (1H, t, J=10.8 Hz), 3.30 (1H, br s), 3.59-3.67 (1H, m), 3.84-3.93 (1H, m), 4.09 (1H, m), 4.10 (1H, d, J=8.7 Hz), 4.49 (1H, d, J=8.7 Hz), 6.77 (1H, d, J=1.8 Hz), 6.90 (1H, dd, J=5.5, 1.4 Hz), 7.08 (1H, s), 7.10 (1H, dd, J=8.2, 1.8 Hz), 7.28 (1H, d, J=8.7 Hz), 7.53 (1H, d, J=8.7 Hz), 7.66 (1H, s), 8.09 (1H, d, J=5.0 Hz).

MS (ESI) m/z: 601 $(M+H)^+$.

Example 79

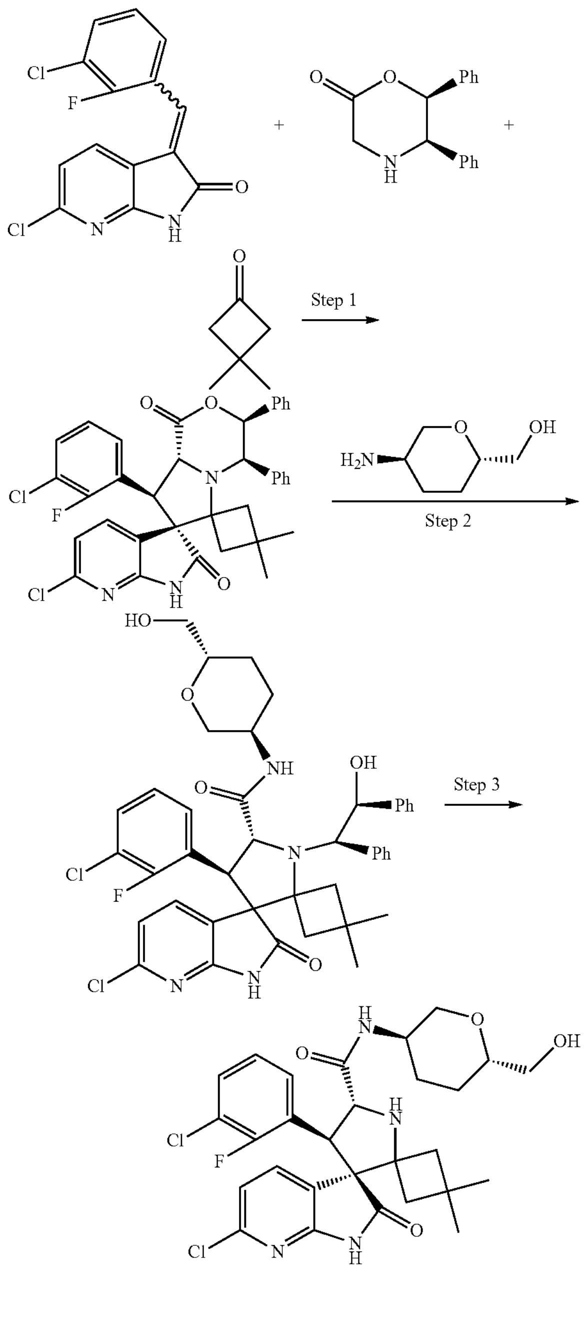

Step 1

(3'S,4'R,8'S,8'S,8a'R)-6"-chloro-8'-(3-chloro-2-fluorophenyl)-3,3-dimethyl-3',4'-diphenyl-3',4',8',8a'-tetrahydro-1'H-dispiro[cyclobutane-1,6'-pyrrolo[2,1-c][1,4]oxazine-7',3"-pyrrolo[2,3-b]pyridine]-1',2"(1"H)-dione The compound (0.93 g, 3.00 mmol) obtained in Reference Example 1 and 3,3-dimethylcyclobutanone (Tetrahedron, 1968, 6017-6028) (0.30 g, 3.00 mmol) were used and treated in the same way as in Step 1 of Example 9 to give 1.10 g (51%) of the title compound as a yellow solid.

$^1$H-NMR (400 MHz, $CDCl_3$) δ: 0.71 (3H, s), 0.92 (3H, s), 1.66 (1H, d, J=13.2 Hz), 1.85 (1H, d, J=13.2 Hz), 2.45 (1H, d, J=14.2 Hz), 2.62 (1H, d, J=14.2 Hz), 4.60 (1H, d, J=9.3 Hz), 4.83 (1H, d, J=9.3 Hz), 5.04 (1H, d, J=4.4 HZ), 6.39 (1H, d, J=4.4 Hz), 6.86 (1H, d, J=7.8 Hz), 6.99 (1H, t, J=7.8 Hz), 7.04 (1H, d, J=7.8 Hz), 7.10-7.25 (12H, m), 7.77 (1H, s).

Step 2

(4'S,5'R)-6"-chloro-4'-(3-chloro-2-fluorophenyl)-1'-[(1R,2S)-2-hydroxy-1,2-diphenylethyl]-N-[(3R,6S)-6-(hydroxymethyl)tetrahydro-2H-pyran-3-yl]-3,3-dimethyl-2"-oxo-1",2"-dihydrodispiro[cyclobutane-1,2'-pyrrolidine-3',3"-pyrrolo[2,3-b]pyridine]-5'-carboxamide The compound (430 mg, 0.67 mmol) obtained in Step 1 above and the compound (263 mg, 2.00 mmol) obtained in Step 3 of Reference Example 2 were used as starting materials and treated in the same way as in Step 1 of Example 20 to give 390 mg (76%) of the title compound as a brown amorphous solid.

MS (ESI) m/z: 773 $(M+H)^+$.

Step 3

(3'R, 4'S,5'R)-6"-chloro-4'-(3-chloro-2-fluorophenyl)-N-[(3R,6S)-6-(hydroxymethyl)tetrahydro-2H-pyran-3-yl]-3,3-dimethyl-2"-oxo-1",2"-dihydrodispiro[cyclobutane-1,2'-pyrrolidine-3',3"-pyrrolo[2,3-b]pyridine]-5'-carboxamide The compound (390 mg, 0.50 mmol) obtained in Step 2 above was used as a starting material and treated in the same way as in Step 3 of Example 1 to give 150 mg (52%) of the title compound as a colorless solid.

$^1$H-NMR (400 MHz, $CD_3OD$) δ: 0.69 (3H, s), 1.33 (3H, s), 1.38-1.64 (3H, m), 1.71-1.79 (1H, m), 1.83 (1H, dd, J=12.8, 3.2 Hz), 2.00 (1H, dd, J=12.4, 3.2 Hz), 2.10 (1H, d, J=12.4 Hz), 2.24 (1H, d, J=12.4 Hz), 3.11 (1H, t, J=10.8 Hz), 3.33-3.41 (1H, m); 3.49 (2H, d, J=5.0 Hz), 3.73-3.83 (1H, m), 3.88-3.94 (1H, m), 4.34 (1H, d, J=9.2 Hz), 4.45 (1H, d, J=9.2 Hz), 7.05 (1H, t, J=8.0 Hz), 7.11 (1H, d, J=7.8 Hz), 7.23-7.27 (1H, m), 7.52 (1H, t, J=7.1 Hz), 7.88 (1H, dd, J=7.8, 2.3 Hz),

MS (ESI) m/z: 577 $(M+H)^+$.

Example 80

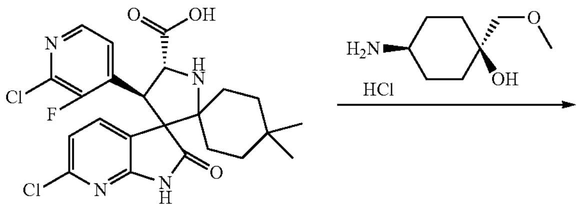

-continued

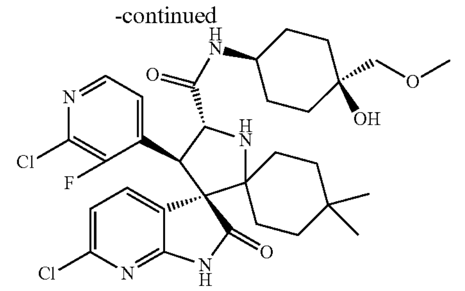

(3'R, 4'S,5'R)-6"-chloro-4'-(2-chloro-3-fluoropyridin-4-yl)-N-[cis-4-hydroxy-4-(methoxymethyl)cyclohexyl]-4,4-dimethyl-2"-oxo-1",2"-dihydrodispiro[cyclohexane-1,2'-pyrrolidine-3',3"-pyrrol[2,3-b]pyridine]-5'-carboxamide The compound (79 mg, 0.16 mmol) obtained in Step 1 of Example 47 and the compound (40 mg, 0.20 mmol obtained in Step 2 of Reference Example 31 were used as starting materials and treated in the same way as in Step 2 of Example 12 to give 63 mg (62%) of the title compound as a colorless solid.

$^1$H-NMR (400 MHz, $CDCl_3$) δ: 0.68 (3H, s), 0.95 (3H, s), 1.80-1.17 (16H, m), 2.19 (1H, s), 3.21 (3H, s), 3.39 (3H, s), 3.58-3.74 (1H, m), 4.45-4.47 (1H, m), 4.67 (1H, d, J=8.7 Hz), 7.06 (1H, d, J=8.3 Hz), 7.46-7.51 (2H, m), 7.60-7.63 (1H, m), 8.07 (1H, d, J=5.0 Hz), 8.17 (1H, s),

MS (ESI) m/z: 634 $(M+H)^+$.

Example 81

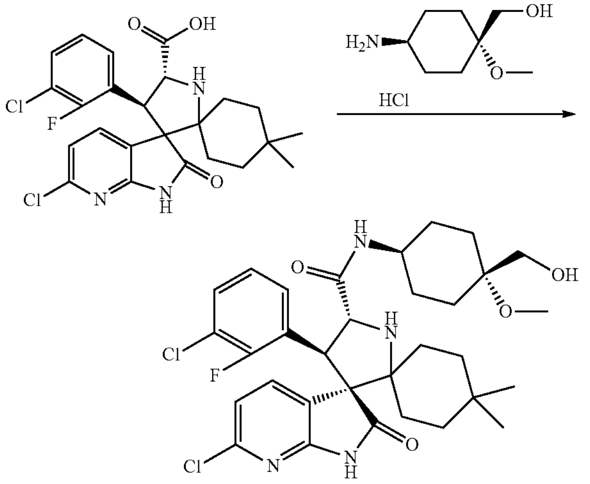

(3'R, 4'S,5'R)-6"-chloro-4'-(3-chloro-2-fluorophenyl)-N-[trans-4-(hydroxymethyl)-4-methoxycyclohexyl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (71 mg, 0.15 mmol) obtained in Step 1 of Example 49 and the compound (42 mg, 0.21 mmol) obtained in Step 4 of Reference Example 29 were used as starting materials and treated in the same way as in Step 2 of Example 12 to give 65 mg (71%) of the title compound as a colorless solid.

$^1$H-NMR (500 MHz, $CDCl_3$) δ: 0.70 (3H, s), 0.95 (3H, s), 1.14-1.24 (2H, in), 1.34-1.70 (11H, m), 1.76-1.79 (1H, m), 1.87-1.92 (3H, m), 3.18-3.22 (4H, m), 3.60 (2H, d, J=5.7 Hz), 3.83-3.89 (1H, m), 4.48 (1H, d, J=9.2 Hz), 4.68 (1H, d, J=9.7 Hz), 6.96 (1H, t, J=8.0 Hz), 7.05 (1H, d, J=8.0 Hz), 7.14-7.18 (1H, m), 7.48 (1H, C, J=6.3 Hz), 7.63 (2H, dd, J=8.0, 2.3 Hz), 7.87 (1H, s).

MS (ESI) m/z: 633 (M+H)$^+$.

Example 82

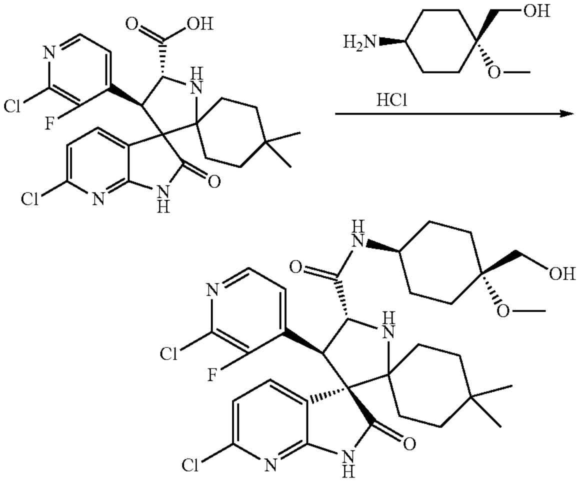

(3'R, 4'S,5'R)-6"-chloro-4'-(2-chloro-3-fluoropyridin-4-yl)-N-[trans-4-(hydroxymethyl)-4-methoxycyclohexyl]-4,4-dimethyl-2"-oxo-1",2'-dihydrodispiro [cyclohexane-1,2'-pyrrolidine-3',3"-pyrrolo[2,3-b] pyridine]-5'-carboxamide The compound (96 mg, 0.20 mmol) obtained in Step 1 of Example 47 and the compound (42 mg, 0.22 mmol) obtained in Step 4 of Reference Example 29 were used as starting materials and treated in the same way as in Step 2 of Example 12 to give 26 mg (21%) of the title compound as a colorless solid.

$^1$H-NMR (400 MHz, $CDCl_3$) δ: 0.70 (3H, s), 0.95 (3H, s), 1.14-1.26 (2H, m), 1.35-1.74 (12H, m), 1.88-1.94 (3H, m), 3.21-3.25 (4H, m), 3.60 (2H, d, J=5.5 Hz), 3.82-3.90 (1H, m), 4.47 (1H, d, J=8.7 Hz), 4.65 (1H, d, J=9.2 Hz), 7.07 (1H, d, J=7.8 Hz), 7.47 (1H, t, J=5.0 Hz), 7.59-7.63 (2H, m), 8.02 (1H, s), 8.08 (1H, d, J=5.0 Hz).

MS (ESI) m/z: 634 (M+H)$^+$.

Example 83

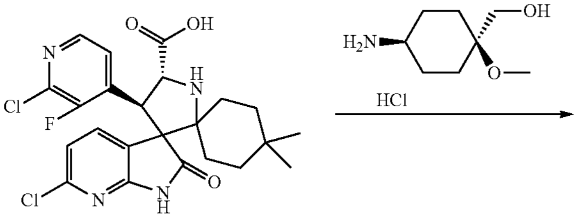

-continued

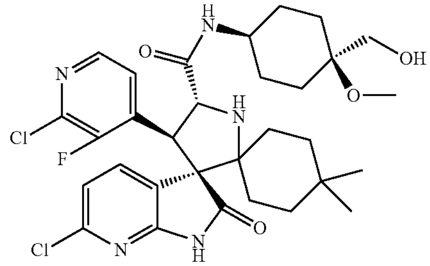

(3'R, 4'S,5'R)-6"-chloro-4'-(2-chloro-3-fluoropyridin-4-yl)-N-[cis-4-(hydroxymethyl)-4-methoxycyclohexyl]-4,4-dimethyl-2"-oxo-1",2"-dihydrodispiro [cyclohexane-1,2'-pyrrolidine-3',3"-pyrrolo[2,3-b] pyridine]-5'-carboxamide The compound (67 mg, 0.14 mmol) obtained in Step 1 of Example 47 and the compound (0.11 mmol) obtained in Step 6 of Reference Example 29 were used as starting materials and treated in the same way as in Step 2 of Example 12 to give 36 mg (53%) of the title compound as a colorless solid.

$^1$H-NMR (400 MHz, $CDCl_3$) δ: 0.69 (3H, s), 0.96 (3H, s), 1.14-1.83 (15H, m), 1.90-1.99 (2H, m), 3.21-3.26 (4H, m), 3.41-3.53 (2H, m), 3.66-3.76 (1H, m), 4.45 (1H, d, J=8.7 Hz), 4.68 (1H, d, J=9.2 Hz), 7.07 (1H, d, J=7.8 Hz), 7.46-7.50 (2H, m), 7.61-7.63 (1H, m), 8.08 (2H, d, J=5.0 Hz).

MS (ESI) m/z: 634 (M+H)$^+$.

Example 84

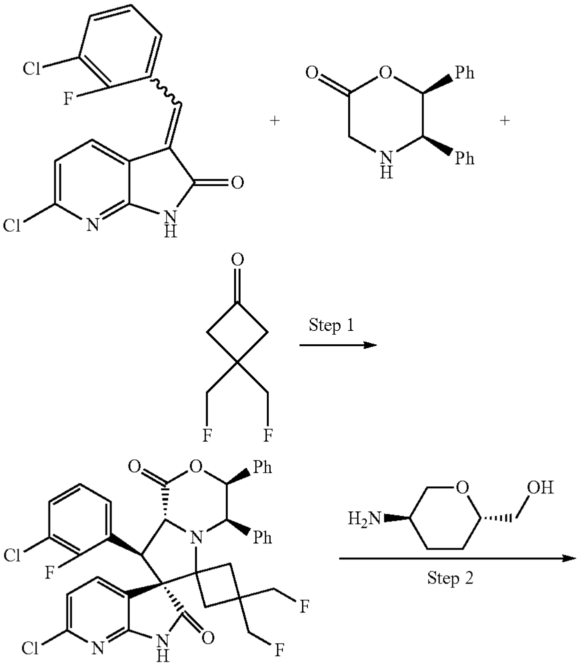

-continued

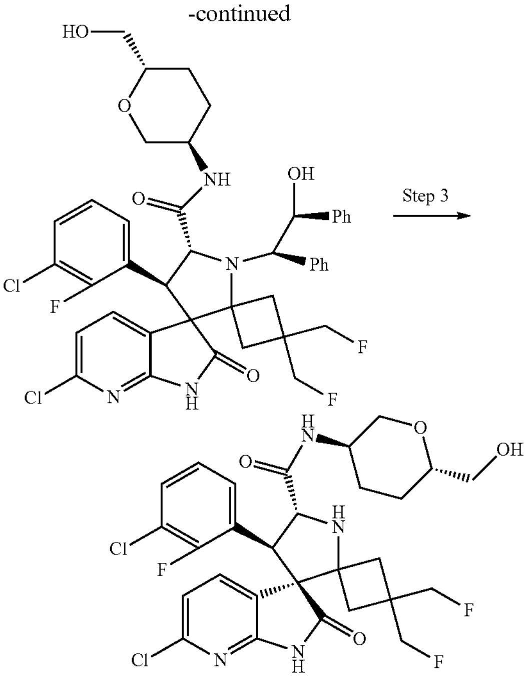

Step 1

(3'S,4'R, 7'S,8'S, 8a'R)-6"-chloro-8'-(3-chloro-2-fluorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-pyrrolo[2,3-b]pyridine]-1',2" (1"H)-dione The compound (4.60 g, 15.0 mmol) obtained in Reference Example 1 above and the compound (2.21 g, 16.5 mmol) obtained in Step 2 of Reference Example 21 were used as starting materials and treated in the same way as in Step 1 of Example 9 to give 1.77 g (11%) of the title compound as a pale yellow solid.

$^1$H-NMR (400 MHz, $CDCl_3$) δ: 1.87 (1H, d, J=14.2 Hz), 2.23 (1H, d, J=14.2 Hz), 2.76 (1H, d, J=14.2 Hz), 2.88 (1H, d, J=14.2 Hz), 3.90-3.96 (1H, m), 4.02-4.08 (1H, m), 4.15 (1H, dd, J=15.3, 9.8 Hz), 4.27 (1H, dd, J=15.3, 9.8 Hz), 4.57 (1H, d, J=9.6 Hz), 4.80 (1H, d, J=9.6 Hz), 5.20 (1H, dd, J=4.1, 1.8 Hz), 6.39 (1H, d, J=4.1 Hz), 6.87 (1H, d, J=7.8 Hz), 6.96 (2H, t, J=8.0 Hz), 7.05-7.09 (1H, m), 7.10-7.13 (2H, m), 7.14-7.25 (10H, m), 7.92 (1H, s).

Step 2

(4'S,5+R)-6"-chloro-4'-(3-chloro-2-fluorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-pyrrolo[2,3-b]pyridine]-5'-carboxamide The compound (339 mg, 0.50 mmol) obtained in Step 1 above and the compound (197 mg, 1.50 mmol) obtained in Step 3 of Reference Example 2 were used as starting materials and treated in the same way as in Step 1 of Example 20 to give 198 mg (49%) of the title compound as a brown amorphous solid.

MS (ESI) m/z: 809 $(M+H)^+$.

Step 3

(3'R, 4'S,5'R)-6"-chloro-4'-(3-chloro-2-fluorophenyl)-3,3-bis(fluoromethyl)-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-pyrrolo[2,3-b]pyridine]-5'-carboxamide The compound (198 mg, 0.24 mmol) obtained in Step 2 above was used as a starting material and treated in the same way as in Step 2 of Example 10 to give 80 mg (53%) of the title compound as a colorless solid.

$^1$H-NMR (400 MHz, $CD_3CD$) δ: 1.36-1.48 (1H, m), 1.53-1.64 (1H, m), 1.71-1.81 (2H, m), 1.87-1.93 (1H, m), 2.03-2.13 (2H, m), 2.42 (1H, d, J=12.8 Hz), 3.11 (1H, t, J=10.5 Hz), 3.32-3.40 (1H, m), 3.49 (2H, d, J=5.0 Hz), 3.74-3.85 (1H, m), 3.86-4.06 (3H, m), 4.41 (1H, d, J=9.6 Hz), 4.48 (1H, d, J=9.2 Hz), 4.61-4.80 (2H, m), 7.06 (1H, t, J=8.0 Hz), 7.11 (1H, d, J=7.8 Hz), 7.24-7.28 (1H, m), 7.52 (1H, t, J=6.6 Hz), 7.92 (1H, dd, J=8, 0, 2.1 Hz).

MS (ESI) m/z: 613 $(M+H)^+$.

Example 85 (Isomer A) and 86 (Isomer A)

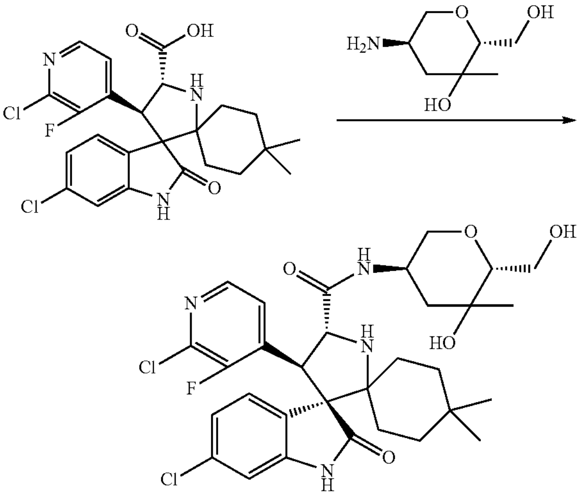

(3'R, 4'S,5'R)-6"-chloro-4'-(2-chloro-3-fluoropyridin-4-yl)-N-[(3R,6R)-5-hydroxy-6-(hydroxymethyl)-5'-methyltetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (60 mg, 0.12 mmol) obtained in Step 1 of Example 17 and the compound (21 mg, 0.13 mmol) obtained in Step 3 of Reference Example 32 were used as starting materials and treated in the same way as in Step 2 of Example 12 to separately give 35 mg (46%: isomer A) and 15 mg (20%: isomer B) of the title compound as colorless solids.

Isomer A:

$^1$H-NMR (400 MHz, $CDCl_3$) δ: 0.68 (3H, s), 0.95 (3H, s), 1.09-1.28 (3H, m), 1.32 (3H, s), 1.36-1.76 (5H, m), 1.98-2.11 (2H, m), 2.33 (1H, s), 3.04-3.27 (2H, m), 3.30-3.38 (1H, m), 3.70-4.10 (4H, m), 4.40-4.50 (1H, m), 4.64 (1H, d,

J=9.2 Hz), 6.73 (1H, d, J=1.8 Hz), 7.04-7.12 (1H, m), 7.29-7.35 (2H, m), 7.46-7.57 (2H, m), 8.06 (1H, d, J=5.5 Hz).

MS (ESI) m/z: 635 $(M+H)^+$.

Isomer B:

$^1$H-NMR (400 MHz, $CDCl_3$) δ: 0.58 (3H, s), 0.94 (31, s), 1.11-1.76 (11H, m), 2.00-2.07 (1H, m), 2.37-2.44 (2H, m), 3.08-3.30 (4H, m), 3.82-3.96 (2H, m), 4.11-4.20 (1H, m), 4.21-4.33 (1H, m), 4.43 (1H, d, J=9.0 Hz), 4.62 (1H, d, J=9.0 Hz), 6.69 (1H, d, J=1.8 Hz), 7.05-7.10 (1H, m), 7.29-7.34 (1H, m), 7.46-7.62 (3H, m), 8.06 (1H, d, J=5.0 Hz).

MS (ESI) m/z: 635 $(M+H)^+$.

Example 87

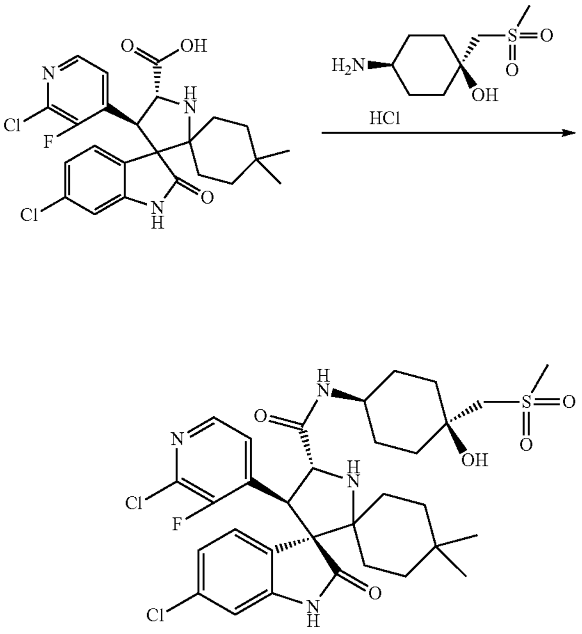

(3'R, 4'S,5'R)-6"-chloro-4'-(2-chloro-3-fluoropyridin-4-yl)-N-{cis-4-hydroxy-4-[(methylsulfonyl) methyl] cyclohexyl}-4,4-dimethyl-2"-oxo-1",2'-dihydrodispiro[cyclohexane-1,2'-pyrrolidine-3',3"-indole]-5'-carboxamide The compound (89 mg, 0.18 mmol) obtained in Step 1 of Example 17 and the compound (0.20 mmol) obtained in Step 3 of Reference Example 33 were used as starting materials and treated in the same way as in Step 2 of Example 12 to give 84 mg (67%) of the title compound as a colorless solid.

$^1$H-NMR (500 MHz, DMSO-$d_6$) δ: 0.60 (3H, s), 0.90 (3H, s), 0.93-1.00 (1H, m), 1.11-1.14 (1H, m), 1.22-1.25 (1H, m), 1.41-1.64 (9H, m), 1.67-1.76 (2H, m), 1.84-1.91 (2H, m), 3.00 (3H, s), 3.22 (2H, s), 3.44-3.49 (1H, m), 3.56 (1H, d, J=11.5 Hz), 4.44 (1H, t, J=9.7 Hz), 4.55 (1H, d, J=9.2 Hz), 4.86 (1H, s), 6.71 (1H, d, J=2.3 Hz), 7.06 (1H, dd, J=8.3, 2.0 Hz), 7.50 (1H, dd, J=8.3, 2.0 Hz), 7.63 (1H, t, J=5.2 Hz), 7.74 (1H, d, J=8.0 Hz), 8.18 (1H, d, J=5.2 Hz), 10.61 (1H, s).

MS (ESI) m/z: 681 $(M+H)^+$.

Example 88

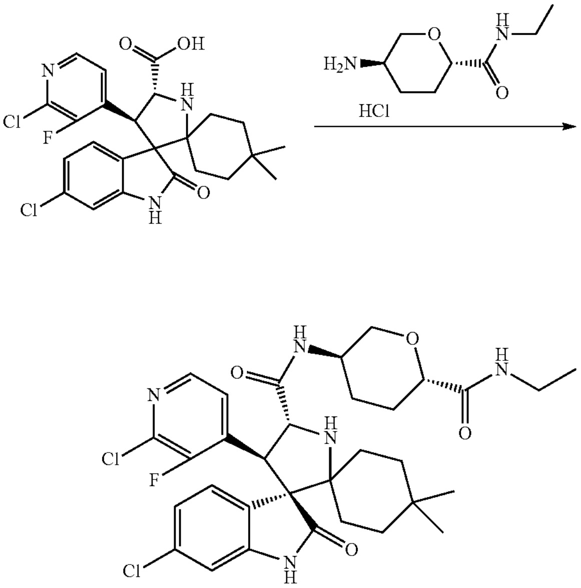 [SMILES: CC1(C)CCC2(CC1)N[C@@H](C(=O)O)[C@H](c1ccnc(Cl)c1F)C21C(=O)Nc2cc(Cl)ccc21 ; CCNC(=O)[C@@H]1CC[C@@H](N)CO1 ; Cl ; CCNC(=O)[C@@H]1CC[C@@H](NC(=O)[C@@H]2NC3(CCC(C)(C)CC3)[C@@]3(C(=O)Nc4cc(Cl)ccc43)[C@H]2c2ccnc(Cl)c2F)CO1]

(3'R, 4'S,5'R)-6"-chloro-4'-(2-chloro-3-fluoropyridin-4-yl)-N-[(3R,6S)-6-(ethylcarbamoyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (160 mg, 0.33 mmol) obtained in Step 1 of Example 17 and the compound (87 mg, 0.40 mmol) obtained in Step 2 of Reference Example 34 were used as starting materials and treated in the same way as in Step 2 of Example 12 to give 143 mg (67%) of the title compound as a colorless solid.

$^1$H-NMR (400 MHz, $CDCl_3$) δ: 0.68 (3H, s), 0.95 (3H, s), 1.15 (3H, t, J=7.2 Hz), 1.16-1.24 (2H, m), 1.35-1.41 (1H, m), 1.43-1.62 (5H, m), 1.70-1.77 (2H, m), 2.09-2.15 (1H, m), 2.28-2.34 (1H, m), 3.13 (1H, t, J=10.7 Hz), 3.25-3.36 (2H, m), 3.74-3.79 (1H, m), 3.85-3.94 (1H, m), 4.11 (1H, dd, J=11.7, 3.9 Hz), 4.44 (1H, d, J=8.8 Hz), 4.64 (1H, d, J=9.0 Hz), 6.52 (1H, t, J=5.5 Hz), 6.73 (m, d, J=1.7 Hz), 7.07 (1H, dd, J=8.1, 2.0 Hz), 7.31 (1H, dd, J=8.2, 2.1 Hz), 7.48-7.52 (2H, m), 7.62 (1H, s), 8.05 (1H, d, J=5.1 Hz).

MS (ESI) m/z: 646 $(M+H)^+$.

Example 89 (Isomer A) and 90 (Isomer B)

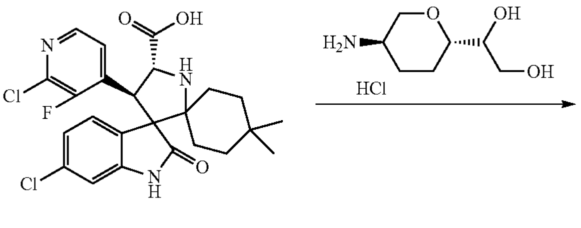

-continued

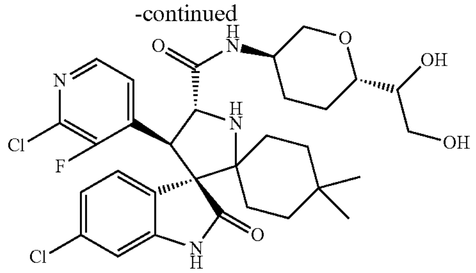

(3'R, 4'S,5'R)-6"-chloro-4'-(2-chloro-3-fluoropyridin-4-yl)-N-[(3R,6S)-6-(1,2-dihydroxyethyl)tetrahydro-2H-pyran-3-yl]-4,4-dimethyl-2"-oxo-1",2"-dihydrodispiro[cyclohexane-1,2f-pyrrolidine-3',3"=indole]-5'-carboxamide The compound (332 mg, 0.67 mmol) obtained in Step 1 of Example 17 and the compound (160 mg, 0.80 mmol) obtained in Step 3 of Reference Example 35 were used as starting materials and treated in the same way as in Step 2 of Example 12 to give a mixture of diastereomers. The mixture of diastereomers obtained was resolved and purified by chiral column liquid chromatography (fractionation conditions: CHIRALPAK IA, [n-hexane:ethanol=1:1 (v/v)] to separately give 100 mg (23%: isomer A) and 174 mg (40%: isomer B) of the title compounds as colorless solids.

Isomer A:

$^1$H-NMR (400 MHz, $CDCl_3$) δ: 0.68 (3H, s), 0.95 (38, s), 1.11-1.26 (2H, m), 1.33-1.39 (1H, m), 1.42-1.63 (5H, m), 1.70-1.76 (2H, m), 1.82-1.89 (1H, m), 2.10-2.16 (2H, m), 2.56 (1H, d, J=6.4 Hz), 3.09 (1H), t, J=10.5 Hz), 3.27 (1H, br s), 3.40-3.45 (1H, m), 3.61-3.66 (1H, m), 3.69-3.75 (2H, m), 3.84-3.93 (1H, m), 4.03-4.08 (1H, m), 4.43 (1H, d, J=9.2 Hz), 4.64 (1H, d, J=9.2 Hz), 6.72 (1H, d, J=1.8 Hz), 7.07 (1H, dd, J=8.0, 2.1 Hz), 7.31 (1H, dd, J=8.0, 2.1 Hz), 7.43-7.51 (3H, m), 8.05 (1H, d, J=5.0 Hz).

MS (ESI) m/z: 635 $(M+H)^+$.

Isomer B:

$^1$H-NMR (400 MHz, $CDCl_3$) δ: 0.68 (3H, s), 0.95 (3H, s), 1.10-1.24 (2H, m), 1.33-1.38 (1H, m), 1.43-1.54 (3H, m), 1.57-1.79 (5H, m), 2.09-2.14 (1H, m), 2.20-2.25 (1H, m), 2.77 (1H, d, J=4.1 Hz), 3.12 (1H, t, J=10.5 Hz), 3.31 (1H, br s), 3.37-3.43 (1H, m), 3.53-3.59 (1H, m), 3.62-3.67 (1H, m), 3.71-3.78 (1H, m), 3.86-3.94 (1H, m), 4.06-4.11 (1H, m), 4.43 (1H, d, J=9.2 Hz), 4.64 (1H, d, J=9.2 Hz), 6.73 (1H, d, J=1.8 Hz), 7.07 (1H, dd, J=8.2, 1.8 Hz), 7.31 (1H, dd, J=8.0, 2.1 Hz), 7.46-7.51 (3H, m), 8.05 (1H, d, J=5.5 Hz).

MS (ESI) m/z: 635 $(M+H)^+$.

Example 91

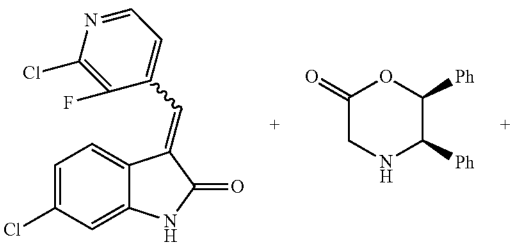

-continued

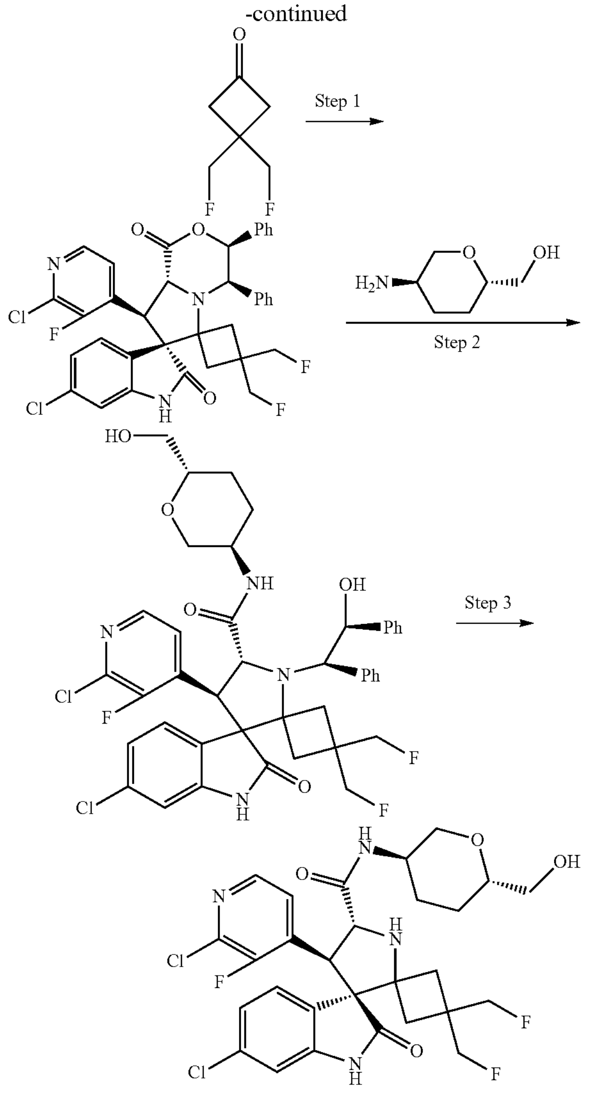

Step 1

(3'S,4'R, 7'S,8'S,8a'R)-6"-chloro-8'-(2-chloro-3-fluoropyridin-4-yl)-3,3-bis(fluoromethyl)-3',4'-diphenyl-3',4',8',8a'-tetrahydro-1'H-dispiro[cyclobutane-1,6"-pyrrolo[2,1-c][1,4]oxazine-7',3"-indole]-1',2" (1"H)-dione The compound (5.0 g, 17.2 mmol) obtained in Reference Example 8 and the compound (2.88 g, 21.5 mmol) obtained in Step 2 of Reference Example 21 were used as starting materials and treated in the same way as in Step 1 of Example 9 to give 10.2 g (87%) of the title compound as a pale yellow amorphous solid.

$^1$H-NMR (400 MHz, $CDCl_3$) δ: 1.92 (1H, d, J=14.7 Hz), 2.35 (1H, d, J=14.7 Hz), 2.84 (1H, d, J=14.2 Hz), 3.07 (1H, d, J=14.2 Hz), 3.90-3.98 (1H, m), 4.02-4.10 (1H, m), 4.23-4.30 (1H, m), 4.35-4.42 (1H, m), 4.52 (1H, d, J=9.6 Hz), 4.69 (1H, d, J=9.6 Hz), 5.22-5.25 (1H, m), 6.30 (1H, d, J=4.1 Hz), 6.78 (1H, d, J=8.3 Hz), 6.84 (1H, t, 0=4.8 Hz), 6.89 (1B, d, J=1.8 Hz), 6.94 (1H, dd, J=8.3, 1.8 Hz), 7.14-7.27 (10H, m), 7.97 (1H, d, J=5.0 Hz), 8.00 (1H, s).

MS (ESI) m/z: 678 $(M+H)^+$.

Step 2

(4'S,5'R)-6"-chloro-4'-(2-chloro-3-fluoropyridin-4-yl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (203 mg, 0.30 mmol) obtained in Step 1 above was used as a starting material and treated in the same way as in Step 1 of Example 20 to give 153 mg (63%) of the title compound as a pale yellow amorphous solid.

MS (ESI) m/z: 809 $(M+H)^+$.

Step 3

(3'R, 4'S,5'R)-6"-chloro-4'-(2-chloro-3-fluoropyridin-4-yl)-3,3-bis(fluoromethyl)-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (153 mg, 0.19 mmol) obtained in Step 2 above was dissolved in acetonitrile (10 ml) and water (3 ml), cerium (IV) diammonium nitrate (207 mg, 0.38 mmol) was added under ice cooling and the resulting mixture was stirred for 10 minutes. Potassium carbonate (104 mg, 0.76 mmol) was added to the reaction mixture and the precipitated insoluble matter was removed by filtration through celite. The filtrate was diluted with ethyl acetate, washed with brine and dried over anhydrous sodium sulfate. The solvent was evaporated, the residue was purified by NH-silica gel column chromatography (chloroform:methanol=100:0→40:1) and then the residue was dissolved in 2-propanol (10 ml) and stirred at 50° C. for 2 days. The solvent was evaporated under reduced pressure and then the residue was purified by chiral column liquid chromatography [fractionation conditions; CHIRALPAK IC, n-hexane: ethanol=2:3 (v/v)] to give 67 mg (57%) of the title compound as a colorless solid.

$^1$H-NMR (400 MHz, $CD_3OD$) δ: 1.37-1.49 (1H, m), 1.55-1.78 (2H, m), 1.85-1.91 (1H, m), 2.00-2.20 (2H, m), 2.48 (1H, d, J=12.8 Hz), 3.16 (1H, t, J=10.5 Hz), 3.33-3.41 (1H, m), 3.45-3.51 (2H, m), 3.74-3.94. (4H, m), 4.39 (1H, d, J=9.2 Hz), 4.50 (1H, d, J=9.2 Hz), 4.60-4.77 (2H, m), 6.84 (1H, d, J=1.8 Hz), 7.13 (1H, dd, J=8.0, 2.1 Hz), 7.54 (1H, dd, J=8.0, 2.1 Hz), 7.60 (1H, t, J=5.0 Hz), 8.06 (1H, d, J=5.0 Hz).

MS (ESI) m/z: 613 $(M+H)^+$.

Example 92

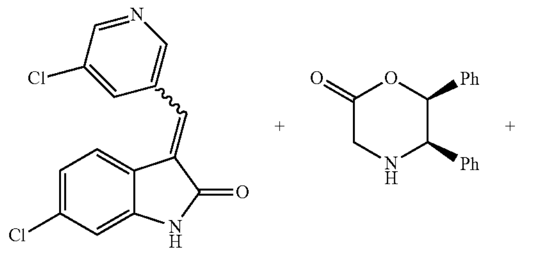

-continued

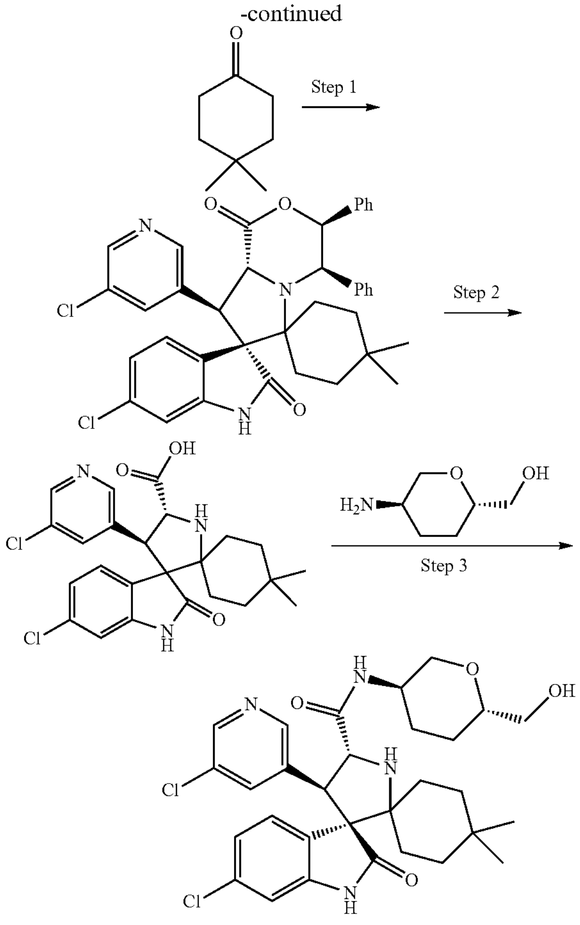

Step 1

(3'S,4'R, 7'S,8'R, 8a'R)-6"-chloro-8'-(5-chloropyridin-3-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-indole]-1',2" (1"H)-dione The compound (1.35 g, 4.65 mmol) obtained in Reference Example 36 was used as a starting material and created in the same way as in Step 1 of Example 9 to give 2.33 g (77%) of the title compound as a yellow solid.

$^1$H-NMR (400 MHz, $CDCl_3$) δ: 0.56 (3H, s), 0.67 (3H, s), 0.81-1.01 (1H, m), 1.16-1.44 (4H, m), 1.74-1.83 (1H, m), 0.1.86-1.97 (1H, m), 2.16-2.27 (1H, m), 4.48 (1H, d, J=11.0 Hz), 4.82 (1H, d, J=3.7 Hz), 5.03 (1H, d, J=11.0 Hz), 6.61-6.68 (2H, m), 6.77-6.84 (2H, m), 6.92-6.98 (2H, m), 7.10-7.29 (9H, m), 7.47-7.50 (1H, m), 8.14 (1H, d, J=1.4 Hz), 8.34 (1H, d, J=2.3 Hz).

MS (APCI) m/z: 652 $(M+H)^+$.

Step 2

(4'R, 5'R)-6"-chloro-4'-(5-chloropyridin-3-yl)-4,4-dimethyl-2"-oxo-1",2"-dihydrodispiro[cyclohexane-1,2"-pyrrolidine-3',3"-indole]-5'-carboxylic acid The compound (2.29 g, 3.52 mmol) obtained in Step 1 above was used as a starting material and treated in the same way as in Step 1 of Example 12 to give 827 mg (50%) of the title compound as a light brown solid, MS (APCI) m/z: 474 $(M+H)^+$.

Step 3

(3'R, 4'R, 5'R)-6"-chloro-4'-(5-chloropyridin-3-yl)-N-[(3R,6S)-6-(hydroxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (200 mg, 0.42 mmol) obtained in Step 2 above and the compound (83 mg, 0.63 mmol) obtained in Step 3 of Reference Example 2 were used as starting materials and treated in the same way as in Step 2 of Example 12 to give 23 mg: (9%) of the title compound as a pale yellow solid.

$^1$H-NMR (400 MHz, $CD_3OD$) δ: 0.67-0.71 (3H, m), 0.93-0.96 (3H, m), 1.15-1.24 (2H, m), 1.27-1.66 (5H, m), 1.69-1.86 (4H, m), 2.02-2.10 (1H, m), 3.11-3.53 (4H, m), 3.73-3.82 (1H) m), 3.94-3.98 (1H, m), 4.26 (1H, d, J=9.2 Hz), 4.61 (1H, d, J=9.2 Hz), 6.76 (1H, d, J=1.8 Hz), 7.10 (1H, dd, J=8.0, 2, 1 Hz), 7.54 (1H, d, J=8.3 Hz), 7.78 (1H, t, 3=2.1 Hz), 8.07 (1H, d, J=1.8 Hz), 8.28 (1H, d, J=2.3 Hz).

MS (ESI) m/z: 587 $(M+H)^+$.

Example 93 (Isomer A) and 94 (Isomer B)

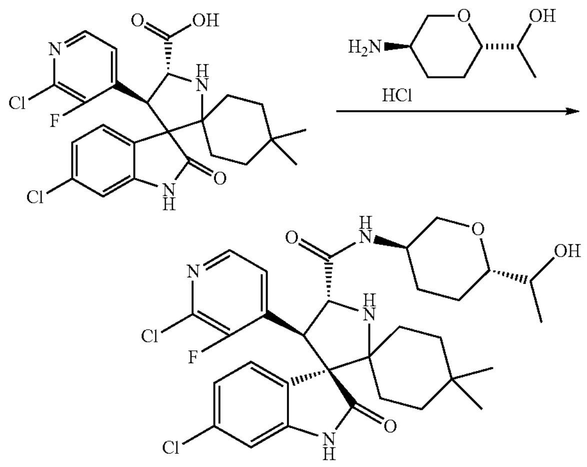

(3'R,4'S,5'R)-6"-chloro-4'=(2-chloro-3-fluoropyridin-4-yl)-N-{(3R,6S)-6-[1-hydroxyethyl]tetrahydro-2-pyran-3-yl}-4,4-dimethyl-2"-oxo-1",2"-dihydrodispiro[cyclohexane-1,2'-pyrrolidine-3',3"-indole]-5'-carboxamide The compound (300 mg, 0.61 mmol) obtained in Step 1 of Example 17 and the compound (133 mg, 0.73 mmol) obtained in Step 3 of Reference Example 30 were used as starting materials and treated in the same way as in Step 2 of Example 12 to give a mixture of diastereomers. The mixture of diastereomers obtained was resolved and purified by chiral column liquid chromatography [fractionation conditions: CHIRALCEL OD-H, n-hexane:ethanol=7:3 (v/v)] to separately give 42 mg (11%; isomer A) and 233 mg (61%: isomer B) of the title compounds as colorless solids.

Isomer A:

$^1$H-NMR (400 MHz, $CDCl_3$) δ: 0.68 (3H, s), 0.95 (3H, s), 1.09-1.25 (5H, m), 1.34-1.65 (5H, m), 1.69-1.79 (3H, m), 2.07 (1H, d, J=4.4 Hz), 2.10-2.15 (1H, m), 3.13 (1H, L, J=10.6 Hz), 3.20-3.25 (1H, m), 3.27 (1H, br s), 3.82-3.91 (2H, m), 4.04-4.09 (1H, m), 4.43 (1H, d, J=9.0 Hz), 4.65 (1H, d, J=9.0 Hz), 6.72 (1H, d, J=2.0 Hz), 7.07 (1H, dd, J=8.1, 2.0 Hz), 7.31 (1H, dd, J=8.1, 2.2 Hz), 7.40 (1H, s), 7.46 (1H, d, J=8.8 Hz), 7.49 (1H, t, J=5.0 Hz), 8.05 (1H, d, J=5.1 Hz).

MS (ESI) m/z: 619 $(M+H)^+$.

Isomer B:

$^1$H-NMR (400 MHz, $CDCl_3$) δ: 0.68 (3H, s), 0.95 (3H, s), 1.16 (3H, d, J=6.3 Hz), 1.17-1.24 (3H, m), 1.32-1.39 (1H, m), 1.42-1.64 (4H, m), 1.67-1.79 (3H, m), 2.08-2.14 (1H, m), 2.64 (1H, d, J=2.4 Hz), 3.02-3.08 (1H, m), 3.10 (1H, t, J=10.6 Hz), 3.27 (1H, br s); 3.60-3.65 (1H, m), 3.85-3.91 (1H, m), 4.05-4.10 (1H, m), 4.44 (1H, d, J=9.0 Hz), 4.65 (1H, d, J=9.0 Hz), 6.73 (1H, d, J=2.0 Hz), 7.07 (1H, dd, J=8.1, 2.0 Hz), 7.31 (1H, dd, J=8.1, 2.0 Hz), 7.36 (1H, s), 7.46 (1H, d, J=8.5 Hz), 7.49 (1H, t, J=5.0 Hz), 8.05 (1H, d, J=5.0 Hz).

MS (ESI) m/z: 619 $(M+H)^+$.

Example 95

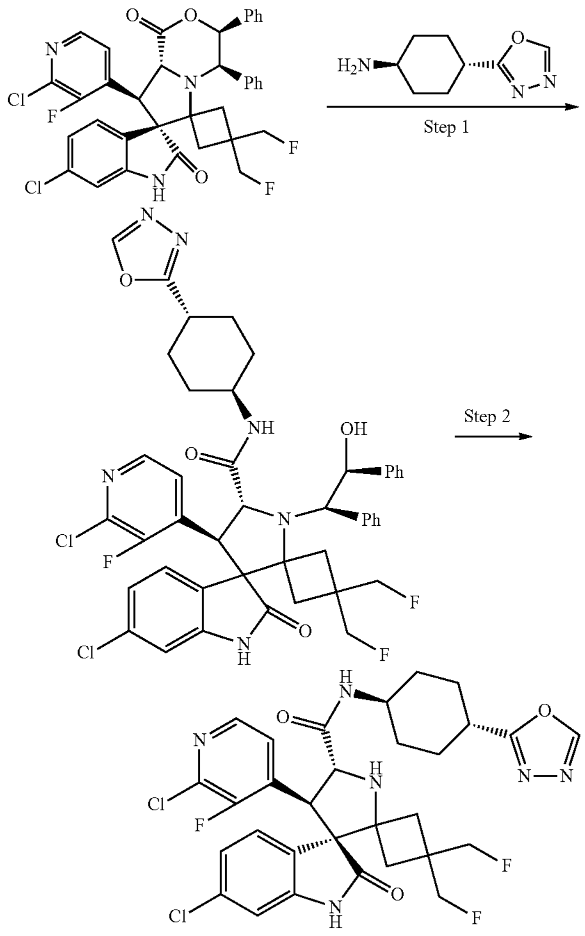

Step 1

(4'5, 5'R)-6"-chloro-4'-(2-chloro-3-fluoropyridin-4-yl)-3,3-bis(fluoromethyl)-1'-[(1R,2S)-2-hydroxy-1,2-diphenylethyl]-N-[trans-4-(1,3,4-oxadiazol-2-yl) cyclohexyl]-2"-oxo-1",2"-dihydrodispiro [cyclobutane-1,2'-pyrrolidine-3',3"-indole]-5'-carboxamide The compound (203 mg, 0.30 mmol) obtained in Step 91 of Example 1 was used as a starting material and treated in the same way as in Step 1 of Example 5 to give 60 mg (23%) of the title compound as a colorless amorphous solid.

MS (ESI) m/z: 845 $(M+H)^+$.

Step 2

(3'R, 4'S,5'R)-6"-chloro-4'-(2-chloro-3-fluoropyridin-4-yl)-3,3-bis(fluoromethyl)-N-[trans-4-(1,3,4-oxadiazol-2-yl)cyclohexyl]-2"-oxo-1",2'-dihydrodispiro[cyclobutane-1,2'-pyrrolidine-3',3"-indole]-5'-carboxamide The compound (60 mg, 0.07 mmol) obtained in Step 1 above was used as a starting material and treated in the same way as in Step 3 of Example 91 to give 23 mg (58%) of the title compound as a colorless solid [fractionation conditions: CHIRALPAK IC, n-hexane:ethanol=1:4 (v/v)].

$^1$H-NMR (400 MHz, $CD_3OD$) δ: 1.49-1.57 (2H, m), 1.67-1.75 (3H, m), 1.91 (1H, d, J=12.8 Hz), 2.03-2.11 (3H, m); 2.22 (2H, t, J=15.6 Hz), 2.49 (1H, d, J=12.4 Hz), 2.99-3.04 (1H, m), 3.70-3.76 (1H, m), 3.81 (1H, s), 3.92 (1H, s), 4.39 (1H, d, J=9.2 Hz), 4.52 (1H, d, J=9.2 Hz), 4.64 (1H, dd, J=15.6, 9.2 Hz), 4.76 (1H, dd, J=14.7, 8.7 Hz), 6.85 (1H, d, J=1.8 Hz), 7.13 (1H, dd, J=8.2, 1.8 Hz), 7.55 (1H, dd, J=8.2, 1.8 Hz), 7.62 (1H, t, J=5.0 Hz), 8.07 (1H, d, J=5.0 Hz), 8.84 (1H, s),

MS (ESI) m/z: 649 $(M+H)^+$.

Example 96

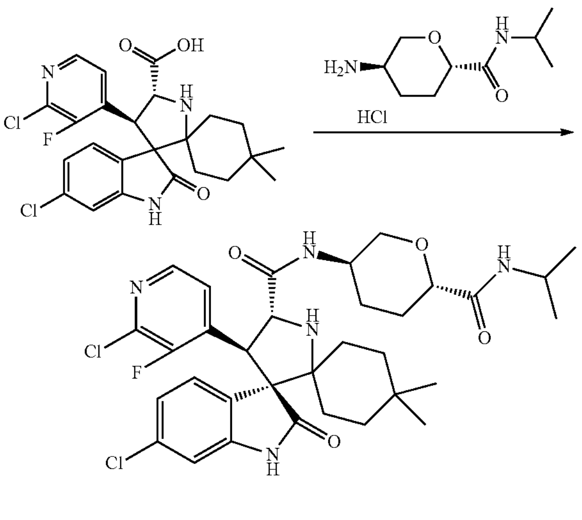

(3'R, 4'S,5'R)-6"-chloro-4'-(2-chloro-3-fluoropyridin-4-yl)-N-[(3R,6S)-6-(isopropylcarbamoyl)tetrahydro-2H-pyran-3-yl]-4,4-dimethyl-2'-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (80 mg, 0.36 mmol) obtained in Step 2 of Reference Example 37 were used as starting materials and treated in the same way as in Step 2 of Example 12 to give 182 mg (92%) of the title compound as a colorless solid.

$^1$H-NMR (400 MHz, $CDCl_3$) δ: 0.68 (3H, s), 0.95 (3H, s), 1.16 (6H, d, J=6.4 Hz), 1.17-1.22 (2H, m), 1.34-1.39 (1H, m), 1.44-1.77 (7H, m), 2.08-2.16 (1H, m), 2.27-2.34 (1H, m), 3.13 (1H, t, J=10.8 Hz), 3.28 (1H, br s), 3.71-3.76 (1H, m), 3.84-3.93 (1H, m), 4.01-4.14 (2H, m), 4.44 (1H, d, J=8.7 Hz), 4.64 (1H, d, J=9.2 Hz), 6.36 (1H, d, J=8.2 Hz), 6.73 (1H, d, J=1.8 Hz), 7.07 (1H, dd, J=7.8, 1.8 Hz), 7.31 (1H, dd, J=8.2, 2.3 Hz), 7.48-7.52 (2H, m), 7.61 (1H, s), 8.05 (1H, d, J=5.0 Hz).

MS (ESI) m/z: 662 $(M+H)^+$.

Example 97

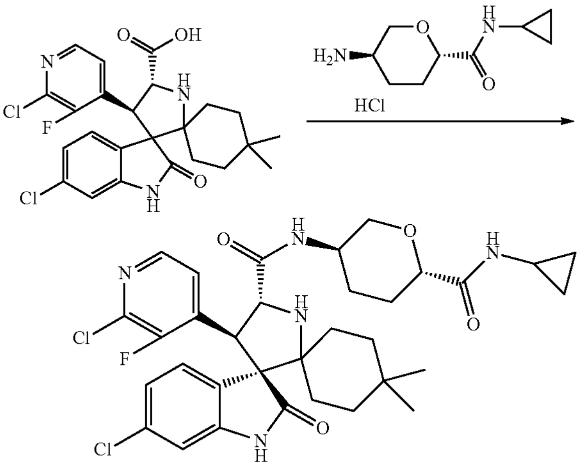

(3'R, 4'S,5'R)-6"-chloro-4'-(2-chloro-3-fluoropyridin-4-yl)-N-[(3R,6S)-6-(cyclopropylcarbamoyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (79 mg, 0.36 mmol) obtained in Step 2 of Reference Example 38 were used as starting materials and treated in the same way as in Step 2 of Example 12 to give 163 mg (82%) of the title compound as a colorless solid.

$^1$H-NMR (400 MHz, $CDCl_3$) δ: 0.50-0.55 (2H, m), 0.68 (3H, s), 0.71-0.80 (2H, m), 0.95 (3H, s), 1.09-1.25 (2H, m), 1.33-1.80 (8H, m), 2.09-2.15 (1H, m), 2.27-2.33 (1H, m), 2.69-2.75 (1H, m), 3.11 (1H, t, J=10.8 Hz), 3.27 (1H, br s), 3.73-3.78 (1H, m), 3.85-3.91 (1H, m), 4.06-4.12 (1H, m), 4.43 (1H, d, J=9.2 Hz), 4.63 (1H, d, J=9.2 Hz), 6.57 (1H, d, J=3.7 Hz), 6.74 (1H, d, J=1.8 Hz), 7.07 (1H, dd, J=8.0, 2.1

Hz), 7.30 (1H, dd, J=8.2, 2.3 Hz), 7.47-7.52 (2H, m), 7.68 (1H, s), 8.04 (1H, d, J=5.0 Hz).

MS (ESI) m/z: 658 $(M+H)^+$.

Example 98

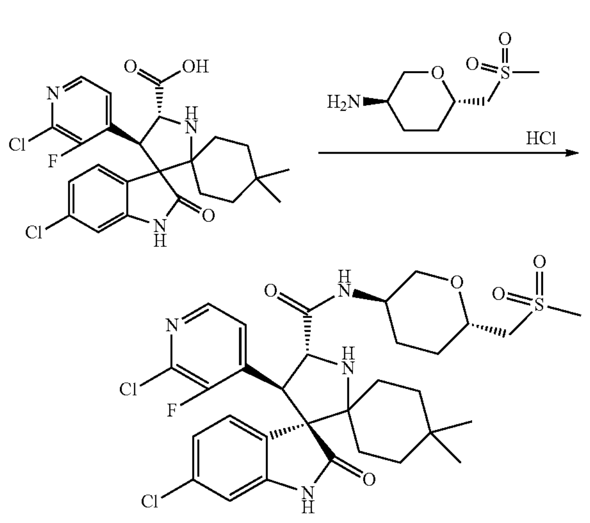

(3'R, 4'S,5'R)-6"-chloro-4'-(2-chloro-3-fluoropyridin-4-yl)-4,4-dimethyl-N-{(3R,6S)-6-[(methylsulfonyl)methyl]tetrahydro-2H-pyran-3-yl}-2"-oxo-1",2"-dihydrodispiro[cyclohexane-1,2'-pyrrolidine-3',3"-indole]-5'-carboxamide The compound (94 mg, 0.19 mmol) obtained in Step 1 of Example 17 and the compound (0.21 mmol) obtained in Step 2 of Reference Example 39 were used as starting materials and treated in the same way as in Step 2 of Example 12 to give 86 mg (68%) of the title compound as a colorless solid.

$^1$H-NMR (400 MHz, DMSO-$d_6$) δ: 0.59 (3H, s), 0.90 (3H, s), 0.92-1.00 (1H, m), 1.10-1.13 (1H, m), 1.19-1.22 (1H, m), 1.38-1.88 (9H, m), 2.96 (3H, s), 3.15-3.22 (2H, m), 3.41 (1H, dd, J=14.9, 8.9 Hz), 3.50-3.52 (1H, m), 3.60-3.77 (3H, m), 4.46 (1H, t, J=9.4 Hz), 4.57 (1H, d, J=8.7 Hz), 6.71 (1H, d, J=2.3 Hz), 7.06 (1H, dd, J=8.3, 1.8 Hz), 7.50 (1H, dd, J=8.3, 1.8 Hz), 7.63 (1H, t, J=5.0 Hz), 7.82 (1H, d, J=8.3 Hz), 8.18 (1H, d, J=5.0 Hz), 10.61 (1H, s).

MS (ESI) m/z: 667 $(M+H)^+$.

Example 99

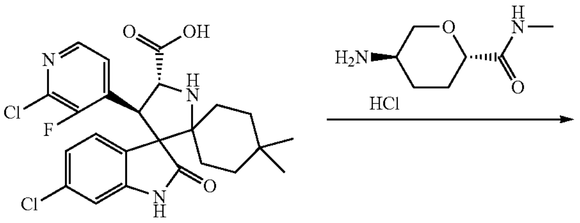

-continued

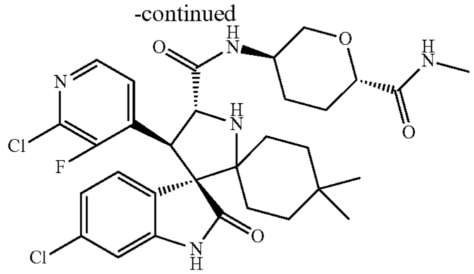

(3'R, 4'S,5'R)-6"-chloro-4'-(2-chloro-3-fluoropyridin-4-yl)-N-[(3R,6S)-6-(methylcarbamoyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (70 mg, 0.36 mmol) obtained in Step 2 of Reference Example 40 were used as starting materials and treated in the same way as in Step 2 of Example 12 to give 157 mg (83%) of the title compound as a colorless solid.

$^1$H-NMR (400 MHz, $CDCl_3$) δ: 0.68 (3H, s), 0.95 (3H, s); 1.11-1.27 (2H, m), 1.34-1.39 (1H, m), 1.44-1.60 (5H, m), 1.69-1.78 (2H, m), 2.09-2.15 (1H, m), 2.28-2.34 (1H, m), 2.82 (3H, d, J=5.0 Hz), 3.13 (1H, t, J=10.5 Hz), 3.27 (1H, br s), 3.76-3.81 (1H, m), 3.85-3.93 (1H, m), 4.12 (1H, dd, J=10.8, 3.0 Hz), 4.43 (1H, d, J=8.7 Hz), 4.64 (1H, d, J=9.2 Hz), 6.52-6.58 (1H, m), 6.73 (1H, d, J=1.8 Hz), 7.07 (1H, dd, J=8.0, 2.1 Hz), 7.31 (1H, dd, J=8.2, 2.3 Hz), 7.50 (2H, t, J=5.0 Hz), 7.62 (1H, s), 8.05 (1H, d, J=5.0 Hz).

MS (ESI) m/z: 632 $(M+H)^+$.

Example 100

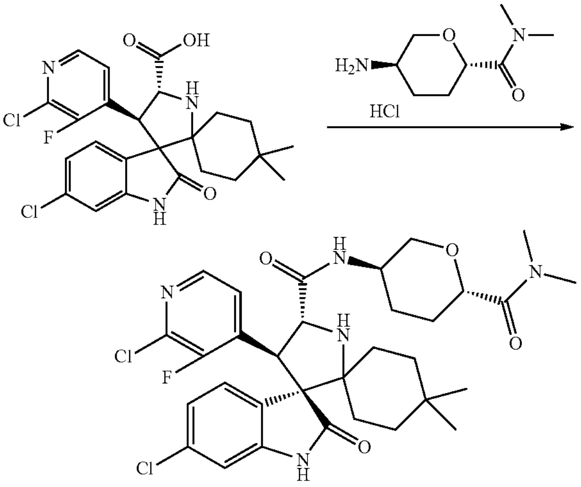

(3'R, 4'S,5'R)-6"-chloro-4'-(2-chloro-3-fluoropyridin-4-yl)-N-[(3R,6S)-6-(dimethylcarbamoyl)tetrahydro-2H-pyran-3-yl]-4,4-dimethyl-2"-oxo-1",2"-dihydrodispiro[cyclohexane-1,2'-pyrrolidine-3',3'"-indole]-5'-carboxamide The compound (150 mg, 0.30 mmol) obtained in Step 1 of Example 17 and the compound (75 mg, 0.36 mmol)

obtained in Step 2 of Reference Example 41 were used as starting materials and treated in the same way as in Step 2 of Example 12 to give 136 mg (70%) of the title compound as a colorless solid.

$^1$H-NMR (400 MHz, $CDCl_3$) δ: 0.68 (3H, s), 0.95 (3H, s), 1.13-1.27 (2H, m), 1.35-1.40 (1H, m), 1.44-1.59 (4H, m), 1.71-1.78 (2H, m), 1.87-2.02 (2H, m), 2.16-2.22 (1H, m), 2.95 (3H, s), 3.09 (3H, s), 3.25 (1H, t, J=10.1 Hz), 3.27 (1H, br s), 3.89-3.99 (1H, m), 4.06 (1H, dd, J=10.8, 3.4 Hz), 4.12 (1H, dd, J=9.4, 3.0 Hz), 4.45 (1H, d, J=9.2 Hz), 4.65 (1H, d, J=9.2 Hz), 6.73 (1H, d, J=1.8 Hz), 7.06 (1H, dd, J=8.2, 1.8 Hz), 7.32 (1H, dd, J=8.2, 1.8 Hz), 7.50 (1H, t, J=5.0 Hz), 7.61 (1H, d, J=8.7 Hz), 7.69 (1H, s), 8.04 (1H, d, J=5.0 Hz).

MS (ESI) m/z: 646 $(M+H)^+$.

Example 101

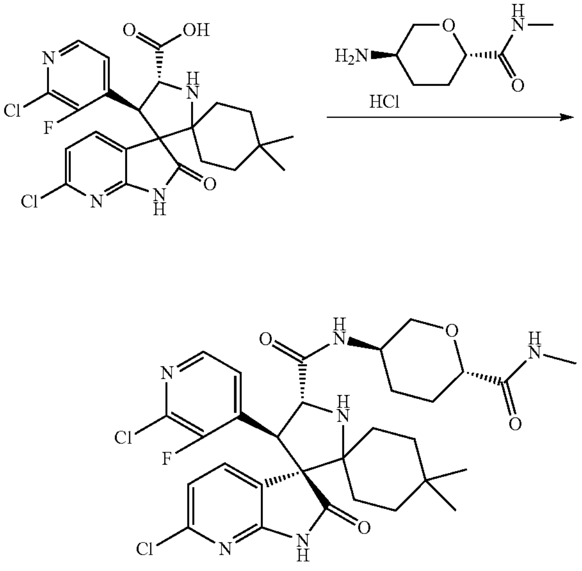

(3'R, 4'S,5'R)-6"-chloro-4'-(2-chloro-3-fluoropyridin-4-yl)-4,4-dimethyl-N-[(3R,6S)-6-(methylcarbamoyl)tetrahydro-2H-pyran-3-yl]-2"-oxo-1",2"-dihydrodispiro[cyclohexane-1,2'-pyrrolidine-3',3"-pyrrolo[2,3-b]pyridine]-5'-carboxamide The compound (150 mg, 0.30 mmol) obtained in Step 1 of Example 47 and the compound (59 mg, 0.30 mmol) obtained in Step 2 of Reference Example 40 were used as starting materials and treated in the same way as in Step 2 of Example 12 to give 94 mg (49%) of the title compound as a colorless solid.

$^1$H-NMR (400 MHz, $CDCl_3$) δ: 0.70 (3H, s), 0.96 (3H, s), 1.13-1.27 (2H, m), 1.34-1.40 (1H, m), 1.45-1.74 (7H, m), 2.08-2.14 (1H, m), 2.29-2.34 (1H, m), 2.83 (3H, d, J=5.0 Hz), 3.13 (1H, t, J=10.8 Hz), 3.21-3.27 (1H, m), 3.77-3.81 (1H, m), 3.84-3.91 (1H, m), 4.08-4.13 (1H, m), 4.41-4.48 (1H, m, 4.65 (1H, d, J=9.2 Hz), 6.52-6.57 (1H, m), 7.08 (1H, d, J=8.2 Hz), 7.41-7.47 (2H, m), 7.61 (1H, dd, J=7.8, 2.3 Hz), 8.08 (2H, d, J=5.0 Hz).

MS (ESI) m/z: 633 $(M+H)^+$.

Example 162

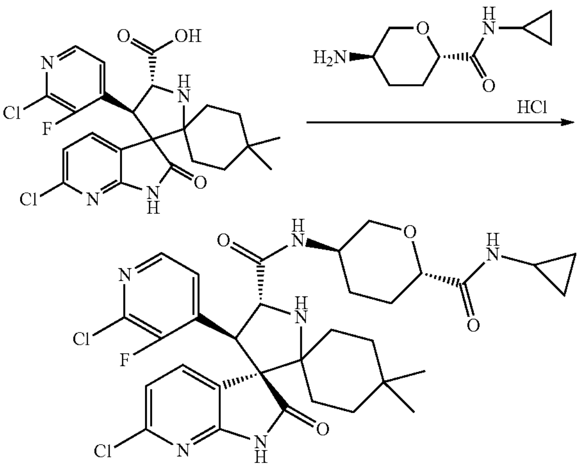

(3'R, 4'S,5'R)-6"-chloro-4'-(2-chloro-3-fluoropyridin-4-yl)-N-[(3R,6S)-6-(cyclopropylcarbamoyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (150 mg, 0.30 mmol) obtained in Step 1 of Example 47 and the compound (60 mg, 0.27 mmol) obtained in Step 2 of Reference Example 38 were used as starting materials and treated in the same way as in Step 2 of Example 12 to give 106 mg (54%) of the title compound as a colorless solid.

$^1$H-NMR (400 MHz, $CDCl_3$) δ: 0.51-0.54 (2H, m), 0.70 (3H, s), 0.75-0.80 (2H, m), 0.96 (3H, s), 1.13-1.19 (1H, m), 1.20-1.28 (1H, m), 1.34-1.39 (1H, m), 1.43-1.76 (7H, m), 2.07-2.13 (1H, m), 2.27-2.33 (1H, m), 2.70-2.75 (1H, m), 3.11 (1H, t, J=10.8 Hz), 3.24 (1H, br s), 3.76 (1H, dd, J=11.0, 2.3 Hz), 3.85-3.90 (1H, m), 4.08 (1H, dd, J=10.8, 3.0 Hz), 4.45 (1H, d, J=8.7 Hz), 4.65 (1H, d, J=9.2 Hz), 6.56 (1H, d, J=3.7 Hz), 7.07 (1H, d, J=8.2 Hz), 7.42 (1H, d, J=8.7 Hz), 7.45 (1H, t, J=5.0 Hz), 7.61 (1H, dd, J=7.8, 2.3 Hz), 8.08 (1H, d, J=5.0 Hz), 8.26 (1H, br s).

MS (ESI) m/z; 659 $(M+H)^+$.

Example 103

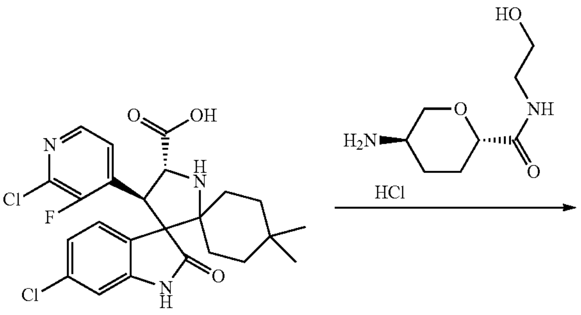

-continued

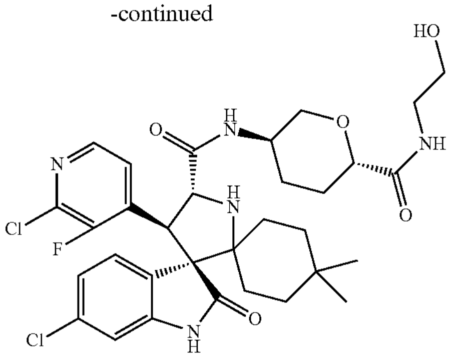

(3'R, 4'S,5'R)-6"-chloro-4'-(2-chloro-3-fluoropyridin-4-yl)-N-{(3R,6S)-6-[(2-hydroxyethyl) carbamoyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (81 mg, 0.36 mmol) obtained in Step 2 of Reference Example 42 were used as starting materials and treated in the same way as in Step 2 of Example 12 to give 86 mg (43%) of the title compound as a colorless solid.

$^1$H-NMR (400 MHz, $CDCl_3$) δ: 0.68 (3H, s), 0.95 (3H, s), 1.13-1.28 (2H, m), 1.33-1.40 (1H, m), 1.45-1.65 (5H, m), 1.68-1.81 (2H, m), 2.10-2.17 (1H, m), 2.27-2.36 (2H, m), 3.14 (1H, t, J=10.6 Hz), 3.27 (1H, br s), 3.40-3.48 (2H, m), 3.70-3.75 (2H, m), 3.80 (1H, dd, J=11.1, 2.3 Hz), 3.86-3.95 (1H, m), 4.11-4.16 (1H, m), 4.44 (1H, d, J=9.0 Hz), 4.64 (1H, d, J=9.0 Hz), 6.71 (1H, d, J=2.0 Hz), 6.85-6.89 (1H, m), 7.07 (1H, dd, J=8.2, 1.8 Hz), 7.24-7.26 (1H, m), 7.31 (1H, dd, J=7.9, 2.3 Hz), 7.44 (1H, d, J=8.1 Hz), 7.47 (1H, t, J=5.0 Hz), 8.04 (1H, d, J=5.1 Hz).

MS (ESI) m/z: 662 $(M+H)^+$.

Example 104

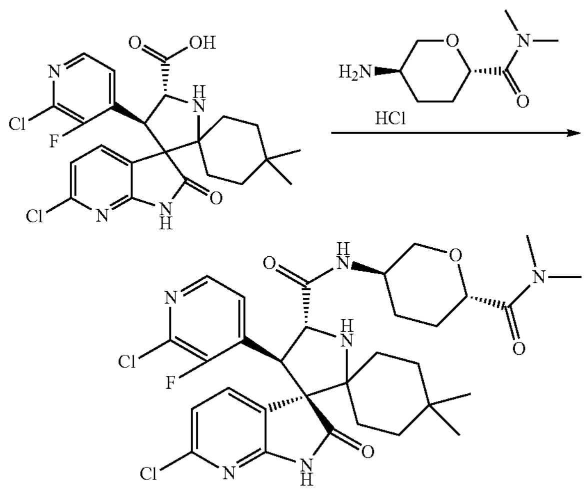

(3'R, 4'S,5'R)-6"-chloro-4'-(2-chloro-3-fluoropyridin-4-yl)-N-[(3R,6S)-6-(dimethylcarbamoyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (150 mg, 0.30 mmol) obtained in Step 1 of Example 47 and the compound (75 mg, 0.36 mmol) obtained in Step 2 of Reference Example 41 were used as starting materials and treated in the same way as in Step 2 of Example 12 to give 105 mg (54%) of the title compound as a colorless solid.

$^1$H-NMR (400 MHz, $CDCl_3$) δ: 0.70 (3H, s), 0.96 (3H, s), 1.13-1.29 (2H, m), 1.36-1.41 (1H, m), 1.46-1.66 (5H, m), 1.72-1.77 (1H, m), 1.88-2.05 (2H, m), 2.15-2.23 (1H, m), 2.96 (3H, s), 3.09 (3H, s), 3.23-3.29 (2H, m), 3.90-3.97 (1H, m), 4.03-4.07 (1H, m), 4.13 (1H, dd, J=9.6, 3.2 Hz), 4.46 (1H, d, J=9.2 Hz), 4.67 (1H, d, J=9.2 Hz), 7.08 (1H, d, J=7.8 Hz), 7.45 (1H, t, J=5.0 Hz), 7.54 (1H, d, J=8.7 Hz), 7.62 (1H, dd, J=8.0, 2.5 Hz), 8.08 (1H, d, J=5.0 Hz), 8.12 (1H, br s).

MS (ESI) m/z: 647 $(M+H)^+$.

Example 105

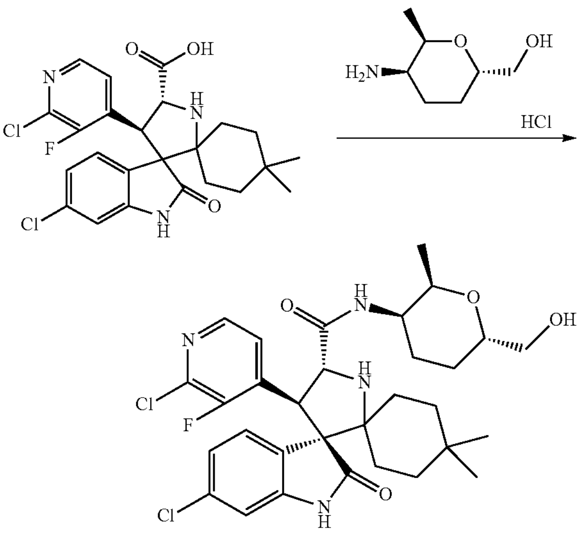

(3'R, 4'S,5'R)-6"-chloro-4'-(2-chloro-3-fluoropyridin-4-yl)-N-[(2R,3R,6S)-6-(hydroxymethyl)-2-methyltetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (85 mg, 0.17 mmol) obtained in Step 1 of Example 17 and the compound (38 mg, 0.21 mmol) obtained in Step 7 of Reference Example 43 were used as starting materials and treated in the same way as in Step 2 of Example 12 to give 43 mg (40%) of the title compound as a colorless solid.

$^1$H-NMR (400 MHz, $CDCl_3$) δ: 0.69 (3H, s), 0.95 (3H, s), 1.12-1.26 (6H, m), 1.35-1.94 (10H, m), 3.28 (1H, br s), 3.47-3.58 (1H, m), 3.68-4.17 (4H, m), 4.49 (1H, d, J=9.17 Hz), 4.65 (1H, d, J=9.17 Hz), 6.74 (1H, d, J=1.83 Hz), 7.07 (1H, dd, J=8.25, 1.83 Hz), 7.20-7.25 (1H, m), 7.30-7.35 (1H, m), 7.49-7.53 (1H, m), 7.78 (1H, d, J=8.71 Hz), 8.06 (1H, d, J=5.04 Hz).

MS (ESI) m/z: €19 $(M+H)^+$.

Example 106

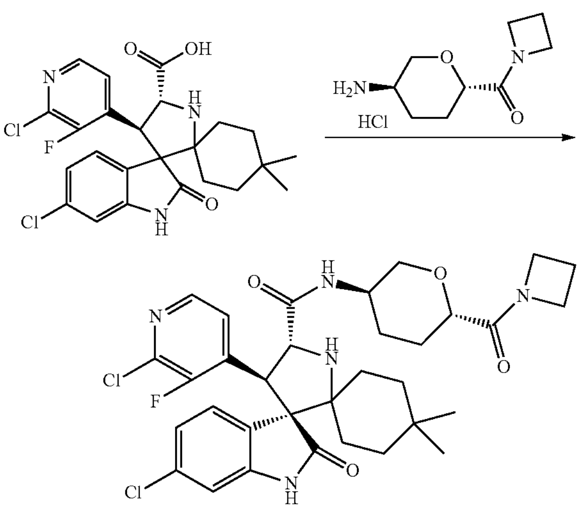

(3'R, 4+S,5'R)—N-[(3R,6S)-6-(azetidin-1-ylcarbonyl)tetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5H-carboxamide The compound (150 mg, 0.30 mmol) obtained in Step 1 of Example 17 and the compound (99 mg, 0:45 mmol) obtained in Step 2 of Reference Example 44 were used as starting materials and treated in the same way as in Step 2 of Example 12 to give 26 mg (13%) of the title compound as a colorless solid.

$^1$H-NMR (400 MHz, $CDCl_3$) δ: 0.68 (3H, s), 0.95 (3H, s), 1.12-1.23 (2H, m), 1.33-1.40 (1H, m), 1.45-1.65 (5H, m), 1.68-1.84 (3H, m), 2.05-2.15 (2H, m), 2.23-2.31 (2H, m), 3.13 (1H, t, J=10.3 Hz), 3.26 (1H, s), 3.86-3.92 (1H, m), 3.93 (1H, dd, J=10.5, 2.3 Hz), 4.04 (2H, t, J=7.6 Hz), 4.05-4.08 (1H, m), 4.32 (2H, t, J=7.8 Hz), 4.43 (1H, d, J=9.6 Hz), 4.64 (1H, d, J=9.2 Hz), 6.74 (1H, d, J=1.8 Hz), 7.07 (1H, dd, J=8.2, 1.8 Hz), 7.29-7.33 (1H, m), 7.49 (1H, t, J=4.8 Hz), 7.54 (1H, d, J=8.2 Hz), 8.05 (1H, d, J=5.0 Hz).

MS (ESI) m/z: 660 $(M+H)^+$.

Example 107

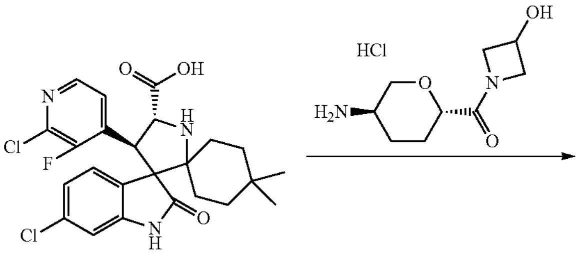

-continued

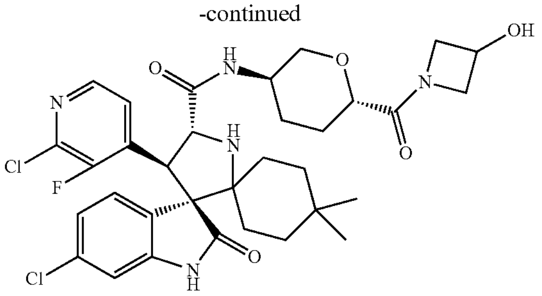

(3'R, 4'S,5'R)-6"-chloro-4'-(2-chloro-3-fluoropyridin-4-yl)-N-{(3R,6S)-6-[(3-hydroxyazetidin-1-yl)carbonyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (106 mg, 0.45 mmol) obtained in Step 2 of Reference Example 45 were used as starting materials and treated in the same way as in Step 2 of Example 12 to give 60 mg (30%) of the title compound as a colorless solid, $^1$H-NMR (400 MHz, $CDCl_3$) δ: 0.68 (3H, s), 0.95 (3H, s), 1.11-1.23 (2H, m), 1.33-1.40 (1H, m), 1.45-1.65 (4H, m), 1.67-1.83 (3H, m), 2.06-2.17 (2H, m), 2.42-2.58 (1H, m), 3.12 (1H, t, J=10.3 Hz), 3.25 (1H, br s), 3.83-3.91 (2H, m), 3.94 (1H, dd, J=10.5, 1.8 Hz), 4.01-4.07 (1H, m), 4.14 (1H, dd, J=10.5, 4.1 Hz), 4.23-4.28 (1H, m), 4.44 (1H, d, J=8.7 Hz), 4.50-4.56 (1H, m), 4.59-4.66 (2H, m), 6.72 (1H, d, J=1.8 Hz), 7.07 (1H, dd, J=8.0, 2.1 Hz), 7.31 (1H, dd, J=8.0, 2.1 HZ), 7.50 (1H, t, J=4.8 Hz), 7.54-7.58 (2H, m), 8.05 (1H, d, J=5.0 Hz).

MS (ESI) m/z: 674 $(M+H)^+$.

Example 108

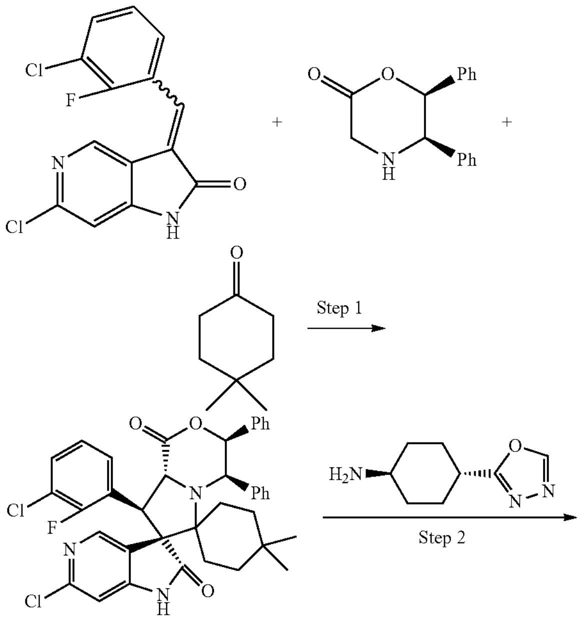

-continued

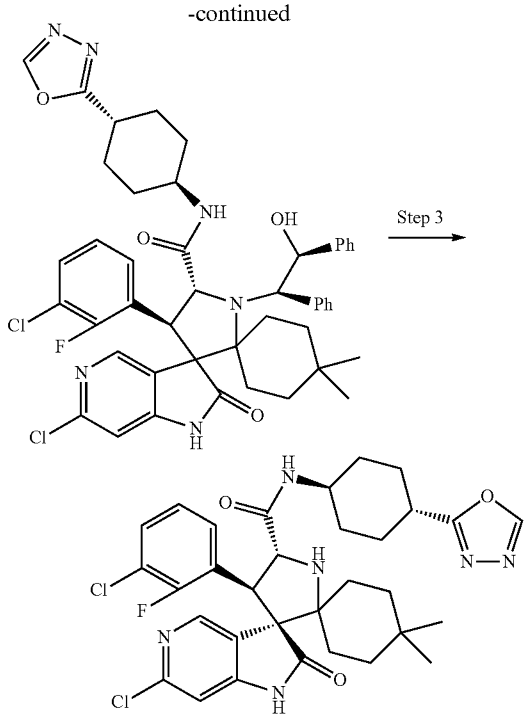

Step 1

(3'S,4'R, 7'S,8'S,8a'R)-6"-chloro-8'-(3-chloro-2-fluorophenyl)-4,4-dimethyl-3',4'-diphenyl-3',4',8',8a'-tetrahydro-1'H-dispiro[cyclohexane-1,6'-pyrrolo[2,1-c][1,4]oxazine-7',3"-pyrrolo[3,2-c]pyridine]-1',2"(1"B)-dione The compound (3.94 g, 12.7 mmol) obtained in Reference Example 46 was used as a starting material and treated in the same way as in Step 1 of Example 9 to give 6.51 g (76%) of the title compound as a yellow amorphous solid.

$^1$H-NMR (400 MHz, $CDCl_3$) δ: 0.20 (3H, s), 0.54 (3H, s), 0.94-1.01 (3H, m), 1.29-1.42 (4H, m), 1.83-1.85 (1H, m), 2.22-2.26 (1H, m), 4.60 (1H, d, J=11.2 Hz), 4.84 (1H, d, J=3.2 Hz), 5.36 (1H, d, J=11.2 Hz), 6.74 (2H, d, J=6.6 Hz), 6.87 (1H, s), 7.05-7.32 (1H, m), 7.79 (1H, t, J=6.7 Hz), 8.22 (2H, s).

Step 2

(4'S,5'R)-6"-chloro-4'-(3-chloro-2-fluorophenyl)-1'-[(1R,2S)-2-hydroxy-1,2-diphenylethyl]-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-pyrrolo[3,2-c]pyridine]-5'-carboxamide The compound (1.38 g, 2.06 mmol) obtained in Step 1 above the compound (1.03 g, 6.17 mmol) obtained in Step 3 of Reference Example 3 were used as starting materials and treated in the same way as in Step 1 of Example 5 to give 0.95 g (55%) of the title compound as a pale yellow amorphous solid.

MS (ESI) m/z: 837 $(M+H)^+$.

Step 3

(3'R, 4'S, S'R)-6"-chloro-4'-(3-chloro-2-fluorophenyl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-pyrrolo[3,2-c]pyridine]-5'-carboxamide The compound (950 mg, 1.18 mmol) obtained in Step 2 above was used as a starting material and treated in the same way as in Step 3 of Example 1 to give 350 mg (46%) of the title compound as a colorless solid.

$^1$H-NMR (400 MHz, $CD_3OD$) δ: 0.73 (3H, s), 0.97 (3H, s); 1.12-1.24 (2H, m), 1.38-2.26 (14H, m), 3.01-3.04 (1H, m), 3.68-3.72 (1H, m), 4.57 (1H, d, J=9.3 Hz), 4.75 (1H, d, J=9.3 Hz), 6.79 (1H, s), 7.05 (1H, t, J=8.1 Hz), 7.22-7.26 (1H, m), 7.55-7.61 (1H, m), 8.31 (1H, d, J=2.4 Hz), 8.85 (1H, s),

MS (ESI) m/z: 641 $(M+H)^+$.

Example 109

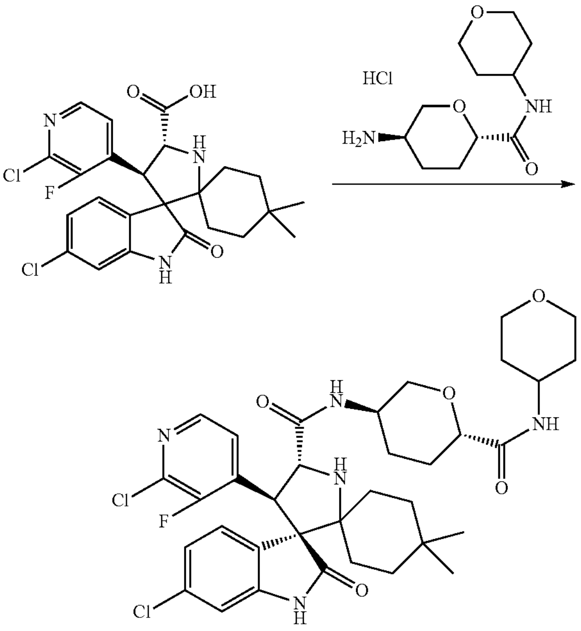

(3'R, 4'S,5'R)-6"-chloro-4'-(2-chloro-3-fluoropyridin-4-yl)-4,4-dimethyl-2"-Oxo-N-[(3R,6S)-6-(tetrahydro-2H-pyran-4-ylcarbamoyl)tetrahydro-2H-pyran-3-yl]-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (95 mg, 0.36 mmol) obtained in Step 2 of Reference Example 47 were used as starting materials and treated in the same way as in Step 2 of Example 12 to give 121 mg (57%) of the title compound as a colorless solid.

$^1$H-NMR (400 MHz, $CDCl_3$) δ: 0.68 (3H, s), 0.95 (3H, s), 1.11-1.25 (2H, m), 1.37 (1H, d, J=12.8 Hz), 1.47-1.77 (9H, m), 1.83-1.91 (2H, m), 2.10-2.16 (1H, m), 2.28-2.34 (1H, m), 3.14 (1H, t, J=10.5 Hz), 3.29 (1H, br s), 3.43-3.51 (2H, m), 3.76 (1H, d, J=8.7 Hz), 3.86-4.02 (4H, m), 4.12 (1H, dd,

J=10.8, 3.4 Hz), 4.44 (1H, d, J=8.7 Hz), 4.64 (1H, d, J=9.2 Hz), 6.46 (1H, d, J=8.2 Hz), 6.73 (1H, d, J=1.8 Hz), 7.07 (1H, dd, J=8.2, 1.8 Hz), 7.31 (1H, dd, J=8.0, 2.1 Hz), 7.49-7.52 (2H, m), 7.65 (1H, s), 8.05 (1H, d, J=5.0 Hz).

MS (ESI) m/z: 702 $(M+H)^+$.

Example 110

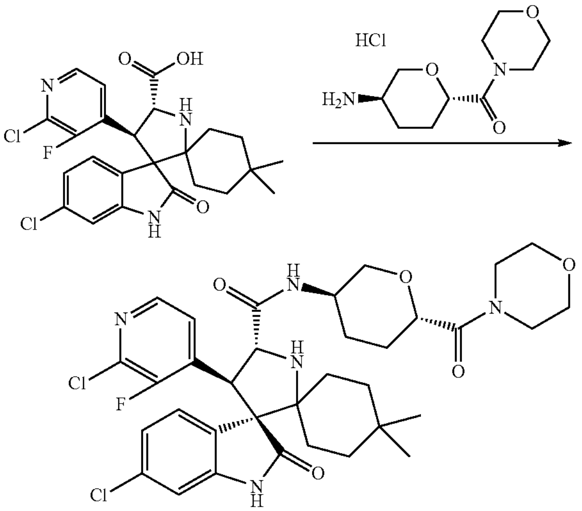

(3'R, 4'S,5'R)-6"-chloro-4'-(2-chloro-3-fluoropyridin-4-yl)-4,4-dimethyl-N-[(3R,6S)-6-(morpholin-4-ylcarbonyl)tetrahydro-2H-pyran-3-yl]-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (112 mg, 0.45 mmol) obtained in Step 2 of Reference Example 48 were used as starting materials and treated in the same way as in Step 2 of Example 12 to give 98 mg (47%) of the title compound as a colorless solid.

$^1$H-NMR (400 MHz, $CDCl_3$) δ: 0.68 (3H, s), 0.95 (3H, s), 1.11-1.25 (2H, m), 1.37 (1H, d, J=12.8 Hz), 1.45-1.65 (4H, m), 1.71-1.81 (2H, m), 1.93-2.01 (2H, m), 2.16-2.23 (1H, m), 3.24 (1H, dd, J=11.0, 9.2 Hz), 3.26 (1H, br s); 3.52-3.59 (2H, m), 3.63-3.73 (6H, m), 3.90-3.97 (1H, m), 4.03 (1H, dd, J=10.1, 3.7 Hz), 4.10 (1H, dd, J=8.0, 3.4 Hz), 4.45 (1H, 3, J=9.2 Hz), 4.64 (1H, d, J=8.7 Hz), 6.73 (1H, d, J=1.8 Hz), 7.07 (1H, dd, J=8.2, 1.8 Hz), 7.31 (1H, dd, J=8.0, 2.1 Hz), 7.48-7.52 (2H, m), 7.62 (1H, d, J=8.7 Hz), 8.05 (1H, d, J=5.5 Hz).

MS (ESI) m/z: 688 $(M+H)^+$.

Example 111

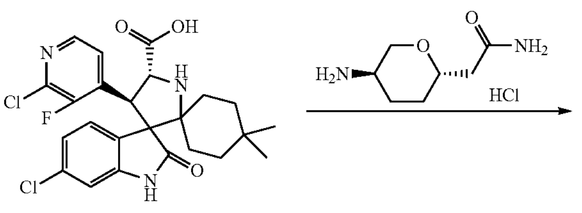

-continued

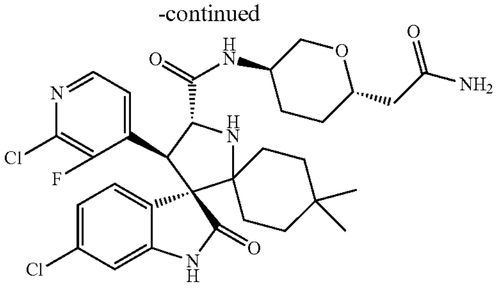

(3'R, 4'S,5'R)—N-[(3R,6S)-6-(2-amino-2-oxoethyl)tetrahydro-2H-pyran-3-yl]-6"-chloro-4'-(2-chloro-3-fluoropyridin-4-yl)-4,4-dimethyl-2"-oxo-1",20-dihydrodispiro[cyclohexane-1,2'-pyrrolidine-3',3"-indole]-5'-carboxamide The compound (89 mg, 0.18 mmol) obtained in Step 1 of Example 17 and the compound (0.15 mmol) obtained in Step 3 of Reference Example 49 were used as starting materials and treated in the same way as in Step 2 of Example 12 to give 31 mg (32%) of the title compound as a colorless solid.

$^1$H-NMR (500 MHz, $CDCl_3$) δ: 0.67 (3H, s), 0.94 (3H, s), 1.11-1.26 (2H, m), 1.36 (1H, dd, J=12.9, 2.0 Hz), 1.45-1.82 (8H, m), 2.07-2.10 (1H, m); 2.37-2.46 (2H, m), 3.14 (1H, t, J=10.6 Hz), 3.29 (1H, s), 3.65-3.71 (1H, m), 3.85-3.93 (1H, m), 4.03-4.06 (1H, m), 4.44 (1H, d, J=9.2 Hz), 4.62 (1H, d, J=9.2 Hz), 5.68 (1H, s), 6.29 (1H, s), 6.71 (1H, d, J=1.7 Hz), 7.05 (1H, dd, J=8.3, 2.0 Hz), 7.27-7.30 (2H, m), 7.49-7.53 (2H, m), 8.04 (1H, d, J=5.2 Hz), 8.42 (1H, s).

MS (ESI) m/z: 654 $(M+Na)^+$.

Example 112

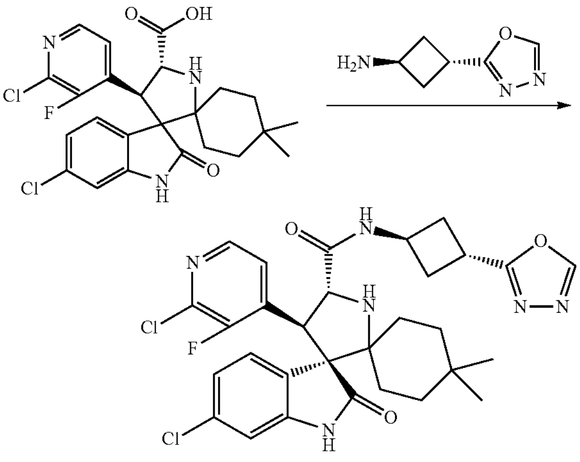

(3'R, 4'S, S'R)-6"-chloro-4'-(2-chloro-3-fluoropyridin-4-yl)-4,4-dimethyl-N-[trans-3-(1,3,4-oxadiazol-2-yl)cyclobutyl]-2"-oxo-1",2"-dihydrodispiro[cyclohexane-1,2'-pyrrolidine-3',3"-indole]-5-carboxamide The compound (1.00 g, 2.03 mmol) obtained in Step 1 of Example 17 and the compound (391 mg, 2.81 mmol) obtained in Step 3 of Reference Example 50 were used as starting materials and treated in the same way as in Step 2 of Example 12 to give 753 mg (60%) of the title compound as a colorless solid.

$^1$H-NMR (400 MHz, $CD_3OD$) δ: 0.69 (3H, s), 0.98 (3H, s), 1.12-1.24 (2H, m), 1.33-1.40 (1H, m), 1.52-1.69 (2H, m), 1.77=1.92 (3H, m), 2.60-2.80 (4H, m), 3.76-3.82 (1H, m), 4.56 (1H, d, J=9.2 Hz), 4.57-4.65 (1H, m), 4.70 (1H, d, J=9.2 Hz), 6.77 (1H, d, J=2.3 Hz), 7.07 (1H, dd, J=8.0, 2.1 Hz), 7.47 (1H, dd, J=8.2, 2.3 Hz), 7.66 (1H, t, J=5.0 Hz), 7.90 (1H, s), 8.06 (1H, d, J=5.0 Hz), 8.89 (1H, s).

MS (ESI) m/z: 613 $(M+H)^+$.

Example 113

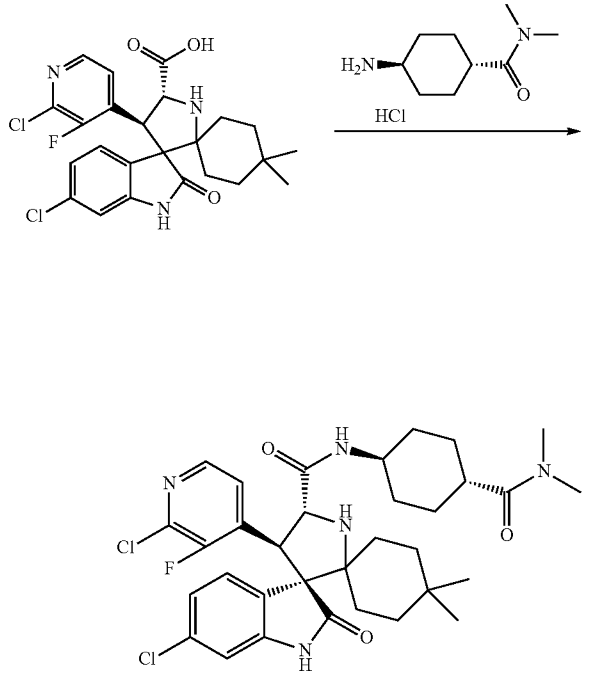

(3'R, 4'S,5'R)-6"-chloro-4'-(2-chloro-3-fluoropyridin-4-yl)-N-[trans-4-(dimethylcarbamoyl)cyclohexyl]-4,4-dimethyl-2"-oxo-1",2"-dihydrodispiro [cyclohexane-1,2'-pyrrolidine-3',3"-indole]-5'-carboxamide The compound (29 mg, 0.06 mmol) obtained in Step 1 of Example 17 and trans-4-amino-N,N-dimethylcyclohexanecarboxamide hydrochloride (WO2008/068171) (17 mg, 0.08 mmol) were used as starting materials and treated in the same way as in Step 2 of Example 12 to give 36 mg (100%) of the title compound as a colorless solid.

$^1$H-NMR (400 MHz, $CDCl_3$) δ: 0.67 (3H, s), 0.95 (3H, s), 1.08-1.40 (6H, m), 1.42-1.55 (2H, m), 1.56-1.91 (6H, m), 2.00-2.13 (2H, m), 2.44-2.55 (1H, m), 2.93 (3H, s), 3.06 (3H, s), 3.66-3.79 (1H, m), 4.44 (1H, d, J=8.7 Hz), 4.65 (1H, d, J=8.7 Hz), 6.71 (1H, d, J=1.8 Hz), 7.05 (1H, dd, J=8.3, 1.8 Hz), 7.31 (1H, dd, J=8.3, 2.3 Hz), 7.49-7.57 (2H, m), 8.03 (1H, d, J=5.0 Hz), 8.09 (1H, s).

MS (ESI) m/z: 644 $(M+H)^+$.

Example 114

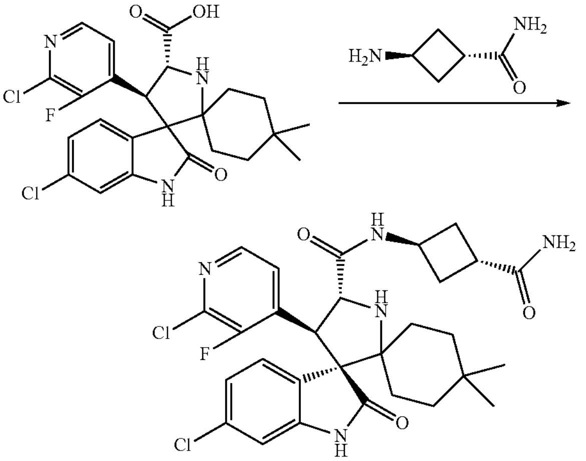

(3'R, 4'S,5'R)—N-(trans-3-carbamoylcyclobutyl)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide The compound (90 mg, 0.18 mmol) obtained in Step 1 of Example 17 and the compound (21 mg, 0.18 mmol) obtained in Step 2 of Reference Example 51 were used as starting materials and treated in the same way as in Step 2 of Example 12 to give 66 mg (61%) of the title compound as a colorless solid.

$^1$H-NMR (400 MHz, $CDCl_3$) δ: 0.68 (38, s), 0.95 (3H, s), 1.11-1.79 (8H, m), 2.24-2.41 (2H, m), 2.61-2.75 (2H, m), 2.99-3.09 (1H, m), 3.73 (1H, br s), 4.40-4.52 (2H, m), 4.65 (1H, d, J=9.17 Hz), 5.39 (2H, br s), 6.73 (1H, d, J=1.8 Hz), 7.07 (1H, dd, J=8.25, 1.8 Hz), 7.30-7.35 (1H, m), 7.41 (1H, s), 7.46-7.51 (1H, m), 7.85 (1H, d, J=7.8 Hz), 8.05 (1H, d, J=5.0 Hz).

MS (ESI) m/z: 588 $(M+H)^+$.

Example 115

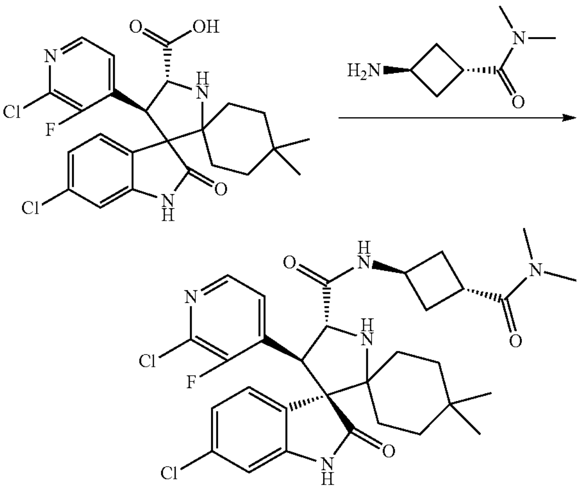

(3'R, 4'S,5'R)-6"-chloro-4'-(2-chloro-3-fluoropyridin-4-yl)-N-[trans-3-(dimethylcarbamoyl)cyclobutyl]-4,4-dimethyl-2"-oxo-1",2"-dihydrodispiro[cyclohexane-1,2'-pyrrolidine-3',3"-indole]-5'-carboxamide The compound (90 mg, 0.18 mmol) obtained in Step 1 of Example 17 and the compound (26 mg, 0.18 mmol) obtained in Step 2 of Reference Example 52 were used as starting materials and treated in the same way as in Step 2 of Example 12 to give 35 mg (31%) of the title compound as a colorless solid.

$^1$H-NMR (400 MHz, $CDCl_3$) δ: 0.69 (3H, s), 0.95 (3H, s), 1.11-1.78 (8H, m), 2.19-2.38 (2H, m), 2.66-2.81 (2H, m), 2.90 (3H, s), 2.96 (3H, s), 3.23-3.37 (2H, m), 4.25-4.36 (1H, m), 4.43 (1H, d, J=9.0 Hz), 4.66 (1H, d, J=9.0 Hz), 6.73 (1H, d, J=1.8 Hz), 7.07 (1H, dd, J=7.8, 1.83 Hz), 7.31-7.41 (2H, m), 7.47-7.51 (1H, m), 7.87 (1H, d, J=7.3 Hz), 8.04 (1H, d, J=5.0 Hz).

MS (ESI) m/z: 616 $(M+H)^+$.

Example 116

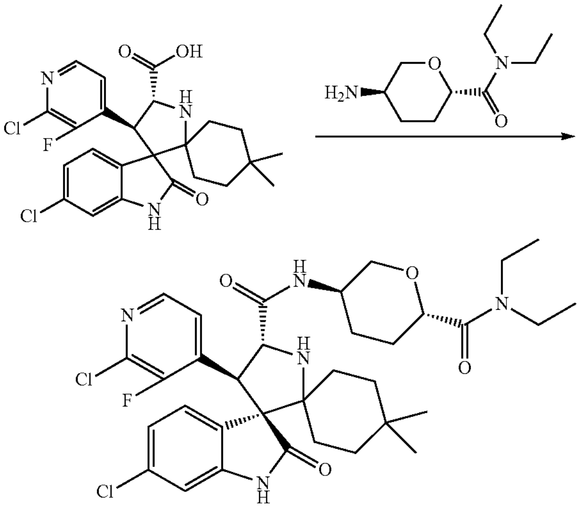

(3'R, 4'S,5'R)-6"-chloro-4'-(2-chloro-3-fluoropyridin-4-yl)-N-[(3R,6S)-6-(diethylcarbamoyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (73 mg, 0.36 mmol) obtained in Step 2 of Reference Example 53 were used as starting materials and treated in the same way as in Step 2 of Example 12 to give 124 mg (61%) of the title compound as a colorless solid.

$^1$H-NMR (400 MHz, $CDCl_3$) δ: 0.68 (3H, s), 0.95 (3H, s), 1.12 (3H, t, J=7.1 Hz), 1.19 (3H, t, J=7.1 Hz), 1.20-1.23 (2H, m), 1.37 (1H, d, J=11.0 Hz), 1.46-1.67 (4H, m), 1.71-1.80 (2H, m), 1.86-1.93 (1H, m), 1.97-2.06 (1H, m), 2.17-2.25 (1H, m), 3.23-3.51 (6H, m), 3.90-3.99 (1H, m); 4.05 (1H, dd, J=12.4, 4.6 Hz), 4.09 (1H, dd, J=9.4, 3.0 Hz), 4.42-4.47 (1H, m), 4.65 (1H, d, J=9.2 Hz), 6.74 (1H, d, J=1.8 Hz), 7.07 (1H, dd, J=8.0, 2.1 Hz), 7.32 (1H, dd, J=8.2, 2.3 Hz), 7.42 (1H, s), 7.49 (1H, t, J=5.0 Hz), 7.62 (1H, d, J=8.2 Hz), 8.05 (1H, d, J=5.5 Hz).

MS (ESI) m/z: 674 $(M+H)^+$.

Example 117

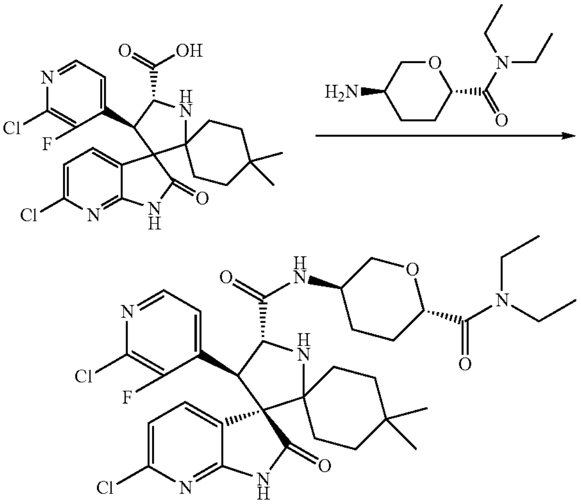

(3'R, 4'S,5'R)-6"-chloro-4'-(2-chloro-3-fluoropyridin-4-yl)-N-[(3R,6S)-6-(diethylcarbamoyl)tetrahydro-2H-pyran-3-yl]-4,4-dimethyl-2"-oxo-1",2"-dihydrodispiro[cyclohexane-1,2'-pyrrolidine-3',3"-pyrrolo[2,3-b]pyridine]-5'-carboxamide The compound (150 mg, 0.30 mmol) obtained in Step 1 of Example 47 and the compound (72 mg, 0.36 mmol) obtained in Step 2 of Reference Example 53 were used as starting materials and treated in the same way as in Step 2 of Example 12 to give 129 mg (68%) of the title compound as a colorless solid.

$^1$H-NMR (400 MHz, $CDCl_3$) δ: 0.70 (38, s), 0.96 (3H, s), 1.13 (3H, t, J=7.1 Hz), 1.18 (3H, t, J=7.1 Hz), 1.20-1.27 (2H, m), 1.38 (1H, d, J=9.2 Hz), 1.46-1.66 (5H, m), 1.73-1.77 (1H, m), 1.86-1.92 (1H, m), 1.97-2.07 (1H, m), 2.16-2.23 (1H, m), 3.22-3.48 (6H, m), 3.90-3.98 (1H, m), 4.04 (1H, dd, J=10.8, 3.0 Hz), 4.09 (1H, dd, J=9.2, 3.2 Hz), 4.46 (1H, d, J=8.7 Hz), 4.67 (1H, d, J=9.2 Hz), 7.07 (1H, d, J=7.8 Hz), 7.45 (1H, t, J=5.0 Hz), 7.56 (1H, d, J=8.2 Hz), 7.63 (1H, dd, J=7.8, 2.3 Hz), 8.08 (1H, d, J=5.5 Hz), 8.28 (1H, s).

MS (ESI) m/z: 675 $(M+H)^+$.

Example 118

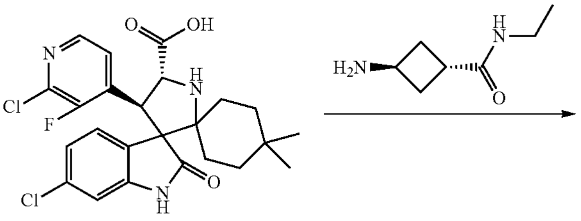

-continued

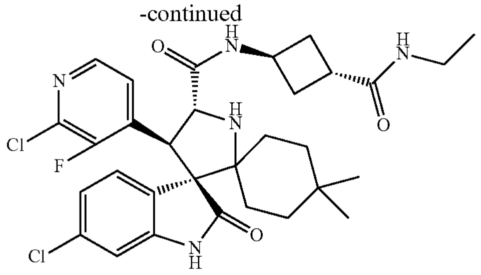

(3'R,4'S,5'R)-6"-chloro-4'-(2-chloro-3-fluoropyridin-4-yl)-N-[trans-3-(ethylcarbamoyl)cyclobutyl]-4,4-dimethyl-2"-oxo-1",2"-dihydrodispiro[cyclohexane-1,2'-pyrrolidine-3',3"-indole]-5'-carboxamide The compound (110 mg, 0.22 mmol) obtained in Step 1 of Example 17 and the compound (41 mg, 0.29 mmol) obtained in Step 2 of Reference Example 54 were used as starting materials and treated in the same way as in Step 2 of Example 12 to give 42 mg (31%) of the title compound as a colorless solid.

$^1$H-NMR (400 MHz, $CD_3OD$) δ: 0.69 (3H, s), 0.96 (3H, s), 1.07-1.40 (7H, m), 1.51-1.91 (4H, m), 2.22-2.35 (2H, m), 2.47-2.61 (2H, m), 2.96-3.06 (1H, m), 3.20 (2H, q, J=7.3 Hz), 4.41-4.56 (2H, m), 4.67 (1H, d, J=9.2 Hz), 6.77 (1H, d, J=2.1 Hz), 7.06 (1H, dd, J=8.0, 2.1 Hz), 7.43-7.50 (1H, m), 7.62-7.68 (1H, m), 8.05 (1H, d, J=5.0 Hz).

MS (ESI) m/z: 616 $(M+H)^+$.

Example 119

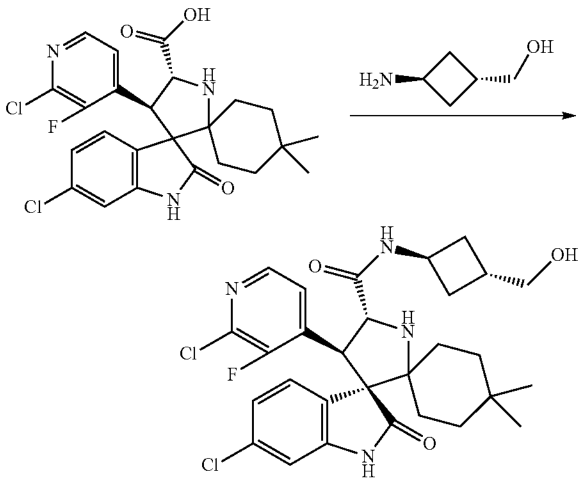

(3'R,4'S,5'R)-6"-chloro-4'-(2-chloro-3-fluoropyridin-4-yl)-N-[trans-3-(hydroxymethyl)cyclobutyl]-4,4-dimethyl-2"-oxo-1",2"-dihydrodispiro[cyclohexane-1,2'-pyrrolidine-3',3"-indole]-5'-carboxamide The compound (55 mg, 0.11 mmol) obtained in Step 1 of Example 17 and the compound (11 mg, 0.11 mmol) obtained in Step 2 of Reference Example 55 were used as starting materials and treated in the same way as in Step 2 of Example 12 to give 55 mg (86%) of the title compound as a colorless solid.

$^1$H-NMR (400 MHz, $CD_3OD$), δ: 0.69 (3H, s), 0.96 (3H, s), 1.08-1.42 (4H, m), 1.51-1.92 (4H, m), 2.05-2.49 (5H, m), 3.60 (2H, d, J=6.9 Hz), 4.26-4.37 (1H, m), 4.53 (1H, d, J=9.2 Hz), 4.66 (1H, d, J=9.2 Hz), 6.77 (1H, d, J=1.8 Hz), 7.06 (1H, dd, J=8.3, 1.83 Hz), 7.43-7.50 (1H, m), 7.63-7.69 (1H, m), 8.05 (1H, d, J=5.0 Hz).

MS (ESI) m/z: 575 $(M+H)^+$

Example 120

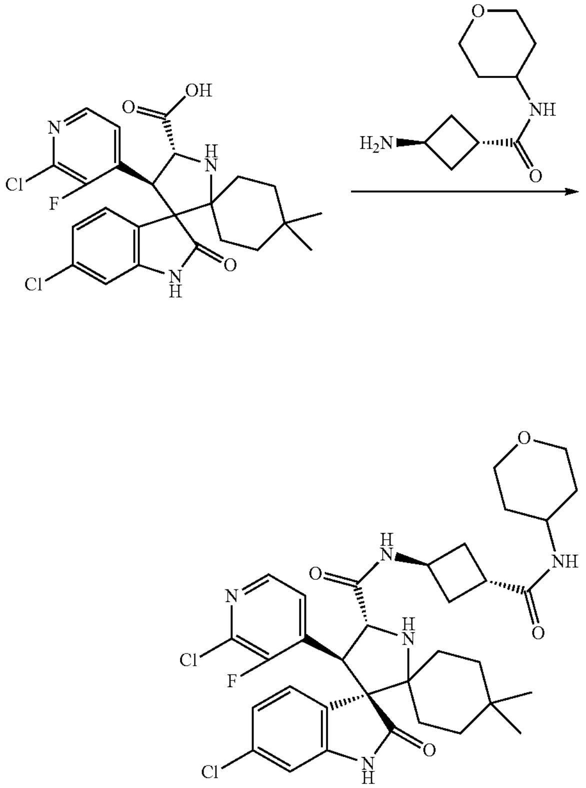

(3'R, 4'S,5'R)-6"-chloro-4'-(2-chloro-3-fluoropyridin-4-yl)-4,4-dimethyl-2"-oxo-N-[trans-3-(tetrahydro-2H-pyran-4-ylcarbamoyl)cyclobutyl]-1",2"-dihydrodispiro[cyclohexane-1,2'-pyrrolidine-3',3"-indole]-5'-carboxamide The compound (95 mg, 0.19 mmol) obtained in Step 1 of Example 17 and the compound (46 mg, 0.23 mmol) obtained in Step 2 of Reference Example 56 were used as starting materials and treated in the same way as in Step 2 of Example 12 to give 66 mg (51%) of the title compound as a colorless solid.

$^1$H-NMR (400 MHz, $CD_3OD$) δ: 0.69 (3H, s), 0.96 (38, s), 1.09-1.91 (12H, m), 2.22-2.36 (2H, m), 2.47-2.61 (2H, m), 2.96-3.06 (1H, m), 3.41-3.52 (2H, m), 3.81-3.97 (3H, m), 4.48 (1H; t, J=7.8 Hz), 4.54 (1H, d, J=9.2 Hz), 4.67 (1H, d, J=9.2 Hz), 6.77 (1H, d, J=2.1 Hz), 7.06 (1H, ad, J=8.1; 2.1 Hz), 7.46 (1H, dd, J=8.1, 2.1 Hz), 7.62-7.68 (1H, m), 8.05 (1H, d, J=5.0 Hz).

MS (ESI) m/z: 672 $(M+H)^+$.

Example 121

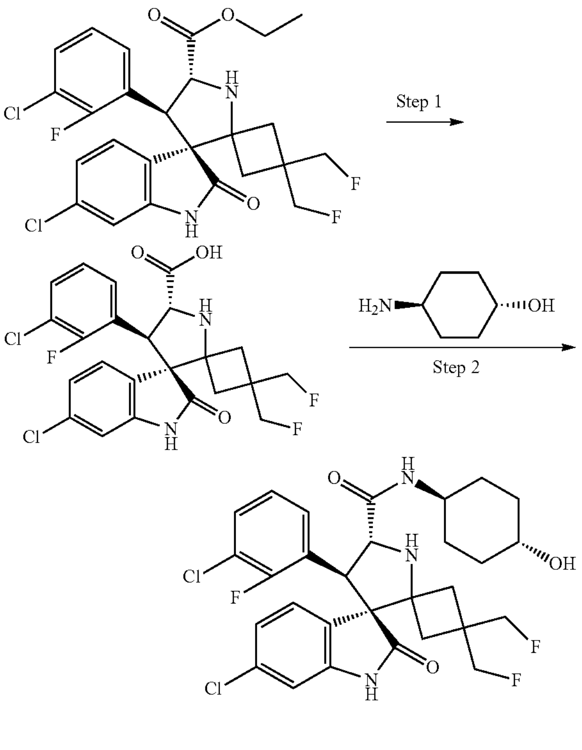

Step 1

(3'R, 4'S,5'R)-6"-chloro-4'-(3-chloro-2-fluorophenyl)-3,3-bis(fluoromethyl)-2"-oxo-1",2"-dihydrodispiro[cyclobutane-1,2'-pyrrolidine-3',3"-indole]-5'-carboxylic acid The compound (1.95 g, 3.70 mmol) obtained in Step 2 of Reference Example 57 was dissolved in ethanol (37 ml), 1N sodium hydroxide solution (7.4 ml, 7.40 mmol) was added and the resulting mixture was stirred under heating at 50° C. for 1 hour. After cooling, the reaction mixture was neutralized by addition of 1N hydrochloric acid (7.4 ml, 7.40 mmol) at 0° C. and the solvent was evaporated under reduced pressure. The residue obtained was collected by filtration and dried to give 2.02 g (100%) of the title compound as a colorless solid.

$^1$H-NMR (400 MHz, $CD_3OD$) δ: 1.92 (1H, d, J=14.2 Hz), 2.44 (1H, d, J=14.2 Hz), 2.59 (1H, d, J=14.7 Hz), 2.91 (1H, d, J=14.7 Hz), 3.75 (1H, dd, J=15.1, 10.5 Hz), 3.87 (1H, dd, J=14, 4, 9.4 Hz), 4.48 (1H, d, J=10.5 Hz), 4.54 (1H, dd, J=15.8, 9.4 Hz), 4.66 (1H, dd, J=15.8, 9.4 Hz), 4.78 (1H, d, J=10.5 Hz), 6.84 (1H, d, J=1.8 Hz), 7.07-7.12 (1H, m), 7.17 (1H, dd, J=8.2, 1.8 Hz), 7.27-7.33 (1H, m), 7.54-7.59 (1H, m), 7.67 (1H, dd, J=8.2, 2.3 Hz).

Step 2

(3'R, 4'S,5'R)-6"-chloro-4'-(3-chloro-2-fluorophenyl)-3,3-bis(fluoromethyl)-N-(trans-4-hydroxycyclohexyl)-2"-oxo-1",2"-dihydrodispiro[cyclobutane-1, 2'-pyrrolidine-3',3"-indole]-5'-carboxamide The compound (70 mg, 0.14 mmol) obtained in Step 1 above and trans-4-aminocyclohexanol (19.4 mg, 0.17 mmol) were used as starting materials and treated in the same way as in Step 2 of Example 12 to give 56 mg (67%) of the title compound as a colorless solid.

$^1$H-NMR (400 MHz, $CD_3OD$) δ: 1.25-1.42 (5H, m), 1.68 (1H, dd, J=13.7, 2.3 Hz), 1.81-2.00 (5H, m), 2.07 (1H, d, J=12.8 Hz), 2.47 (1H, d, J=12.8 Hz), 3.50-3.64 (2H, m), 3.76-3.93 (2H, m), 4.36 (1H, d, J=9.2 Hz), 4.44 (1H, d, J=9.2 Hz), 4.58-4.76 (2H, m), 6.80 (1H, d, J=2.3 Hz), 7.00-7.05 (1H, m), 7.10 (1H, dd, J=8.2, 1.8 Hz), 7.20-7.25 (1H, m), 7.50 (1H, dd, J=8.2, 2.3 Hz), 7.53-7.58 (1H, m).

MS (ESI) m/z: 596 $(M+H)^+$.

Example 122

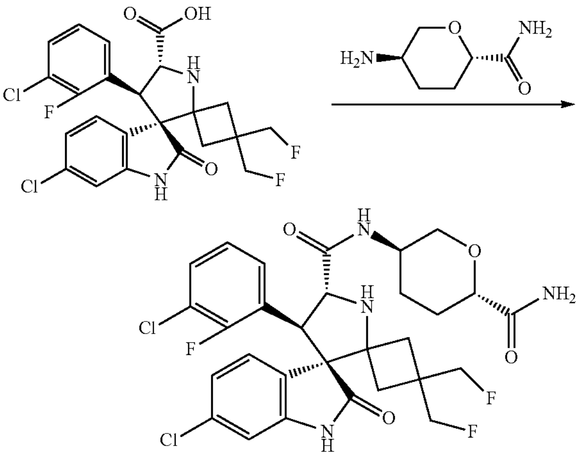

(3'R, 4'S,5'R)—N-[(3R, 6S)-6-carbamoyltetrahydro-2H-pyran-3-yl]-6"-chloro-4'-(3-chloro-2-fluorophenyl)-3,3-bis(fluoromethyl)-2"-oxo-1",2"-dihydrodispiro[cyclobutane-1,2-pyrrolidine-3',3"-indole]-5'-carboxamide The compound (70 mg, 0.14 mmol) obtained in Step 1 of Example 121 and the compound (26.8 mg, 0.17 mmol) obtained in Step 3 of Reference Example 28 were used as starting materials and treated in the same way as in Step 2 of Example 12 to give 72 mg (86%) of the title compound as a colorless solid.

$^1$H-NMR (400 MHz, $CD_3OD$) δ: 1.52-1.71 (3H, m), 1.89 (1H, d, J=13.3 Hz), 2.04-2.19 (3H, m), 2.48 (1H, d, J=13.3 Hz), 3.17 (1H, t, J=10.5 Hz), 3.74-3.92 (4H, m), 3.94-4.00 (1H, m), 4.39 (1H, d, J=9.2 Hz), 4.46 (1H, d, J=9.2 Hz), 4.59-4.77 (2H, m), 6.81 (1H, d, J=1.8 Hz), 7.00-7.06 (1H, m), 7.11 (1H, dd, J=8.2, 1.8 Hz), 7.20-7.25 (1H, m), 7.50 (1H, dd, J=8.2, 2.3 Hz), 7.52-7.57 (1H, m).

MS (ESI) m/z: 625 $(M+H)^+$.

Example 123

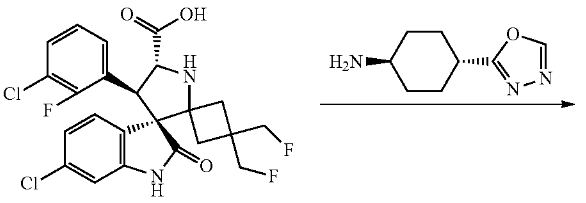

-continued

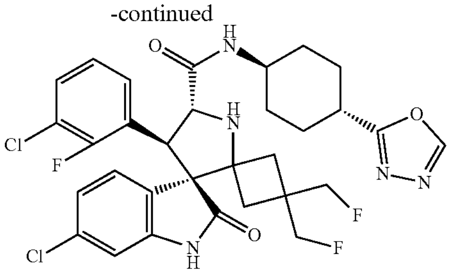

(3'R, 4"S,5'R)-6'-chloro-4'-(3-chloro-2-fluorophenyl)-3,3-bis(fluoromethyl)-N-[trans-4-(1,3,4-oxadiazol-2-yl)cyclohexyl]-2"-oxo-1",2"-dihydrodispiro[cyclobutane-1,2'-pyrrolidine-3',3"-indole]-5'-carboxamide The compound (80 mg, 0.16 mmol) obtained in Step 1 of Example 121 and the compound (32 mg, 0.19 mmol) obtained in Step 3 of Reference Example 3 were used as starting materials and treated in the same way as in Step 2 of Example 12 to give 91 mg (87%) of the title compound as a colorless solid.

$^1$H-NMR (400 MHz, $CD_3OD$) δ: 1.37-1.58 (2H, m), 1.64-1.80 (3H, m), 1.90 (1H, d, J=13.3 Hz), 1.99 (1H, d, J=12.4 Hz), 2.07-2.27 (4H, m), 2.49 (1H, d, J=13.3 Hz), 2.96-3.04 (1H, m), 3.67-3.75 (1H, m), 3.79-3.91 (2H, m), 4.39 (1H, d, J=9.2 Hz), 4.47 (1H, d, J=9.2 Hz), 4.59-4.78 (2H, m), 6.81 (1H, d, J=2.3 Hz), 7.01-7.06 (1H, m), 7.11 (1H, dd, J=8.2, 1.8 Hz), 7.20-7.26 (1H, m), 7.51 (1H, dd, J=8.2, 2.3 Hz), 7.54-7.59 (1H, m), 8.85 (1H, d, J=1.4 Hz).

MS (ESI) m/z: 648 $(M+H)^+$.

Example 124

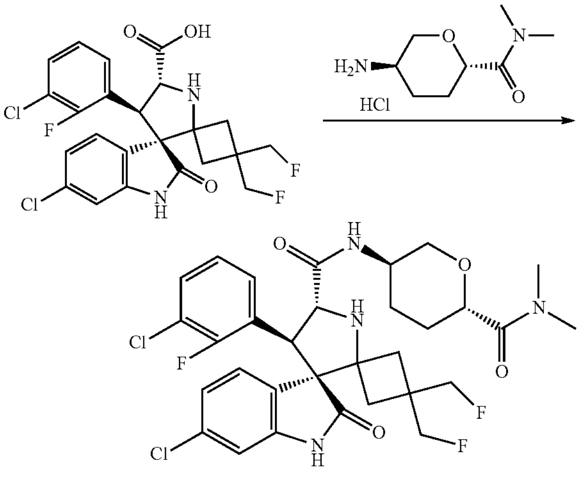

(3'R, 4'S,5'R)-6"-chloro-4'-(3-chloro-2-fluorophenyl)-N-[(3R,6S)-6-(dimethylcarbamoyl)tetrahydro-2H-pyran-3-yl]-3,3-bis(fluoromethyl)-2"-oxo-1",2"-dihydrodispiro[cyclobutane-1,2'-pyrrolidine-3',3"-indole]-5'-carboxamide The compound (80 mg, 0.16 mmol) obtained in Step 1 of Example 121 and the compound (33.1 mg, 0.19 mmol)

obtained in Step 2 of Reference Example 41 were used as starting materials and treated in the same way as in Step 2 of Example 12 to give 79 mg (75%) of the title compound as a colorless solid.

$^1$H-NMR (400 MHz, $CD_3OD$) δ: 1.62-1.73 (2H, m), 1.77-1.92 (3H, m), 2.07 (1H, d, J=13.3 Hz), 2.11-2.18 (1H, m), 2.49 (1H, d, J=13.3 MHz), 2.92 (3H, s), 3.09 (3H, s), 3.23 (1H, t, J=10.1 Hz), 3.77-3.95 (4H, m), 4.22 (1H, dd, J=9.8, 3.4 Hz), 4.38 (1H, d, J=9.2 Hz), 4.46 (1H, d, J=9.2 Hz), 4.60-4.77 (2H, m), 6.81 (1H, d, J=1.8 Hz), 7.00-7.06 (1H, m), 7.11 (1H, dd, J=8.0, 2.1 Hz), 7.20-7.25 (1H, m), 7.51 (1H, dd, J=8.0, 2.1 Hz), 7.52-7.57 (1H, m).

MS (ESI) m/z: 653 $(M+H)^+$.

Example 125

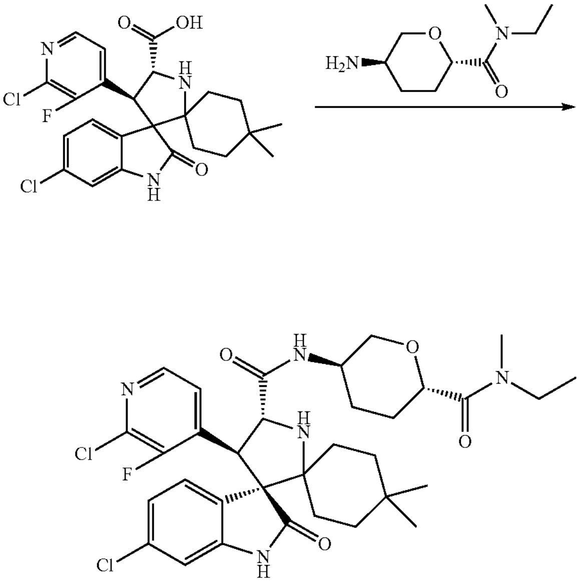

(3'R, 4'S,5'R)-6"-chloro-4'-(2-chloro-3-fluoropyridin-4-yl)-N-{(3R,6S)-6-[ethyl(methyl)carbamoyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (67 mg, 0.36 mmol) obtained in Step 2 of Reference Example 58 were used as starting materials and treated in the same way as in Step 2 of Example 12 to give 122 mg (62%) of the title compound as a colorless solid.

$^1$H-NMR (400 MHz, $CDCl_3$) δ: 0.68 (3H, s), 0.95 (3H, s), 1.11-1.26 (5H, m); 1.37 (1H, d, J=11.0 Hz), 1.45-1.66 (4H, m), 1.70-1.78 (2H, m), 1.88-2.02 (2H, m), 2.15-2.23 (1H, m), 2.91-3.05 (3H, m), 3.25 (1H, t, J=9.8 Hz), 3.28 (1H, br s), 3.34-3.51 (2H, m), 3.92-3.98 (1H, m), 4.03-4.07 (1H, m), 4.08-4.13 (1H, m), 4.45 (1H, d, J=9.2 Hz), 4.65 (1H, d, J=9.2 Hz), 6.73 (1H, d, J=1.8 Hz), 7.06 (1H, dd, J=8.2, 1.8 Hz), 7.31 (1H, dd, J=8.0, 2.1 Hz), 7.50 (1H, t, J=5.0 Hz), 7.63 (1H, d, J=8.2 Hz), 7.80 (1H, s), 8.04 (1H, d, J=5.0 Hz).

MS (ESI) m/z: 660 $(M+H)^+$.

Example 126

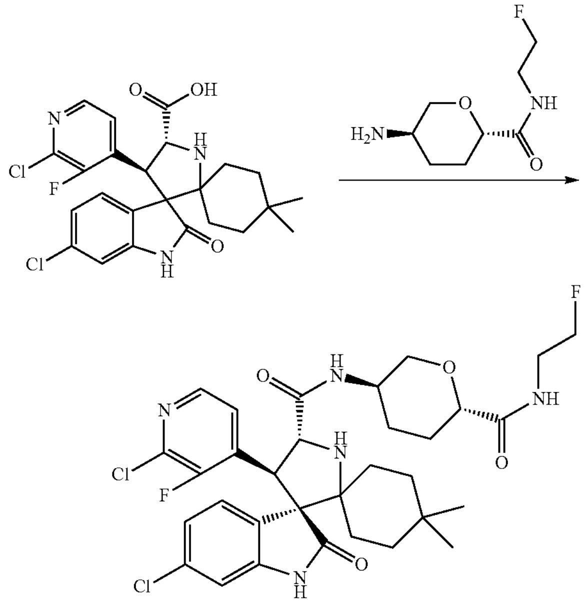

(3'R, 4'S,5'R)-6"-chloro-4'-(2-chloro-3-fluoropyridin-4-yl)-N-{(3R,6S)-6-[{2-fluoroethyl}carbamoyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (68 mg, 0.36 mmol) obtained in Step 2 of Reference Example 59 were used as starting materials and treated in the same way as in Step 2 of Example 12 to give 97 mg (49%) of the title compound as a colorless solid.

$^1$H-NMR (400 MHz, $CDCl_3$) δ: 0.68 (3H, s), 0.95 (3H, s), 1.11-1.25 (2H, m), 1.32-1.83 (8H, m), 2.11-2.18 (1H, m), 2.27-2.33 (1H, m), 3.15 (1H, t, J=10.8 Hz), 3.28 (1H, br s), 3.49-3.69 (2H, m), 3.81 (1H, dd, J=11.0, 2.3 Hz), 3.86-3.95 (1H, m), 4.07-4.15 (1H, m), 4.40-4.50 (2H, m), 4.52-4.57 (1H, m), 4.64 (1H, d, J=9.2 Hz), 6.73 (1H, d, J=1.8 Hz), 6.91 (1H, t, J=6.0 Hz), 7.07 (1H, dd, J=8, 2, 1.8 Hz), 7.31 (1H, dd, J=8.0, 2.1 Hz), 7.48-7.53 (2H, m), 7.60 (1H, s), 8.05 (1H, d, J=5.5 Hz).

MS (ESI) m/z: 664 $(M+H)^+$.

Example 127

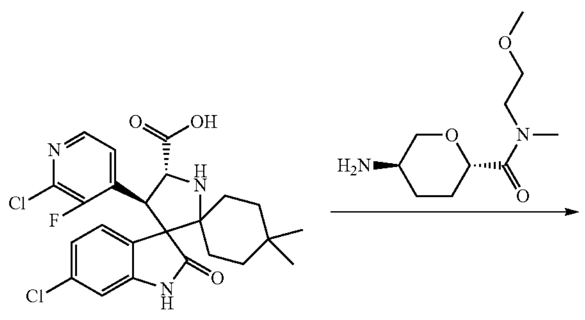

-continued

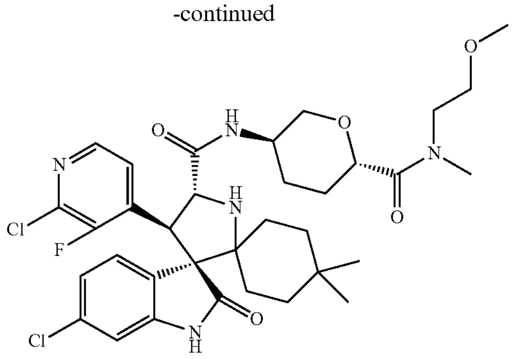

(3'R, 4'S,5'R)-6"-chloro-4'-(2-chloro-3-fluoropyridin-4-yl)-N-{(3R,6S)-6-[(2-methoxyethyl)(methyl)carbamoyl]tetrahydro-2H-pyran-3-yl}-4,4-dimethyl-2"-oxo-1",2"=dihydrodispiro[cyclohexane-1,2'-pyrrolidine-3',3"-indole]-5'-carboxamide The compound (150 mg, 0.30 mmol) obtained in Step 1 of Example 17 and the compound (78 mg, 0.36 mmol) obtained in Step 2 of Reference Example 60 were used as starting materials and treated in the same way as in Step 2 of Example 12 to give 143 mg (698) of the title compound as a colorless solid.

$^1$H-NMR (400 MHz, $CDCl_3$) δ: 0.68 (3H, s), 0.95 (3H, s), 1.10-1.25 (2H, m), 1.34-1.41 (1H, m), 1.45-1.67 (4H, m), 1.71-1.78 (2H, m), 1.88-2.03 (2H, m), 2.16-2.23 (1H, m), 2.96-3.14 (3H, m), 3.18-3.28 (1H, m), 3.33 (3H, s), 3.38-3.80 (5H, m), 3.91-3.97 (1H, m), 4.02-4.07 (1H, m), 4.14-4.21 (1H, m), 4.45 (1H, d, J=9.2 Hz), 4.65 (1H, d, J=8.7 Hz), 6.73 (1H, d, J=2.3 Hz), 7.07 (1H, dd, J=8.2, 1.8 Hz), 7.32 (1H, dd, J=8.0, 2.1 Hz), 7.50 (1H, t, J=5.0 Hz), 7.59-7.64 (21, m)+8.04 (1H, d, J=5.0 Hz).

MS (ESI) m/z: 690 $(M+H)^+$.

Example 128

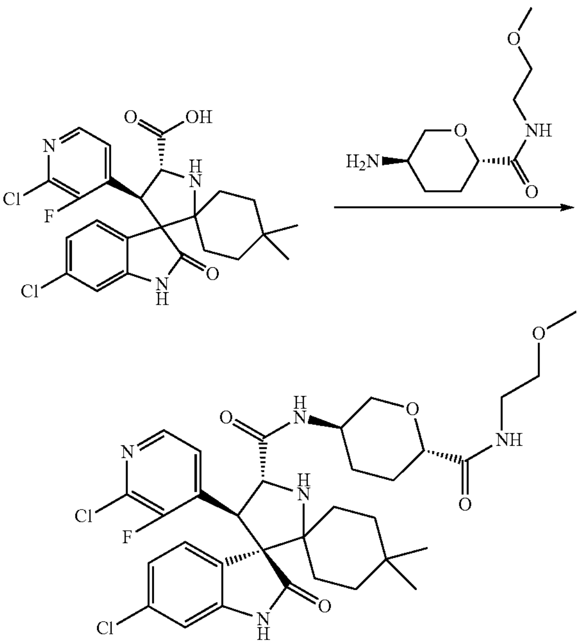

(3'R, 4'S,5'R)-6"-chloro-4'-(2-chloro-3-fluoropyridin-4-yl)-N-{(3R,6S)-6-[(2-methoxyethyl) carbamoyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (73 mg, 0.36 mmol) obtained in Step 2 of Reference Example 61 were used as starting materials and treated in the same way as in Step 2 of Example 12 to give 121 mg (60%) of the title compound as a colorless solid.

$^1$H-NMR (400 MHz, $CDCl_3$) δ: 0.68 (3H, s), 0.95 (3H, s), 1.11-1.81 (10H, m), 2.10-2.16 (1H, m), 2.26-2.33 (1H, m), 3.14 (1H, t, J=10.5 Hz), 3.27 (1H, br s), 3.36 (3H, s), 3.40-3.53 (4H, m), 3.79 (1H, dd, J=11.2, 2.5 Hz), 3.86-3.96 (1H, m), 4.12 (1H, m), 4.44 (1H, d, J=8.7 Hz), 4.64 (1H, d, J=9.2 Hz), 6.73 (1H, d, J=1.8 Hz), 6.84-6.88, (1H, m), 7.07 (1H, dd, J=8.0, 2.1 Hz), 7.31 (1H, dd, J=8.2, 2.3 Hz), 7.48-7.52 (2H, m), 7.61 (1H, s), 8.05 (1H, d, J=5.5 Hz).

MS (ESI) m/z: 676 $(M+H)^+$.

Example 129

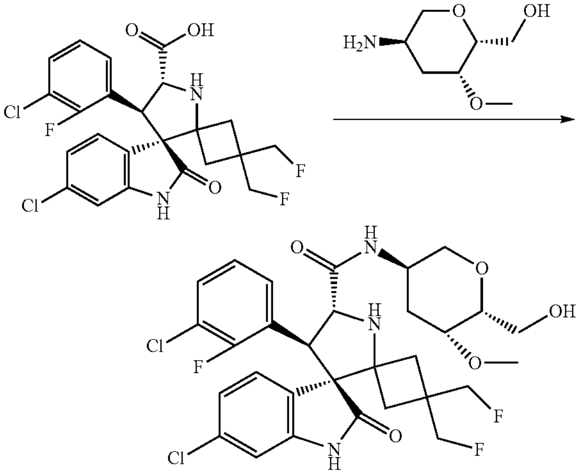

(3'R,4'S,5'R)-6"-chloro-4'-(3-chloro-2-fluorophenyl)-3,3-bis(fluoromethyl)-N-[(3R,5R,6R)-6-(hydroxymethyl)-5-methoxytetrahydro-2H-pyran-3-yl]-2"-oxo-1",2"-dihydrodispiro[cyclobutane-1,2'-pyrrolidine-3',3"-indole]-5'-carboxamide The compound (100 mg, 0.20 mmol) obtained in Step 1 of Example 121 and the compound (65 mg, 0.40 mmol) obtained in Step 5 of Reference Example 27 were used as starting materials and treated in the same way as in Step 2 of Example 12 to give 95 mg (74%) of the title compound as a colorless solid.

$^1$H-NMR (400 MHz, $CDCl_3$) δ: 1.41-1.50 (1H, m), 1.65-1.86 (2H, m), 2.03-2.17 (2H, m), 2.36-2.52 (2H, m), 3.14-3.22 (1H, m), 3.41 (3H, s), 3.45-3.55 (2H, m), 3.66-4.32 (7H, m); 4.40 (2H, br s), 4.54-4.82 (2H, m), 6.79 (1H, d, J=2.3 Hz), 6.93-6.99 (1H, m), 7.11-7.23 (3H, m), 7.36-7.48 (3H, m),

MS (ESI) m/z: 642 $(M+H)^+$.

Example 130

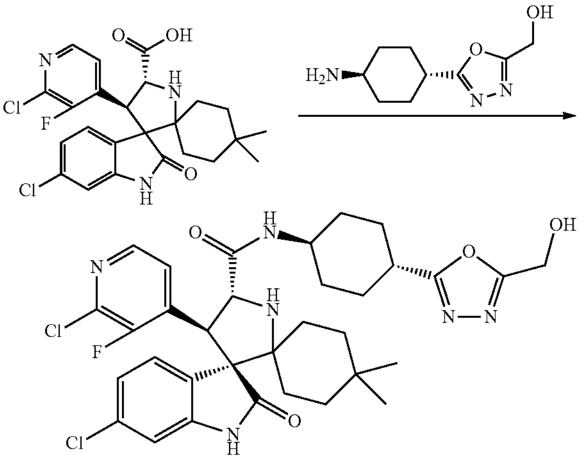

(3'R, 4'S,5'R)-6"-chloro-4'-(2-chloro-3-fluoropyridin-4-yl)-N-{trans-4-[5-(hydroxymethyl)-1,3,4-oxadiazol-2-yl]cyclohexyl}-4,4-dimethyl-2"-oxo-1",2"-dihydrodispiro[cyclohexane-1,2'-pyrrolidine-3',3"-indole]-5'-carboxamide The compound (64 mg, 0.12 mmol) obtained in Step 1 of Example 17 and the compound (27 mg, 0.13 mmol) obtained in Step 3 of Reference Example 62 were used as starting materials and treated in the same way as in Step 2 of Example 12 to give 55 mg (67%) of the title compound as a colorless solid.

$^1$H-NMR (500 MHz, $CDCl_3$) δ: 0.68 (3H, s), 0.96 (3H, s), 1.11-1.28 (2H, m), 1.31-1.43 (3H, m), 1.45-1.81 (7H, m), 2.10-2.28 (4H, m), 2.72-2.86 (1H, m), 2.87-2.97 (1H, m), 3.18-3.43 (1H, m), 3.72-3.82 (1H, m), 4.45 (1H, d, J=9.2 Hz), 4.66 (1H, d, J=9.2 Hz), 4.83 (2H, s), 6.74 (1H, d, J=2.3 Hz), 7.07 (1H, dd, J=8.3, 2.0 Hz), 7.30-7.34 (1H, m), 7.49-7.53 (1H, m), 7.57-7.65 (2H, m), 8.05 (1H, d, J=5.2 Hz).

MS (ESI) m/z: 611 $(M+H)^+$.

Example 131

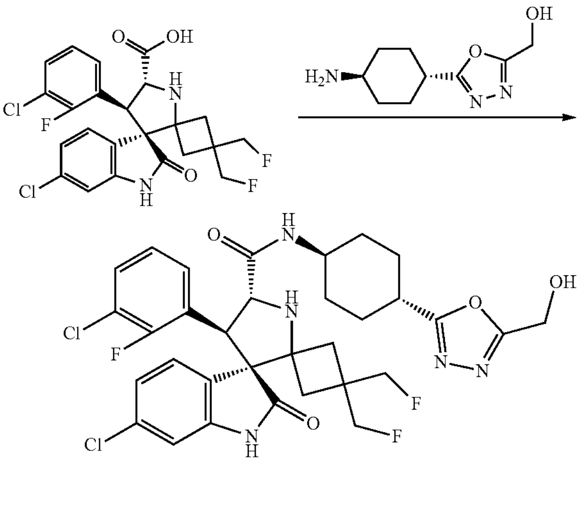

(3'R, 4'S,5'R)-6"-chloro-4'-(3-chloro-2-fluorophenyl)-3,3-bis(fluoromethyl)-N-[trans-4-[5-(hydroxymethyl)-1,3,4-oxadiazol-2-yl]cyclohexyl]-2"-oxo-1",2"-dihydrodispiro[cyclobutane-1,2'-pyrrolidine-3',3"-indole]-5'-carboxamide The compound (60 mg, 0.12 mmol) obtained in Step 1 of Example 121 and the compound (26 mg, 0, 13 mmol) obtained in Step 3 of Reference Example 62 were used as starting materials and created in the same way as in Step 2 of Example 12 to give 46 mg (57%) of the title compound as a colorless solid.

$^1$H-NMR (500 MHz, $CD_3OD$) δ: 1.37-1.47 (1H, m), 1.47-1.57 (1H, m), 1.63-1.78 (3H, m), 1.86-1.93 (1H, m), 1.94-2.02 (1H, m), 2.06-2.13 (2H, m), 2.14-2.27 (2H, m), 2.45-2.53 (1H, m), 2.97 (1H, tt, J=12.0, 3.7 Hz), 3.71 (1H, tt, J=11.5, 4.0 Hz), 3.77-3.93 (2H, m), 4.39 (1H, d, J=9.2 Hz), 4.47 (1H; d, J=9.2 Hz), 4.61-4.77 (4H, m), 6.81 (1H, di J=1.7 Hz), 7.00-7.06 (1H, m), 7.11 (1H, dd, J=8.0, 1.7 Hz), 7.20-7.25 (1H, m), 7.48-7.53 (1H, m), 7.54-7.59 (1H, m).

MS (ESI) m/z: 678 $(M+H)^+$.

Example 132

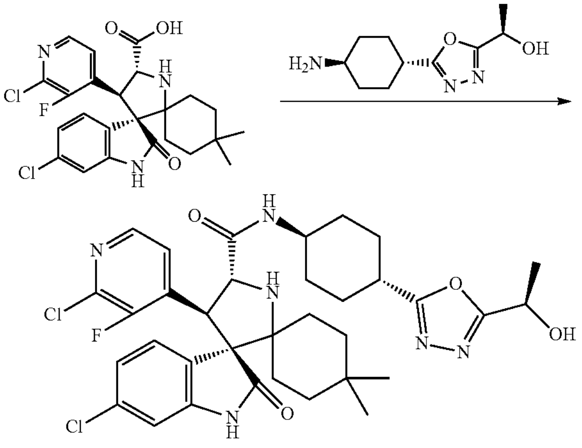

(3'R, 4'S, S'R)-6"-chloro-4'-(2-chloro-3-fluoropyridin-4-yl)-N-(trans-4-{5-[(1R)-1-hydroxyethyl]-1,3,4-oxadiazol-2-yl}cyclohexyl)-4,4-dimethyl-2"-oxo-1",2"-dihydrodispiro[cyclohexane-1,2'-pyrrolidine-3',3"-indole]-5'-carboxamide The compound (74 mg, 0.14 mmol) obtained in Step 1 of Example 17 and the compound (33 mg, 0.16 mmol) obtained in Step 3 of Reference Example 63 were used as starting materials and treated in the same way as in Step 2 of Example 12 to give 71 mg (73%) of the title compound as a colorless solid.

$^1$H-NMR (500 MHz, $CDCl_3$) δ: 0.68 (3H, s), 0.96 (3H, s), 1.12-1.27 (2R, m), 1.29-1.43 (3H, m), 1.44-1.55 (2H, m), 1.56-1.81 (8H, m), 2.09-2.28 (4H, m), 2.86-2.99 (2H, m), 3.20-3.40 (1H, m), 3.71-3.82 (1H, m), 4.45 (1H, d, J=9.2 Hz), 4.66 (1H, d, J=9.2 Hz), 5.01-5.11 (1H, m), 6.74 (1H, d, J=1.72 Hz), 7.05-7.08 (1H, m), 7.30-7.34 (1H, m), 7.50-7.53 (1H, m), 7.60 (1H, d, J=8.6 Hz), 7.79 (1H, s), 8.04 (1H, d, J=5.2 Hz).

MS (ESI) m/z: 685 $(M+H)^+$.

Example 133

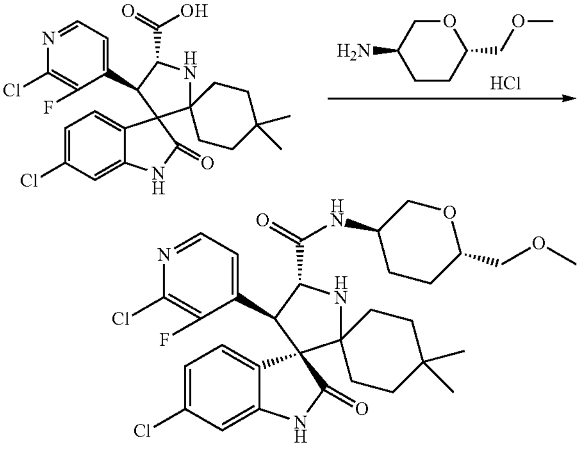

(3'R, 4'S,5'R)-6"-chloro-4'-(2-chloro-3-fluoropyridin-4-yl)-N-[(3R,6S)-6-(methoxymethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (150 mg, 0.30 mmol) obtained in Step 1 of Example 17 and the compound (70 mg, 0.36 mmol) obtained in Step 2 of Reference Example 64 were used as starting materials and treated in the same way as in Step 2 of Example 12 to give 156 mg (84%) of the title compound as a pale orange solid.

$^1$H-NMR (400 MHz, $CDCl_3$) δ: 0.67 (3H, s), 0.95 (3H, s), 1.08-1.65 (8H, m), 1.68-1.77 (3H, m), 2.08-2.14 (1H, m), 3.13 (1H, t, J=10.8 Hz), 3.27 (1H, br s), 3.33-3.45 (5H, m), 3.48-3.55 (1H, m), 3.87-3.96 (1H, m), 4.04-4.10 (1H, m), 4.43 (1H, d, J=9.2 Hz), 4.65 (1H, d, J=8.7 Hz), 6.73 (1H, d, J=1.8 Hz), 7.06 (1H, dd, J=8.2, 1.8 Hz), 7.31 (1H, dd, J=8.0, 2.1 Hz), 7.46-7.51 (3H, m), 8.04 (1H, d, J=5.0 Hz).

MS (ESI) m/z: 619 $(M+H)^+$.

Example 134

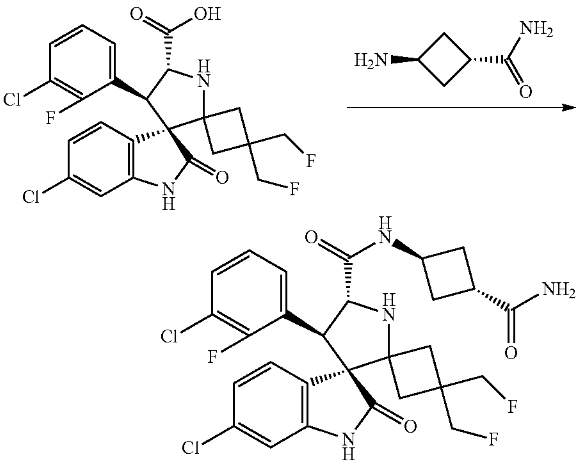

(3'R, 4'S,5'R)—N-(trans-3-carbamoylcyclobutyl)-6"-chloro-4'-(3-chloro-2-fluorophenyl)-3,3-bis(fluoromethyl)-2"-oxo-1",2"-dihydrodispiro[cyclobutane-1,2'-pyrrolidine-3',3"-indole]-5'-carboxamide The compound (75 mg, 0.15 mmol) obtained in Step 1 of Example 121 and the compound (19 mg, 0.17 mmol) obtained in Step 2 of Reference Example 51 were used as starting materials and treated in the same way as in Step 2 of Example 12 to give 66 mg (74%) of the title compound as a colorless solid.

$^1$H-NMR (400 MHz, $CD_3OD$) δ: 1.67 (1H, d, J=13.3 Hz), 1.89 (1H, d, J=13.3 Hz), 2.08 (1H, d, J=11.5 Hz), 2.19-2.37 (2H, m), 2.44-2.63 (3H, m), 3.00-3.09 (1H, m), 3.78-3.90 (2H, m), 4.34-4.50 (4H, m), 4.59-4.81 (2H, m), 6.81 (1H, d, J=2.3 Hz), 7.00-7.13 (1H, m), 7.19-7.26 (1H, m), 7.48-7.59 (2H, m).

MS (ESI) m/z: 595 $(M+H)^+$:

Example 135

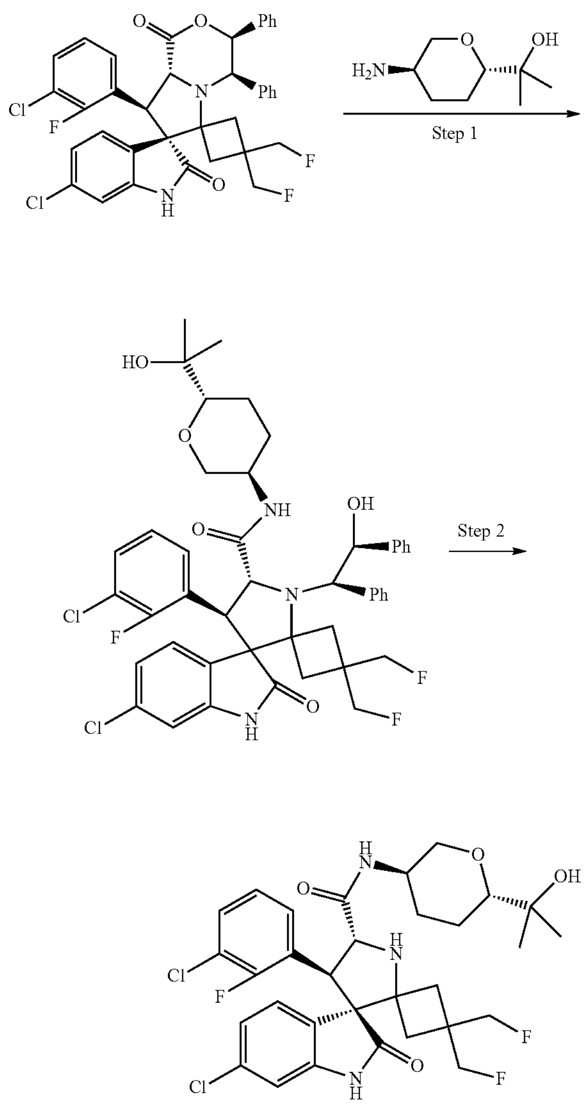

Step 1

(4'S,5'R)-6"-chloro-4'-(3-chloro-2-fluorophenyl)-3,3-bis(fluoromethyl)-1'-[(1R, 2S)-2-hydroxy-1,2-diphenylethyl]-N-[(3R,6S)-6-(1-hydroxy-1-methylethyl) tetrahydro-2H-pyran-3-yl]-2"-oxo-1",2"-dihydrodispiro[cyclobutane-1,2'-pyrrolidine-3',3"-indole]-5'-carboxamide The compound (200 mg, 0.30 mmol) obtained in Step 1 of Example 38 and the compound (159 mg, 1.00 mmol) obtained in Step 2 of Reference Example 5 were used as starting materials and treated in the same way as in Step 1 of Example 20 to give 118 mg (47%) of the title compound as a brown amorphous solid.

MS (ESI) m/z: 836 $(M+H)^+$.

Step 2

(3'R, 4'S,5'R)-6"-chloro-4'-(3-chloro-2-fluorophenyl)-3,3-bis(fluoromethyl)-N-[(3R,6S)-6-(1-hydroxy-1-methylethyl)tetrahydro-2H-pyran-3-yl]-2"-oxo-1",2"-dihydrodispiro[cyclobutane-1,2'-pyrrolidine-3',3"-indole]-5'-carboxamide The compound (118 mg, 0.14 mmol) obtained in Step 1 above was used as a starting material and treated in the same way as in Step 3 of Example 91 to give 40 mg (44%) of the title compound as a colorless solid [fractionation conditions: CHIRALPAK IC, n-hexane:ethanol=7:3 (v/v)], $^1$H-NMR (400 MHz, $CD_3OD$) δ: 1.14 (3H, s), 1.16 (3H, s), 1.44-1.60 (2H, m), 1.68 (1H, d, J=13.7 Hz), 1.83 (1H, d, J=10.5 Hz), 1.89 (1H, d, J=12.8 Hz), 2.02-2.12 (2H, m), 2.48 (1H, d, J=12.8 Hz), 3.05-3.10 (2H, m), 3.71-3.95 (4H, m), 4.38 (1H, d, J=9.2 Hz), 4.45 (1H, d, J=9.2 Hz), 4.59-4.76 (2H, m), 6.81 (1H, d, J=1.8 Hz), 7.03 (1H, t, J=8.5 Hz), 7.11 (1H, dd, J=8.2, 1.8 Hz), 7.21-7.25 (1H, m), 7.50 (1H, dd, J=8.2, 2.3 Hz), 7.52-7.56 (1H, m).

MS (ESI) m/z: 640 $(M+H)^+$.

Example 136

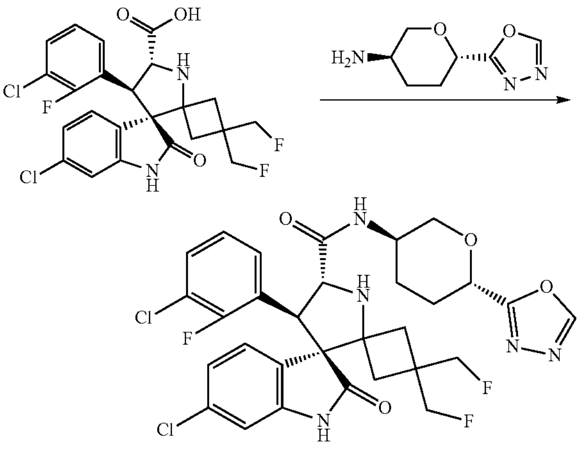

(3'R, 4'S,5'R)-6"-chloro-4'-(3-chloro-2-fluorophenyl)-3,3-bis(fluoromethyl)-N-[(3R,6S)-6-(1,3,4-oxadiazol-2-yl)tetrahydro-2H-pyran-3-yl]-2"-oxo-1",2"-dihydrodispiro[cyclobutane-1,2'-pyrrolidine-3',3"-indole]-5'-carboxamide The compound (80 mg, 0.16 mmol) obtained in Step 1 of Example 121 and the compound (33 mg, 0.19 mmol) obtained in Step 6 of Reference Example 18 were used as starting materials and treated in the same way as in Step 2 of Example 12 to give 79 mg (75%) of the title compound as a colorless amorphous solid.

$^1$H-NMR (400 MHz, $CDCl_3$) δ: 1.66-1.76 (2H, m), 1.85 (1H, dd, J=13.3, 2.7 Hz), 2.04-2.35 (4H, m), 2.40 (1H, d, J=13.3 Hz), 3.33-3.40 (1H, m), 3.78-4.13 (5H, m), 4.36-4.44 (2H, m), 4.56-4.82 (3H, m), 6.75 (1H, d, J=1.8 Hz), 6.86-6.91 (1H, m), 7.11-7.16 (2H, m), 7.38 (1H, dd, J=8.1, 2.2 Hz), 7.41-7.45 (1H, m), 7.66 (1H, d, J=8.1 Hz), 7.85 (1H, s), 8.43 (1H, s).

MS (ESI) m/z: 650 $(M+H)^+$.

Example 137

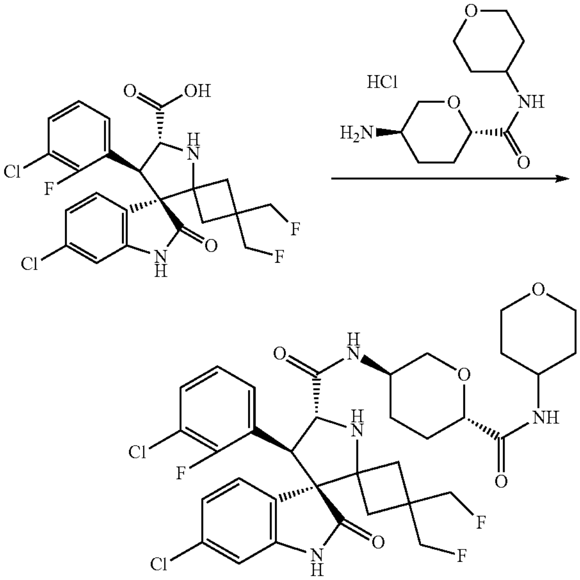

(3'R, 4'S,5'R)-6"-chloro-4'-(3-chloro-2-fluorophenyl)-3,3-bis(fluoromethyl)-2"-oxo-N-[(3R,6S)-6-(tetrahydro-2H-pyran-4-ylcarbamoyl)tetrahydro-2H-pyran-3-yl]-1",2"-dihydrodispiro[cyclobutane-1,2'-pyrrolidine-3',3"-indole]-5'-carboxamide The compound (70 mg, 0.14 mmol) obtained in Step 1 of Example 121 and the compound (45 mg, 0.17 mmol) obtained in Step 2 of Reference Example 47 were used as starting materials and treated in the same way as in Step 2 of Example 12 to give 79 mg (79%) of the title compound as a colorless amorphous solid.

$^1$H-NMR (400 MHz, $CDCl_3$) δ: 1.44-1.71. (5H, m), 1.81-1.91 (3H, m), 2.03 (1H, d, J=13.3 Hz), 2.14-2.21 (1H, m), 2.27-2.33 (1H, m), 2.39 (1H, d, J=12.8 Hz), 3.10 (1H, t, J=10.8 Hz), 3.43-3.51 (2H, m), 3.74-4.03 (8H, m), 4.09-4.15 (1H, m), 4.33-4.41 (2H, m), 4.55-4.76 (2H, m), 6.46 (1H, d, J=8.2 Hz), 6.77 (1H, d, J=1.8 Hz), 6.87-6.92 (1H, m), 7.11-7.17 (2H, m), 7.37 (1H, dd, J=8, 0, 2.1 Hz), 7.41-7.47 (2H, m), 7.92 (1H, s).

MS (ESI) m/z: 709 $(M+H)^+$.

Example 138

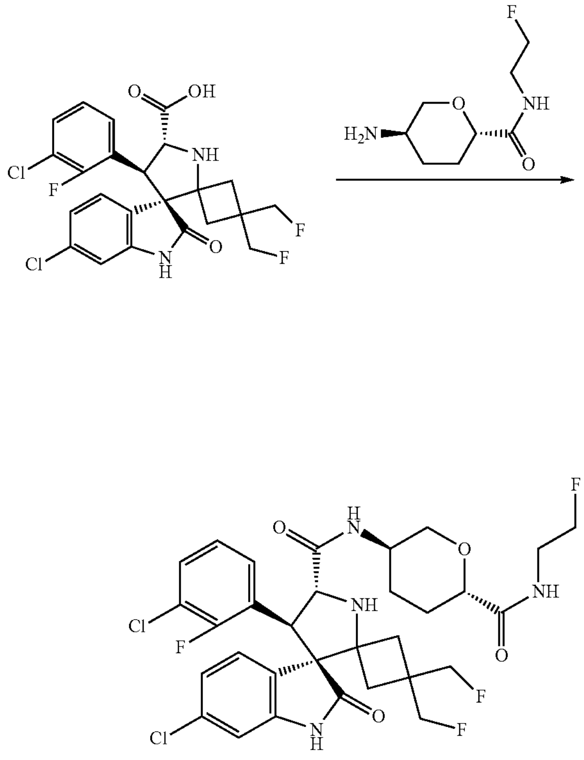

(3'R, 4'S,5'R)-6"-chloro-4'-(3-chloro-2-fluorophenyl)-N-{(3R,6S)-6-[(2-fluoroethyl) carbamoyl]tetrahydro-2H-pyran-3-yl}-3,3-bis(fluoromethyl)-2"-oxo-1",2"-dihydrodispiro[cyclobutane-1,2'-pyrrolidine-3',3"-indole]-5'-carboxamide The compound (70 mg, 0:14 mmol) obtained in Step 1 Of Example 121 and the compound (32 mg, 0.17 mmol) obtained in Step 2 of Reference Example 59 were used as starting materials and treated in the same way as in Step 2 of Example 12 to give 64 mg (68%) of the title compound as a colorless amorphous solid.

$^1$H-NMR (400 MHz, $CDCl_3$) δ: 1.47-1.71 (3H, m), 1.84 (1H, dd, J=13.7, 2.8 Hz), 2.01-2.07 (1H, m), 2.16-2.22 (1H, m), 2.27-2.33 (1H, m), 2.39 (1H, d, J=12.8 Hz), 3.12 (1H, t, J=10.8 Hz), 3.47-3.70 (2H, m), 3.78-4.02 (5H, m), 4.10-4.16 (1H, m), 4.35-4.40 (2H, m), 4.44 (1H, t, J=4.8 Hz), 4.54-4.77 (3H, m), 6.78 (1H, d, J=1.8 Hz), 6.89 (1H, t, J=6.0 Hz), 6.93 (1H, t, J=8.0 Hz), 7.12-7.18 (2H, m), 7.37 (1H, dd, J=8.0, 2.2 Hz), 7.41-7.47 (3H, m).

MS (ESI) m/z: 671 $(M+H)^+$.

Example: 139

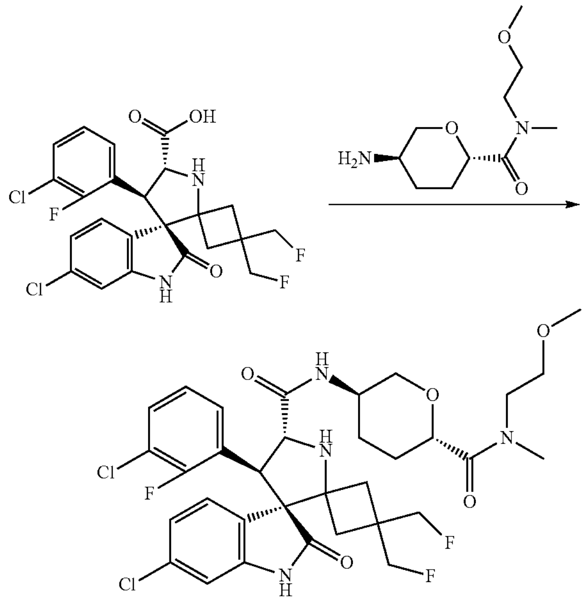

(3'R, 4'S,5'R)-6"-chloro-4'-(3-chloro-2-fluorophenyl)-3,3-bis(fluoromethyl)-N-[(3R,6S)-6-[(2-methoxyethyl)(methyl)carbamoyl]tetrahydro-2H-pyran-3-yl]-2"-oxo-1",2"-dihydrodispiro [cyclobutane-1,2'-pyrrolidine-3',3"-indole]-5'-carboxamide The compound (70 mg, 0.14 mmol) obtained in Step 1 of Example 121 and the compound (36 mg, 0.17 mmol) obtained in Step 2 of Reference Example 60 were used as starting materials and treated in the same way as in Step 2 of Example 12 to give 49 mg (52%) of the title compound as a colorless amorphous solid.

$^1$H-NMR (400 MHz, $CDCl_3$) δ: 1.39-1.61 (3H, m), 1.70 (1H, dd, J=13.4, 2.4 Hz), 1.81-2.11 (4H, m), 2.21-2.30 (1H, m), 2.41 (1H, d, J=12.7 Hz), 2.91-3.17 (2H, m), 3.23 (1H, t, J=9.8 Hz), 3.32 (3H, s), 3.49-3.63 (3H, br s), 3.78-4.23 (6H, m), 4.38 (2H, s), 4.54-4.75 (2H, m), 6.75 (1H, d, J=1.8 Hz), 6.88-6.93 (1H, m), 7.10-7.16 (2H, m), 7.25-7.30 (1H, m), 7.35-7.47 (3H, m).

MS (ESI) m/z: 697 $(M+H)^+$.

Example 140

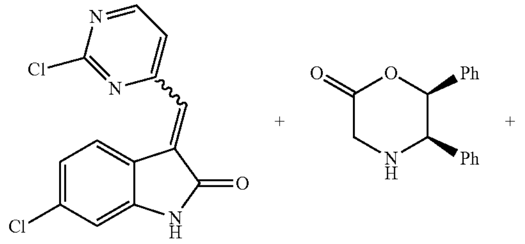

-continued

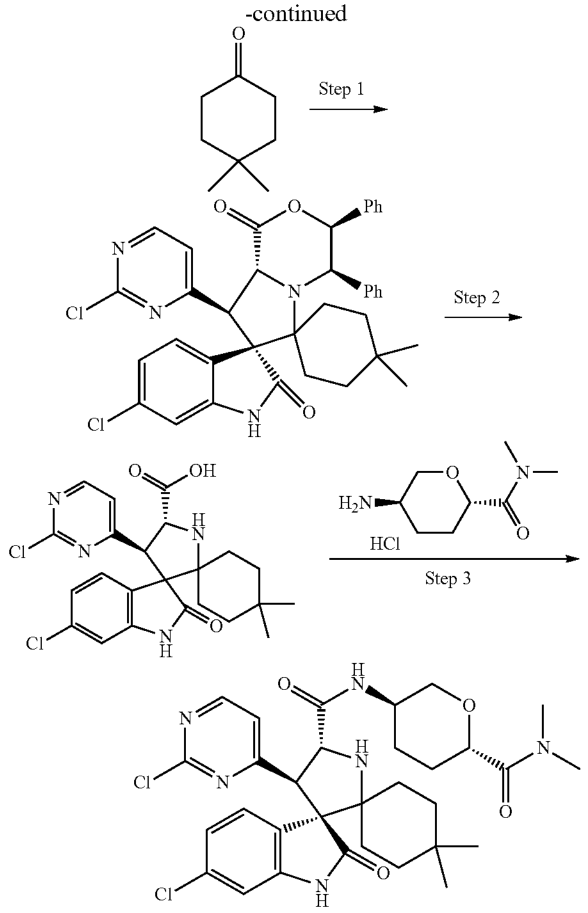

Step 1

(3'S,4'R, 7'S,8'R, 8a'R)-6"-chloro-8'-(2-chloropyrimidin-4-yl)-4,4-dimethyl-3',4'-diphenyl-3',4',8',8a'-tetrahydro-1'A-dispiro[cyclohexane-1,6'-pyrrolo[2,1-c][1,4]oxazine-7',3"-indole]-1',2" (1"H)-dione The compound (3.80 g, 13.0 mmol) obtained in Reference Example 65 was used as a starting material and treated in the same way as in Step 1 of Example 9 to give 4.48 g (53%) of the title compound as a pale yellow solid.

$^1$H-NMR (500 MHz, $CD_3OD$) δ: 0.33 (3H, s), 0.59 (3H, s); 0.93-1.55 (6H, m), 2.07-2.16 (1H, m), 2.23-2.32 (1H, m), 4.57 (1H, d, J=9.7 Hz), 4.93 (1H, d, J=3.4 Hz), 5.60 (1H, d, J=9.7 Hz), 6.73-6.76 (1H, m), 6.80-6.93 (4H, m), 6.97-7.10 (3H, m), 7.10-7.37 (7H, m), 8.43 (1H, d, J=5.2 Hz).

MS (FAB) m/z: 653 $(M+H)^+$.

Step 2

(4'R, 5'R)-6"-chloro-4'-(2-chloropyrimidin-d-yl)-4,4-dimethyl-2"-oxo-1",2"-dihydrodispiro[cyclohexane-1,2'-pyrrolidine-3',3"-indole]-5'-carboxylic acid The compound (952 mg, 1.46 mmol) obtained in Step 1 above was used as a starting material and treated in the same way as in Step 1 of Example 12 to give 314 mg (45%) of the title compound as a brown solid.

MS (FAB) m/z: 475 $(M+H)^+$.

Step 3

(3'R, 4'R, 5'R)-6"-chloro-4'-(2-chloropyrimidin-4-yl)-N-[(3R,6S)-6-(dimethylcarbamoyl)tetrahydro-2H-pyran-3-yl]-4,4-dimethyl-2"-oxo-1",2"-dihydro-dispiro[cyclohexane-1,2'=pyrrolidine-3',3"-indole]-5'-carboxamide The compound (120 mg, 0.25 mmol) obtained in Step 2 above and the compound (51 mg, 0.30 mmol) obtained in Step 2 of Reference Example 41 were used as starting materials and treated in the same way as in Step 2 of Example 12 to give 62 mg (68%) of the title compound as a colorless amorphous solid.

$^1$H-NMR (400 MHz, $CDCl_3$) δ: 0.66 (3H, s), 0.93 (3H, s), 1.13-1.73 (9H, m), 1.90-2.08 (2H, m), 2.17-2.25 (1H, m), 2.97 (3H, s), 3.11 (3H, s), 3.26-3.35 (1H, m), 3.98-4.08 (1H, m), 4.11-4.17 (2H, m), 4.33-4.42. (2H, m), 6.94 (1H, d, J=1.7 Hz), 7.01 (1H, dd, J=8.1, 2.0 Hz), 7.13 (1H, d, J=8.1 Hz), 7.67 (1H, d, J=5.4 Hz), 7.72 (1H, d, J=8.3 Hz), 7.85 (1H, s), 8.39 (1H, d, J=5.1 Hz).

MS (ESI) m/z: 629 $(M+H)^+$.

Example 141

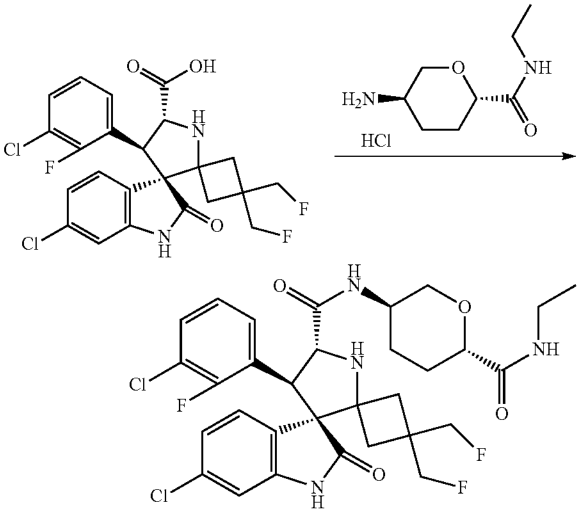

(3'R, 4'S,5'R)-6"-chloro-4'-(3-chloro-2-fluorophenyl)-N-[(3R, (S)-6-(ethylcarbamoyl)tetrahydro-2H-pyran-3-yl]-3,3-bis(fluoromethyl)-2"-oxo-1",2"-dihydrodispiro[cyclobutane-1,2'-pyrrolidine-3',3"-indole]-5'-carboxamide The compound (150 mg, 0.30 mmol) obtained in Step 1 of Example 121 and the compound (62 mg, 0.36 mmol) obtained in Step 2 of Reference Example 34 were used as starting materials and treated in the same way as in Step 2 of Example 12 to give 94 mg (48%) of the title compound as a colorless solid.

$^1$H-NMR (400 MHz, $CDCl_3$) δ: 1.15 (3H, t, J=7.3 Hz), 1.48-1.60 (2H, m), 1.68 (1H, dd, J=13.5, 2.5 Hz), 1.83-1.86 (1H, m), 2.03 (1H, d, J=11.4 Hz), 2.13-2.20 (1H, m), 2.25-2.35 (1H, m), 2.39 (1H, d, J=13.3 Hz), 3.10 (1H, t, J=10.8 Hz), 3.24-3.36 (2H, m), 3.71-3.98 (5H, m), 4.12 (1H, ddd, J=10.9, 4.8, 1.3 Hz), 4.37 (2H, s), 4.54-4.75 (2H, m), 6.51 (1H, t, J=5.7 Hz), 6.77 (1H, d, J=1.8 Hz), 6.92 (1H, t, J=8.0 Hz), 7.10-7.18 (2H, m), 7.37 (1H, dd, J=8, 0, 2.1 Hz), 7.40-7.47 (2H, m), 7.68 (1H, s).

MS (ESI) m/z: 653 $(M+H)^+$.

Example 142

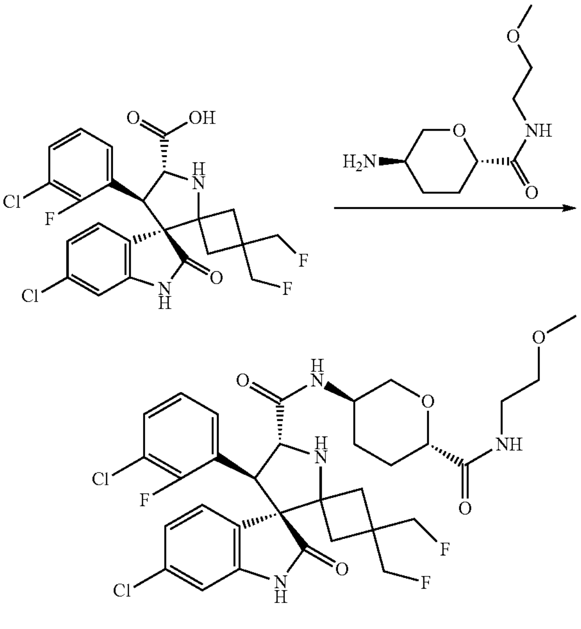

(3'R, 4'S,5'R)-6"-chloro-4'-(3-chloro-2-fluorophenyl)-3,3-bis(fluoromethyl)-N-{(3R,6S)-6-[(2-methoxyethyl)carbamoyl]tetrahydro-2H-pyran-3-yl}-2"-oxo-1",2"-dihydrodispiro[cyclobutane-1,2'-pyrrolidine-3',3"-indole]-5'-carboxamide The compound (150 mg, 0.30 mmol) obtained in Step 1 of Example 121 and the compound (73 mg, 0.36 mmol) obtained in Step 2 of Reference Example 61 were used as starting materials and treated in the same way as in Step 2 of Example 12 to give 116 mg (57%) of the title compound as a colorless solid.

$^1$H-NMR (400 MHz, $CDCl_3$)): 1.47-1.63 (2H, m), 1.68 (1H, dd, J=13.3, 2.7 Hz), 1.84 (1H, dd, J=13.3, 2.7 Hz), 2.03 (1H, d, J=12.4 Hz), 2.13-2.21 (1H, m), 2.27-2.31 (1H, m), 2.38 (1B, d, J=12.8 Hz), 3.10 (1H, t, J=10.8 Hz), 3.36 (3H, s), 3.44-3.47 (4H, m), 3.77-4.01 (5H, m), 4.12 (1H, ddd, J=10.9, 4.3, 1.4 Hz), 4.37 (2H, s), 4.54-4.75 (2H, m), 6.77 (1H, d, J=1.8 Hz), 6.82-6.87 (1H, m), 6.92 (1H, t, J=8.0 Hz), 7.12-7.17 (2H, m), 7.37 (1H, dd, J=8.0, 2.1 Hz), 7.41-7.46 (2H, m), 7.60 (1H, s).

MS (ESI) m/z: 683 $(M+H)^+$.

Example 143

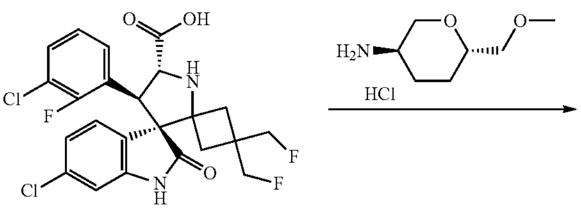

-continued

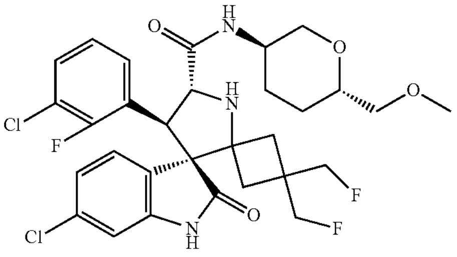

(3'R, 4'S,5'R)-6"-chloro-A'-(3-chloro-2-fluorophenyl)-3,3-bis(fluoromethyl)-N-[(3R,6S)-6-(methoxymethyl)tetrahydro-2H-pyran-3-yl]-2"-oxo-1",2"-dihydrodispiro[cyclobutane-1,2'-pyrrolidine-3',3"-indole]-5'-carboxamide The compound (150 mg, 0.30 mmol) obtained in Step 1 of Example 121 and the compound (70 mg, 0.36 mmol) obtained in Step 2 of Reference Example 64 were used as starting materials and treated in the same way as in Step 2 of Example 12 to give 121 mg (64%) of the title compound as a colorless solid.

$^1$H-NMR (400 MHz, $CDCl_3$) δ: 1.40-1.55 (2H, m), 1.63-1.76 (2H, m), 1.83 (1H, dd, J=13.5, 3.0 Hz), 2.04 (1H, dd, J=12.4, 2.7 Hz), 2.12-2.19 (1H, m), 2.37 (1H, d, J=12.4 Hz), 3.09 (1H, t, J=10.8 Hz), 3.34-3.45 (5H, m), 3.48-3.55 (1H, m), 3.78-4.02 (4H, m), 4.07 (1H, ddd, J=10.6, 4.3, 1.5 Hz), 4.38 (2H, s), 4.55-4.76 (2H, m), 6.76 (1H, d, J=1.8 Hz), 6.88-6.92 (1H, m), 7.11-7.16 (2H, m), 7.35-7.40 (2H, m), 7.41-7.45 (1H, m), 7.53 (1H, s).

MS (ESI) m/z: 626 $(M+H)^+$.

Example 144

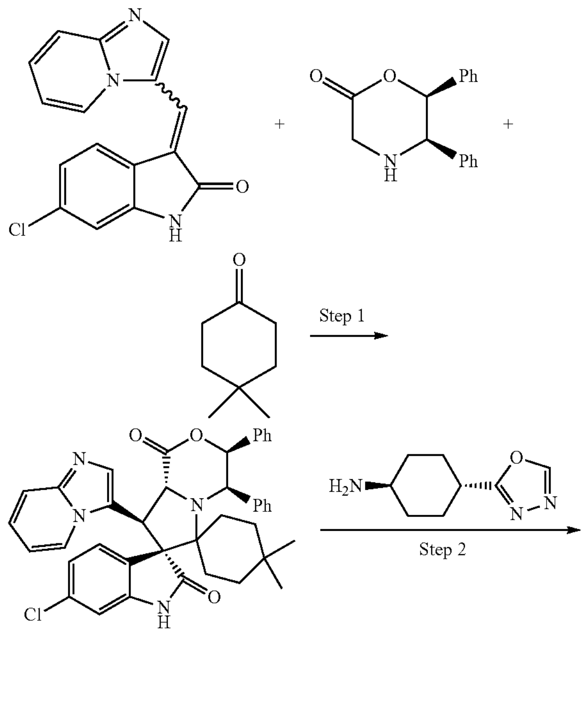

-continued

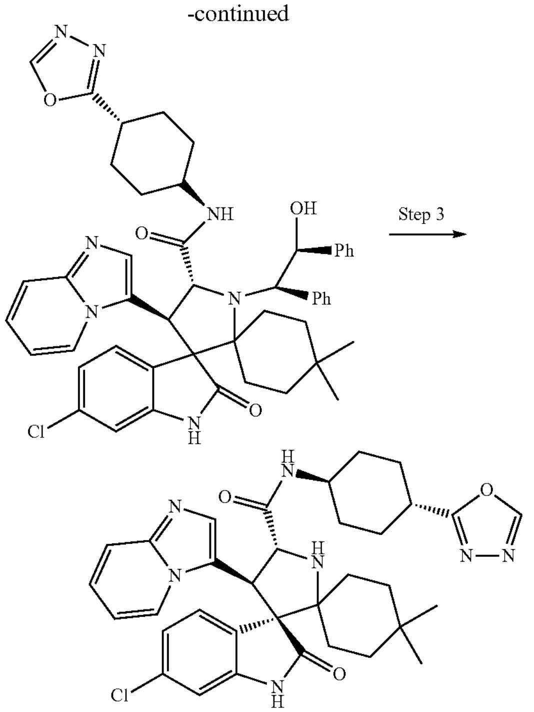

Step 1

(3'S,4'R,7'S,8'R, 8a'R)-6"-chloro-8'-imidazo[1,2-a]pyridin-3-yl-4,4-dimethyl-3',4'-diphenyl-3',4",8',8a'-tetrahydro-1'H-dispiro[cyclohexane-1,6'-pyrrolo[2,1-c] [1,4]oxazine-7',3"-indole]-1",2" (1"H)-dione The compound (550 mg, 1.86 mmol) obtained in Reference Example 66 was used as a starting material and treated in the same way as in Step 1 of Example 9 to give 344 mg (28%) of the title compound as a yellow amorphous solid.

$^1$H-NMR (400 MHz, $CDCl_3$) δ: 0.26 (3H, s), 0.54 (3H, s), 0.96-1.00 (2H, m), 1.07-1.10 (2H, m), 1.31-1.39 (4H, m), 1.69-1.71 (4H, m), 1.96-1.99 (1H, m), 2.25-2.28 (1H, m), 4.64 (1H, d, J=10.7 Hz), 4.91 (1H, d, J=2.9 Hz), 5.45 (1H, d, J=10.5 Hz), 6.31 (1H, d, J=8.3 Hz), 6.46 (1H, dd, J=8.3, 1.7 Hz), 6.52 (1H, t, J=6.8 Hz), 6.78 (1H, d, J=1.7 Hz), 6.82-6.84 (2H, m), 7.01-7.28 (16H, m), 7.52 (1H, d, J=9.0 Hz), 8.02-8.05 (1H, m), 8.21 (1H, br s).

MS (ESI) m/z: 658 $(M+H)^+$.

Step 2

(4'R, 5'R)-6"-chloro-1'-[(1R, 2S)-2-hydroxy-1,2-diphenylethyl]-4'-(imidazo[1,2-a]pyridin-3-yl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-indole]-5'-carboxamide The compound (344 mg, 0.52 mmol) obtained in Step 1 above and the compound (265 mg, 1.57 mmol) obtained in Step 3 of Reference Example 3 were used as starting materials and treated in the same way as in Step 1 of Example 5 to give 239 mg (55%) of the title compound as a pale yellow amorphous solid.

MS (ESI) m/z: 824 $(M+H)^+$.

Step 3

(3'R, 4'R, 5'R)-6"-chloro-4'-imidazo[1; 2-a]pyridin-3-yl-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-indole]-5'-carboxamide The compound (239 mg, 0.29 mmol) obtained in Step 2 above was used as a starting material and treated in the same way as in Step 3 of Example 1 to give 81 mg (44%) of the title compound as a colorless solid.

$^1$H-NMR (400 MHz, $CD_3OD$) δ: 0.70 (3H, s), 0.95 (3H, s), 1.13-1.22 (2H, m), 1.27-1.88 (10H, m), 1.94-2.02 (2H, m), 2.06-2.27 (3H, m), 3.01 (1H, tt, J=12.1, 4.1 Hz), 3.69 (1H, tt, J=12.1, 4.1 Hz), 4.49 (1H, d, J=8.7 Hz), 6.68 (1H, d, J=1.8 Hz, 6.72 (1H, td, J=6.9, 0.9 Hz), 6.98 (1H, dd, J=8.2, 1.8 Hz), 7.13 (1H, td, J=8.0, 1.4 Hz), 7.36 (1H, d, J=9.2 Hz), 7.62 (1H, s), 7.66 (1H, d, J=7.8 Hz), 7.89 (1H, s), 8.23 (1H, d, J=7.3 Hz), 8.84 (1H, s).

MS (ESI) m/z: 628 $(M+H)^+$.

Example 145

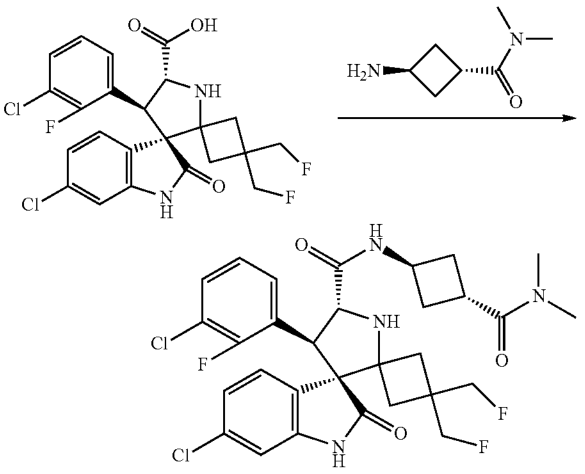

(3'R, 4'S,5'R)-6"-chloro-4'-(3-chloro-2-fluorophenyl)-N-[trans-3-(dimethylcarbamoyl)cyclobutyl]-3,3-bis(fluoromethyl)-2"-oxo-1",2"-dihydrodispiro[cyclobutane-1,2'-pyrrolidine-3',3"-indole]-5'-carboxamide The compound (80 mg, 0.16 mmol) obtained in Step 1 of Example 121 and the compound (39 mg, 0.27 mmol) obtained in Step 2 of Reference Example 52 were used as starting materials and treated in the same way as in Step 2 of Example 12 to give 72 mg (72%) of the title compound as a colorless solid.

$^1$H-NMR (400 MHz, $CDCl_3$) δ: 1.69 (1H, dd, J=13.5, 3.0 Hz), 1.86 (1H, dd, J=13.5, 3.0 Hz), 2.10 (1H, dd, J=12.8, 2.8 Hz), 2.21-2.31 (2H, m), 2.40 (1H, d, J=12.8 Hz), 2.70-2.81 (2H, m), 2.90 (3H, s), 2.96 (3H, s), 2.97 (1H, dd, J=6.2, 1.6 Hz), 3.28-3.36 (1H, m), 3.79-4.00 (2H, m), 4.30-4.38 (1H, m), 4.39 (2H, s), 4.59-4.82 (2H, m), 6.78 (1H, d, J=1.8 Hz), 6.93 (1H, t, J=8.0 Hz), 7.12-7.17 (2H, m), 7.40 (1H, dd, J=7.8, 2.3 Hz), 7.43-7.48 (1H, m), 7.50 (1H, s), 7.77 (1H, d, J=7.3 Hz).

MS (ESI) m/z: 623 $(M+H)^+$.

Example 146 (Isomer A) and 147 (Isomer B)

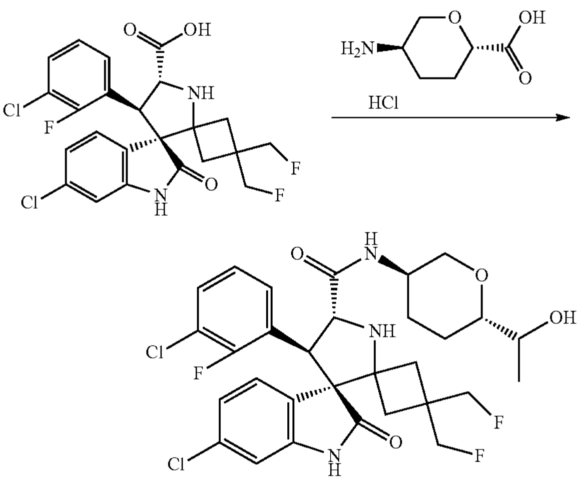

(3'R, 4'S,5'R)-6"-chloro-4'-(3-chloro-2-fluorophenyl)-3,3-bis(fluoromethyl)-N-{(3R,6S)-6-[1-hydroxyethyl]tetrahydro-2H-pyran-3-yl}-2"-oxo-1",2"-dihydrodispiro[cyclobutane-1,2'-pyrrolidine-3',3"-indole]-5'-carboxamide The compound (300 mg, 0.6 mmol) obtained in Step 1 of Example 121 and the compound (131 mg, 0.72 mmol) obtained in Step 3 of Reference Example 30 were used as starting materials and treated in the same way as in Step 2 of Example 12 to give a mixture of diastereomers. The mixture of diastereomers obtained was resolved and purified by chiral column liquid chromatography [fractionation conditions: CHIRALPAK IC, n-hexane:ethanol=3:2 (v/v)] to separately give 161 mg (42%: isomer A) and 86 mg (23%: isomer B) of the title compounds as colorless solids.

Isomer A:

$^1$H-NMR (400 MHz, $CDCl_3$) δ: 1.15 (3H, d, J=6.4 Hz), 1.44 (1H, ddd, J=24.5, 12.1, 4.1 Hz), 1.61-1.75 (3H, m), 1.84 (1H, dd, J=13.3, 2.7 Hz), 2.01-2.09 (2H, m), 2.13-2.22 (1H, m), 2.38 (1H, d, J=13.3 Hz), 3.09 (1H, t, J=10.5 Hz), 3.23 (1H, dt, J=11.3, 2.9 Hz), 3.79-3.99 (5H, m), 4.07 (1H, dq, J=10.5, 2.3 Hz), 4.38 (2H, s), 4.55-4.76 (2H, m), 6.92 (1H, t, J=8.0 Hz), 7.12-7.16 (2H, m), 7.36-7.40 (2H, m), 7.43-7.45 (1H, m), 7.52 (1H, s).

MS (ESI) m/z: 626 $(M+H)^+$.

Isomer B:

$^1$H-NMR (400 MHz, $CDCl_3$) δ: 1.16 (3H, d, J=6.4 Hz), 1.39-1.50 (2H, m), 1.67 (1H, dd, J=13.3, 2.7 Hz), 1.72-1.78 (1H, m), 1.83 (1H, dd, J=13.7, 3.2 Hz), 2.04 (1H, d, J=12.8 Hz), 2.12-2.18 (1H, m), 2.38 (1H, d, J=12.4 Hz), 2.64 (1H, s), 3.03-3.09 (2H, m), 3.58-3.67 (1H, m), 3.83 (1H, dd, J=23.8, 9.2 Hz), 3.88-4.03 (3H, m), 4.08 (1H, ddd, J=11.0, 4.2, 1.4 Hz), 4.38 (2H, s), 4.55-4.76 (2H, m), 6.77 (1H, d, J=1.8 Hz), 6.91 (1H, t, J=8.0 Hz), 7.12-7.17 (2H, m), 7.35-7.41 (2H, m), 7.44 (1H, t, J=6.6 Hz), 7.50 (1H, s).

MS (ESI) m/z: 626 $(M+H)^+$.

Example 148

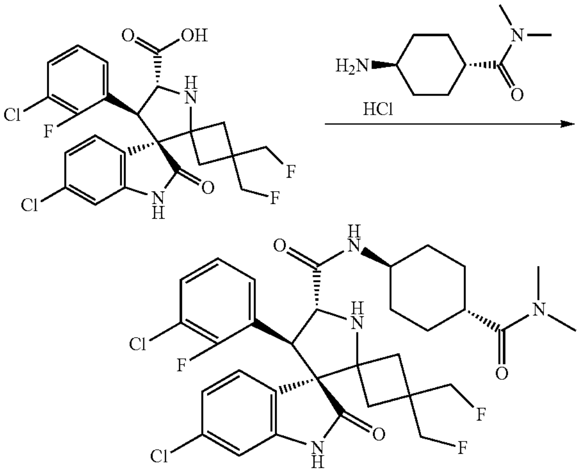

(3'R, 4'S,5'R)-6"-chloro-4'-(3-chloro-2-fluorophenyl)-N-[trans-4-(dimethylcarbamoyl)cyclohexyl]-3,3-bis(fluoromethyl)-2"-oxo-1",2"-dihydrodispiro[cyclobutane-1,2'-pyrrolidine-3',3"-indole]-5'-carboxamide The compound (70 mg, 0.14 mmol) obtained in Step 1 of Example 121 and trans-4-amino-N,N-dimethylcyclohexanecarboxamide hydrochloride (WO2008/068171) (29 mg, 0.17 mmol) were used as starting materials and treated in the same way as in Step 2 of Example 12 to give 62 mg (68%) of the title compound as a colorless amorphous solid.

$^1$H-NMR (400 MHz, $CDCl_3$) δ: 1.15-1.34 (2H, m), 1.61-1.87 (6H, m), 2.01-2.15 (3H, m), 2.36 (1H, d, J=12.9 Hz), 2.45-2.54 (1H, m), 2.93 (3H, s), 3.06 (3H, s), 3.70-4.03 (4H, m), 4.34-4.40 (2H, m), 4.56-4.79 (2H, m), 6.72 (1H, d, J=2.0 Hz), 6.85-6.91 (1H, m), 7.08-7.14 (2H, m), 7.36 (1H, d, J=8.2, 2.1 Hz), 7.41-7.47 (2H, m), 8.19 (1H, s).

MS (ESI) m/z: 651 $(M+H)^+$.

Example 149

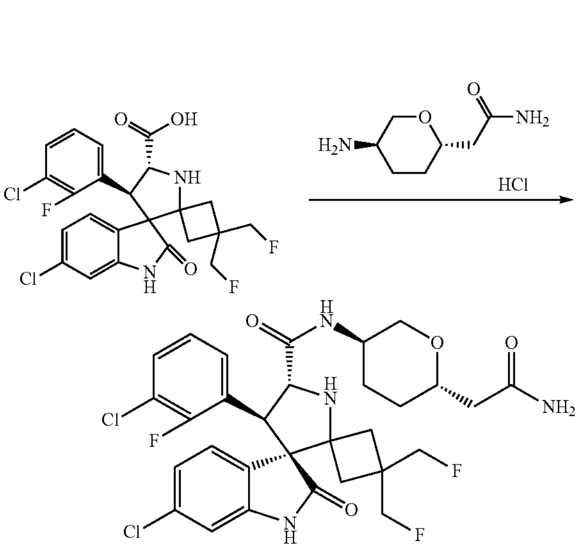

(3'R, 4'S,5'R)—N-[(3R,6S)-6-(2-amino-2-oxoethyl)tetrahydro-2H-pyran-3-yl]-6"-chloro-4'-(3-chloro-2-fluorophenyl)-3,3-bis(fluoromethyl)-2"-oxo-1",2"-dihydrodispiro[cyclobutane-1,2'-pyrrolidine-3',3"-indole]-5'-carboxamide The compound (60 mg, 0.12 mmol) obtained in Step 1 of Example 121 and the compound (28 mg, 0.14 mmol) obtained in Step 3 of Reference Example 49 were used as starting materials and treated in the same way as in Step 2 of Example 12 to give 29 mg (38%) of the title compound as a solid.

$^1$H-NMR (500 MHz, $CDCl_3$) δ: 1.46-1.57 (2H, m), 1.66-1.69 (1H, m), 1.79-1.85 (2H, m), 2.02-2.05 (1H, m), 2.13-2.15 (1H, m), 2.37-2.46 (3H, m), 3.10 (1H, t, J=10.9 Hz), 3.66-3.70 (1H, m), 3.80-4.08 (5H, m), 4.35-4.40 (2H, m), 4.56-4.75 (2H, m), 5.35 (1H, s), 6.21 (1H, s), 6.78 (1H, d, J=1.7 Hz), 6.94 (1H, t, J=7.7 Hz), 7.12-7.17 (2H, m), 7.36-7.40 (2H, m), 7.46-7.43 (1H, m), 7.52 (1H, s).

MS (ESI) m/z: 639 $(M+H)^+$:

Example 150

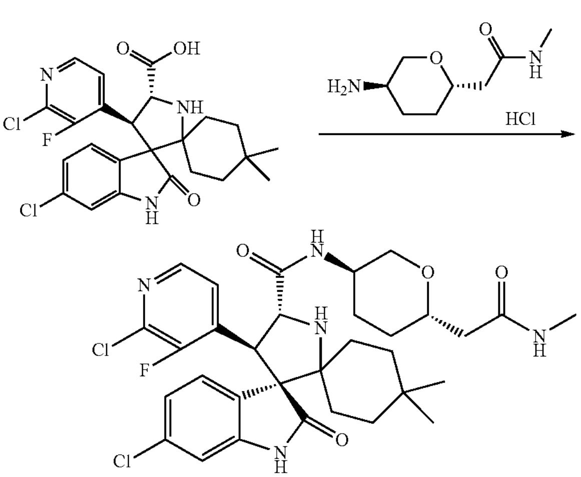

(3'R, 4'S,5'R)-6"-chloro-4'-(2-chloro-3-fluoropyridin-4-yl)-4,4-dimethyl-N-{(3R,6S)-6-[2-(methylamino)-2-oxoethyl]tetrahydro-2H-pyran-3-yl}-2"-oxo-1",2"-dihydrodispiro[cyclohexane-1,2'-pyrrolidine-3',3"-indole]-5'-carboxamide The compound (99 mg, 0.20 mmol) obtained in Step 1 of Example 17 and the compound (180 mg, 0.22 mmol) obtained in Step 3 of Reference Example 67 were used as starting materials and treated in the same way as in Step 2 of Example 12 to give 35 mg (27%) of the title compound as a solid.

$^1$H-NMR (500 MHz, DMSO-dd) δ: 0.59 (3H, s), 0.90-0.99 (4H, m), 1.10-1.13 (1H, m), 1.19-1.33 (2H, m), 1.40-1.43 (1H, m), 1.48-1.60 (3H, m), 1.70-1.76 (3H, m), 1.82-1.86 (1H, m), 2.14 (1H, dd, J=14.3, 5.2 Hz), 2.23 (1H, dd, J=14.0, 7.7 Hz), 2.54 (3H, d, J=4.6 Hz), 3.08 (1H, t, J=10.3 Hz), 3.52-3.50 (1H, m), 3.58-3.67 (3H, m), 4.45 (1H, t, J=9.5 Hz), 4.56 (1H, d, J=9.2 Hz), 6.71 (1H, d, J=2.3 Hz), 7.06 (1H, dd, J=8.3, 2.0 Hz), 7.50 (1H, dd, J=8.3, 2.0 Hz), 7.63 (1H, t, J=4.9 Hz), 7.79-7.74 (2H, m), 8.17 (1H, d, J=5.2 Hz), 10.62 (1H, s).

MS (ESI) m/z: 646 $(M+H)^+$.

Example 151

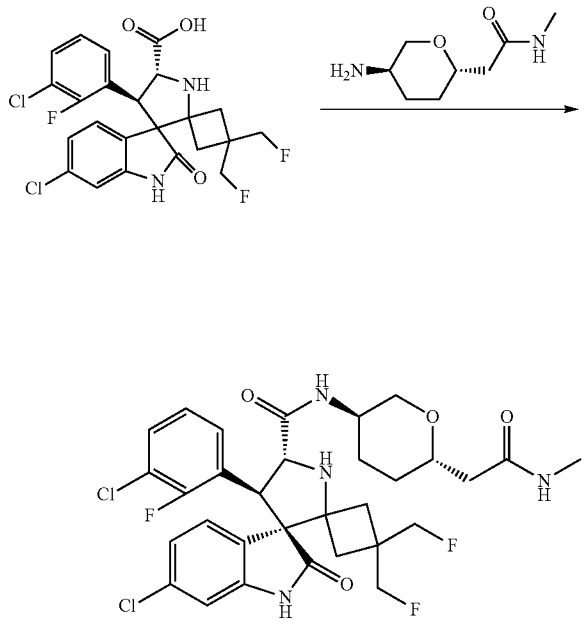

(3'R, 4'S,5'R)-6"-chloro-4'-(3-chloro-2-fluorophenyl)-3,3-bis(fluoromethyl)-N-{(3R,6S)-6-[2-(methylamino)-2-oxoethyl]tetrahydro-2H-pyran-3-yl}=2"-oxo-1",2"-dihydrodispiro[cyclobutane-1,2'-pyrrolidine-3',3'-indole]-5'-carboxamide The compound (81 mg, 0.16 mmol) obtained in Step 1 of Example 121 and the compound (197 mg, 0.24 mmol) obtained in Step 3 of Reference Example 67 were used as starting materials and treated in the same way as in Step 2 of Example 12 to give 28 mg (26%) of the title compound as a solid.

$^1$H-NMR (500 MHz, $CDCl_3$) δ: 1.46-1.52 (2H, m), 1.66-1.69 (1H, m), 1.75-1.85 (2H, m), 2.01-2.04 (1H, m), 2.11-2.13 (1H, m), 2.36-2.39 (3H, m), 2.79 (3H, d, J=4.6 Hz), 3.09 (1H, t, J=10.9 Hz), 3.67-3.69 (1H, m), 3.80-4.05 (5H, m), 4.35-4.39 (2H, m), 4.56-4.74 (2H, m), 6.15-6.16 (1H, m), 6.78 (1H, s), 6.93 (1H, t, J=7.7 Hz), 7.16-7.12 (2H, m), 7.36-7.46 (3H, m), 7.56 (1H, s).

MS (ESI) m/z: 653 $(M+H)^+$.

Example 152

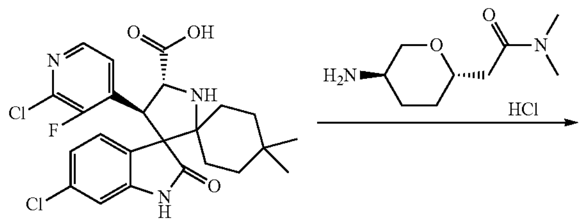

-continued

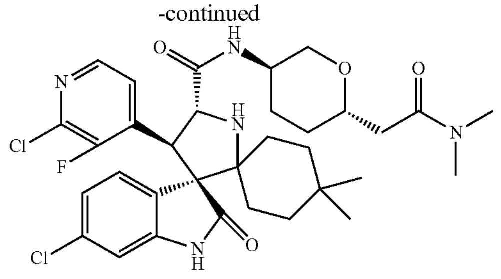

(3'R, 4'S,5'R)-6"-chloro-4'-(2-chloro-3-fluoropyridin-4-yl)-N-{(3R,6S)-6-[2-(dimethylamino)-2-oxoethyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide The compound (98 mg, 0.20 mmol) obtained in step 1 of Example 17 and the compound (53 mg, 0.24 mmol) obtained in Step 2 of Reference Example 68 were used as starting materials and treated in the same way as in Step 2 of Example 12 to give 82 mg (62%) of the title compound as a solid.

$^1$H-NMR (500 MHz, $CDCl_3$) δ: 0.67 (3H, s), 0.95 (3H, s), 1.11-1.26 (2H, m), 1.34-1.62 (5H, m), 1.71-1.77 (2H, m), 1.91-1.93 (1H, m), 2.07-2.09 (1H, m), 2.34 (1H, dd, J=15, 2, 5.4 Hz), 2.67 (1H, dd, J=15.2, 6.6 Hz), 2.95 (3H, s), 3.01 (3H, s), 3.13 (1H, t, J=10.6 Hz), 3.27 (1H, br s), 3.82-4.00 (3H, m), 4.43 (1H, d, J=9.2 Hz), 4.64 (1H, d, J=9.2 Hz), 6.73 (1H, s), 7.06 (1H, d, J=6.9 Hz), 7.31 (1H, d, J=8.0 Hz), 7.51-7.44 (3H, m), 8.05 (1H, d, J=5.2 Hz).

MS (ESI) m/z: 660 $(M+H)^+$.

Example 153

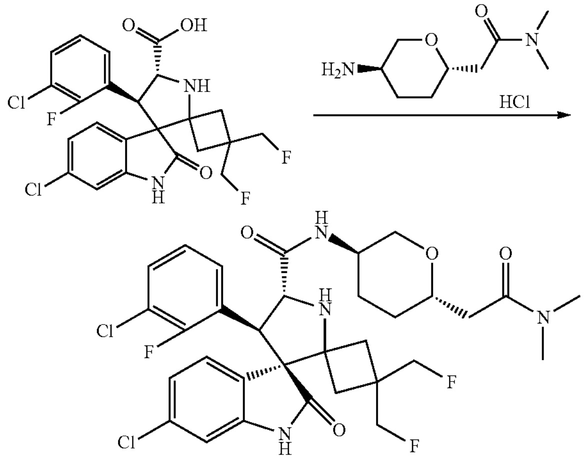

(3'R, 4'S,5'R)-6"-chloro-4'-(3-chloro-2-fluorophenyl)-N-{(3R,6S)-6-[2-(dimethylamino)-2-oxoethyl]tetrahydro-2H-pyran-3-yl}-3,3-bis(fluoromethyl)-2"-oxo-1",2"-dihydrodispiro[cyclobutane-1,2'-pyrrolidine-3',3'-indole]-5'-carboxamide The compound (81 mg, 0.16 mmol) obtained in Step 1 of Example 121 and the compound (53 mg, 0.24 mmol)

obtained in Step 2 of Reference Example 68 were used as starting materials and treated in the same way as in Step 2 of Example 12 to give 58 mg (54%) of the title compound as a solid.

$^1$H-NMR (500 MHz, $CDCl_3$) δ: 1.44-1.50 (2H, m), 1.66-1.68 (1H, m), 1.82-1.92 (2H, m), 2.01-2.12 (2H, m), 2.31-2.39 (2H, m), 2.67 (1H, dd, J=15.5, 6.9 Hz), 2.95 (3H, s), 3.01 (3H, s), 3.09 (1H, t, J=10.6 Hz), 3.83-3.99 (6H, m), 4.37 (2H, s), 4.57-4.74 (2H, m), 6.77 (1H, s), 6.92 (1H, t, J=7.7 Hz), 7.12-7.15 (2H, m), 7, 36-7.37 (2H, m), 7.43-7.46 (1H, m), 7.57-7.54 (1H, m).

MS (ESI) m/z: 667 $(M+H)^+$.

Example 154

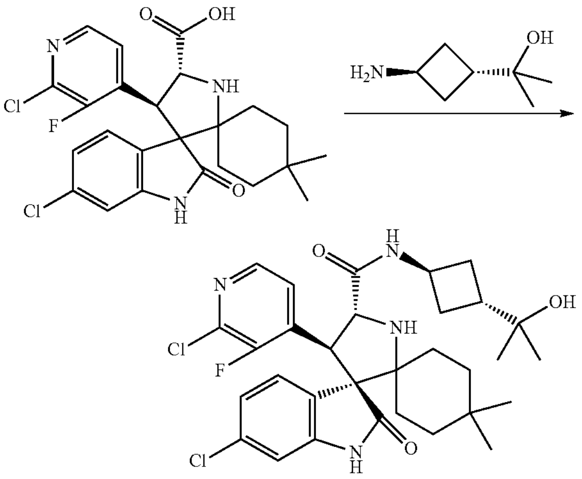

(3'R, 4'S,5'R)-6'-chloro-4'-(2-chloro-3-fluoropyridin-4-yl)-N-[trans-3-(2-hydroxypropan-2-yl)cyclobutyl]-4,4-dimethyl-2"-oxo-1",2"-dihydrodispiro[cyclohexane-1,2'-pyrrolidine-3',3"-indole]-5'-carboxamide The compound (45 mg, 0.09 mmol) obtained in Step 1 of Example 17 and the compound (13 mg, 0.10 mmol) obtained in Step 2 of Reference Example 69 were used as starting materials and treated in the same way as in Step 2 of Example 12 to give 38 mg (69%) of the title compound as a solid.

$^1$H-NMR (400 MHz, $CDCl_3$) δ: 0.69 (3H, s), 0.96 (3H, s), 1.05-2.10 (16H, m), 2.31-2.46 (3H, m), 3.34 (1H, br s), 4.22-4.34 (1H, m), 4.43 (1H, d, J=8.90 Hz), 4.66 (1H, d, J=8.90 Hz), 6.72 (1H, d, J=1.83 Hz), 7.07 (1H, dd, J=8.25, 1.83 Hz), 7.27-7.35 (2H, m), 7.47-7.53 (1H, m), 7.82-7.89 (1H, m), 8.05 (1H, d, J=5.04 Hz).

MS (ESI) m/z: 603 $(M+H)^+$.

Example 155

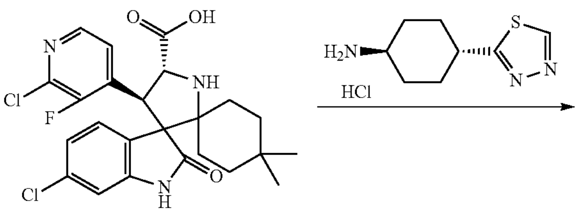

-continued

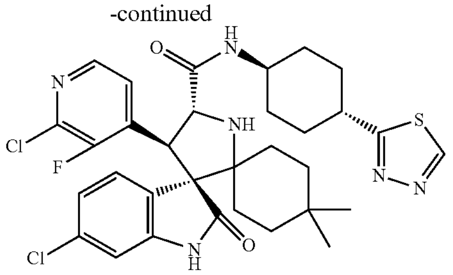

(3'R, 4'S,5'R)-6"-chloro-4'-(2-chloro-3-fluoropyridin-4-yl)-4,4-dimethyl-2"-oxo-N-[trans-4-(1,3,4-thiadiazol-2-yl)cyclohexyl]-1",2"-dihydrodispiro[cyclohexane-1,2'-pyrrolidine-3',3"-indole]-5'-carboxamide The compound (84 mg, 0.16 mmol) obtained in Step 1 of Example 17 and the compound (46 mg, 0.18 mmol) obtained in Step 3 of Reference Example 70 were used as starting materials and treated in the same way as in Step 2 of Example 12 to give 76 mg (72%) of the title compound as a solid.

$^1$H-NMR (500 MHz, $CDCl_3$) δ: 0.68 (3H, s), 0.96 (3H, s), 1.12-1.26 (2H, m), 1.34-1.55 (5H, m), 1.60-1.81 (5H, m), 2.10-2.20 (2H, m), 2.25-2.35 (2H, m), 3.18-3.43 (2H, m), 3.76-3.87 (1H, m), 4.46 (1H, d, J=8.88 Hz), 4.66 (1H, d, J=8.88 Hz), 6.73 (1H, d, J=1.72 Hz), 7.06 (1H, dd, J=8.31, 2.00 Hz), 7.29-7.34 (1H, m), 7.50-7.55 (1H, m), 7.63 (1H, d, J=8.59 Hz), 7.98 (1H, s), 8.04 (1H, d, J=5.15 Hz), 9.05 (1H, s).

MS (ESI) m/z: 657 $(M+H)^+$.

Example 156

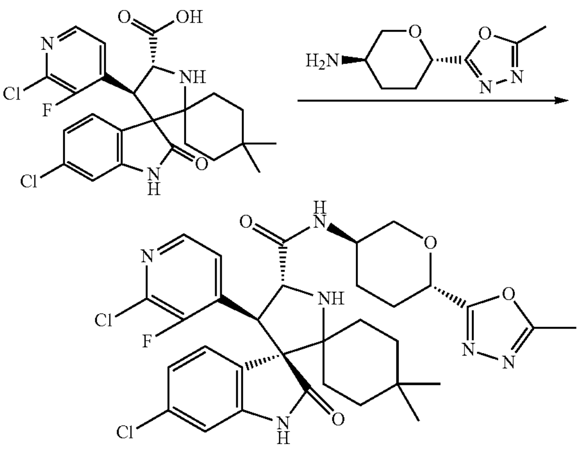

(3'R, 4'S,5'R)-6"-chloro-4'-(2-chloro-3-fluoropyridin-4-yl)-4,4-dimethyl-N-[(3R,6S)-6-(5-methyl-1,3,4-oxadiazol-2-yl)tetrahydro-2H-pyran-3-yl]-2"-oxo-1",2"-dihydrodispiro[cyclohexane-1,2'-pyrrolidine-3',3"-indole]-5 (=carboxamide The compound (204 mg, 0.39 mmol) obtained in Step 1 of Example 17 and the compound (79 mg, 0.43 mmol) obtained in Step 2 of Reference Example 71 were used as starting materials and treated in the same way as in Step 2 of Example 12 to give 165 mg (64%) of the title compound as a solid.

$^1$H-NMR (500 MHz, $CDCl_3$) δ: 0.69 (3H, s), 0.96 (3H, s), 1.11-1.27 (2H, m), 1.35-1.43 (1H, m), 1.44-1.55 (2H, m), 1.60-1.83 (4H, m), 2.07-2.28 (3H, m), 2.55 (3H, s), 3.14-3.43 (2H, m), 3.98-4.07 (1H, m), 4.08-4.15 (1H, m), 4.47 (1H, d, J=9.16 Hz), 4.65 (1H, d, J=9.16 Hz), 4.69 (1H, dd, J=9.74, 2.86 Hz), 5.73 (1H, d, J=1.72 Hz), 7.06 (1H, dd, J=8.02, 1.72 Hz), 7.29-7.33 (1H, m), 7.49-7.53 (1H, m), 7.69 (1H, d, J=8.59 Hz), 8.04 (1H, d, J=5.15 Hz), 8.08 (1H, s).

MS (ESI) m/z: 657 $(M+H)^+$.

Example 157

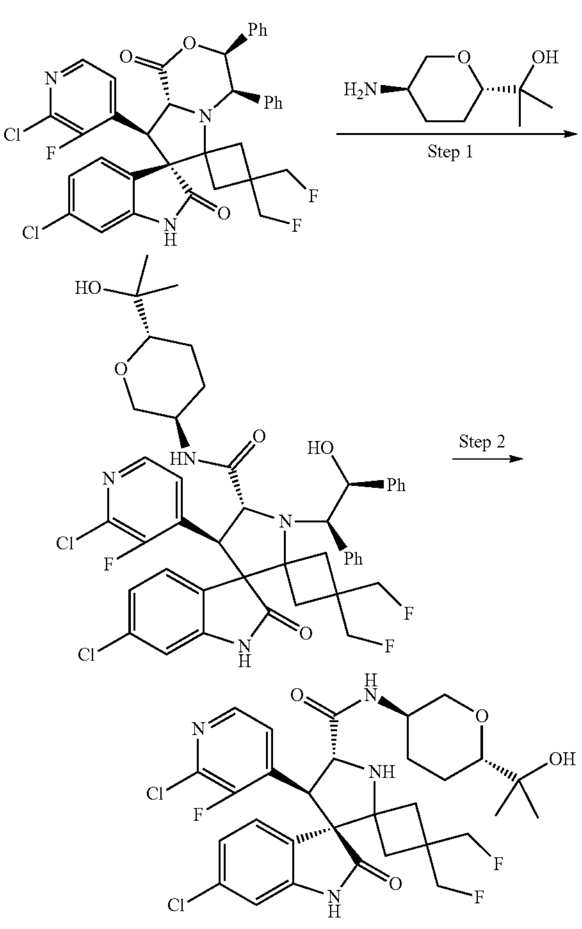

Step 1

(4'S,5'R)-6"-chloro-4'-(2-chloro-3-fluoropyridin-4-yl)-3,3-bis(fluoromethyl)-1'-[(1R,2S)-2-hydroxy-1,2-diphenylethyl]-N-[(3R,6S)-6-(1-hydroxy-1-methylethyl)tetrahydro-2H-pyran-3-yl]-2"-oxo-1",2'-dihydrodispiro[cyclobutane-1,2'-pyrrolidine-3',3"-indole]-5'-carboxamide The compound (267 mg, 1.55 mmol) obtained in Step 2 of Reference Example 5 and triethylamine (0.23 ml, 2.06 mmol) were added to a tetrahydrofuran solution (5.5 ml) of the compound (350 mg, 0.52 mmol) obtained in Step 1 of Example 91 and the resulting mixture was stirred at 60° C. for 36 hours. After cooling, saturated ammonium chloride solution was added, followed by extraction with ethyl acetate. The organic layer was washed with brine and then dried over anhydrous magnesium sulfate. The solvent was evaporated and the residue was purified by silica gel column chromatography [chloroform:methanol=100:0→11:1 (v/v)] to give 232 mg (538) of the title compound as a solid, MS (ESI) m/z: 837 $(M+H)^+$.

Step 2

(3'R, 4'S,5'R)-6'-chloro-4'-(2-chloro-3-fluoropyridin-4-yl)-3,3-bis(fluoromethyl)-N-[(3R,6S)-6-(1-hydroxy-1-methylethyl)tetrahydro-2H-pyran-3-yl]-2"-oxo-1",2"-dihydrodispiro[cyclobutane-1,2'-pyrrolidine-3',3'-indole]-5'-carboxamide The compound (162 mg, 0.38 mmol) obtained in Step 1 above was used as a starting material and treated in the same way as in Step 3 of Example 91 to give 58 mg (51%) of the title compound as a solid [fractionation conditions: CHIRALPAK IC, n-hexane:ethanol=1:1 (v/v)].

$^1$H-NMR (400 MHz, $CDCl_3$) δ: 1.15 (3H, s), 1.19 (3H, s), 1.39-1.59 (2H, m), 1.62-1.88 (3H, m), 2.03 (1H, d, J=11.9 Hz), 2.16 (1H, d, J=12.4 Hz), 2.38 (1H, d, J=12.8 Hz), 2.48 (1H, s), 3.04-3.13 (2H, m), 3.78-4.11 (5H, m), 4.32-4.41 (2H, m), 4.53-4.79 (2H, m), 6.80 (1H, s), 7.14 (1H, d, J=7.8 Hz), 7.36 (2H, d, J=7.8 Hz), 7.44 (1H, t, J=4.6 Hz), 7.88 (JH, s), 8.04 (1H, d, J=5.0 Hz).

MS (ESI) m/z: 641 $(M+H)^+$.

Example 158

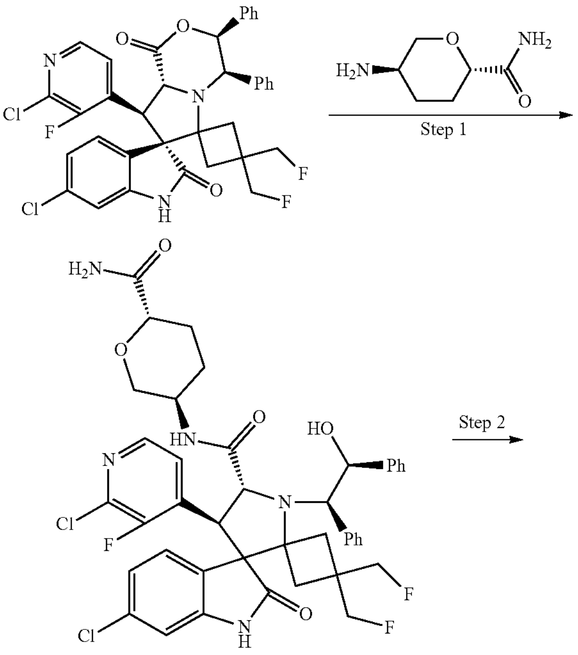

-continued

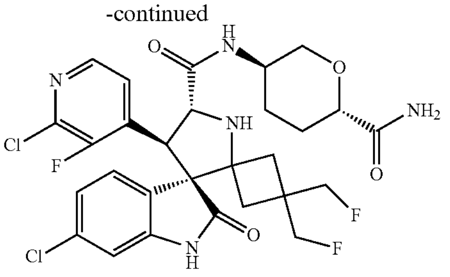

Step 1

(3'S,4'S, S'R)-N-[(3R,6S)-6-carbamoyltetrahydro-2H-pyran-3-yl]-6"-chloro-4'-(2-chloro-3-fluoropyridin-4-yl)-3,3-bis(fluoromethyl)-1'-[(1R,2S)-2-hydroxy-1,2-diphenylethyl]-2"-oxo-1",2"-dihydrodispiro[cyclobutane-1,2'-pyrrolidine-3,3'-indole]-5'-carboxamide The compound (300 mg, 0.44 mmol) obtained in Step 1 of Example 91 and the compound (240 mg, 1.33 mmol) obtained in Step 3 of Reference Example 28 were used as starting materials and treated in the same way as in Step 1 of Example 20 to give 180 mg (50%) of the title compound as a solid.

MS (ESI) m/z: 822 $(M+H)^+$.

Step 2

(3'R, 4'S,5'R)—N-[(3R,6S)-6-carbamoyltetrahydro-2H-pyran-3-yl]-6"-chloro-4'-(2-chloro-3-fluoropyridin-4-yl)-3,3-bis(fluoromethyl)-2"-oxo-1",2"-dihydrodispiro[cyclobutane-1,2'-pyrrolidine-3',3"-indole]-5'-carboxamide The compound (150 mg, 0.18 mmol) obtained in Step 1 above was used as a starting material and treated in the same way as in Step 3 of Example 91 to give 76 mg (59%) of the title compound as a solid [fractionation conditions: CHIRALPAK IC, n-hexane:ethanol=3:2 (v/v)].

$^1$H-NMR (400 MHz, $CDCl_3$) δ: 1.47-1.74 (3H, m), 1.85 (1H, d, J=13.3 Hz), 2.03 (1H, d, J=12.8 Hz), 2.16-2.43 (3H, m), 3.14 (1H, t, J=10.5 Hz), 3.76-4.16 (6H, m), 4.29-4.43 (2H, m), 4.53-4.76 (2H, m), 5.70 (1H, s), 6.51 (1H, s), 6.83 (1H, s), 7.14 (1H, d, J=7.3 Hz), 7.35 (1H, d, J=7.8 Hz), 7.41-7.47 (2H, m), 8.05 (1H, d, J=5.0 Hz), 8.30 (1H, s).

MS (ESI) m/z: 626 $(M+H)^+$.

Example 159

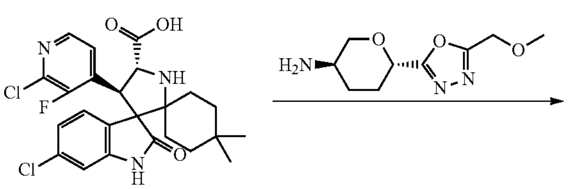

-continued

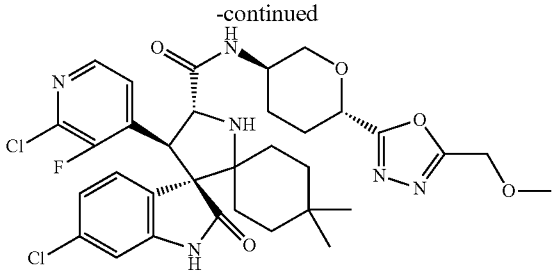

(3'R, 4'S,5'R)-6"-chloro-4'-(2-chloro-3-fluoropyridin-4-yl)-N-{trans-4-[5-(methoxymethyl)-1,3,4-oxadiazol-2-yl]cyclohexyl}-4,4-dimethyl-2"-oxo-1",2"-dihydrodispiro[cyclohexane-1,2'-pyrrolidine-3',3"-indole]-5"-carboxamide The compound (174 mg, 0.34 mmol) obtained in Step 1 of Example 17 and the compound (78 mg, 0.37 mmol) obtained in Step 3 of Reference Example 12 were used as starting materials and treated in the same way as in Step 2 of Example 12 to give 168 mg (73%) of the title compound as a solid.

$^1$H-NMR (400 MHz, $CDCl_3$) δ: 0.68 (3H, s), 0.96 (3H, s), 1.10-1.26 (2H, m), 1.30-1.55 (5H, m), 1.58-1.82 (5H, m), 2.08-2.29 (4H, m), 2.87-2.97 (1H, m), 3.19-3.39 (1H, m), 3.45 (3H, s), 3.71-3.85 (1H, m), 4.46 (1H, d, J=8.7 Hz), 4.62 (2H, s), 4.65 (1H, d, J=8.7 Hz), 6.70 (1H, d, J=1.8 Hz), 7.01-7.06 (1H, m), 7.28-7.33 (1H, m), 7.50-7.55 (1H, m), 7.64 (1H, d, J=8.2 Hz), 8.02 (1H, d, J=5.5 Hz), 8.50 (1H, s).

MS (ESI) m/z: 685 $(M+H)^+$.

Example 160

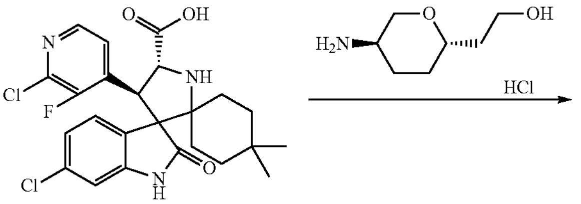

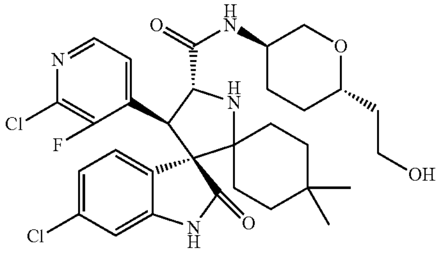

(3'R, 4'S,5'R)-6"-chloro-4'-(2-chloro-3-fluoropyridin-4-yl)-N-[(3R,6S)-6-(2-hydroxyethyl)tetrahydro-2H-pyran-3-yl]-4,4-dimethyl-2"-oxo-1",2"-dihydrodispiro[cyclohexane-1,2'-pyrrolidine-3',3"-indole]-5'-carboxamide The compound (101 mg, 0.20 mmol) obtained in Step 1 of Example 17 and the compound (19 mg, 0.10 mmol) obtained in Step 2 of Reference Example 73 were used as starting materials and treated in the same way as in Step 2 of Example 12 to give 21 ng (33%) of the title compound as a solid.

$^1$H-NMR (500 MHz, $CDCl_3$) δ: 0.68 (3H, s), 0.95 (3H, s), 1.15-1.22 (2H, m), 1.35-1.72 (11H, m), 2.07-2.09 (1H, m), 2.42 (1H, br s), 3.12 (1H, t, J=10.6 Hz), 3.28 (1H, br s), 3.53 (1H, br s), 3.77 (2H, br s), 3.89-3.89 (1H, m), 4.02-4.04 (1H, m), 4.43 (1H, d, J=8.6 Hz), 4.64 (1H, d, J=8.6 Hz), 6.72 (1H, br s), 7.07 (1H, d, J=7.4 Hz), 7.30-7.32 (1H, m), 7.46-7.50 (3H, m), 8.05 (1H, d, J=4.6 Hz).

MS (ESI) m/z: 619 $(M+H)^+$.

Example 161

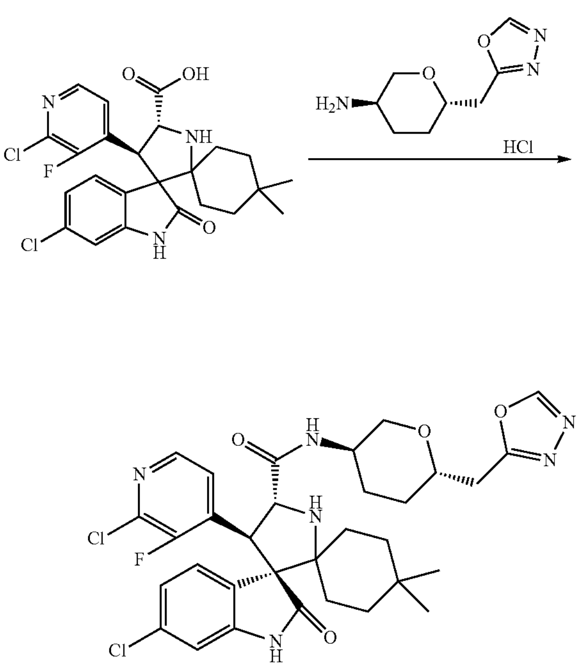

(3'R, 4'S,5'R)-6"-chloro-4'-(2-chloro-3-fluoropyridin-4-yl)-4,4-dimethyl-N-[(3R,6S)-6-(1,3,4-oxadiazol-2-ylmethyl)tetrahydro-2H-pyran-3-yl]-2"-oxo-1",2"-dihydrodispiro[cyclohexane-1,2'-pyrrolidine-3',3"-indole]-5'-carboxamide The compound (200 mg, 0.41 mmol) obtained in Step 1 of Example 17 and the compound (58 mg, 0.26 mmol) obtained in Step 3 of Reference Example 74 were used as starting materials and treated in the same way as in Step 2 of Example 12 to give 72 mg (42%) of the title compound as a solid.

$^1$H-NMR (500 MHz, DMSO-dc) δ: 0.59 (3H, s), 0.90-0.99 (4H, m), 1.10-1.12 (1H, m), 1.19-1.21 (1H, m), 1.41-1.63 (5H, m), 1.71-1.76 (2H, m), 1.83-1.88 (2H, m), 3.00-3.15 (3H, m), 3.51 (1H, d, J=9.7 Hz), 3.71-3.65 (3H, m), 4.45 (1H, t, J=9.2 Hz), 4.57 (1H, d, J=8.6 Hz), 6.71 (1H, d, J=1.7 Hz), 7.06 (1H, d, J=6.3 Hz), 7.50 (1H, d, J=7.4 Hz), 7.63 (1H, t, J=4.6 Hz), 7.80 (1H, d, J=8.0 Hz), 8.17 (1H, d, J=5.2 Hz), 9.14 (1H, s), 10.62 (1H, s).

MS (ESI) m/z: 657 $(M+H)^+$.

Example 162

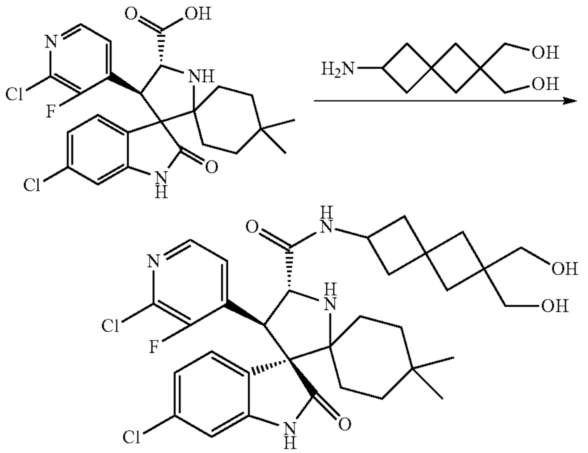

(3'R, 4'S,5'R)—N-[6,6-bis(hydroxymethyl)spiro[3.3]hepta-2-yl]-6"-chloro-4'-(2-chloro-3-fluoropyridin-4-yl)-4,4-dimethyl-2'-oxo-1",2"-dihydrodispiro[cyclohexane-1,2'-pyrrolidine-3',3"-indole]-5'-carboxamide The compound (98 mg, 0.20 mmol) obtained in Step 1 of Example 17 and the compound (38 mg, 0.20 mmol) obtained in Step 5 of Reference Example 75 were used as starting materials and treated in the same way as in Step 2 of Example 12 to give 76 mg (56%) of the title compound as a solid.

$^1$H-NMR (400 MHz, $CD_3OD$) δ: 0.68 (3H, s), 0.95 (3H, s), 1.13-1.22 (2H, m), 1.33-1.36 (1H, m), 1.55-1.57 (2H, m), 1.72-1.87 (5H, m), 1.97-2.00 (4H, m), 2.36-2.47 (2H, m), 3.46-3.54 (4H, m), 4.09-4.17 (1H, m), 4.51 (1H, d, J=9.2 MHz), 4.65 (1H, d, J=9.2 Hz), 6.76 (1H, d, J=1.8 Hz), 7.06 (1H, dd, J=8.0, 1.8 Hz), 7.45 (1H, dd, J=8.0, 2.1 Hz), 7.65 (1H, m), 8.05 (1H, d, J=5.5 Hz).

MS (ESI) m/z: 649 $(M+H)^+$.

Example 163

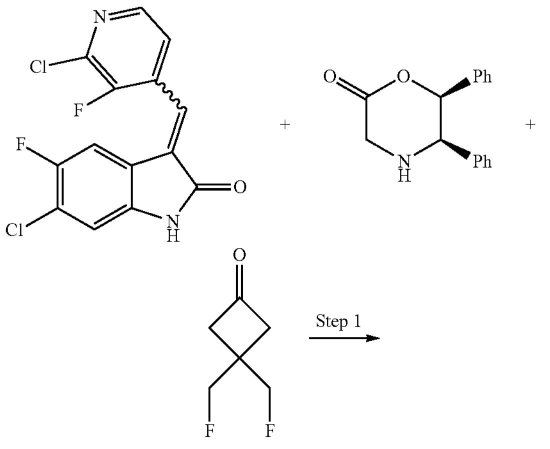

-continued

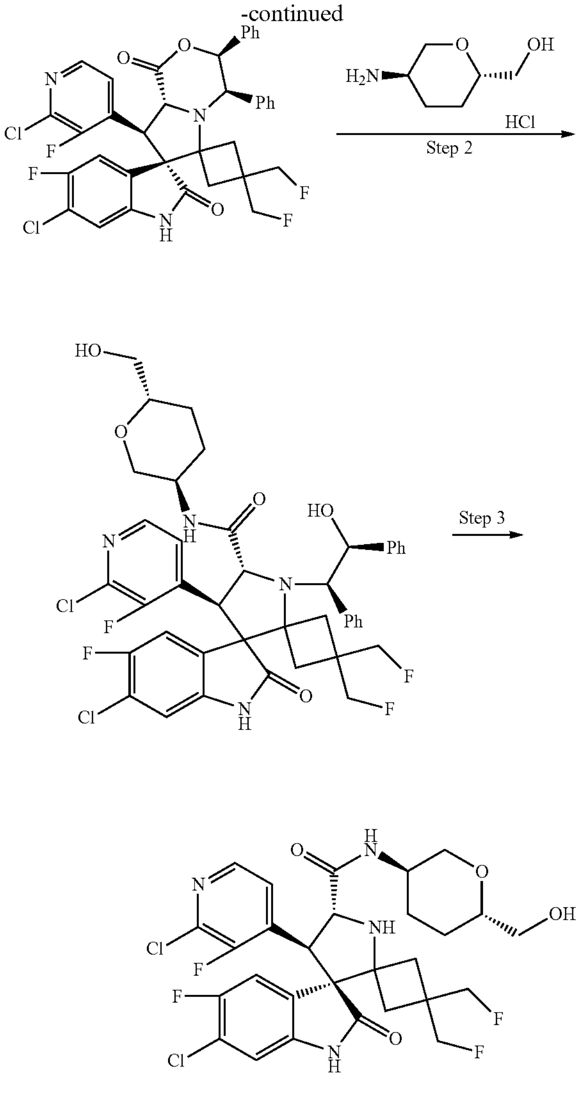

Step 1

(3'S,4'R, 7'S,8'S,8a'R)-6"-chloro-8'-(2-chloro-3-fluoropyridin-4-yl)-5"-fluoro-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2" (1'H)-dione The compound (402 mg, 3.0 mmol) obtained in Step 2 of Reference Example 21 and the compound (981 mg, 3.00 mmol) obtained in Reference Example 11 were used as starting materials and treated in the same way as in Step 1 of Example 9 to give 1.20 g (57%) of the title compound as a solid.

$^1$H-NMR (400 MHz, $CDCl_3$) δ: 1.74 (1H, d, J=14.2 Hz), 2.42 (1H, d, J=14.7 Hz), 2.84 (1H, d, J=14.7 Hz), 3.19 (1H, d, J=14.2 Hz), 4.00-4.04 (1H, m), 4.12-4.15 (1H, m), 4.31 (1H, t, J=10.1 Hz), 4.43 (1H, t, J=9.6 Hz), 4.53 (1H, d, J=9.6 Hz), 4.65 (1H, d, J=10.1 Hz), 5.26 (1H, t, J=3.2 Hz), 6.29 (1H, d, J=4.1 Hz), 6.78-6.79 (2H, m), 6.90 (1H, d, J=6.0 Hz), 7.16-7.18 (2H, m), 7.21-7.29 (8H, m), 7.73 (1H, s), 7.98 (1H, d, J=5.0 Hz).

Step 2

(4'S,5'R)-6"-chloro-4'-(2-chloro-3-fluoropyridin-4-yl)-5"-fluoro-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (348 mg, 0.50 mmol) obtained in Step 1 above and the compound (251 mg, 1.50 mmol) obtained in Step 1 of Reference Example 2 were used as starting materials and treated in the same way as in Step 1 of Example 20 to give 353 mg (85%) of the title compound as a solid.

MS (ESI) m/z: 827 $(M+H)^+$.

Step 3

(3'R, 4'S,5'R)-6"-chloro-4'-(2-chloro-3-fluoropyridin-4-yl)-5"-fluoro-3,3-bis(fluoromethyl)-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (353 mg, 0.43 mmol) obtained in Step 2 above was used as a starting material and treated in the same way as in Step 3 of Example 91 to give 140 mg (52%) of the title compound as a solid.

$^1$H-NMR (400 MHz, $CD_3OD$) δ: 1.42-1.46 (1H, m), 1.59-1.65 (1H, m), 1.71-1.79 (2H, m), 1.84-1.91 (1H, m), 1.99-2.13 (2H, m), 2.46 (1H, d, J=13.3 Hz), 3.16 (1H, t, J=10.5 Hz), 3.37-3.39 (1H, m), 3.50 (2H, d, J=5.0 Hz), 3.76-3.84 (1H, m), 3.88 (1H, s), 3.90-3.93 (1H, m), 4.00 (1H, s), 4.40 (1H, d, J=9.2 Hz), 4.51 (1H, d, J=9.2 Hz), 4.60-4.82 (2H, m), 6.90 (1H, d, J=6.0 Hz), 7.60-7.61 (2H, m), 8.08 (1H, d, J=5.0 Hz).

Example 164

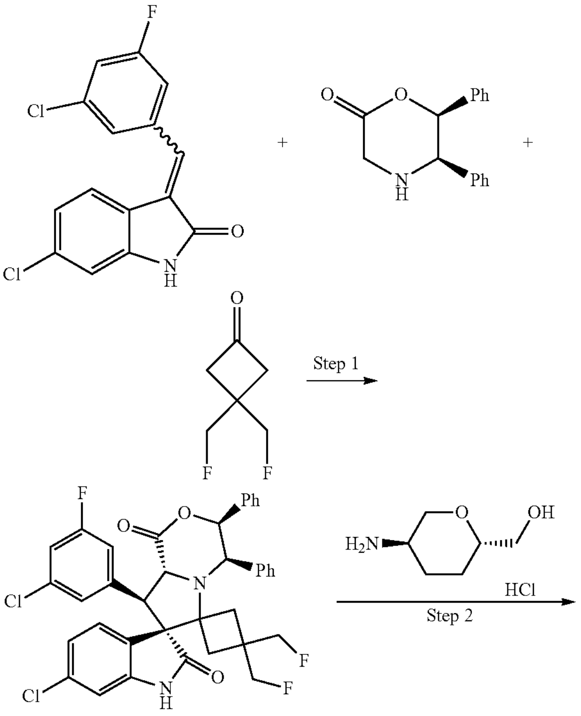

-continued

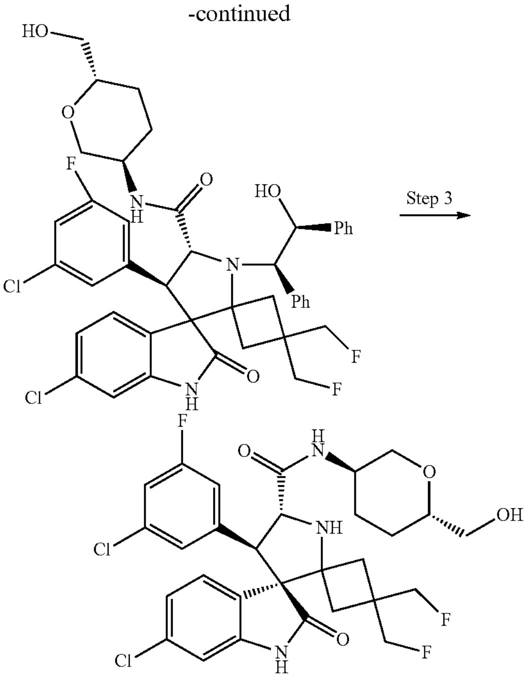

Step 1

(3'S,4"R, 7'S,8'R, 8a'R)-6"-chloro-8'-(3-chloro-5=fluorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2"(1"H)-dione The compound (402 mg, 3.00 mmol) obtained in Step 2 of Reference Example 21 and the compound (981 mg, 3.00 mmol) obtained in Reference Example 6 were used as starting materials and treated in the same way as in Step 1 of Example 9 to give 1.32 g (65%) of the title compound as a solid.

$^1$H-NMR (400 MHz, $CDCl_3$) δ: 1.68 (1H, d, J=15.1 Hz), 2.45 (1H, d, J=14.2 Hz), 2.88 (1H, d, J=14.2 Hz), 3.30 (1H, d, J=14.7 Hz), 4.02 (1H, d, J=12.4 Hz), 4.07 (1H, d, J=10.1 Hz), 4.14-4.19 (1H, m), 4.39 (1H, dd, J=13.1, 9.4 Hz), 4.50 (1H, dd, J=: 12.8, 9.6 Hz), 4.61 (1H, d, J=9.6 Hz), 5.24 (1H, t, J=3.4 Hz), 6.18 (1H, d, J=3.7 Hz), 6.54 (1H, d, J=9.6 Hz), 6.75 (1H, s), 6.81 (1H, d, J=1.8 Hz), 6.87-6.90 (2H, m), 6.97 (1H, dd, J=8, 2, 1.8 Hz), 7.21-7.30 (10H, m), 7.54 (1H, s).

Step 2

(4'R, 5'R)-6"-chloro-4'-(3-chloro-5-fluorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (338 mg, 0.50 mmol) obtained in Step 1 above and the compound (251 mg, 1.50 mmol) obtained in Step 1 of Reference Example 2 were used as starting materials and treated in the same way as in Step 1 of Example 20 to give 335 mg (83%) of the title compound as a solid.

MS (ESI) m/z: 808 (M+H)$^+$.

Step 3

(3'R, 4'R, 5'R)-6"-chloro-4'-(3-chloro-5-fluorophenyl)-3,3-bis(fluoromethyl)-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (335 mg, 0.41 mmol) obtained in Step 2 above was used as a starting material and treated in the same way as in Step 3 of Example 91 to give 97 mg (38%) of the title compound as a solid.

$^1$H-NMR (400 MHz, $CD_3OD$) δ: 1.41-1.45 (1H, m), 1.51-1.78 (3H, m), 1.88 (1H, d, J=12.8 Hz), 1.98-2.11 (2H, m), 2.46 (1H, d, J=12.8 Hz), 3.11 (1H, t, J=10.8 Hz), 3.33-3.40 (1H, m), 3.49 (2H, d, J=5.0 Hz), 3.74-3.84 (2H, m), 3.87-3.94 (3H, m), 4.47 (1H, d, J=9.6 Hz), 4.56-4.78 (2H, m), 6.84 (1H, d, J=2.3 Hz), 6.87 (1H, m), 6.93-6.97 (1H, m), 7.00-7.03 (1H, m), 7.14 (1H, dd, J=8.2, 1.8 Hz), 7.57 (1H, d, J=8.2 Hz).

Example 165

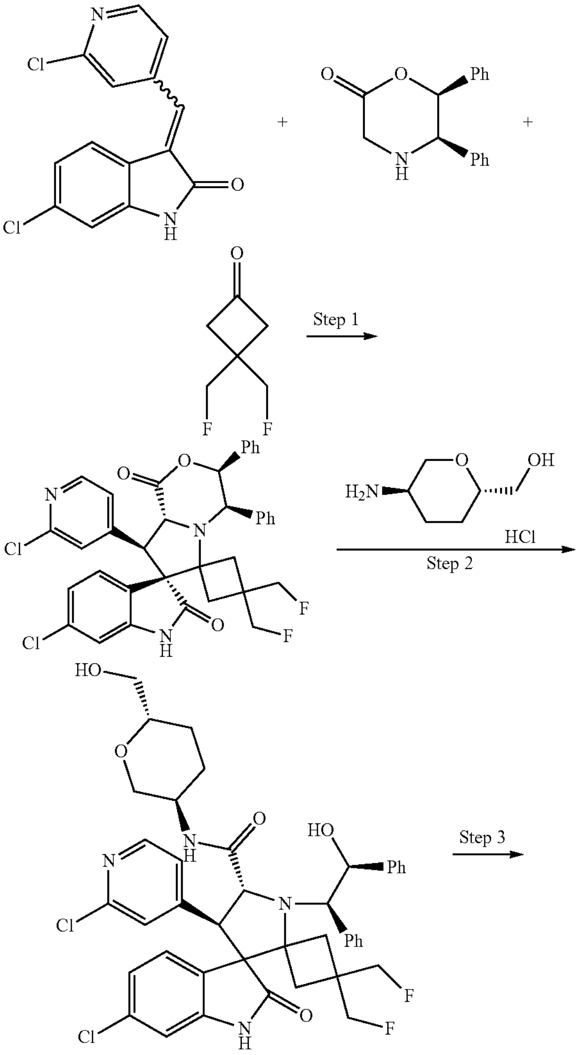

-continued

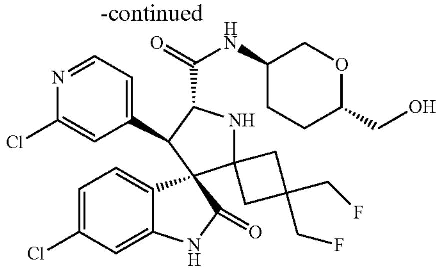

Step 1

(3'S,4'R, 7'S,8'R, 8a'R)-6"-chloro-8'-(2-chloropyridin-4-yl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2" (1"H)-dione The compound (402 mg, 3.00 mmol) obtained in Step 2 of Reference Example 21 and the compound (873 mg, 3.00 mmol) obtained in Reference Example 4 were used as starting materials and treated in the same way as in Step 1 of Example 9 to give 1.35 g (68%) of the title compound as a solid.

$^{1}$H-NMR (400 MHz, $CDCl_3$) δ: 1.65 (1H, d, J=14.9 Hz), 2.46 (1H, d, J=14.9 Hz), 2.88 (1H, d, J=14.4 Hz), 3.32 (1H, d, J=13.7 Hz), 4.01-4.10 (2H, m), 4.13-4.21 (1H, m), 4.39 (1H, dd, J=13.2, 9.5 Hz), 4.51 (1H, dd, J=12, 9, 9.5 Hz), 4.65 (1H, d, J=10.0 Hz), 5.26 (1H, t, J=3, 5 Hz), 6.19 (1H, d, J=3.9 Hz), 6.76 (1H, dd, J=5.2, 1.6 Hz), 6.80 (1H, d, J=1.7 Hz), 6.91-6.95 (3H, m), 7.20-7.27 (10H, m), 7.85 (1H, s), 8.11 (1H, d, J=5.4 Hz).

Step 2

(3'S,4'R, 5'R)-6'-chloro-4'-(2-chloropyridin-4-yl)-3,3-bis(fluoromethyl)-1'-[(1R, 2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2"-pyrrolidine-3',3"-indole]-5'-carboxamide A methanol solution (5 ml) of the compound (330 mg, 0.50 mmol) obtained in Step 1 above and the compound (251 mg, 1.50 mmol) obtained in Step 1 of Reference Example 2 were used as starting materials and treated in the same way as in Step 1 of Example 20 to give 222 mg (56%) of the title compound as a solid.

$^{1}$H-NMR (400 MHz, $CDCl_3$) δ: 1.25-1.29 (1H, m), 1.46-1.51 (2H, m), 1.51-1.64 (1H, m), 1.99 (1H, dd, J=7.3, 4.6 Hz), 2.11 (1H, d, J=12.2 Hz), 2.63 (1H, d, J=16.6 Hz), 2.70 (1H, t, J=10.6 Hz), 2.82 (1H, d, J=14.9 Hz), 3.27-3.31 (1H, m), 3.46-3.60 (3H, m), 3.81-3.84 (2H, m), 3.93-3.97 (2H, m), 4.05 (1H, d, J=2.4 Hz), 4.18 (1H, s), 4.30 (1H, s), 4.44 (1H, dd, J=12.6, 9.6 Hz), 4.56 (1H, dd, J=12.5, 9.8 Hz), 4.80 (1H, d, J=2.9 Hz), 5.32 (1H, d, J=8.1 Hz), 5.62 (1H, s), 6.61 (1H, dd, J=5.4, 1.5 Hz), 6.80-6.83 (3H, m), 6.89 (1H, dd, J=8.1, 2.0 Hz), 7.05-7.19 (6H, m), 7.29-7.32 (4H, m), 7.65 (1H, s), 8.05 (1H, d, J=5.1 Hz).

Step 3

(3'R, 4'R, 5'R)-6"-chloro-4'-(2-chloropyridin-4-yl)-3,3-bis(fluoromethyl)-N-[(3R,6S)-6-(hydroxymethyl)tetrahydro-2H-pyran-3-yl]-2'-oxo-1",2"-dihydro-dispiro[cyclobutane-1,2'-pyrrolidine-3',3"-indole]-5'-carboxamide The compound (222 mg, 0.28 mmol) obtained in Step 2 above was used as a starting material and treated in the same way as in Step 3 of Example 91 to give 80 mg (56%) of the title compound as a colorless solid [fractionation conditions: CHIRALPAK IC, n-hexane: 2-propanol=2:3 (v/v)].

$^{1}$H-NMR (400 MHz, $CD_3OD$) δ: 1.40-1.46 (1H, m), 1.54-1.80 (3H, m), 1.88 (1H, d, J=12.4 Hz), 1.98-2.11 (2H, m); 2.47 (1H, d, J=13.3 Hz), 3.15 (1H, t, J=10.5 Hz), 3.36-3.39 (1H, m), 3.50 (2H, d, J=5.0 Hz), 3.75-3.85 (2H, m), 3.88-4.00 (3H, m), 4.55 (1H, d, J=9.2 Hz), 4.60-4.80 (2H, m), 6.86 (1H, d, J=1.8 Hz), 7.09-7.18 (2H, m), 7.20-7.30 (1H, m), 7.60 (1H, d, J=8.2 Hz), 8.10 (1H, d, J=5.5 Hz).

MS (ESI) m/z: 599 $(M+H)^+$.

Example 166

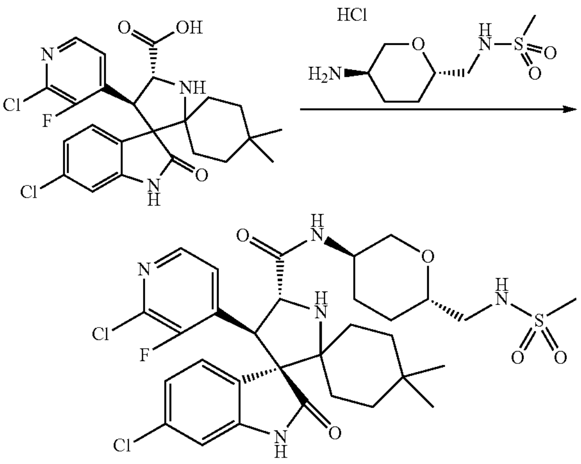

(3'R, 4'S,5'R)-6"-chloro-4'-(2-chloro-3-fluoropyridin-4-yl)-4,4-dimethyl-N-[(3R,6S)-6-{[(methylsulfonyl)amino]methyl}tetrahydro-2H-pyran-3-yl]-2"-oxo-1",2"-dihydrodispiro[cyclohexane-1,2'-pyrrolidine-3',3"-indole]-5'-carboxamide The compound (199 mg, 0.40 mmol) obtained in Step 1 of Example 17 and the compound (81 mg, 0.33 mmol) obtained in Step 2 of Reference Example 76 were used as starting materials and treated in the same way as in Step 2 of Example 12 to give 184 mg (83%) of the title compound as a solid.

$^{1}$H-NMR (500 MHz, $CDCl_3$) δ: 0.68 (3H, s), 0.95 (3H, s), 1.12-1.22 (2H, m), 1.34-1.37 (1H, m), 1.43-1.62 (5H, m), 1.68-1.78 (3H, m), 2.09-2.11 (1H, m), 2.96 (3H, s), 3.02-3.12 (2H, m), 3.26-3.32 (2H, m), 3.45-3.50 (1H, m), 3.88-3.88 (1H, m), 4.02-4.05 (1H, m), 4.42-4.45 (1H, m), 4.64 (1H, d, J=9.2 Hz), 4.74 (1H, dd, J=8.0, 4.0 Hz), 6.73 (1H, d, J=1.7 Hz), 7.07 (1H, dd, J=8.3, 2.0 Hz), 7.31 (1H, dd, J=8.3, 2.0 Hz), 7.37 (1H, s), 7.50-7.47 (2H, m), 8.05 (1H, d, J=5.2 Hz).

MS (ESI) m/z: 682 $(M+H)^+$.

Example 167

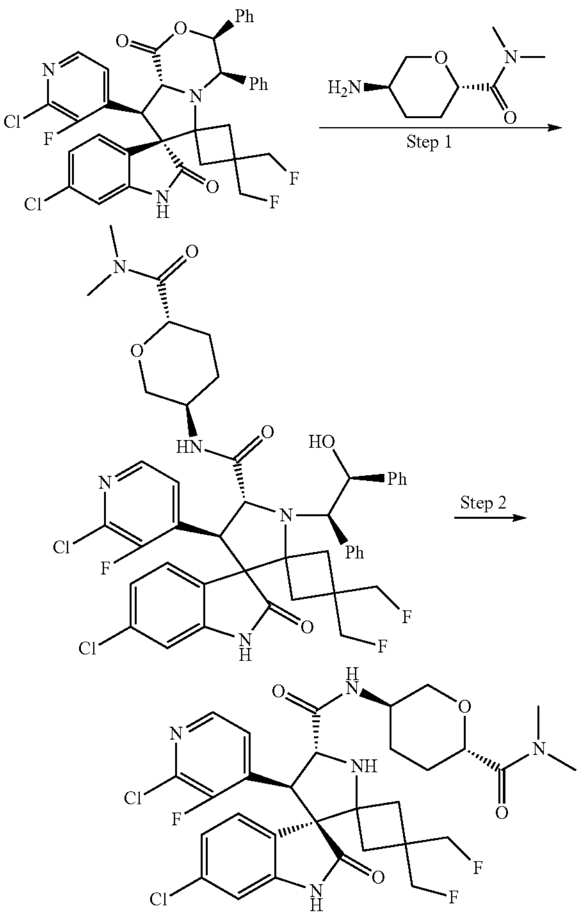

Step 1

(4'S,5'R)-6"-chloro-4'-(2-chloro-3-fluoropyridin-4-yl)-N-[(3R,6S)-6-(dimethylcarbamoyl)tetrahydro-2H-pyran-3-yl]-3,3-bis(fluoromethyl)-1'-[(1R,2S)-2-hydroxy-1,2-diphenylethyl]-2"-oxo-1",2"-dihydrodispiro[cyclobutane-1,2'-pyrrolidine-3',3"-indole]-5'-carboxamide The compound (350 mg, 0.52 mmol) obtained in Step 1 of Example 91 and the compound (267 mg, 1.55 mmol) obtained in Step 2 of Reference Example 77 were used as starting materials and treated in the same way as in Step 1 of Example 157 to give 232 mg (53%) of the title compound as a solid.

MS (ESI) m/z: 850 $(M+H)^+$.

Step 2

(3'R, 4'S,5'R)-6"-chloro-4'-(2-chloro-3-fluoropyridin-4-yl)-N-[(3R,6S)-6-(dimethylcarbamoyl)tetrahydro-2H-pyran-3-yl]-3,3-bis(fluoromethyl)-2"-oxo-1"', 2"'-dihydrodispiro[cyclobutane-1,2'-pyrrolidine-3',3"-indole]-5"-carboxamide The compound (320 mg, 0.38 mmol) obtained in Step 1 above was used as a starting material and treated in the same way as in Step 3 of Example 91 to give 138 mg (56%) of the title compound as a solid. [fractionation conditions: CHIRALPAK IC, n-hexane:ethanol=2:3 (v/v)].

$^1$H-NMR (400 MHz, $CDCl_3$) δ: 1.52-1.63 (2H, m), 1.69 (1H, dd, J=13.5, 2.5 Hz), 1.82-2.08 (4H, m), 2.21-2.31 (1H, m), 2.39 (1H, d, J=12.8 Hz), 2.96 (3H, s), 3.09 (3H, s), 3.24 (1H, dd, J=10.5, 8.7 Hz), 3.79-4.09 (4H, m), 4.16 (1H, dd, J=9.2, 3.2 Hz), 4.34-4.41 (2H, m), 4.54-4.78 (2H, m), 6.83 (1H, d, J=1.8 Hz), 7.15 (1H, dd, J=8.3, 1.8 Hz), 7.37 (1H, dd, J=8, 0, 2.1 Hz), 7.44 (16, t, J=4.8 Hz), 7.55 (1H, d, J=8.3 Hz), 7.68 (1H, br s), 8.05 (1H, d, J=5.0 Hz).

MS (ESI) m/z: 654 $(M+H)^+$.

Example 168

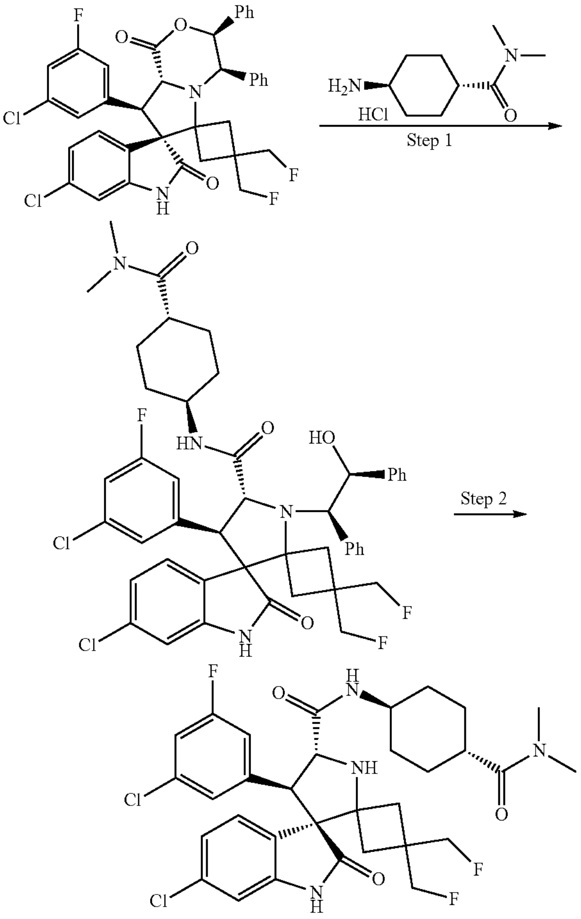

Step 1

(4+R, S'R)-6"-chloro-4'-(3-chloro-5-fluorophenyl)-N-[trans-4-(dimethylcarbamoyl)cyclohexyl]-3,3-bis(fluoromethyl)-1'-[(1,2S)-2-hydroxy-1,2-diphenylethyl]-2"-oxo-1",2"-dihydrodispiro[cyclobutane-1,2'-pyrrolidine-3',3'-indole]-5'-carboxamide The compound (339 mg, 0.50 mmol) obtained in Step 1 of Example 164 and trans-4-amino-N,N-dimethylcyclohexanecarboxamide (144 mg, 0.85 mmol) were used as starting materials and treated in the same way as in Step 1 of Example 20 to give 178 mg (42%) of the title compound as a colorless solid.

MS (ESI) m/z: 847 $(M+H)^+$.

Step 2

(3'R, 4'R, 5'R)-6"-chloro-4'-(3-chloro-5-fluorophenyl)-N-[trans-4-(dimethylcarbamoyl)cyclohexyl]-3,3-bis(fluoromethyl)-2"-oxo-1",2"-dihydrodispiro[cyclobutane-1,2'-pyrrolidine-3',3"-indole]-5'-carboxamide The compound (178 mg, 0.21 mmol) obtained in Step 1 above was used as a starting material and treated in the same way as in Step 3 of Example 91 to give 60 mg (44%) of the title compound as a solid.

$^1$H-NMR (400 MHz, $CD_3OD$) δ: 1.26-1.71 (3H, m), 1.75-2.09 (6H, m), 2.46 (1H, d, J=12.8 Hz), 2.60-2.72 (1H, m), 2.91 (3H, s), 3.11 (3H, s), 3.59-3.71 (1H, m), 3.79 (1H, s), 3.88-3.94 (2H, m), 4.45 (1H, d, J=9.6 Hz), 4.56-4.75 (2H, m), 6.84 (1H, d, J=1.8 Hz), 6.87-6.99 (2H, m), 7.02 (1H, br s), 7.14 (1H, dd, J=8.0, 1.6 Hz), 7.57 (1H, d, J=8.2 Hz),

MS (ESI) m/z: 653 $(M+H)^+$.

Example 169

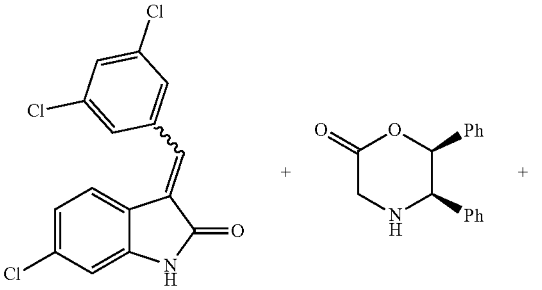

+

+

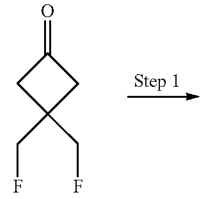

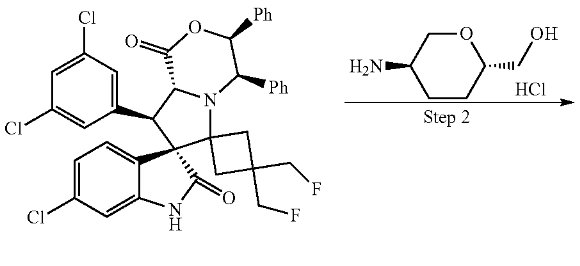

-continued

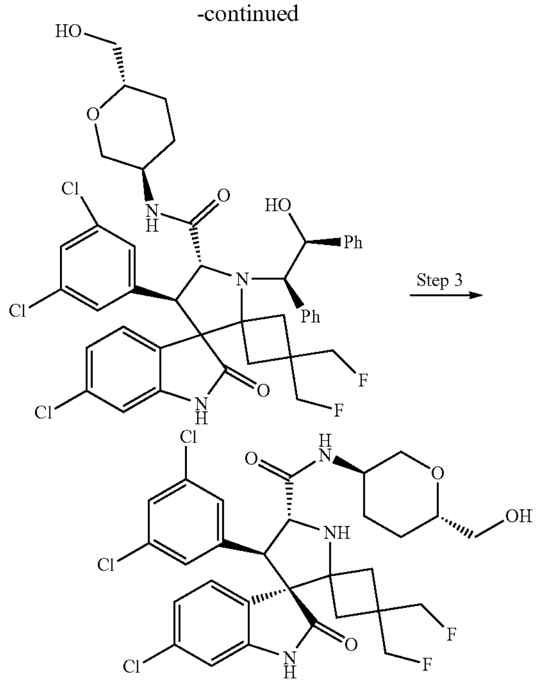

Step 1

(3'S,4'R, 7'S,8'R, 8a'R)-6"-chloro-8'-(3,5-dichlorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2" (1"H)-dione The compound (402 mg, 3.00 mmol) obtained in Step 2 of Reference Example 21 and the compound (974 mg, 3.00 mmol) obtained in Reference Example 78 were used as starting materials and treated in the same way as in Step 1 of Example 9 to give 1.27 g (61%) of the title compound as a solid.

$^1$H-NMR (400 MHz, $CDCl_3$) δ: 1.70 (1H, d, J=15.1 Hz), 2.46 (1H, d, J=14.7 Hz), 2.89 (1H, d, J=13.3 Hz), 3.30 (1H, d, J=14.7 Hz), 3.99-4.10 (2H, m), 4.11-4.22 (1H, m), 4.39 (1H, dd, J=12, 8, 9.6 Hz), 4.51 (1H, dd, J=12.8, 9.6 Hz), 4.60 (1H, d, J=10.1 Hz), 5.24 (1H, t, J=3.4 Hz), 6.17 (1H, d, J=4.1 Hz), 6.78-6.84 (3H, m), 6.91 (1H, d, J=8.2 Hz), 6.98 (1H, dd, J=8, 2, 1.8 Hz), 7.15 (1H, t, J=1.8 Hz), 7.16-7.34 (10H, m), 7.52 (1H, s).

Step 2

(4'R, 5'R)-6"-chloro-4'-(3,5-dichlorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (347 mg, 0.50 mmol) obtained in Step 1 above and the compound (197 mg, 1.50 mmol) obtained in Step 1 of Reference Example 2 were used as starting materials and treated in the same way as in Step 1 of Example 20 to give 285 mg (69%) of the title compound as a solid.

MS (ESI) m/z: 825 $(M+H)^+$.

Step 3

(3'R, 4'R, 5'R)-6"-chloro-4'-(3,5-dichlorophenyl)-3,3-bis(fluoromethyl)-N-[(3R,6S)-6-(hydroxymethyl) tetrahydro-2H-pyran-3-yl]-2"-oxo-1",2"-dihydro-dispiro[cyclobutane-1,2'-pyrrolidine-3',3"-indole]-5'-carboxamide The compound (285 mg, 0.35 mmol) obtained in Step 2 above was used as a starting material and treated in the same way as in Step 3 of Example 91 to give 99 mg (16%) of the title compound as a solid.

$^1$H-NMR (400 MHz, $CD_3OD$) δ: 1.38-1.48 (1H, m), 1.53-1.65 (1H, m); 1.68 (1H, dd, J=13.7, 2.3 Hz), 1.75-1.78 (1H, m), 1.88 (1H, d, J=13.7 Hz), 2.01-2.12 (2H, m), 2.46 (1H, d, J=13.3 Hz), 3.12 (1H, t, J=10.8 Hz), 3.34-3.40 (1H, m), 3.49 (2H, d, J=5.5 Hz), 3.76-3.84 (2H, m), 3.88-3.95. (3H, m), 4.47 (1H, d, J=9.2 Hz), 4.57-4.76 (2H, m), 6.85 (1H, d, J=1.8 Hz), 7.12-7.17 (3H, m), 7.18-7.20 (1H, m), 7.57 (1H, d, J=8.2 Hz).

Example 170

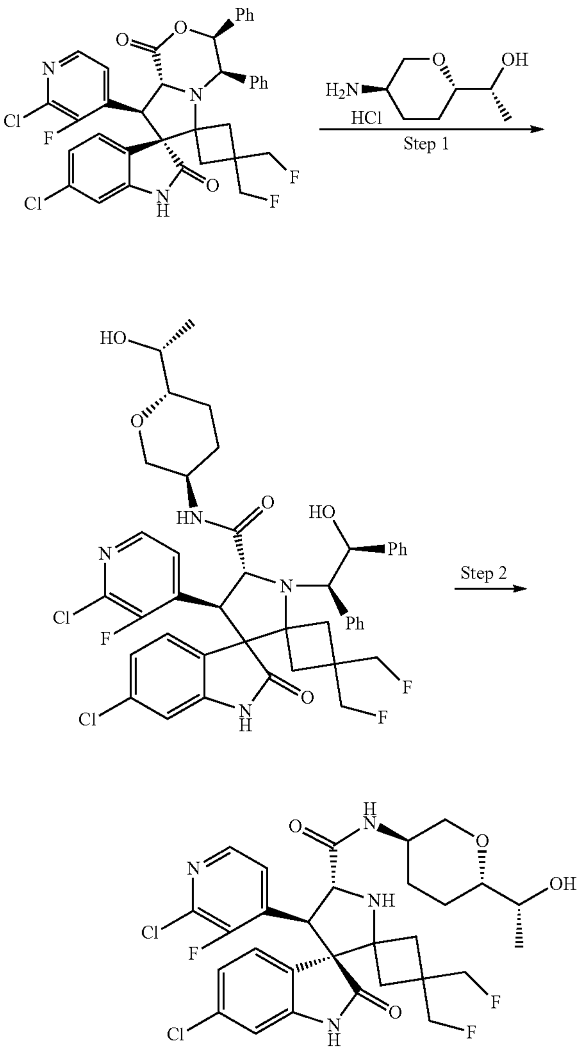

Step 1

(4'S,5'R)-6"-chloro-4'-(2-chloro-3-fluoropyridin-4-yl)-3,3-bis(fluoromethyl)-1'-[(1R,2S)-2-hydroxy-1,2-diphenylethyl]-N-{(3R,6S)-6-[(1R)-1-hydroxyethyl] tetrahydro-2H-pyran-3-yl}-2"-oxo-1",2"-dihydrodispiro[cyclobutane-1,2'-pyrrolidine-3',3"-indole]-5'-carboxamide The compound (500 mg, 0.74 mmol) obtained in Step 1 of Example 91 and the compound (321 mg, 2.21 mmol) obtained in Step 4 of Reference Example 79 were used as starting materials and treated in the same way as in Step 1 of Example 157 to give 378 mg (62%) of the title compound as a solid.

MS (ESI) m/z: 823 $(M+H)^+$.

Step 2

(3'R, 4'S,5'R)-6"-chloro-4'-(2-chloro-3-furopyridinyl-4-yl)-3,3-bis(fluoromethyl)-N-{(3R,6S)-6-[(1R)-1-hydroxyethyl]tetrahydro-2H-pyran-3-yl}-2"-oxo-1",2"-dihydrodispiro[cyclobutane-1,2'-pyrrolidine-3',3'-indole]-5'-carboxamide The compound (360 mg, 0.44 mmol) obtained in Step 1 above was used as a starting material and treated in the same way as in Step 3 of Example 91 to give 186 mg (68%) of the title compound as a solid [fractionation conditions: CHIRALPAK IC, n-hexane:ethanol=3:2 (v/v)];

$^1$H-NMR ($CDCl_3$) δ: 1.15 (3H, d, J=6.4 Hz), 1.38-1.89 (5H, m), 2.00-2.23 (3H, m), 2.38 (1H, d, J=12.4 Hz), 3.10 (1H, t, J=10.5 Hz), 3.23 (1H, d, J=11.0 Hz), 3.77-4.10 (6H, m), 4.32-4.41 (2H, m), 4.53-4.77 (2H, m), 6.81 (1H, s), 7.15 (1H, d, J=8.3 Hz), 7.33-7.39 (2H, m), 7.44 (1H, t, J=4.6 Hz), 7.65 (1H, s), 8.05 (1H, d, J=5.0 Hz).

MS (ESI) m/z: 627 $(M+H)^+$.

Example 171

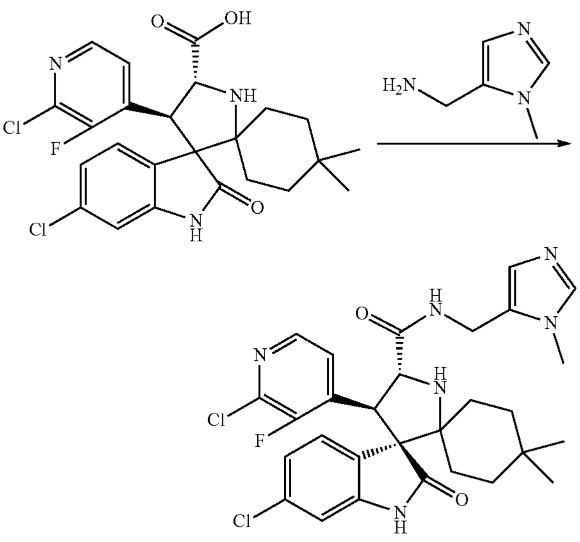

(3'R, 4'S, S'R)-6"-chloro-4'-(2-chloro-3-fluoropyridin-4-yl)-4,4-dimethyl-N-[(1-methyl-1H-imidazol-5-yl)methyl]-2"-oxo-1",2"-dihydrodispiro[cyclohexane-1,2"-pyrrolidine-3',3"-indole]-5'-carboxamide The compound (400 mg, 0.81 mmol) obtained in Step 1 of Example 17 and 1-(1-methyl-1H-imidazole-5-yl)methanamine (95 mg, 0.98 mmol) were used as starting materials and treated in the same way as in Step 2 of Example 12 to give 188 mg (41%) of the title compound as a solid.

$^1$H-NMR (400 MHz, $CDCl_3$) δ: 0.64 (3H, s), 0.88 (3H, s), 1.09-1.26 (3H, m), 1.37-1.52 (2H, m), 1.59-1.82 (3H, m), 3.21-3.28 (1H, m), 3.62 (3H, s), 4.40-4.53 (3H, m), 4.64 (1H, d, J=9.2 Hz), 6.72 (1H, s), 7.00-7.08 (2H, m), 7.29 (1H, d, J=8.7 Hz), 7.45 (1H, s), 7.52 (1H, t, J=5.0 Hz), 7.83 (1H, t, J=5.0 Hz), 8.05 (1H, d, J=5.0 Hz), 8.45 (1H, s).

MS (ESI) m/z: 585 $(M+H)^+$.

Example 172

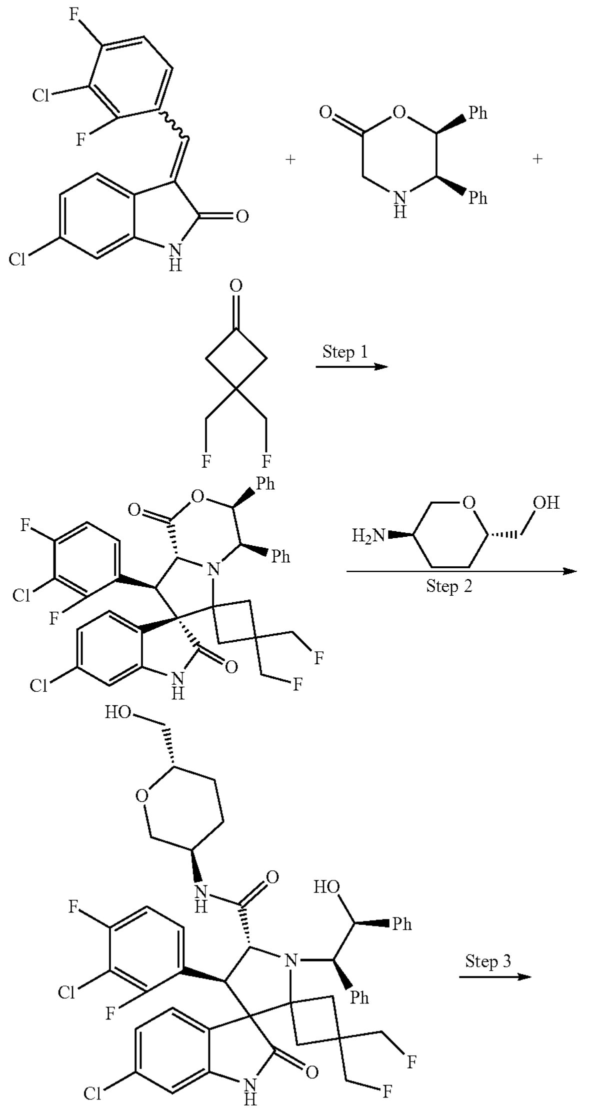

-continued

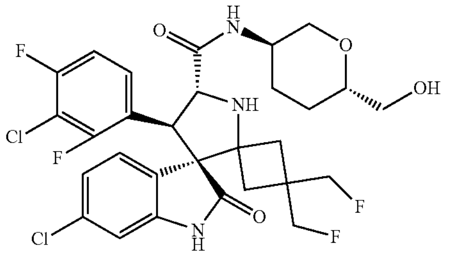

Step 1

(3'S,4'R,7'S,8'S,8a'R)-6"-chloro-8'-(3-chloro-2,4-difluorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3'-indole]-1',2"(1"H)-dione The compound (402 mg, 3.00 mmol) obtained in Step 2 of Reference Example 21 and the compound (978 mg, 3.00 mmol) obtained in Reference Example 80 were used as starting materials and treated in the same way as in Step 1 of Example 9 to give 1.20 g (58%) of the title compound as a solid.

$^1$H-NMR (400 MHz, $CDCl_3$) δ: 1.87 (1H, d, J=13.8 Hz), 2.32 (1H, d, J=14.2 Hz), 2.83. (1H; d, J=14.2 Hz), 3.01 {1}, d, J=14.7 Hz), 3.89-3.95 (1H, m), 4.01-4.07 (1H, m), 4.24 (1H, dd, J=14.2, 9.6 Hz), 4.36 (1H, dd, J=14.0, 9.4 Hz), 4.48 (1H, d, J=10.1 Hz), 4.68 (1H, d, J=10.1 Hz), 5.22 (1H, t, J=3.2 Hz), 6.32 (1H, d, J=3.7 Hz), 6.72-6.80 (2H, m), 6.84-6.89 (2H, m), 6.92 (1H, dd, J=8.3, 1.8 Hz), 7.09-7.16 (2), m), 7.20-7.25 (8H, m), 7.62 (1H, 8).

Step 2

(3'S,4'S,5'R)-6"-chloro-4'~ (3-chloro-2,4-difluorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (348 mg, 0.50 mmol) obtained in Step 1 above was used as a starting material and treated in the same way as in Step 1 of Example 20 to give 400 mg (96%) of the title compound as a solid.

$^1$H-NMR (400 MHz, $CDCl_3$) δ: 1.17-1.30 (1H, m), 1.42-1.56 (2H, m), 1.62 (2H, d, J=11.5 Hz), 2.10 (1H, d, J=11.0 Hz), 2.58 (1H, d, J=15.6 Hz), 2.70 (1H, t, J=10.5 Hz), 2.85 (1H, d, J=15.1 Hz), 3.25-3.34 (1H, m), 3.40 (1H, d, J=14.7 Hz), 3.50 (1H, dd, J=11.5, 6.9 Hz), 3.58 (1H, dd, J=11.7, 3.0 Hz), 3.82 (1H, d, J=9.6 Hz), 3.88 (1H, dd, J=10.5, 2.8 Hz), 3.91-4.03 (1H, m), 4.09 (1H, s), 4.20 (2H, d, J=9.6 Hz), 4.35 (1H, s), 4.45 (1H, t, J=10.1 Hz), 4.57 (1H, t, J=10.1 Hz), 4.83 (1H, d, J=3.2 Hz), 5.22 (1H, d, J=7.8 Hz), 5.61, (1H, s), 6.47-6.52 (1H, m), 6.63 (1H, dd, J=8.9, 6.2 Hz), 6.77-6.85 (2H, m), 6.89 (1H, dd, J=8.0, 1.6 Hz), 7.08-7.16 (4H, m), 7.20-7.31 (4H, m), 7.26 (2H, d, J=6.9 Hz), 8.07 (1H, s).

Step 3

(3'R,4'S,5'R)-6"-chloro-4'-(3-chloro-2,4-difluorophenyl)-3,3-bis(fluoromethyl)-N-[(3R,6S)-6-(hydroxymethyl)tetrahydro-2H-pyran-3-yl]-2'-oxo-1",2"-dihydrodispiro[cyclobutane-1,2'-pyrrolidine-3',3"-indole]-5'-carboxamide The compound (400 mg, 0.48 mmol) obtained in Step 2 above was used as a starting material and treated in the same way as in Step 3 of Example 91 to give 120 mg (40%) of the title compound as a solid.

$^1$H-NMR (400 MHz, $CD_3OD$) δ: 1.37-1.50 (1H, m), 1.53-1.79 (3H, m), 1.88 (1H, d, J=13.6 Hz), 2.02-2.12 (2H, m), 2.47 (1H, d, J=13.6 Hz), 3.12 (1H, t, J=10.4 Hz), 3.35-3.41 (1H, m), 3.49 (2H, d, J=5.4 Hz), 3.74-3.84 (2H, m), 3.86-3.92 (2H, m), 4.33 (1H, d, J=9.5 Hz), 4.44 (1H, d, J=9.5 Hz), 4.57-4.78 (2H, m), 6.82 (1H, br s), 6.98-7.02 (1H, m), 7.08-7.14 (1H, m), 7.47-7.53 (1H, m), 7.55-7.63 (1H, m).

MS (ESI) m/z: 632 $(M+H)^+$.

Example 173

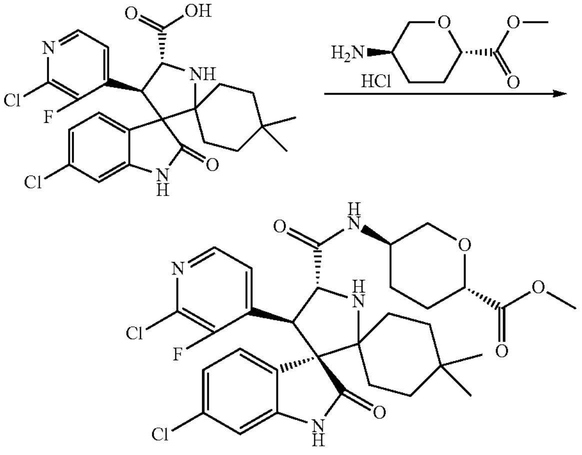

Methyl (2S,5R)-5-({[(3'S,4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3'-indole]-5'-yl] carbonyl}amino)tetrahydro-2H-pyran-2-carboxylate The compound (34.0 g, 69.1 mmol) obtained in Step 1 of Example 17 and the compound (12.6 g, 64.3 mmol) obtained in Step 1 of Reference Example 18 were used as starting materials and treated in the same way as in Step 2 of Example 12 to give 31.5 g (76%) of the title compound as a solid.

$^1$H-NMR (400 MHz, $CDCl_3$) δ: 0.68 (3H, s), 0.95 (3H, s), 1.15-1.26 (2H, m), 1.33-1.40 (1H, m), 1.42-2.03 (7H, m), 2.08-2.17 (2H, m); 3.22-3.31 (2H, m), 3.79 (3H, s), 3.91-4.07 (2H, m), 4.15 (1H, dd, J=11.3, 4.1 Hz), 4.40-4.49 (1H, m), 4.64 (1H, d, J=9.1 Hz), 6.73 (1H, d, J=1.8 Hz), 7.07 (1H, dd, J=8.2, 2.0 Hz), 7.31 (1H, dd, J=8.2, 2.0 Hz), 7.49 (2H, t, J=4.8 Hz), 7.61 (1H, d, J=8.6 Hz), 8.05 (1H, d, J=5.4 Hz).

MS (ESI) m/z: 633 $(M+H)^+$.

Example 174

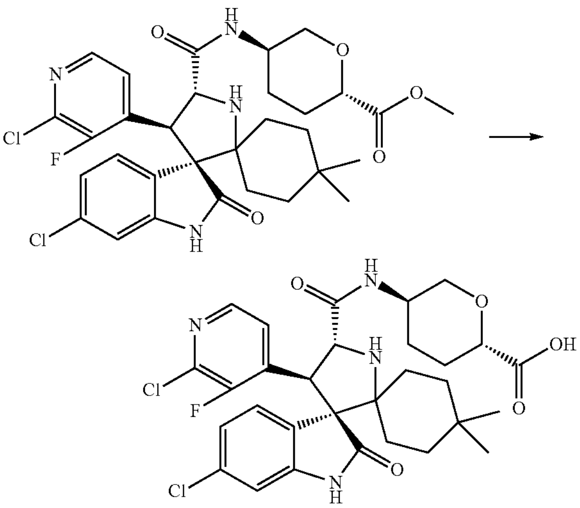

(2S,5R)-5-({[(3'B, 4'S,5'R)-6"-chloro-4'-(2-chloro-3-fluoropyridin-4-yl)-4,4-dimethyl-2"-oxo-1'", 2"-dihydrodispiro[cyclohexane-1,2-pyrrolidine-3',3"-indole]-5'-yl]carbonyl}amino)tetrahydro-2H-pyran-2-carboxylic acid 1N sodium hydroxide solution (3 ml) was added to a methanol (10 ml) solution of the compound (1.00 g, 1.58 mmol) obtained in Example 173 and the resulting mixture was stirred at room temperature for 18 hours. 1N hydrochloric acid was added to the reaction mixture to adjust its pH to approximately 6 to 7, followed by extraction with ethyl acetate. The organic layer was washed with brine and dried over anhydrous magnesium sulfate. The solvent was evaporated under reduced pressure to give 577 mg (60%) of the title compound as a solid.

$^1$H-NMR (400 MHz, DMSO-$d_6$) δ: 0.58 (3H, s), 0.89 (3H, s), 0.91-0.99 (1H, m), 1.07-1.13 (1H, m), 1.17-1.23 (1H, m), 1.37-1.76 (7H, m), 1.82-1.88 (1H, m), 1.92-1.99 (1H, m), 3.15-3.22 (1H, m), 3.56-3.91 (3H, m), 4.41-4.57 (2H, m), 6.70 (1H, d, J=2.3 Hz), 7.05 (1H, dd, J=8.2, 1.8 Hz), 7.50 (1H, d, J=7.2 Hz), 7.62 (1H, t, J=5.0 Hz), 7.84 (1N, d, J=8.6 Hz), 8.16 (1H, d, J=5.0 Hz), 10.62 (1H, br s).

MS (ESI) m/z: 619 $(M+H)^+$.

Example 175

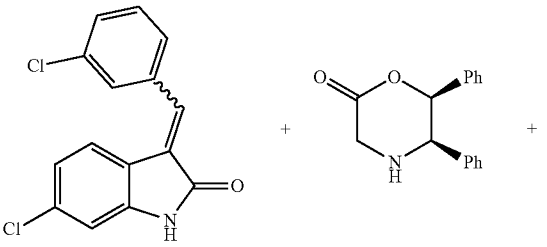

-continued

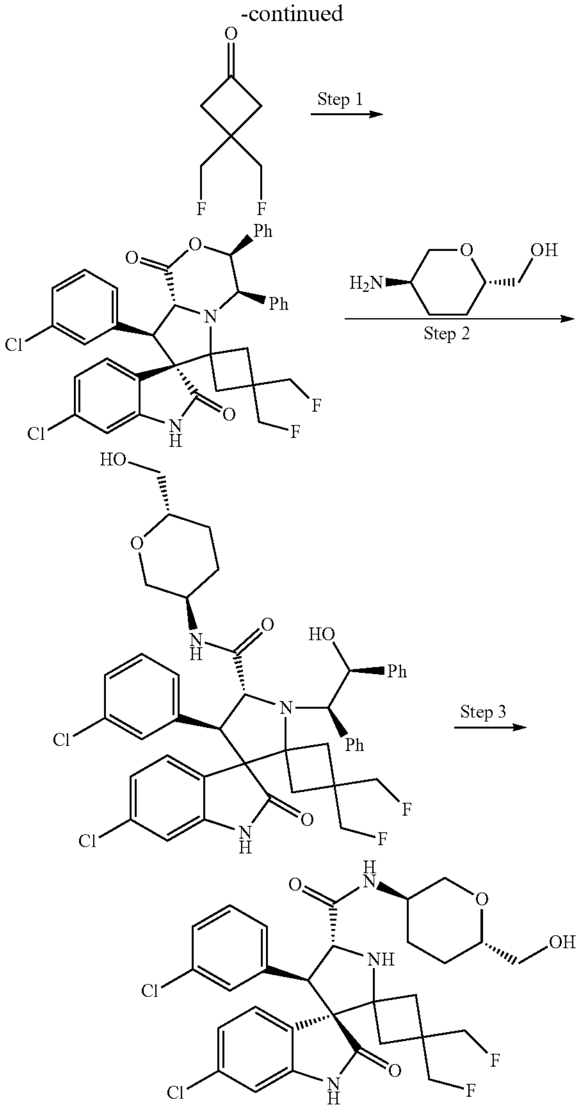

Step 1

(3'S,4'R, 7'S,8'R, 8a'R)-6"-chloro-8'-(3-chlorophenyl)-3,3-bis(fluoromethyl)-3',4'-diphenyl-3',4',8',8a'-tetrahydro-1'H-dispiro[cyclobutane-1,6'-pyrrolo[2,1-c][1,4]oxazine-7',3"-indole]-1',2" (1"H)-dione The compound (760 mg, 2.6 mmol) obtained in Reference Example 81 and the compound (402 mg, 3.00 mmol) obtained in Step 2 of Reference Example 21 were used as starting materials and treated in the same way as in Step 1 of Example 9 to give 1.20 g (70%) of the title compound as a solid.

$^1$H-NMR (400 MHz, $CDCl_3$) δ: 1.70 (1H, d, J=14.0 Hz), 2.45 (1H, d, J=14.5 Hz), 2.90 (1H, d, J=14.0 Hz), 3.29 (1H, d, J=14.0 Hz), 3.98-4.18 (3H, m), 4.38 (1H, dd, J=14.0, 9.5 Hz), 4.50 (1H, dd, J=14.0, 9.5 Hz), 4.66 (1H, d, J=10.0 Hz), 5.24 (1H, t, J=3.2 Hz), 6.18 (1H, d, J=3.6 Hz), 6.77-6.82 (2H, m), 6.89 (1H, d, J=8.2 Hz), 6.93-6.96 (2H, m), 7.03 (1H, t, J=7.9 Hz), 7.11-7.15 (1H, m), 7.18-7.34 (10H, m), 7.65 (1H, s).

Step 2

(4'R, 5'R)-6"-chloro-4'-(3-chlorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (330 mg, 0.50 mmol) obtained in Step 1 above was used as a starting material and treated in the same way as in Step 1 of Example 20 to give 343 mg (86%) of the title compound as a solid.

MS (ESI) m/z: 790 $(M+H)^+$.

Step 3

(3'R, 4'R, 5'R)-6"-chloro-4'-(3-chlorophenyl)-3,3-bis(fluoromethyl)-N-[(3R,6S)-6-(hydroxymethyl)tetrahydro-2H-pyran-3-yl]-2"-oxo-1",2"-dihydrodispiro[cyclobutane-1,2'-pyrrolidine-3',3"-indole]-5'-carboxamide The compound (343 mg, 0.43 mmol) obtained in Step 2 above was used as a starting material and treated in the same way as in Step 3 of Example 91 to give 90 mg (35%) of the title compound as a solid.

$^1$H-NMR (400 MHz, $CD_3OD$) δ: 1.36-1.50 (1H, m), 1.53-1.80 (3H, m), 2.06 (2H, d, J=12.4 Hz), 2.47 (1H, d, J=12.4 Hz), 3.09 (1H, t, J=10.5 Hz), 3.34-3.38 (1H, m), 3.49 (2H, d, J=5.5 Hz), 3.77-3.83 (2H, m), 3.85-3.95 (3H, m), 4.49 (1H, d, J=9.2 Hz), 4.57-4.78 (2H, m), 6.81 (1H, d, 3-1.8 Hz), 7.03-7.14 (4H, m), 7.19-7.21 (1H, m), 7.56 (1H, d, J=8.2 Hz).

Example 176

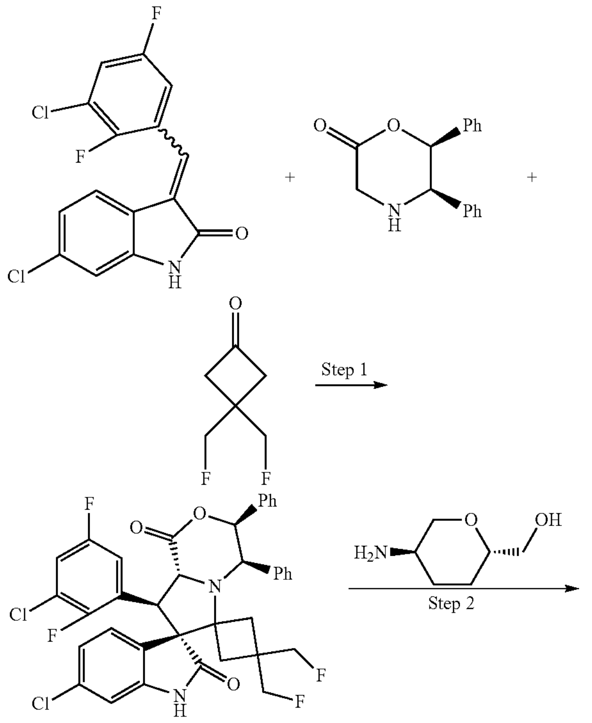

-continued

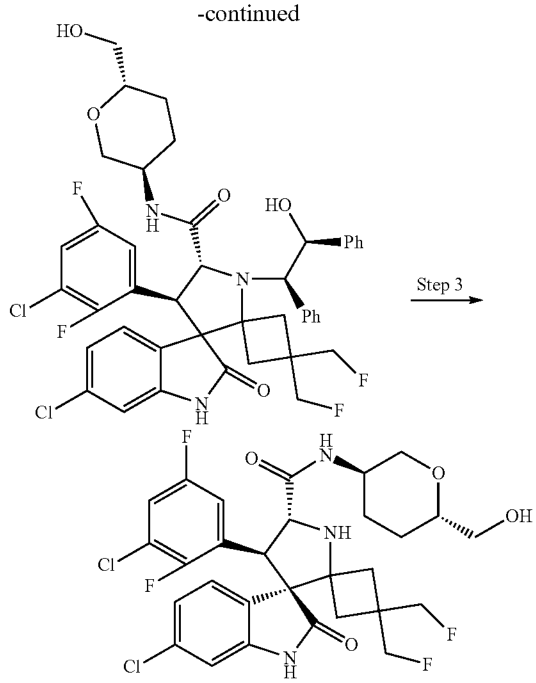

Step 1

(3'S,4'R, 7'S,8'S,8a'R)-6"-chloro-8'-(3-chloro-2,5-difluorophenyl)-3,3-bis(fluoromethyl)-3',4'-diphenyl-3',4',8',8a'-tetrahydro-1'H-dispiro[cyclobutane-1, 6'-pyrrolo[2,1-c][1,4]oxazine-7',3"-indole]-1',2" (1"H)-dione The compound (978 mg, 3.00 mmol) obtained in Reference Example 82 was used as a starting material and treated in the same way as in Step 1 of Example 9 to give 1.50 g (70%) of the title compound as a solid.

$^1$H-NMR (400 MHz, $CDCl_3$) δ: 1.93 (1H, d, J=14.5 Hz), 2.30 (1H, d, J=14.5 Hz), 2.81 (1H, d, J=14.0 Hz), 2.92 (16, d, J=14.0 Hz), 3.87 (1H, t, J=11.6 Hz), 3.99 (1H, t, J=11.8 Hz), 4.21 (1H, dd, J=14.0, 9.5 Hz), 4.33 (1H, dd, J=14.3, 9.7 Hz), 4.50 (1H, d, J=9.5 Hz), 4.61 (1H, d, J=9.1 Hz), 5.22 (1H, s), 6.34 (1H, d, J=3.6 Hz), 6.62-6.72 (2H, m), 6.88-7.02 (3H, m), 7.10-7.17 (2H, m), 7.19-7.31 (8H, m), 7.81 (1H, s).

Step 2

(4'S,5'R)-6"-chloro-4'-(3-chloro-2,5-difluorophenyl)-3,3-bis(fluoromethyl)-1'-[(1R,2S)-2-hydroxy-1,2-diphenylethyl]-N-[(3R,6S)-6-(hydroxymethyl)tetrahydro-2H-pyran-3-yl]-2"-oxo-1",2"-dihydrodispiro [cyclobutane-1,2'-pyrrolidine-3',3"-indole]-5'-carboxamide The compound (348 mg, 0.50 mmol) obtained in Step 1 above was used as a starting material and treated in the same way as in Step 1 of Example 20 to give 321 mg (78%) of the title compound as a solid.

MS (ESI) m/z: 826 $(M+H)^+$.

Step 3

(3'R, 4'S,5'R)-6"-chloro-4'-(3-chloro-2,5-difluorophenyl)-3,3-bis(fluoromethyl)-N-[(3R,6S)-6-(hydroxymethyl)tetrahydro-2H-pyran-3-yl]-2"-oxo-1", 2"-dihydrodispiro[cyclobutane-1,2'-pyrrolidine-3',3"-indole]-5'-carboxamide The compound (321 mg, 0.39 mmol) obtained in Step 2 above was used as a starting material and treated in the same way as in Step 3 of Example 91 to give 125 mg (51%) of the title compound as a solid.

$^1$H-NMR (400 MHz, $CD_3OD$) δ: 1.37-1.50 (1H, m), 1.53-1.79 (3H, m); 1.88 (1H, d, J=13.7 Hz), 2.02-2.12 (2H, m), 2.47 (1H, d, J=12.8 Hz), 3.12 (1H, d, J=10.5 Hz), 3.33-3.41 (1H, m), 3.49 (2H, d, J=5.0 Hz), 3.75-3.85 (2H, m), 3.88-3.92 (2H, m), 4.36 (1H, d, J=9.6 Hz), 4.41 (1H, d, J=9.2 Hz), 4.58-4.78 (2H, m), 6.83 (1H, d, J=1.8 Hz), 7.06-7.14 (2H, m), 7.31-7.35 (1H, m), 7.50 (1H, dd, J=8.0, 2.1 Hz).

Example 177

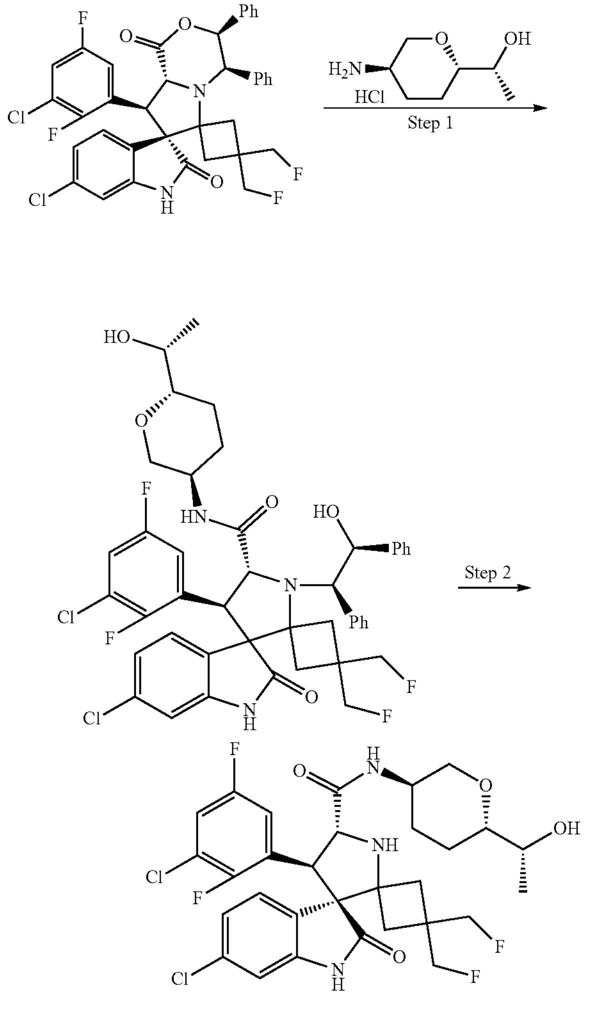

Step 1

(4'S,5'R)-6"-chloro-4'-(3-chloro-2,5-difluorophenyl)-3,3-bis(fluoromethyl)-1'-[(1R,2S)-2-hydroxy-1,2-diphenylethyl]-N-{(3R, 6S)-6-[(1R)-1-hydroxyethyl] tetrahydro-2H-pyran-3-yl}-2"-oxo-1",2"-dihydrodispiro[cyclobutane-1,2'-pyrrolidine-3",3"-indole]-5'-carboxamide The compound (348 mg, 0.50 mmol) obtained in Step 1 of Example 176 and the compound (272 mg, 1.50 mmol) obtained in Step 4 of Reference Example 79 were used as starting materials and treated in the same way as in Step 1 of Example 20 to give 303 mg (72%) of the title compound as a solid.

MS (ESI) m/z: 840 $(M+H)^+$.

Step 2

(3'R, 4'S,5'R)-6"-chloro-4'-(3-chloro-2,5-difluoro-phenyl)-3,3-bis(fluoromethyl)-N-{(3R,6S)-6-[(1R)-1-hydroxyethyl]tetrahydro-2H-pyran-3-yl}-2"-oxo-1"1,2"-dihydrodispiro[cyclobutane-1,2'-pyrrolidine-3',3"-indole]-5'-carboxamide The compound (303 mg, 0.36 mmol) obtained in Step 1 above was used as a starting material and treated in the same way as in Step 3 of Example 91 to give 135 mg (58%) of the title compound as a solid.

$^1$H-NMR (400 MHz, $CD_3OD$) δ: 1.15 (3H, d, J=6.4 Hz), 1.40-1.62 (2H, m), 1.68 (1H, d, J=13.3 Hz), 1.88 (2H, d, J=12.8 Hz), 2.02-2.13 (2H, m), 2.47 (1H, d, J=12.8 Hz), 3.08-3.13 (2H, m), 3.59-3.65 (1H, m), 3.74-3.82 (2H, m), 3.86-3.93 (2H, m), 4.36 (1H, d, J=9.6 Hz), 4.41 (1H, d, J=9.2 Hz), 4.56-4.78 (2H, m), 6.83 (1H, d, J=1.8 Hz), 7.06-7.14 (2H, m), 7.31-7.35 (1H, m), 7.50 (1H, dd, J=8.0, 2.1 Hz).

Example 178

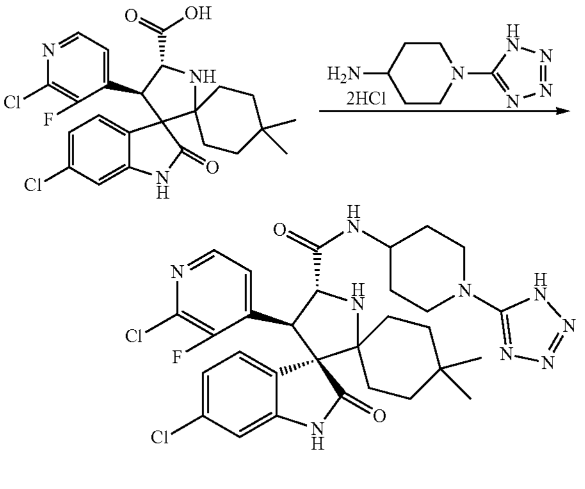

(3'R, 4'S,5'8)-6"-chloro-4'-(2-chloro-3-fluoropyridin-4-yl)-4,4-dimethyl-2"-oxo-N-[1-(1H-tetrazol-5-yl) piperidin-4-yl]-1",2"-dihydrodispiro[cyclohexane-1, 2'-pyrrolidine-3',3"-indole]-5'-carboxamide The compound (148 mg, 0.30 mmol) obtained in Step 1 of Example 17 and the compound (72 mg, 0.30 mmol) obtained in Step 3 of Reference Example 83 were used as starting materials and treated in the same way as in Step 2 of Example 12 to give 170 mg (538) of the title compound as a solid.

$^1$H-NMR (400 MHz, $CD_3OD$) δ: 0.67 (3H, s), 0.91 (3H, s), 1.09-1.23 (2H, m), 1.27-1.34 (1H, m), 1.51-1.83 (7H, m), 1.91-2.05 (2H, m), 3.16-3.27 (2H, m), 3.80-3.95 (3H, m), 4.56 (1H, d, J=9.2 Hz), 4.69 (1H, d, J=9.2 Hz), 6.77 (1H, d, J=1.8 Hz), 7.07 (1H, dd, J=7.8, 1.8 Hz), 7.46 (1H, dd, J=8.2, 1.8 Hz), 7.67 (1H, t, J=5.0 Hz), 8.06 (1H, d, J=5.0 Hz).

Example 179

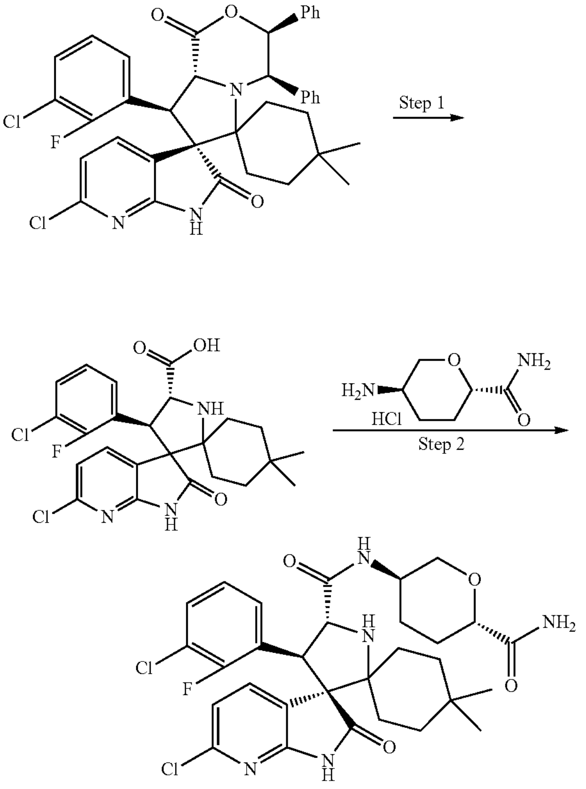

Step 1

(4'S,5'R)-6"-chloro-4'-(3-chloro-2-fluorophenyl)-4,4-dimethyl-2"-oxo-1",2"-dihydrodispiro[cyclohexane-1,2'-pyrrolidine-3',3"-pyrrolo[2,3-b]pyridine]-5'-carboxylic acid The compound (18.2 g, 27.0 mmol) obtained in Step 2 of Example 1 was used as a starting material and treated in the same way as in Step 1 of Example 17 to give 3.1 g (23%) of the title compound as a solid.

$^1$H-NMR (500 MHz, DMSO-$d_6$) δ: 0.65-0.66 (3H, m), 0.86-0.88 (3H, m), 1.03-1.63 (6.6H, m), 1.77-1.83 (0.7H, m), 1.98-2.01 (0.7H, m), 4.27 (0.3H, d, J=9.2 Hz), 4.52-4.55 (1H, m), 4.72 (0.7H, d, J=9.7 Hz), 6.88 (0.38, d, J=8.0 Hz), 7.11-7.19 (2H, m), 7.38-7.42 (1H, m); 7.51-7.55 (1H, m), 7.95 (0.7H, dd, J=8.0, 2.3 Hz), 11.32-11.31 (1H, m).

Step 2

(3'R, 4'S,5'R)—N-[(3R,6S)-6-carbamoyltetrahydro-2H-pyran-3-yl]-6"-chloro-4'-(3-chloro-2-fluorophenyl)-4,4-dimethyl-2"-oxo-1",2"-dihydrodispiro[cyclohexane-1,2'-pyrrolidine-3',3"-pyrrolo[2,3-b]pyridine]-5'-carboxamide The compound (248 mg, 0.50 mmol) obtained in Step 1 above and the compound (104 mg, 0.57 mmol) obtained in Step 2 of Reference Example 84 were used as starting materials and treated in the same way as in Step 2 of Example 12 to give 258 mg (83%) of the title compound as a solid, $^1$H-NMR (500 MHz, $CDCl_3$) δ: 0.70 (3H, s), 0.96 (3H, s), 1.16-1.27 (2H, m), 1.36-1.67 (7H, m), 1.76-1.78 (1H, m), 2.11-2.15 (1H, m), 2.26-2.30 (1H, m), 3.14 (1H, t, J=10.9 Hz), 3.22 (1H, br s), 3.80 (1H, dd, J=11.5, 2.3 Hz), 3.87-3.93 (1H, m), 4.11-4.14 (1E, m), 4.43-4.50 (1H, m), 4.68 (1H, d, J=9.7 Hz), 5.50 (1H, d, J=4.0 Hz), 6.49 (1H, d, J=4.6 Hz), 6.97 (1H, t, J=8.0 Hz), 7.05 (1H, d, J=7.4 Hz), 7.16-7.19 (1H, m), 7.46-7.49 (2H, ml, 7.62, (1H, dd, J=8.0, 2.3 Hz), 8.13 (1H, s).

MS (ESI) m/z: 618 $(M+H)^+$.

Example 180

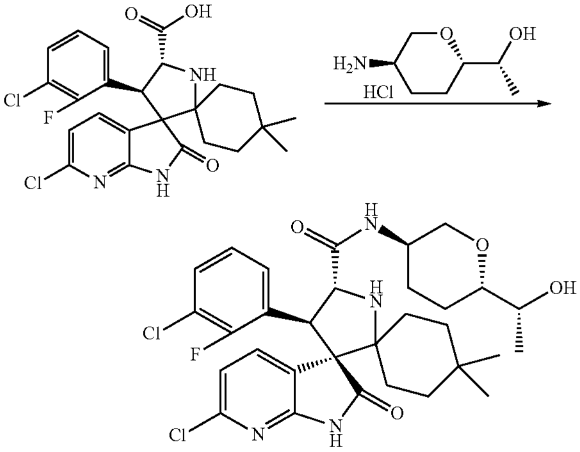

(3'R, 4'S,5'R)-6"-chloro-4'-(3-chloro-2-fluorophenyl)-N-{(3R,6S)-6-[(1R)-1-hydroxyethyl]tetrahydro-2H-pyran-3-yl}-4,4-dimethyl-2"-oxo-1",2"-dihydrodispiro[cyclohexane-1,2'-pyrrolidine-3',3"-pyrrolo[2,3-b]pyridine]-5'-carboxamide The compound (250 mg, 0.51 mmol) obtained in Step 1 of Example 179 and the compound (104 mg, 0.57 mmol) obtained in Step 4 of Reference Example 79 were used as starting materials and treated in the same way as in Step 2 of Example 12 to give 282 mg (90%) of the title compound as a solid.

$^1$H-NMR (500 MHz, $CDCl_3$) δ: 0.70 (3H, s), 0.96 (3H, s), 1.14-1.24 (5H, m), 1.35-1.64 (7H, m), 1.72-1.79 (2H, m), 2.07-2.13 (2H, m), 3.12 (1H, t, J=10.6 Hz), 3.21-3.24 (2H, m), 3.82-3.90 (2H, m), 4.06-4.09 (1H, m), 4.46 (1H, d, J=9.2 Hz), 4.69 (1H, d, J=9.2 Hz), 6.96 (1H, t, J=7.7 Hz), 7.05 (1H, d, J=8.0 Hz), 7.16 (1H, c, J=6.9 Hz), 7.43-7.48 (2H, m), 7.63 (1H, dd, J=7.4, 2.3 Hz), 8.03 (1H, s).

MS (ESI) m/z: 619 $(M+H)^+$.

Example 181

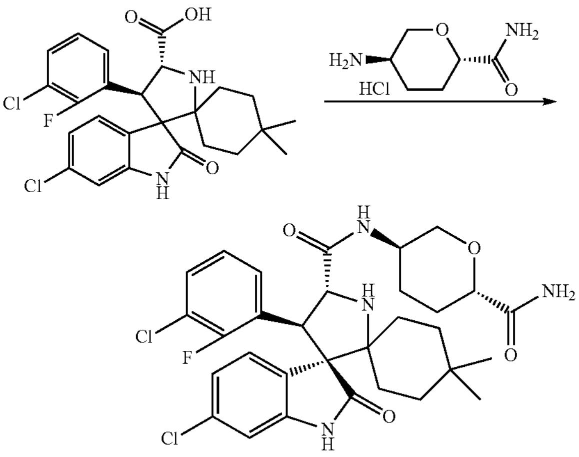

(3'R, 4'S,5'R)-N-[(3R, 6S)-6-carbamoyltetrahydro-2H-pyran-3-yl]-6"-chloro-4'-(3-chloro-2-fluorophenyl)-4,4-dimethyl-2"-oxo-1",2"-dihydrodispiro[cyclohexane-1,2'-pyrrolidine-3',3'-indole]-5'-carboxamide The compound (250 mg, 0.51 mmol) obtained in Step 1 of Example 12 and the compound (100 mg, 0.56 mmol) obtained in Step 2 of Reference Example 84 were used as starting materials and treated in the same way as in Step 2 of Example 12 to give 222 mg (71%) of the title compound as a solid.

$^1$H-NMR (500 MHz, DMSO-$d_6$) δ: 0.60 (3H, s), 0.90 (3H, s), 0.95 (1H, td, J=13.7, 4.0 Hz), 1.10-1.12 (1H, m), 1.20-1.24 (1H, m), 1.40-1.65 (5H, m); 1.70-1.76 (2H, m), 1.87-1.91 (1H, m), 1.97-2.01 (1H, m), 3.16 (1H, t, J=10.6 Hz), 3.48 (1H, d, J=10.9 Hz), 3.64-3.71 (2H, m), 3.76-3.79 (1H, m), 4.38 (1H, t, J=9.7 Hz), 4.58 (1H, d, J=9.2 Hz), 6.68 (1H, d, J=1.7 Hz), 7.04 (1H, dd, J=8.0, 2.3 Hz), 7.15-7.09 (3H, m), 7.31-7.34 (1H, m), 7.45 (1H, dd, J=8.3, 2.0 Hz), 7.57 (1H, t, J=6.6 Hz), 7.83 (1H, d, J=8.0 Hz), 10.53 (1H, s).

MS (ESI) m/z: 617 $(M+H)^+$.

Example 182

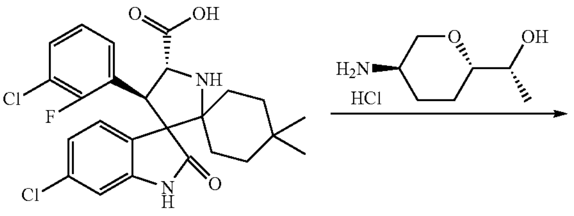

-continued

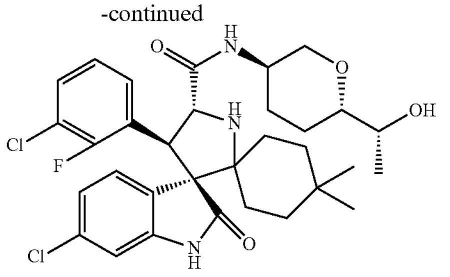

(3'R, 4'S,5'R)-6"-chloro-4'-(3-chloro-2-fluorophenyl)-N-{(3S,6S)-6-[(1R)-1-hydroxyethyl]tetrahydro-2H-pyran-3-yl}-4,4-dimethyl-2'-oxo-1",2"-dihydrodispiro[cyclohexane-1,2'-pyrrolidine-3',3"-indole]-5-carboxamide The compound (247 mg, 0.50 mmol) obtained in Step 1 of Example 12 and the compound (104 mg, 0.57 mmol) obtained in Step 4 of Reference Example 79 were used as starting materials and treated in the same way as in Step 2 of Example 12 to give 261 mg (84%) of the title compound as a solid.

$^1$H-NMR (500 MHz, $CDCl_3$) δ: 0.68 (3H, s), 0.94 (3H, s), 1.11-1.21 (5H, m), 1.34-1.39 (1H, m), 1.43 (1H, td, J=12.2, 3.6 Hz), 1.48-1.53 (1H, m), 1.56-1.64 (3H, m), 1.71-1.76 (3H, m), 2.08 (1H, d, J=4.6 Hz), 2.13 (1H, d, J=12.0 Hz), 3.12 (1H, L, J=10.6 Hz), 3.21-3.25 (2H, m), 3.82-3.92 (2H, m), 4.06-4.09 (1H, m), 4.44 (1H, d, J=8.0 Hz), 4.67 (1H, d, J=9.2 Hz), 6.68 (1H, d, J=2.3 Hz), 6.91 (1H, t, J=8.0 Hz), 7.05 (1H, dd, J=8.0, 1.7 Hz), 7.11-7.14 (1H, m), 7.33 (1H, dd, J=8.0, 2.3 Hz), 7.40 (1H, s), 7.47-7.52 (2H, m).

MS (ESI) m/z: 618 $(M+H)^+$.

Example 183

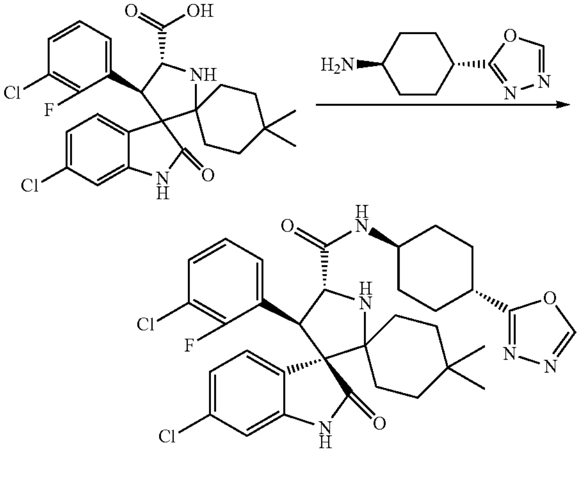

(3'R, 4'S,5'R)-6'-chloro-4'-(3-chloro-2-fluorophenyl)-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-indole]-5'-carboxamide The compound (250 mg, 0.51 mmol) obtained in Step 1 of Example 12 and the compound (100 mg, 0.60 mmol) obtained in Step 3 of Reference Example 3 were used as starting materials and treated in the same way as in Step 2 of Example 12 to give 251 mg (778) of the title compound as a solid.

$^1$H-NMR (500 MHz, $CDCl_3$) δ: 0.69 (3H, s), 0.96 (3H, s), 1.12-1.26 (2H, m), 1.32-1.43 (3H, m), 1.48-1.80 (7H, m), 2.15-2.25 (4H, m), 2.93-2.98 (1H, m), 3.24 (1H, br s), 3.76-3.82 (1H, m), 4.46 (1H, d, J=9.2 Hz), 4.68 (1H, d, J=9.2 Hz), 6.69 (1H, s), 6.89 (1H, t, J=8.0 Hz), 7.05 (1H, d, J=6.9 Hz), 7.12 (1H, t, J=7.2 Hz), 7.33 (1H, d, J=6.9 Hz), 7.55-7.50 (2H, m), 7.64 (1H, d, J=8.6 Hz), 8.34 (1H, s).

MS (ESI) m/z: 640 $(M+H)^+$.

Example 184

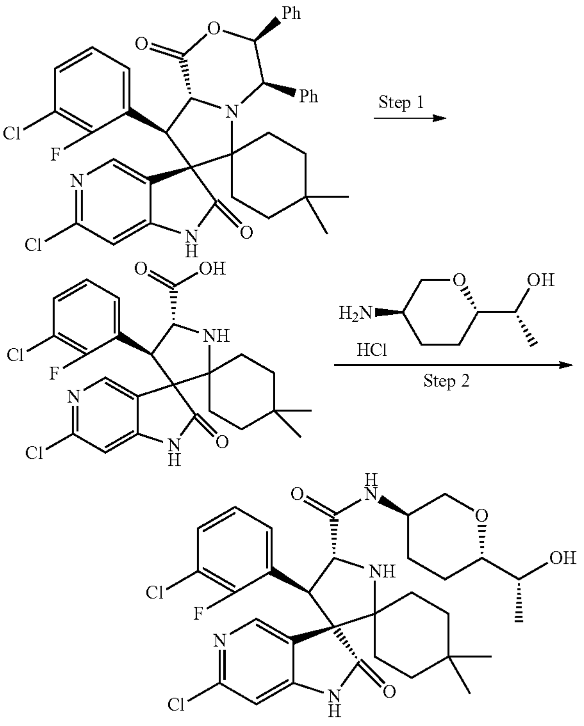

Step 1

(4'S,5'R)-6"-chloro-4'-(3-chloro-2-fluorophenyl)-4,4-dimethyl-2"-oxo-1",2"-dihydrodispiro[cyclohexane-1,2'-pyrrolidine-3',3"-pyrrolo[3,2-c]pyridine]-5'-carboxylic acid 1N sodium hydroxide solution (1.8 ml) was added to a methanol (10 ml) solution of the compound (1.00 g, 1.49 mmol) obtained in Step 1 of Example 108 and the resulting mixture was stirred at 70° C. for 5 hours. 65% Aqueous methanol (15 ml) solution of cerium (IV) diammonium nitrate (3.2 g, 5.96 mmol) was added dropwise to the reaction mixture under ice cooling and the resulting mixture was stirred at the same temperature for 30 minutes. Subsequently, the reaction mixture was rendered weakly acidic (pH 4 to 5) by addition of 1N sodium hydroxide solution and then concentrated under reduced pressure. After extraction with ethyl acetate, the organic layer was washed with brine. The organic layer was dried over anhydrous magnesium sulfate and filtered and then the solvent in the filtrate was evaporated under reduced pressure. The residue obtained was solidified by addition of diethyl ether to give 480 mg (65%) of the title compound as a solid.

MS (ESI) m/z: 492 $(M+H)^+$.

Step 2

(3'R, 4'S,5'R)-6"-chloro-4'-(3-chloro-2-fluorophenyl) =N-{(3R,6S)-6-[(1R)-1-hydroxyethyl]tetrahydro-2H-pyran-3-yl}-4,4-dimethyl-2"-oxo-1",2"-dihydro-dispiro[cyclohexane-1,2'-pyrrolidine-3',3'-pyrrolo[3,2-c]pyridine]-5'-carboxamide The compound (300 mg, 0.61 mmol) obtained in Step 1 above and the compound (111 mg, 0.61 mmol) obtained in Step 4 of Reference Example 79 were used as starting materials and treated in the same way as in Step 2 of Example 12 to give 67 mg (18%) of the title compound as a solid.

$^1$H-NMR (400 MHz, $CD_3OD$) δ: 0.72 (3H, s), 0.96 (3E, s), 1.15 (3H, d, J=6.3 Hz), 1.17-1.25 (2H, m), 1.28-1.63 (6H, m), 1.73-1.95 (3H, m), 2.06-2.11 (1H, m), 3.13 (2H, t, J=10.6 Hz), 3.59-3.65 (1H, m), 3.72-3.80 (1H, m), 3.88-3.95 (1H, m), 4.55 (1H, d, J=9.1 Hz), 4.75 (1H, d, J=9.1 Hz), 6.79 (1H, s), 7.05 (1H, t, J=8.2 Hz), 7.24 (1H, t, J=6.8 Hz), 7.56 (1H, t, J=6.8 Hz), 8.31 (1H, d, J=2.7 Hz).

MS (ESI) m/z: 619 $(M+H)^+$.

Example 185

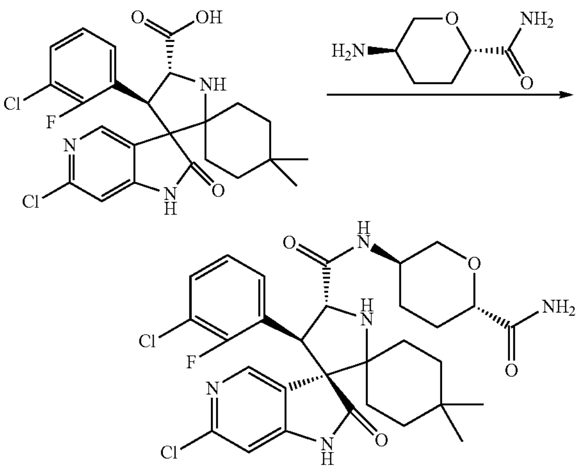

(3'R, 4'S,5'R)—N-[(3R,6S)-6-carbamoyltetrahydro-2H-pyran-3-yl]-6"-chloro-4'-(3-chloro-2-fluorophenyl)-4,4-dimethyl-2"-oxo-1",2"-dihydrodispiro[cyclohexane-1,2-pyrrolidine-3',3"-pyrrolo[3,2-c] pyridine]-5'-carboxamide The compound (300 mg, 0.61 mmol) obtained in Step 1 of Example 185 and the compound (110 mg, 0.61 mmol) obtained in Step 3 of Reference Example 28 were used as starting materials and treated in the same way as in Step 2 of Example 12 to give 155 mg (41%) of the title compound as a solid.

$^1$H-NMR (400 MHz, $CD_3OD$) δ: 0.72 (3H, s), 0.96 (3H, s), 1.11-1.24 (2H, m), 1.36-1.41 (1H, m), 1.51-1.95 (7H, m), 2.09-2.19 (2H, m), 3.23 (1H, t, J=10.6 Hz), 3.77-3.86 (2H, m), 4.00 (1H, dq, 0=10.5, 2.1 Hz), 4.56 (1H, d, J=9.1 Hz), 4.76 (1H, d, J=9.1 Hz), 6.79 (1H, s), 7.05 (1H, t, J=8.2 Hz), 7.22-7.27 (1H, m), 7.57 (1H, t, J=6.3 Hz), 8.31 (1H, d, J=2.3 Hz).

MS (ESI) m/z: 618 $(M+H)^+$.

Example 186

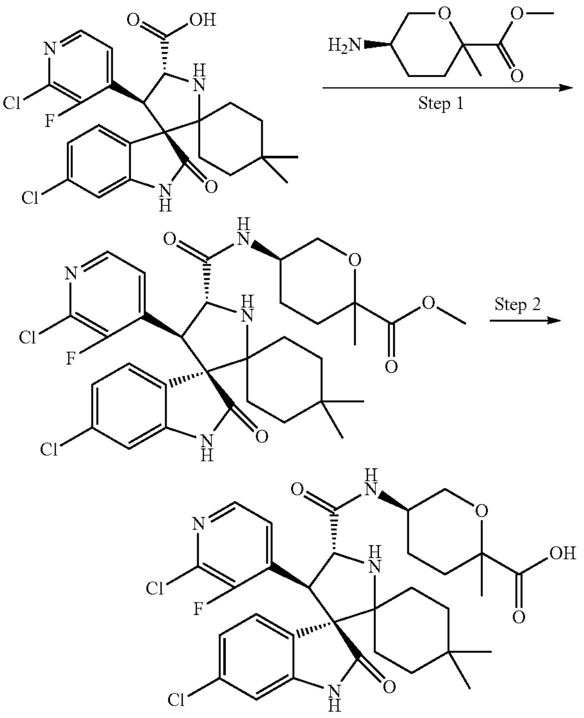

Step 1

Methyl (5R)-5-({[(3'R, 4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-yl]carbonyl}amino)-2-methyltetrahydro-2H-pyran-2-carboxylate The compound (492 mg, 1.0 mmol) obtained in Step 1 of Example 17 and the compound (119 mg, 0.70 mmol) obtained in Step 3 of Reference Example 85 were used as starting materials and treated in the same way as in Step 2 of Example 12 to give 321 mg (71%) of the title compound as a solid.

$^1$H-NMR (400 MHz, $CDCl_3$) δ: 0.69 (3H, s), 0.96 (3H, s), 1.14-1.26 (2H, m), 1.36-1.41 (1H, m), 1.46 (3R, s), 1.49-1.56 (2H, m), 1.63-1.90 (6H, m), 2.19-2.26 (1H, m), 3.19-3.23 (1H, m), 3.72-3.77 (1H, m), 3.80 (3H, s), 3.84 (1H, dd, J=12.7, 2.3 Hz), 3.86-3.91 (1H, m), 4.52-4.57 (1H, m), 4.64 (1H, d, J=9.5 Hz), 6.73 (1H, d, J=1.8 Hz), 7.07 (1H, dd, J=8.2, 1.8 Hz), 7.34 (1H, dd, J=8.4, 2.5 Hz), 7.43 (1H, s), 7.51 (1H, t, J=5.0 Hz), 8.05 (1H, d, J=5.4 Hz), 8.14 (1H, d, J=8.2 Hz).

MS (ESI) m/z: 647 $(M+H)^+$.

Step 2

(5R)-5-({[(3'R, 4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-yl]carbonyl}amino)-2-methyltetrahydro-2H-pyran-2-carboxylic acid The compound (280 mg, 0.43 mmol) obtained in Step 1 above was used as a starting material and treated in the same way as in Example 174 to give 222 mg (818) of the title compound as a solid.

$^1$H-NMR (400 MHz, DMSO-$d_6$) δ: 0.60 (3H, s), 0.89 (3H, s), 0.95-1.01 (1H, m), 1.10-1.18 (1H, m), 1.28-1.86 (12H, m), 1.98-2.04 (1H, m), 3.37-3.39 (1H, m), 3.47-3.59 (1H, m), 3.62-3.80 (2H, m), 4.48-4.54 (1H, m), 6.70 (1H, s), 7.05 (1H, d, J=8.2 Hz), 7.54 (1H, d, J=7.7 Hz), 7.58-7.65 (1H, m), 8.10 (1H, d, J=7.2 Hz), 8.18 (1H, d, J=4.1 Hz), 10.63 (1H, br s).

MS (ESI) m/z: 633 $(M+H)^+$.

Example 187

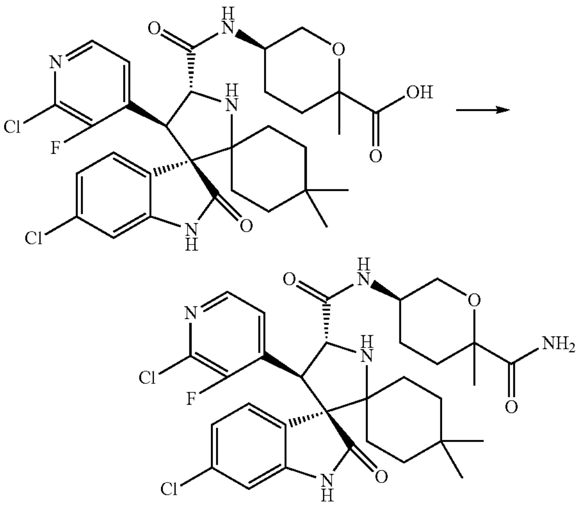

(3'R, 4'S,5'R)—N-[(3R)-6-carbamoyl-6-methyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide The compound (150 mg, 0.24 mmol) obtained in Example 187 was used as a starting material and treated in the same way as in Step 1 of Reference Example 16 to give 116 mg (76%) of the title compound as a solid.

$^1$H-NMR (400 MHz, $CDCl_3$) δ: 0.59 (3H, s), 0.36 (3H, s), 1.16-1.27 (2H, m), 1.38-1.43 (1H, m), 1.47 (3H, s), 1.49-1.56 (2H, m), 1.68-1.80 (5H, m), 1.83-1.91 (1H, m), 2.15-2.21 (1H, m), 3.28 (1H, br s), 3.62. (1H, dd, J=12.0, 4.8 Hz), 3.82-3.93 (2H, m), 4.51 (1H, d, J=9.5 Hz), 4.64 (1H, d, J=9.5 Hz), 5.52 (1H, d, J=3.6 Hz), 6.49 (1H, d, J=3.6 Hz), 6.73 (1H, d, J=1.8 Hz), 7.07 (1H, dd, J=8.2, 1.8 Hz), 7.34 (1H, dd, J=8.4, 2.0 Hz), 7.51 (1H, t, J=5.0 Hz), 7.70 (1H, s), 7.93 (1H, d, J=7.7 Hz), 8.05 (1H, d, J=5.0 Hz).

MS (ESI) m/z: 632 $(M+H)^+$.

Example 188

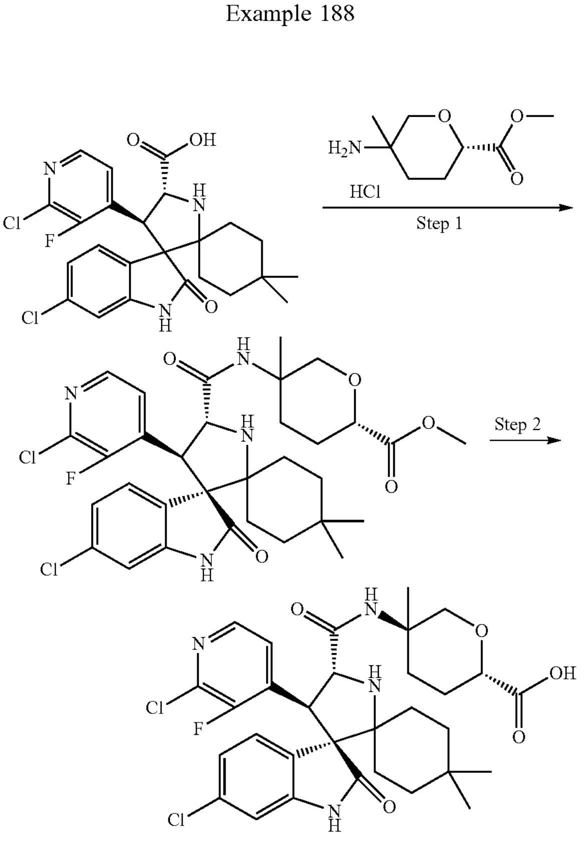

Step 1

Methyl (2S)-5-({[(3"R, 4'S,5'R)-6'-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-yl]carbonyl}amino)-5-methyltetrahydro-2H-pyran-2-carboxylate 1-Chloro-N, N, 2-trimethylprop-1-en-1-amine (0.13 ml, 1.00 mmol) was added to a tetrahydrofuran (8 ml) solution of the compound (492 mg, 1.00 mmol) obtained in Step 1 of Example 17, the resulting mixture was stirred for 1 minute, then a tetrahydrofuran (6 ml) solution of the compound (210 mg, 1.00 mmol) obtained in Step 2 of Reference Example 85 combined with triethylamine (0.42 ml, 3.00 mmol) was added dropwise. The resulting mixture was stirred at room temperature for 16 hours. Subsequently, 1-ethyl-3-(3-dimethylaminopropyl) carbodiimide hydrochloride (191 mg, 1.00 mmol) was added to the reaction mixture and the resulting mixture was stirred at room temperature for 5 hours. The reaction mixture was diluted with ethyl acetate, then washed with saturated sodium bicarbonate solution, and brine in that order, and dried over anhydrous magnesium sulfate. The solvent was evaporated under reduced pressure and the residue obtained was purified by silica gel chromatography [chloroform:methanol=50:1 (v/v)] to give 62 mg (10%) of the title compound as a solid.

$^1$H-NMR (400 MHz, $CDCl_3$) δ: 0.67 (3H, s), 0.93-0.98 (1H, m), 0.93 (3H, s), 1.10-1.53 (12H, m), 1.94-1.99 (1H, m), 2.31-2.37 (1H, m), 2.92 (1H, br s), 3.28-3.33 (1H, m), 3.75-3.80 (1H, m), 3.81 (3H, s), 3.91-3.96 (1H, m), 4.42

(1H, d, J=9.1 Hz), 4.64 (1H, d, J=9.1 Hz), 6.74 (1H, d, J=2.3 Hz), 7.07 (1H, dd, J=8.2, 1.8 Hz), 7.31 (1H, dd, J=7, 7, 2.7 Hz), 7.41 (1H, s), 7.47-7.53 (2H, m), 8.05 (1H, d, J=5.4 Hz).

MS (ESI) m/z: 647 $(M+H)^+$.

Step 2

(2S)-5-({[(3'R, 4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-yl]carbonyl}amino)-5-methyltetrahydro-2H-pyran-2-carboxylic acid The compound (130 mg, 0.20 mmol) obtained in Step 1 above was used as a starting material and treated in the same way as in Example 174 to give 35 mg (28%) of the title compound as a solid.

$^1$H-NMR (400 MHz, DMSO-dc) δ: 0.57 (3H, s), 0.86 (3H, s), 0.92-1.23 (4H, m), 1.26 (3H, s), 1.29-1.79 (7H, m), 2.16-2.22 (1H, m), 3.24-3.30 (1H, m), 3.52-3.58 (1H, m), 3.60-3.70 (1H, m), 4.42 (1H, d, J=8.6 Hz), 4.56 (1H, d, J=9.1 Hz), 6.70 (1H, d, J=1.8 Hz), 7.04 (1H, dd, J=8.2, 2.3 Hz), 7.48 (1H, dd, J=8.2, 1.8 Hz), 7.61 (1H, t, J=5.2 Hz), 7.86 (1H, d, J=8.6 Hz), 8.16 (1H, d, J=5.0 Hz), 10.61 (1H, s).

MS (ESI) m/z: 633 $(M+H)^+$.

Example 189

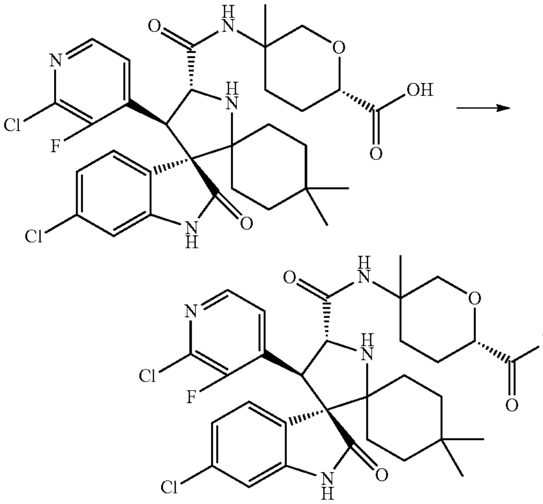

(3'R, 4'S,5'R)—N-[(6S)-6-carbamoyl-3-methyltetrahydro-2H-pyran-3-yl]-6"-chloro-4'-(2-chloro-3-fluoropyridin-4-yl)-4,4-dimethyl-2"-oxo-1'1,2"-dihydrodispiro[cyclohexane-1,2'-pyrrolidine-3',3"-indole]-5'-Carboxamide The compound (23 mg, 0.04 mmol) obtained in Step 2 of Example 189 was used as a starting material and treated in the same way as in Step 1 of Reference Example 16 to give 11 mg (48%) of the title compound as a solid.

$^1$H-NMR (400 MHz, $CDCl_3$) δ: 0.66 (3H, s), 0.92 (3H, s), 1.11-1.40 (4H, m), 1.44 (3H, s), 1.46-1.77 (6H, m), 1.92-1.97 (1H, m), 2.24-2.29 (1H, m), 3.40 (1H, dd, J=11.1, 7.0 Hz), 3.85-4.00 (2H, m), 4.47 (1H, d, J=9.1 Hz), 4.61 (1H, d, J=9.5 Hz), 5.48 (1H, d, J=4.1 Hz), 6.53 (1H, d, J=4.1 Hz), 6.73 (1H, d, J=1.8 Hz), 7.07 (1H, dd, J=8, 2, 1.8 Hz), 7.31 (1H, dd, J=8.2, 2.3 Hz), 7.50 (1H, t, J=5.0 Hz), 7.60 (1H, s), 7.70 (1H, d, J=8.2 Hz), 8.05 (1H, d, J=5.0 Hz).

MS (ESI) m/z: 632 $(M+H)^+$.

Example 190

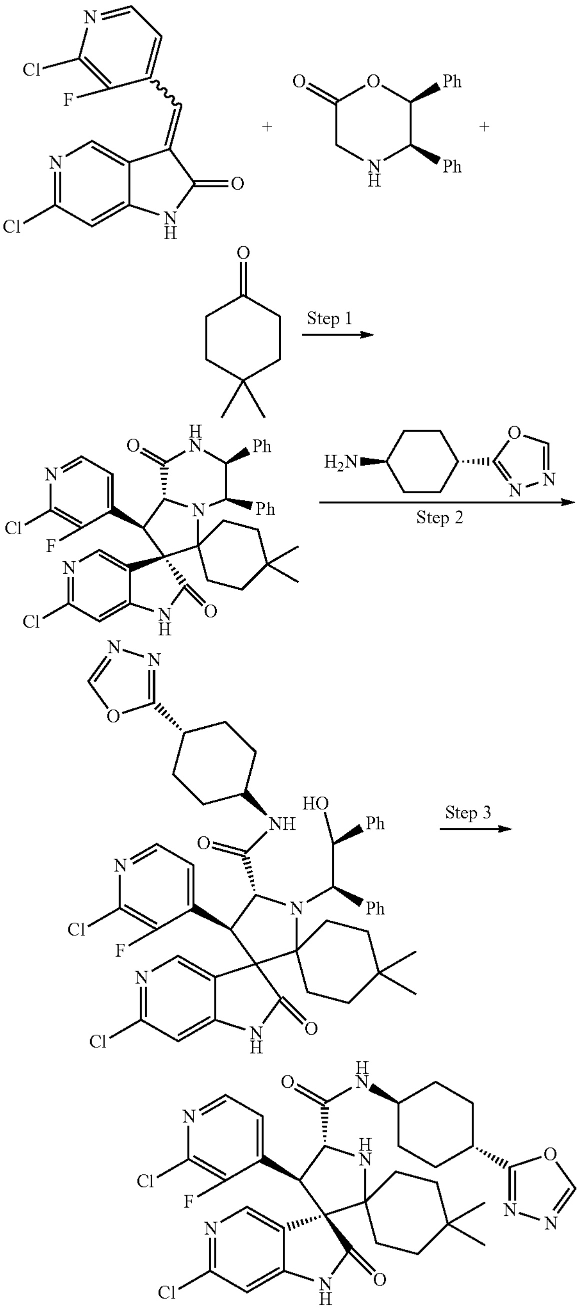

Step 1

(3'S,4'R, 7'S,8'S,8a'R)-6"-chloro-8'-(2-chloro-3-fluoropyridine-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-pyrrolo[3,2-c]pyridine]-1',2"(1"H)-dione The compound (3.00 g, 9.67 mmol) obtained in Reference Example 86 was used as a starting material and treated in the same way as in Step 1 of Example 9 to give 5.00 g (77%) of the title compound as a solid.

$^{1}$H-NMR ($CDCl_3$) δ: 0.22 (3H, s), 0.54 (3H, s), 0.93-1.09 (3H, m), 1.24-1.37 (3H, m), 1.75-1.82 (1H, m), 2.20-2.27 (1H, m), 4.56 (1H, d, J=11.0 Hz), 4.82 (1H, d, J=3.2 Hz), 5.29 (1H, d, J=11.0 Hz), 6.73 (1H, d, J=6.9 Hz), 6.90-6.93 (1H, m), 7.03-7.06 (1H, m), 7.09-7.25 (10H, m), 7.78 (1H, t, J=4.8 Hz), 7.93 (1H, s), 8.33 (1H, d, J=5.0 Hz).

MS (ESI) m/z: 671 $(M+H)^+$.

Step 2

(4'S,5'R)-6"-chloro-4'-(2-chloro-3-fluoropyridin-4-yl)-1'-[(1R,2S)-2-hydroxy-1,2-diphenylethyl]-4,4-dimethyl-N-[trans-4-(1,3,4-oxadiazol-2-yl)cyclohexyl]-2"-oxo-1",2"-dihydrodispiro[cyclohexane-1,2'-pyrrolidine-3',3"-pyrrolo[3,2-c]pyridine]-5'-carboxamide The compound (300 mg, 0.45 mmol) obtained in Step 1 above and the compound (242 mg, 1.34 mmol) obtained in Step 3 of Reference Example 3 were used as starting materials and treated in the same way as in Step 2 of Example 12 to give 177 mg (47%) of the title compound as a solid.

MS (ESI) m/z: 838 $(M+H)^+$.

Step 3

(3'R, 4'S,5'R)-6"-chloro-4'-(2-chloro-3-fluoropyridin-4-yl)-4,4-dimethyl-N-[trans-4-(1,3,4-oxadiazol-2-yl)cyclohexyl]-2-oxo-1",2"-dihydrodispiro[cyclohexane-1,2'-pyrrolidine-3',3"-pyrrolo[3,2-c]pyridine]-5'-carboxamide The compound (145 mg, 0.17 mmol) obtained in Step 2 above was used as a starting material and treated in the same way as in Step 3 of Example 1 to give 62 mg (56%) of the title compound as a solid.

$^{1}$H-NMR (400 MHz, $CD_3OD$) δ: 0.72 (3H, s), 0.97 (3H, s), 1.09-1.26 (2H, m), 1.37-1.94 (10H, m), 2.01-2.29 (4H, m), 2.98-3.09 (1H, m), 3.67-3.75 (1H, m), 4.61 (1H, d, J=9.2 Hz), 4.75 (1H, d, J=9.2 Hz), 6.84 (1H, s), 7.64 (1H, t, J=5.0 Hz), 8.09 (1H, d, J=5.0 Hz), 8.36 (1H, s), 8.85 (1H, s),

MS (ESI) m/z: 642 $(M+H)^+$.

Example 191

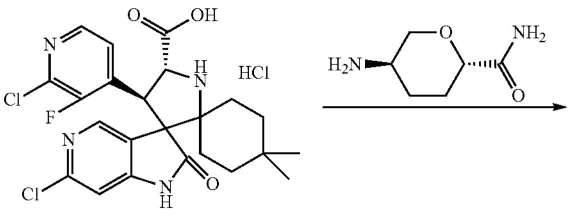

-continued

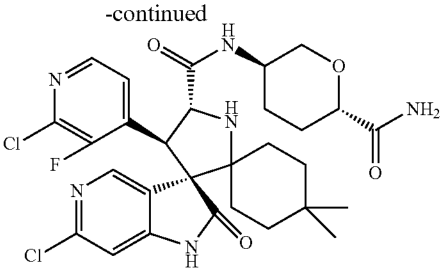

(4'S,5'R)—N-[3R, 6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-pyrrolo[3,2-c]pyridine]-5'-carboxamide The compound (60 mg, 0.11 mmol) obtained in Step 3 of Reference Example 87 and the compound (20.5 mg, 0.11 mmol) obtained in Step 3 of Reference Example 28 were used as starting materials and treated in the same way as in Step 2 of Example 12 to give 26 mg (37%) of the title compound as a solid.

$^{1}$H-NMR (400 MHz, $CD_3OD$) δ: 0.71 (3H, s), 0.96 (3H, s), 1.10-1.41 (4H, m), 1.49-1.91 (7H, m), 2.06-2.20 (2H, m), 3.77-3.87 (2H, m), 3.98-4.04 (1H, m), 4.60 (1H, d, J=9.2 Hz), 4.76 (1H, d, J=9.2 Hz), 6.83 (1H, s), 7.62 (1H, t, J=5.0 Hz), 8.09 (1H, d, J=5.0 Hz), 8.35 (1H, d, J=1.8 Hz).

MS (ESI) m/z: 619 $(M+H)^+$.

Example 192

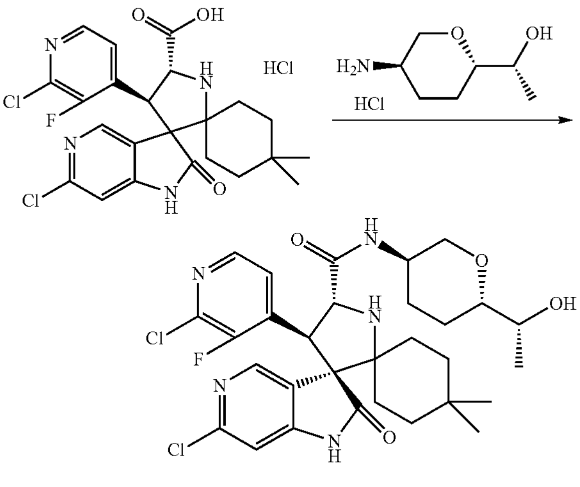

6"-Chloro-4'-(2-chloro-3-fluoropyridin-4-yl)-N-{(3R,6S)-6-[(1R)-1-hydroxyethyl]tetrahydro-2H-pyran-3-yl}-4,4-dimethyl-2"-oxo-1",2"-dihydrodispiro[cyclohexane-1,2'-pyrrolidine-3',3"-pyrrolo[3,2-c]pyridine]-5'-carboxamide The compound (40 mg, 0.76 mmol) obtained in Step 3 of Reference Example 87 and the compound (14 mg, 0.76 mmol) obtained in Step 4 of Reference Example 79 were used as starting materials and treated in the same way as in Step 2 of Example 12 to give 18 mg (39%) of the title compound as a solid.

$^1$H-NMR (400 MHz, $CDCl_3$) δ: 0.73 (3H, s), 0.98 (3H, s), 1.13-1.30 (3H, m), 1.18 (3H, d, J=6.4 Hz), 1.39-1.81 (9H, m), 2.12-2.21 (2H, m), 3.15 (1H, t, J=10.8 Hz), 3.24-3.29 (1H, m), 3.84-3.93 (2H, m), 4.04-4.09 (1H, m), 4.49 (1H, d, J=9.2 Hz), 4.71 (1H, d, J=9.2 Hz), 6.72 (1H, s), 7.45-7.49 (2H, m), 8.09 (1H, d, J=5.0 Hz), 8.31-8.34 (2H, m).

MS (ESI) m/z: 620 $(M+H)^+$.

Example 193

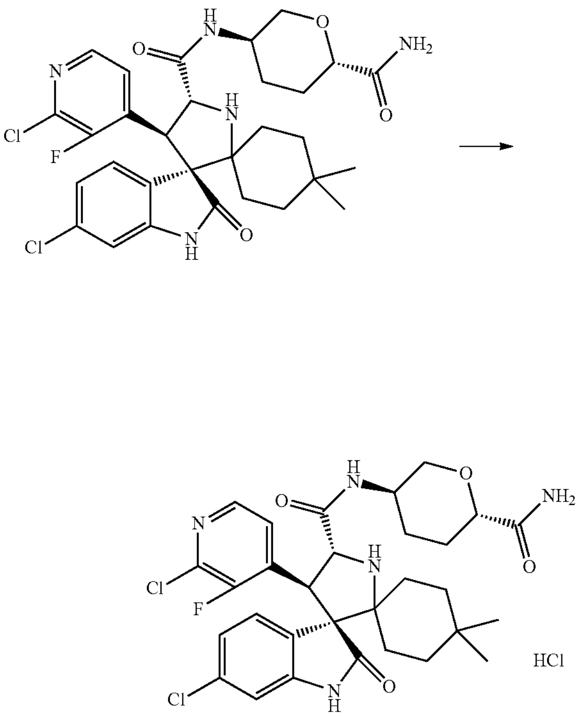 [SMILES: CC1(C)CCC2(CC1)N[C@@H](C(=O)N[C@@H]1CC[C@@H](C(N)=O)OC1)[C@H](c1ccnc(Cl)c1F)[C@]21C(=O)Nc2cc(Cl)ccc21 ; CC1(C)CCC2(CC1)N[C@@H](C(=O)N[C@@H]1CC[C@@H](C(N)=O)OC1)[C@H](c1ccnc(Cl)c1F)[C@]21C(=O)Nc2cc(Cl)ccc21 ; Cl]

(3'R, 4'S, S'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide hydrochloride water/2-propanol (IPA) solvate Concentrated hydrochloric acid (0.026 ml, 0.31 mmol) was added to a 2-propanol (2.0 ml) solution of the compound (192 mg, 0.31 mmol) obtained in Example 70 and the resulting mixture was dissolved by heating. After stirring at room temperature for 18 hours, the precipitate was collected by filtration to give 173 mg (85%) of the title compound as a solid.

$^1$H-NMR (500 MHz, DMSO-$d_6$) δ: 0.62 (3H, s), 0.92 (3H, s), 1.09-1.58 (6H, m), 1.65-2.07 (5H, m), 2.53-2.94 (1H, m), 3.29-3.73 (5H, m), 4.56-4.76 (1H, m), 4.85-5.23 (1H, m), 6.80 (1H, s), 7.01-7.13 (2H, m), 7.14-7.20 (1H, m), 7.49-7.74 (2H, m), 8.19-8.42 (1H, m), 8.61-9.08 (1H, m), 10.41 (1H, br s), 11.25 (1H, br s).

Anal. Calcd for $C_{30}H_{34}Cl_2FN_5O_4 \cdot HCl \cdot 0.75H_2O \cdot IPA$: C, 54.48; H, 6.03; N, 9.63. Found: C, 54.47; H, 6.14; N, 9.65.

Example 194

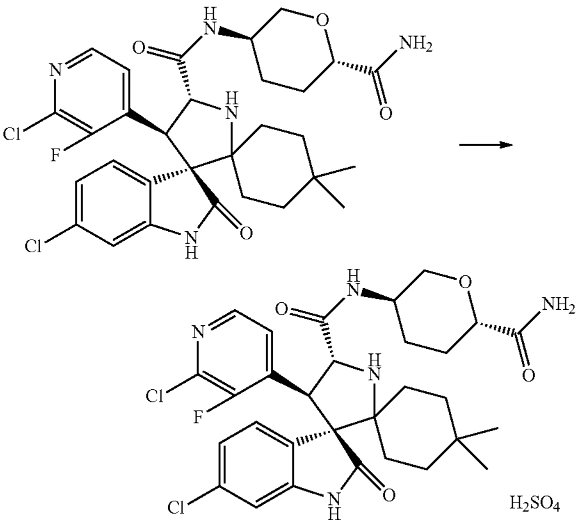

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide sulfate water/2-propanol (IPA) solvate Concentrated sulfuric acid (0.005 ml, 0.08 mmol) was added to a 2-propanol (0.5 ml) solution of the compound (52 mg, 0.08 mmol) obtained in Example 70 and the resulting mixture was dissolved by heating. After stirring at room temperature for 2 days, the precipitate was collected by filtration to give 20 mg (34%) of the title compound as a solid.

$^1$H-NMR (500 MHz, DMSO-$d_6$) δ: 0.62 (3H, s), 0.92 (31, s), 1.13-1.61 (6H, m), 1.67-2.09 (5H, m), 2.45-2.88 (1H, m), 3.47-4.01 (5H, m), 4.58-4.77 (1H, m), 4.83-5.11 (1H, m), 6.79 (1H, s), 6.98-7.25 (3H, m), 7.51-7.73 (2H, m), 8.20-8.41 (1H, m), 8.51-8.73 (1H, m), 8.79-9.05 (1H, m), 10.35 (1H, br s), 11.18 (1H, br s).

Anal. Calcd for $C_{30}H_{34}Cl_2FN_5O_4 \cdot H_2SO_4 \cdot 0.25H_2O \cdot IPA$: C, 49.94; H, 5.71; N, 8.82. Found: G, 49.74; H, 5.71; N, 8.85.

Example 195

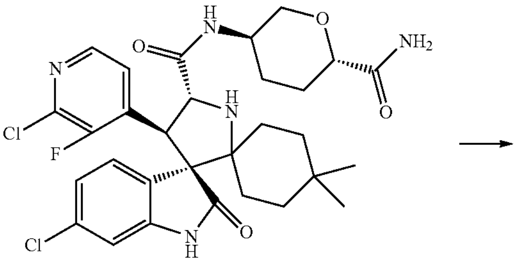

-continued

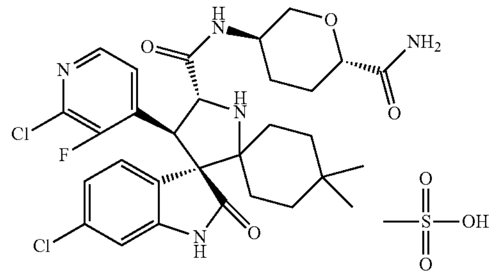

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide methanesulfonate hydrate Methanesulfonic acid (0.006 ml, 0.09 mmol) was added to a 2-propanol (0.5 ml) solution of the compound (54 mg, 0.09 mmol) obtained in Example 70 and the resulting mixture was dissolved by heating. After stirring at room temperature for 3 days, the precipitate was collected by filtration to give 27 mg (43%) of the title compound as a solid.

$^1$H-NMR (400 MHz, $CDCl_3$) δ: 0.74 (3H, s), 1.03 (3H, s), 1.28-1.43 (2H, m), 1.44-1.82 (4H, m), 1.84-2.10 (3H, m), 2.14-2.28 (2H, m), 2.56-2.79 (4H, m), 3.09-3.25 (1H, m), 3.72-3.80 (1H, m), 3.81-3.94 (2H, m), 4.72-4.85 (1H, m), 5.35-5.54 (1H, m), 5.69-5.88 (1H, m), 6.55-6.68 (1H, m), 6.90 (1H, s), 7.08 (1H, dd, J=7.8, 1.8 Hz), 7.28-7.35 (1H, m), 7.81-7.95 (1H, m), 8.14-8.36 (2H, m), 8.44-8.89 (1H, m), 9.83 (1H, br s); 11.03 (1H, br s).

Anal. Calcd for $C_{30}H_{34}Cl_2FN_5O_4{\cdot}CH_3SO_3H{\cdot}H_2O$: C, 50.82; H, 5.50; N, 9.56. Found: C, 50.78; H, 5.51, N, 9.53.

Example 196

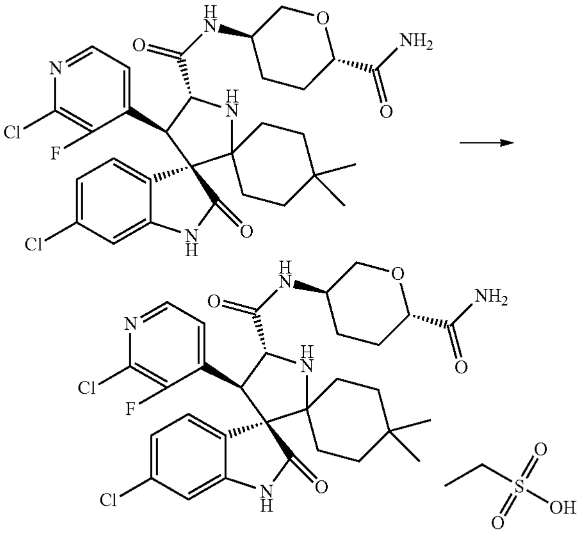

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide ethanesulfonate hydrate Ethanesulfonic acid (0.024 ml, 0.30 mmol) was added to a 2-propanol (2.4 ml) solution of the compound (183 mg, 0.30 mmol) obtained in Example 70 and the resulting mixture was dissolved by heating. After stirring at room temperature for 23 hours, the precipitate was collected by filtration to give 177 mg (82%) of the title compound as a solid.

$^1$H-NMR (400 MHz, DMSO-da) δ: 0.62 (3H, s), 0.92 (3H, 8), 1.05 (3H, t, J=7.4 Hz), 1.09-1.59 (6H, m), 1.62-2.06 (5H, m), 2.38 (2H, q, J=7.4 Hz), 2.59-3.07 (1H, m), 3.27-3.79 (5H, m), 4.53-4.76 (1H, m), 4.78-5.16 (1H, m), 6.79 (1H, s), 7.00-7.23 (3H, m), 7.51-7.75 (2H, m), 8.21-8.41 (1H, m), 8.48-9.07 (1H, m), 10.35 (1H, br s), 11.19 (1H, br s).

Anal. Calcd for $C_{30}H_{34}Cl_2FN_5O_4{\cdot}C_2H_5SO_3H{\cdot}H_2O$: C, 51.54; H, 5.54; N, 9.39. Found: C, 51.42, H, 5.65; N, 9.35.

Example 197

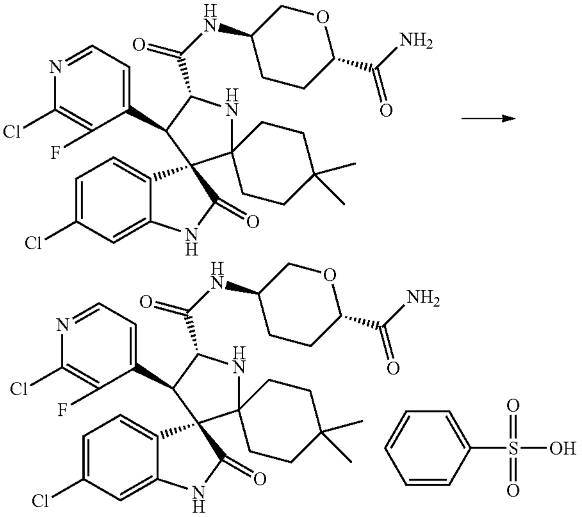

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide benzenesulfonate hydrate Benzenesulfonic acid monohydrate (30 mg, 0.17 mmol) was added to a 2-propanol (1.0 ml) solution of the compound (104 mg, 0.17 mmol) obtained in Example 70 and the resulting mixture was dissolved by heating. After stirring at room temperature for 24 hours, the precipitate was collected by filtration to give 116 mg (89%) of the title compound as a solid.

$^1$H-NMR (400 MHz, $CDCl_3$) δ: 0.69 (3H, s), 0.88 (3H, s), 1.09-1.85 (7H, m), 1.88-2.19 (4H, m), 2.53-2.77 (1H, m); 2.95-3.10 (1H, m), 3.53-3.69 (1H, m), 3.71-3.89 (2H, m), 4.68-4.85 (1H, m), 5.47-5.80 (2H, m), 6.52 (1H, s), 6.77-

6.90 (1H, m), 7.03-7.11 (1H, m), 7.24-7.44 (5H, m), 7.63-7.98 (4H, m), 8.09-8.43 (1H, m), 10.16 (1H, br s), 10.96 (1H, br s).

Anal. Calcd for $C_{30}H_{34}Cl_2FN_5O_4 \cdot C_6H_5SO_3H \cdot 1.5H_2O$: C, 53.80; H, 5.39; N, 8.71. Found: C, 53.89; H, 5.40; N, 8.80.

Example 198

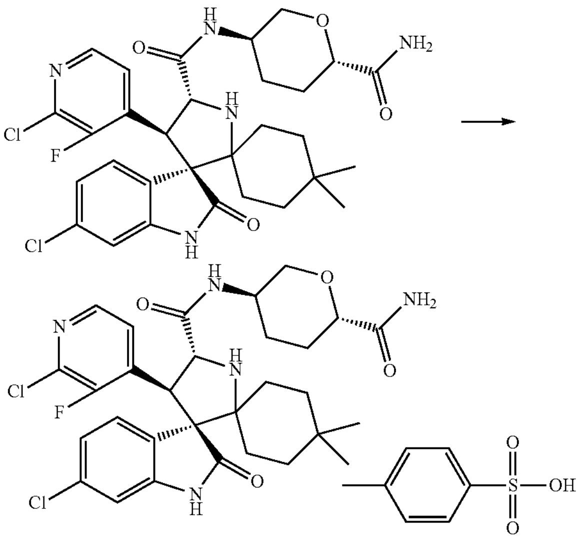

(3'R, 4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide p-toluenesulfonate hydrate P-toluenesulfonic acid monohydrate (16 mg, 0.08 mmol) was added to a 2-propanol (0.5 ml) solution of the compound (52 mg, 0.08 mmol) obtained in Example 70 and the resulting mixture was dissolved by heating. After stirring at room temperature for 4 hours, the precipitate was collected by filtration to give 48 mg (72%) of the title compound as a solid.

$^1$H-NMR (400 MHz, DMSO-$d_6$) δ: 0.63 (3H, s), 0.92 (3H, s), 1.09-1.59 (6H, m), 1.66-2.03 (5H, m), 2.29 (3H, s), 2.70-2.91 (1H, m), 3.34-3.74 (5H, m), 4.67 (1H, d, J=10.1 Hz), 4.80-5.11 (1H, m), 6.80 (1H, s), 7.02-7.22 (5H, m), 7.43-7.52 (2H, m), 7.55-7.70 (2H, m), 8.23-8.39 (1H, m), 8.45-8.74 (1H, m), 10.33 (1H, br s), 11.14 (1H, br s).

Anal. Calcd for $C_{30}H_{34}Cl_2FN_5O_4 \cdot C_6H_4CH_3SO_3H \cdot 1.5H_2O$: C, 54.34; H, 5.55; N, 8.56. Found: C, 54.06; H, 5.45; N, 8.50.

Example 199

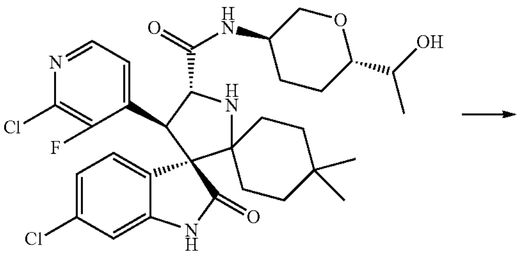

-continued

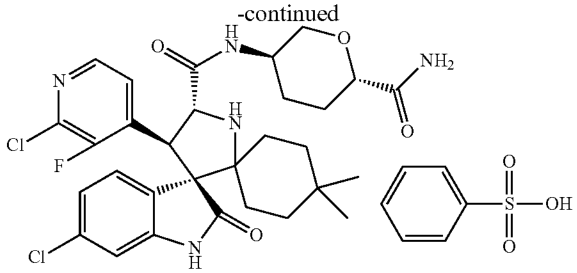

(3'R, 4'S,5'R)-6"-chloro-4'-(2-chloro-3-fluoropyridin-4-yl)-N-{(3R,6S)-6-[1-hydroxyethyl]tetrahydro-2H-pyran-3-yl}-4,4-dimethyl-2"-oxo-1",2"-dihydrodispiro[cyclohexane-1,2'-pyrrolidine-3',3"-indole]-5'-carboxamide benzenesulfonate hydrate Benzenesulfonic acid monohydrate (19 mg, 0.11 mmol) was added to an acetonitrile (0.6 ml) solution of the compound (isomer A) (67 mg, 0.11 mmol) obtained in Example 93 and the resulting mixture was dissolved by heating. After stirring at room temperature for 26 hours, the precipitate was collected by filtration to give 62 mg (80%) of the title compound as a solid.

$^1$H-NMR (400 MHz, $CDCl_3$) δ: 0.72 (3H, s), 0.98 (3H, s), 1.04 (3H, d, J=6.4 Hz), 1.21-2.09 (12H, m), 2.59-2.73 (1H, m), 2.86-3.05 (2H, m), 3.67-3.87 (3H, m), 4.74 (1H, d, J=10.5 Hz), 5.52-5.70 (1H, m), 6.84 (1H, s), 7.05 (1H, dd, J=8.2, 1.8 Hz), 7.23-7.29 (1H, m), 7.30-7.40 (3H, m), 7.69 (2H, d, J=6.4 Hz), 7.83-7.98 (2H, m), 8.04-8.17 (1H, m), 8.44 (1H, br s), 9.88 (1H, br s), 10.93 (1H, br s).

Anal. Calcd for $C_{31}H_{37}Cl_2FN_5O_4 \cdot C_6H_5SO_3H \cdot 1.75H_2O$: C, 55.09; H, 5.87; N, 8.24. Found: C, 54.68; H, 5.62; N, 8.73.

REFERENCE EXAMPLES

Reference Example 1

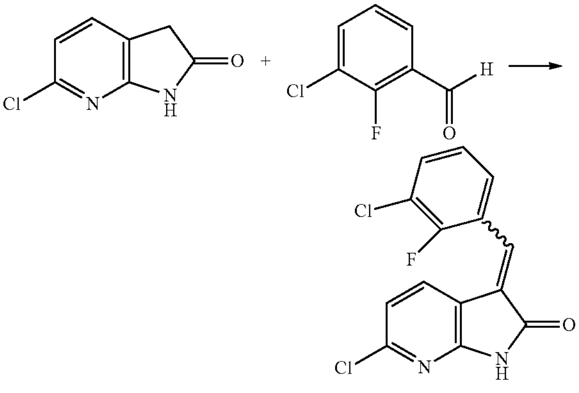

(3E/Z)-6-chloro-3-(3-chloro-2-fluorobenzylidene)-1,3-dihydro-2H-pyrrolo[2,3-b]pyridin-2-one N,N-diisopropylethylamine (0.10 ml) was added to a methanol (30 ml) solution of 6-chloro-1,3-dihydro-2H-pyrrolo[2,3-b]pyridin-2-one (633 mg, 3.75 mmol) and 3-chloro-2-fluorobenzaldehyde (0.45 ml, 3.83 mmol) and the resulting mixture was heated to reflux for 18 hours. After cooling, the precipitate was collected by filtration, washed with cold methanol, and dried to give 920 mg (79%) of the title compound as a yellow solid.

$^1$H-NMR (400 MHz, DMSO-$d_6$) δ: 7.02 (1H, d, J=8.0 Hz), 7.30 (1H, t, J=8.0 Hz), 7.53 (1H, d, J=7.8 Hz), 7.66-7.78 (3H, m), 11.4 (1H, s).

Reference Example 2

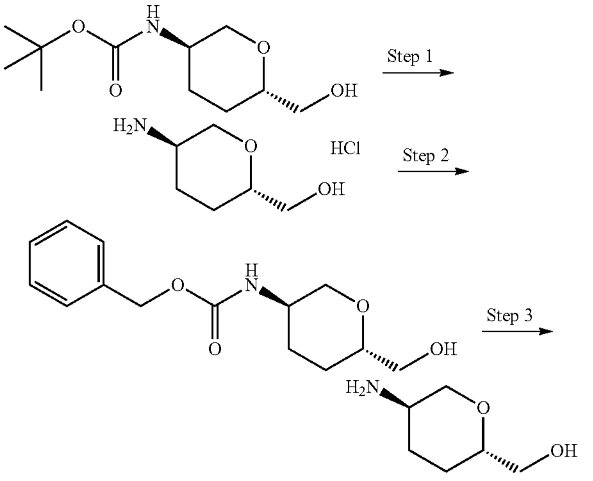

Step 1

2-Amino-1,5-anhydro-2,3,4-trideoxy-D-erythro-hexitol hydrochloride 1,5-Anhydro-2-[(text-butoxycarbonyl)amino]-2,3,4-trideoxy-D-erythro-hexitol (Eur. J. Org. Chem., 2003, 2418-2427) (6.00 g, 0.03 mol) was dissolved in methanol (20 ml), 4N hydrochloric acid/1,4-dioxane solution (60 ml) was added and the resulting mixture was stirred at room temperature for 1 hour. The reaction solvent was evaporated under reduced pressure to give 4.5 g (100%) of the title compound as a colorless solid, $^1$H-NMR (400 MHz, DMSO-$d_6$) δ: 1.25 (1H, dad, J=24.3, 13.3, 3.7 Hz), 1.52 (1H, ddd, J=24.7, 12.4, 3.9 Hz), 1.66-1.72 (1H, m), 2.03-2.09 (1H, m), 2.97-3.06 (1H, m), 3.19-3.37 (4H, m), 3.96-4.00 (1H, m).

MS (ESI) m/z: 132 (M+H)$^+$.

Step 2

1,5-Anhydro-2-{[(benzyloxy) carbonyl]amino}-2,3,4-trideoxy-D-erythro-hexitol

The compound (3.5 g, 21.0 mmol) obtained in Step 1 above was dissolved in 5N aqueous sodium hydroxide solution (40 ml) and benzyloxycarbonyl chloride (3.3 ml, 23.0 mmol) was added dropwise at 0° C., After stirring at room temperature for 16 hours, the reaction mixture was rendered acidic by addition of 1N hydrochloric acid, followed by extraction with ethyl acetate. The organic layer was washed with brine and dried over anhydrous magnesium sulfate. The solvent was evaporated under reduced pressure, diethyl ether and hexane were added to the residue obtained and then the slurry was filtered and dried to give 2.06 g (378) of the title compound as a colorless solid.

$^1$H-NMR (400 MHz, DMSO-$d_6$) δ: 1.33 (1H, dad, J=24.5, 12.3, 3.9 Hz), 1.48 (1H, ddd, J=24.3, 13.2, 3.5 Hz), 1.61-1.67 (1H, m), 1.95-2.00 (1H, m), 2.09-2.16 (1H, m), 3.05 (1H, t; J=10.6 Hz), 3.34-3.41 (1H, m), 3.50-3.55 (1H, m), 3.57-3.64 (1H, m), 3.65-3.72 (1H, m), 4.11-4.17 (1H, m), 4.48 (1H, br s), 5.06-5.13 (2H, m), 7, 32-7.38 (5H, m).

MS (ESI) m/z; 266 (M+H)$^+$.

Step 3

2-Amino-1,5-anhydro-2,3,4-trideoxy-D-erythro-hexitol

The compound (2.00 g, 7.54 mmol) obtained in Step 2 above was dissolved in methanol (30 ml), 10% palladium carbon (300 mg) was added and the resulting mixture was stirred at room temperature for 4 hours in a hydrogen atmosphere. The catalyst was removed by filtration through celite and then the filtrate was concentrated under reduced pressure and dried to give 1.13 g (100%) of the title compound as a colorless solid.

$^1$H-NMR (400 MHz, DMSO-$d_6$) δ: 1.07-1.20 (2H, m), 1.54-1.61 (1H, m), 1.82-1.88 (1H, m), 2.50-2.56 (1H, m), 2.82 (1H, t, J=10.5 Hz), 3.08-3.14 (1H, m), 3.24 (1H, dd, J=11.2, 4.8 Hz), 3.33 (1H, dd, J=11.0, 6.0 Hz), 3.73 (1H, dq, J=10.8, 2.2 Hz).

MS (ESI) m/z: 132 (M+H)$^+$.

Reference Example 3

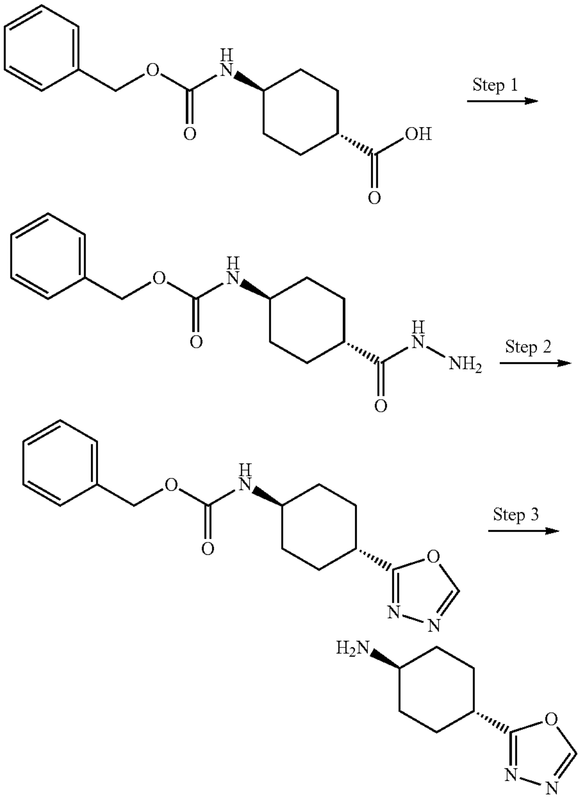

Step 1

Benzyl [trans-4-(hydrazinocarbonyl)cyclohexyl] carbamate

Hydrazine monohydrate (1.42 ml, 23.4 mmol), 1-hydroxybenzotriazole (2.44 g, 18.0 mmol), and 1-ethyl-3-(3-dimethylaminopropyl) carbodiimide hydrochloride (4.49 g, 23.4 mmol) were added to an N,N-dimethylformamide (75 ml) solution of trans-4-(carbobenzoxyamino)cyclohexanecarboxylic acid (5.00 g, 18.0 mmol) at room temperature and the resulting mixture was stirred for 3 days. Water (150 ml) was added to the reaction mixture and the precipitated solid was collected by filtration and dried under reduced pressure to give 4.52 g (86%) of the title compound as a colorless solid.

$^1$H-NMR (500 MHz, $CDCl_3$) δ: 1.09-1.20 (2H, m), 1.56-1.67 (2H, m), 1.86-1.94 (2H, m), 1.96-2.05 (1H, m), 2.07-2.17 (2H, m), 3.43-3.57 (1H, m), 3.65-4.05 (2H, m), 4.54-4.63 (1H, m), 5.08 (2H, s), 6.68 (1H, s), 7.30-7.39 (5H, m).

Step 2

Benzyl [trans-4-(1,3,4-oxadiazol-2-yl)cyclohexyl] carbamate

Trimethyl orthoformate (2 ml) and a boron trifluoride-diethyl ether complex (0.02 ml, 0.17 mmol) were added to an N,N-dimethylacetamide (20 ml) solution of the compound (1.00 g, 3.43 mmol) obtained in Step 1 above at room temperature and the resulting mixture was stirred at 50° C. for 8 hours under nitrogen atmosphere. The reaction mixture was cooled, triethylamine (0.29 ml, 2.06 mmol) was added at room temperature, the resulting mixture was stirred overnight, then water was added and the precipitated solid was collected by filtration and dried to give 0.91 g (88%) of the title compound as a colorless solid.

$^1$H-NMR (500 MHz, $CDCl_3$) δ: 1.23-1.34 (2H, m), 1.67-1.80 (2H, m), 2.15-2.24 (4H, m), 2.85-2.95 (1H, m), 3.52-3.65 (1H, m), 4.59-4.69 (1H, m), 5.10 (2H, s), 7.30-7.38 (5H, m), 8.33 (1H, s).

Step 3

Trans-4-(1,3,4-oxadiazol-2-yl)cyclohexanamine

The compound (2.35 g, 9.45 mmol) obtained in Step 2 above was used as a starting material and treated in the same way as in Step 3 of Reference Example 2 to give 1.55 g (98%) of the title compound as a pale yellow solid.

$^1$H-NMR (500 MHz, $CDCl_3$) δ: 1.21-1.31 (2H, m), 1.62-1.72 (2H, m), 1.74-1.90 (2H, m), 1.98-2.05 (2H, m), 2.14-2.21 (2H, m), 2.73-2.80 (1H, m), 2.85-2.93 (1H, m), 8.38 (1H, s).

Reference Example 4

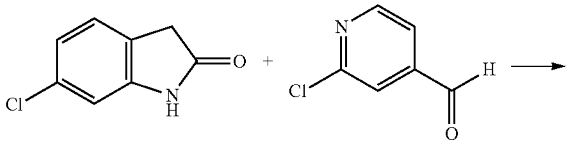

-continued

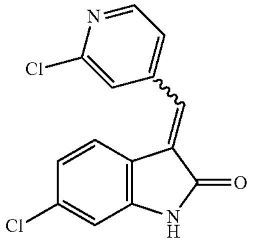

(3E/Z)-6-chloro-3-[(2-chloropyridin-4-yl)methylene]-1,3-dihydro-2H-indol-2-one

N,N-diisopropylethylamine (22.5 ml, 135 mmol) was added to a methanol (2000 ml) solution of 6-chloro-1,3-dihydro-2H-indol-2-one (14) g, 841 mmol) and 2-chloroisonicotinaldehyde (131 g, 925 mmol) and the resulting mixture was heated to reflux for 16 hours. After cooling, the precipitate was collected by filtration, washed with cold methanol, and dried to give 194 g (79%) of the title compound as an orange solid.

MS (ESI) m/z: 291 $(M+H)^+$.

Reference Example 5

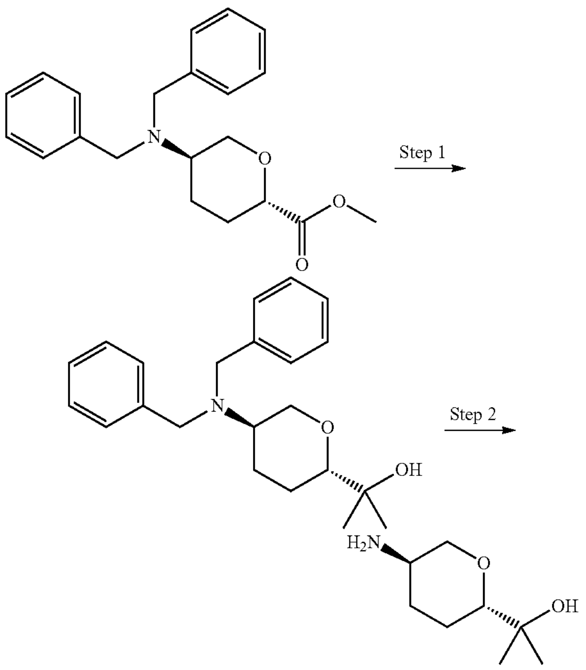

Step 1

2-[(2S,5R)-5-(dibenzylamino)tetrahydro-2H-pyran-2-yl]propan-2-ol

Methyl 2,5-anhydro-3,4,5-trideoxy-5-(dibenzylamino)-L-erythro-hexonate (16.0 g, 47.0 mmol) was dissolved in tetrahydrofuran (200 ml) under nitrogen atmosphere, methyl magnesium bromide/tetrahydrofuran solution (1.06 mol/l, 300 ml, 0.32 mol) was added dropwise at 0° ° C. and then the resulting mixture was stirred at room temperature for 16 hours. After ice cooling again, aqueous ammonium chloride solution (300 ml) was gradually added to the reaction mixture and the resulting mixture was stirred for 30 minutes. The reaction mixture was diluted with ethyl acetate and the organic layer was washed with brine. The organic layer was dried over anhydrous magnesium sulfate and the solvent was evaporated under reduced pressure. The residue obtained was purified by silica gel column chromatography [n-hexane:ethyl acetate=3:1 (v/v)] to give 15.5 g (97%) of the title compound as a pale yellow oil.

$^1$H-NMR (400 MHz, $CDCl_3$) δ: 1.08 (3H, s), 1.14 (3H, s), 1.26-1.36 (1H, m), 1.53-1.62 (1H, m), 1.69-1.75 (1H, m), 2.04-2.10 (1H, m), 2.40 (1H, s), 2.69-2.77 (1H, m), 3.00 (1H, dd, J=11.4, 1.8 Hz), 3.41 (1H, t, J=10.8 Hz), 3.61-3.71 (4H, m), 4.03-4.08 (1H, m), 7.20-7.37 (10H, m).

MS (ESI) m/z: 340 $(M+H)^+$.

Step 2

2-[(2S,5R)-5-aminotetrahydro-2H-pyran-2-yl] propan-2-ol

The compound (15.5 g, 46.0 mmol) obtained in Step 1 above was dissolved in ethanol (300 ml), 20% palladium hydroxide (3.0 g) was added and the resulting mixture was stirred at room temperature for 2 days under a hydrogen atmosphere. The catalyst was removed by filtration through celite and then the solvent in the filtrate was evaporated under reduced pressure and dried to give 7.10 g (98%) of the title compound as a colorless solid.

$^1$H-NMR (400 MHz, DMSO-$d_6$) δ: 1.00 (3H, s), 1.06 (3H, s), 1.27-1.37 (1H, m), 1.45-1.54 (1H, m), 1.74-1.80 (1H, m), 2.04-2.12 (1H, m), 2.92 (1H, d, J=11.4 Hz), 2.96-3.01 (1H, m), 3.24 (1H, t, J=10.8 Hz), 4.00-4.05, (1H, m), 4.28 (1H, br s), 8.16 (2H, br s).

MS (ESI) m/z: 160 $(M+H)^+$.

Reference Example 6

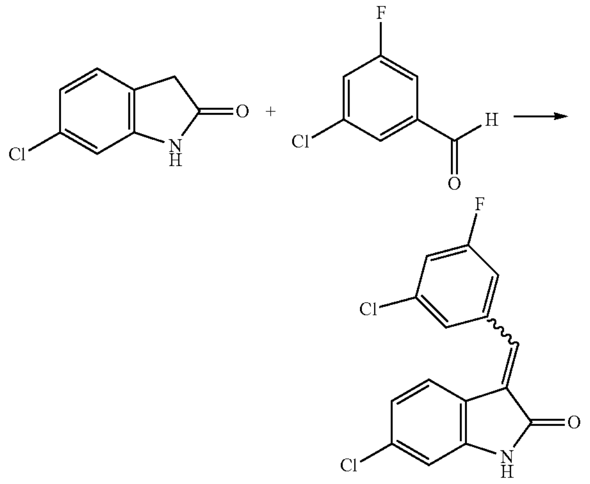

(3E/Z)-6-chloro-3-(3-chloro-5-fluorobenzylidene)-1,3-dihydro-2H-indol-2-one

3-Chloro-5-fluorobenzaldehyde (3.00 g, 18.9 mmol) was used as a starting material and treated in the same way as. In Reference Example 4 to give 3.19 g (56%) of the title compound as a yellow solid.

$^1$H-NMR (400 MHz, DMSO-$d_6$) δ: 6.89-6.91 (1H, m), 6.93-6.97 (1H, m), 7.34 (1H, d, J=8.3 Hz), 7.52-7.58 (2H, m), 7.58-7.62 (2H, m), 10.84 (1H, s),

MS (APCI) m/z: 308 $(M+H)^+$.

Reference Example 7

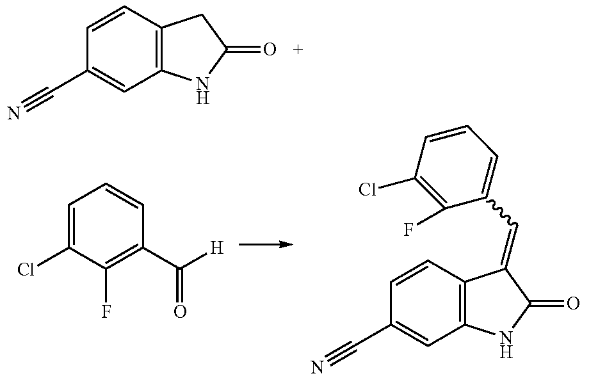

(3E/Z)-3-(3-chloro-2-fluorobenzylidene)-2-oxo-2,3-dihydro-1H-indole-6-carbonitrile 2-Oxo-2,3-dihydro-1H-indole-6-carbonitrile (400 mg, 2.53 mmol) was used as a starting material and treated in the same way as in Reference Example 1 to give 685 mg (91%) of the title compound as a brown solid.

$^1$H-NMR (400 MHz, DMSO-$d_6$) δ: 7.24-7.42 (4H, m), 7.72-7.80 (3H, m), 11.07 (1H, s).

Reference Example 8

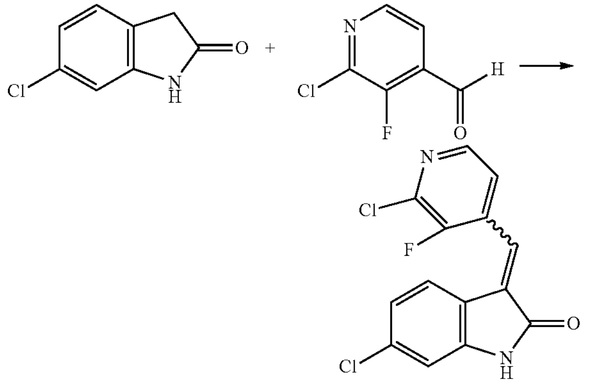

(3E/Z)-6-chloro-3-[(2-chloro-3-fluoropyridin-4-yl)methylene]-1,3-dihydro-2H-indol-2-one 2-Chloro-3-fluoro isonicotinaldehyde (2.20 g, 13.8 mmol) was used as a starting material and treated in the same way as in Reference Example 4 to give 3.37 g (83%) of the title compound as a yellow solid.

MS (APCI) m/z: 309 $(M+H)^+$.

Reference Example 9

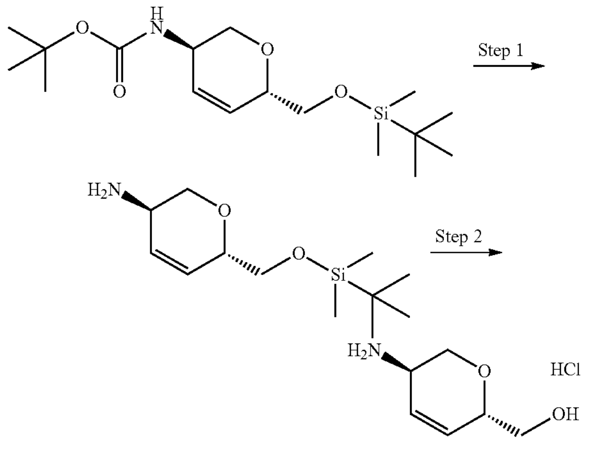

Step 1

2-Amino-1,5-anhydro-6-O-[tert-butyl(dimethyl)silyl]-2,3,4-trideoxy-D-erythro-hex-3-enitol 1,5-Anhydro-2-[(tert-butoxycarbonyl)amino]-6-O-[tert-butyl(dimethyl)silyl]-2,3,4-trideoxy-D-erythro-hex-3-enitol (Eur. J. Org. Chem, 2003, 2418-2427) (1.02 g, 2.97 mmol); tert-butyldimethylsilyl trifluoromethanesulfonate (4.10 ml, 17.8 mmol), and 2,6-lutidine (1.73 ml, 14.9 mmol) were mixed with dichloromethane (3 ml) and the resulting mixture was stirred at room temperature for 2 hours. Saturated ammonium chloride solution (50 ml) was added to the reaction mixture, followed by extraction with dichloromethane. The organic layer was washed with brine and dried over anhydrous sodium sulfate. The solvent was evaporated under reduced pressure and the residue obtained was purified by silica gel column chromatography {chloroform: methanol=40:1→9:1 (v/v)} to give 295 mg (41%) of the title compound as a light brown oil.

$^1$H-NMR (400 MHz, $CDCl_3$) δ: 0.07 (6H, s), 0.90 (9H, s), 1.43 (2M, br s), 3.23 (1H, dd, J=10.9, 7.9 Hz), 3.39-3.4:4 (1H, m), 3.54 (1H, dd, J=10.3, 5.9 Hz), 3.69 (1H, dd, J=10.3, 6.1 Hz), 4.06 (1H, dd, J=11.5, 5.6 Hz), 4.03-4.12 (1H, m), 5.78 (1H, dt, J=10.4, 1.8 Hz), 5.83-5.87 (1H, m).

MS (ESI) m/z: 244 $(M+H)^+$.

Step 2

2-Amino-1,5-anhydro-2,3,4-trideoxy-D-erythro-hex-3-enitol hydrochloride

The compound (1.0 g, 3.0 mmol) obtained in Step 1 above was dissolved in 1,4-dioxane (4 ml), 4N hydrochloric acid/1,4-dioxane solution (10 ml) was added and the resulting mixture was stirred at room temperature for 2 hours. The solvent was evaporated under reduced pressure to give 620 mg (100%) of the title compound as a light brown solid.

$^1$H-NMR (400 MHz, DMSO-$d_6$) δ: 3.38 (1H, dd, J=11.2, 4.8 Hz), 3.46 (1H, dd, J=11.4, 6.4 Hz), 3.52-3.59 (1H, m), 3.64-3.70 (1H, m), 4.04 (1H, dd, J=11.4, 4.6 Hz), 4.05-4.09 (1H, m), 5.89 (1H, dt, J=10.5, 2.7 Hz), 6.05-6.08 (1H, m), 8.31 (2H, br s).

MS (ESI) m/z: 130 $(M+H)^+$.

Reference Example 10

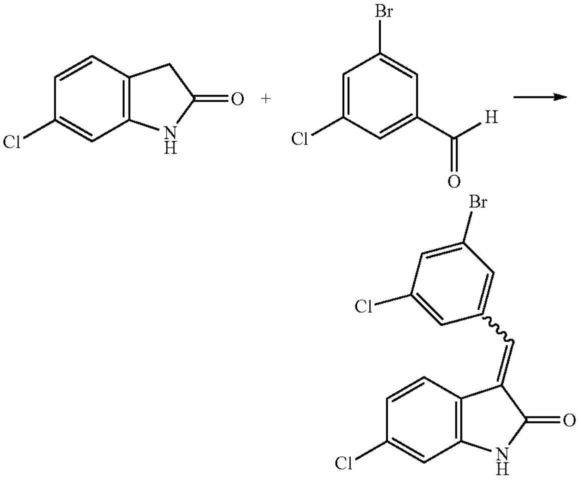

(3E/Z)-3-(3-bromo-5-chlorobenzylidene)-6-chloro-1,3,4-dihydro-2H-indol-2-one

3-Bromo-5-chlorobenzaldehyde (4.90 g, 22.4 mmol) was used and treated in the same way as in Reference Example 4 to give 8.11 g (98%) of the title compound as a yellow solid.

MS (FAB) m/z: 367 $(M+H)^+$.

Reference Example 11

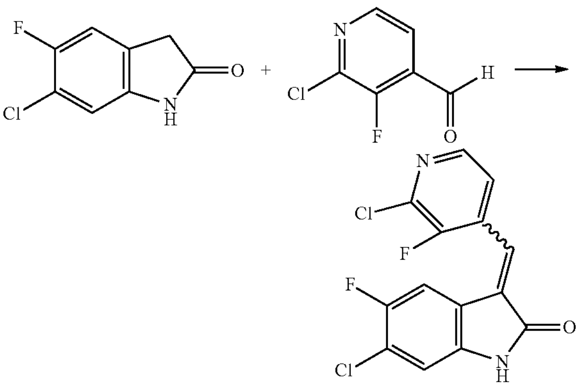

(3E/Z)-6-chloro-3-[(2-chloro-3-fluoropyridin-4-yl)methylene]-5-fluoro-1,3-dihydro-2H-indol-2-one 6-Chloro-5-fluoro-1,3-dihydro-2H-indol-2-one (928 mg, 5.0 mmol) was used as a starting material and treated in the same way as in Reference Example 8 to give 1.6 g (97%) of the title compound as a yellow solid.

$^1$H-NMR (400 Mhz, DMSO-$d_6$) δ: 7.03 (1H, dd, J=6.3, 0.7 Hz), 7.18 (1H, d, J=9.3 Hz), 7.55 (1H, s), 7.79 (1H, t, J=5.0 Hz), 8.41 (1H, d, J=4.9 Hz), 10.94 (1H, s).

Reference Example 12

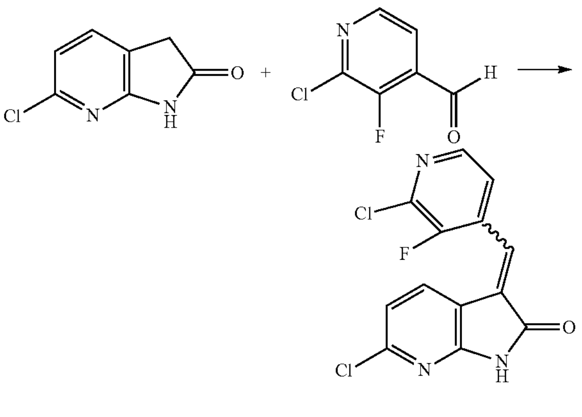

(3E/Z)-6-chloro-3-[(2-chloro-3-fluoropyridin-4-yl) methylene]-1,3-dihydro-2H-pyrrolo[2,3-b]pyridin-2-one 2-Chloro-3-fluoro isonicotinaldehyde (1.14 g, 7.16 mmol) was used as a starting material and treated in the same way as in Reference Example 1 to give 1.46 g (69%) of the title compound as a brown solid.

$^1$H-NMR (500 MHz, DMSO-d$_6$) δ: 7.02 (0.7H, d, J=8.0 Hz), 7.18 (0.3H, d, J=8.0 Hz), 7.54 (0.7H, d, J=8.0 Hz), 7.63 (0.78, s), 7.78 (0.7H, t, J=4.9 Hz), 7.89 (0.3H, s), 7.99 (0.3H, d, J=5.2 Hz), 8.18 (0.3H, d, J=8.0 Hz), 8.33 (0.3H, d, J=5.2 Hz), 8.40 (0.7H, d, J=5.2 Hz).

Reference Example 13

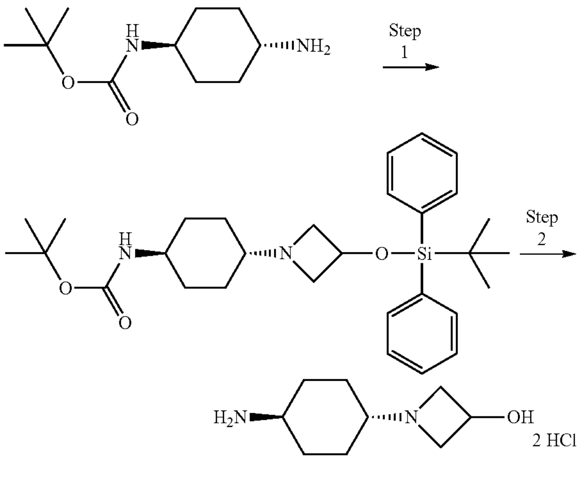

Step 1

Tert-butyl [trans-4-(3-[tert-butyl(diphenyl)silyl)oxy] azetidin-1-yl)cyclohexyl]carbamate 1,3-Dibromo-2-propanol (1.70 ml, 16.5 mmol) and sodium carbonate (15.9 g, 150 mmol) were added to an ethanol (300 ml) solution of tert-butyl(trans-4-aminocyclohexyl)carbamate (3.21 g, 15.0 mmol) and the resulting mixture was stirred under heating to reflux overnight. After cooling, insoluble matter was removed by filtration through celite and then the filtrate was concentrated under reduced pressure. The residue was diluted with water, followed by extraction with ethyl acetate. Then the organic layer was washed with brine. The organic layer was dried over anhydrous sodium sulfate and then the solvent was evaporated under reduced pressure. The residue was dissolved in N,N-dimethylformamide (15 ml) and imidazole (2.45 g, 36.0 mmol) and tert-butyldiphenylchlorosilane (4.29 ml, 16.5 mmol) were added under ice cooling. After stirring at room temperature for 1 hour, the reaction mixture was diluted with ethyl acetate and washed with water and brine in that order. The organic layer was dried over anhydrous magnesium sulfate, then the solvent was evaporated under reduced pressure and the residue was purified by silica gel column chromatography [chloroform; methanol=10:0→10:1 (v/v)] to give 2.45 g (32%) of the title compound as a colorless solid.

$^1$H-NMR (400 MHz, CDCl$_3$) δ: 1.01-1.13 (4H, m), 1.06 (9H, s), 1.46 (9H, s), 1.74-1.80 (2H, m), 1.93-2.03 (3H, m), 2.87 (2H, t, J=7.2 Hz), 3.35-3.43 (1H, m), 3.51 (2H, t, J=6.9 Hz), 4.42 (1H, t, J=6.3 Hz), 7.37-7.41 (4H, m), 7.42-7.47 (2H, m), 7.61-7.65 (4H, m).

Step 2

1-(Trans-4-aminocyclohexyl)azetidin-3-ol dihydrochloride

The compound (2.45 g, 4.82 mmol) obtained in Step 1 above was suspended in methanol (9 ml), 4N hydrochloric acid/1,4-dioxane solution (18 ml) was added and the resulting mixture was stirred at room temperature. After 48 hours, diethyl ether was added to the reaction mixture and the precipitated solid was collected by filtration and dried to give 1.08 g (92%) of the title compound as a colorless solid.

$^1$H-NMR (400 MHz, CD$_3$OD) δ: 1.33-1.56 (4H, m), 2.11-2.21 (4H, m), 3.13-3.15 (1H, m), 3.22-3.26 (1H, m), 3.92-3.99 (2H, m), 4.36-4.39 (2H, m), 4.56-4.67 (1H, m).

Reference Example 14

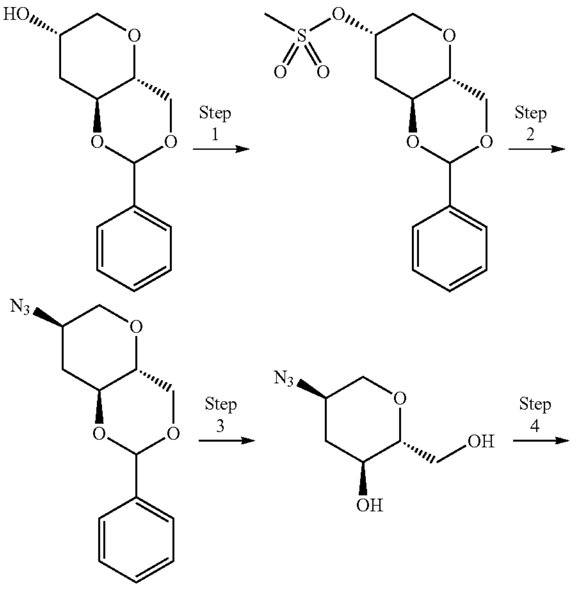

-continued

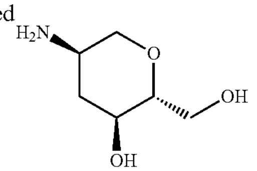

Step 1

1,5-Anhydro-4,6-O-benzylidene-3-deoxy-2-O-(methylsulfonyl)-D-arabino-hexitol

Methanesulfonyl: chloride (4.70 ml, 61.0 mmol) was added to a dichloromethane (250 ml) solution of 1,5-anhydro-4,6-O-benzylidene-3-deoxy-D-arabino-hexitol (WO2005/049582) (12.0 g, 50.8 mmol) and triethylamine (8.50 ml, 61.0 mmol) under ice cooling. After stirring at the same temperature for 45 minutes, water was added and the resulting mixture was subjected to extraction with chloroform. The organic layer was washed with brine and dried over anhydrous sodium sulfate. The solvent was evaporated under reduced pressure to give the title compound.

Step 2

1,5-Anhydro-2-azido-4,6-O-benzylidene-2,3-dideoxy-D-ribo-hexitol

An N,N-dimethylformamide (380 ml) solution of the compound (16.0 g, 50.8 mmol) obtained in Step 1 above combined with sodium azide (6.60 g, 102 mmol) was stirred at 80° C. for 66 hours. N,N-dimethylformamide was evaporated under reduced pressure, then ether was added and the organic layer was washed with water and brine and then dried over anhydrous sodium sulfate. The solvent was evaporated under reduced pressure, n-hexane was added and the precipitated solid was collected by filtration to give 7.50 g (56%) of the title compound as a colorless solid.

$^1$H-NMR (400 MHz, $CDCl_3$) δ: 1.68-1.79 (1H, m), 2.49-2.57 (1H, m), 3.23-3.35 (2H, m), 3.54-3.72 (3H, m), 4.01-4.09 (1H, m), 4.31 (1H, dd, J=10.6, 4.6 Hz), 5.54 (1H, s), 7.33-7.52 (5H, m).

Step 3

1,5-Anhydro-2-azido-2,3-dideoxy-D-ribo-hexitol

The compound (8.00 g, 30.6 mmol) obtained in Step 2 above was dissolved in acetic acid (160 ml) and water (40 ml) and the resulting solution was stirred at 90° C. for 1 hour and then concentrated under reduced pressure. The residue was purified by silica gel column chromatography [n-hexane:ethyl acetate=3:1→1:3 (v/v)] to give 4.70 g (89%) of the title compound as a colorless solid.

$^1$H-NMR (400 MHz, $CDCl_3$) δ: 1.47-1.58 (1H, m), 1.95-2.02 (1H, m), 2.26 (1H, d, J=5.0 Hz), 2.45-2.53 (1H, m), 3.11-3.21 (2H, m), 3.47-3.57 (1H, m), 3.66-3.75 (1H, m), 3.77-3.91 (2H, m), 3.97-4.04 (1H, m).

Step 4

2-Amino-1,5-anhydro-2,3-dideoxy-D-ribo-hexitol

10% Palladium carbon (120 mg) was added to a methanol (14 ml) solution of the compound (500 mg, 2.89 mmol) obtained in Step 3 above and the resulting mixture was stirred for 6 hours under hydrogen atmosphere. The catalyst was removed by filtration through celite and then the solvent was evaporated under reduced pressure to give 341 mg (80%) of the title compound as a colorless solid.

$^1$H-NMR (400 MHz, DMSO-$d_6$) δ: 1.00-1.10 (1H, m), 1:38 (2H, br s), 2.01-2.10 (1H, m), 2.55-2.65 (1H, m), 2.71-2.78 (1H, m), 2.78-2.95 (1H, m), 3.13-3.24 (1H, m), 3.29-3.39 (1H, m), 3.61-3.72 (2H, m), 4.36-4.44 (1H, m), 4.70 (1H, d, J=5.50 Hz).

MS (ESI) m/z: 148 $(M+H)^+$.

Reference Example 15

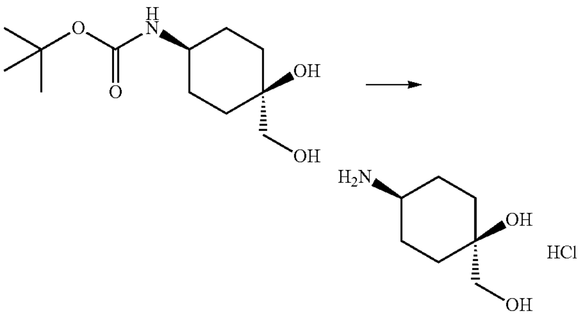

Cis-4-amino-1-(hydroxymethyl)cyclohexanol hydrochloride tert-Butyl[cis-4-hydroxy-4-(hydroxymethyl)cyclohexyl]carbamate (WO2010/027500) (376 mg, 1.53 mmol) was used as a starting material and treated in the same way as in Step 1 of Reference Example 2 to give the title compound as a colorless solid.

Reference Example 16

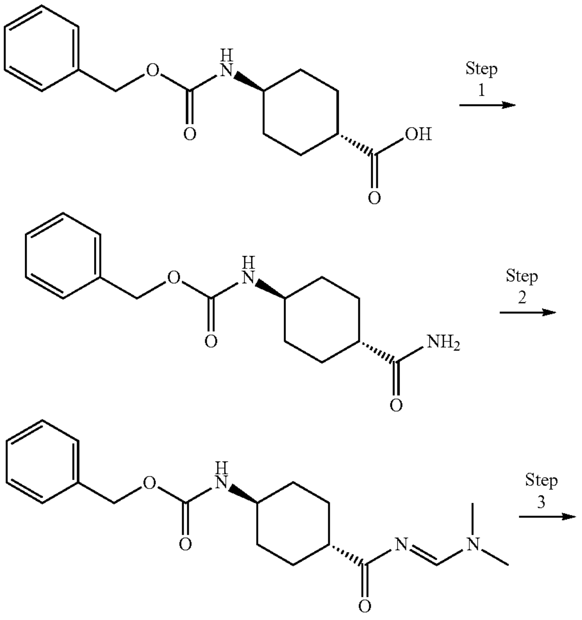

-continued

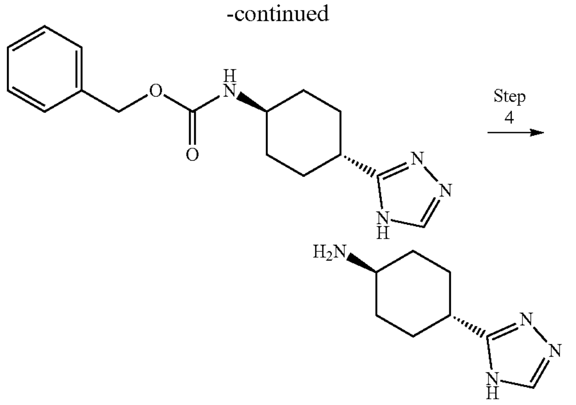

1 above was stirred at 120° ° C. for 3 hours. The solvent was evaporated under reduced pressure, then diethyl ether was added and the precipitated solid was collected by filtration to give 0.97 g (67%) of the title compound as a colorless solid.

$^1$H-NMR (400 MHz, $CDCl_3$) δ: 1.09-1.22 (2H, m), 1.51-1.60 (2H, m), 1.97-2.14 (4H, m), 2.22-2.34 (1H, m), 3.06 (3H, s), 3.10 (3H, s), 3.41-3.58 (1H, m), 4.53-4.64 (1H, m), 5.09 (2H, s), 7.29-7.37 (5H, m), 8.39 (1H, s).

MS (ESI) m/z: 332 $(M+H)^+$.

Step 1

Benzyl (trans-4-carbamoylcyclohexyl) carbamate

Triethylamine (1.4 ml, 10.1 mmol) was added to an N,N-dimethylformamide (120 ml) solution of trans-4-[((benzyloxy)carbonyl]amino)cyclohexanecarboxylic acid (1, 40 g, 5.10 mmol), ammonium chloride (0.54 g, 10.1 mmol), 1-hydroxybenzotriazole (0.39 g, 2.50 mmol), and 1-ethyl-3-(3-dimethylaminopropyl) carbodiimide hydrochloride (1.35 g, 7.10 mmol) and the resulting mixture was stirred at room temperature for 19 hours. Water was added and the precipitated solid was collected by filtration to give 1.20 g (86%) of the title compound as a colorless solid.

$^1$H-NMR (400 MHz, DMSO-$d_6$) δ: 1.07-1.21 (2H, m), 1.26-1.41 (2H, m), 1.68-1.87 (4H, m), 1.92-2.04 (1H, m), 3.15-3.27 (1H, m), 4.99 (2H, s), 6.67 (1H, br s), 7.12-7.21 (2H, m), 7.27-7.40 (5H, m).

MS (ESI) m/z: 277 $(M+H)^+$.

Step 2

Benzyl (trans-4-{[(E)=(dimethylamino)methylidene] carbamoyl}cyclohexyl) carbamate An N,N-dimethylformamide dimethyl acetal (20 ml) solution of the compound (1.20 g, 4.34 mmol) obtained in Step 1 above was stirred at 120° ° C. for 3 hours.

Step 3

Benzyl [trans-4-(4H-1,2,4-triazol-3-yl)cyclohexyl] carbamate

Hydrazine monohydrate (0.21 ml, 3.51 mmol) was added to an acetic acid (25 ml) solution of the compound (970 mg, 2.93 mmol) obtained in Step 2 above and the resulting mixture was stirred at room temperature for 2 hours. Water was added and the precipitated solid was collected by filtration to give 717 mg (82%) of the title compound as a colorless solid.

$^1$H-NMR (400 MHz, DMSO-$d_6$) δ: 1.23-1.58 (4H, m), 1.85-2.05 (4H, m), 2.47-2.55 (1H, m), 3.29-3.36 (1H, m), 5.01 (2H, s), 7.22-7.40 (6H, m).

MS (ESI) m/z: 301 $(M+H)^+$.

Step 4

Trans-4-(4H-1,2,4-triazol-3-yl)cyclohexanamine

The compound (360 mg, 1.20 mmol) obtained in Step 3 above was used as a starting material and treated in the same way as in Step 3 of Reference Example 2 to give 63 mg (31%) of the title compound as a colorless solid.

$^1$H-NMR (400 MHz, $CD_3OD$) δ: 1.22-1.38 (2H, m), 1.56-1.70 (2H, m), 1.95-2.11 (4H, m), 2.67-2.84 (2H, m), 8.05 (1H, s).

Reference Example 17

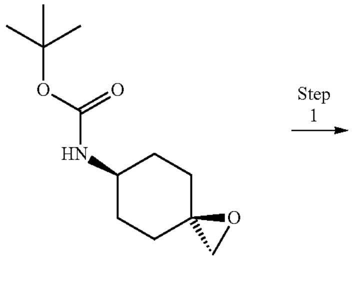

-continued

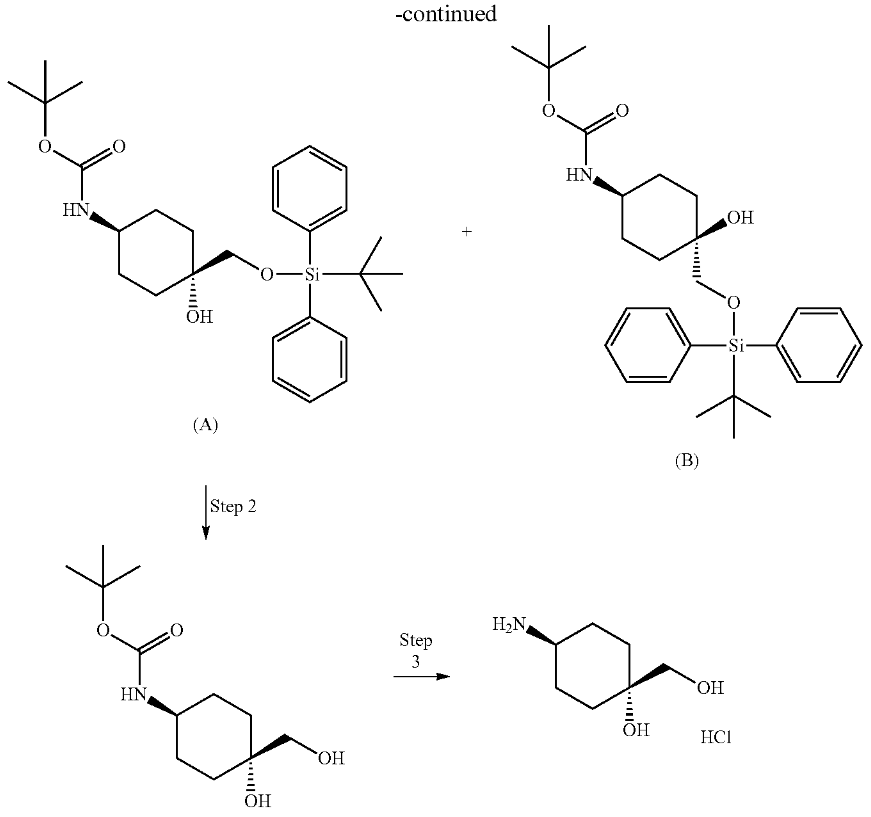

(A)

(B)

Step 1

Tert-butyl [trans-4-({[tert-butyl (diphenyl)silyl] oxy}methyl)-4-hydroxycyclohexyl] carbamate (A)

Cis-tert-butyl-1-oxaspiro[2.5]oct-6-ylcarbamate (WO2010/027500) (4.15 g, 18.3 mmol) was dissolved in 1,2-dimethoxyethane (50 ml) and water (200 ml), potassium hydroxide (5.13 g, 91.5 mmol) was added and the resulting mixture was heated to reflux for 3 hours. After cooling, the precipitate was removed by filtration and the filtrate was subjected to extraction with ethyl acetate. The organic layer was washed with brine and then dried over anhydrous magnesium sulfate. The solvent was evaporated under reduced pressure to give 2.33 g of a mixture of tert-butyl [cis-4-hydroxy-4-(hydroxymethyl)cyclohexyl]carbamate and tert-butyl [trans-4-hydroxy-4-(hydroxymethyl)cyclohexyl]carbamate as a colorless solid. The mixture above was dissolved in N,N-dimethylformamide (20 ml), tert-butyldiphenylchlorosilane (4.13 g, 15.0 mmol) and imidazole (2.74 g, 40.0 mmol) were added and the resulting mixture was stirred at room temperature for 1 hour. The reaction mixture was diluted with ethyl acetate, washed with water and brine, and dried over anhydrous magnesium sulfate. The solvent was evaporated under reduced pressure and the residue obtained was purified by silica gel column chromatography [acetonitrile:benzene=1:9 (v/v)] to give 0.81 g (9%) of the title compound as a colorless amorphous solid.

$^{1}$H-NMR (400 MHz, $CDCl_3$) δ: 1.07 (9H, 9), 1.17-1.27 (2H, m), 1.43 (9H, s), 1.53-1.66 (4H, m), 1.85-1.91 (2H, m), 2.54 (1H, s), 3.53 (2H, s), 3.61 (1H, m), 4.38 (1H, m), 7.38-7.47 (6H, m), 7.64-7.66 (4H, m).

MS (APCI) m/z: 482 $(M-H)^-$.

Step 2

Tert-butyl [trans-4-hydroxy-4-(hydroxymethyl)cyclohexyl]carbamate

Tetrabutylammonium fluoride/tetrahydrofuran solution (1.0 mol/1, 2.0 ml) was added to a tetrahydrofuran (8 ml) solution of the compound (0.80 g, 1.65 mmol) obtained in Step 1 above and the resulting mixture was stirred at room temperature for 1 hour. The solvent was evaporated under reduced pressure and the residue was purified by silica gel column chromatography [chloroform:methanol=9:1 (v/v)] to give 372 mg (92%) of the title compound as a colorless solid.

$^{1}$H-NMR (400 MHz, DMSO-$d_6$) δ: 1.19-1.31 (4H, m), 1.37 (9H, s), 1.61-1.67 (4H, m), 3.24 (2H, d, J=5.5 Hz), 3.34 (1H, m), 3.94 (1H, s), 4.33 (1H, t, J=6.0 Hz), 6.63 (1H, d, J=6.9 Hz).

MS (FAB) m/z: 246 $(M+H)^+$.

Step 3

Trans-4-amino-1-(hydroxymethyl)cyclohexanol hydrochloride

The compound (67 mg, 0.27 mmol) obtained in Step 2 above was used as a starting material and treated in the same way as in Step 1 of Reference Example 2 to give the title compound as a colorless solid.

Reference Example 18

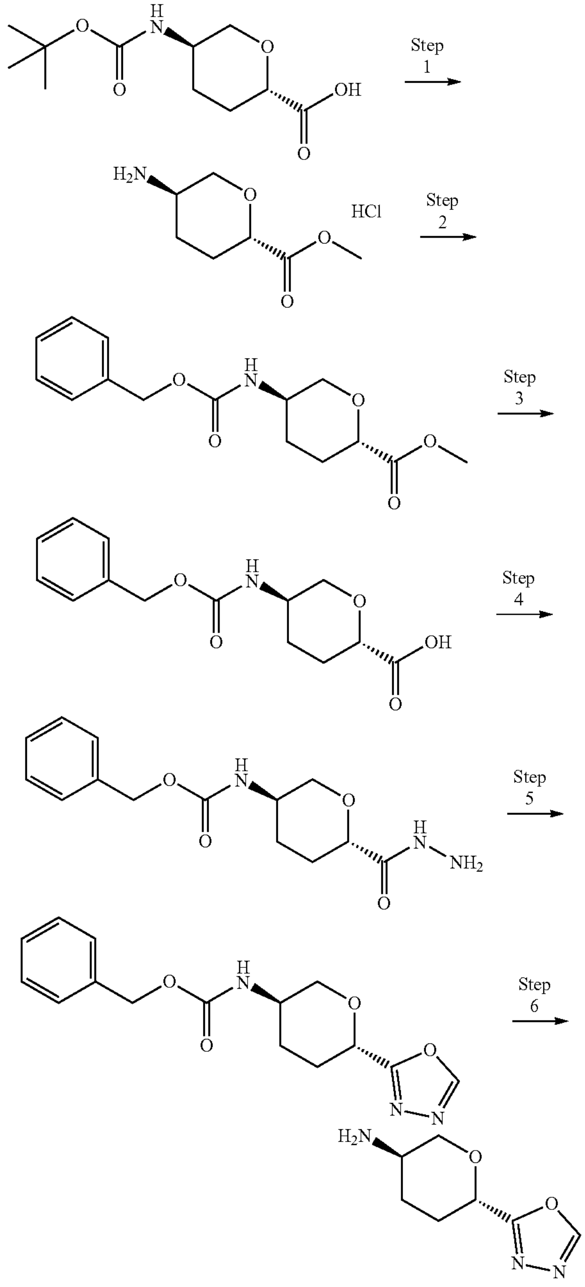

Step 1

Methyl 5-amino-2,6-anhydro-3,4,5-trideoxy-L-erythro-hexonate hydrochloride 4N hydrochloric acid/1,4-dioxane solution (20 ml) was added to a methanol (5 ml) solution of 2,6-anhydro-5-[(tert-butoxycarbonyl)amino]-3,4,5-trideoxy-L-erythro-hexonic acid (Eur. J. Org. Chem., 2003, 2418-2427) (1.00 g, 4.08 mmol) at room temperature and the resulting mixture was stirred for 20 hours. The reaction mixture was concentrated under reduced pressure to give 0.80 g (100%) of the title compound.

MS (ESI) m/z: 160 $(M+B)^+$.

Step 2

Methyl 2,6-anhydro-5-{[(benzyloxy) carbonyl] amino}-3,4,5-trideoxy-L-erythro-hexonate The compound (0.80 g, 4.08 mmol) obtained in Step 1 above was dissolved in acetonitrile (10 ml) and water (20 ml), sodium bicarbonate (1.71 g, 30.4 mmol) and carbobenzoxy chloride (0.72 ml, 4.89 mmol) were added under ice cooling and the resulting mixture was stirred at 5° C. for 21 hours. Saturated sodium bicarbonate solution was added to the reaction mixture, followed by extraction with dichloromethane:methanol [10:1 (v/v)]. The organic layer was dried over anhydrous sodium sulfate. The solvent was concentrated under reduced pressure and the residue obtained was purified by silica gel column chromatography [n-hexane:ethyl acetate=17:3→3:2 (v/v)] to give 0.97 g (81%) of the title compound as a colorless solid.

$^1$H-NMR (400 MHz, $CDCl_3$) δ: 1.38-1.54 (1H, m), 1.66-1.85 (1H, m), 2.03-2.16 (2H, m), 3.12-3.23 (1H, m), 3.70-3.80 (4H, m), 3.91-4.01 (1H, m), 4.15-4.25 (1H, m), 4.66-4.79 (1H, m), 5.01-5.17 (2H, m), 7.29-7.39 (5H, m).

Step 3

2,6-Anhydro-5-{[(benzyloxy)carbonyl]amino}-3,4,5-trideoxy-L-erythro-hexonic acid 1N sodium hydroxide solution (55.4 ml, 55.4 mmol) was added to a tetrahydrofuran (110 ml) solution of the compound (3.12 g, 27.7 mmol) obtained in Step 2 above at room temperature and the resulting mixture was stirred for 2 hours. 10% Citric acid solution was added under ice cooling, followed by extraction with ethyl acetate. Then the organic layer was washed with brine. The organic layer was dried over anhydrous sodium sulfate, then the solvent was concentrated under reduced pressure and the residue was dried under reduced pressure to give 7.78 g (100%) of the title compound as a colorless solid.

$^1$H-NMR (400 MHz, $CD_3OD$) δ: 1.45-1.73 (2H, m), 1.98-2.16 (2H, m), 3.10-3.20 (1H, m), 3.51-3.64 (1H, m), 3.85-3.95 (1H, m), 4.00-4.09 (1H, m), 5.06 (2H, s), 6.93-7.08 (1H, m), 7.22-7.44 (5H, m).

Step 4

Benzyl [(3R,6S)-6-(hydrazinocarbonyl)tetrahydro-2H-pyran-3-yl]carbamate

Hydrazine monohydrate (0.23 ml, 3.86 mmol), 1-hydroxybenzotriazole (434 mg, 3.21 mmol), and 1-ethyl-3-(3-dimethylaminopropyl)carbodiimide hydrochloride (740 mg, 3.86 mmol) were added to an N,N-dimethylformamide (16 ml) solution of the compound (898 mg, 3.21 mmol) obtained in Step 3 above at room temperature and the resulting mixture was stirred for 18 hours. The reaction mixture was subjected to extraction with chloroform:methanol [10:1 (v/v)] and the organic layer was washed with saturated sodium bicarbonate solution and then dried over anhydrous sodium sulfate. The solvent was concentrated under reduced pressure and the residue obtained was purified by silica gel column chromatography [dichloromethane:methanol=49:1→13:1 (v/v)] to give 811 mg (86%) of the title compound as a colorless solid.

$^1$H-NMR (400 MHz; $CD_3OD$) δ: 1.42-1.60 (2H, m), 2.00-2.16 (2H, m), 3.11 (1H, t, J=10.8 Hz), 3.50-3.62 (1H, m), 3.75-3.83 (1H, m), 4.02-4.11 (1H, m), 5.06 (2H, s), 7.26-7.37 (5H, m).

MS (ESI) m/z: 294 $(M+H)^+$.

Step 5

Benzyl [(3S,6S)-6-(1,3,4-oxadiazol-2-yl)tetrahydro-2H-pyran-3-yl]carbamate

The compound (2.27 g, 7.74 mmol) obtained in Step 4 above was used as a starting material and treated in the same way as in Step 2 of Reference Example 3 at room temperature to give 2.00 g (85%) of the title compound as a colorless solid.

$^1$H-NMR (500 MHz, $CDCl_3$) δ: 1.49-1.63 (1H, m), 2.04-2.30 (3H, m), 3.27-3.37 (1H, m), 3.76-3.90 (1H, m), 4.14-4.22 (1H, m), 4.66-4.77 (2H, m), 5.04-5.19 (2H, m), 7.31-7.40 (5H, m), 8.41 (1H, s).

MS (ESI) m/z: 304 $(M+H)^+$.

Step 6

(3R,6S)-6-(1,3,4-oxadiazol-2-yl)tetrahydro-2H-pyran-3-amine

The compound (749 mg, 2.47 mmol) obtained in Step 5 above was used as a starting material and treated in the same way as in Step 3 of Reference Example 2 to give 418 mg (100%) of the title compound as a light brown solid.

$^1$H-NMR (500 MHz, $CDCl_3$) δ: 1.36-1.48 (1H, m), 1.98-2.10 (1H, m), 2.12-2.25 (2H, m), 2.93-3.02 (1H, m), 3.18-3.25 (1H, m), 4.04-4.11 (1H, m), 4.63-4.69 (1H, m), 8.42 (1H, s).

Reference Example 19

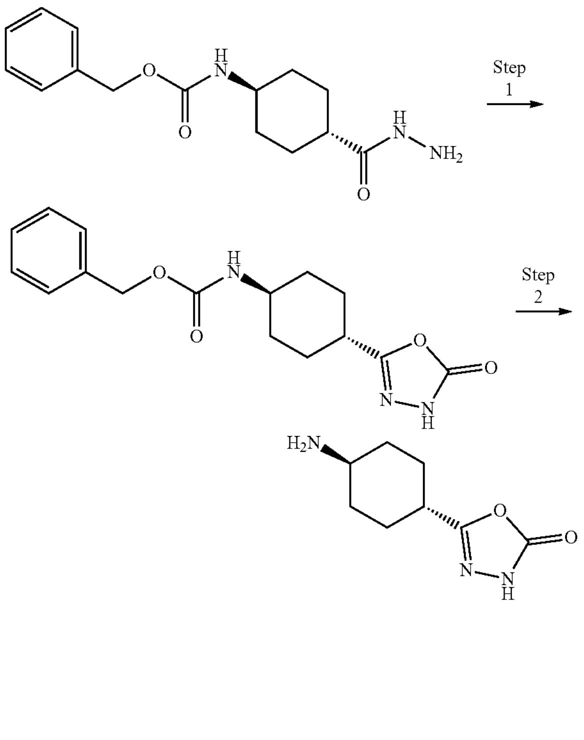

Step 1

Benzyl [trans-4-(5-oxo-4,5-dihydro-1,3,4-oxadiazol-2-yl)cyclohexyl]carbamate

Triphosgene (0.36 g, 1.17 mmol) was added to a 1,4-dioxane (15 ml) suspension of the compound (1.00 g, 3.43 mmol) obtained in Step 1 of Reference Example 3 under ice cooling and the resulting mixture was stirred at room temperature for 20 hours. Water was added to the reaction mixture, the resulting mixture was stirred for 70 minutes and then the solid was collected by filtration and dried under reduced pressure to give 685 mg (638) of the title compound as a colorless solid.

$^1$H-NMR (500 MHz, $CDCl_3$) δ: 1.17-1.28 (2H, m), 1.54-1.65 (2H, m), 2.05-2.21 (4H, m), 2.46-2.56 (1H, m), 3.47-3.61 (1H, m), 4.58-4.66 (1H, m), 5.09 (2H, s), 7.29-7.39 (5H, m), 8.12 (1H, s).

Step 2

5-(Trans-4-aminocyclohexyl)-1,3,4-oxadiazol-2(3H)-one

The compound (685 mg, 2.16 mmol) obtained in Step 1 above was used as a starting material and treated in the same way as in Step 3 of Reference Example 2 to give 341 mg (86%) of the title compound as a colorless solid.

$^1$H-NMR (500 MHz, $CD_3OD$) δ: 1.21-1.32 (2H, m), 1.40-1.51 (2H, m), 1.88-2.05 (4H, m), 2.43-2.51 (1H, m), 2.75-2.83 (1H, m).

Reference Example 20

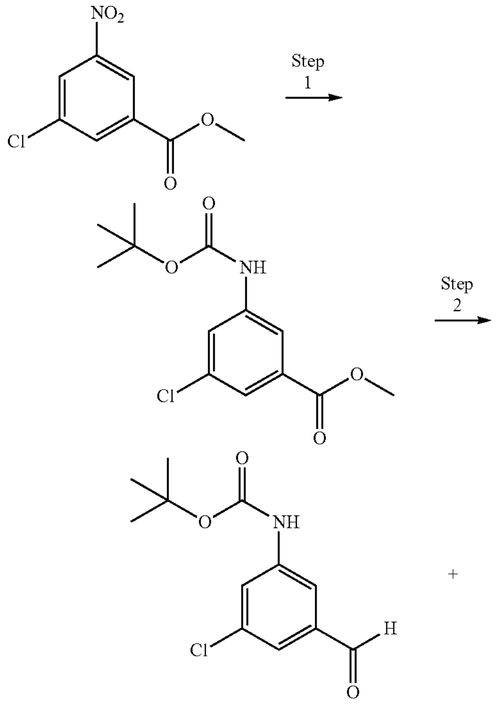

-continued

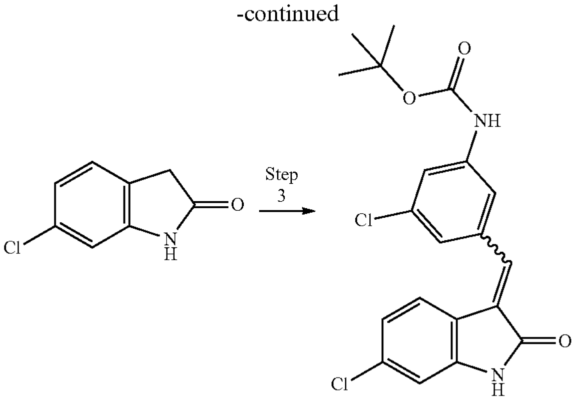

Step 1

Methyl 3-[(tert-butoxycarbonyl)amino]-5-chlorobenzoate

Zinc powder (7.54 g, 116 mmol) and acetic acid (23 ml) were added to a methanol (230 ml) solution of methyl 3-chloro-5-nitrobenzoate (5.00 g, 23.0 mmol) under ice cooling and the resulting mixture was heated to reflux for 4 hours. The reaction mixture was filtered through celite and then saturated sodium bicarbonate solution was added to the filtrate, followed by extraction with ethyl acetate. The organic layer was dried over anhydrous sodium sulfate, then the solvent was concentrated under reduced pressure and the residue obtained was dissolved in tetrahydrofuran (250 ml). Di-tert-butyl dicarbonate (7.52 g, 34.5 mmol) and 4-dimethylaminopyridine (141 mg, 1.16 mmol) were added and the resulting mixture was heated at 50° C. for 16 hours. Saturated sodium bicarbonate solution was added to the reaction mixture, followed by extraction with ethyl acetate. The organic layer was dried over anhydrous sodium sulfate. The solvent was evaporated under reduced pressure and the residue obtained was purified by silica gel column chromatography [n-hexane:ethyl acetate=2:1 (v/v)] to give 2.77 g (41%) of the title compound as a colorless solid.

$^1$H-NMR (400 MHz, $CDCl_3$) δ: 1.51 (9H, s), 3.91 (3H, s), 6.61 (1H, br s), 7.66-7.68 (1H, m), 7.74-7.77 (1H, m), 7.80-7.85 (1H, m).

MS (FAB) m/z: 286 $(M+H)^+$.

Step 2

Tert-butyl (3-chloro-5-formylphenyl) carbamate

Lithium borohydride (294 mg, 1.40 mmol) was added to a tetrahydrofuran (100 ml) solution of the compound (2.67 g, 9.36 mmol) obtained in Step above under ice cooling and the resulting mixture was stirred at room temperature for 3 days and then stirred at 50° C. for 2 hours. Water was added to the reaction mixture, followed by extraction with ethyl acetate. The organic layer was washed with brine and then dried over anhydrous sodium sulfate. The solvent was evaporated under reduced pressure and the residue was dissolved in dichloromethane (100 ml): Dimethyl sulfoxide (2.00 ml, 28.1 mmol), N,N-diisopropylethylamine (4.81 ml, 28.1 mmol), and a sulfur trioxide-pyridine complex (4.38 g, 28.1 mmol) were added and the resulting mixture was stirred at room temperature for 16 hours. Saturated sodium bicarbonate solution was added to the reaction mixture, followed by extraction with ethyl acetate. The organic layer was washed with brine and then dried over anhydrous sodium sulfate. The solvent was evaporated under reduced pressure and the residue obtained was purified by silica gel column chromatography [n-hexane:ethyl acetate=4:1 (v/v)] to give 2.21 g (92%) of the title compound as a colorless solid.

$^1$H-NMR (400 MHz, $CDCl_3$) δ: 1.53 (9H, s), 6.65 (1H, br s), 7.50-7.54 (1H, m), 7.71-7.74 (1H, m), 7.75-7.78 (1H, m), 9.92 (1H, s),

MS (FAB) m/z: 256 $(M+H)^+$.

Step 3

Tert-butyl {3-chloro-5-[(3E/Z)-(6-chloro-2-oxo-1,2-dihydro-3H-indol-3-ylidene)methyl]phenyl}carbamate 6-Chloro-1,3-dihydro-2H-indol-2-one (1.31 g, 7.85 mmol) and the compound (2.01 g, 7.85 mmol) obtained in Step 2 above were dissolved in methanol (40 ml) at room temperature and N,N-diisopropylethylamine (0.21 ml, 1.25 mmol) was added; After heating to reflux for 24 hours, saturated sodium bicarbonate solution was added to the reaction mixture, followed by extraction with ethyl acetate. The organic layer was washed with brine and then dried over anhydrous sodium sulfate. The solvent was evaporated under reduced pressure and the residue was purified by silica gel column chromatography [n-hexane:ethyl acetate=4:1 (v/v)] to give 2.53 g (82%) of the title compound as an orange solid.

MS (FAB) m/z: 405 $(M+H)^+$.

Reference Example 21

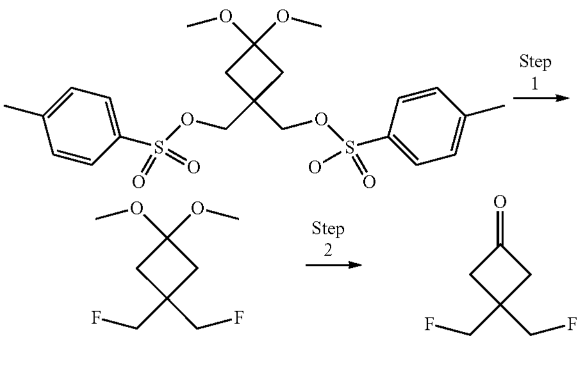

Step 1

1,1-Bis(fluoromethyl)-3,3-dimethoxycyclobutane

Tetrabutylammonium fluoride/tetrahydrofuran solution (1.0 mol/1, 74.3 ml, 74.3 mmol) was added to a tetrahydrofuran (5 ml) solution of (3,3-dimethoxycyclobutane-1,1-diyl)bis(methylene) bis(4-methylbenzenesulfonate) (9.0 g, 18.6 mmol) and the resulting mixture was stirred at 50° C. for 20 hours. After cooling, tetrabutylammonium fluoride/tetrahydrofuran solution (1.0 mol/1, 37.1 ml, 37.1 mmol) was further added and the resulting mixture was stirred at 50° C. for 12 hours. After cooling, saturated sodium bicarbonate solution was added at 0° ° C., followed by extraction with diethyl ether. The organic layer was washed with saturated ammonium chloride solution and brine and then dried over anhydrous magnesium sulfate. The solvent was evaporated under reduced pressure (80 mmHg, 17° C.) and the residue was purified by silica gel column chromatography [n-hexane:ether=9:1→1:1 (v/v)] to give 3.90 g (95%) of the title compound as a colorless oil.

$^1$H-NMR (400 MHz, $CDCl_3$) δ: 2.05 (4H, m), 3.15 (6H, s), 4.39-4.51 (4H, m).

Step 2

3,3-Bis(fluoromethyl)cyclobutanone 1N hydrochloric acid (61.7 ml, 61.7 mmol) was added to a tetrahydrofuran (42 ml) solution of the compound (2.8 g, 12.3 mmol) obtained in Step 1 above at 0° ° C. After stirring at room temperature for 13 hours, the reaction mixture was diluted with diethyl ether at 0° C. and saturated sodium bicarbonate solution was added for extraction. The organic layer was washed with brine and then dried over anhydrous magnesium sulfate. The solvent was evaporated under reduced pressure (110 mmHg, 17° C.) to give 3.63 g (100%) of the title compound as a colorless oil, $^1$H-NMR (400 MHz, $CDCl_3$) δ: 2.99-3.04 (4H, m), 4.53-4.66 (4H, m).

Reference Example 22

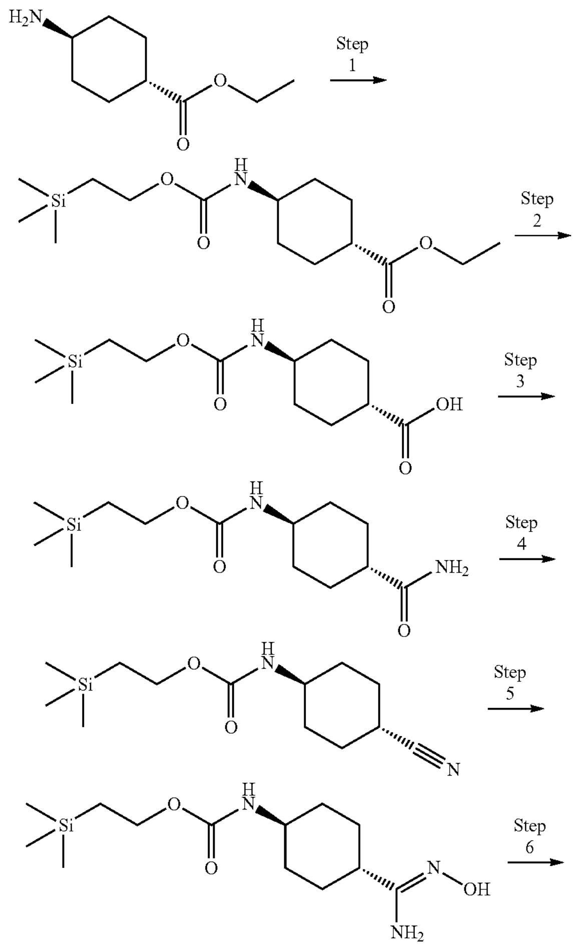

-continued

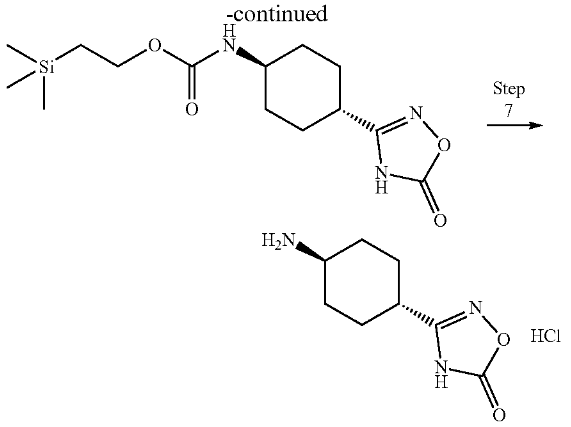

Step 1

Ethyl trans-4-({[2-(trimethylsilyl)ethoxy] carbonyl}amino)cyclohexanecarboxylate Ethyl trans-4-amino)cyclohexanecarboxylate (J. Med. Chem., 1971, 14, 600-614) (29.5 g, 143 mmol) was dissolved in 1,4-dioxane (290 ml) and water (290 ml), triethylamine (30.0 ml, 215 mmol) and 1-[2-(trimethylsilyl) ethoxycarbonyloxy]pyrrolidine-2,5-dione (40.8 g, 157 mmol) were added under ice cooling and the resulting mixture was stirred at room temperature for 2 days. The reaction mixture was concentrated and then the residue was diluted with ethyl acetate and washed with 10% aqueous citric acid solution, saturated sodium bicarbonate solution, and brine in that order. The organic layer was dried over anhydrous sodium sulfate and the solvent was concentrated under reduced pressure to give 44.3 g (93%) of the title compound as colorless needle-like crystals.

$^1$H-NMR (500 Mhz, $CDCl_3$) δ: 0.03 (9H, s), 0.92-1.01 (2H, m), 1.08-1.18 (2H, m), 1.25 (3H/t, J=7.2 Hz), 1.48-1.59 (2H, m), 1.97-2.11 (4H, m), 2.21 (1H, tt, J=12.3, 3.7 Hz), 3.38-3.54 (1H, m), 4.07-4.19 (4H, m), 4.38-4.49 (1H, m).

Step 2

Trans-4-({[2-(trimethylsilyl) ethoxy] carbonyl}amino)cyclohexanecarboxylic acid

The compound (44.3 g, 140 mmol) obtained in Step 1 above was dissolved in tetrahydrofuran (500 ml) and water (100 ml), lithium hydroxide monohydrate (11.8 g, 281 mmol) was added at room temperature and the resulting mixture was stirred for 2 days. Lithium hydroxide monohydrate (2.95 g, 70.2 mmol) was further added, the resulting mixture was further stirred for 27 hours, then the reaction mixture was concentrated and 10% aqueous citric acid solution was added to the residue, followed by extraction with ethyl acetate. The organic layer was washed with brine and then dried over anhydrous sodium sulfate and the solvent was concentrated under reduced pressure to give 40.0 g (99%) of the title compound as a colorless solid.

$^1$H-NMR (500 MHz, $CDCl_3$) δ: 0.04 (9H, s), 0.92-1.02 (2H, m), 1.10-1.20 (2H, m); 1.47-1.63. (2H, m), 2.01-2.13 (4H, m), 2.23-2.31 (1H, m), 3.40-3.55 (1H, m), 4.08-4.20 (2H, m), 4.41-4.50 (1H, m).

Step 3

2-(Trimethylsilyl)ethyl (trans-4-carbamoylcyclohexyl)carbamate

The compound (3.23 g, 11.2 mmol) obtained in Step 2 above and ammonium chloride (1.20 g, 22.5 mmol) were used as starting materials and treated in the same way as in Step 1 of Reference Example 16 to give 3.16 g (98%) of the title compound as a colorless solid.

$^1$H-NMR (500 MHz, $CDCl_3$) δ: 0.04 (9H, s), 0.92-1.01 (2H, m), 1.09-1.20 (2H, m), 1.52-1.62 (2H, m), 1.95-2.02 (2H, m), 2.06-2.15 (2H, m), 3.40-3.54 (2H, m), 4.08-4.19 (2H, m), 4.38-4.49 (1H, m), 5.17-5.27 (1H, m), 5.35-5.45 (1H, m).

Step 4

2-(Trimethylsilyl)ethyl (trans-4-cyanocyclohexyl)carbamate

Anhydrous trifluoroacetic acid (2.30 ml, 16.6 mmol) was added to a dichloromethane (60 ml) solution of the compound (3.16 g, 11.0 mmol) obtained in Step 3 above combined with triethylamine (3.10 ml, 22.1 mmol) under ice cooling. After stirring at room temperature for 75 minutes, saturated sodium bicarbonate solution was added to the reaction mixture. After extraction with dichloromethane, the organic layer was dried over anhydrous sodium sulfate. The solvent was concentrated under reduced pressure and the residue obtained was purified by silica gel column chromatography [n-hexane:ethyl acetate=19:1→3:2 (v/v)] to give 3.06 q (100%) of the title compound as a pale yellow solid.

$^1$H-NMR (500 MHz, $CDCl_3$) δ: 0.04 (9H, s), 0.92-1.01 (2H, m), 1.14-1.24 (2H, m), 1.64-1.75 (2H, m), 2.05-2.15 (4H, m), 2.37-2.45 (1H, m), 3.43-3.59 (1H, m), 4.10-4.18 (2H, x), 4.39-4.52 (1H, m).

Step 5

2-(Trimethylsilyl)ethyl {trans-4-[(Z)-amino (hydroxyimino)methyl]cyclohexyl}carbamate Aqueous hydroxylamine solution (50% w/w, 0.68 ml, 11.1 mmol) was added to an ethanol (40 ml) solution of the compound (1.03 g, 3.71 mmol) obtained in Step 4 above at room temperature and the resulting mixture was heated to reflux for 21 hours. After cooling, the reaction mixture was Concentrated under reduced pressure to give the title compound as a colorless solid.

Step 6

2-(Trimethylsilyl)ethyl [trans-4-(5-oxo-4,5-dihydro-1,2,4-oxadiazol-3-yl)cyclohexyl]carbamate Carbonyldiimidazole (1.24 g, 7.43 mmol) was added to a tetrahydrofuran (20 ml) solution of the compound (1.12 g, 3.71 mmol) obtained in Step 5 above under ice cooling and the resulting mixture was stirred at 50° C. for 24 hours. The reaction mixture was diluted with dichloromethane:methanol [10:1 (v/v)] and washed with 10% aqueous citric acid solution and saturated sodium bicarbonate solution in that order and then the organic layer was dried over anhydrous sodium sulfate. The solvent was concentrated under reduced pressure and the residue obtained was purified by silica gel column chromatography [n-hexane:ethyl acetate=9:1→13:7→dichloromethane:methanol=49:1→19:1 (v/v)] to give 757 mg (62%) of the title compound as a colorless solid.

$^1$H-NMR (500 MHz; $CDCl_3$) δ: 0.05 (9H, s), 0.94-1.02 (2H, m), 1.22-1.33 (2H, m), 1.62-1.75 (2H, m), 2.00-2.09 (2H, m), 2.14-2.22 (2H, m), 2.55-2.65 (1H, m), 3.44-3.58 (1H, m), 4.18-4.24 (2H, m), 4.61 (1H, d, J=8.0 Hz).

Step 7

3-(Trans-4-aminocyclohexyl)-1,2,4-oxadiazol-5 (4H)-one hydrochloride 4N hydrochloric acid/1,4-dioxane solution (3.5 ml) was added to the compound (349 mg, 1.06 mmol) obtained in Step 6 above at room temperature and the resulting mixture was stirred for 23 hours. The reaction mixture was concentrated under reduced pressure to give 234 mg (100%) of the title compound as a colorless solid.

$^1$H-NMR (500 MHz, $CD_3OD$) δ: 1.45-1.67 (4H, m), 2.11-2.19 (4H, m), 2.59-2.68 (1H, m), 3.10-3.19 (1H, m).

Reference Example 23

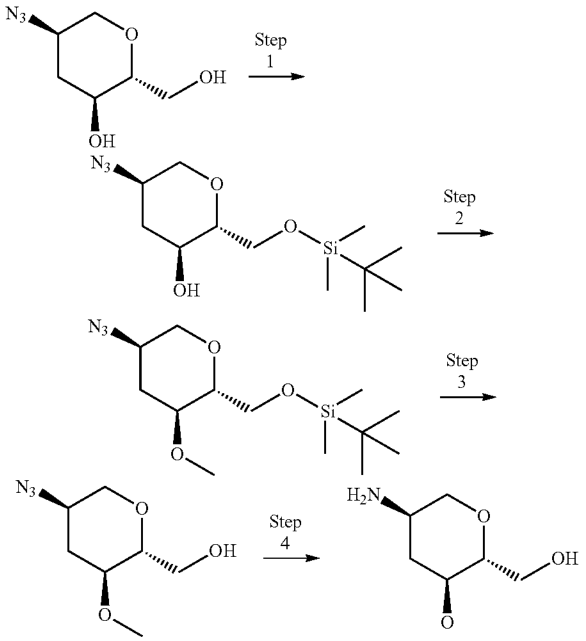

Step 1

1,5-Anhydro-2-azido-6-O-[tert-butyl(dimethyl)silyl]-2,3-dideoxy-D-ribo-hexitol

A dichloromethane (4 mi) solution of tert-butyldimethylchlorosilane (381 mg, 2.54 mmol) was added to a dichloromethane (10 ml) solution of 1,5-anhydro-2-azido-2,3-dideoxy-D-ribo-hexitol (440 mg, 2.54 mmol) and triethylamine (0.46 ml, 3.30 mmol) under ice cooling. After stirring at room temperature for 50 hours, the reaction mixture was diluted with chloroform and the organic layer was washed with water and brine. The organic layer was dried over anhydrous sodium sulfate, then the solvent was evaporated under reduced pressure and the residue was purified by silica gel column chromatography [n-hexane: ethyl acetate=10:1→4:1 (v/v)] to give 650 mg (89%) of the title compound as a colorless oil.

$^1$H-NMR (400 MHz, $CDCl_3$) δ: 0.07-0.10 (6H, m), 0.88 (9H, s), 1.41-1.53 (1H, m), 2.39-2.49 (1H, m), 3.06-3.18 (2H, m), 3.41-3.57 (2H, m), 3.62-3.71 (2H, m), 3.88-3.96 (2H, m).

MS (ESI) m/z: 310/(M+Na)$^+$.

Step 2

1,5-Anhydro-2-azido-6-O-[tert-buty] (dimethyl) silyl)-2,3-dideoxy-4-O-methyl-D-ribo-hexitol Sodium hydride (60% oil, 136 mg, 3.39 mmol) was added to a tetrahydrofuran (11 ml) solution of the compound (650 mg, 2.26 mmol) obtained in Step 1 above under ice cooling, the resulting mixture was stirred for 5 minutes and then methyl iodide (0.42 ml, 6.78 mmol) was added. After stirring at the same temperature for 1 hour, saturated ammonium chloride solution was added, the resulting mixture was subjected to extraction with ethyl acetate and the organic layer was washed with brine. The organic layer was dried over anhydrous sodium sulfate and then the solvent was evaporated under reduced pressure to give the title compound.

Step 3

1,5-Anhydro-2-azido-2,3-dideoxy-4-O-methyl-D-ribo-hexitol

Tetrabutylammonium fluoride/tetrahydrofuran solution (1.0 mol/l, 3.6 ml, 3.60 mmol) was added to a tetrahydrofuran (7 ml) solution of the compound (2.26 mmol) obtained in Step 2 above and the resulting mixture was stirred at room temperature for 16 hours. The solvent was evaporated under reduced pressure and water was added, followed by extraction with ethyl acetate. The organic solvent was dried over anhydrous sodium sulfate, the solvent was evaporated under reduced pressure and the residue obtained was purified by silica gel column chromatography [n-hexane:ethyl acetate=4:1→1:1 (v/v)] to give 329 mg (78%) of the title compound as a colorless oil.

$^1$H-NMR (400 MHz, $CDCl_3$) δ: 1.34-1.44 (1H, m), 1.90-1.97 (1H, m), 2.61-2.69 (1H, m), 3.13-3.29 (3H, m), 3.39 (3H, s), 3.42-3.53 (1H, m), 3.65-3.73 (1H, m), 3.81-3.89 (1H, m), 3.97-4.04 (1H, m).

Step 4

2-Amino-1,5-anhydro-2,3-dideoxy-4-O-methyl-D-ribo-hexitol

The compound (329 mg, 1.76 mmol) obtained in Step 3 above was used as a starting material and treated in the same way as in Step 4 of Reference Example 14 to give 283 mg (100%) of the title compound as a colorless oil, $^1$H-NMR (400 MHz, $CD_3OD$) δ: 1.04-1.15 (1H, m), 2.45-2.54 (1H, m), 2.73-2.84 (1H, m), 2.94-3.08 (2H, m), 3.11-3.21 (1H, m), 3.35 (3H, s), 3.58 (1H, dd, J=11.69, 5.73 Hz), 3.74-3.81 (1H, m), 3.84-3.92 (1H, m).

MS (ESI) m/z: 162 (M+H)$^+$.

Reference Example 24

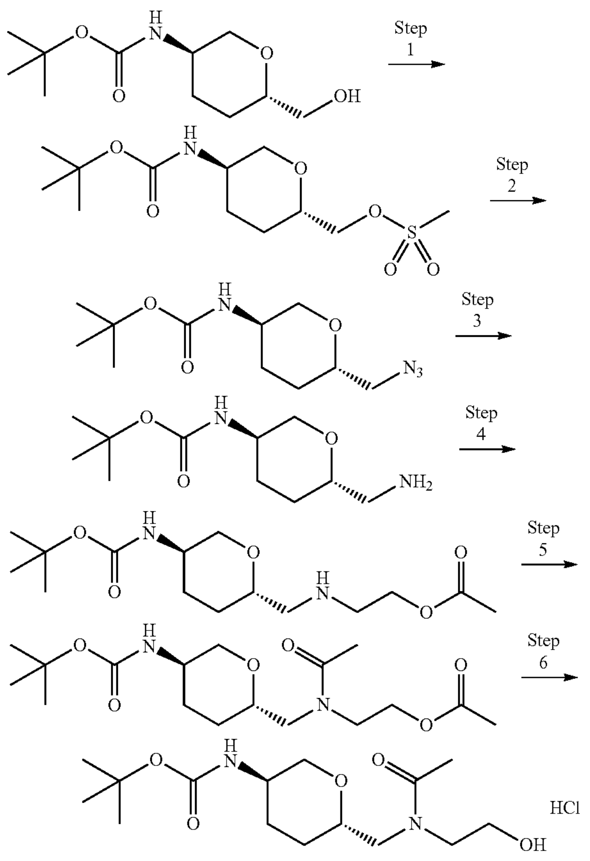

Step 1

1,5-Anhydro-2-[(tert-butoxycarbonyl)amino]-2,3,4-trideoxy-6-O-(methylsulfonyl)-D-erythro-hexitol The same starting material (2.38 g, 10.30 mmol) as in Step 1 of Reference Example 2 was used and treated in the same way as in Step 1 of Reference Example 14 to give 1.34 g (42%) of the title compound as a colorless solid.

$^1$H-NMR (500 MHz, $CDCl_3$) δ: 1.28-1.36 (1H, m), 1.44-1.54 (9H, m), 1.72 (1H, do, J=13.0, 3.1 Hz), 2.12-2.17 (1H, m), 3.02 (1H, t, J=10.6 Hz), 3.05 (3H, s), 3.53-3.64 (2H, m), 4.13-4.10 (1H, m), 4.28-4.15 (3H, m).

MS (FAB) m/z: 310 (M+H)$^+$.

Step 2

1,5-Anhydro-6-azido-2-[(tert-butoxycarbonyl)amino]-2,3,4,6-tetradeoxy-D-erythro-hexitol The compound obtained in Step 1 above was used as a starting material and treated in the same way as in Step 2 of Reference Example 14 to give the title compound.

$^1$H-NMR (400 MHz, $CDCl_3$) δ: 1.23-1.34 (1H, m), 1.44 (9H, =), 1.46-1.53 (1H, m), 1.66-1.71 (1H, m), 2.09-2.15 (1H, m), 3.02 (1H, t, J=10, 8 Hz), 3.21 (1H, dd, J=12.6, 3.9 Hz), 3.30 (1H, dd, J=12.8, 6.9 Hz), 3.39-3.45 (1H, m), 3.60-3.64 (1H, m), 4.12 (1H, dq, J=10.9, 2.3 Hz), 4.24 (1H, br s).

MS (ESI) m/z: 279 (M+Na)$^+$.

Step 3

6-Amino-1,5-anhydro-2-[(tert-butoxycarbonyl)amino]-2,3,4,6-tetradeoxy-D-erythro-hexitol The compound obtained in Step 2 above was used as a starting material and treated in the same way as in Step 4 of Reference Example 14 to give the title compound.

$^1$H-NMR (400 MHz, DMSO-$d_6$) δ: 1.13-1.32 (2H, m), 1.35 (9H, s), 1.60-1.65 (1H, m), 1.78-1.84 (1H, m), 2.50 (2H, d, J=5.9 Hz), 2.91 (1H, t, J=10.6 Hz), 3.01-3.08 (1H, m), 3.25-3.30 (1H, m), 3.74-3.79 (1H, m), 6.72 (1H, d, J=8.1 Hz).

Step 4

6-[(2-Acetoxyethyl)amino]-1,5-anhydro-2-[(tert-butoxycarbonyl)amino]-2,3,4,6-tetradeoxy-D-erythro-hexitol The compound (500 mg, 2.17 mmol) obtained in Step 3 above was dissolved in dichloromethane (10 ml), 2-oxoethyl acetate (243 mg, 2.39 mmol) was added and the resulting mixture was stirred at room temperature for 1 hour. Then sodium triacetoxyborohydride (920 mg, 4.34 mmol) was added and the resulting mixture was stirred at room temperature for 3 hours. After reaction, saturated sodium bicarbonate solution (50 ml) was added and the resulting mixture was further stirred for 1 hour. The reaction mixture was diluted with dichloromethane and the organic layer was washed with brine. The organic layer was dried over anhydrous sodium sulfate and the solvent was evaporated under reduced pressure. The residue obtained was purified by silica gel column chromatography [chloroform:methanol=40:1→20:1 (v/v)] to give 544 mg (64%) of the title compound as a colorless oil.

$^1$H-NMR (400 MHz, $CDCl_3$) δ: 1.23-1.33 (1H, m), 1.39-1.49 (10H, m), 1.65-1.71 (1H, m), 2.06-2.15 (4H, m), 2.61-2.70 (2H, m), 2.80-2.90 (2H, m), 2.99 (1H, t, J=10.5 Hz), 3.34-3.40 (1H, m), 3.56-3.62 (1H, m), 4.05-4.19 (3H, m), 4.24 (1H, br s).

MS (ESI) m/z: 317 $(M+H)^+$.

Step 5

6-[(2-Acetoxyethyl) (acetyl)amino]-1,5-anhydro-2-{(tert-butoxycarbonyl)amino}-2,3,4,6-tetradeoxy-D-erythro-hexitol The compound (264 mg, 0.83 mmol) obtained in Step 4 above was dissolved in dichloromethane (8 ml), acetic anhydride (0:50 ml, 5.30 mmol) was added and the resulting mixture was stirred at room temperature for 1 hour. Then pyridine (0.10 ml, 1.24 mmol) was added and the resulting mixture was further stirred for 1 hour. Saturated brine (20 ml) was added to the reaction mixture and the resulting mixture was stirred for 1 hour, followed by extraction with dichloromethane. The organic layer was washed with saturated sodium bicarbonate solution and brine in that order and dried over anhydrous magnesium sulfate. The solvent was evaporated under reduced pressure and the residue obtained was purified by silica gel column chromatography [chloroform:methanol=40:1 (v/v)] to give 244 mg (82%) of the title compound as a colorless amorphous solid.

$^1$H-NMR (400 MHz, $CDCl_3$) δ: 1.15-1.40 (3H, m), 1.43 (9H, s), 1.71-1.76 (1H, m), 2.05 and 2.06 (total 3H, each s), 2.11 and 2.15 (total 3H, each s), 2.82-3.02 (2H, m), 3.24-3.78 (5H, m), 4.01-4.30 (4H, m).

MS (ESI) m/z: 359 $(M+H)^+$.

Step 6

6-[(2-Acetoxyethyl) (acetyl)amino]-2-amino-1,5-anhydro-2,3,4,6-tetradeoxy-D-erythro-hexitol hydrochloride The compound (240 mg, 0.67 mmol) obtained in Step 5 above was used as a starting material and treated in the same way as in Step 1 of Reference Example 2 to give the title compound as a colorless amorphous solid.

Reference Example 25

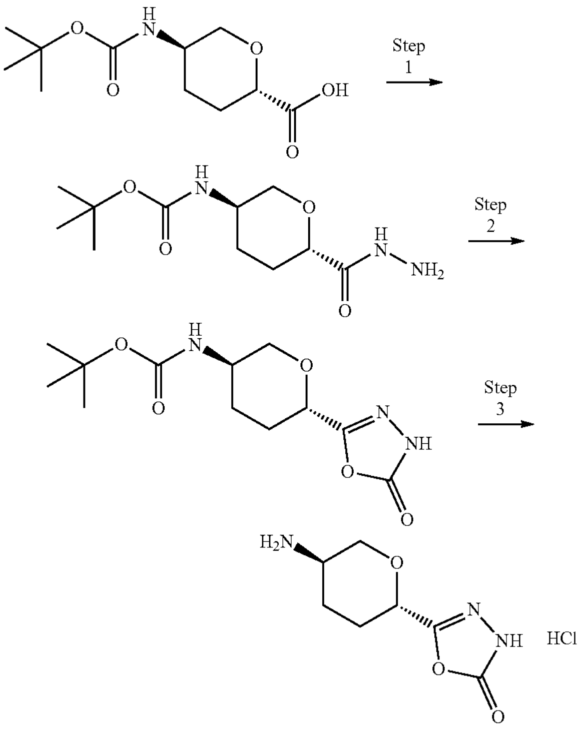

Step 1

Tert-butyl [(3R,6S)-6-(hydrazinocarbonyl)tetrahydro-2H-pyran-3-yl]carbamate

The same starting material (1.52 g, 6.20 mmol) as in Step 1 of Reference Example 18 was used and treated in the same way as in Step 4 of Reference Example 18 to give 1.33 g (83%) of the title compound as a colorless solid.

$^1$H-NMR (500 MHz, $CDCl_3$) δ: 1.30-1.60 (11H, m), 2.10-2.18 (1H, m), 2.20-2.28 (1H, m), 3.03 (1H, t, J=10.9 Hz), 3.55-3.68 (1H, m), 3.81 (1H, dd, J=11.7, 2.6 Hz), 4.12-4.19 (1H, m), 4.27-4.38 (1H, m), 7.63 (1H, s).

MS (ESI) m/z: 260 $(M+H)^+$.

Step 2

Tert-butyl [(3R,6S)-6-(5-oxo-4,5-dihydro-1,3,4-oxadiazol-2-yl)tetrahydro-2H-pyran-3-yl]carbamate The compound (1.33 g, 5.13 mmol) obtained in Step 1 above was used as a starting material and treated in the same way as in Step 1 of Reference Example 19 to give 1.10 g (75%) of the title compound as a colorless solid.

$^1$H-NMR (500 MHz, $CD_3OD$) δ: 1.38-1.58 (10H, m), 1.84-1.95 (1H, m), 1.96-2.03 (1H, m), 2.05-2.13 (1H, m), 3.20 (1H, t, J=10.6 Hz), 3.48-3.59 (1H, m), 3.97-4.05 (1H, m), 4.28 (1H, dd, J=10.6, 2.6 Hz), 6.59-6.71 (1H, m).

MS (ESI) m/z: 286 $(M+H)^+$.

Step 3

5-[(2S,5R)-5-aminotetrahydro-2H-pyran-2-yl]-1,3,4-oxadiazol-2 (3H)-one hydrochloride The compound (1.10 g, 3.86 mmol) obtained in Step 2 above was used as a starting material and treated in the same way as in Step 1 of Reference Example 2 to give 688 mg (81%) of the title compound as a colorless solid.

$^1$H-NMR (400 MHz, $CD_3OD$) δ: 1.70-1.82 (1H, m), 1.94-2.06 (1H, m), 2.08-2.17 (1H, m), 2.25-2.34 (1H, m), 3.29-3.38 (1H, m), 3.54 (1H, do, J=11.5, 9.16 Hz), 4.07-4.15 (1H, m), 4.49 (1H, dd, J=9.6, 3.2 MHz).

MS (ESI) m/z: 186 $(M+H)^+$.

Reference Example 26

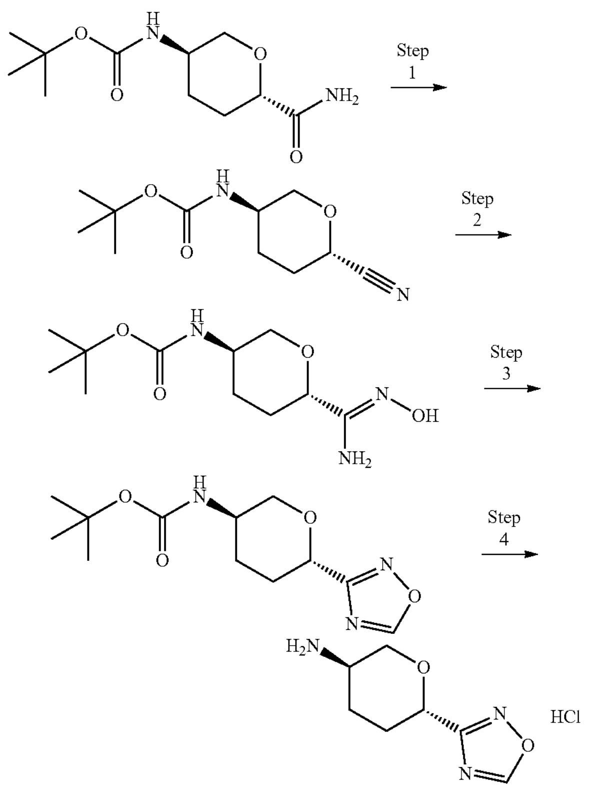

Step 1

Tert-butyl [(3R,6S)-6-cyanotetrahydro-2H-pyran-3-yl]carbamate

Tert-butyl [(3R, 6S)-6-carbamoyltetrahydro-2H-pyran-3-yl]carbamate (WO2006/125974) (1.54 g, 6.30 mmol) was used as a starting material and treated in the same way as in Step 4 of Reference Example 22 to give 1.39 g (978) of the title compound as a colorless solid.

$^1$H-NMR (500 MHz, $CDCl_3$) δ: 1.45 (9H, s), 1.74-1.90 (2H, m), 2.00-2.20 (2H, m), 3.52-3.67 (1H, m), 3.70-3.83, (1H, m), 4.05 (1H, dd, J=12.0, 2.9 Hz), 4.56-4.67 (1H, m), 4.85-4.98 (1H, m).

Step 2

Tert-butyl {(3R,6S)-6-[(Z)-amino (hydroxyimino) methyl]tetrahydro-2H-pyran-3-yl}carbamate The compound (1.39 g, 6.14 mmol) obtained in Step 1 above was used as a starting material and treated in the same way as in Step 5 of Reference Example 22 to give 1.59 g (100%) of the title compound as a colorless solid.

Step 3

Tert-butyl [(3R,6S)-6-(1,2,4-oxadiazol-3-yl)tetrahydro-2H-pyran-3-yl]carbamate

Trimethyl orthoformate (6.0 ml) was added to an N,N-dimethylacetamide (20 ml) solution of the compound (1.59 g, 6.14 mmol) obtained in Step 2 above at room temperature under nitrogen atmosphere and then a boron trifluoride-diethyl ether complex (0.08 ml, 0.61 mmol) was added. After stirring at 50° C. for 21 hours, the reaction mixture was cooled, triethylamine (0.86 ml, 6.14 mmol) was added at room temperature and the resulting mixture was stirred for 80 minutes. The reaction mixture was diluted with dichloromethane:methanol [10:1 (v/v)] and washed with saturated sodium bicarbonate solution and then the organic layer was dried over anhydrous sodium sulfate. The solvent was concentrated under reduced pressure and the residue obtained was purified by silica gel column chromatography [n-hexane:ethyl acetate=9:1→7:3 (v/v)] to give 1.46 g (898) of the title compound as a colorless solid.

$^1$H-NMR (400 MHz, $CDCl_3$) δ: 1.39-1.63 (10H, m), 1.95-2.29 (3H, m), 3.20-3.36 (1H, m), 3.68-3.86 (1H, m), 4.17-4.29 (2H, m), 4.43-4.58 (1H, m), 4.60-4.68 (1H, m), 8.74 (1H, s).

Step 4

(3R,6S)-6-(1,2,4-oxadiazol-3-yl)tetrahydro-2H-pyran-3-amine hydrochloride

The compound (1.46 g, 5.43 mmol) obtained in Step 3 above was used as a starting material and treated in the same way as in Step 1 of Reference Example 2 to give 988 mg (88%) of the title compound as a colorless solid.

$^1$H-NMR (400 MHz, $CD_3OD$) δ: 1.75-1.88 (1H, m), 1.99-2.11 (1H, m), 2.16-2.25 (1H, m), 2.26-2.35 (1H, m), 3.32-3.41 (1H, m), 3.58 (1H, dd, J=11.5, 9.6 Hz), 4.14-4.21 (1H, m), 4.76-4.81 (1H, m), 9.28 (1H, s).

Reference Example 27

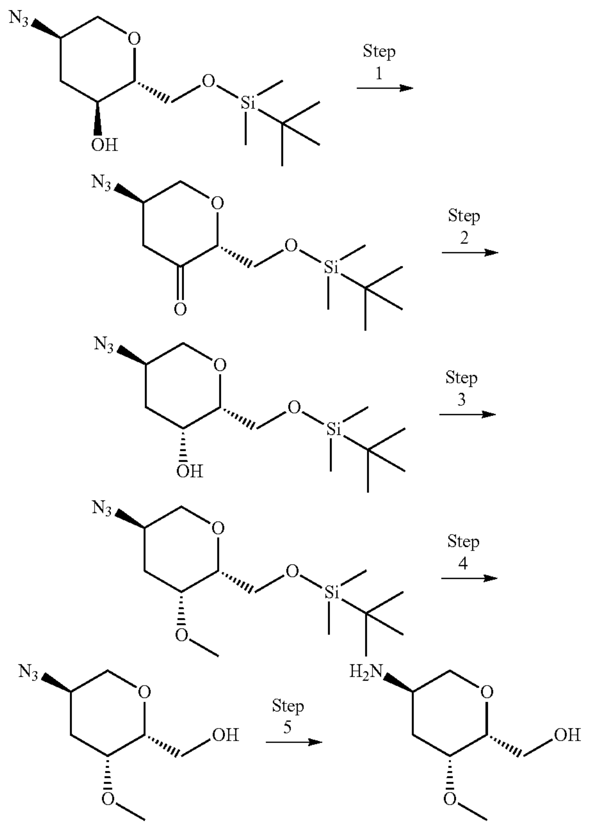

Step 1

2,6-Anhydro-5-azido-1-O-[tert-butyl(dimethyl)silyl]-4,5-dideoxy-L-erythro-hex-3-ulose A Dess-Martin reagent (876 mg, 2.00 mmol) was added to a dichloromethane (10 ml) solution of 1,5-anhydro-2-azido-6-O-[tert-butyl(dimethyl)silyl]-2,3-dideoxy-D-ribo-hexitol (450 mg, 1.25 mmol) under ice cooling and the resulting mixture was stirred for 75 minutes. Aqueous sodium thiosulfate solution was added under ice cooling, then the resulting mixture was subjected to extraction with ether and the organic layer was washed with brine. The organic layer was dried over anhydrous sodium sulfate, then the solvent was evaporated under reduced pressure and the residue was purified by silica gel column chromatography [n-hexane: ethyl acetate 50:1→20:1 (v/v)] to give 272 mg (76%) of the title compound as a colorless oil.

$^1$H-NMR (400 MHz, $CDCl_3$) δ: 0.02 (3H, s), 0.04 (3H, s), 0.85 (9H, s), 2.55 (1H, dd, J=16.1, 6.4 Hz), 2.86 (1H, dd, J=16.1, 5.7 Hz), 3.58-3.67 (1H, m), 3.87-4.00 (3H, m), 4.06-4.16 (1H, m), 4.31-4.39 (1H, m).

MS (ESI) m/z: 308 (M+Na)$^+$.

Step 2

1,5-Anhydro-2-azido-6-O-[tert-butyl(dimethyl)silyl]-2,3-dideoxy-D-xylo-hexitol

Lithium tri-sec-butylborohydride/tetrahydrofuran solution (1.0 mol/1, 0.83 ml, 0.83 mmol) was added to a tetrahydrofuran (2.5 ml) solution of the compound (169 mg, 0.59 mmol) obtained in Step 1 above at −78° C. and the resulting mixture was stirred at −78° ° C. for 45 minutes, 1N hydrochloric acid was added, the resulting mixture was subjected to extraction with ethyl acetate and the organic layer was washed with brine. The organic layer was dried over anhydrous sodium sulfate, then the solvent was evaporated under reduced pressure and the residue was purified by silica gel column chromatography [n-hexane:ethyl acetate=20:1→12:1 (v/v)] to give 101 mg (59%) of the title compound as a colorless oil.

$^1$H-NMR (400 MHz, $CDCl_3$) δ: 0.07 (3H, s), 0.08 (3H, s), 0.88 (9H, s), 1.49-1.58 (1H, m), 2.28-2.36 (1H, m), 3.14-3.27 (2H, m), 3.43-3.48 (1H, m), 3.85-3.96 (3H, m), 4.03-4.15 (2H, m).

MS (ESI) m/z: 288 (M+H)$^+$.

Step 3

1,5-Anhydro-2-azido-6-O-[tert-butyl(dimethyl)silyl]-2,3-dideoxy-4-C-methyl-D-xylo-hexitol The compound (160 mg, 0.56 mmol) obtained in Step 2 above was used as a starting material and treated in the same way as in Step 2 of Reference Example 23 to give the title compound.

Step 4

1,5-Anhydro-2-azido-2,3-dideoxy-4-O-methyl-D-xylo-hexitol

The compound (0.56 mmol) obtained in Step 3 above was used as a starting material and treated in the same way as in Step 3 of Reference Example 23 to give 62 mg (60%) of the title compound as a colorless solid.

$^1$H-NMR (400 MHz, $CDCl_3$) δ: 1.43-1.52 (1H, m), 2.10 (1H, dd, J=9.2, 2.8 Hz), 2.47-2.56 (1H, m), 3.21-3.29 (1H, m), 3.40 (3H, s), 3.41-3.46 (1H, m), 3.51-3.55 (1H, m), 3.64-3.91 (3H, m), 4.09-4.17 (1H, m).

Step 5

2-Amino-1,5-anhydro-2,3-dideoxy-4-O-methyl-D-xylo-hexitol

The compound (62 mg, 0.33 mmol) obtained in Step 4 above was used as a starting material and treated in the same way as in Step 4 of Reference Example 14 to give 53 mg (100%) of the title compound as a colorless solid.

$^1$H-NMR (400 MHz, $CD_3OD$) δ: 1.19-1.30 (1H, m), 2.35-2.44 (1H, m), 2.93-3.10 (2H, m), 3.28-3.32 (1H, m), 3.35 (38) s), 3.45-3.51 (1H, m), 3.56-3.67 (2H, m), 3.87-3.96 (1H, m).

MS (ESI) m/z: 162 (M+H)$^+$.

Reference Example 28

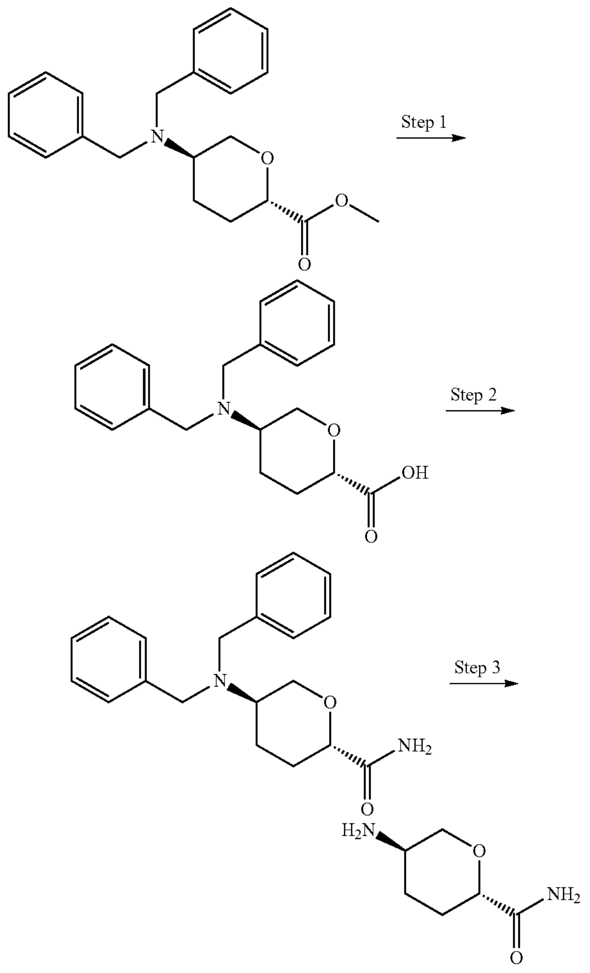

Step 1

2,6-Anhydro-3,4,5-trideoxy-5-(dibenzylamino)-L-erythro-hexonic acid

The same starting material (1.60 g, 4.70 mmol) as in Step 1 of Reference Example 5 was dissolved in methanol (30 ml), 1N sodium hydroxide solution (10 ml) was gradually added under ice cooling and then the resulting mixture was stirred at room temperature for 3 hours. Dowex 50W-X8 was added to the reaction mixture to adjust its pH to 5 to 6, insoluble matter was removed by filtration and then the filtrate was concentrated under reduced pressure to give 1.7 g (100%) of the title compound as a colorless amorphous solid.

$^1$H-NMR (400 MHz, $CDCl_3$) δ: 1.18-1.26 (1H, m), 1.36-1.48 (1H, m), 1.79-1.97 (2H, m), 2.62 (1H, t, J=11.0 Hz), 3.18 (1H, t, J=10.4 Hz), 3.40 (1H, d, J=11.5 Hz), 3.51-3.61 (4H, m), 3.90-3.99 (1H, m), 7.12-7.38 (10H, m).

MS (ESI) m/z: 326 $(M+H)^+$.

Step 2

(2S,5R)-5-(dibenzylamino)tetrahydro-2H-pyran-2-carboxamide

The compound (870 mg, 2.67 mmol) obtained in Step 1 above was dissolved in N,N-dimethylformamide (30 ml), 1-hydroxybenzotriazole (361 mg, 2.67 mmol) and 1-ethyl-3-(3-dimethylaminopropyl) carbodiimide hydrochloride (614 mg, 3.20 mmol) were added and the resulting mixture was stirred at room temperature for 15 minutes. Ammonium chloride (285 mg, 5.44 mmol) and N,N-diisopropylethylamine (1.86 ml, 10.7 mmol) were added and the resulting mixture was stirred at room temperature for 8 hours. The reaction mixture was diluted with ethyl acetate and the organic layer was washed with saturated sodium bicarbonate solution and brine in that order and dried over anhydrous sodium sulfate. The solvent was evaporated under reduced pressure to give 495 mg (57%) of the title compound as a colorless solid.

$^1$H-NMR (400 MHz, $CDCl_3$) δ: 1.35-1.45 (1H, m), 1.60-1.70 (1H, m), 2.10-2.18 (1H, m), 2.21-2.28 (1H, m), 2.76 (1H, tt, J=11.4, 4.0 Hz), 3.44 (1H, t, J=10.9 Hz), 3.67 (4H, q. J=14.2 Hz), 3.71-3.73 (1H, m), 4.04 (1H, dq, J=11.0, 2.1 Hz), 5.35 (1H, s), 6.40 (1H, s), 7.21-7.36 (10H, m).

MS (ESI) m/z: 325 $(M+H)^+$.

Step 3

(2S,5R)-5-aminotetrahydro-2H-pyran-2-carboxamide

The compound (490 mg, 1.51 mmol) obtained in Step 2 above was used as a starting material and treated in the same way as in Step 2 of Reference Example 5 to give 215 mg (99%) of the title compound as a colorless solid.

$^1$H-NMR (400 MHz, DMSO-$d_6$) δ: 1.11-1.22 (1H, m), 1.25-1.35 (1H, m), 1.83-1.91 (2H, m), 2.51-2.60 (1H, m), 2.90 (1H, t, J=10.5 Hz), 3.52 (1H, d, J=11.9 Hz), 3.78-3.84 (1H, m), 6.99 (1H, br s), 7.09 (1H, br s).

MS (ESI) m/z: 145 $(M+H)^+$.

Reference Example 29

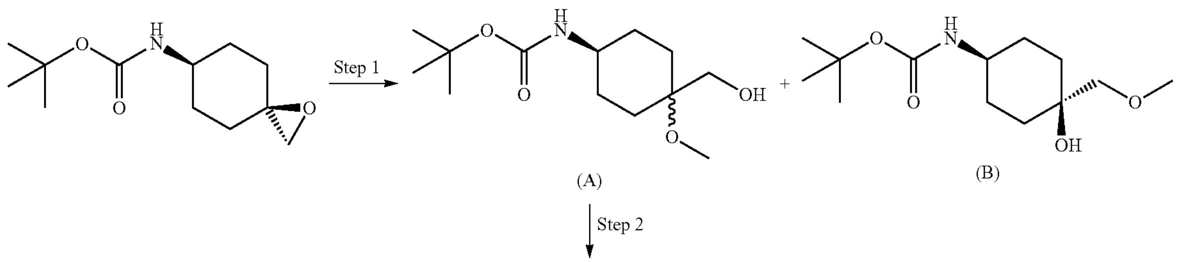

-continued

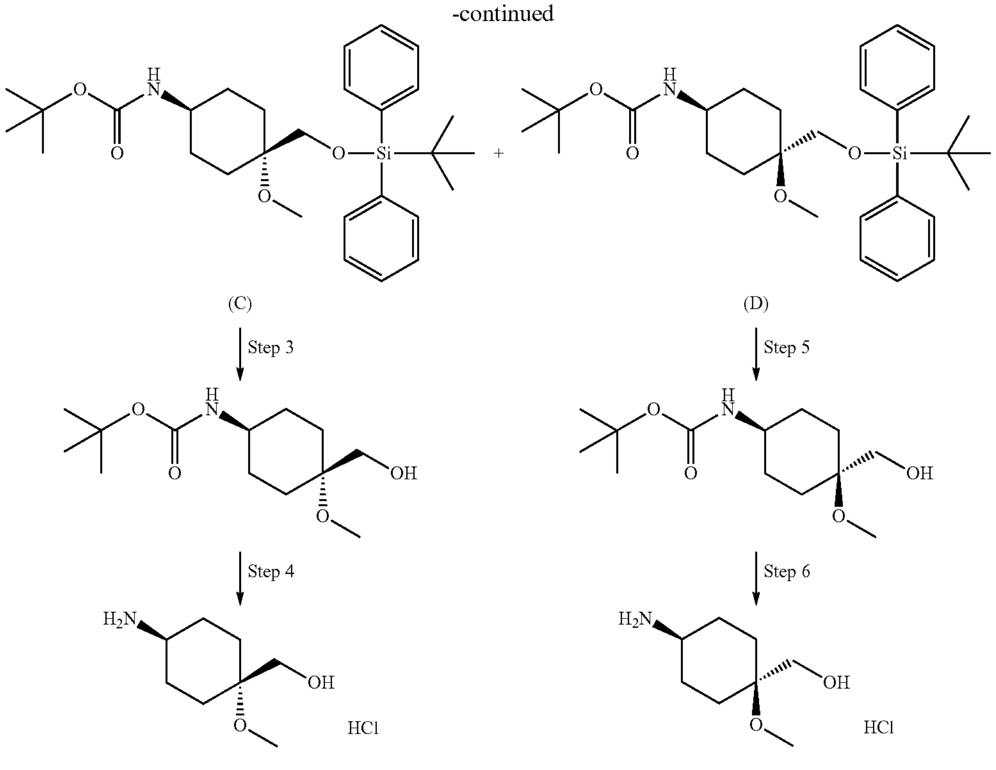

Step 1

Tert-butyl [4-(hydroxymethyl)-4-methoxycyclo-hexyl]carbamate (A)

Concentrated sulfuric acid (0.10 ml, 1.90 mmol) was added to a methanol (10 ml) solution of the same starting material (1.14 g, 5.02 mmol) as in Step 1 of Reference Example 17 and the resulting mixture was stirred overnight at room temperature. Potassium carbonate (1.34 g, 9.70 mmol) was added, followed by extraction with chloroform. The organic Layer was washed with water and brine and then dried over anhydrous sodium sulfate. The solvent was evaporated under reduced pressure and the residue obtained was purified by silica gel column chromatography (ethyl acetate) to separately give 422 mg (34%) of the title compound and 239 mg (18%) of the compound (B) as colorless amorphous solids.

$^1$H-NMR (500 MHz, $CDCl_3$) δ: 1.22-1.38 (3H, m), 1.44 (9H, s), 1.63 (3H, t, J=6.3 Hz), 1.80-1.83 (1H, m), 1.87-1.93 (2H, m), 3.19 (0.6H, s), 3.21 (2.4H, s), 3.45 (0.4H, d, =5.7 Hz), 3.55-3.61 (2.6H, m), 4.41-4.52 (1H, m).

Step 2

Tert-butyl [trans-4-({[tert-butyl (diphenyl)silyl] oxy}methyl)-4-methoxycyclohexyl]carbamate (C) and tert-butyl [cis-4-({[tert-butyl (diphenyl)silyl] oxy}methyl)-4-methoxycyclohexyl]carbamate (D)

Tert-butyldiphenylchlorosilane (667 mg, 2.4 mmol) and imidazole (441 mg, 6.5 mmol) were added to an N,N-dimethylformamide (4 ml) solution of the compound (A) (413 mg, 1.59 mmol) obtained in Step 1 above and the resulting mixture was stirred overnight at room temperature. The reaction mixture was diluted with ethyl acetate, washed with water and brine and then dried over anhydrous magnesium sulfate. The solvent was evaporated under reduced pressure and the residue obtained was purified by silica gel column chromatography [n-hexane:ethyl acetate=90:10 (v/v)] to separately give 513 mg of the title compound (C) (65%, highly polar compound) and 123 mg of the title compound (D) (168, low polar compound) as colorless amorphous solids.

Compound (C):

$^1$H-NMR (400 MHz, $CDCl_3$) δ: 1.08 (9H, s), 1.25-1.33 (2H, m), 1.45 (OH, s), 1.52-1.59 (2H, m), 1.63-1.70 (2H, m), 1.76-1.84 (2H, m), 3.23 (3H, s), 3.58 (2H, s), 3.61-3.67 (1H, m), 4.42-4.48, (1H, m), 7.37-7.47 (6H, m), 7.66-7.68 (4H, m).

Compound (D):

$^1$H-NMR (400 MHz, $CDCl_3$) δ: 1.05 (9H, s), 1.3:1-1.44 (13H, m), 1.77-1.85 (4H, m), 3.18 (3H, s), 3.39 (1H, m), 3.49 (2H, s), 4.42 (1H, d, J=6.9 Hz), 7.36-7.45 (6H, m), 7.64-7.66 (4H, m).

Step 3

Tert-butyl [trans-4-(hydroxymethyl)-4-methoxycy-clohexyl]carbamate

The compound (C) (511 mg, 1.03 mmol) obtained in Step 2 above was used as a starting material and treated in the same way as in Step 2 of Reference Example 17 to give 243 mg (91%) of the title compound as a colorless amorphous solid.

$^1$H-NMR (500 MHz, $CDCl_3$) δ: 1.31-1.38 (2H, m), 1.44 (3H, s), 1.63 (4H, t, J=6.3 Hz), 1.83 (1H, t, J=6.0 Hz), 1.87-1.93 (2H, m), 3.21 (3H, s), 3.55-3.60 (3H, m), 4.47-4.51 (1H, m).

MS (FAB) m/z: 260 $(M+H)^+$.

Step 4

(Trans-4-amino-1-methoxycyclohexyl)methanol hydrochloride

The compound (46 mg, 0.175 mmol) obtained in Step 3 above was used as a starting material and treated in the same way as in Step 1 of Reference Example 2 to give the title compound as a colorless solid.

Step 5

Tert-butyl [cis-4-(hydroxymethyl)-4-methoxycyclohexyl]carbamate

The compound (D) (127 mg, 0,254 mmol) obtained in Step 2 above was used as a starting material and treated in the same way as in Step 2 of Reference Example 17 to give 59 mg (89%) of the title compound as a colorless amorphous solid, $^1$H-NMR (500 MHz, $CDCl_3$) δ: 1.25 (2H, td, J=13.6, 3.6 Hz), 1.37 (2H, dq, J=3.4, 12.6 Hz), 1.44 (9H, s), 1.71 (1H, t, J=5.7 Hz), 1.80-1.83 (2H, m), 1.88-1.93 (2H, m), 3.19 (3H, s), 3.41-3.45 (3H, m), 4.43-4.46 (1H, m).

MS (FAB) m/z: 260 $(M+H)^+$.

Step 6

(Cis-4-amino-1-methoxycyclohexyl) methanol hydrochloride

The compound (30 mg, 0.115 mmol) obtained in Step 5 above was used as a starting material and treated in the same way as in Step 1 of Reference Example 2 to give the title compound as a colorless solid.

Reference Example 30

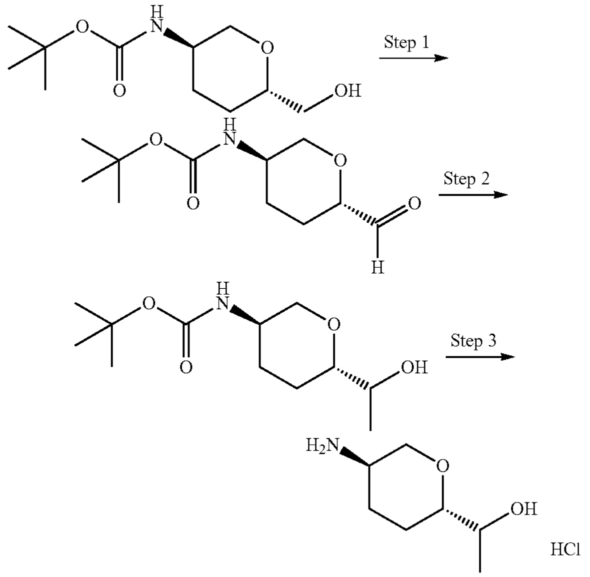

Step 1

2,6-Anhydro-5-[(tert-butoxycarbonyl)amino]-3,4,5-trideoxy-L-erythro-hexose

Dichloromethane (5 ml) and dimethyl sulfoxide (0.21 ml, 2.85 mmol) were mixed under nitrogen atmosphere, a dichloromethane (5 ml) solution of oxalyl chloride (0.21 ml, 2.50 mmol) was added dropwise at −78° C. and the resulting mixture was stirred for 30 minutes. A dichloromethane (5 ml) solution of the same starting material (440 mg, 1.90 mmol) as in Step 1 of Reference Example 2 was added dropwise at the same temperature and the resulting mixture was stirred for 1 hour. Then a dichloromethane (4 ml) solution of N,N-diisopropylethylamine (1.65 ml, 9.50 mmol) was added dropwise and the resulting mixture was stirred at the same temperature for 1 hour, warmed to room temperature, and further stirred for 1 hour. The reaction solvent was evaporated under reduced pressure and the residue was purified by silica gel column chromatography [n-hexane:ethyl acetate=1:1→1:2 (v/v)] to give 347 mg (80%) of the title compound as a colorless solid.

$^1$H-NMR (400 MHz, $CDCl_3$) δ: 1.36-1.44 (1H, m), 1.45 (9H, s), 1.53-1.63 (1H, m), 1.94-2.01 (1H, m), 2.10-2.17 (1H, m), 3.15 (1H, t, J=10.5 Hz), 3.59-3.67 (1H, m), 3.73 (1H, dd, J=11.0, 2.7 Hz), 4.17 (1H, dq, J=11.0, 2.1 Hz), 4.38 (1H, br s), 9.65 (1H, s).

Step 2

1,5-Anhydro-2-[(tert-butoxycarbonyl)amino]-2,3, 4,7-trideoxy-D-erythro-heptitol

The compound (2.80 g) obtained in Step 1 above was dissolved in diethyl ether (30 ml), methyl magnesium bromide/tetrahydrofuran solution (1.1 mol/l, 54.0 ml, 59.4 mmol) was added dropwise at 0° ° C. under nitrogen atmosphere and then the resulting mixture was stirred at room temperature for 16 hours. Methanol (5 ml) was gradually added, followed by extraction with ethyl acetate. The organic layer was washed with aqueous ammonium chloride solution and brine in that order and dried over anhydrous magnesium sulfate. The solvent was evaporated under reduced pressure and the residue was purified by silica gel column chromatography [n-hexane:ethyl acetate=2:1→1:1 (v/v)] to give 1.07 g (73%) of the title compound as a colorless solid.

$^1$H-NMR (400 MHz, $CDCl_3$) δ: 1.14 (3H, d, J=6.4 Hz), 1.23-1.32 (1H, m), 1.34-1.43 (1H, m), 1.44 (9H, s), 1.66-1.72 (1H, m), 2.08-2.14 (1H, m), 2.64 (1H, br s), 2.99 (1H, t, J=10.8 Hz), 3.56-3.64 (2H, m), 4.09-4.15 (1H, m), 4.25 (1H, br s).

MS (ESI) m/z: 2.68 $(M+Na)^+$.

Step 3

2-Amino-1,5-anhydro-2,3,4,7-tetradeoxy-D-erythro-heptitol hydrochloride

The mixture (700 mg, 2.85 mmol) obtained in Step 2 above was used as a starting material and treated in the same way as in Step 1 of Reference Example 2 to give 484 mg (93%) of the title compound as a colorless solid.

$^1$H-NMR (400 MHz, DMSO-$d_6$) δ: 1.06 (3H, d, J=6.4 Hz), 1.35-1.46 (1H, m), 1.53-1.64 (1H, m), 1.66-1.73 (1H, m), 2.11-2.18 (1H, m), 2.99-3.14 (2H, m), 3.31 (1H, t, J=10.8 Hz), 3.55-3.63 (1H, m), 4.05-4.12 (1H, m).

MS (ESI) m/z: 146 $(M+H)^+$.

Reference Example 31

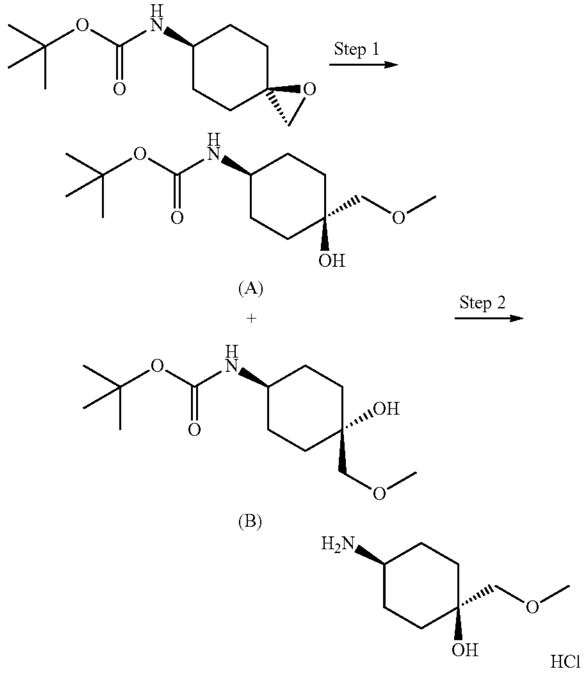

Step 1

Tert-butyl [cis-4-hydroxy-4-(methoxymethyl)cyclohexyl] carbamate (A) and tert-butyl [trans-4-hydroxy-4-(methoxymethyl)cyclohexyl]carbamate (B)

Sodium methylate/methanol solution (28% w/w, 2.0 ml, 10.0 mmol) was added to a methanol (7 ml) solution of the same starting material (0.75 g, 3.31 mmol) as in Step 1 of Reference Example 17 and the resulting mixture was stirred at 60° C. for 2 hours. Water was added, followed by extraction with ethyl acetate. The organic layer was washed with brine and then dried over anhydrous sodium sulfate. The solvent was evaporated under reduced pressure and the residue obtained was purified by silica gel column chromatography [n-hexane:ethyl acetate=1:1 (v/v)] to give 619 mg of the title compound (A) (72%, low polar compound) as a colorless amorphous solid. Also, 61 mg of the title compound (B) (7%, highly polar compound) was obtained as a colorless amorphous solid.

Compound (A):

$^1$H-NMR (400 MHz, $CDCl_3$) δ: 1.35 (2H, td, J=13.3, 4.0 Hz), 1.44 (98, s), 1.47-1.57 (2H, m), 1.70-1.75 (2H, m), 1.79-1.83 (2H, m), 2.06 (1H, s), 3.20 (2H, s), 3.38-3.43 (4H, m), 4.45-4.43 (1H, m).

MS (FAB) m/z: 260 $(M+H)^+$.

Compound (B):

$^1$H-NMR (500 MHz, $CDCl_3$) δ: 1.33-1.40 (2H, m), 1.44 (9H, s), 1.51-1.56 (2H, m), 1.64-1.69 (2H, m), 1.91-1.96 (2H, m) ¿ 2.33 (1H, s), 3.31 (2H, s), 3.40 (3H, s), 3.61-3.64 (1H, m), 4.49-4.53 (1H, m).

MS (FAB) m/z: 260 $(M+H)^+$.

Step 2

Cis-4-amino-1-(methoxymethyl)cyclohexanol hydrochloride

The compound (A) (80 mg, 0.31 mmol) obtained in Step 1 above was used as a starting material and treated in the same way as in Step 1 of Reference Example 2 to give the title compound as a colorless solid.

Reference Example 32

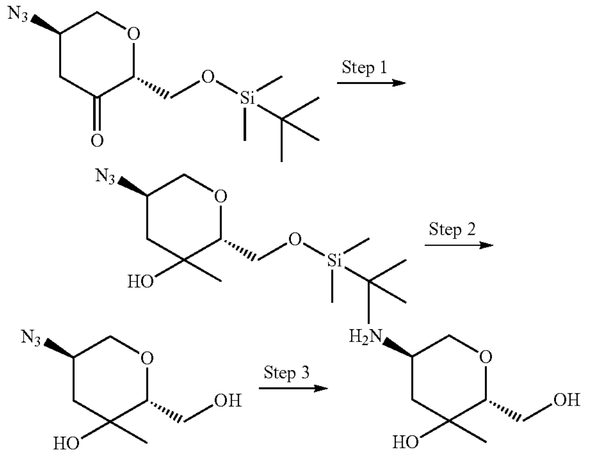

Step 1

1,5-Anhydro-2-azido-6-O-[tert-butyl(dimethyl)silyl]-2,3-dideoxy-4-C-methyl-D-erythro-hexitol Methylmagnesium bromide (1.06 mol/1, 0.47 ml, 0.50 mmol) was added to a tetrahydrofuran (1.4 ml) solution of the compound (80 mg, 0.28 mmol) obtained in Step 1 of Reference Example 27 at −40° C. and the resulting mixture was gradually warmed to −10° C. 1N hydrochloric acid was added and the resulting mixture was subjected to extraction with ethyl acetate. The organic layer was washed with saturated sodium bicarbonate solution and brine and dried over anhydrous sodium sulfate. The solvent was evaporated under reduced pressure and the residue was purified by silica gel column chromatography [n-hexane:ethyl acetate=50:1→20:1 (v/v)] to give 58 mg of a mixture of the title diastereomers (69%) as a colorless oil.

MS (ESI) m/z: 324 $(M+Na)^+$.

Step 2

1,5-Anhydro-2-azido-2,3-dideoxy-4-C-methyl-D-erythro-hexitol

The mixture (58 mg, 0.19 mmol) obtained in Step 1 above was used as a starting material and treated in the same way as in Step 3 of Reference Example 23 to give 25 mg (70%) of the title compound as a colorless oil.

Step 3

2-Amino-1,5-anhydro-2,3-dideoxy-4-C-methyl-D-erythro-hexitol

The mixture (25 mg, 0.13 mmol) obtained in Step 2 above was used as a starting material and treated in the same way as in Step 4 of Reference Example 14 to give 21 mg (100%) of the title compound as a colorless oil.

MS (ESI) m/z: 162 $(M+H)^+$.

Reference Example 33

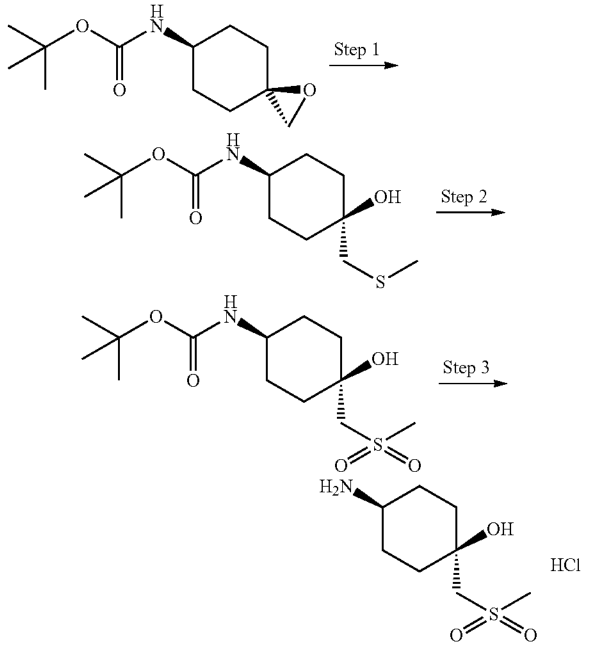

Step 1

Tert-butyl [cis-4-hydroxy-4-[(methylthio)methyl] cyclohexyl]carbamate

A methanol (5 ml) solution of the same starting material (1.00 g, 4.41 mmol) as in Step 1 of Reference Example 17 combined with sodium methanethiolate (465 mg, 6.64 mmol) was stirred for 1 hour. The reaction mixture was diluted with ethyl acetate, washed with water, saturated sodium bicarbonate solution, and brine in that order and then dried over anhydrous sodium sulfate. The solvent was evaporated under reduced pressure and the residue obtained was purified by silica gel column chromatography [ethyl acetate:benzene=3:7 (v/v)] to give 766 mg (638) of the title compound as a colorless solid.

$^1$H-NMR (500 MHz, $CDCl_3$) δ: 1.37-1.44 (11H, m), 1.49-1.57 (2H, m), 1.74 (2H, dq, J=14.2, 3, 1 Hz), 1.80-1.83 (2H, m), 2.15 (1H, s), 2.17 (3H, s), 2.61 (2H, s), 3.37-3.44 (1H, m), 4.43-4.45 (1H, m).

MS (FAB) m/z: 276 $(M+H)^+$.

Step 2

Tert-butyl {cis-4-hydroxy-4-[(methylsulfonyl) methyl] cyclohexyl}carbamate

M-chloroperbenzoic acid (25% hydrated, 538 mg, 2.34 mmol) was added to a dichloromethane (5 ml) solution of the compound (276 mg, 1.00 mmol) obtained in Step 1 above under ice cooling and the resulting mixture was stirred for 1 hour. The reaction mixture was diluted with ethyl acetate, washed with water, saturated sodium bicarbonate solution, and brine in that order and then dried over anhydrous sodium sulfate. The solvent was evaporated under reduced pressure and the residue obtained was purified by silica gel column chromatography [ethyl acetate:n-hexane=7:3 (v/v)] to give 292 mg (95%) of the title compound as a colorless solid.

$^1$H-NMR (500 MHz, $CDCl_3$) δ: 1.44. (9H, s), 1.51-1.62 (4H, m), 1.80-1.86 (2H, m), 2.03-2.10 (2H, m), 3.00 (3H, s), 3.19-3.21 (3H, m), 3.40-3.46 (1H, m), 4.40-4.46 (1H, m).

MS (FAB) m/z: 308 $(M+H)^+$.

Step 3

Cis-4-amino-1-[(methylsulfonyl)methyl] cyclohexanol hydrochloride

The compound (62 mg, 0.20 mmol) obtained in Step 2 above was used as a starting material and treated in the same way as in Step 1 of Reference Example 2 to give the title compound as a colorless solid.

Reference Example 34

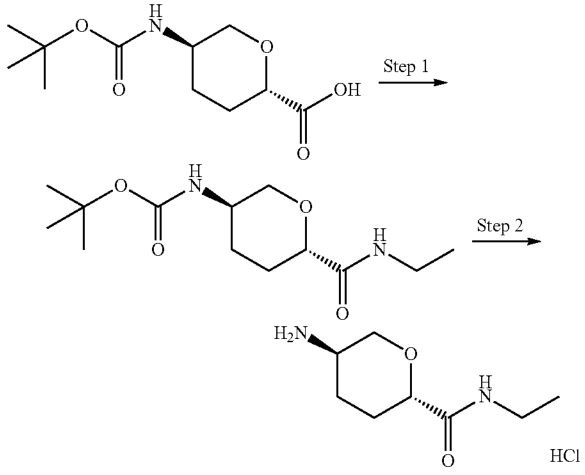

Step 1

Tert-butyl [(3R,6S)-6-(ethylcarbamoyl)tetrahydro-2H-pyran-3-yl]carbamate

The same starting material (500 mg, 2.04 mmol) as in Step 1 of Reference Example 18 and ethylamine hydrochloride (250 mg, 3.06 mmol) were used as starting materials and treated in the same way as in Step 2 of Reference Example 28 to give 123 mg (22%) of the title compound as a colorless solid.

$^1$H-NMR (400 MHz, $CDCl_3$) δ: 1.16 (3H, t, J=7.3 Hz), 1.32-1.54 (11H, m), 2.09-2.15 (1H, m), 2.21-2.28 (1H, m), 3.04 (1H, t, J=10.7 Hz), 3.25-3.36 (2H, m), 3.60 (1H, br s), 3.70 (1H, dd, J=11.6, 2.6 Hz), 4.12-4.18 (1H, m), 4.30 (1H, s), 6.50 (1H, br s).

MS (ESI) m/z: 295 $(M+Na)^+$.

Step 2

(2S,5R)-5-amino-N-ethyltetrahydro-2H-pyran-2-carboxamide hydrochloride

The compound (120 mg, 0.44 mmol) obtained in Step 1 above was used and treated in the same way as in Step 1 of Reference Example 2 to give 87 mg (95%) of the title compound as a colorless amorphous solid.

$^1$H-NMR (400 MHz, DMSO-$d_6$) δ: 0.98 (3H, t, J=7.2 Hz), 1.37-1.47 (1H, m), 1.56 (1H, ddd, J=23.8, 12.2, 3.7 Hz), 1.96-2.08 (2H, m), 3.04-3.13 (3H, m), 3.54-3.59 (1H, m), 3.71" (1H, dd, J=11.2, 2.4 Hz), 4.02-4.07 (1H, m), 7.69 (1H, t, J=5.5 Hz).

MS (ESI) m/z: 173 $(M+H)^+$.

Reference Example 35

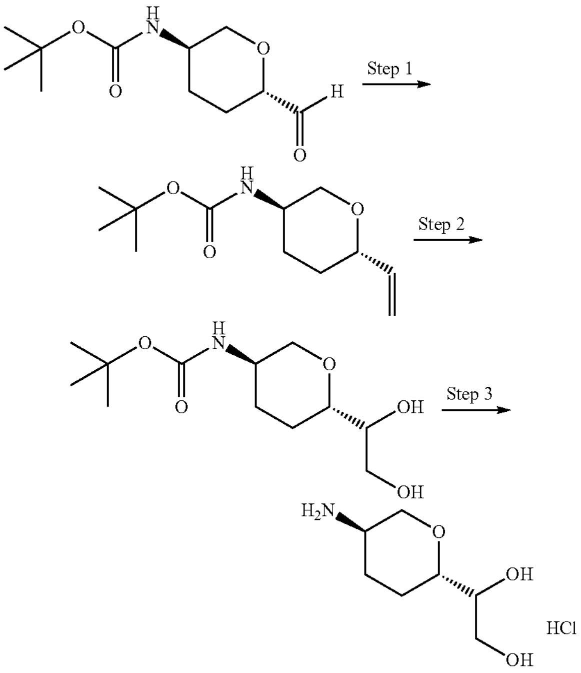

Step 1

Tert-butyl [(3R,6S)-6-vinyltetrahydro-2H-pyran-3-yl]carbamate

N-butyllithium/n-hexane solution (1.65 mol/l, 6.60" ml; 10.9 mmol) was added dropwise to a tetrahydrofuran (100 ml) suspension of methyltriphenylphosphonium bromide (3.90 g, 10.9 mmol) at −78° ° C. under nitrogen atmosphere and the resulting mixture was stirred for 15 minutes and then stirred at 0° C. for 45 minutes. After cooling to −78° C. again, a tetrahydrofuran (6 ml)/hexamethylphosphoric acid triamide (3 ml) solution of the compound (1.00 g, 4.36 mmol) obtained in Step 1 of Reference Example 30 was added dropwise and the resulting mixture was stirred at the same temperature for 30 minutes and then stirred at room temperature for 1 hour. Water (100 ml) was added, followed by extraction with diethyl ether. The organic layer was washed with brine and dried over anhydrous magnesium sulfate. The solvent was evaporated under reduced pressure and the residue was purified by silica gel column chromatography [n-hexane:ethyl acetate=4:1 (v/v)] to give 553 mg (56%) of the title compound as a colorless solid:

$^1$H-NMR (400 MHz, $CDCl_3$) δ: 1.33 (1H, ddd, J=24.0, 12.4, 3.9 Hz), 1.44 (9H, s), 1.47-1.56 (1H, m), 1.78 (1H, dq, J=13.6, 3.3 Hz), 2.06-2.14 (1H, m), 3.06 (1H, t, J=10.5 Hz), 3.61 (1H, br s), 3.71-3.77 (1H, m), 4.08-4.13 (1H, m), 4.28 (1H, br s), 5.12 (1H, dt, J=10.7, 1.3 Hz), 5.24 (1H, at, J=17.4, 1.6 Hz), 5.85 (1H, dq, 3=17.4, 5.3 Hz).

MS (ESI) m/z: 228 $(M+H)^+$.

Step 2

1,5-Anhydro-2-[(tert-butoxycarbonyl)amino]-2,3,4-trideoxy-D-erythro-heptitol

The compound (230 mg, 1.01 mmol) obtained in Step 1 above was dissolved in a mixture of tert-butanol (5 ml), ethyl acetate (1.5 ml), and water (6 ml). Methanesulfonamide (115 mg, 1.2 mmol) and AD-mix-α (1.7 g) were added and the resulting mixture was stirred at room temperature for 16 hours. Sodium bisulfite (2 g) was gradually added and the resulting mixture was further stirred for 15 minutes. After extraction with ethyl acetate, the organic layer was washed with brine and dried over anhydrous magnesium sulfate. The solvent was evaporated under reduced pressure and the residue was purified by silica gel column chromatography [chloroform:methanol=9:1 (v/v)] to give 206 mg (79%) of the title compound as a colorless solid.

$^1$H-NMR (400 MHz, $CDCl_3$) δ: 1.23-1.36 (1H, m), 1.44 (9H, s), 1.51-1.82 (3H, m), 2.09-2.16 (1H, m), 2.22-2.29 (1H, m), 2.61 and 2.78 (total 1H, each d, J=5.0 and 3.7 Hz), 3.01 (2H, t, J=10.3 Hz), 3.30-3.35 (1H, m), 3.51-3.56 (1H, m), 3.59-3.65 (1H, m), 3.69-3.75 (1H, m), 4.08-4.16 (1H, m), 4.27 (1H, br s).

MS (ESI) m/z: 284 $(M+Na)^+$.

Step 3

2-Amino-1,5-anhydro-2,3,4-trideoxy-D-erythro-heptitol hydrochloride

The compound (200 mg, 0.77 mmol) obtained in Step 2 above was used as a starting material and treated in the same way as in Step 1 of Reference Example 2 to give 166 mg (100%) of the title compound as a colorless amorphous solid.

MS (ESI) m/z: 162 $(M+H)^+$.

Reference Example 36

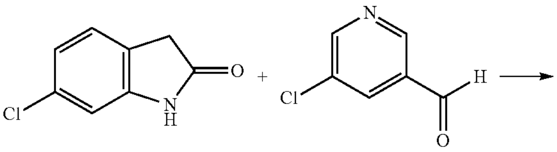

-continued

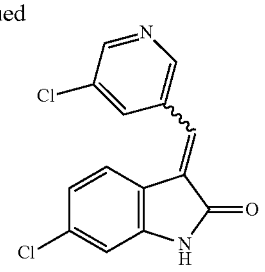

6-Chloro-3-[(5-chloropyridin-3-yl)methylene]-1,3-dihydro-2H-indol-2-one

5-Chloronicotinaldehyde (2.04 g, 14.4 mmol) was: used as a starting material and treated in the same way as in Reference Example 4 to give 3.48 g (878) of the title compound as a yellow solid.

MS (APCI) m/z: 291 $(M+H)^+$.

Reference Example 37

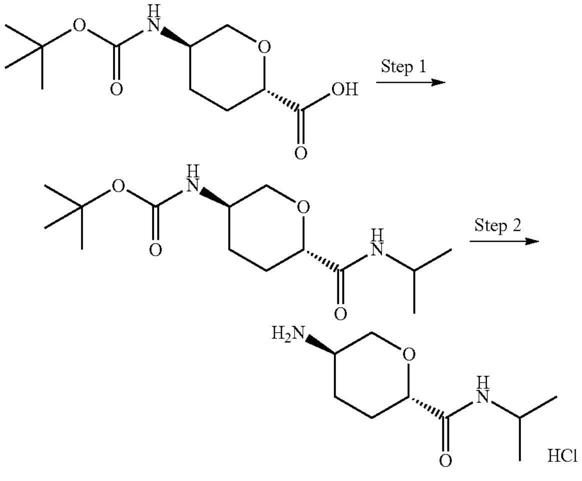

Step 1

Tert-butyl [(3R,6S)-6-(isopropylcarbamoyl)tetrahydro-2H-pyran-3-yl]carbamate

The same starting material (400 mg, 1.63 mmol) as in Step 1 of Reference Example 18 and isopropylamine (0.21 ml, 2.45 mmol) were used as starting materials and treated in the same way as in Step 2 of Reference Example 28 to give 363 mg (78%) of the title compound as a colorless solid.

$^1$H-NMR (400 MHz, $CDCl_3$) δ: 1.16 (6H, d, J=6.4 Hz), 1.33 (1H, ddd, J=24.7, 12.4, 3.9 Hz), 1.43-1.54 (10H, m), 2.09-2.16 (1H, m), 2.21-2.27 (1H, m), 3.03 (1H, t, J=10.5 Hz), 3.60 (1H, br s), 3.67 (1H, dd, J=11.4, 2.7 Hz), 4.01-4.11 (1H, m), 4.12-4.17 (1H, m), 4.29 (1H, br s), 6.34, (1H, d, J=7.3 Hz).

MS (BSI) m/z: 309 $(M+Na)^+$.

Step 2

(2S,5R)-5-amino-N-isopropyltetrahydro-2H-pyran-2-carboxamide hydrochloride

The compound (350 mg, 1.22 mmol) obtained in Step 1 above was used as a starting material and treated in the same way as in Step 1 of Reference Example 2 to give 198 mg (73%) of the title compound as a colorless solid.

$^1$H-NMR (400 MHz, DMSO-$d_6$); 1.04 (6H, d, J=6.6 Hz), 1.42 (1H, ddd, J=24.4, 13.0, 3.6 Hz), 1.58 (1H, ddd, J=24.4, 12.3, 3.8 Hz), 1.93-1.99 (1H, m), 2.06-2.11 (1H, m), 3.04-3.12 (1H, m), 3.31-3.33 (1H, m, 3.69 (1H, dd, J=11.2, 2.4 Hz), 3.82-3.90 (1H, m), 4.07-4.12 (1H, m), 7.43 (1H, d, J=8.1 Hz).

MS (ESI) m/z: 187 $(M+H)^+$.

Reference Example 38

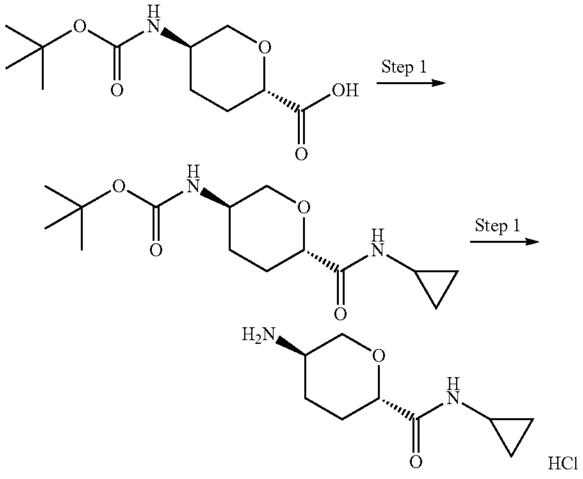

Step 1

Tert-butyl [(3R,6S)-6-(cyclopropylcarbamoyl)tetrahydro-2H-pyran-3-yl]carbamate

The same starting material (400 mg, 1, 63 mmol) as in Step 1 of Reference Example 18 and cyclopropylamine (0.21 ml, 2.45 mmol) were used as starting materials and treated in the same way as in Step 2 of Reference Example 28 to give 231 mg (50%) of the title compound as a colorless solid.

$^1$H-NMR (400 MHz, $CDCl_3$) δ: 0.49-0.54 (2H, m), 0.74-0.80 (2H, m), 1.27-1.38 (1H, m), 1.42-1.53 (10H, m), 2.08-2.14 (1H, m), 2.20-2.27 (1H, m), 2.68-2.74 (1H, m), 3.01 (1H, t, J=10.6 Hz), 3.57 (1H, br s), 3.68 (1H, dd, J=11.5, 2.4 Hz), 4.09-4.14 (1H, m), 4.29 (1H, br s), 6.54 (1H, s).

MS (ESI) m/z: 307 $(M+Na)^+$.

Step 2

(2S,5R)-5-amino-N-cyclopropyltetrahydro-2H-pyran-2-carboxamide hydrochloride

The compound (220 mg, 0.77 mmol) obtained in Step 1 above was used as a starting material and treated in the same way as in Step 1 of Reference Example 2 to give 128 mg (75%) of the title compound as a colorless solid.

$^1$H-NMR (400 MHz, DMSO-$d_6$) δ: 0.43-0.47 (2H, m), 0.56-0.60 (2H, m), 1.39-1.50 (1H, m), 1.57 (1H, dad, J=23.6, 12.1, 3.4 Hz), 1.92-1.99 (1H, m), 2.03-2.11 (1H, m), 2.60-2.67 (1H, m), 3.02-3.12 (1H, m), 3.28-3.32 (1H, m), 3.69 (1H, dd, J=11.0, 2.3 Hz), 4.05 (1H, dq, J=11.0, 2.3 Hz), 7.72 (1H, d, J=4.6 Hz).

MS (ESI) m/z: 185 $(M+H)^+$.

Reference Example 39

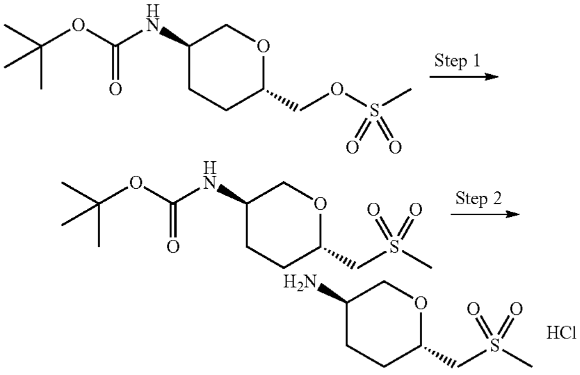

Step 1

Tert-butyl {(3R,6S)-6-[(methylsulfonyl)methyl]tetrahydro-2H-pyran-3-yl}carbamate An N,N-dimethylformamide (5 ml) solution of the compound (621 mg, 2.01 mmol) obtained in Step 1 of Reference Example 24 combined with sodium methanethiolate (297 mg, 4.24 (mol) was stirred overnight at room temperature. The reaction mixture was diluted with ethyl acetate, washed with water, 1N hydrochloric acid, saturated sodium bicarbonate solution, and brine in that order and then dried over anhydrous sodium sulfate. The solvent was evaporated under reduced pressure, the residue obtained was dissolved in dichloromethane (20 ml), m-chloroperbenzoic acid (258 hydrated, 1.9 g, 8.2 mmol) was added and the resulting mixture was stirred for 1 hour. The reaction mixture was diluted with ethyl acetate, washed with water, saturated sodium bicarbonate solution, and brine in that order and then dried over anhydrous sodium sulfate. The solvent was evaporated under reduced pressure and the residue obtained was purified by silica gel column chromatography [ethyl acetate:n-hexane=1:1 (v/v)] and subsequently purified by NH-silica gel column chromatography [ethyl acetate:n-hexane=1:1 (v/v)] to give 505 mg (86%) of the title compound as a colorless solid.

$^1$H-NMR (400 MHz, $CDCl_3$) δ: 1.30-1.56 (11H, m), 1.76 (1H, dq, J=13.4, 3.1 Hz), 2.10-2.16 (1H, m), 2.92-2.99 (4H, m), 3.05 (1H, t, J=10.8 Hz), 3.23 (1H, dd, J=15.1, 9.6 Hz), 3.57-3.64 (1H, m), 3.83-3.89 (1H, m), 4.07-4.12 (1H, m), 4.23-4.29 (1H, m).

MS (FAB) m/z: 294 $(M+H)^+$.

Step 2

(3R,6S)-6-[(methylsulfonyl)methyl]tetrahydro-2H-pyran-3-amine hydrochloride

The compound (61 mg, 0.21 mmol) obtained in Step 1 above was used as a starting material and treated in the same way as in Step 1 of Reference Example 2 to give the title compound as a colorless solid.

Reference Example 40

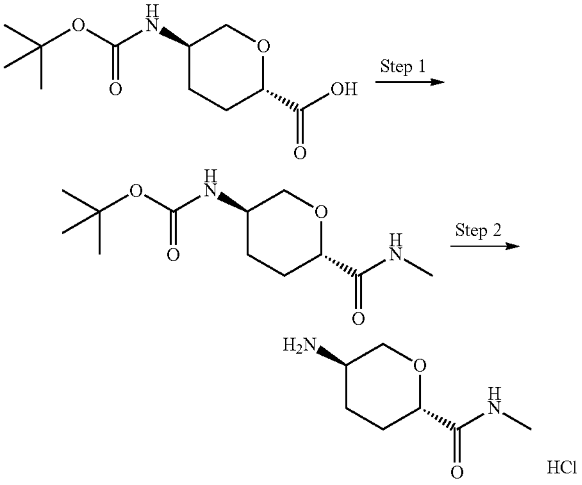

Step 1

Tert-butyl [(3R,6S)-6-(methylcarbamoyl)tetrahydro-2H-pyran-3-yl]carbamate

The same starting material (400 mg, 1.63 mmol) as in Step 1 of Reference Example 18 and aqueous methylamine solution (40% w/w, 0.27 ml, 3.26 mmol) were used as starting materials and treated in the same way as in Step 2 of Reference Example 28 to give 191 mg (45%) of the title compound as a colorless solid.

$^1$H-NMR (400 MHz, $CDCl_3$) δ: 1.32-1.55 (11H, m), 2.08-2.16 (1H, m), 2.20-2.29 (1H, m), 2.82 (3H, d, J=5.1 Hz), 3.04 (1H, C, J=10.6 Hz), 3.57-3.64 (1H, m), 3.72 (1H, dd, J=11.5, 2.4 Hz), 4.13-4.19 (1H, m), 4.28 (1H, br s), 6.53 (1H, s).

MS (ESI) m/z: 259 $(M+H)^+$.

Step 2

(2S,5R)-5-amino-N-methyltetrahydro-2H-pyran-2-carboxamide hydrochloride

The compound (190 mg, 0.74 mmol) obtained in Step 1 above was used as a starting material and treated in the same way as in Step 1 of Reference Example 2 to give 124 mg (86%) of the title compound as a colorless solid.

$^1$H-NMR (400 MHz, DMSO-$d_6$) δ: 1.36-1.47 (1H, m), 1.58 (1H, ddd, J=24.0, 12.1, 3.7 Hz), 1.96-2.02 (1H, m), 2.04-2.10 (1H, m), 2.57 (3H, d, J=4.6 Hz), 3.04-3.12 (1H, m), 3.35 (1H, t, J=10.3 Hz), 3.72 (1H, dd, J=11.2, 2.5 Hz), 4.05-4.09 (1H, m), 7.67 (1H, d, J=4.6 Hz).

MS (ESI) m/z: 159 $(M+H)^+$.

Reference Example 41

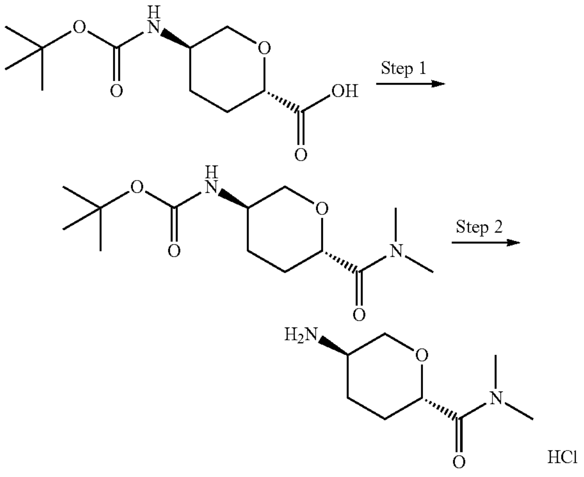

Step 1

Tert-butyl [(3R,6S)-6-(dimethylcarbamoyl)tetrahydro-2H-pyran-3-yl]carbamate

The same starting material (400 mg, 1.63 mmol) as in Step 1 of Reference Example 18 and aqueous dimethylamine solution (50% w/w, 0.29 ml, 3.26 mmol) were used as starting materials and treated in the same way as in Step 2 of Reference Example 28 to give 328 mg (74%) of the title compound as a colorless solid.

$^1$H-NMR (400 MHz, $CDCl_3$) δ: 1.41-1.42 (1H, m), 1.44 (9H, s), 1.83-2.00 (2H, m), 2.16-2.22 (1H, m), 2.95 (3H, s), 3.07 (3H, s), 3.08-3.15 (1H, m), 3.66 (1H, br s), 4.04 (1H, dd, J=10.0, 3.2 Hz), 4.11 (1H, dd, J=10.7, 3.2 Hz), 4.40 (1H, br s).

MS (ESI) m/z: 273 $(M+H)^+$.

Step 2

(2S,5R)-5-amino-N,N-dimethyltetrahydro-2H-pyran-2-carboxamide hydrochloride

The compound (320 mg, 1.17 mmol) obtained in Step 1 above was used as a starting material and treated in the same way as in Step 1 of Reference Example 2 to give 289 mg (78%) of the title compound as a colorless solid.

$^1$H-NMR (400 MHz, DMSO-$d_6$) δ: 1.55-1.75 (3H, m), 2.07-2.13 (11, m), 2.99 (38, s), 3.07-3.13 (1H, m), 3.15 (3H, s), 3.38 (1H, t, J=10.5 Hz), 3.97-4.01 (1H, mi, 4.13 (1H, dd, J=8.9, 3.4 Hz).

MS (ESI) m/z: 173 $(M+H)^+$.

Reference Example 42

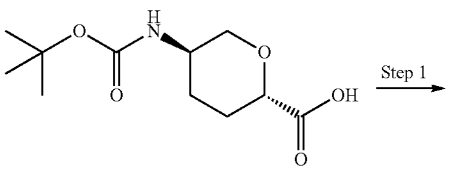

-continued

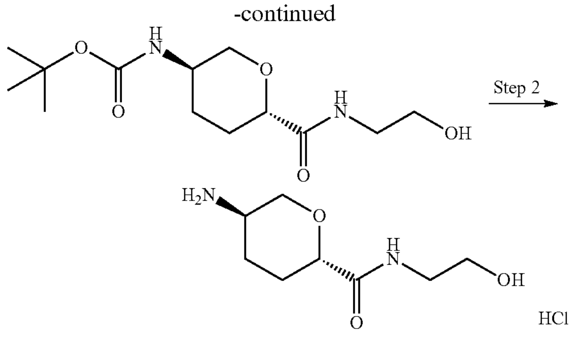

Step 1

Tert-butyl {(3R,6S)-6-[(2-hydroxyethyl) carbamoyl] tetrahydro-2H-pyran-3-yl}carbamate The same starting material (400 mg, 1.63 mmol) as in Step 1 of Reference Example 18 and 2-aminoethanol (0.15 ml, 2.45 mmol) were used as starting materials and treated in the same way as in Step 2 of Reference Example 28 to give 313 mg (67%) of the title compound as a colorless solid.

$^1$H-NMR (400 MHz, $CDCl_3$) δ: 1.33-1.41 (1H, m), 1.44 (9H, s), 1.48-1.57 (1H, m), 2.10-2.18 (1H, m), 2.21-2.28 (1H, m), 2.78 (1H, br s), 3.05 (1H, t, J=10.8 Hz), 3.38-3.51 (2H, m), 3.58-3.63 (1H, m), 3.70-3.77 (3H, m), 4.13-4.19 (1H, m), 4.33 (1H, br s), 6.97 (1H, br s).

MS (ESI) m/z: 289 $(M+H)^+$.

Step 2

(2S,5R)-5-amino-N-(2-hydroxyethyl)tetrahydro-2H-pyran-2-carboxamide hydrochloride The compound (310 mg, 1.07 mmol) obtained in Step 1 above was used as a starting material and treated in the same way as in Step 1 of Reference Example 2 to give 310 mg (100%) of the title compound as a colorless amorphous solid, $^1$H-NMR (400 MHz, DMSO-$d_6$) δ: 1.38-1.48 (1H, m), 1.54-1.64 (1H, m), 1.97-2.04 (1H, m), 2.06-2.12 (1H, m), 3.06-3.17 (2H, m), 3.34-3.47 (4H, m), 3.71-3.79 (1H, m), 4.07-4.13 (1H, m), 7.56 (1H, t, J=5.7 Hz).

MS (ESI) m/z: 189 $(M+H)^+$.

Reference Example 43

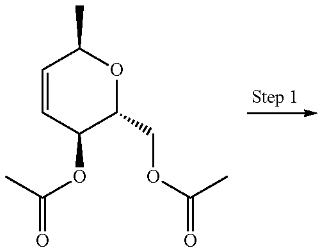

-continued

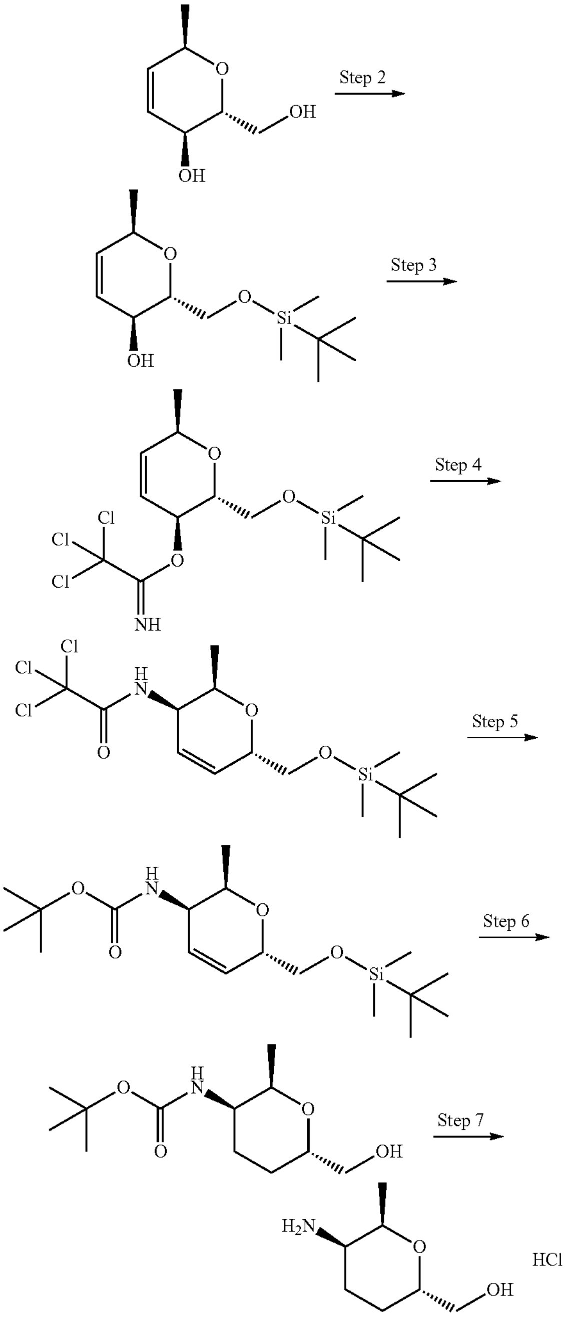

Step 1

2,6-Anhydro-1,3,4-trideoxy-D-arabino-hept-3-enitol

Sodium methoxide/methanol solution (28% w/w, 0.40 ml, 2.1 mmol) was added to a methanol (15 ml) solution of 5,7-di-O-acetyl-2,6-anhydro-1,3,4-trideoxy-D-arabino-hept-3-enitol (Synlett, 1996, 185, and Tetrahedron: Asymm., 2003, 14, 757) (1.56 g, 6.83 mmol) and the resulting mixture was stirred at room temperature for 3 hours. DOWEX 50WX8-200 was added to the reaction mixture to adjust its pH to 4 and then insoluble matter was removed by filtration. The filtrate was concentrated under reduced pressure to give the title compound.

Step 2

2,6-Anhydro-7-O-[tert-butyl(dimethyl)silyl]-1,3,4-trideoxy-D-arabino-hept-3-enitol The compound (6.83 mmol) obtained in Step 1 above was used as a starting material and treated in the same way as in Step 1 of Reference Example 23 to give the title compound.

Step 3

2,6-Anhydro-7-O-[tert-butyl(dimethyl)silyl]-1,3,4-trideoxy-5-O-(2,2,2-trichloroethanimidoyl)-D-arabino-hept-3-enitol 1,8-Diazabicyclo[5.4.0]undec-7-ene (1.00 ml, 6.83 mmol) was added to a dichloromethane (22 ml) solution of the compound (6.83 mmol) obtained in Step 2 above combined with trichloroacetonitrile (0.82 ml, 8.20 mmol) under ice cooling and the resulting mixture was stirred at room temperature for 1 hour. The solvent in the reaction mixture was evaporated under reduced pressure and the residue was dissolved in chloroform and added dropwise into n-hexane: ethyl acetate [4:1 (v/v)] mixed solvent. The resulting insoluble matter was removed by filtration through celite and the solvent in the filtrate was evaporated under reduced pressure. The residue obtained was purified by silica gel column chromatography [n-hexane:ethyl acetate=99: 1→10:1 (v/v)] to give 2.1 g (778) of the title compound as a colorless oil.

$^1$H-NMR (400 MHz, $CDCl_3$) δ: 0.04 (6H, s), 0.87 (9H, s), 1.30 (3H, d, J=6.4 Hz), 3.74-3.91 (3H, m), 4.36-4.46 (1H, m), 5.25-5.30 (1H, m), 5.86-5.93 (2H, m), 8.34 (1H, s).

Step 4

2,6-Anhydro-7-O-[tert-butyl(dimethyl)silyl]-1,3,4,5-tetradeoxy-3-[(trichloroacetyl)amino]-D-arabino-hept-4-enitol Potassium carbonate (50 mg, 0.36 mmol) was added to an o-dichlorobenzene (11 ml) solution of the compound (2.13 g, 5.29 mmol) obtained in Step 3 above and the resulting mixture was stirred under heating at 180° C. for 4 hours. After cooling to room temperature, insoluble matter was removed by filtration through celite and then the solvent in the filtrate was evaporated under reduced pressure to give the title compound.

Step 5

2,6-Anhydro-3-[(tert-butoxycarbonyl)amino]-7-O-[tert-butyl(dimethyl)silyl]-1,3,4,5-tetradeoxy-D-arabino-hept-4-enitol Potassium hydroxide (0.89 g) was added to a 2-propanol (9 ml) solution of the compound (5.29 mmol) obtained in Step 4 above and the resulting mixture was stirred for 28 hours. Insoluble matter was removed by filtration through celite, the solvent was evaporated under reduced pressure and the residue obtained was dissolved in dichloromethane (9 ml). Di-tert-butyl dicarbonate (1.38 g, 6.35 mmol) was added under ice cooling and the resulting mixture was stirred at room temperature for 4 hours. Water was added, the resulting mixture was subjected to extraction with chloroform and the organic layer was washed with brine and then dried over anhydrous sodium sulfate. The solvent was evaporated under reduced pressure and the residue was purified by silica gel column chromatography [n-hexane: ethyl acetate=30:1→10:1 (v/v)] to give 1.3 g (71%) of the title compound as a colorless oil.

$^1$H-NMR (400 MHz, $CDCl_3$) δ: 0.04 (3H, s), 0.04 (3H, s), 0.87 (9H, s), 1.15 (3H, d, J=6.0 Hz), 1.42 (9H, s), 3.62 (1H, dd, J=10.6, 5.50 Hz), 3.72 (1H, dd, J=10.6, 6.4 Hz), 3.84-3.92 (1H, m), 3.96-4.04 (1H, m), 4.13-4.20 (1H, m), 4.59 (1H, d, J=9.6 Hz), 5.83-5.89 (1H, m), 5.92-6.01 (1H, m).

Step 6

2,6-Anhydro-3-[(tert-butoxycarbonyl)amino]-1,3,4,5-tetradeoxy-D-arabino-heptitol The compound (960 mg, 2.68 mmol) obtained in Step 5 above was dissolved in ethyl acetate (5 ml) and ethanol (5 ml), platinum (IV) oxide (18 mg, 0.08 mmol) was added and the resulting mixture was stirred for 19 hours under hydrogen atmosphere. The catalyst was removed by filtration through celite, then the solvent in the filtrate was evaporated under reduced pressure and the residue was purified by silica gel column chromatography [n-hexane:ethyl acetate=9:1→2:3 (v/v)] to give 524 mg (79%) of the title compound as a colorless solid.

$^1$H-NMR (400 MHz, $CDCl_3$) δ: 1.17 (3H, d, J=6.9 Hz), 1.41-1.93 (14H, m), 3.45-3.83 (4H, m), 4, 08-4.18 (1H, m); 4.54-4.66 (1H, m).

Step 7

3-Amino-2,6-anhydro-1,3,4,5-tetradeoxy-D-arabino-heptitol hydrochloride

The compound (524 mg, 2.14 mmol) obtained in Step 6 above was used as a starting material and treated in the same way as in Step 1 of Reference Example 2 to give 355 mg (92%) of the title compound as a colorless solid.

$^1$H-NMR (400 MHz, $CD_3OD$) δ: 1.24 (3H, d, J=6.9 Hz), 1.44-1.55 (1H, m), 1.76-2.04 (3H, m), 3.27-3.34 (1H, m), 3.52 (1H, dd, J=11.5, 4.6 Hz), 3.61-3.69 (1H, m), 3.75-3.84 (1H, m), 4.11-4.19 (1H, m).

Reference Example 14

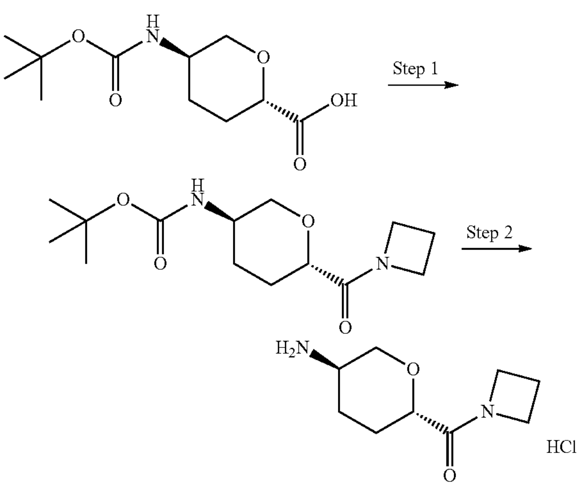

Step 1

Tert-butyl [(3S,6S)-6-(azetidin-1-ylcarbonyl)tetrahydro-2H-pyran-3-yl]carbamate

The same starting material (400 mg, 1.63 mmol) as in Step 1 of Reference Example 18 and azetidine hydrochloride (305 mg, 3.26 mmol) were used as starting materials and treated in the same way as in Step 2 of Reference Example 28 to give 244 mg (53%) of the title compound as a colorless solid,

$^1$H-NMR (400 MHz, $CDCl_3$) δ: 1.29-1.39 (1H, m), 1.44 (9H, s), 1.68-1.78 (1H, m), 1.98-2.05 (1H, m), 2.08-2.16 (1H, m), 2.23-2.30 (2H, m), 3.02 (1H, t, J=10.3 Hz), 3.56-3.66 (1H, m), 3.86 (1H, dd, J=11.2, 2.5 Hz), 4.04 (2H, t, J=7.8 Hz), 4.10 (1H, dq, J=10.6, 2.1 Hz), 4.31 (2H, t, J=7.8 Hz), 4.33 (1H, br s).

MS (ESI) m/z: 285 $(M+H)^+$.

Step 2

(3R,6S)-6-(azetidin-1-ylcarbonyl)tetrahydro-2H-pyran-3-amine hydrochloride

The compound obtained in Step 1 above was used as a starting material and treated in the same way as in Step 1 of Reference Example 2 to give 210 mg (100%) of the title compound as a colorless amorphous solid.

$^1$H-NMR (400 MHz, DMSO-$d_6$) δ: 1.42-1.51 (1H, m), 1.55-1.61 (1H, m), 1.78-1.85 (1H, m), 1.95-2.03 (1H, m), 2.14-2.22 (2H, m), 3.07-3.11 (1H, m), 3.59 (1H, t, J=6.7 Hz), 3.84 (2H, t, J=7.6 Hz), 3.95-4.01 (1H, m), 4.04-4.10 (1H, m), 4.20 (2H, t, J=7.8 Hz).

MS (ESI) m/z: 185 $(M+H)^+$.

Reference Example 45

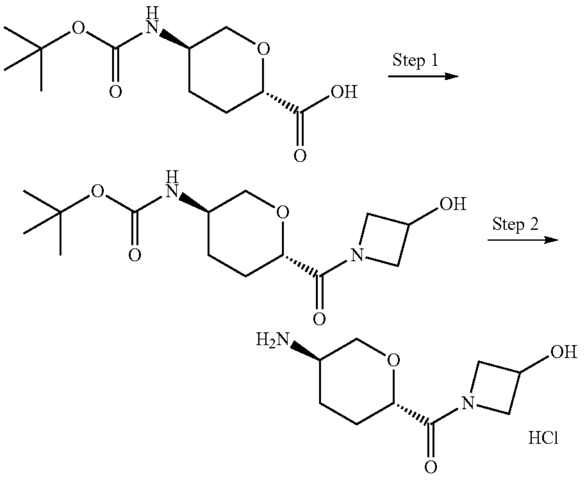

Step 1

Tert-butyl {(3R,6S)-6-[(3-hydroxyazetidin-1-yl)carbonyl]tetrahydro-2H-pyran-3-yl}carbamate The same starting material (400 mg, 1.63 mmol) as in Step 1 of Reference Example 18 and 3-hydroxyazetidine hydrochloride (267 mg, 2.45 mmol) were used as starting materials and treated in the same way as in Step 2 of Reference Example 28 to give 261 mg (53%) of the title compound as a colorless solid.

$^1$H-NMR (400 MHz, $CDCl_3$) δ: 1.33-1.42 (1H, m), 1.44 (9H, s), 1.64-1.76 (1H, m), 2.01-2.07 (1H, m), 2.08-2.15 (1H, m); 2.37 (1H, d, J=5.6 Hz), 3.01 (1H, td, J=10.5, 2.8 Hz), 3.60 (1H, br s), 3.82-3.91 (2H, m), 4.06-4.17 (2H, m), 4.23-4.30 (1H, m), 4.35 (1H, br s), 4.51-4.57 (1H, m), 4.60-4.68 (1H, m).

MS (ESI) m/z: 301 $(M+H)^+$.

Step 2

1-{[(2S,5R)-5-aminotetrahydro-2H-pyran-2-yl] carbonyl}azetidin-3-ol hydrochloride The compound (310 mg, 1.03 mmol) obtained in Step 1 above was used as a starting material and treated in the same way as in Step 1 of Reference Example 2 to give 249 mg (100%) of the title compound as a colorless amorphous solid.

$^1$H-NMR (400 MHz, DMSO-$d_6$) δ: 1.53-1.61 (2H, m), 1.78-1.83 (1H, m), 2.04-2.07 (1H, m), 3.05-3.13 (1H, m), 3.30 (1H, dd, J=10.9, 6.0 Hz), 3.57 (1H, dd, J=11.2, 3.7 Hz), 3.85-4.07 (4H, m), 4.34-4.46 (2H, m).

MS (ESI) m/z: 201 $(M+H)^+$.

Reference Example 46

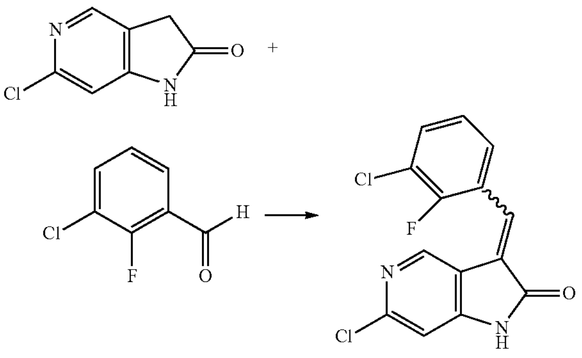

(3E/Z)-6-chloro-3-(3-chloro-2-fluorobenzylidene)-1, 3-dihydro-2H-pyrrolo[3,2-c]pyridin-2-one 6-Chloro-1,3-dihydro-2H-pyrrolo[3,2-c]pyridin-2-one (3.00 g, 17.8 mmol) was used as a starting material and treated in the same way as in Reference Example 1 to give 3.94 g (72%) of the title compound as a yellow solid.

$^1$H-NMR (DMSO-$d_6$) δ: 6.98 (1H, 8), 7.41 (1H, t, J=7.9 Hz), 7.70 (1H, s), 7.78 (2H, q, J=7.0 Hz), 8.09 (1H, s), 11.38 (1H, br s).

MS (ESI) m/z: 309 $(M+H)^+$.

Reference Example 47

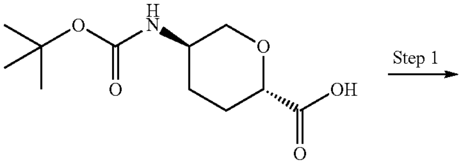

-continued

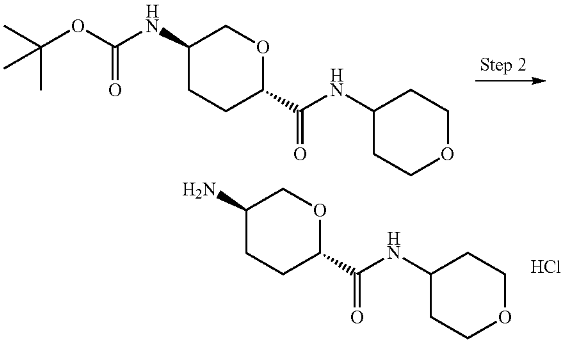

Step 1

Tert-butyl [(3R,6S)-6-(tetrahydro-2H-pyran-4-ylcarbamoyl)tetrahydro-2H-pyran-3-yl]carbamate The same starting material (400 mg, 1, 63 mmol) as in Step 1 of Reference Example 18 and tetrahydropyran-4-ylamine hydrochloride (270 mg, 1.96 mmol) were used as starting materials and treated in the same way as in Step 2 of Reference Example 28 to give 355 mg (66%) of the title compound as a colorless solid.

$^1$H-NMR (400 MHz, $CDCl_3$) δ: 1.35 (1H, ddd, J=24.6, 12.3, 3.8 Hz), 1.44 (9H, s), 1.45-1.56 (3H, m), 1.84-1.92 (2H, m), 2.10-2.16 (1H, m), 2.22-2.27 (1H, m), 3.04 (1H, t, J=10.8 Hz), 3.48 (2H, td, J=11.7, 2.1 Hz), 3.59-3.63 (1H, m), 3.70 (1H, dd, J=11.4, 2.3 Hz), 3.92-4.02 (3H, m), 4.13-4.19 (1H, m), 4.30-4.32 (1H, m), 6.45 (1H, d, J=7.8 Hz).

MS (ESI) m/z: 351 $(M+H)^+$.

Step 2

(2S,5S)-5-amino-N-(tetrahydro-2H-pyran-4-yl)tetrahydro-2H-pyran-2-carboxamide hydrochloride The compound (350 mg, 1.07 mmol) obtained in Step 1 above was used as a starting material and treated in the same way as in Step 1 of Reference Example 2 to give 236 mg (838) of the title compound as a colorless solid.

$^1$H-NMR (400 MHz, DMSO-$d_6$) δ: 1.40-1.64 (6H, m), 1.93-1.99 (1H, m), 2.06-2.13 (1H, m), 3.04-3.12 (1H, m), 3.30 (2H, td, J=11.7, 2.3 Hz), 3.37 (1H, t, J=9.4 Hz), 3.72 (1H, dd, J=11.2, 2.5 Hz), 3.74-3.82 (3H, m), 4.11 (1H, dq, J=10.5, 2.1 Hz), 7.63 (1H, d, J=7.8 Hz).

MS (ESI) m/z: 229 $(M+H)^+$.

Reference Example 48

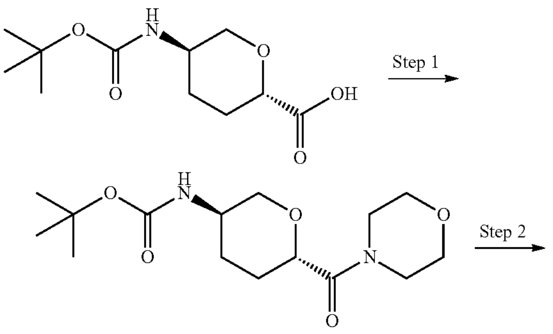

-continued

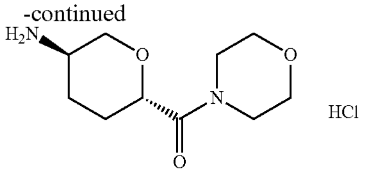

Step 1

Tert-butyl [(3R,6S)-6-(morpholin-4-ylcarbonyl)tetrahydro-2H-pyran-3-yl]carbamate The same starting material (400 mg, 1.63 mmol) as in Step 1 of Reference Example 18 and morpholine (0.17 ml, 1.96 mmol) were used as starting materials and treated in the same way as in Step 2 of Reference Example 28 to give 344 mg (67%) of the title compound as a colorless solid.

$^1$H-NMR (400 MHz, $CDCl_3$) δ: 1.37-1.43 (1H, m), 1.44 (9H, s), 1.87-1.99 (2H, m), 2.15-2.22 (1H, m), 3.11 (1H, t, J=10.1 Hz), 3.50-3.74 (9H, m), 4.01 (1H, dd, J=8.5, 3.9 Hz), 4.06-4.12 (1H, m), 4.41 (1H, s).

MS (ESI) m/z: 315 $(M+H)^+$.

Step 2

(3R,6S)-6-(morpholin-4-ylcarbonyl)tetrahydro-2H-pyran-3-amine hydrochloride

The compound (340 mg, 1.08 mmol) obtained in Step 1 above was used as a starting material and treated in the same way as in Step 1 of Reference Example 2 to give 283 mg (100%) of the title compound as a colorless amorphous solid.

$^1$H-NMR (400 MHz, DMSO-da) δ: 1.58-1.78 (3H, m), 2.08-2.13 (1H, m), 3.06-3.13 (1H, m), 3.41-3.58 (9H, m), 3.99 (1H, dd, J=10.8, 2.5 Hz), 4.15 (1H, dd, J=9.6, 3.2 Hz).

MS (ESI) m/z: 215 $(M+H)^+$.

Reference Example 49

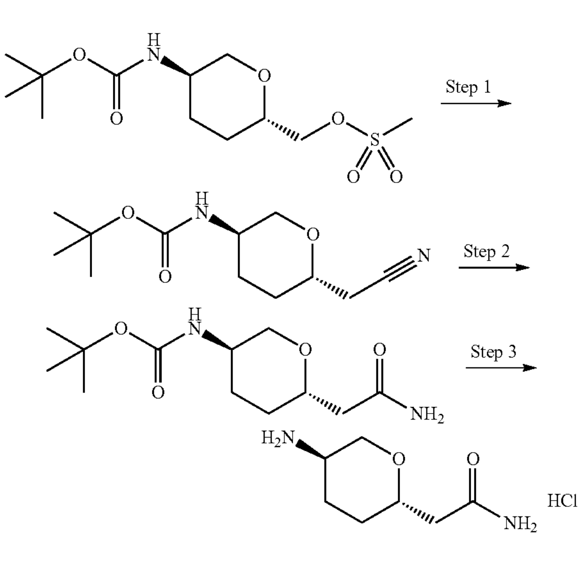

Step 1

Tert-butyl [(3R,6S)-6-(cyanomethyl)tetrahydro-2H-pyran-3-yl] carbamate

Potassium cyanide (741 mg, 11.4 mmol) was added to an N,N-dimethylformamide (10 ml) solution of the compound (678 mg, 2.19 mmol) obtained in Step 1 of Reference Example 24 and the resulting mixture was stirred overnight at 100° C. The reaction mixture was diluted with ethyl acetate, washed with brine and then dried over anhydrous sodium sulfate. The solvent was evaporated under reduced pressure and the residue obtained was purified by silica gel column chromatography [ethyl acetate; chloroform=1:4 (v/v)] to give 392 mg (74%) of the title compound as a colorless solid.

$^1$H-NMR (500 MHz, $CDCl_3$) δ: 1.20-1.57 (11H, m), 1.87 (1H, dq, J=13.5, 3.1 Hz), 2.13-2.16 (1H, m), 2.48-2.58 (2H, m), 3.04 (1H, t, J=10.9 Hz), 3.50-3.56 (1H, m), 3.60-3.65 (1H, m), 4.09-4.12 (1H, m), 4.23-4.28 (1H, m).

MS (FAB) m/z: 241 $(M+H)^+$.

Step 2

Tert-butyl [(3R,6S)-6-(2-amino-2-oxoethyl)tetrahydro-2H-pyran-3-yl]carbamate

The compound (60 mg, 0.25 mmol) obtained in Step 1 above was added to a mixture of sodium hydroxide (94 mg, 2.36 mol), ethanol (5 ml), and 30% aqueous hydrogen peroxide solution (5 ml) and the resulting mixture was stirred overnight at room temperature. The reaction mixture was diluted with ethyl acetate, washed with brine and then dried over anhydrous sodium sulfate. The solvent was evaporated under reduced pressure and the residue obtained was purified by silica gel column chromatography [methanol:chloroform=5:95 (v/v)] to give 9 mg (13%) of the title compound as a colorless solid.

$^1$H-NMR (500 MHz, $CDCl_3$) δ: 1.28-1.54 (11H, m), 1.73-1.76 (1H, m), 2.08-2.10 (1H, m), 2.35-2.44 (2H, m), 3.04 (1H, t, J=10.9 Hz), 3.59-3.64 (2H, m), 4.09-4.12 (1H, m), 4.32 (1H, d, J=8.0 Hz), 5.46 (1H, br s), 6.30 (1H, br s).

MS (FAB) m/z: 259 $(M+H)^+$.

Step 3

2-[(2S,5R)-5-aminotetrahydro-2H-pyran-2-yl]acetamide hydrochloride

The compound (39 mg, 0.15 mmol) obtained in Step 2 above was used and treated in the same way as in Step 1 of Reference Example 2 to give the title compound as a colorless solid.

Reference Example 50

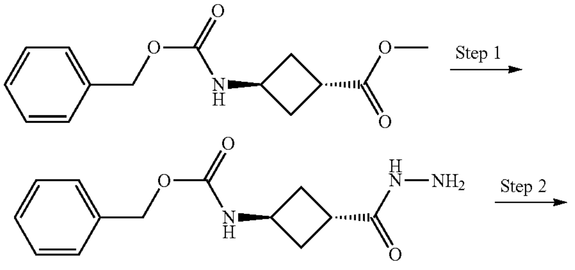

-continued

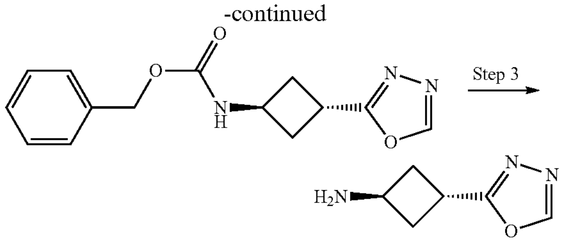

Step 1

Benzyl [trans-3-(hydrazinecarbonyl)cyclobutyl]carbamate

Hydrazine monohydrate (10 ml) was added to a methanol (50 ml) solution of methyl trans-3-{[(benzyloxy) carbonyl] amino}cyclobutanecarboxylate (Neurochemical Research, 1980, 5, 393-400) (995 mg, 3.78 mmol) at room temperature and the resulting mixture was stirred for 24 hours. The precipitated solid was collected by filtration, washed with water and then dried to give 760 mg (76%) of the title compound as a colorless solid.

$^1$H-NMR (400 MHz, $CDCl_3$) δ: 2.21-2.25 (2H, m), 2.61-2.64 (2H, m), 2.81-2.87 (1H, m), 3.87 (2H, br s), 4.36 (1H, q, J=7.5 Hz), 4.83 (1H, br s), 5.09 (2H, s), 6.54 (1H, br s), 7.30-7.35 (5H, m).

MS (ESI) m/z: 265 $(M+H)^+$.

Step 2

Benzyl [trans-3-(1,3,4-oxadiazol-2-yl)cyclobutyl] carbamate

The compound (760 mg, 2.89 mmol) obtained in Step 1 above was used as a starting material and treated in the same way as in Step 2 of Reference Example 3 to give 1.00 g (99%) of the title compound as a colorless solid.

$^1$H-NMR (400 MHz, $CDCl_3$) δ: 2.52-2.58 (2H, m), 2.76-2.79 (2H, m), 3.67-3.72 (1H, m), 4.48-4.52 (1H, m), 5.10 (2H, s), 5.15 (1H, br s), 7.30-7.41 (5H, m), 8.37 (1H, s); MS (ESI) m/z: 274 $(M+H)^+$.

Step 3

Trans-3-(1,3,4-oxadiazol-2-yl)cyclobutanamine

The compound (1.00 g, 3.66 mmol) obtained in Step 2 above was used as a starting material and treated in the same way as in Step 3 of Reference Example 2 to give 391 mg (77%) of the title compound as a colorless oil.

$^1$H-NMR (400 MHz, $CDCl_3$) δ: 2.21-2.29 (2H, m), 2.67-2.74 (2H, m), 3.64-3.71 (1H, m), 3.83-3.91 (1H, m), 8.35 (1H, s).

MS (ESI) m/z: 140 $(M+H)^+$.

Reference Example 51

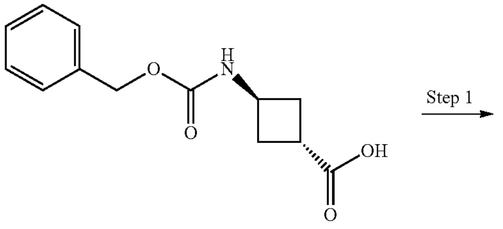

-continued

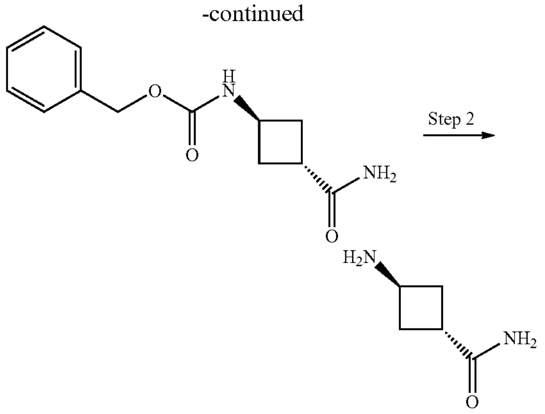

Step 1

Benzyl (trans-3-carbamoylcyclobutyl) carbamate trans-3-{[(Benzyloxy) carbonyl] amino}cyclobutanecarboxylic acid (110 mg, 0.44 mmol) was used as a starting material and treated in the same way as in Step 1 of Reference Example 16 to give 47 mg (43%) of the title compound as a colorless solid.

$^1$H-NMR (400 MHz, $CDCl_3$) δ: 2.10-2.34 (2H, m), 2.59-2.71 (2H, m), 2.90-3.01 (1H, m), 4.29-4.41 (1H, m), 4.95 (1H, br s), 5.09 (2H, s), 5.30 (2H, br s), 7.29-7.40 (5H, m), MS (SSI) m/z: 249 $(M+H)^+$.

Step 2

Trans-3-aminocyclobutanecarboxamide

The compound (21 mg, 0.19 mmol) obtained in Step 1 above was used as a starting material and treated in the same way as in Step 3 of Reference Example 2 to give 21 mg (97%) of the title compound as a colorless solid.

$^1$H-NMR (400 MHz, $CD_3OD$) δ: 1.96-2.09 (2H, m), 2.39-2.52 (2H, m), 2.94-3.04 (1H, m), 3.54-3.69 (1H, m).

Reference Example 52

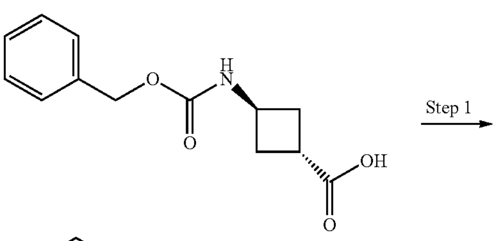

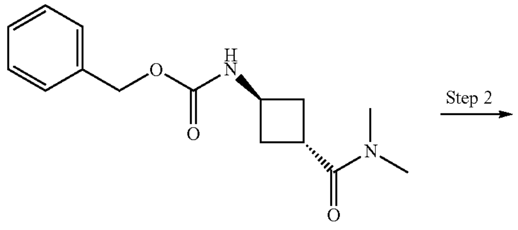

-continued

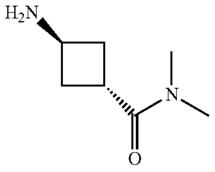

Step 1

Benzyl [trans-3-(dimethylcarbamoyl)cyclobutyl] carbamate

The same starting material as in Step 1 of Reference Example 51 and aqueous dimethylamine solution (50% w/w, 0.16 ml, 1.77 mmol) were used as starting materials and treated in the same way as in Step 2 of Reference Example 28 to give 48 mg (39%) of the title compound as a colorless solid.

MS (ESI) m/z: 277 $(M+H)^+$.

Step 2

Trans-3-amino-N,N-dimethylcyclobutanecarboxamide

The compound (48 mg, 0.17 mmol) obtained in Step 1 above was used as a starting material and treated in the same way as in Step 3 of Reference Example 2 to give 26 mg (100%) of the title compound as a colorless solid.

$^1$H-NMR (400 MHz, $CD_3OD$) δ: 2.07-2.17 (2H, m), 2.45-2.56 (2H, m), 2.93 (3H, s), 2.95 (3H, s), 3.33-3.42 (1H, m), 3.51-3.62 (1H, m).

MS (ESI) m/z: 143 $(M+H)^+$.

Reference Example 53

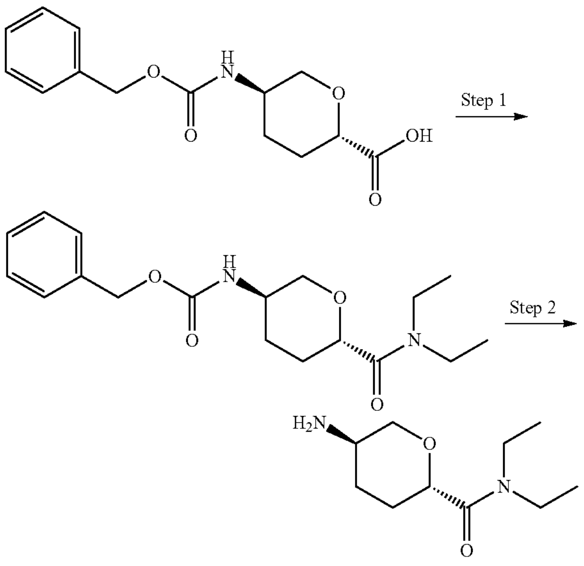

Step 1

Benzyl [(3R,6S)-6-(diethylcarbamoyl)tetrahydro-2H-pyran-3-yl] carbamate

The compound (400 mg, 1.43 mmol) obtained in Step 3 of Reference Example 18 and diethylamine (0.22 ml, 2.15 mmol) were used as starting materials and treated in the same way as in Step 2 of Reference Example 28 to give 514 mg (100%) of the title compound as a colorless amorphous solid.

$^1$H-NMR (400 MHz, $CDCl_3$) δ: 1.12 (3H, t, J=7.1 Hz), 1.18 (3H, t, J=7.1 Hz), 1.41-1.48 (1H, m), 1.80-1.87 (1H, m), 1.93-2.03 (1H, m), 2.18-2.23 (1H, m), 3.13-3.20 (1H, m), 3.28-3.47 (4H, m), 3.71-3.76 (1H, m), 4.02 (1H, dd, J=8.9, 2.6 Hz), 4.12 (1H, dd, J=11.2, 3.2 Hz), 4.69-4.73 (1H, m), 5.06-5.12 (2H, m), 7.30-7.39 (5H, m).

MS (ESI) m/z: 335 $(M+H)^+$.

Step 2

(2S,5R)-5-amino-N,N-diethyltetrahydro-2H-pyran-2-carboxamide)

The compound (480 mg, 1.43 mmol) obtained in Step 1 above was used as a starting material and treated in the same way as in Step 3 of Reference Example 2 to give 282 mg (98%) of the title compound as a colorless amorphous solid.

$^1$H-NMR (400 MHz, DMSO-$d_6$) δ: 0.98 (3H, t, J=6.9 Hz), 1.10 (3H, t, J=6.9 Hz), 1.50 (1H, ddd, J=23.5, 11.8, 4.7 Hz), 1.63-1.75 (2H, m), 2.01-2.08 (1H, m), 2.92-3.00 (1H, m), 3.12-3.20 (1H, m), 3.23-3.39 (4H, m), 3.92 (1H, dq, J=10.8, 2.1 Hz), 4.02 (1H, dd, J=9.6, 3.7 Hz).

MS (ESI) m/z: 201 $(M+H)^+$.

Reference Example 54

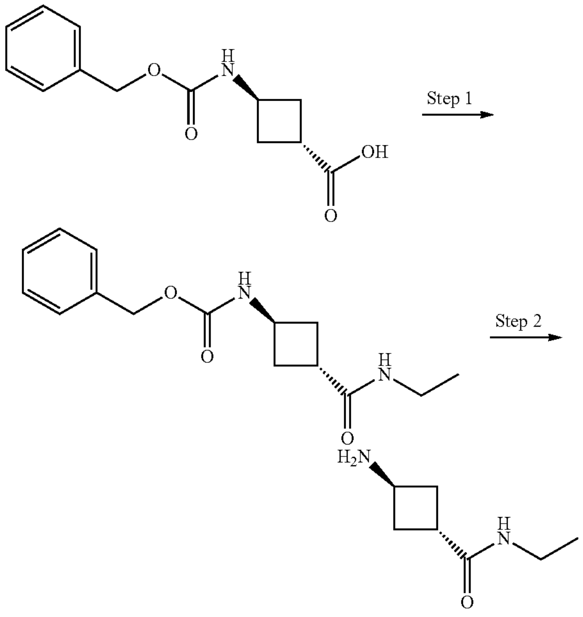

Step 1

Benzyl [trans-3-(ethylcarbamoyl)cyclobutyl]carbamate

The same starting material as in Step 1 of Reference Example 51 and ethylamine hydrochloride (79 mg, 0.96 mmol) were used as starting materials and treated in the same way as in Step 2 of Reference Example 28 to give 85 mg (64%) of the title compound as a colorless solid.

$^1$H-NMR (400 MHz, $CDCl_3$) δ: 1.13 (3H, t, J=7.3 Hz), 2.04-2.30 (2H, m), 2.57-2.67 (2H, m), 2.77-2.91 (1H, m), 3.25-3.35 (2H, m), 4.29-4.41 (1H, m), 4.91-5.15 (3H, m), 5.37 (1H) br si, 7.29-7.39 (5H, m).

MS (ESI) m/z: 277 $(M+H)^+$.

Step 2

Trans-3-amino-N-ethylcyclobutanecarboxamide

The compound (84 mg, 0.30 mmol) obtained in Step 1 above was used as a starting material and treated in the same way as in Step 3 of Reference Example 2 to give 43 mg. (100%) of the title compound as a colorless oil:

$^1$H-NMR (400 MHz, $CD_3OD$) δ: 1.10 (3H, t, J=7.1 Hz), 1.95-2.06 (2H, m), 2.38-2.49 (2H, m), 2.87-2.99 (1H, m), 3.14-3.23 (2H, m), 3.57-3.68 (1H, m).

MS (ESI) m/z: 143 $(M+H)^+$.

Reference Example 55

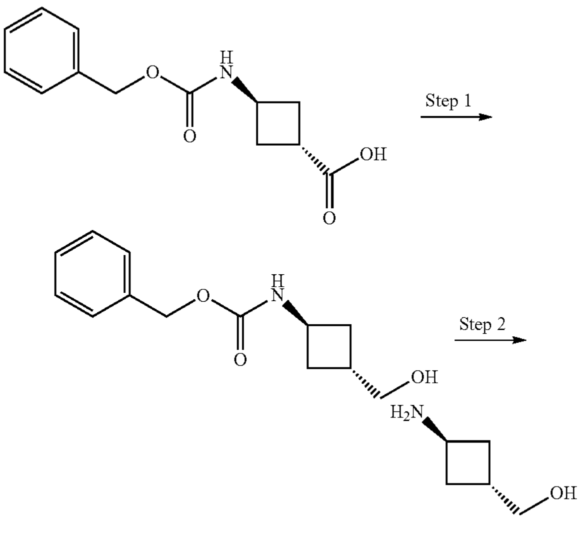

Step 1

Benzyl [trans-3-(hydroxymethyl)cyclobutyl]carbamate

Isobutyl chloroformate (0.14 ml, 1.04 mmol) and triethylamine (0.15 ml, 1.04 mmol) were added in that order to a tetrahydrofuran (4 ml) solution of the same starting material (260 mg, 1.04 mmol) as in Step 1 of Reference Example 51 under ice cooling, and the resulting mixture was stirred at the same temperature for 10 minutes. Insoluble matter was removed by filtration through celite, methanol (1 ml) was added to the filtrate and sodium borohydride (79 mg, 2.09 mmol) was added under ice cooling. After stirring for 30 minutes, 1N hydrochloric acid was added. The solvent was evaporated under reduced pressure, the residue was subjected to extraction with ethyl acetate and the organic layer was washed with brine and then dried over anhydrous sodium sulfate. The solvent was evaporated under reduced pressure and the residue was purified by silica gel column chromatography [n-hexane:ethyl acetate=3:1→1:1 (v/v)] to give 111 mg (45%) of the title compound as a colorless solid.

$^1$H-NMR (400 MHz, $CDCl_3$) δ: 1.36 (1H, br s), 1.95-2.08 (2H, m), 2.15-2.27 (2H, m), 2.32-2.47 (1H, m), 3.68 (2H, d, J=7.3 Hz), 4.17-4.33 (1H, m), 4.93 (1H, br s), 5.08 (2H, s), 7.29-7.39 (5H, m).

MS (ESI) m/z: 236 $(M+H)^+$.

Step 2

(Trans-3-aminocyclobutyl)methanol

The compound (34 mg, 0.14 mmol) obtained in Step 1 above was used as a starting material and treated in the same way as in Step 3 of Reference Example 2 to give 11 mg (75%) of the title compound as a colorless solid.

$^1$H-NMR (400 MHz, $CD_3OD$) δ: 1.83-1.94 (2H, m), 2.04-2.15 (2H, m), 2.26-2.39 (1H, m), 3.42-3.52 (1H, m), 3.55 (2H, d, J=7.3 Hz).

Reference Example 56

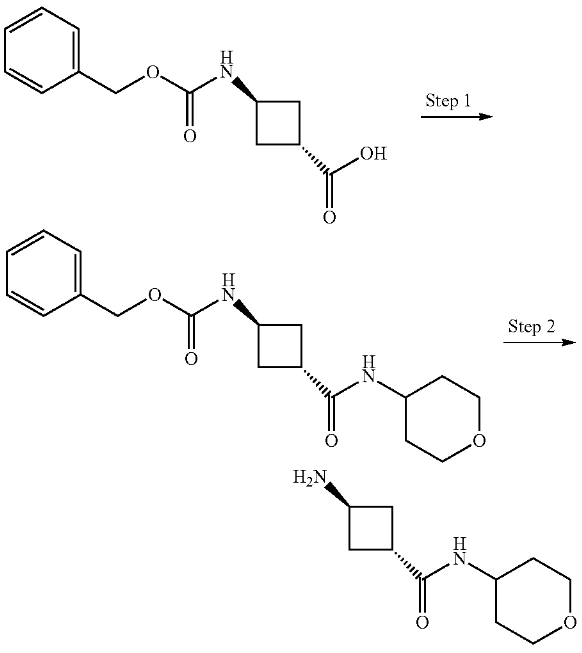

Step 1

Benzyl [trans-3-(tetrahydro-2H-pyran-4-ylcarbamoyl)cyclobutyl] carbamate

The same starting material as in Step 1 of Reference Example 51 and 4-aminotetrahydropyran hydrochloride (99 mg, 0.72 mmol) were used as starting materials and treated in the same way as in Step 2 of Reference Example 28 to give 104 mg (65%) of the title compound as a colorless solid.

$^{1}$H-NMR (DMSO-06) δ: 1.27-1.41 (2H, m), 1.61-1.71 (2H, m); 2.01-2.13 (2H, m), 2.22-2.31 (2H, m), 2.72-2.82 (1H, m), 3.28-3.35 (2H, m), 3.67-3.86 (3H, m), 4.09-4.22 (1H, m), 4.99 (2H, s), 7.28-7.40 (5H, m), 7.58 (1H, d, J=8.3 Hz), 7.70 (1H, d, J=7.8 Hz).

MS (ESI) m/z: 333 $(M+H)^{+}$.

Step 2

Trans-3-amino-N-(tetrahydro-2H-pyran-4-yl)cyclobutanecarboxamide

The compound (78 mg, 0.23 mmol) obtained in Step 1 above was used as a starting material and treated in the same way as in Step 3 of Reference Example 2 to give 47 mg (100%) of the title compound as a colorless solid.

$^{1}$H-NMR (400 MHz, $CD_3OD$) δ: 1.41-1.56 (2H, m), 1.74-1.84 (2H, m), 1.95-2.06 (2H, m), 2.38-2.48 (2H, m), 2.88-2.98 (1H, m), 3.41-3.51 (2H, m), 3.58-3.68 (1H, m), 3.80-3.97 (3H,

MS (ESI) m/z: 199 $(M+H)^{+}$.

Reference Example 57

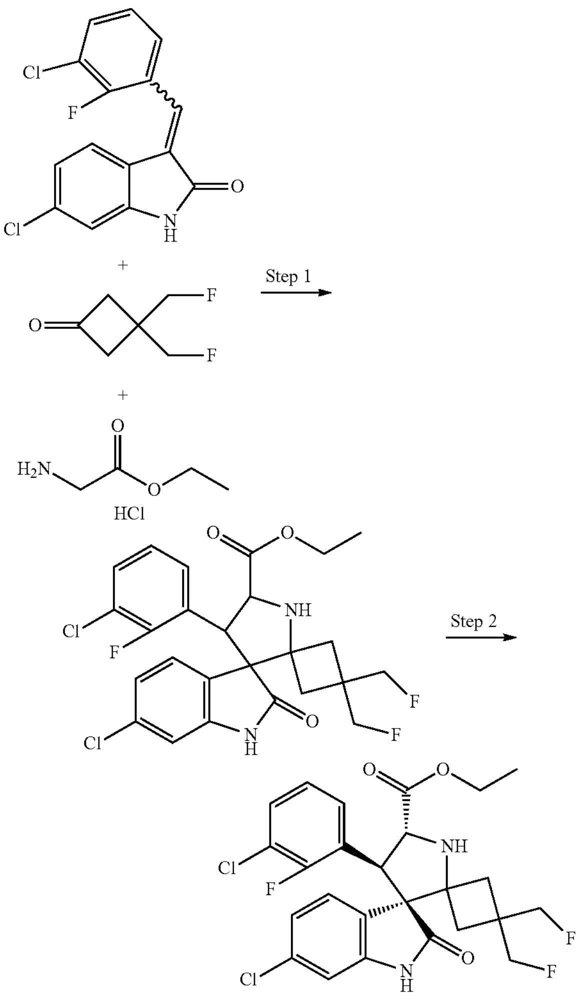

Step 1

Ethyl 6"-chloro-4'-(3-chloro-2-fluorophenyl)-3,3-bis(fluoromethyl)-2"-oxo-1",2"-dihydrodispiro[cyclobutane-1,2'-pyrrolidine-3',3"-indole]-5'-carboxylate (racemate)

Glycine ethyl ester hydrochloride (6.98 g, 50 mmol) and the compound (6.70 g, 50.0 mmol) obtained in Step 1 of Reference Example 21 were dissolved in tetrahydrofuran (210 ml) and N,N-dimethylformamide (210 ml), triethylamine (7.6 ml, 54.5 mmol) and molecular sieves 4A (powder) (18.8 g) were added and the resulting mixture was stirred at 70° C. for 1 hour. (3E/Z)-6-chloro-3-(3-chloro-2-fluorobenzylidene)-1,3-dihydro-2H-indol-2-one (WO2006/091646) (14.0 g, 45.4 mmol) was added to the reaction mixture and the resulting mixture was stirred at 70° ° C. for 14 hours. Glycine ethyl ester hydrochloride (1.58 g, 11.4 mmol) and the compound (1.52 g, 11.4 mmol) obtained in Step 2 of Reference Example 21 were further added to the reaction mixture and the resulting mixture was further stirred at 70° C. for 18 hours. After cooling, insoluble matter was removed by filtration through celite and the filtrate was concentrated under reduced pressure. Saturated sodium bicarbonate solution was added to the residue, followed by extraction with ethyl acetate. The organic layer was washed with water and brine and then dried over anhydrous magnesium sulfate. The solvent was evaporated under reduced pressure and the residue obtained was purified by silica gel column chromatography [n-hexane:ethyl acetate=9:1→1:1 (v/v)] to give 5.31 g (22%) of the title compound.

Step 2

Ethyl (3R,4'S,5'R)-6"-chloro-4'-(3-chloro-2-fluorophenyl)-3,3-bis(fluoromethyl)-2"-oxo-1",2"-dihydrodispiro[cyclobutane-1,2'-pyrrolidine-3',3"-indole]-5'-carboxylate The racemate (5.31 g, 10.1 mmol) obtained in Step 1 above was fractionated and purified by chiral column liquid chromatography [fractionation conditions: CHIRALPAK IC, n-hexane:tetrahydrofuran=4:1 (v/v)] to give 2.33 g (44%) of the title compound.

$^{1}$H-NMR (400 MHz, $CDCl_3$) δ: 1.19 (3H, t, J=7.1 Hz), 1.70 (1H, d, J=13.7 Hz), 1.83-1.89 (1H, m), 2.20 (1H, d, J=12.8 Hz), 2.42 (1H, dd, J=12.8, 2.7 Hz), 3.66-3.76 (1H, m); 3.77-3.96 (2H, m), 4.09-4.22 (2H, m), 4.45 (1H, d, J=9.5 Hz), 4.48 (1H, d, J=9.5 Hz), 4.54-4.78 (2H, m), 6.81 (1H; d, J=1.8 Hz), 6.96 (1H, td, J=8.0, 1.2 Hz), 7.13 (1H, dd, J=8.0, 2.1 Hz), 7.16-7.21 (1H, m), 7.36 (1H, br s), 7.40 (1H, dd, 0=8.1, 2.0 Hz), 7.44-7.48 (1H, m).

Reference Example 58

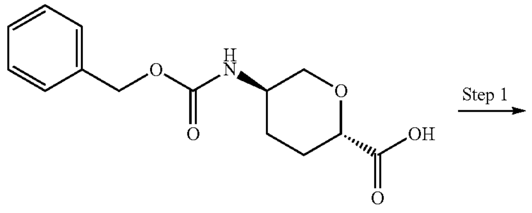

-continued

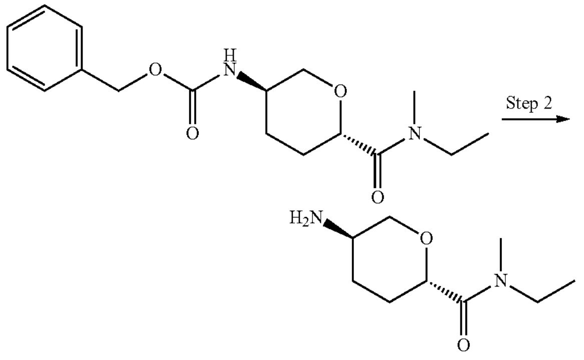

Step 1

Benzyl {(3R,6S)-6-[ethyl(methyl) carbamoyl]tetrahydro-2H-pyran-3-yl}carbamate

The compound (400 mg, 1.43 mmol) obtained in Step 3 of Reference Example 18 and N-methylethanamine (0.19 ml, 2.15 mmol) were used as starting materials and treated in the same way as in Step 2 of Reference Example 28 to give 466 mg (100%) of the title compound as a colorless amorphous solid.

$^1$H-NMR (400 MHz, $CDCl_3$) δ: 1.11 and 1.18 (total 3H, each t, J=7.1 Hz), 1.39-1.50 (1H, m), 1.82-1.90 (1H, m), 1.92-2.01 (1H, m), 2.16-2.25 (1H, m), 2.91 and 3.03 (total 3H, each s), 3.17 (1H, t, J=10.3 Hz), 3.33-3.49 (2H, m), 3.71-3.78 (1H, m), 4.01-4.07 (1H, m), 4.10-4.15 (1H, m), 4.68 (1H, d, J=6.9 Hz), 5.06-5.13 (2H, m), 7.31-7.38 (5H, m).

MS (ESI) m/z: 321 $(M+H)^+$.

Step 2

(2S,5R)—S-amino-N-ethyl-N-methyltetrahydro-2H-pyran-2-carboxamide

The compound (450 mg, 1.40 mmol) obtained in Step 1 above was used as a starting material and treated in the same way as in Step 3 of Reference Example 2 to give 240 mg (92%) of the title compound as a colorless amorphous solid.

$^1$H-NMR (400 MHz, DMSO-$d_6$) δ: 1.00-1.12 (3H, m), 1.49-1.55 (1H, m), 1.68-1.75 (2H, m), 2.04-2.11 (1H, m), 2.76-2.83 (1H, m), 2.91-3.00 (1H, m), 3.19 (3H, s), 3.27 (1H, t, J=10.3 Hz), 3.31-3.38 (1H, m), 3.94 (1H, dd, J=11.0, 4.6 Hz), 4.06 (1H, t, J=6.4 Hz).

MS (ESI) m/z: 187 $(M+H)^+$.

Reference Example 59

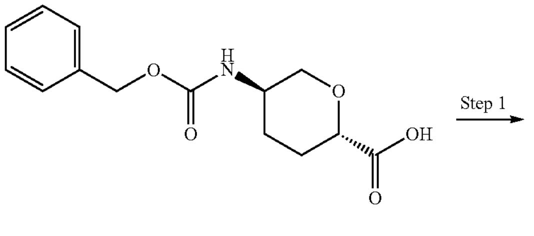

-continued

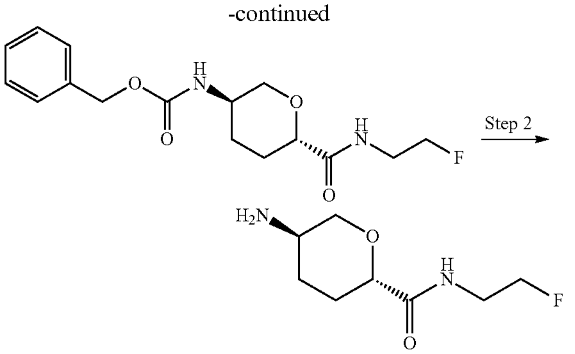

Step 1

Benzyl {(3R,6S)-6-[(2-fluoroethyl) carbamoyl]tetrahydro-2H-pyran-3-yl}carbamate

The compound (400 mg, 1.43 mmol) obtained in Step 3 of Reference Example 18 and 2-fluoroethanamine hydrochloride (214 mg, 2.15 mmol) were used as starting materials and treated in the same way as in Step 2 of Reference Example 28 to give 310 mg (96%) of the title compound as a colorless solid.

$^1$H-NMR (400 MHz, $CDCl_3$) δ: 1.32-1.45 (1H, m), 1.50-1.59 (1H, m), 2.13-2.19 (1H, m), 2.26 (1H, dq, J=13.7, 3.2 Hz), 3.08 (1H, t, J=10.8 Hz), 3.48-3.78 (4H, m), 4.18-4.23 (1H, m), 4.42-4.57 (3H, m), 5.06-5.14 (2H, ml, 6.89 (1H, br s), 7.31-7.39 (5H, m).

MS (ESI) m/z: 325 $(M+H)^+$.

Step 2

(2S,5R)-5-amino-N-(2-fluoroethyl)tetrahydro-2H-pyran-2-carboxamide

The compound (300 mg, 0.92 mmol) obtained in Step 1 above was used as a starting material and treated in the same way as in Step 3 of Reference Example 2 to give 140 mg (80%) of the title compound as a colorless solid.

$^1$H-NMR (400 MHz, DMSO-$d_6$) δ: 1.13-1.36 (2H, m), 1.86-1.93 (2H, m), 2.53-2.61 (1H, m), 2.93 (1H, t, J=10.5 Hz), 3.30-3.44 (2H, m), 3.61 (1H, dd, J=11.2, 2.5 Hz), 3.84 (1H, dq, J=11.0, 2.1 Hz), 4.33-4.80 (2H, m), 7.74 (1H, br s).

MS (ESI) in/z: 191 $(M+H)^+$.

Reference Example 60

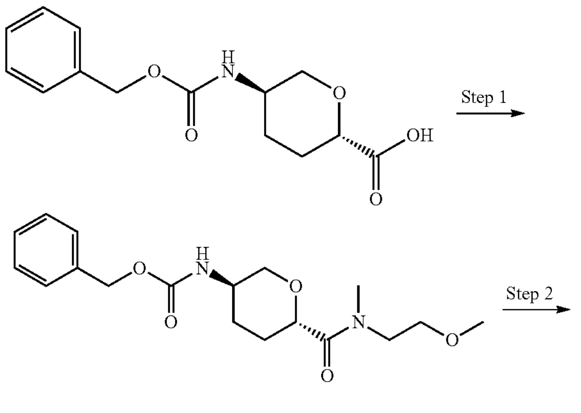

-continued

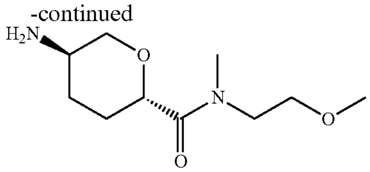

Step 1

Benzyl {(3R,6S)-6-[(2-methoxyethyl)(methyl) carbamoyl]tetrahydro-2H-pyran-3-yl}carbamate The compound (400 mg, 1.43 mmol) obtained in Step 3 of Reference Example 18 and (2-methoxyethyl)methylamine (191 mg, 2.15 mmol) were used as starting materials and treated in the same way as in Step 2 of Reference Example 28 to give 442 mg (88%) of the title compound as a colorless amorphous solid.

$^1$H-NMR (400 MHz, $CDCl_3$) δ: 1.41-1.46 (1H, m), 1.82-1.99 (2H, m), 2.17-2.23 (1H, m), 2.96 and 3.12 (total 3H, each s), 3.15-3.20 (1H, m), 3.33 and 3.33 (total 3H, each s), 3.48-3.56 (3H, m), 3.70-3.78 (2H, m), 4.04-4.17 (2H, m), 4.67 (1H, br s), 5.05-5.14 (2H, m), 7.30-7.39 (5H, m).

MS (ESI) m/z: 351 $(M+H)^+$.

Step 2

(2S,5R)-5-amino-N-(2-methoxyethyl)-N-methyltetrahydro-2H-pyran-2-carboxamide

The compound (440 mg, 1.26 mmol) obtained in Step 1 above was used as a starting material and treated in the same way as in Step 3 of Reference Example 2 to give 264 mg (978) of the title compound as a colorless amorphous solid.

$^1$H-NMR (400 MHz, DMSO-$d_6$) δ: 1.53-1.73 (3H, m), 2.06-2.12 (1H, m), 2.80 and 3.02 (total 3H, each s), 3.05-3.13 (1H, m), 3.21 and 3.25 (total 3H, each s), 3.35-3.41 (3H, m), 3.42-3.67 (2H, m), 3.95-4.01 (1H, m), 4.11-4.17 (1H, m), 8.10 (2H, br s).

MS (ESI) m/z: 217 $(M+H)^+$.

Reference Example 61

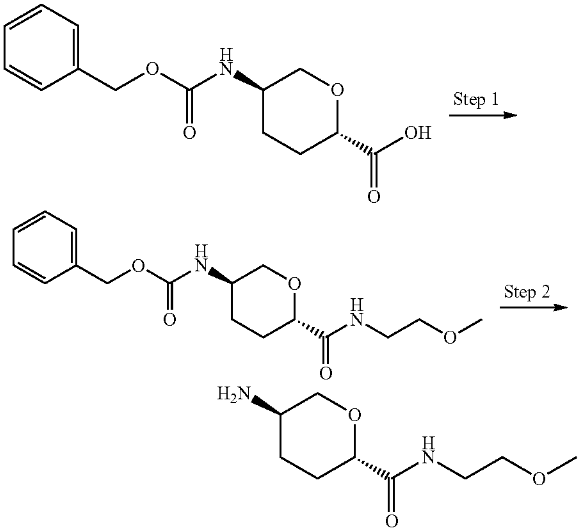

Step 1

Benzyl {(3R,6S)-6-[(2-methoxyethyl) carbamoyl] tetrahydro-2H-pyran-3-yl}carbamate The compound (600 mg, 2.15 mmol) obtained in Step 3 of Reference Example 18 and 2-methoxyethylamine (0.28 ml, 3.23 mmol) were used as starting materials and treated in the same way as in Step 2 of Reference Example 28 to give 359 mg (50%) of the title compound as a colorless solid.

$^1$H-NMR (400 MHz, $CDCl_3$) δ: 1.33-1.42 (1H, m), 1.50-1.57 (1H, m), 2.12-2.17 (1H, m), 2.25 (1H, dq, J=13.6, 3.2 Hz), 3.07 (1H, t, J=10.6 Hz), 3.37 (3H, s), 3.41-3.50 (4H, m), 3.68-3.72 (1H, m), 3.74 (1H, dd, J=11.5, 2.4 Hz), 4.17-4.22 (1H, m), 4.52 (1H, d, J=6.6 Hz), 5.06-5.14 (2H, m) 6.84 (1H, br s), 7.31-7.39 (5H, m).

MS (ESI) m/z: 337 $(M+H)^+$.

Step 2

(2S,5R)-5-amino-N-(2-methoxyethyl)tetrahydro-2H-pyran-2-carboxamide

The compound (350 mg, 1.04 mmol) obtained in Step 1 above was used as a starting material and treated in the same way as in Step 3 of Reference Example 2 to give 220 mg (100%) of the title compound as a colorless oil.

$^1$H-NMR (400 MHz, DMSO-$d_6$) δ: 1.12-1.22 (1H, m), 1.24-1.34 (1H, m), 1.85-1.92 (2H, m), 2.53-2.60 (1H, m), 2.91 (1H, t, J=10.5 Hz), 3.16-3.27 (5H, m), 3.32 (28, t, J=6.0 Hz), 3.58 (1H, dd, J=11.4, 2.3 Hz), 3.83 (1H, ddd, J=11.0, 4.2, 1.8 Hz), 7.46 (1H, s).

MS (ESI) m/z: 203 $(M+H)^+$.

Reference Example 62

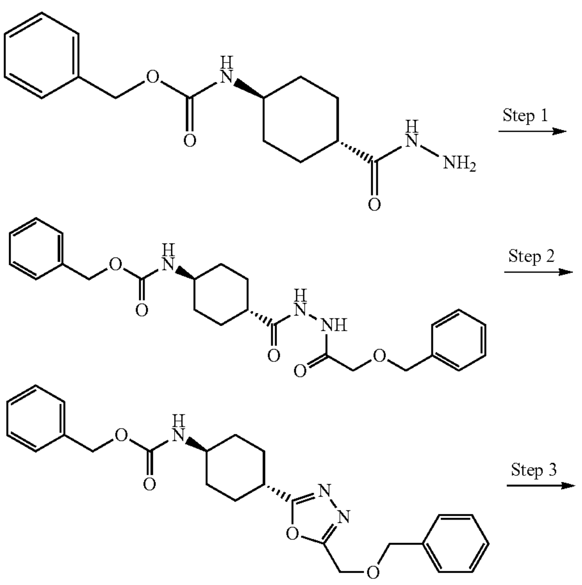

-continued

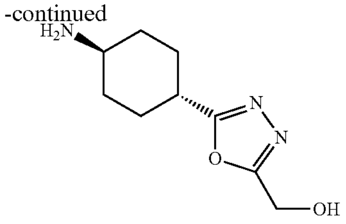

Step 1

Benzyl [trans-4-({2-[(benzyloxy)acetyl] hydrazino}carbonyl)cyclohexyl]carbamate

The compound (507 mg, 1.74 mmol) obtained in Step 1 of Reference Example 3 and benzyloxyacetic acid (0.28 ml, 1.92 mmol) were used as starting materials and treated in the same way as in Step 2 of Reference Example 28 to give 695 mg (918) of the title compound as a colorless solid.

$^1$H-NMR (500 MHz, $CDCl_3$) δ: 1.08-1.21 (2H, m), 1.61-1.72 (2H, m), 1.90-2.02 (2H, m), 2.06-2.21 (3H, m), 3.39-3.63 (1H, m), 4.10 (2H, s), 4.50-4.70 (3H, m), 5.08 (2H, s), 7.29-7.42 (10H, m), 7.94-8.03 (1H, m), 8.80-8.88 (1H, m).

Step 2

Benzyl (trans-4-(5-[(benzyloxy)methyl]-1,3,4-oxadiazol-2-yl)cyclohexyl) carbamate Hexachloroethane (205 mg, 0.87 mmol), triethylamine (0.29 ml, 2.08 mmol), and the compound (152 mg, 0.35 mmol) obtained in Step 1 above were added to a dichloromethane (9 ml) solution of triphenylphosphine (273 mg, 1.04 mmol) under ice cooling and the resulting mixture was stirred at room temperature for 24 hours. The reaction mixture was diluted with dichloromethane:methanol [10:1 (v/v)], washed with 10% aqueous citric acid solution, and dried over anhydrous sodium sulfate. The solvent was concentrated under reduced pressure and the residue was purified by silica gel column chromatography [n-hexane: ethyl acetate=2:1→1:1 (v/v)] to give 125 mg (86%) of the title compound as a colorless solid.

$^1$H-NMR (500 MHz, $CDCl_3$) δ: 1.20-1.33 (2H, m), 1.64-1.82 (2H, m), 2.11-2.23 (4H, m), 2.78-2.88 (1H, m), 3.50-3.64 (1H, m), 4.62 (2H, s), 4.67 (2H, s), 4.71-4.79 (1H, m), 5.09 (2H, s), 7.28-7.39 (10H, m).

MS (ESI) m/z: 422 $(M+H)^+$.

Step 3

[5-(Trans-4-aminocyclohexyl)-1,3,4-oxadiazol-2-yl] methanol

The compound (125 mg, 0.30 mmol) obtained in Step 2 above was used as a starting material and treated in the same way as in Step 3 of Reference Example 2 to give 52 mg (89%) of the title compound as a colorless solid.

$^1$H-NMR (500 MHz, $CD_3OD$) δ: 1.22-1.35 (2H, m), 1.58-1.69 (2H, m), 1.97-2.04 (2H, m), 2.11-2.22 (2H, m), 2.64-2.72 (1H, m), 2.85-2.95 (1H, m), 4.71 (2H, s).

Reference Example 63

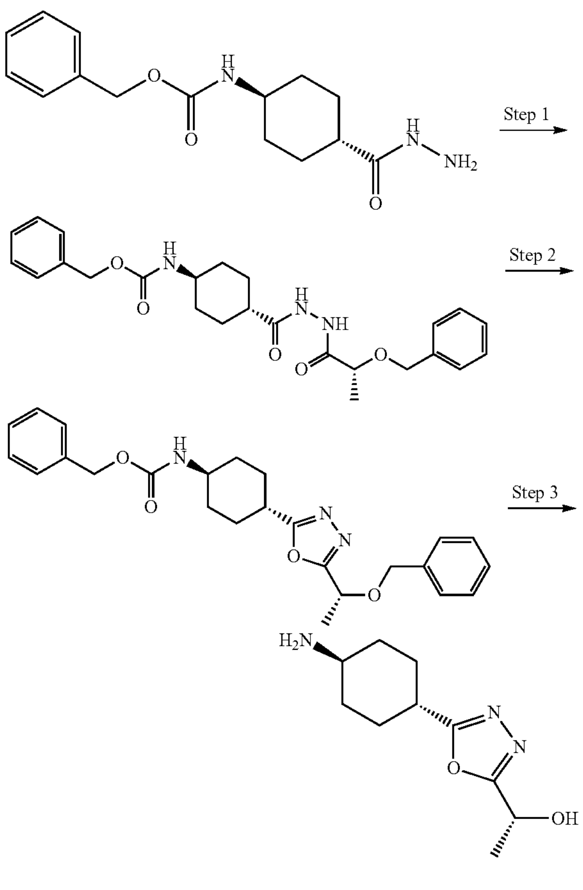

Step 1

Benzyl [trans-4-({2-[(2R)-2-(benzyloxy) propanoyl] hydrazino}carbonyl)cyclohexyl] carbamate The compound (504 mg, 1.73 mmol) obtained in Step 1 of Reference Example 3 and (R)-(+)-2-(benzyloxy) propionic acid (386 mg, 2.08 mmol) were used as starting materials and treated in the same way as in Step 2 of Reference Example 28 to give 687 mg (88%) of the title compound as a colorless solid:

$^1$H-NMR (500 MHz, DMSO-$d_6$) δ: 1.28-1.39 (2H, m), 1.44 (3H, d, J=6.4 Hz), 1.50-1.64 (2H, m), 1.87-1.96 (2H, m), 1.96-2.06 (2H, m), 2.21-2.32 (1H, m), 3.33-3.46 (1H, m), 4.12 (1H, q, J=6.4 Hz), 4.57 (1H, d, J=12.0 Hz), 4.75 (1H, d, J=12.0 Hz), 5.15 (2H, s), 7.37 (1H, d, J=7.5 Hz), 7.41-7.57 (10H, m), 9.86-9.90 (1H, m), 9.92-9.97 (1H, m).

Step 2

Benzyl (trans-4-{5-[(1R)-1-(benzyloxy)ethyl]-1,3,4-oxadiazol-2-yl}cyclohexyl) carbamate The compound (687 mg, 1.52 mmol) obtained in Step 1 above was used as a starting material and treated in the same way as in Step 2 of Reference Example 62 to give 606 mg (92%) of the title compound as a colorless oil:

$^1$H-NMR (500 MHz, $CDCl_3$) δ: 1.22-1.33 (2H, m), 1.61 (3H, d, J=6.9 Hz), 1.65-1.78 (2H, m), 2.12-2.25 (4H, m), 2.78-2.88 (1H, m), 3.51-3.65 (1H, m), 4.51 (1H, d, J=11.5. Hz), 4.56 (1H, d, J=11.5 Hz), 4.59-4.69 (1H, m), 4.80 (1H, q, J=6.7 Hz), 5.10 (2H, s), 7.23-7.43 (10H, m).

MS (ESI) m/z: 436 $(M+H)^+$.

Step 3

(1R)-1-[5-(trans-4-aminocyclohexyl)-1,3,4-oxadiazol-2-yl]ethanol

The compound (606 mg, 1.39 mmol) obtained in Step 2 above was used as a starting material and treated in the same way as in Step 3 of Reference Example 2 to give 288 mg (99%) of the title compound as a light brown oil.

$^1$H-NMR (400 MHz, $CD_3OD$) δ: 1.21-1.36 (2H, m), 1.53-1.70 (5H, m), 1.95-2.05 (2H, m), 2.11-2.22 (2H, m), 2.64-2.74 (1H, m), 2.84-2.96 (1H, m), 4.98 (1H, q, J=6.7 Hz).

Reference Example 64

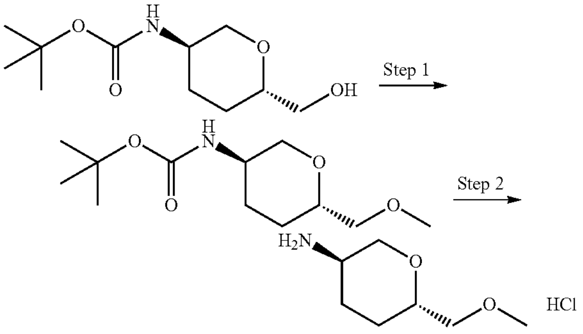

Step 1

1,5-Anhydro-2-[(tert-butoxycarbonyl)amino]-2,3,4-trideoxy-6-O-methyl-D-erythro-hexitol The same starting material (500 mg, 2.16 mmol) as in Step 1 of Reference Example 2 was used and treated in the same way as in Step 2 of Reference Example 23 to give 433 mg (82%) Of the title compound as a colorless solid.

$^1$H-NMR (400 MHz, $CDCl_3$) δ: 1.28 (1H, ddd, J=24.6, 12.5, 4.0 Hz), 1.41-1.48 (10H, m), 1.65-1.73 (1H, m), 2.08-2.15 (1H, m), 3.02 (1H, t, J=10.8 Hz), 3.34-3.46 (CH, m), 3.60-3.65 (1H, m), 4.11 (1H, dd, J=11.2, 3.4 Hz), 4.24 (1H, br s).

MS (ESI) m/z: 268 $(M+Na)^+$.

Step 2

2-Amino-1,5-anhydro-2,3,4-trideoxy-6-O-methyl-D-erythro-hexitol hydrochloride

The compound (420 mg, 1.71 mmol) obtained in Step 1 above was used as a starting material and treated in the same way as in Step 1 of Reference Example 2 to give 360 mg (100%) of the title compound as a colorless amorphous solid.

¿H-NMR (400 MHz, DMSO-$d_6$) δ: 1.24-1.35 (1H, m), 1.47-1.56 (1H, m), 1.64-1.69 (1H, m), 2.01-2.07 (1H, m), 3.00-3.07 (1H, m), 3.22 (3H, s), 3.24-3.31 (2H, m), 3.40-3.46 (2H, m), 3.97 (1H, dq, J=10.9, 2.2 Hz).

MS (ESI) m/z: 146 $(M+H)^+$.

Reference Example 65

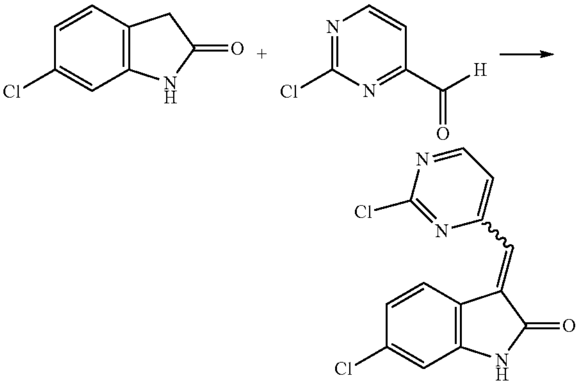

6-Chloro-3-[(2-chloropyrimidin-4-yl)methylene]-1,3-dihydro-2H-indol-2-one

2-Chloropyrimidine-4-carbaldehyde (3.05 g, 21.4 mmol) was used as a starting material and treated in the same way as in Reference Example 4 to give 5.02 g (80%) of the title compound as a red solid.

$^1$H-NMR (500 MHz, DMSO-$d_6$) δ: 6.92 (1H, d, J=2.3 Hz), 7.10 (1H, dd, J=8.3, 2.0 Hz), 7.52 (1H, s), 8.00 (1H, d, J=5.2 Hz), 8.83 (1H, d, J=8.0 Hz), 8.95 (1H, d, J=4.6 Hz), 10.94 (1H, s).

MS (ESI) m/z: 291 $(M+H)^+$.

Reference Example 66

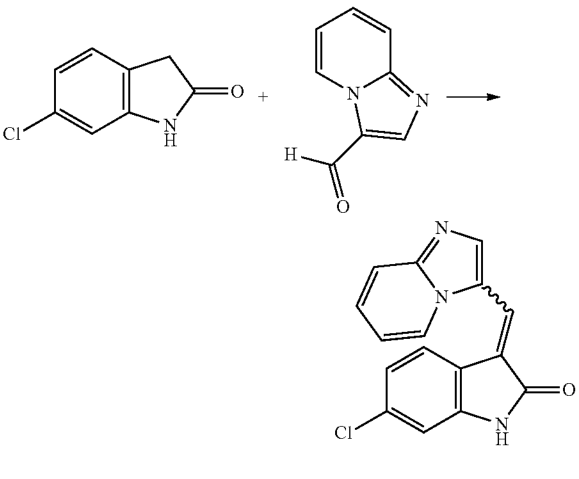

(3E/Z)-6-chloro-3-(imidazo[1,2-a]pyridin-3-ylmethylene)-1,3-dihydro-2H-indol-2-one Imidazo[1,2-a]pyridine-3-carbaldehyde (2.67 g, 18:3 mmol) was used as a starting material and treated in the same way as in Reference Example 4 to give 2.44 g (45%) of the title compound as an orange solid.

MS (ESI) m/z: 295 $(M+H)^+$.

Reference Example 67

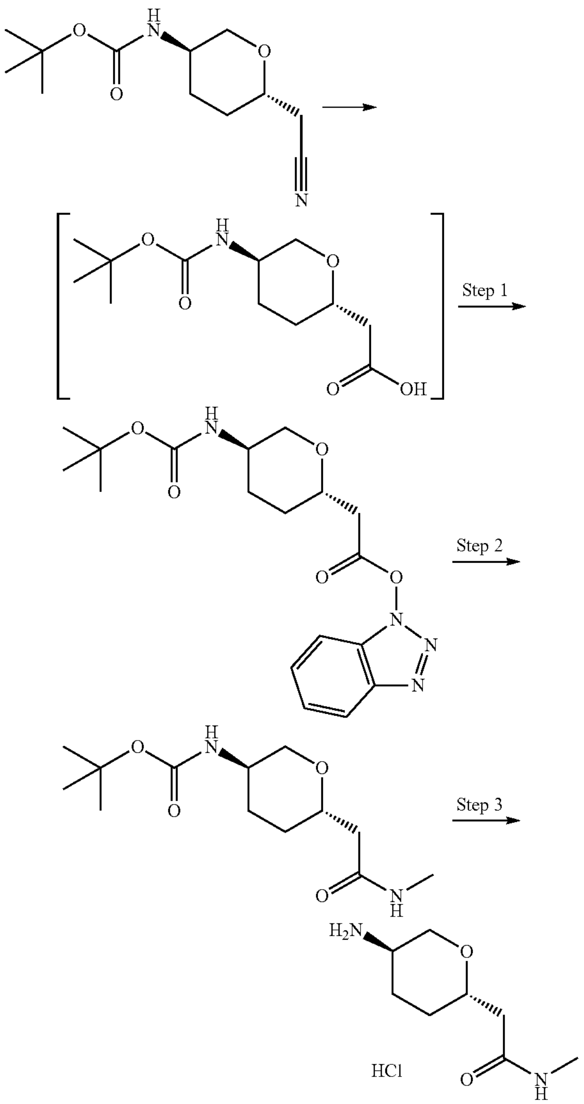

Step 1

Text-butyl {(3R,6S)-6-[2-(1H-benzotriazol-1-yloxy)-2-oxoethyl]tetrahydro-2H-pyran-3-yl}carbamate Concentrated hydrochloric acid (40 ml) was added to the compound (1.99 g, 8.28 mmol) obtained in Step 1 of Reference Example 49, concentrated sulfuric acid (20 ml) was added under ice cooling and then the resulting mixture was stirred at 100° C. for 2 hours. Ice (300 g) was added to the reaction mixture under ice cooling and then the resulting mixture was rendered basic by gradual addition of sodium bicarbonate (84 g). The reaction mixture was diluted with dioxane (400 ml), di-t-butyl dicarbonate (11.5 g, 53.0 mmol) was added under ice cooling and then the resulting mixture was stirred at room temperature for 24 hours. The reaction mixture was rendered acidic by addition of citric acid (53 g), followed by extraction with ethyl acetate. The organic layer was washed with brine and then dried over anhydrous sodium sulfate. The solvent was evaporated under reduced pressure, and the residue obtained was dissolved in methylene chloride (20 ml), 1-Hydroxybenzotriazole (2.24 g, 16.6 mmol) and 1-ethyl-3-(3-dimethylaminopropyl) carbodiimide hydrochloride (3.17 g, 16.5 mmol) were added and the resulting mixture was stirred at room temperature for 24 hours. Brine was added to the reaction mixture, followed by extraction with ethyl acetate. The organic layer was washed with saturated sodium bicarbonate solution and brine in that order and then dried over anhydrous magnesium sulfate. The solvent was evaporated under reduced pressure and the residue obtained was purified by silica gel column chromatography [methanol:chloroform=5:95 (v/v)] to give 2.27 g (738) of the title compound as a solid.

MS (FAB) m/z: 377 $(M+H)^+$.

Step 2

Tert-butyl {(3R,6S)-6-[2-(methylamino)-2-oxoethyl]tetrahydro-2H-pyran-3-yl}carbamate Methylamine/tetrahydrofuran solution (2.0 mol/l) ml) was added to a tetrahydrofuran (5 ml) solution of the compound (378 mg, 1.00 mmol) obtained in Step 1 above and the resulting mixture was stirred at room temperature for 1 hour. The reaction mixture was diluted with ethyl acetate, washed with water, saturated sodium bicarbonate solution, and brine in that order and then dried over anhydrous sodium sulfate. The solvent was evaporated under reduced pressure and the residue obtained was purified by silica gel column chromatography [methanol:ethyl acetate=5:95 (v/v)] to give 135 mg (49%) of the title compound as a solid.

$^1$H-NMR (500 MHz, $CDCl_3$) δ: 1.27-1.35 (1H, m), 1.44-1.50 (10H, m), 1.72-1.75 ($^1$H, m), 2.06-2.10 (1H, m), 2.36 (2H, d, J=6.3 Hz), 2.80 (3H, d, J=5.2 Hz), 3.02 (1H, t, J=10.6 Hz), 3.58-3.63 (2H, m), 4.07-4.11 (1H, m), 4.28 (1H, br s), 6.22 (1H, br s).

MS (FAB) m/z: 273 $(M+H)^+$;

Step 3

2-[(2, 5R)-5-aminotetrahydro-2H-pyran-2-yl]-N-methylacetamide

The compound (60 mg, 0.22 mmol) obtained in Step 2 above was used as a starting material and treated in the same way as in Step 1 of Reference Example 2 to give the title compound as a solid.

Reference Example 68

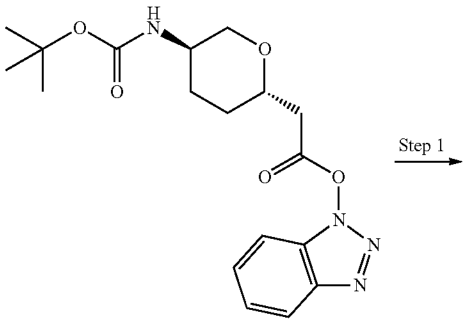

-continued

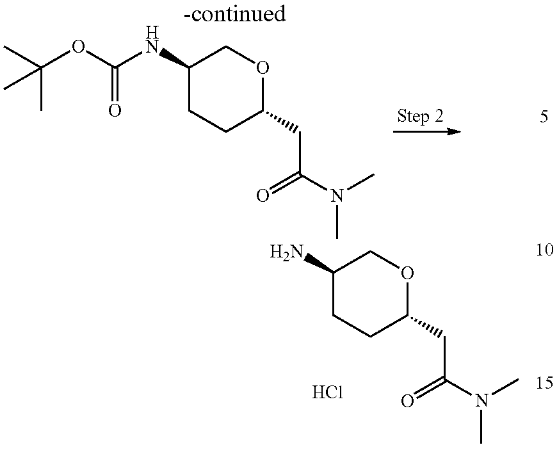

Step 1

Tert-butyl {(3R,6S)-6-[2-(dimethylmethylamino)-2-oxoethyl]tetrahydro-2H-pyran-3-yl}carbamate The compound (385 mg, 1.00 mmol) obtained in Step 1 of Reference Example 67 and aqueous dimethylamine solution (40 wt %, 0.25 ml, 2.00 mmol) were used as starting materials and treated in the same way as in Step 2 of Reference Example 67 to give 168 mg (57%) of the title compound as a solid.

$^1$H-NMR (500 MHz, $CDCl_3$) δ: 1.28-1.45 (11H, m), 1.85-1.88 (1H, m), 2.06-2.09 (1H, m), 2.32 (1H, dd, J=15.2, 5.4 Hz), 2.66 (1H, dd, J=15.2, 7.2 Hz), 2.95 (3H, s), 3.00-3.05 (4H, m), 3.59-3.62 (1H, m), 3.74-3.79 (1H, m), 4.01-4.04 (1H, m), 4.32-4.30 (1H, m).

MS (FAB) m/z: 287 $(M+H)^+$.

Step 2

2-[(2S,5R)-5-aminotetrahydro-2H-pyran-2-yl]-N,N-dimethylacetamide

The compound (69 mg, 0.24 mmol) obtained in Step 1 above was used as a starting material and treated in the same way as in Step 1 of Reference Example 2 to give the title compound as a solid.

Reference Example 69

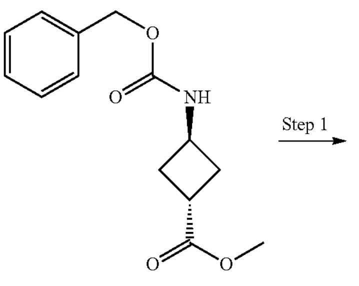

-continued

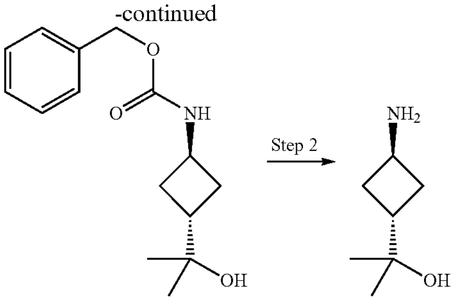

Step 1

Benzyl [trans-3-(2-hydroxypropan-2-yl)cyclobutyl] carbamate

The same starting material (99 mg, 0.38 mmol) as in Step 1 of Reference Example 50 was used and treated in the same way as in Step 1 of Reference Example 5 to give 55 mg (55%) of the title compound as an oil.

$^1$H-NMR (400 MHz, $CDCl_3$) δ: 1.16 (CH, s), 1.87-2.01 (2H, m), 2.27-2.41 (4H, m), 4.06-4.18 (1H, m), 4.94 (1H, br s), 5.09 (2H, s), 7.30-7.39 (5H, m).

MS (ESI) m/z: 2.64 $(M+H)^+$.

Step 2

2-(Trans-3-aminocyclobutyl) propan-2-ol

The compound (55 mg, 0.21 mmol) obtained in Step 1 above was used as a starting material and treated in the same way as in Step 3 of Reference Example 2 to give 24 mg (89%) of the title compound as an oil.

$^1$H-NMR (400 MHz, $CD_3OD$) δ: 1.11 (6H, s), 1.76-1.86 (2H, m), 2.24-2.42 (3H, m), 3.36-3.46 (1H, m).

Reference Example 70

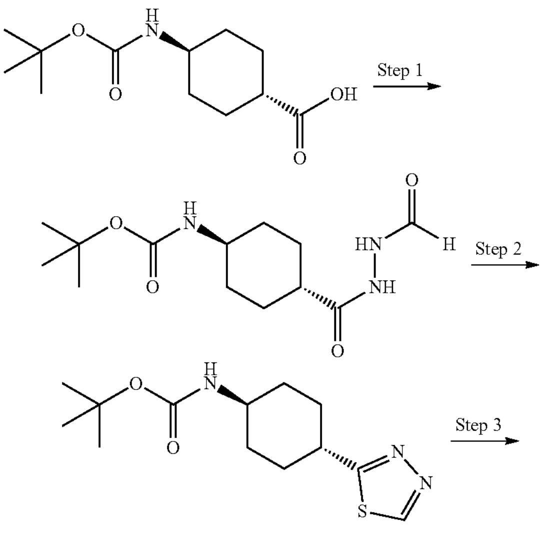

-continued

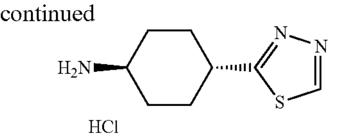

Step 1

Tert-butyl {trans-4-[(2-formylhydrazino)carbonyl]cyclohexyl}carbamate

The same starting material (500 mg, 2.06 mmol) as in Step 1 of Reference Example 3 and formohydrazide (123 mg, 2.06 mmol) were used as starting materials and treated in the same way as in Step 4 of Reference Example 18 to give 459 mg (78%) of the title compound as a solid.

MS (ESI) m/z: 286 $(M+H)^+$.

Step 2

Tert-butyl [trans-4-(1,3,4-thiazol-2-yl)cyclohexyl]carbamate

A Lawesson's reagent (651 mg, 1.61 mmol) was added to a toluene (18 ml) suspension of the compound (459 mg, 1.61 mmol) obtained in Step 1 above at room temperature and the resulting mixture was heated to reflux for 2.5 hours. After cooling, insoluble matter was removed by filtration and the filtrate was concentrated under reduced pressure. The residue obtained was purified by medium pressure silica gel column chromatography (hexane:ethyl acetate=3:1→1:1) to give 225 mg (49%) of the title compound as a solid.

$^1$H-NMR (400 MHz, $CDCl_3$) δ: 1.26-1.37 (2H, m), 1:45 (9H, s), 1.64-1.75 (2H, m), 2.11-2.31 (4H, m), 3.13-3.23 (1H, ml; 3.44-3.61 (1H, m), 4.40-4.57 (1H, m), 9.04 (1H, s).

Step 3

Trans-4-(1,3,4-thiazol-2-yl)cyclohexanamine hydrochloride 4N hydrochloric acid/1,4-dioxane (2.0 ml) and dichloromethane (0.5 ml) were added to the compound (51 mg, 0.18 mmol) obtained in Step 2 above at room temperature and the resulting mixture was stirred for 3 hours. The reaction mixture was concentrated under reduced pressure to give 46 mg (99%) of the title compound as a solid.

$^1$H-NMR (400 MHz, $CD_3OD$) δ: 1.56-1.66 (2H, m), 1.72-1.83 (2H, m), 2.15-2.22 (2H, m), 2.28-2.35 (2H, m), 3.18-3.34 (2H, m), 9.38 (1H, s).

Reference Example 71

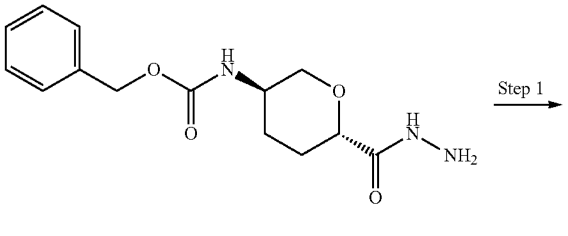

-continued

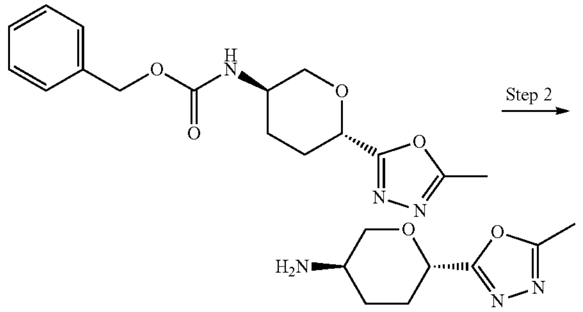

Step 1

Benzyl [(3R,6S)-6-(5-methyl-1,3,4-oxazol-2-yl)tetrahydro-2H-pyran-3-yl]carbamate The compound (401 mg, 1.37 mmol) obtained in Step 4 of Reference Example 18 and trimethyl orthoacetate (1.01 ml, 7.94 mmol) were used as starting materials and treated in the same way as in Step 2 of Reference Example 3 to give 139 mg (30%) of the title compound as a solid.

$^1$H-NMR (400 MHz, $CDCl_3$) δ: 1.48-1.63 (11, m), 1.99-2.29 (3H, m), 2.54 (3H, s), 3.24-3.36 (1H, m), 3.74-3.90 (1H, m), 4.12-4.23 (1H, m), 4.55-4.69 (1H, m), 4.72-4.85 (1H, m), 5.02-5.20 (2H, m), 7.29-7.43 (5H, m).

Step 2

(3R,6S)-6-(5-methyl-1,3,4-oxazol-2-yl)tetrahydro-2H-pyran-3-amine

The compound (139 mg, 0.44 mmol) obtained in Step 1 above was used as a starting material and treated in the same way as in Step 3 of Reference Example 2 to give 79 mg (99%) of the title compound as an oil, $^1$H-NMR (400 MHz, $CD_3OD$) δ: 1.40-1.50 (1H, m), 1.89-1.99 (1H, m), 2.03-2.10 (1H, m), 2.10-2.18 (1H, m), 2.53 (3H, s), 2.78-2.86 (1H, m), 3.18-3.26 (1H, m), 3.37-4.03 (2H, m), 4.59 (1H, dd, J=11.17, 2.58 Hz).

Reference Example 72

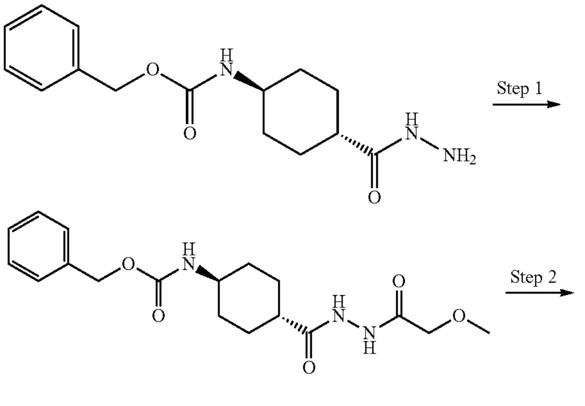

-continued

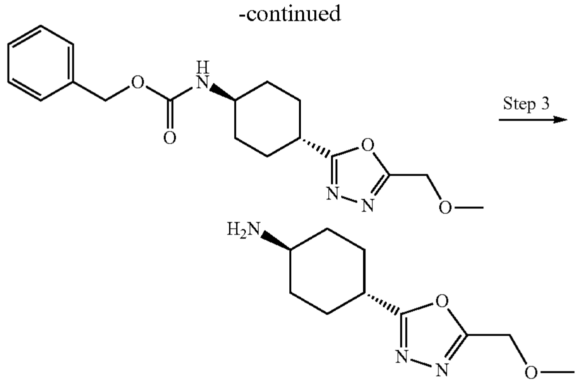

Step 1

Benzyl (trans-4-{[2-(methoxyacetyl) hydrazino] carbonyl}cyclohexylcarbamate

1-Hydroxybenzotriazole (231 mg, 1.71 mmol) and 1-ethyl-3-(3-dimethylaminopropyl) carbodiimide hydrochloride (394 mg, 2.05 mmol) were added to an N,N-dimethylformamide (10 ml) suspension of the compound (499 mg, 1.71 mmol) obtained in Step 1 of Reference Example 3 combined with methoxyacetic acid (0.16 ml, 2.05 mmol) and the resulting mixture was stirred at room temperature for 24 hours. Water was added to the reaction mixture and the precipitated solid was collected by filtration and dried to give 553 mg (894) of the title compound as a solid.

$^1$H-NMR (400 MHz, DMSO-$d_6$) δ: 1.11-1.23 (2H, m), 1.34-1.47 (2H, m), 1.70-1.79 (2H, m), 1.80-1.90 (2H, m), 2.05-2.15 (1H, m), 3.18-3.28 (1H, m), 3.31 (3H, s), 3.88 (2H, s), 5.00 (2H, s), 7.21 (1H, d, J=8.02 Hz), 7.27-7.41 (5H, m), 9.61-9.74 (2H, m).

Step 2

Benzyl {trans-4-[5-(methoxymethyl)-1,3,4-oxazol-2-yl]cyclohexyl}carbamate

The compound (199 mg, 0.55 mmol) obtained in Step 1 above was used as a starting material and treated in the same way as in Step 2 of Reference Example 62 to give the title compound as a mixture with triphenylphosphine oxide.

Step 3

Trans-4-[5-(methoxymethyl)-1,3,4-oxazol-2-yl]cyclohexanamine

10% Palladium carbon (200 mg) was added to a methanol (8 ml) solution of the mixture (399 mg) obtained in Step 2 above and the resulting mixture was stirred for 2 hours under hydrogen atmosphere. The catalyst was removed by filtration through celite and then the filtrate was concentrated under reduced pressure. The residue obtained was dissolved in ethyl acetate, followed by extraction with 1N hydrochloric acid. Subsequently, the aqueous layer was rendered basic by addition of 1N sodium hydroxide solution, followed by extraction with chloroform:methanol [5:1 (v/v)]. The organic layer was dried over anhydrous sodium sulfate. The solvent was evaporated under reduced pressure to give 78 mg (67%) of the title compound as an oil.

$^1$H-NMR (400 MHz, $CD_3OD$) δ: 1.22-1.36 (2H, m), 1.57-1.71 (2H, m), 1.96-2.05 (2H, m), 2.12-2.21 (2H, m), 2.65-2.75 (1H, m), 2.85-2.96 (1H, m), 3.42 (3H, s), 4.62 (28, s).

Reference Example 73

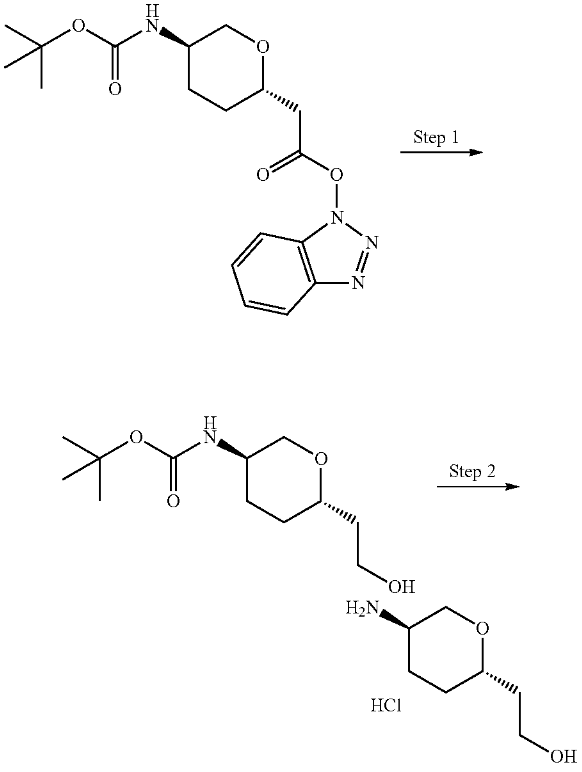

Step 1

Tert-butyl [(3R,6S)-6-(2-hydroxyethyl)tetrahydro-2H-pyran-3-yl]carbamate

The compound (106 mg, 0.28 mmol) obtained in Step 1 of Reference Example 67 was added to a tetrahydrofuran (5 ml) suspension of lithium aluminum hydride (103 mg, 2.70 mmol) under ice cooling and the resulting mixture was stirred at room temperature for 24 hours. Water (0.1 ml) and 5N aqueous sodium hydroxide solution (0.1 ml) were added in that order to the reaction mixture, water (0.1 ml) was further added and the resulting mixture was stirred for 1 hour. After removal by filtration through celite, the solvent was concentrated under reduced pressure. The residue obtained was purified by silica gel column chromatography [ethyl acetate:n-hexane=10:0 (v/v)] to give 15 mg (21%) of the title compound as a solid.

$^1$H-NMR (500 MHz, $CDCl_3$) δ: 1.24-1.33 (1H, m), 1.44-1.54 (10H, m), 1.68-1.78 (3H, m), 2.07-2.09 (1H, m), 2.60 (1H, br s), 3.01 (1H, t, J=10.6 Hz), 3.43-3.48 (1H, m), 3.54-3.62 (1H, m), 3.73-3.79 (2H, m), 4.06-4.09 (1H, m), 4.30 (1H, br s),

MS (FAB) m/z: 246 $(M+H)^+$.

Step 2

2-[(2S,5R)-5-aminotetrahydro-2H-pyran-2-yl]ethanol

The compound (25 mg, 0.10 mmol) obtained in Step 1 above was used as a starting material and treated in the same way as in Step 1 of Reference Example 2 to give the title compound as a solid.

Reference Example 74

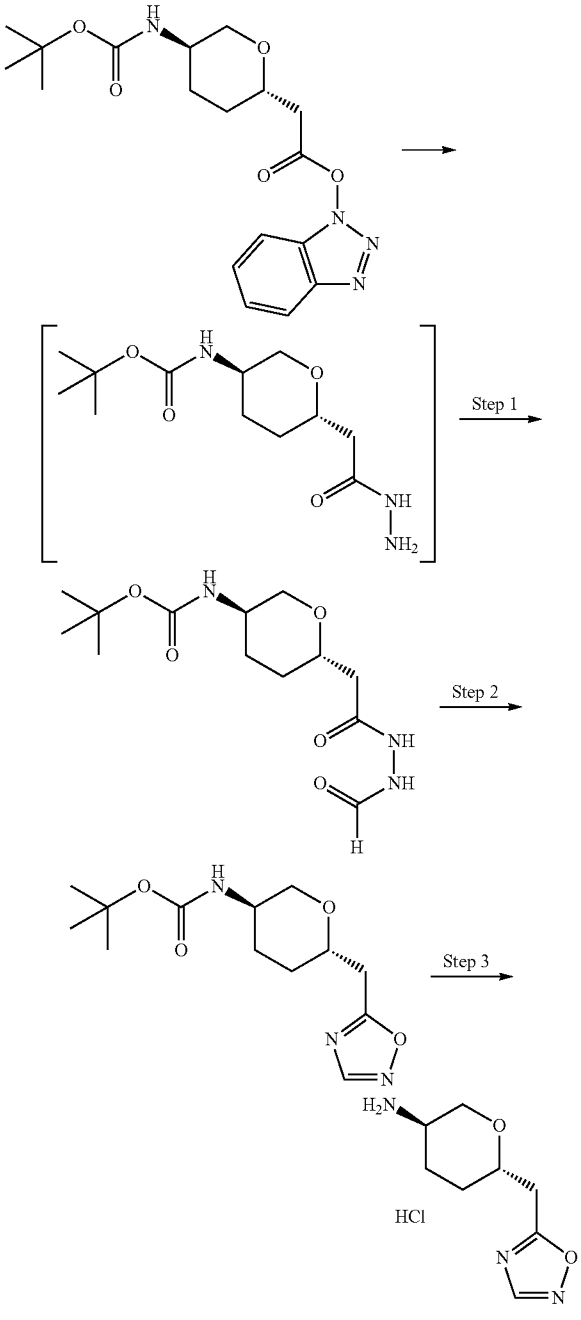

Step 1

Tert-butyl {(3R,6S)-6-[2-(2-formylhydrazino)-2-oxoethyl]tetrahydro-2H-pyran-3-yl}carbamate Hydrazine monohydrate (0.06 ml, 1.2 mmol) was added to a tetrahydrofuran (5 ml) solution of the compound (397 mg, 1.10 mmol) obtained in Step 1 of Reference Example 67 and the resulting mixture was stirred at room temperature for 2 hours. Formic acid (0.09 ml, 2.40 mmol) and 1-ethyl-3-(3-dimethylaminopropyl) carbodiimide hydrochloride (461 mg, 2.40 mmol) were added to the reaction mixture and the resulting mixture was stirred at room temperature for 24 hours. Water was added to the reaction mixture, followed by extraction with chloroform:2-propanol [3:1 (v/v)]. The organic layer was. Washed with saturated sodium bicarbonate solution and brine in that order and dried over anhydrous sodium sulfate. The solvent was concentrated under reduced pressure and the residue obtained was purified by silica gel column chromatography [chloroform:methanol=90:10 (v/v)] to give 118 mg (37%) of the title compound as a solid:

$^1$H-NMR (500 MHz, DMSO-$d_6$) δ: 1.21-1.41 (11H, m), 1.69-1.72 (1H, m), 1.81-1.84 (1H, m), 2.19-2.34 (2H, m), 2.92 (1H, t, J=10.8 Hz), 3.28-3.33 (1H, m), 3.49-3.55 (1H, m); 3.74-3.71 (1H, m), 6.74 (1H, d, J=7.8 Hz), 7.97 (1H, s), 9.93 (2H, s).

MS (FAB) m/z: 302 $(M+H)^+$.

Step 2

Tert-butyl [(3R,6S)-6-(1,3,4-oxazol-2-ylmethyl) tetrahydro-2H-pyran-3-yl]carbamate The compound (114 mg, 0.38 mmol) obtained in Step 1 above was used as a starting material and treated in the same way as in Step 2 of Reference Example 62 to give 73 mg (688) of the title compound as a solid.

$^1$H-NMR (500 MHz, $CDCl_3$) δ: 1.27-1.37 (1H, m), 1.43-1.58 (10H, m), 1.82-1.87 (1H, m), 2.10-2.15 (1H, m), 2.98-3.15 (3H, m), 3.61-3.61 (1H, m), 3.70-3.77 (1H, m), 4.03-4.08 (1H, m), 4.24-4.24 (1H, m), 8.35 (1H, s).

Step 3

(3R,6S)-6-(1,3,4-oxazol-2-ylmethyl)tetrahydro-2H-pyran-3-amine

The compound (73 mg, 0.26 mmol) obtained in Step 2 above was used as a starting material and treated in the same way as in Step 1 of Reference Example 2 to give the title compound as a solid.

Reference Example 75

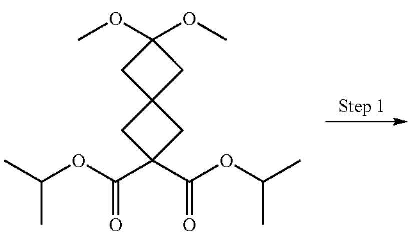

-continued

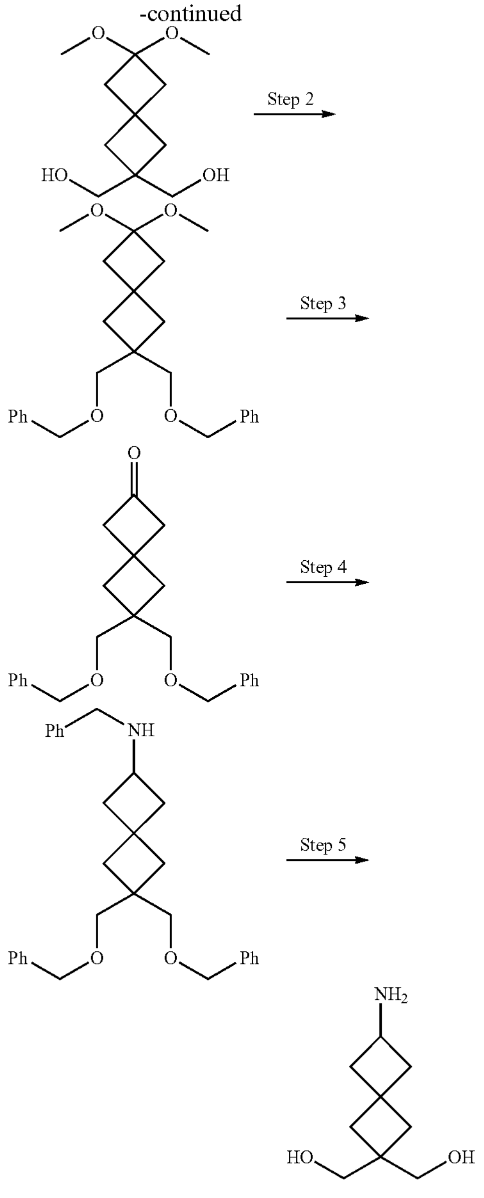

Step 1

(6,6-Dimethoxyspiro[3.3]heptane-2,2-diyl) dimethanol

Diisopropyl 6,6-dimethoxyspiro[3,3]heptane-2,2-dicarboxylate (5.60 g, 17.1 mmol) was used as a starting material and treated in the same way as in Step 1 of Reference Example 73 to give 1.56 g (42%) of the title compound as a solid.

$^1$H-NMR (400 MHz, $CDCl_3$) δ: 1.92 (4H, 8), 2.21 (5E, s), 2.36 (2H, br s), 3.12 (6H, s), 3.69 (4H, d, J=4.6 Hz).

Step 2

2,2-Bis[(benzyloxy)methyl]-6,6-dimethoxyspiro[3.3]heptane

Sodium hydride (755 mg, 17.3 mmol) was added to a dimethylformamide (40 ml)/tetrahydrofuran (20 ml) solution of the compound (1.56 g, 7.20 mmol) obtained in Step 1 above under ice cooling, the resulting mixture was stirred at room temperature for 10 minutes, then benzyl bromide (2.06 ml, 17.3 mmol) was added and the resulting mixture was stirred for 24 hours. Saturated ammonium chloride solution was added to the reaction mixture, followed by extraction with ethyl acetate. The organic layer was washed with brine and then dried over anhydrous sodium sulfate. The solvent was evaporated under reduced pressure and the residue obtained was purified by silica gel column chromatography [n-hexane:ethyl acetate=4:1 (v/v)] to give 2.25 g (79%) of the title compound as an oil.

$^1$H-NMR (400 MHz, $CDCl_3$) δ: 1.96 (4H, s), 2.12 (4H, s), 3.10 (6H, s), 3.43 (4H, s), 4.51 (4H, s), 7.26-7.32 (10H, m).

Step 3

6,6-Bis[(benzyloxy)methyl]spiro[3.3]heptan-2-one

The compound (2.25 g, 5.67 mmol) obtained in Step 2 above was used as a starting material and treated in the same way as in Step 2 of Reference Example 21 to give 1.70 g (86%) of the title compound as an oil.

$^1$H-NMR (400 MHz, $CDCl_3$) δ: 2.17 (4H, s), 3.01 (4H, s), 3.47 (4H, s), 4.52 (4H, s), 7.27-7.36 (10H, m).

Step 4

N-Benzyl-6,6-bis[(benzyloxy)methyl]spiro[3.3]heptan-2-amine

Benzylamine (1.06 ml, 9.70 mmol) and acetic acid (0.56 ml, 9.70 mmol) were added to a dichloromethane (50 ml) solution of the compound (1.70 g, 4.85 mmol) obtained in Step 3 above, the resulting mixture was stirred for 10 minutes under ice cooling and then sodium cyanoborohydride (610 mg, 9.70 mmol) was added to the reaction mixture. After stirring at room temperature for 24 hours, saturated sodium bicarbonate solution was added to the reaction mixture, followed by extraction with ethyl acetate. The organic layer was washed with brine and then dried over anhydrous sodium sulfate. The solvent was evaporated under reduced pressure and the residue obtained was purified by silica gel column chromatography [chloroform: methanol=40:1 (v/v)] to give 1.27 g (60%) of the title compound as an oil.

$^1$H-NMR (400 MHz, $CDCl_3$) δ: 1.49 (2H, br s), 1.67-1.69 (2H, m), 1.85 (2H, s), 1.93 (2H, s), 2.23-2.28 (2H, m), 3.12-3.19 (1H, m), 3.42 (4H, s), 3.65 (2H, s), 4.50 (4H, s), 7.21-7.38 (15H, m).

Step 5

(6-Aminospiro[3.3]heptane-2,2-diyl) dimethanol

20% Palladium hydroxide (254 mg) was added to an ethanol (30 ml) solution of the compound (1.27 g, 2.88 mmol) obtained in Step 4 above and the resulting mixture was stirred at room temperature for 3 days under hydrogen atmosphere. The catalyst was removed by filtration through celite and then the filtrate was concentrated under reduced pressure to give 517 mg (999) of the title compound as an oil.

$^1$H-NMR (400 MHz, $CDCl_3$) δ: 1.62-1.86 (5H, m), 2.17-2.22 (2H, m), 3.15-3.17 (6H, m), 4.58 (48, br s)

Reference Example 76

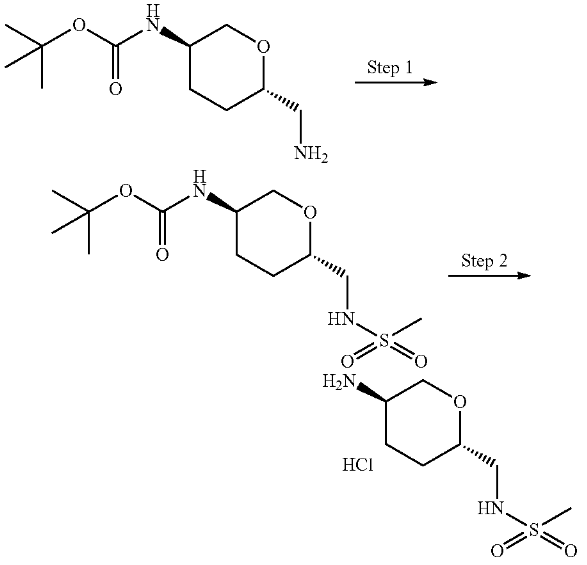

Step 1

1,5-Anhydro-2-[(tert-butoxycarbonyl)amino]-2,3, 4, 6-tetradeoxy-6-[(methylsulfonyl)amino]-D-erythro-hexitol Triethylamine (0.12 ml, 0.88 mmol) and methanesulfonyl chloride (0.05 ml, 0.67 mmol) were added to a dichloromethane (4 ml) solution of the compound (101 mg, 0.44 mmol) obtained in Step 3 of Reference Example 24 under ice cooling and the resulting mixture was stirred for 30 minutes. Water was added, followed by extraction with dichloromethane. The organic layer was washed with saturated ammonia chloride solution, saturated sodium bicarbonate solution, and brine in that order and then dried over anhydrous sodium sulfate. The solvent was evaporated under reduced pressure and the residue obtained was purified by silica gel column chromatography [chloroform: methanol=95:5 (v/v)] to give 105 mg (77%) of the title compound as a solid.

$^1$H-NMR (500 MHz, $CDCl_3$) δ: 1.25-1.35 (1H, m), 1.44-1.51 (10H, m), 1.66-1.72 (1H, m), 2.09-2.12 (1H, m), 2.97-3.06 (5H, m), 3.25-3.31 (1H, m), 3.37-3.43 (1H, m), 3.58 (1H, br s), 4.06-4.10 (1H, m), 4.25 (1H, br s), 4.67 (1H, br s).

MS (FAB) m/z: 309 $(M+H)^+$.

Step 2

2-Amino-1,5-anhydro-2,3,4,6-tetradeoxy-6-[(methylsulfonyl)amino]-D-erythro-hexitol The compound (101 mg, 0.33 mmol) obtained in Step 1 above was used as a starting material and treated in the same way as in Step 1 of Reference Example 2 to give the title compound as a solid.

Reference Example 77

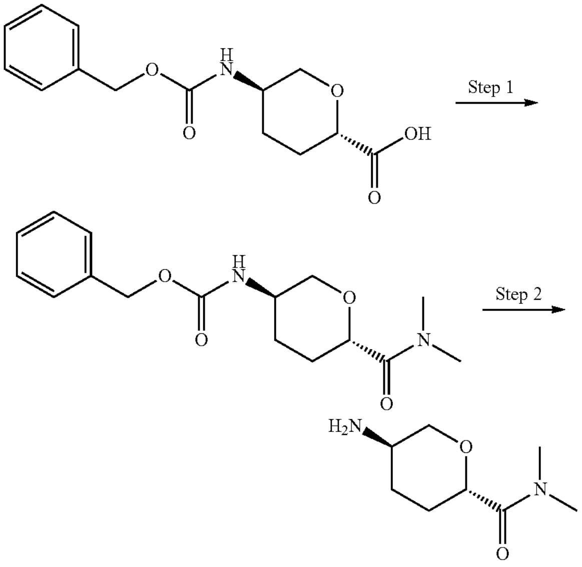

Step 1

Benzyl [(3R,6S)-6-(dimethylcarbamoyl)tetrahydro-2H-pyran-3-yl] carbamate

The compound (200 mg, 0.72 mmol) obtained in Step 3 of Reference Example 18 and dimethylamine hydrochloride (88 mg, 1.07 mmol) were used as starting materials and treated in the same way as in Step 1 of Reference Example 72 to give 177 mg (81%) of the title compound as a solid.

$^1$H-NMR (400 MHz, $CDCl_3$) δ: 1.43 (1H, m), 1.84-2.00 (2H, m), 2.19-2.21 (1H, m), 2.95 (3H, s), 3.07 (3H, s), 3.15-3.18 (1H, m), 3.72=3.75 (1H, m), 4.06 (1H, dd, J=9.8, 2.4 Hz), 4.13 (1H, dd, J=11.0, 4.3 Hz), 4.64-4.66 (1H, m), 5.09 (2H, br s), 7.30-7.40 (5H, m).

MS (ESI) m/z: 307 $(M+H)^+$.

Step 2

(2S,5R)-5-amino-N,N-dimethyltetrahydro-2H-pyran-2-carboxamide

The compound (177 mg, 0.58 mmol) obtained in Step 1 above was used as a starting material and treated in the same way as in Step 3 of Reference Example 2 to give 99 mg (998) of the title compound as an oil.

$^1$H-NMR (400 MHz, $CDCl_3$) δ: 1.22-1.35 (1H, m), 1.75-2.17 (5H, m), 2.93 (1H, m), 2.95 (3H, s), 3.05 (3H, s), 3.07 (1H, m), 3.98-4.04 (2H, m).

MS (ESI) m/z: 173 $(M+H)^+$.

Reference Example 78

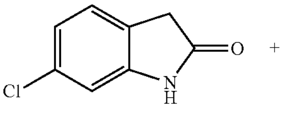

-continued

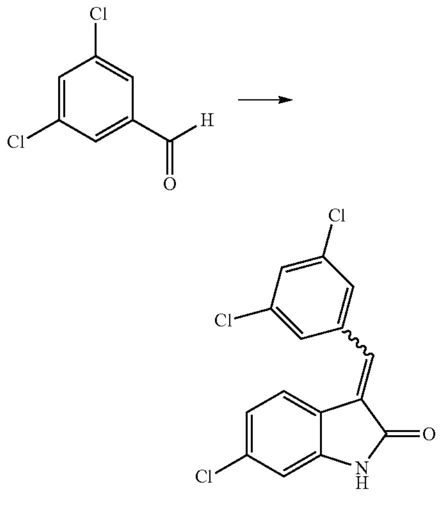

(3E/2)-6-chloro-3-(3,5-dichlorobenzylidene)-1,3-dihydro-2H-indol-2-one 3,5-Dichlorobenzaldehyde (3.50 g, 20.0 mmol) was used as a starting material and treated in the same way as in Reference Example 4 to give 2.60 g (40%) of the title compound as a solid.

$^1$H-NMR (400 MHz, DMSO-$d_6$)): 6.90 (1H, d, J=2.3 Hz), 6.95 (1H, dd, J=8.2, 1.8 Hz), 7.29 (1H, d, J=8.2 Hz), 7.59 (1, s), 7.73 (3H, s), 10.83, (1H, s).

Reference Example 79

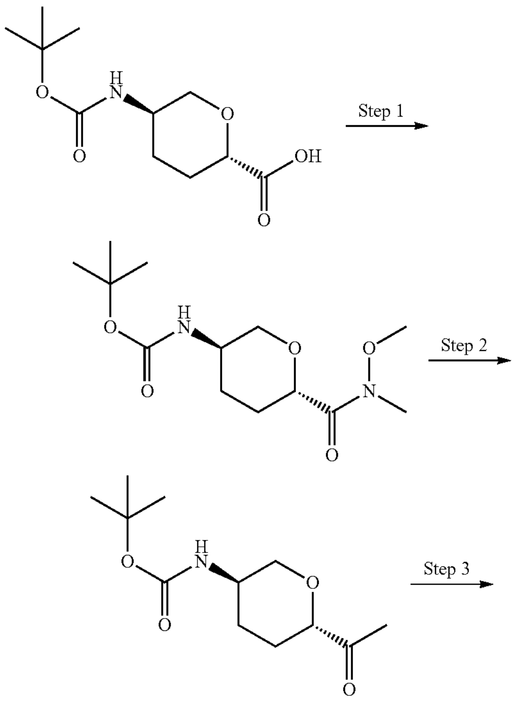

-continued

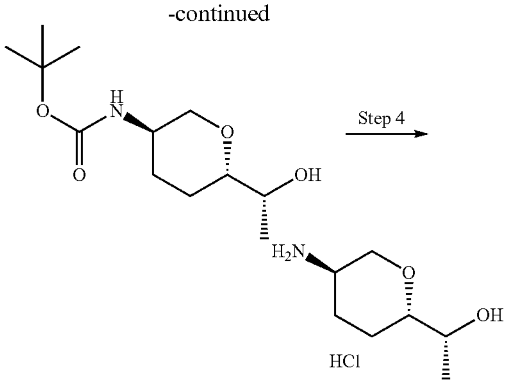

Step 1

Tert-butyl {(3R,6S)-6-[methoxymethyl) carbamoyl] tetrahydro-2H-pyran-3-yl}carbamate The same starting material (70.0 g, 0.29 mol) as in Step 1 of Reference Example 18 and N, O-dimethylhydroxylamine hydrochloride (34.0 g, 0.35 mol) were used as starting materials and treated in the same way as in Step 2 of Example 12 to give 61.0 g (73%) of the title compound as a solid.

$^1$H-NMR (400 MHz, $COCl_3$) δ: 1.44-1.50 (1H, m), 1.44 (9H, s), 1.77-1.93 (2H, m), 2.14-2.22 (1E, m), 3.14-3.19 (1H, m), 3.21 (3H, s), 3.67-3.72 (1H, m), 3.72 (3H, s), 4.20 (2H, dd, J=10.4, 3.6 Hz), 4.39 (1H, br s).

MS (ESI) m/z: 233 $(M-55)^+$.

Step 2

Tert-butyl [(3R,6S)-6-acetyltetrahydro-2H-pyran-3-yl]carbamate

Methylmagnesium bromide/diethyl ether solution (3.0 mol/1, 176 ml, 0.53 mol) was added dropwise to a tetrahydrofuran (600 ml) solution of the compound (61.0 g, 0.21 mol) obtained in Step 1 above under ice cooling under nitrogen atmosphere and then the resulting mixture was stirred at room temperature for 3 hours. Water (200 ml) was added to the reaction mixture under ice cooling, the resulting mixture was stirred and then saturated ammonium chloride solution (100 ml) was added, followed by extraction with ethyl acetate. The organic layer was washed with brine and then dried over anhydrous magnesium sulfate. The solvent was evaporated under reduced pressure and the residue obtained was purified by silica gel column chromatography [n-hexane:ethyl acetate=2:1 (v/v)] to give 38 g (75%) of the title compound as a solid.

$^1$H-NMR (400 MHz, $CDCl_3$) δ: 1.30-1.40 (1H, m), 1.44 (9H, s), 1.48-1.56 (1H, m), 1.96-2.04 (1H, m), 2.11-2.18 (1H, m), 2.20 (3H, s), 3.06 (1H, t, J=10.6 Hz), 3.61-3.65 (1H, m), 3.69 (1H, dd, J=11.3, 2.7 Hz), 4.15 (1H, ddd, J=10.6, 5.0, 2.0 Hz), 4.30 (1H, br s).

MS (ESI) m/z: 266 $(M+Na)^+$.

Step 3

1,5-Anhydro-2-[(tert-butoxycarbonyl)amino]-2,3, 4, 7-tetradeoxy-D-ribo-heptitol

The compound (20.0 g, 82.0 mmol) obtained in Step 2 above was suspended in 0.1 mol/l phosphate buffer solution (pH 6.4, 200 ml) and nicotinamide adenine dinucleotide (oxidized form) (133 mg, 0.20 mmol), ammonium formate (1.26 g, 19.7 mmol), magnesium chloride (19 mg, 0.20 mmol), and isopropyl alcohol (10 ml) were added. Subsequently, 0.1 mol/l phosphate buffer solution (pH 6.4, 10 ml) of CHIRALSCREEN-OH E039 kit (Daicel. Corp.) (1.0 g) was added dropwise. The resulting mixture was stirred at 30° ° C. for 16 hours. Dimethyl sulfoxide (8 ml), isopropyl alcohol (2 ml), and 0.1 mol/l phosphate buffer solution (20 ml) were added to the reaction mixture, then formic acid was added to the reaction mixture to adjust its pH to 6.2 to 6.4 and the resulting mixture was stirred at 37° C. for 8 hours. After extraction with ethyl acetate, insoluble matter was removed by filtration through celite, the filtrate was washed with brine twice and then dried over anhydrous magnesium sulfate and the solvent was evaporated under reduced pressure. The residue obtained was purified by silica gel column chromatography [n-hexane:ethyl acetate=2:1→1:1 (v/v)] to give 17.9 g (89%) of the title compound as a solid.

$^1$H-NMR (400 MHz, $CDCl_3$) δ: 1.14 (3H, d, J=6.4 Hz), 1.26 (1H, ddd, J=24.7, 12.4, 4.1 Hz), 1.44 (9H, s), 1.50-1.60 (1H, m), 1.65-1.71 (1H, m), 2.00-2.04 (1H, m), 2.10-2.17 (1H, m), 3.02 (1H, t, J=10.8 Hz), 3.14-3.19 (1H, m), 3.55-3.62 (1H, m), 3.80-3.87 (1H, m), 4.11 (1H, dq, J=10.6, 2.3 Hz), 4.21-4.26 (1H, m).

MS (ESI) m/z: 268 (M+Na)$^+$.

Step 4

2-Amino-1,5-anhydro-2,3,4,7-tetradeoxy-D-ribo-heptitol hydrochloride

The compound (17.5 g, 71.0 mmol) obtained in Step 3 above was used as a starting material and treated in the same way as in Step 1 of Reference Example 2 to give 12.6 g (98%) of the title compound as a solid.

$^1$H-NMR (400 MHz, DMSO-$d_6$) δ: 1.03 (3H, d, J=6.3 Hz), 1.21-1.33 (1H, m), 1.44-1.55 (1H, m), 1.80-1.87 (1H, m), 2.04-2.11 (1H, m), 2.91-2.95 (1H, m), 2.96-3.03 (1H, m), 3.24 (1H, t, J=10.6 MHz), 3.40-3.45 (1H, m), 3.97-4.02 (1H, m), 4.63 (1, br s).

MS (ESI) m/z: 146 (M+H)$^+$.

Reference Example 80

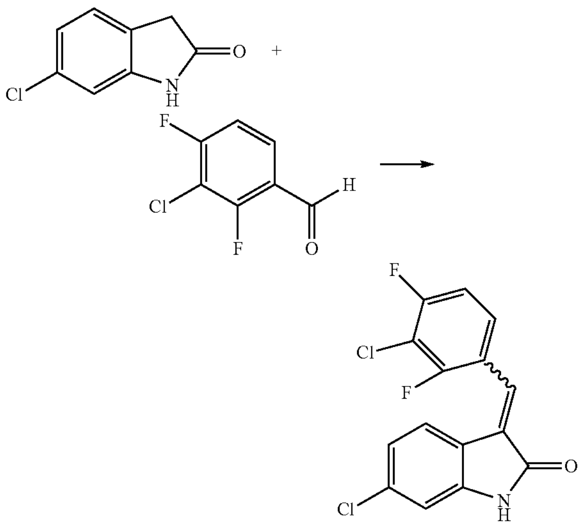

(3E/Z)-6-chloro-3-(3-chloro-2,4-difluorobenzylidene)-1,3-dihydro-2H-indol-2-one

3-Chloro-2,4-difluorobenzaldehyde (4.90 g, 44.9 mmol) was used as a starting material and treated in the same way as in Reference Example 4 to give 8.03 g (56%) of the title compound as a solid.

MS (APCI) m/z: 326 (M+M)$^+$.

Reference Example 81

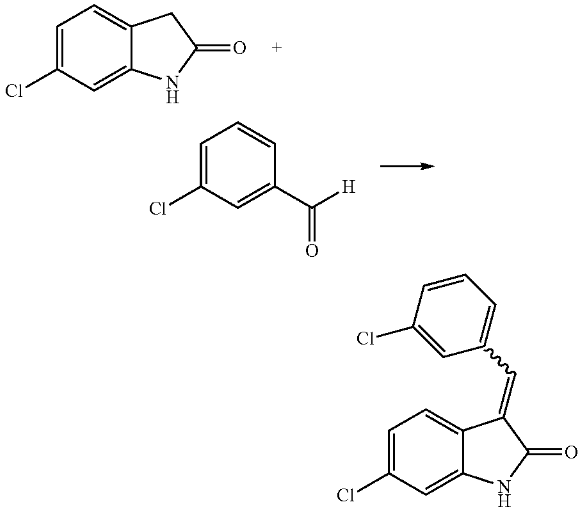

(3E/Z)-6-chloro-3-(3-chlorobenzylidene)-1,3-dihydro-2H-indol-2-one

6-Chloro-1,3-dihydro-2H-indol-2-one (1.67 g, 10.0 mmol) was used as a starting material and treated in the same way as in Reference Example 4 to give 760 mg (268) of the title compound as a solid.

$^1$H-NMR (400 MHz, DMSO-$d_6$) δ: 6.90 (1H, d, J=1.8 Hz), 6.94 (1H, dd, J=8.2, 2.3 Hz), 7.39 (1H, d, J=8.2 Hz), 7.55-7.56 (2H, m), 7.64 (1H, s), 7.65-7.69 (1H, m), 7.74 (1H, s), 10.82 (1H, s).

Reference Example 82

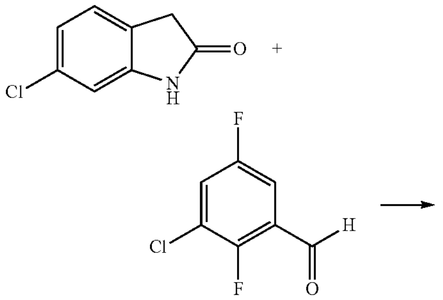

-continued

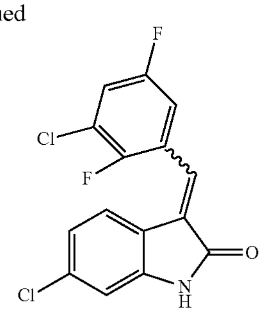

(3E/Z)-6-chloro-3-(3-chloro-2,5-difluorobenzylidene)-1,3-dihydro-2H-indol-2-one

3-Chloro-2,5-difluorobenzaldehyde (6.00 g, 22.0 mmol) was used as a starting material and treated in the same way as in Reference Example 4 to give 2.46 g (34%) of the title compound as a solid.

$^1$H-NMR (400 MHz, DMSO-$d_6$) δ: 6.87-7.10 (2H, m), 7.14-9.17 (4H, m), 10.89-10.96 (1H, m).

Reference Example 83

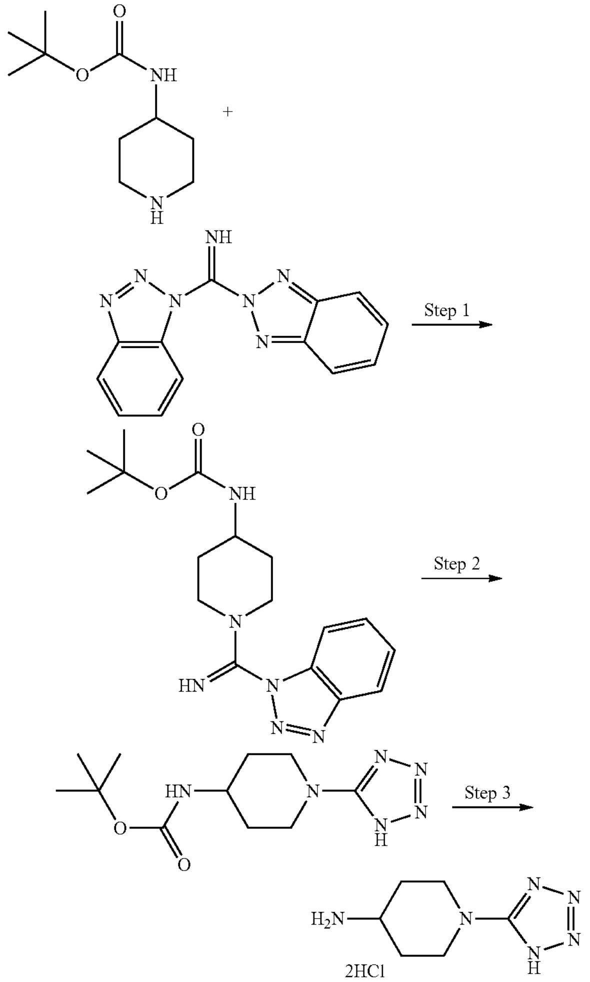

Step 1

Tert-butyl [1-[1H-benzotriazol-1-yl(imino)methyl]piperidin-4-yl]carbamate

A dichloromethane (50 ml) solution of tert-butyl piperidin-4-ylcarbamate (7.50 g) 37.9 mmol) was added dropwise to a dichloromethane (150 ml) solution of 1-(1H-benzotriazol-1-yl)-1-(2H-benzotriazol-2-yl)methanamine (J. Org. Chem. 2000, 65, 8080; and J. Org. Chem. 2003, 68, 4941) (10.0 g, 37.9 mmol) and the resulting mixture was stirred at room temperature for 3 days. 10% Aqueous sodium carbonate solution was added to the reaction mixture, followed by extraction with dichloromethane. The organic layer was washed with brine and then dried over anhydrous sodium sulfate. The solvent was evaporated under reduced pressure to give 10.6 g (81%) of the title compound as an oil.

$^1$H-NMR (400 MHz, $CDCl_3$) δ: 1.45 (9H, s), 1.57-1.62 (2H, m), 2.04 (2H, d, J=11.4 Hz), 3.05-3.12 (2H, m), 3.71 (3H, d, J=13.3 Hz), 4.53 (1H, s), 7.00 (1H, s), 7.46 (1H, t, J=8.2 Hz), 7.60 (1H, t, J=7.6 Hz), 7.71 (1H, s), 8.12 (1H, d, J=8.2 Hz).

Step 2

Tert-butyl [1-(1H-tetrazol-5-yl) piperidin-4-yl]carbamate

Sodium azide (2.00 g, 30.7 mmol) and acetic acid (1.70 ml, 30.7 mmol) were added to a chloroform (300 ml) solution of the compound (10.6 g, 30.7 mmol) obtained in Step 1 above and the resulting mixture was stirred at room temperature for 25 hours; Insoluble matter was removed by filtration and the filtrate was concentrated under reduced pressure. The residue obtained was purified by silica gel column chromatography [chloroform:methanol=30:1→10:1 (v/v)] to give 8.20 g (94%) of the title compound as a solid.

$^1$H-NMR (400 MHz, $CD_3OD$) δ: 1.56-1.44 (11H, m), 1.96-1.92 (2H, m), 3.21-3.14 (2H, m), 3.57 (1H, s), 3.84-3.81 (2H, m).

Step 3

1-(1H-tetrazol-5-yl)piperidin-4-amine dihydrochloride

The compound (8.20 g, 28.6 mmol) obtained in Step 2 above was used as a starting material and treated in the same way as in Step 1 of Reference Example 2 to give 6.90 g (92%) of the title compound as a solid.

$^1$H-NMR (400 MHz, DMSO-$d_6$) δ: 1.57 (2H, dad, J=24.2, 12.3, 4.0 Hz), 1.98 (2H, d, J=10.1 Hz), 3.09 (2H, td, J=12.8, 2.0 Hz), 3.25 (1H, d, J=4.6 Hz), 3.93 (2H, d, J=13.3 Hz), 8.30 (3H, 8).

Reference Example 84

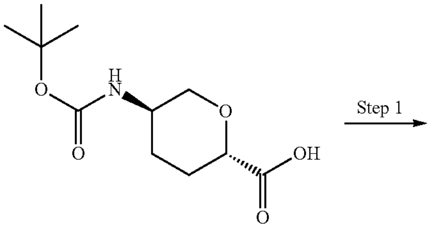

-continued

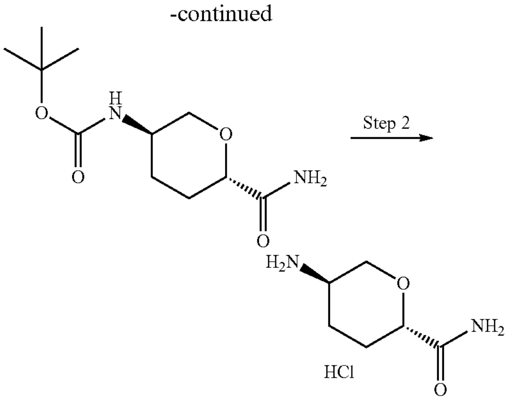

Step 1

Tert-butyl [(3R,6S)-6-carbamoyltetrahydro-2H-pyran-3-yl]carbamate

The same starting material (2.54 g, 10.3 mmol) as in Step 1 of Reference Example 18 and ammonium chloride (1.07 g, 20.0 mmol) were used as starting materials and treated in the same way as in Step 2 of Example 12 to give 1.83 g (75%) of the title compound as a solid.

$^1$H-NMR (400 MHz, $CDCl_3$) δ: 1.35 (1H, ddd, J=24.7, 12.7, 3.9 Hz), 1.44 (9H, s), 1.53-1.63 (1H, m), 2.11-2.18 (1H, m), 2.23 (1H, dq, J=13.6, 3.3 Hz), 3.06 (1H, t, J=10.7 Hz), 3.58-3.67 (1H, m), 3.74 (1H, dd, J=11.5, 2.4 Hz), 4.14-4.20 (1H, m), 4.29 (1H, br a), 5.37 (1H, br s), 6.47 (1H, br s).

MS (ESI) m/z: 267 $(M+Na)^+$.

Step 2

(2S,5R)-5-aminotetrahydro-2H-pyran-2-carboxamide hydrochloride

The compound (1.82 g, 7.45 mmol) obtained in Step 1 above was used as a starting material and treated in the same way as in Step 1 of Reference Example 2 to give 1.31 g (97%) of the title compound as a solid.

$^1$H-NMR (400 MHz, DMSO-$d_6$) δ: 1.39-1.48 (1H, m), 1.57 (1H, ddd, J=23.8, 12.5, 3.9 Hz), 1.95-2.01 (1H, m), 2.04-2.11 (1H, m), 3.07-3.09 (1H, m), 3.31-3.36 (1H, m), 3.67 (1H, dd, J=11.1, 2.6 Hz), 4.03-4.08 (1H, m), 7.12 (2H, s), 7.20 (2H, s).

MS (ESI) m/z: 145 $(M+H)^+$.

Reference Example 85

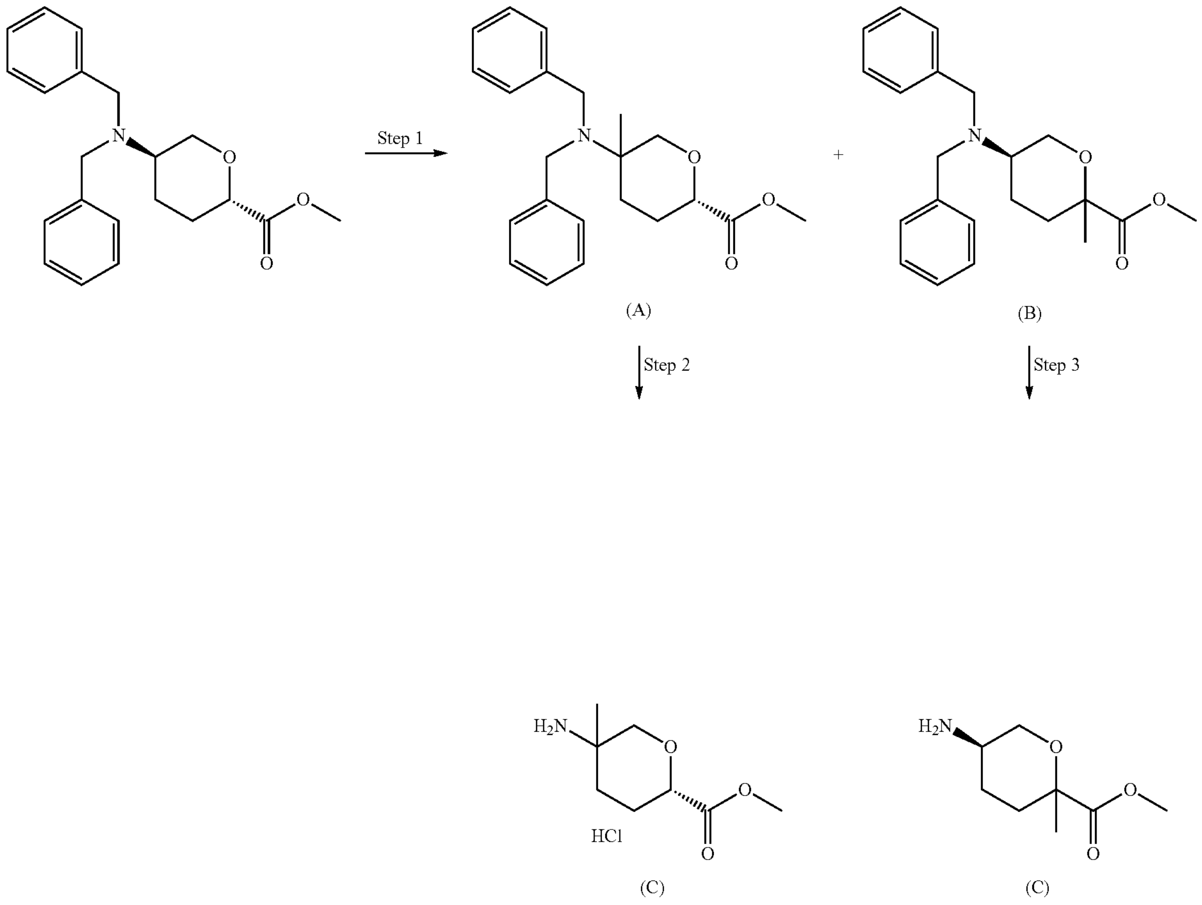

(A)

(B)

(C)

(C)

Step 1

Methyl 2,6-anhydro-3,4,5-trideoxy-5-(dibenzylamino)-5-methyl-L-glycero-hexonate (A) and methyl 2,6-anhydro-3,4, 5-trideoxy-5-(dibenzylamino)-2-methyl-L-glycero-hexonate (B)

Lithium bis(trimethylsilyl)amide/tetrahydrofuran solution (1.0 mol/1, 37 ml, 37.0 mmol) was added dropwise to a tetrahydrofuran (70 ml) solution of the same starting material (6.20 g, 12.0 mmol) as in Step 1 of Reference Example 5 combined with hexamethylphosphoric acid triamide (6.40 ml, 36.0 mmol) at −78° C. under nitrogen atmosphere and then the resulting mixture was stirred at room temperature for 1 hour. After cooling to −78° C. again, methyl iodide (5.5 ml, 90.0 mmol) was added dropwise and the resulting mixture was stirred at room temperature for 16 hours. The reaction mixture was diluted with ethyl acetate and the organic layer was washed with saturated ammonium chloride solution and brine and dried over anhydrous magnesium sulfate. The solvent was evaporated under reduced pressure and the residue obtained was purified by silica gel column chromatography [n-hexane:ethyl acetate=93:7 (v/v)] to give a mixture of the compounds A and B. The mixture obtained was fractionated and purified by chiral column liquid chromatography [fractionation conditions; CHIRALCEL OD-H, n-hexane:ethanol=90:10 (v/v)] to give 1.10 g (178) of the title compound A as an oil. The residue was fractionated and purified by chiral column liquid chromatography [fractionation conditions: CHIRALPAK IC, n-hexane:ethanol=90:10 (v/v)] to give 299 mg (5%) of the title compound B as an oil.

Compound A;

$^1$H-NMR (400 MHz, $CDCl_3$) δ: 1.32 (3H, s), 1.36-1.55 (2H, m), 1.88-1.94 (1H, m), 2.36 (1H, dt, J=13.1, 3.2 Hz), 2.75-2.82 (1H, m), 3.56 (1H, t, J=11.3 Hz), 3.58 (2H, d, J=14.0 Hz), 3.65 (2H, d, J=14.0 Hz), 3.76 (3H, s), 3.87 (1H, dq, J=11.4, 2.2 Hz), 7.19-7.36 (10H, m).

MS (ESI) m/z: 354 $(M+H)^+$.

Compound B:

$^1$H-NMR (400 MHz, $CDCl_3$) δ: 1.45 (3H, s), 1.76-1.92 (4H, m), 2.76-2.83 (1H, m), 3.67 (2H, d, J=14.0 Hz), 3.73 (3H, s), 3.73-3.78 (3H, m), 3.86 (1H, dd, J=11.8, 5.0 Hz), 7.19-7.23 (2H, m), 7.26-7.35 (8H, m).

MS (ESI) m/z: 354 $(M+H)^+$.

Step 2

Methyl 5-amino-2,6-anhydro-3,4,5-trideoxy-5-methyl-L-glycero-hexonate hydrochloride (C)

4N hydrochloric acid/dioxane solution (2 ml) and 10% palladium carbon (200 mg) were added to a methanol (20 ml) solution of the compound A (1.10 g, 3.11 mmol) obtained in Step 1 above and the resulting mixture was stirred at room temperature for 16 hours under hydrogen atmosphere. 20% Palladium hydroxide carbon (200 mg) was further added to the reaction mixture and the resulting mixture was stirred at room temperature for 48 hours under hydrogen atmosphere. The catalyst was removed by filtration through celite and then the filtrate was concentrated under reduced pressure to give 703 mg (100%) of the title compound as a solid.

$^1$H-NMR (400 MHz, DMSO-$d_6$) δ: 1.27 (3H, s), 1.39-1.54 (2H, m), 1.93-2.00 (1H, m), 2.17-2.23 (1H, m), 3.04-3.12 (1H, m), 3.41 (1H, t, J=11.1 Hz), 3.69 (3H, s), 3.83-3.89 (1H, m), 8.17 (2H, br s).

MS (ESI) m/z: 174 $(M+H)^+$.

Step 3

Methyl 2,6-anhydro-3,4,5-trideoxy-5-(dibenzylamino)-2-methyl-L-glycero-hexonate (D)

20% Palladium hydroxide carbon (200 mg) was added to a methanol (6 ml) solution of the compound B (295 mg, 0.83 mmol) obtained in Step 1 above and the resulting mixture was stirred at room temperature for 5 hours under hydrogen atmosphere. The catalyst was removed by filtration through celite and then the filtrate was concentrated under reduced pressure to give 119 mg (838) of the title compound as an oil.

$^1$H-NMR (400 MHz, DMSO-dg) δ: 1.29 (3H, s), 1.55-1.66 (2H, m), 1.73-1.80 (1H, m), 1.84-1.90 (1H, m), 2.84-2.87 (1H, m), 3.46-3.50 (1H, m), 3.60 (1H, dd, J=12.4, 2.7 Hz), 3.65 (3H, s).

MS (ESI) m/z: 174 $(M+H)^+$.

Reference Example 86

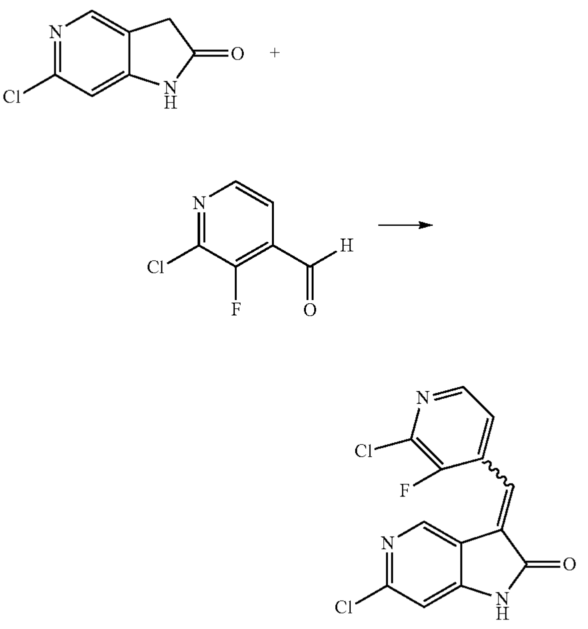

(3E/Z)-6-chloro-3-[(2-chloro-3-fluoropyridin-4-yl) methylene]-1,3-dihydro-2H-pyrrolo[3,2-c]pyrrolidin-2-one 6-Chloro-1,3-dihydro-2H-pyrrolo[3,2-c]pyrrolidin-2-one (7.00 g, 41.5 mmol) and 2-chloro-3-fluoroisonicotinaldehyde monohydrate (7.37 g, 41.5 mmol) were used as starting materials and treated in the same way as in Reference Example 1 to give 5.17 g (40%) of the title compound as a solid.

$^1$H-NMR (400 MHz, DMSO-dc) δ: 7.00 (1H, s), 7.62 (1H, s), 7.84. (1H, t, J=4.8 Hz), 8.10 (1H, s), 8.42 (1H; d, J=4.6 Hz), 11.47 (1H, br s).

MS (ESI) m/z: 310 $(M+H)^+$.

Reference Example 87

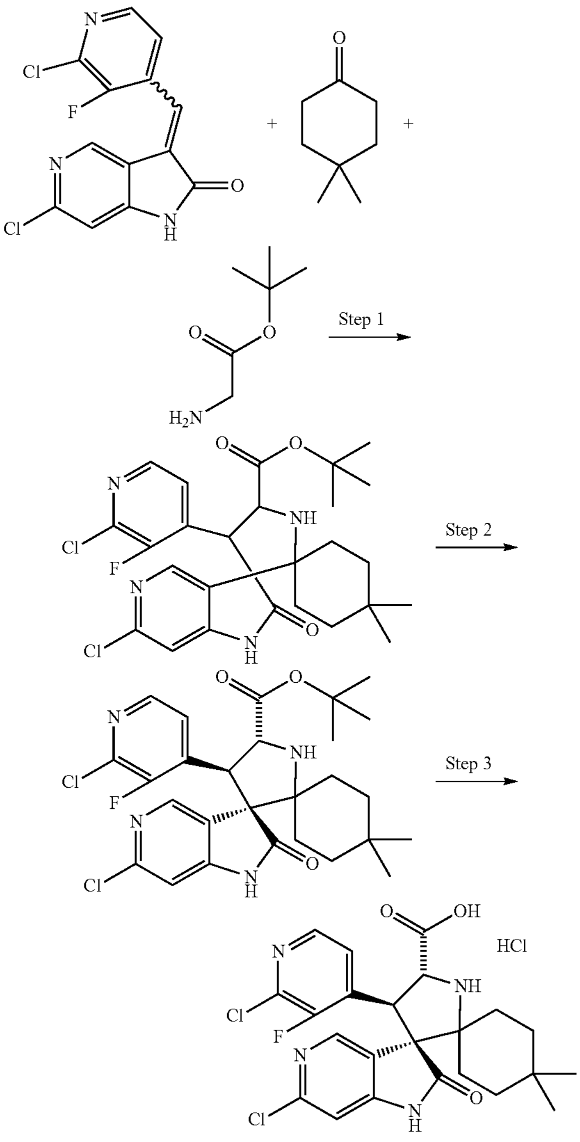

Step 1

6"-Chloro-8'-(2-chloro-3-fluoropyridin-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-pyrrolo[3,2-c]pyridine]-1',2"(1"H)-dione Triethylamine (0.50 ml, 3.56 mmol) and molecular sieves 4A (powder) (1.34 g) were added to a toluene (30 ml) solution of glycine tert-butyl ester (467 mg, 3.56 mmol) and 4,4-dimethylcyclohexanone (449 mg, 3.56 mmol) and the resulting mixture was stirred at 70° C. for 1.5 hours. The compound (1.00 g, 3.23 mmol) obtained in Reference Example 86 was added to the reaction mixture and the resulting mixture was stirred at 70° C. for 3 hours. Glycine tert-butyl ester (106 mg, 0.81 mmol) and 4,4-dimethylcyclohexanone (102 mg, 0.81 mmol) were further added to the reaction mixture and the resulting mixture was stirred at 80° C. for 24 hours. After cooling, insoluble matter was removed by filtration through celite and the filtrate was concentrated under reduced pressure. The residue obtained was purified by silica gel column chromatography [n-hexane; ethyl acetate=100:0→0:100 (v/v)] to give 613 mg (35%) of the title mixture as a solid.

MS (ESI) m/z: 549 $(M+H)^+$.

Step 2

(3'S,4'R, 7'S,8'S,8a'R)-6"-chloro-8'-(2-chloro-3-fluoropyridin-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3"-pyrrolo[3,2-c]pyridine]-1', 2" (1"H)-dione The mixture of isomers (480 mg) obtained in Step 1 above was fractionated and purified by chiral column liquid chromatography [fractionation conditions: CHIRALPAK IA, n-hexane:tetrahydrofuran:ethanol=85:15:5 (v/v)] to give 187 mg (398) of the title compound as a solid.

$^1$H-NMR (400 MHz, $CDCl_3$) δ: 1.19 (3H, t, J=7.1 Hz), 1.70 (1H, d, J=13.7 Hz), 1.87 (1H, d, J=13.7 Hz), 2.20 (1H, d, J=12.8 Hz), 2.42 (1H, dd, J=12.3, 2.7 Hz), 3.70 (1H, s), 3.81 (1H, q, J=9.2 Hz), 3.93 (1H, q, J=9.2 Hz), 4.09-4.22 (2H, m), 4.47 (2H, s), 4.54-4.78 (2H, m), 6.81 (1H, d, J=1.8 Hz), 6.96 (1H, td, J=8.0, 1.2 Hz), 7.13 (1H, dd, J=8.0, 2.1 Hz), 7.16-7.21 (2H, m), 7.38-7.42 (2H, m), 7.44-7.48 (1H, m).

MS (ESI) m/z: 549 $(M+H)^+$.

Step 3

6"-Chloro-4'-(2-chloro-3-fluoropyridin-4-yl)-4,4-dimethyl-2"-oxo-1",2"-dihydrodispiro[cyclohexane-1,2'-pyrrolidine-3',3"-pyrrolo[3,2-c]pyridine]-5'-carboxylic acid hydrochloride Concentrated hydrochloric acid (1.12 ml, 13.7 mmol) was added to the compound (150 mg, 0.27 mmol) obtained in Step 2 above under ice cooling and the resulting mixture was stirred at room temperature for 1 hour. The reaction mixture was concentrated under reduced pressure to give 137 mg (94%) of the title compound as a solid.

$^1$H-NMR (400 MHz, $CD_3OD$) δ: 0.79 (3H, s), 1.04 (3H, s), 1.39-1.66 (4H, m), 1.87-2.12 (3H, m), 2.50 (1H, dd, J=14.2, 3.2 Hz), 5.16 (1H, d, J=10.1 Hz), 5.47 (1H, d, J=10.5 Hz), 6.95 (1H, s), 7.67 (1H, t, J=5.0 Hz), 8.24 (1H, d, J=5.0. Hz), 8.57 (1H, d, J=1.8 Hz).

MS (ESI) m/z: 493 $(M+H)^+$.

PREPARATION EXAMPLES (Preparation Example 1) Powder

5 G of the compound of Example 1, 895 g of lactose, and 100 g of corn starch can be mixed using a blender to give powders.

(Preparation Example 2) Granule

5 G of the compound of Example 5, 895 g of lactose, and 100 g of low-substituted hydroxypropylcellulose are mixed, then 300 g of 10% aqueous hydroxypropylcellulose solution is added and the resulting mixture is kneaded. This product can be granulated using an extrusion granulator and dried to give granules.

(Preparation Example 3) Tablet

5 G of the compound of Example 12, 90 g of lactose, 34 g of corn starch, 20 g of crystalline cellulose, and 1 g of magnesium stearate can be mixed using a blender and then compressed in a tableting machine to give tablets.

TEST EXAMPLES

Test Example 1 Mdm2/p53 Binding Assay

A protein dilution containing 6.25 nM each of His-p53 (fusion protein of a p53 partial protein having p53 amino acids at positions 1 to 132, with a histidine protein) and GST-Mdm2 (fusion protein of an Mdm2 partial protein having Mdm2 amino acids at positions 25 to 108 with leucine residue 33 substituted by glutamic acid, with glutathione transferase) proteins was prepared using a protein buffer solution (20 mM HEPES pH 7.4, 150 mM NaCl, 0.1% BSA). This protein dilution was added in an amount of 8 μl/well to a 384-well plate (384-well low volume NBC, Corning Inc., catalog No: 3676).

Next, a test compound was diluted with DMSO to produce a protein buffer solution containing 10% dilution, and this buffer solution was added in an amount of 4 μl/well to the plate.

Subsequently, a solution containing an XL665-labeled anti-His antibody (HTRF monoclonal anti-6HIS antibody labeled with XL665 (catalog No: 61HISXLB), Schering/Cisbio Bioassays) and a europium (Eu)-labeled anti-GST antibody (HTRF monoclonal anti-GST antibody labeled with europium cryptate, Schering/Cisbio Bioassays, catalog No: 61GSTKLB) at concentrations of 2.5 μg/ml and 0.325 μg/ml, respectively, was prepared using an antibody diluting buffer solution (20 mM HEPES pH 7.4, 150 mM NaCl, 0.1% BSA, 0.5 M KF). These dilutions were added in an amount of 8 μl/well (total reaction solution volume: 20 μl/well). Then the plate was incubated at 25° ° C. for 1 hour.

Time-resolved fluorescence at 620 and 665 nm was measured at an excitation wavelength of 320 nm using a plate reader (ARVOsx, PerkinElmer Co., Ltd. or PHERAstar, BMG LABTECH). Ratio (R) was calculated using the measured values (RFU 620 nm and RFU 665 nm) according to the following formula:

$$R = (RFU\ 665\ \text{nm} - BI - C \times RFU\ 620\ \text{nm})/RFU\ 620\ \text{nm}$$

BI: measured value at 665 nm of reaction solution (only each buffer solution) nonsupplemented with each protein, the compound, and the antibodies $$C\ (\text{correction factor}) = (A - BI)/D$$

A and D: each measured value at 665 nm and 620 nm of reaction solution supplemented with only Eu-labeled anti-GST antibody solution The R value calculated from the well supplemented with His-p53, GST-Mdm2, the test compound, and each antibody was defined as R (sample). The R value calculated from the well supplemented with His-p53, GST-Mdm2, and each antibody but without the test compound was defined as R (control). The R value calculated from the well supplemented with GST-Mdm2 the test compound, and each antibody but without His-p53 was defined as R (background). T/C was calculated from the formula shown below. An $IC_{50}$ value for Mdm2/p53 binding was calculated by sigmoid fitting. The results are shown in Table 1.

$$T/C = (R\ (\text{sample}) - R\ (\text{background}))/(R\ (\text{control}) - R\ (\text{background}))$$

The $IC_{50}$ value of the compound of each Example was as follows:

$0.001 \le IC_{50}$ (μM)<0.05: Example No. 3, 6, 7, 8, 9, 11, 12, 13, 16, 20, 21, 23, 25, 27, 28, 29, 30, 33, 34, 36, 38, 40, 41, 42, 44, 46, 48, 49, 53, 55, 56, 57, 65, 67, 68, 69, 70, 71, 72, 75, 76, 77, 78, 81, 82, 83, 85, 86, 87, 89, 90, 92, 97, 99, 100, 101, 102, 103, 104, 105, 106, 107, 108, 109, 110, 111, 113, 114, 115, 116, 117, 118, 119, 120, 122, 124, 125, 126, 127, 128, 129, 130, 134, 136, 139, 141, 142, 144, 146, 148, 150, 151, 152, 153, 156, 158, 167, 172, 174, 176, 178, 179, 180, 181, 182, 185, 186, 187, 188, 189, 191, 192, 193, $0.05 \le IC_{50}$ (μM)<0.1: Example No. 1, 2, 5, 10, 15, 17, 18, 19, 22, 24, 26, 31, 32, 35, 37, 39, 45, 47, 50, 51, 52, 54, 58, 59, 60, 61, 62, 63, 64, 66, 73, 74, 79, 80, 84, 88, 91, 93, 94, 95, 96, 98, 112, 121, 123, 131, 132, 133, 137, 138, 140, 143, 145, 147, 149, 154, 155, 157, 159, 160, 161, 162, 163, 165, 166, 169, 170, 171, 173, 175, 177, 183, 184, 190.

$0.1 \le IC_{50}$ (μM)<0.5: Example No. 4, 14, 43, 135, 164, 168.

Test Example 2 Cell Growth Inhibition Assay

A cell growth inhibition assay was conducted using a human lung cancer-derived cell line NCI-H460 having wild-type p53.

NCI-H460 cells were suspended in a medium (RPMI1640 medium containing 10% fetal bovine serum) and the suspension was added in an amount of 500 cells/150 μl/well to a 96-well plate. A test compound was dissolved in DMSO and this solution was diluted with medium to prepare a sample solution (DMSO concentration: 1% or lower). On the next day, medium nonsupplemented with the test compound, or the sample solution, was added in an amount of 50 μl/well. Cells were then cultured at 37° ° C. for 3 days in a 5% $CO_2$ atmosphere.

An MTT assay was conducted immediately after the nonsupplemented medium or the sample solution was added. Another MTT assay was conducted after culturing the cells for 3 days. The MIT assays were conducted as shown below.

A 5 mg/ml MTT (3-(4,5-dimethylthiazol-2-yl)-2,5-diphenyltetrazolium bromide, Sigma-Aldrich Co., M-2128) solution was prepared using a phosphate buffer solution (Dulbecco's Phosphate-buffered Saline). This MIT solution was added in an amount of 20 μl/well. Then the plate was cultured at 37° ° C. for 4 hours in a 5% $CO_2$ atmosphere. The plate was centrifuged at 1200 rpm for 5 minutes and then the culture supernatant was removed by aspiration using a dispenser. DMSO was added in an amount of 150 μl/well to dissolve generated formazan. The plate was stirred using a plate mixer for uniform color development from each well. The absorbance of each well was measured at OD 540 nm and at a reference OD (660 nm) using a plate reader (SpectraMax PLUS384, Molecular Devices, CA, USA).

The OD value measured on the day of adding the sample solution was defined as S. The OD value measured three days after addition of the sample solution was defined as T. The OD value measured three days after addition of the DMSO dilution was defined as C. T/C (%) was determined at each concentration according to the formula shown below in order to prepare a dose response curve, from which 50% growth inhibition concentration ($GI_{50}$ value) was calculated.

$$T/C\ (\%) = (T - S)/(C - S) \times 100$$

The $GI_{50}$ values of the compounds of Examples subjected to this test were as follows:

$GI_{50}$ (μM)<0.1: Example No. 20, 31, 35, 70, 99, 100, 110, 113, 116, 156, 160, 182.

$0.1 \leq GI_{50}$ (μM)<0.5: Example No. 1, 8, 13, 16, 17, 18, 23, 24, 32, 34, 38, 51, 57, 67, 69, 77, 88, 90, 93, 94, 96, 97, 107, 109, 111, 112, 115, 117, 154, 161, 162, 183, 184, 185, 188, 191.

$0.5 \leq GI_{50}$ (μM)<1.0: Example No. 3, 7, 11, 14, 25, 26, 40, 47, 53, 54, 108, 114.

$1.0 \leq GI_{50}$ (μM)<5.0: Example No. 2, 4, 5, 6, 28, 29, 30, 164, 179, 180, 186.

$5.0 < GI_{50}$ (μM): Example No. 174

Test Example 3 Anti-Tumor Activity Test

A human osteosarcoma cell line SJSA-1 or SUSA-1-RE (cells in which a p53 reporter gene is incorporated into SJSA-1) is subcutaneously transplanted into nude mice (BALB/C-nu/nu SLC, male, Japan SLC, Inc.). At the point in time when the tumor size reaches approximately 100 to 200 $mm^3$, the mice are divided into groups (6 mice/group). A test compound is suspended in 0.5% methylcellulose solution and orally administered twice a day (bid) at a dose of 50 mg/kg, once a day (qd) at a dose of 50 mg/kg, or once a day (qd) at a dose of 25 mg/kg for 4 consecutive days. After a 2-day drug holiday, the mice are dissected, the tumors are excised and then their weights are measured.

The anti-tumor effect (IR (%)) is calculated according to the following formula:

$$IR\ (\%) = [1 - (\text{average tumor weight of compound} - \text{administered group/average tumor weight of untreated control group})] \times 100.$$

Test Example 4 Metabolic Stability Test

100 μl of 100 mM phosphate buffer solution (pH 7.4) containing 3 μM test compound was added to 100 μl of reaction solution containing 100 mM phosphate buffer solution (pH 7.4), 30 mM glucose 6-phosphate, 10 mM $MgCl_2 \cdot 6H_2O$, 3 units/ml glucose 6-phosphate 1-dehydrogenase, and 0.3 to 1.5 mg/ml human liver microsomes and the mixture was incubated at 37° C. for 20 minutes. Then 70 μl of 100 mM phosphate buffer solution (pH 7.4) containing 3 mM NADP+ was added and the mixture was further incubated at 37° C. for 30 minutes to conduct a microsomal metabolism test. The compound was quantified by the internal standard method using a quadrupole mass spectrometer connected to a high performance liquid chromatography apparatus. The metabolic stability (residual percentage of compound: MS %) was determined according to the following formula;

$$MS\ (\text{human})\ (\%) = (\text{peak area ratio of test compound after addition of } NADP+ \text{ and incubation for 30 minutes}) / (\text{peak area ratio of test compound before addition of } NADP+) \times 100.$$

(peak area ratio: peak area of test compound divided by that of internal standard substance)

Of the compounds of the Examples subjected to this test, the following compounds exhibited an MS % of 30 or more:

70≤MS %≤100: Example No. 1, 2, 3, 4, 6, 8, 9, 10, 11, 12, 13, 14, 15, 16, 17, 18, 20, 23, 24, 25, 29, 30, 31, 34, 36, 38, 39, 40, 41, 43, 45, 46, 51, 53, 54, 56, 57, 60, 63, 64, 65, 67, 69, 70, 76, 77, 79, 84, 5, 87, 88, 90, 91, 92, 93, 94, 95, 98, 103, 106, 107, 108, 109, 110, 122, 123, 124, 125, 126, 149, 151, 156, 157, 158, 159, 163, 164, 165.

50≤MS %<70: Example No. 5, 32, 35, 37, 47, 48, 55, 59, 68, 71, 99, 128, 155.

30≤MS %<50: Example No. 7, 19, 26, 52, 62, 66, 100, 101, 127, 153.

What is claimed is:

1. A compound represented by general formula (1) or a salt thereof:

(1)

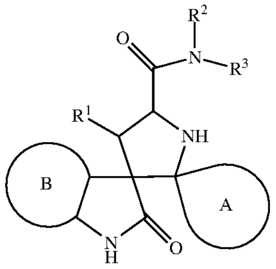

wherein ring A represents a spiro-linked 4- or 6-membered saturated hydrocarbon ring optionally substituted with one or more substituents selected from Group 1, or a spiro-linked 6-membered saturated heterocyclic ring optionally substituted with one or more substituents selected from Group 1;

ring B represents a benzene ring optionally substituted with one or more substituents selected from Group 2, a pyridine ring optionally substituted with one or more substituents selected from Group 2, or a pyrimidine ring optionally substituted with one or more substituents selected from Group 2;

$R^1$ represents an aryl group optionally substituted with one or more substituents selected from Group 3, a heteroaryl group optionally substituted with one or more substituents selected from Group 3, a $C_3$-$C_6$ cycloalkyl group optionally substituted with one or more substituents selected from Group 3, or a $C_3$-$C_6$ cycloalkenyl group optionally substituted with one or more substituents selected from Group 3;

$R^2$ represents a $C_1$-$C_6$ alkyl group optionally substituted with one to three halogen atoms or one to three hydroxy groups, or a hydrogen atom; and $R^3$ represents a group represented by the following general formula (3) or (4):

(3)

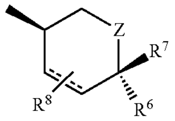

(4)

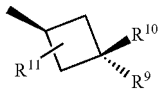

wherein in formula (3), the broken line in the ring structure indicates that the bond may be a double bond, $R^6$ represents a $C_1$-$C_6$ alkyl group optionally substituted with one or more substituents selected from Group 4, a carbamoyl group optionally substituted with one or more substituents selected from Group 5, a 5- or 6-membered nitrogen-containing heteroaryl group optionally substituted with an oxo group or one or more $C_1$-$C_6$ alkyl groups optionally substituted with an oxo group or one hydroxy group, a hydroxy group, or —NR'R", wherein R' and R" each independently represent a $C_1$-$C_6$ alkyl group optionally substituted with one to three halogen atoms, an oxo group, or one to three hydroxy groups, a $C_3$-$C_4$ cycloalkyl group optionally substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group optionally substituted with one or more substituents selected from a $C_1$-$C_6$ alkyl group and a hydroxy group, $R^7$ represents a $C_1$-$C_6$ alkyl group optionally substituted with one hydroxy group, a hydroxy group, or a hydrogen atom, or $R^6$ and $R^7$ may together form a spiro-linked 4- to 6-membered hydrocarbon ring or a spiro-linked 4- to 6-membered nitrogen-containing heterocyclic ring, $R^8$ is absent or represents one or more substituents selected from a hydroxy group, a $C_1$-$C_6$ alkyl group, and a $C_1$-$C_6$ alkoxy group, and Z represents O;

and in formula (4), $R^9$ represents a $C_1$-$C_6$ alkyl group optionally substituted with one or more substituents selected from Group 4, a carbamoyl group optionally substituted with one or more substituents selected from Group 5, a 5- or 6-membered nitrogen-containing heteroaryl group optionally substituted with an oxo group or one or more $C_1$-$C_6$ alkyl groups optionally substituted with an oxo group or one hydroxy group, a hydroxy group, or —NR'R", wherein R' and R" each independently represent a $C_1$-$C_6$ alkyl group optionally substituted with one to three halogen atoms, an oxo group, or one to three hydroxy groups, a $C_3$-$C_4$ cycloalkyl group optionally substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group optionally substituted with one or more substituents selected from a $C_1$-$C_6$ alkyl group and a hydroxy group, $R^{10}$ represents a $C_1$-$C_6$ alkyl group optionally substituted with one hydroxy group, a hydroxy group, or a hydrogen atom, or $R^9$ and $R^{10}$ may together form a spiro-linked 4- to 6-membered hydrocarbon ring or a spiro-linked 4- to 6-membered nitrogen-containing heterocyclic ring, and $R^{11}$ represents one or more substituents selected from a hydroxy group, a $C_1$-$C_6$ alkyl group, and a $C_1$-$C_6$ alkoxy group, wherein Group 1 represents a halogen atom, a $C_1$-$C_6$ alkyl group optionally substituted with one to three halogen atoms, a $C_1$-$C_6$ alkoxy group, or a cyano group, Group 2 represents a halogen atom, a $C_1$-$C_6$ alkyl group optionally substituted with one to three halogen atoms, a $C_3$-$C_4$ cycloalkyl group optionally substituted with one to three halogen atoms, a vinyl group, an ethinyl group, a cyano group, or a $C_1$-$C_6$ alkoxy group, Group 3 represents a halogen atom, a $C_1$-$C_6$ alkyl group optionally substituted with one to three halogen atoms or one to three hydroxy groups, a $C_3$-$C_4$ cycloalkyl group optionally substituted with one to three halogen atoms or one to three hydroxy groups, a vinyl group, an ethinyl group, a cyano group, —OR', —NR'R", —COOR', or —CONHR', wherein R' and R" each independently represent a $C_1$-$C_6$ alkyl group optionally substituted with one to three halogen atoms or one to three hydroxy groups, a $C_3$-$C_4$ cycloalkyl group optionally substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group optionally substituted with one or more substituents selected from a $C_1$-$C_6$ alkyl group and a hydroxy group, Group 4 represents a halogen atom, a hydroxy group, a carbamoyl group, a morpholino group, a $C_1$-$C_6$ alkoxy group, a $C_1$-$C_6$ alkylsulfonyl group, or —NR'R", wherein R' and R" each independently represent a $C_1$-$C_6$ alkyl group optionally substituted with one to three halogen atoms, one to three hydroxy groups, or an oxo group, a $C_3$-$C_4$ cycloalkyl group optionally substituted with one to three halogen atoms or one to three hydroxy groups, or a hydrogen atom, or R' and R" together with the nitrogen atom to which R' and R" are bonded may together form a 4- to 7-membered nitrogen-containing heterocyclic group optionally substituted with one or more substituents selected from a $C_1$-$C_6$ alkyl group and a hydroxy group, and Group 5 represents a $C_1$-$C_6$ alkyl group optionally substituted with one to three halogen atoms, one to three hydroxy groups, or a $C_1$-$C_6$ alkoxy group, a $C_3$-$C_6$ cycloalkyl group, a $C_1$-$C_6$ alkoxy group, or a tetrahydropyranyl group.

2. A compound according to claim 1 represented by general formula (5) or a salt thereof:

(5)

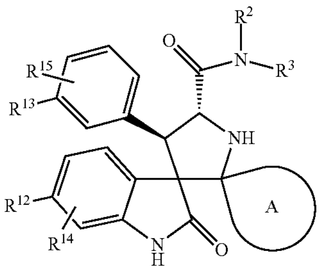

wherein ring A, $R^2$, and $R^3$ have the same meanings as ring A, $R^2$, and $R^3$, respectively, in claim 1;

$R^{12}$ and $R^{13}$ represent a group selected from a halogen atom, a $C_1$-$C_6$ alkyl group optionally substituted with one to three halogen atoms, and a cyano group;

$R^{14}$ is absent or represents one or more substituents selected from a halogen atom, a $C_1$-$C_6$ alkyl group optionally substituted with one to three halogen atoms, and a cyano group; and $R^{15}$ is absent or represents one or more substituents selected from Group 3, wherein Group 3 has the same meaning as Group 3 in claim 1.

3. A compound according to claim 1 represented by general formula (6) or a salt thereof:

(6)

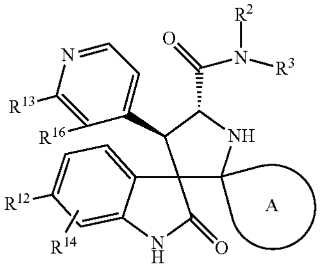

wherein ring A, $R^2$, and $R^3$ have the same meanings as ring A, $R^2$, and $R^3$, respectively, in claim 1;

$R^{12}$, $R^{13}$, and $R^{16}$ represent a group selected from a halogen atom, a $C_1$-$C_6$ alkyl group optionally substituted with one to three halogen atoms, and a cyano group; and $R^{14}$ is absent or represents one or more substituents selected from a halogen atom, a $C_1$-$C_6$ alkyl group optionally substituted with one to three halogen atoms, and cyano group.

4. A compound according to claim 1 represented by general formula (7) or a salt thereof:

(7)

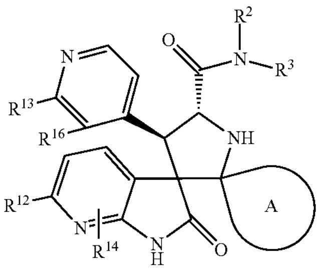

wherein ring A, $R^2$, and $R^3$ have the same meanings as ring A, $R^2$, and $R^3$, respectively, in claim 1;

$R^{12}$, $R^{13}$, and $R^{16}$ represent a group selected from a halogen atom, a $C_1$-$C_6$ alkyl group optionally substituted with one to three halogen atoms, and a cyano group; and $R^{14}$ is absent or represents one or more substituents selected from a halogen atom, a $C_1$-$C_6$ alkyl group optionally substituted with one to three halogen atoms, and a cyano group.

5. A compound according to claim 1 represented by general formula (8) or a salt thereof:

(8)

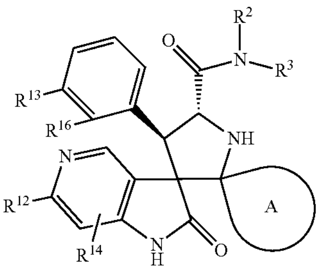

wherein ring A, $R^2$, and $R^3$ have the same meanings as ring A, $R^2$, and $R^3$, respectively, in claim 1;

$R^{12}$, $R^{13}$, and $R^{16}$ represent a group selected from a halogen atom, a $C_1$-$C_6$ alkyl group optionally substituted with one to three halogen atoms, and a cyano group; and $R^{14}$ is absent or represents one or more substituents selected from a halogen atom, a $C_1$-$C_6$ alkyl group optionally substituted with one to three halogen atoms, and a cyano group.

* * * * *